(12) United States Patent
Pinto et al.

(10) Patent No.: US 9,611,274 B2
(45) Date of Patent: *Apr. 4, 2017

(54) MACROCYCLES AS FACTOR XIA INHIBITORS

(71) Applicant: BRISTOL-MYERS SQUIBB COMPANY, Princeton, NJ (US)

(72) Inventors: Donald J. P. Pinto, Churchville, PA (US); James R. Corte, Lawrenceville, NJ (US); Paul J. Gilligan, Wilmington, DE (US); Tianan Fang, Levittown, PA (US); Leon M. Smith, II, Somerset, NJ (US); Yufeng Wang, North Brunswick, NJ (US); Wu Yang, Princeton Junction, NJ (US); William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/942,013

(22) Filed: Nov. 16, 2015

(65) Prior Publication Data

US 2016/0068544 A1 Mar. 10, 2016

Related U.S. Application Data

(62) Division of application No. 14/236,973, filed as application No. PCT/US2012/049706 on Aug. 6, 2012, now Pat. No. 9,221,818.

(60) Provisional application No. 61/515,401, filed on Aug. 5, 2011.

(51) Int. Cl.
| | | |
|---|---|---|
| C07D 487/08 | (2006.01) | |
| C07D 498/06 | (2006.01) | |
| C07D 471/06 | (2006.01) | |
| C07D 487/06 | (2006.01) | |

(52) U.S. Cl.
CPC ......... *C07D 498/06* (2013.01); *C07D 471/06* (2013.01); *C07D 487/06* (2013.01); *C07D 487/08* (2013.01)

(58) Field of Classification Search
CPC .................................................. C07D 487/08
See application file for complete search history.

(56) References Cited

U.S. PATENT DOCUMENTS 9,221,818 B2  12/2015  Pinto et al.

FOREIGN PATENT DOCUMENTS

| WO | WO 2004/080971 A1 | 9/2004 |
|---|---|---|
| WO | WO 2004/094372 A2 | 11/2004 |
| WO | WO 2005/099709 A2 | 10/2005 |
| WO | WO 2005/123050 A2 | 12/2005 |
| WO | WO 2005/123680 A1 | 12/2005 |
| WO | WO 2006/076575 A2 | 7/2006 |
| WO | WO 2006/089005 A2 | 8/2006 |
| WO | WO 2007/070816 A2 | 6/2007 |
| WO | WO 2007/070818 A1 | 6/2007 |
| WO | WO 2007/070826 A1 | 6/2007 |
| WO | WO 2007/076431 A1 | 7/2007 |
| WO | WO 2008/076805 A2 | 6/2008 |
| WO | WO 2008/157162 A1 | 12/2008 |
| WO | WO 2009/114677 A1 | 9/2009 |
| WO | WO 2011/100401 A1 | 8/2011 |
| WO | WO 2011/100402 A1 | 8/2011 |
| WO | WO 2013/022814 A1 | 2/2013 |
| WO | WO 2013/022818 A1 | 2/2013 |
| WO | WO 2013/055984 A1 | 4/2013 |
| WO | WO 2013/056034 A1 | 4/2013 |
| WO | WO 2013/056060 A1 | 4/2013 |
| WO | WO 2014/022766 A1 | 2/2014 |
| WO | WO 2014/022767 A1 | 2/2014 |
| WO | WO 2014/059202 A1 | 4/2014 |
| WO | WO 2014/059203 A1 | 4/2014 |
| WO | WO 2014/059214 A1 | 4/2014 |

*Primary Examiner* — Bruck Kifle
(74) *Attorney, Agent, or Firm* — Hong Liu

(57) ABSTRACT

The present invention provides compounds of Formula (Ia):

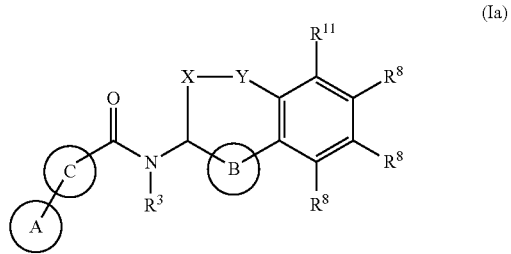

or a stereoisomer, a tautomer, or a pharmaceutically acceptable salt thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

14 Claims, No Drawings

MACROCYCLES AS FACTOR XIA INHIBITORS

CROSS-REFERENCE TO RELATED APPLICATIONS

This application is a divisional application of U.S. patent application Ser. No. 14/236,973, filed Feb. 4, 2014, which is a national phase of International Patent Application No. PCT/US2012/049706, filed Aug. 6, 2012, which claims priority to provisional application, U.S. Ser. No. 61/515,401, filed on Aug. 5, 2011 incorporated by reference herein in their entirety.

FIELD OF THE INVENTION

The present invention relates generally to novel macrocyclic compounds, and their analogues thereof, which are inhibitors of factor XIa and/or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

SUMMARY OF THE INVENTION

The present invention provides novel macrocyclic compounds, their analogues, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two, other agent(s).

These and other features of the invention will be set forth in expanded form as the disclosure continues.

DETAILED DESCRIPTION OF THE INVENTION

I. Compounds of the Invention

In a first aspect, the present invention provides compounds of Formula (I):

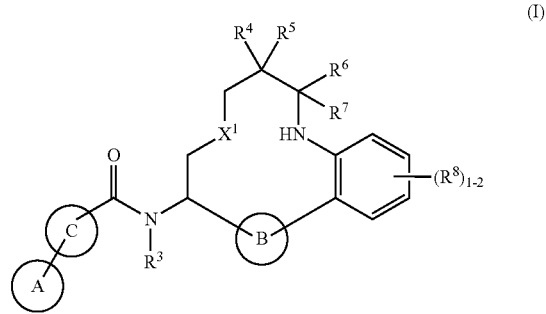

or stereoisomers, tautomers, pharmaceutically acceptable salts, solvates, or prodrugs thereof, wherein:

ring A is selected from aryl and a 5- to 6-membered heterocycle comprising: carbon atoms and 1-4 heteroatoms selected from N, NH, N($C_{1-4}$ alkyl), S(O)$_p$, and O, wherein said aryl and heterocycle are optionally substituted with one or more $R^1$ as valence allows;

ring B is a 5- to 6-membered heterocycle comprising: carbon atoms and 1-4 heteroatoms selected from N, NH, S(O)$_p$, and O, wherein said heterocycle are optionally substituted with one or more $R^{10}$ as valence allows;

ring C is a 4- to 5-membered heterocycle comprising: carbon atoms and 1-4 heteroatoms selected from N, NR$^9$, S(O)$_p$, and O, wherein said heterocycle are optionally substituted with one or more $R^2$ as valence allows;

$X^1$ is selected from $C_{1-4}$ alkylene and $C_{2-4}$ alkenylene; optionally one or more of the carbon atoms of said alkylene and alkenylene may be replaced by O, S(O)$_p$, NH, and N($C_{1-4}$ alkyl);

$R^1$ is, independently at each occurrence, selected from H, halogen, $NO_2$, $C_{1-6}$ alkyl, OH, OMe, and CN;

$R^2$ is selected from H, =O, OH, $NH_2$, $CF_3$, halogen, and $C_{1-4}$ alkyl (optionally substituted with OH), $C_{1-3}$ alkoxy, and $C(O)C_{1-3}$ alkyl;

$R^3$ is selected from H and $C_{1-4}$ alkyl;

alternatively, $R^2$ and $R^3$, together with the atoms to which they are directly or indirectly attached, form a ring wherein said ring is optionally substituted with =O;

$R^4$ is selected from H, $C_{1-4}$ alkyl, hydroxyl, and $C_{3-6}$ cycloalkyl;

$R^5$ is selected from H and $C_{1-4}$ alkyl;

$R^6$ is selected from H, halogen, C(O)OH, and $C(O)O(C_{1-4}$ alkyl);

$R^7$ is selected from H, $C_{1-4}$ alkyl, and $CF_3$;

alternatively, $R^6$ and $R^7$ together are =O;

$R^8$ is, independently at each occurrence, selected from H, halogen, NHC(O)O—$C_{1-4}$ alkyl, CN, OH, O—$C_{1-4}$ alkyl; $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —NHCO($C_{1-4}$ alkyl), —$NHCO_2(CH_2)_{1-2}O(C_{1-4}$ alkyl), —$NHCO_2(CH_2)_{1-3}O(C_{1-4}$ alkyl), $NHCO_2CH_2CH(C_{1-4}$ alkyl)O($C_{1-4}$ alkyl), —$NHCO_2(CH_2)_{1-2}$ OH, —$NHCO_2CH_2CO_2H$, —$CH_2NHCO_2(C_{1-4}$ alkyl), —NHC(O)NH($C_{1-4}$ alkyl), —NHC(O)N($C_{1-4}$ alkyl)$_2$, NHC(O)NH($C_{1-4}$ alkyl)N[5- to 6-membered heterocycle)], —$NHSO_2(C_{1-4}$ alkyl), —$CONH_2$, —CONH($C_{1-4}$ alkyl), —CON($C_{1-4}$ alkyl)$_2$, and —$CH_2CONH_2$;

$R^9$ is selected from H and $C_{1-4}$ alkyl;

$R^{10}$ is, independently at each occurrence, selected from H, halogen, CN, OH, =O, $NH_2$, $C_{3-6}$ cycloalkyl, $C_{1-4}$ alkoxy, $CF_3$, $CH_2OH$, $CO_2H$, $CO_2(C_{1-4}$ alkyl), and CONH; and p is, independently at each occurrence, selected from 0, 1, and 2;

provided the following compounds are excluded

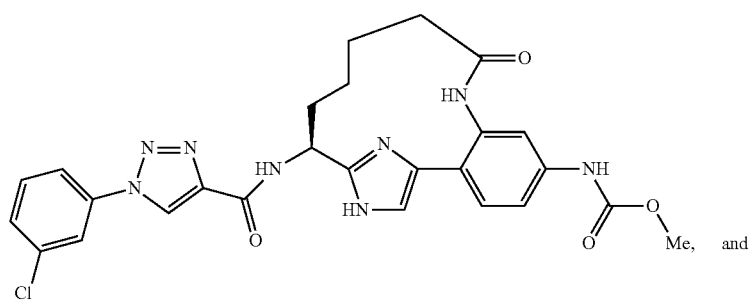

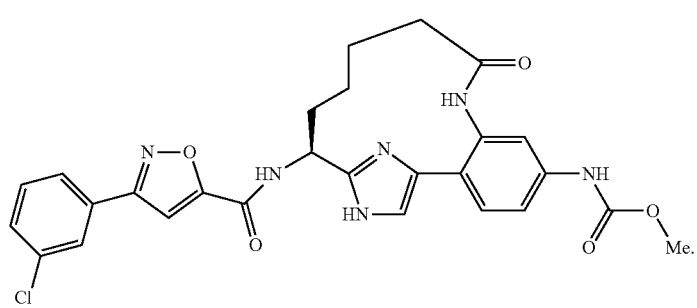

In a second aspect, the present invention provides compounds of Formula (II):

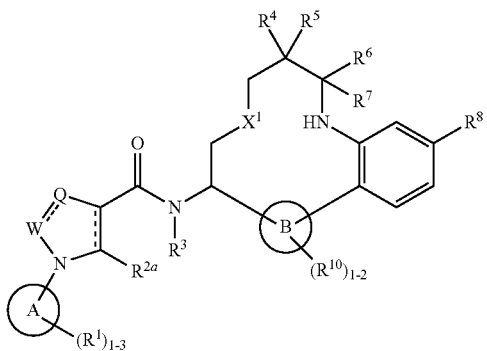

(II)

or stereoisomers, tautomers, pharmaceutically acceptable salts, solvates, or prodrugs thereof, within the scope of the first aspect, wherein:

ring A is selected from aryl and a 6-membered heterocycle comprising: carbon atoms and 1-3 heteroatoms selected from N, NH, and N($C_{1-4}$ alkyl);

ring B is selected from imidazole, pyridine, pyridone, and pyridazine;

$X^1$ is selected from $CH_2$ and CH=CH;

W and Q are each independently selected from N, $NR^9$, $CR^2$, and $CHR^2$; and $R^{2a}$ is selected from H, $NH_2$, and $C_{1-4}$ alkyl.

In a third aspect, the present invention provides compounds of Formula (II), or stereoisomers, tautomers, pharmaceutically acceptable salts, solvates, or prodrugs thereof, within the scope of the second aspect, wherein:

ring A is selected from phenyl and piperidine;

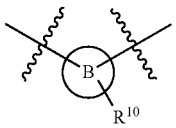

is independently selected from

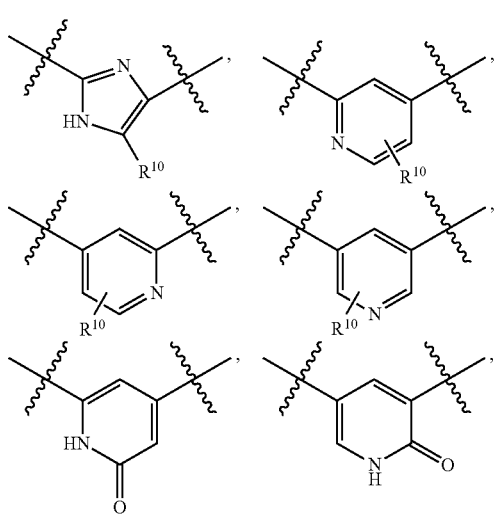

-continued

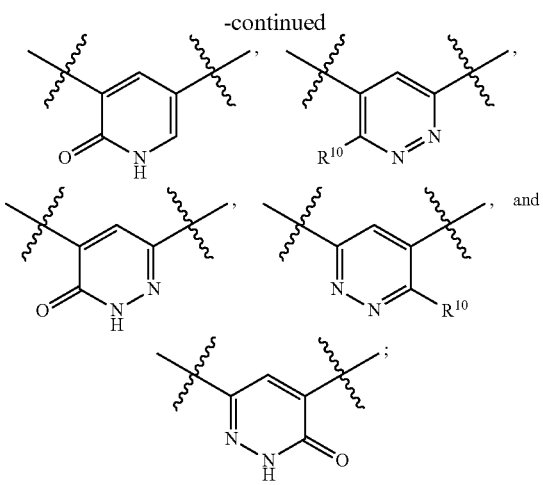

and $R^{10}$ is selected from H, halogen, and CN.

In a fourth aspect, the present invention provides compounds of Formula (III):

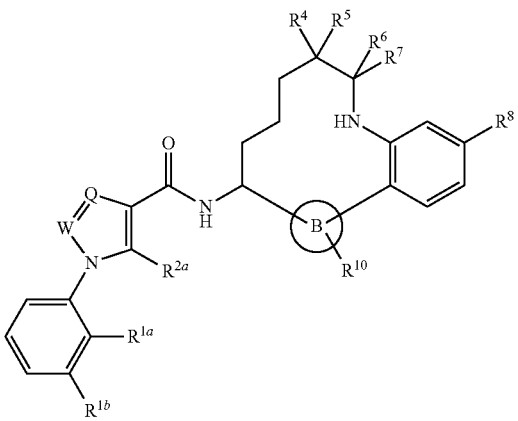

(III)

or stereoisomers, tautomers, pharmaceutically acceptable salts, solvates, or prodrugs thereof, within the scope of the third aspect, wherein:

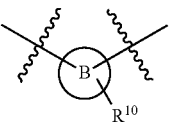

is independently selected from

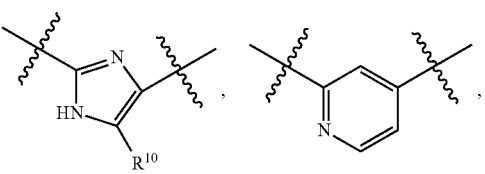

-continued

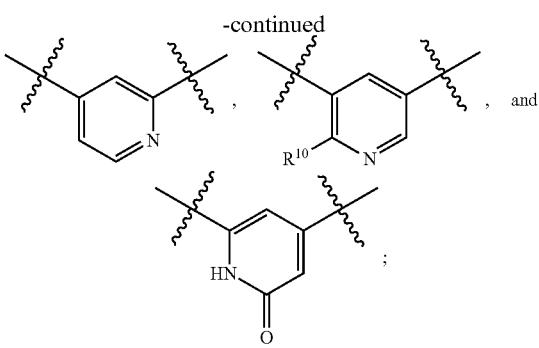

W and Q are each independently selected from N and CR$^2$;

R$^{1a}$ and R$^{1b}$ are each independently selected from H and halogen;

R$^2$ is independently at each occurrence, selected from H and C$_{1-4}$ alkyl optionally substituted with OH;

R$^{2a}$ is selected from H, NH$_2$, and Me;

R$^4$ is selected from H and C$_{1-4}$ alkyl;

R$^5$ is selected from H and C$_{1-4}$ alkyl;

R$^6$ is independently selected from H, C(O)OH, and C(O)O(C$_{1-4}$ alkyl);

R$^7$ is selected from H, C$_{1-4}$ alkyl, and CF$_3$;

alternatively, R$^6$ and R$^7$ together are =O; and

R$^{10}$ is selected from H, halogen and CN.

In a fifth aspect, the present invention provides compounds of Formula (IV):

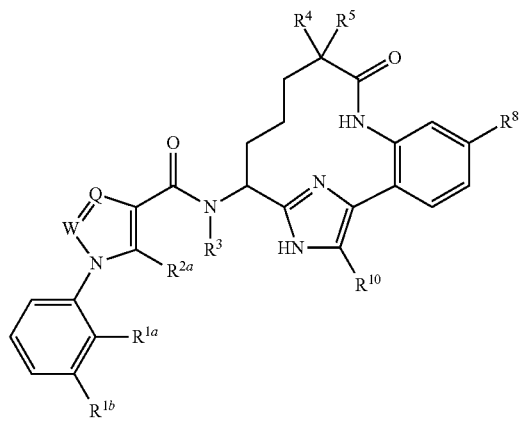

or stereoisomers, tautomers, pharmaceutically acceptable salts, solvates, or prodrugs thereof, within the scope of the fourth aspect, wherein:

W and Q are each independently selected from N and CH;

R$^{1a}$ and R$^{1b}$ are each independently selected from H, F, and Cl;

R$^4$ is selected from H, methyl, ethyl, propyl, isopropyl, and butyl;

R$^5$ is H;

R$^8$ is NHC(O)O—C$_{1-4}$ alkyl; and

R$^{10}$ is selected from H and CN.

In a sixth aspect, the present invention provides compounds of Formula (V):

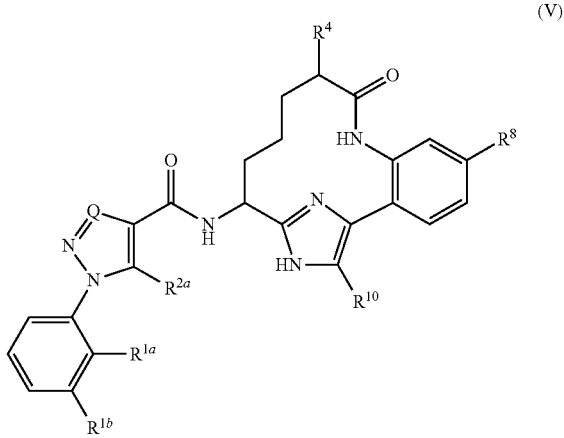

or stereoisomers, tautomers, pharmaceutically acceptable salts, solvates, or prodrugs thereof, within the scope of the fifth aspect, wherein:

R$^{1a}$ is selected from H and F;

R$^{1b}$ is Cl; and

R$^4$ is selected from H, methyl, ethyl, and isopropyl.

In a seventh aspect, the present invention provides compounds of Formula (VI):

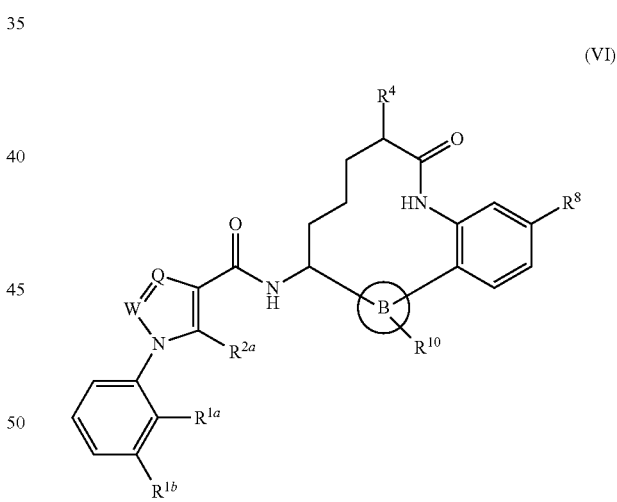

or stereoisomers, tautomers, pharmaceutically acceptable salts, solvates, or prodrugs thereof, within the scope of the fourth aspect, wherein;

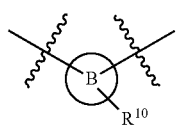

is independently selected from

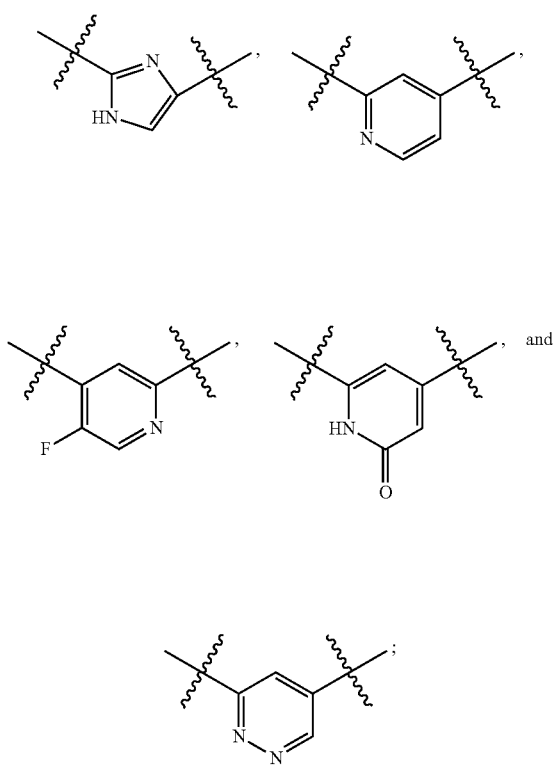

W is selected from N and CH;

Q is selected from N and CH;

$R^{1a}$ and $R^{1b}$ are each independently selected from F and Cl;

$R^4$ is selected from H, methyl, and ethyl; and $R^8$ is NHC(O)OMe.

In another aspect, the present invention provides compounds of Formula (Ia):

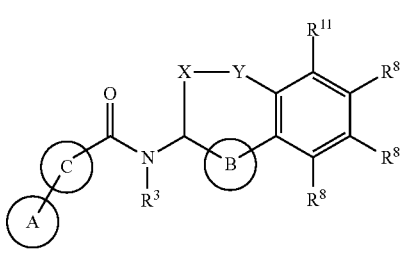

(Ia)

or stereoisomers, tautomers, pharmaceutically acceptable salts, solvates, or prodrugs thereof, wherein:

ring A is selected from aryl and a 5- to 6-membered heterocycle comprising: carbon atoms and 1-4 heteroatoms selected from N, NH, N($C_{1-4}$ alkyl), S(O)$_p$, and O, wherein said aryl and heterocycle are optionally substituted with $R^1$;

ring B is a 5- to 6-membered heterocycle comprising: carbon atoms and 1-4 heteroatoms selected from N, NH, S(O)$_p$, and O, wherein said heterocycle is optionally substituted with $R^{10}$;

ring C is a 4- to 6-membered heterocycle comprising: carbon atoms and 1-4 heteroatoms selected from N, $NR^9$, S(O)$_p$, and O, wherein said heterocycle is optionally substituted with $R^2$;

X is selected from $C_{4-8}$ alkylene and $C_{4-8}$ alkenylene, wherein said alkylene and alkenylene are substituted with $R^4$ and $R^5$; alternatively one or more of the carbon atoms of said alkylene and alkenylene may be replaced by O, C=O, S(O)$_p$, NH, and N($C_{1-4}$ alkyl);

Y is selected from —$CR^6R^7$—NH— and —NH—$CR^6R^7$—;

$R^1$ is selected from H, halogen, $NO_2$, $C_{1-6}$ alkyl, OH, haloalkyl, alkoxy, haloalkoxy, —C(=O)$C_{1-3}$ alkyl, and CN;

$R^2$ is selected from H, =O, OH, $NH_2$, $CF_3$, halogen, $C_{1-4}$ alkyl (optionally substituted with OH), $C_{1-3}$ alkoxy, and C(O)$C_{1-3}$ alkyl;

$R^3$ is selected from H and $C_{1-4}$ alkyl;

alternatively, $R^2$ and $R^3$, together with the atoms to which they are directly or indirectly attached, form a ring;

$R^4$ and $R^5$ are independently selected from H, halogen, $C_{1-6}$ alkyl, OH, $NH_2$, —$CH_2NH_2$, $C_{1-4}$ haloalkyl, —$OCH_2F$, —$OCHF_2$, —$OCF_3$, NH($C_{1-4}$ alkyl), N($C_{1-4}$ alkyl)$_2$, $C_{1-4}$ alkoxy, —$CH_2OH$, and —$CH_2O$($C_{1-4}$ alkyl); when $R^4$ and $R^5$ are not attached to the same carbon atom, they may be taken together with the carbon atoms to which they are attached to form a carbocycle;

$R^6$ is selected from H, halogen, C(O)OH, and C(O)O($C_{1-4}$ alkyl);

$R^7$ is selected from H, $C_{1-4}$ alkyl, and $CF_3$;

alternatively, $R^6$ and $R^7$ together are =O;

$R^8$ is, independently at each occurrence, selected from H, halogen, haloalkyl, CN, —$(CH_2)_n$OH, $NR^{12}R^{12}$, —$CH_2NH_2$, C(O)OH, —$(CH_2)_n$—NHC(O)$OR^{12}$, —NHC(O)$R^{12}$, —NHC(O)C(O)$R^{12}$, —NHC(N=CN)$NHR^{12}$, —NHC(NH)$NHR^{12}$, —N=CHN$R^{12}R^{12}$, —NHC(O)$NR^{12}R^{12}$, —NHS(O)$_2C_{1-4}$ alkyl, —$(CH_2)_n$—CON$R^{12}R^{12}$, —$(CH_2)_nC(O)O(C_{1-4}$ alkyl), —NHC(O)OCH$_2$(C(CH$_2$)$_2$)O—$(CH_2)_n$—$C_{3-10}$ carbocycle, —$(CH_2)_n$—$C_{3-10}$ carbocycle, and —$(CH_2)_n$-4-10-membered heterocycle wherein said carbocycle and heterocycle are optionally substituted with $R^{13}$;

$R^9$ is selected from H and $C_{1-4}$ alkyl;

$R^{10}$ is selected from H, halogen, CN, =O, OH, $NH_2$, $C_{3-6}$ cycloalkyl, $C_{1-4}$ alkyl, $C_{1-4}$ alkoxy, and $C_{1-4}$ haloalkyl;

$R^{11}$ is selected from H, halogen, and methyl;

$R^{12}$ is selected from H, $C_{1-4}$ alkyl (optionally substituted with halogen, hydroxy, alkoxy, carboxy, alkoxycarbonyl), —$(CH_2)_n$—$C_{3-10}$ carbocycle and —$(CH_2)_n$-4-10-membered heterocycle, wherein said carbocycle and heterocycle are optionally substituted with $R^{13}$;

$R^{13}$ is selected from OH, halogen, $C_{1-6}$ alkyl, $C_{3-6}$ cycloalkyl, —$(CH_2)_n$—C(=O)OH, —$(CH_2)_n$—C(=O)O$C_{1-4}$ alkyl, —$(CH_2)_n$—$OC_{1-4}$ alkyl, and =O;

n is, independently at each occurrence, selected from 0, 1, 2, 3, and 4;

p is, independently at each occurrence, selected from 0, 1, and 2;

provided the following compounds are excluded

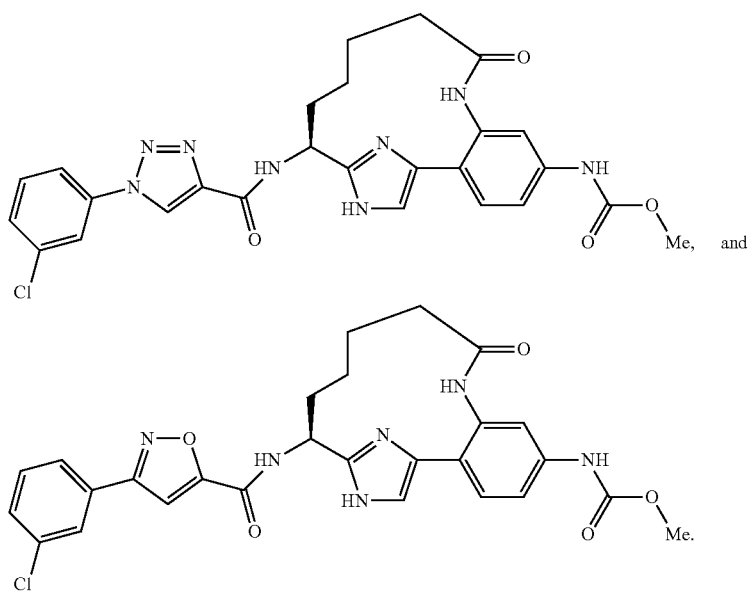

In another aspect, the present invention provides compounds of Formula (Ia), or stereoisomers, tautomers, pharmaceutically acceptable salts, solvates, or prodrugs thereof, wherein:

ring C is a 6-membered heterocycle comprising: carbon atoms and 1-4 heteroatoms selected from N, and $NR^9$, wherein said heterocycle is optionally substituted with $R^2$ and wherein all the variables have the meanings as defined in Formula (Ia).

In another aspect, the present invention provides compounds of Formula (Ia), or stereoisomers, tautomers, pharmaceutically acceptable salts, solvates, or prodrugs thereof, wherein:

$R^8$ is, independently at each occurrence, selected from haloalkyl, —$CH_2OH$, $NR^{12}R^{12}$, —$(CH_2)_n$—$NHC(O)OR^{12}$, —$NHC(O)R^{12}$, —$NHC(O)C(O)R^{12}$, —NHC(N—CN)$NHR^{12}$, —$NHC(NH)NHR^{12}$, —N=$CHNR^{12}R^{12}$, —$(CH_2)_n$—$C_{3-10}$ carbocycle, and —$(CH_2)_n$-4-10-membered heterocycle wherein said carbocycle and heterocycle are optionally substituted with $R^{13}$;

X is selected from —$CR^4R^5$—$CR^4R^5$—, —$CR^4R^5$—$CR^4R^5$—$CR^4R^5$—, and —$CR^4$=$CR^5CR^4R^5$—, wherein one or more —$CR^4R^5$— may be replaced by O or C=O;

$R^4$ is selected from H, F, Cl, OH, and $C_{1-4}$ alkyl;

$R^5$ is selected from H, F, and $C_{1-4}$ alkyl; when $R^4$ and $R^5$ are not attached to the same carbon atom, they may be taken together with the carbon atoms to which they are attached to form a carbocycle;

$R^{11}$ is H;

$R^{12}$ is selected from H, $C_{1-4}$ alkyl (optionally substituted with halogen, hydroxy, alkoxy, carboxy, alkoxycarbonyl), —$(CH_2)_n$—$C_{3-10}$ carbocycle and —$(CH_2)_n$-4-10-membered heterocycle, wherein said carbocycle and heterocycle are optionally substituted with $R^{13}$;

$R^{13}$ is selected from OH, halogen, $C_{1-6}$ alkyl, $C_{3-6}$ cycloalkyl, —$(CH_2)_n$—C(=O)OH, —$(CH_2)_n$—C(=O)$OC_{1-4}$ alkyl, —$(CH_2)_n$—$OC_{1-4}$ alkyl, and =O; and n is, independently at each occurrence, selected from 0, 1, 2, and 3, and wherein all the variables have the meanings as defined in Formula (Ia).

In another aspect, the present invention provides compounds of Formula (IIa):

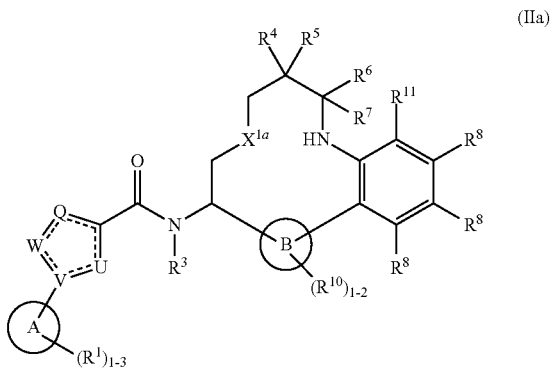

(IIa)

or stereoisomers, tautomers, pharmaceutically acceptable salts, solvates, or prodrugs thereof, wherein:

ring A is selected from aryl and a 5- to 6-membered heterocycle comprising: carbon atoms and 1-3 heteroatoms selected from N, NH, and N($C_{1-4}$ alkyl);

ring B is selected from imidazole, pyridine, pyridone, pyrimidine, and pyridazine;

$X^{1a}$ is selected from $C_{2-4}$ alkylene and $C_{2-4}$ alkenylene wherein said $C_{2-4}$ alkylene and $C_{2-4}$ alkenylene are optionally substituted with $R^4$ and $R^5$; alternatively, one or more of the carbon atoms of said alkylene may be replaced by O and C=O;

U, V, W, and Q are each independently selected from N, $NR^9$, S, O, C, $CR^2$, and $CHR^2$;

--- is an optional bond;

$R^1$ is, independently at each occurrence, selected from H, halogen, $NO_2$, $C_{1-6}$ alkyl, OH, $C_{1-6}$ haloalkyl, $C_{1-6}$ alkoxy, $C_{1-6}$ haloalkoxy, and CN;

$R^2$ is selected from H, =O, OH, $NH_2$, $CF_3$, halogen, $C_{1-4}$ alkyl optionally substituted with OH, $C_{1-3}$ alkoxy, and C(O)$C_{1-3}$ alkyl;

$R^3$ is H;

$R^4$ and $R^5$ are independently selected from H, halogen, $C_{1-6}$ alkyl, OH, and $NH_2$; when $R^4$ and $R^5$ are not attached to the same carbon atom, they may be taken together with the carbon atoms to which they are attached to form a carbocycle;

$R^6$ is selected from H, halogen, C(O)OH, and C(O)O($C_{1-4}$ alkyl);

$R^7$ is selected from H, $C_{1-4}$ alkyl, and $CF_3$;

alternatively, $R^6$ and $R^7$ together are =O;

$R^8$ is, independently at each occurrence, selected from H, halogen, haloalkyl, CN, OH, $NR^{12}R^{12}$, C(O)OH, —$(CH_2)_n$—, —NHC(O)OR$^{12}$, —NHC(O)R$^{12}$, —NHC(O)NR$^{12}R^{12}$, —NHS(O)$_2C_{1-4}$ alkyl, —$(CH_2)_n$—CONR$^{12}R^{12}$, —$(CH_2)_nC$(O)O($C_{1-4}$ alkyl), —$(CH_2)_n$—$C_{3-10}$ carbocycle, and —$(CH_2)_n$-4-10-membered heterocycle optionally substituted with $R^{13}$;

$R^9$ is selected from H and $C_{1-4}$ alkyl;

$R^{10}$ is, independently at each occurrence, selected from H, halogen, CN, =O, OH, $NH_2$, $C_{3-6}$ cycloalkyl, $C_{1-4}$ alkyl, $C_{1-4}$ alkoxy, and $C_{1-4}$ haloalkyl;

$R^{11}$ is H;

$R^{12}$ is selected from H, $C_{1-4}$ alkyl (optionally substituted with halogen, hydroxy, alkoxy, carboxy, alkoxycarbonyl), —$(CH_2)_n$—$C_{3-10}$ carbocycle and —$(CH_2)_n$-4-10-membered heterocycle, wherein said carbocycle and heterocycle are optionally substituted with $R^{13}$;

$R^{13}$ is selected from OH, halogen, $C_{1-6}$ alkyl, $C_{3-6}$ cycloalkyl, —$(CH_2)_n$—C(=O)OH, —$(CH_2)_nC$(=O)O$C_{1-4}$ alkyl, —$(CH_2)_n$—O$C_{1-4}$ alkyl, and =O; and n is, independently at each occurrence, selected from 0, 1, 2, and 3.

In another aspect, the present invention provides compounds of Formula (IIa), or stereoisomers, tautomers, pharmaceutically acceptable salts, solvates, or prodrugs thereof, wherein:

ring A is selected from phenyl, piperidine, and pyridine;

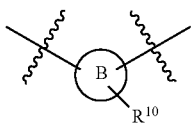

is selected from

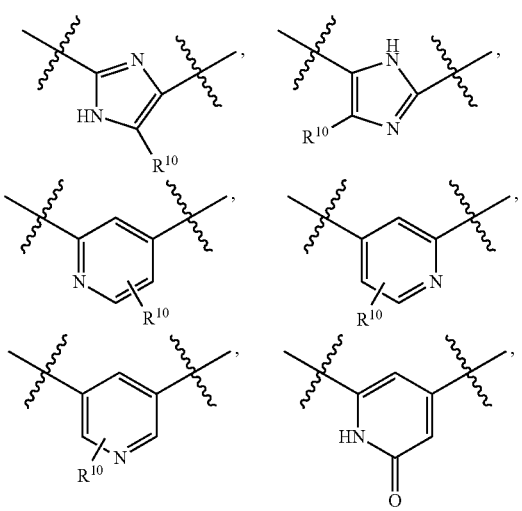

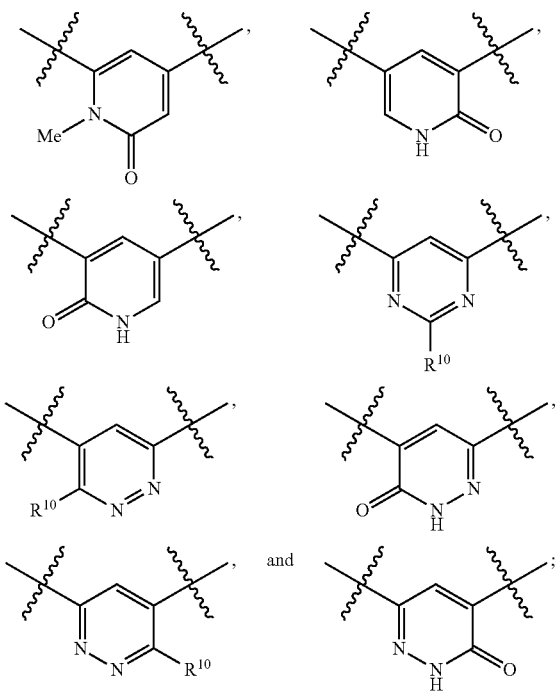

and $R^{10}$ is selected from H, F, Cl, $C_{1-4}$ alkyl, $C_{1-4}$ alkoxy, and CN.

In another aspect, the present invention provides compounds of Formula (IIIa):

(IIIa)

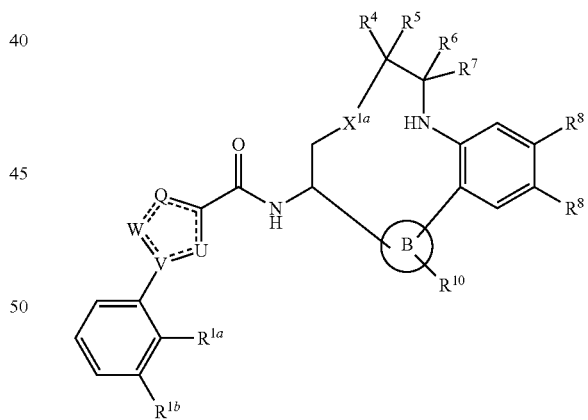

or stereoisomers, tautomers, pharmaceutically acceptable salts, solvates, or prodrugs thereof, wherein:

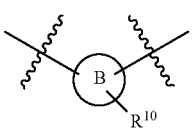

is independently selected from

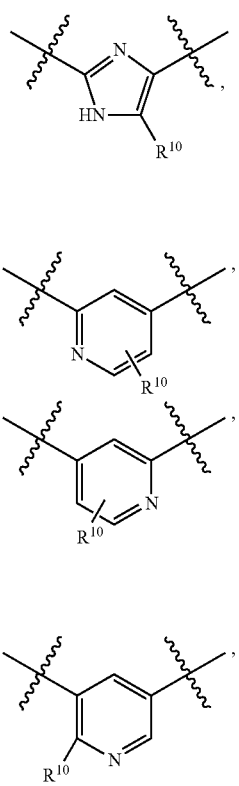

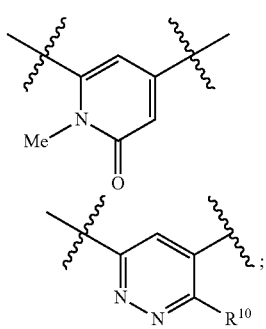

U, V, W, and Q are each independently selected from N, $NR^9$, S, C, $CR^2$, and $CHR^2$;

$X^{1a}$ is selected from —$CR^4R^5$—$CR^4R^5$—, —$CR^4R^5$—$CR^4R^5$—$CR^4R^5$—, and —$CR^4$=$CR^5CR^4R^5$—, wherein one or more —$CR^4R^5$— may be replaced by O or C=O;

$R^{1a}$ and $R^{1b}$ are each independently selected from H, halogen, OH, CN, $CH_3$, $OCH_3$, $CF_3$, and $OCHF_2$;

$R^2$ is selected from H, OH, $NH_2$, $CF_3$, halogen, $C_{1-4}$ alkyl (optionally substituted with OH), $C_{1-3}$ alkoxy, and $C(O)C_{1-3}$ alkyl;

$R^4$ is selected from H, F, Cl, OH, and $C_{1-4}$ alkyl;

$R^5$ is selected from H, F, and $C_{1-4}$ alkyl;

$R^6$ is independently selected from H, C(O)OH, and C(O)O($C_{1-4}$ alkyl);

$R^7$ is selected from H, $C_{1-4}$ alkyl, and $CF_3$;

alternatively, $R^6$ and $R^7$ together are =O;

$R^8$ is, independently at each occurrence, selected from H, halogen, haloalkyl, CN, OH, $NR^{12}R^{12}$, —$CH_2NH_2$, C(O)OH, and —$NHC(O)OR^{12}$, —$(CH_2)_n$—$C_{3-10}$ carbocycle, and —$(CH_2)_n$-4-10-membered heterocycle optionally substituted with $R^{13}$;

$R^9$ is selected from H and $C_{1-4}$ alkyl;

$R^{10}$ is selected from H, halogen, methyl, ethyl, methoxy, ethoxy, and CN;

$R^{12}$ is selected from H, $C_{1-4}$ alkyl (optionally substituted with F, OH, —O($C_{1-4}$ alkyl), —C(O)OH, —C(O)O($C_{1-4}$ alkyl)), —$(CH_2)_n$—$C_{3-10}$ carbocycle and —$(CH_2)_n$-4-10-membered heterocycle, wherein said carbocycle and heterocycle are optionally substituted with $R^{13}$;

$R^{13}$ is selected from OH, halogen, $C_{1-6}$ alkyl, $C_{3-6}$ cycloalkyl, —$(CH_2)_n$—C(=O)OH, —$(CH_2)_n$—C(=O)O$C_{1-4}$ alkyl, —$(CH_2)_n$—O$C_{1-4}$ alkyl, and =O; and n is, independently at each occurrence, selected from 0, 1, 2, and 3.

In another aspect, the present invention provides compounds of Formula (IVa):

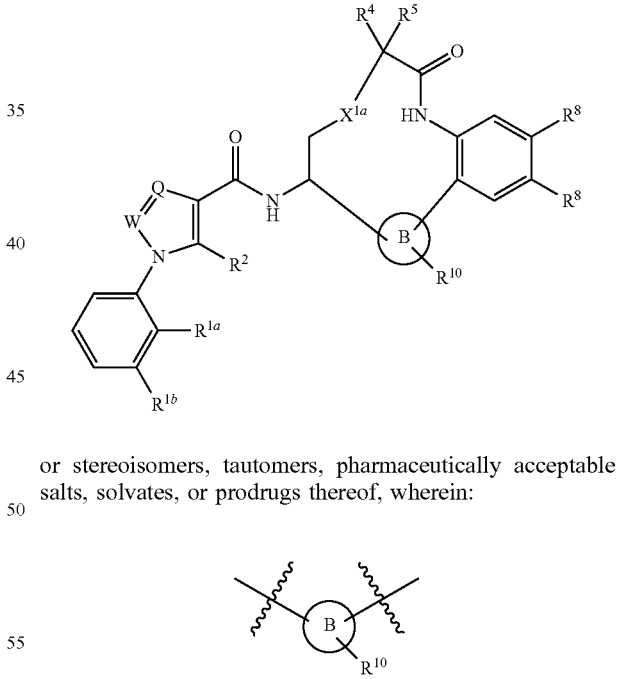

(IVa)

or stereoisomers, tautomers, pharmaceutically acceptable salts, solvates, or prodrugs thereof, wherein:

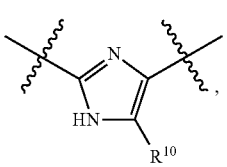

is independently selected from

-continued

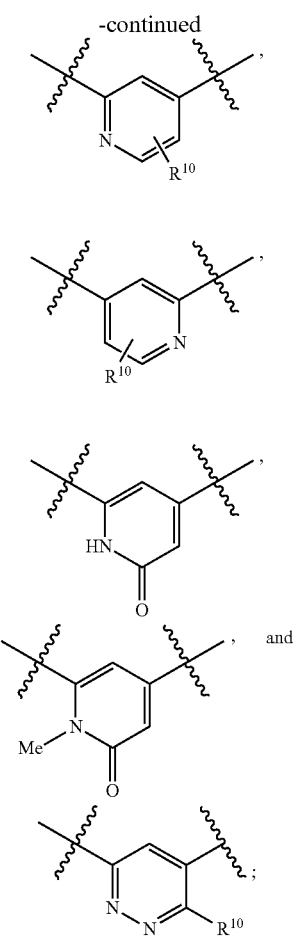

W and Q are each independently selected from N and CR$^2$;

R$^{1a}$ is selected from H, F, and Cl;

R$^{1b}$ is selected from H, F, Cl, OH, CN, CH$_3$, OCH$_3$, CF$_3$, and OCHF$_2$;

R$^2$ is selected from H, OH, NH$_2$, CF$_3$, F, Cl, and C$_{1-4}$ alkyl;

R$^4$ is selected from H, F, methyl, ethyl, propyl, and isopropyl;

R$^5$ is H and F;

R$^8$ is, independently at each occurrence, selected from H, halogen, haloalkyl, CN, OH, NR$^{12}$R$^{12}$, C(O)OH, and —NHC(O)OR$^{12}$, and —(CH$_2$)$_n$-4-10-membered heterocycle optionally substituted with R$^{13}$;

R$^{10}$ is selected from H, halogen, methyl, ethyl, methoxy, ethoxy, and CN;

R$^{12}$ is selected from H, C$_{1-4}$ alkyl (optionally substituted with F, OH, —O(C$_{1-4}$ alkyl), —C(O)OH, —C(O)O(C$_{1-4}$ alkyl)), —(CH$_2$)$_n$—C$_{3-10}$ carbocycle and —(CH$_2$)$_n$-4-10-membered heterocycle, wherein said carbocycle and heterocycle are optionally substituted with R$^{13}$;

R$^{13}$ is selected from OH, halogen, C$_{1-6}$ alkyl, C$_{3-6}$ cycloalkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, and =O; and n is, independently at each occurrence, selected from 0, 1, 2, and 3.

In another aspect, the present invention provides compounds of Formula (Va):

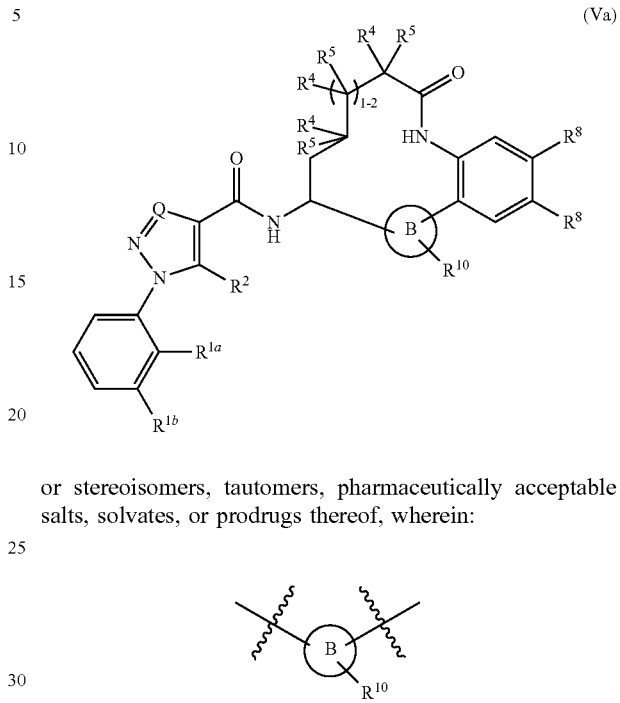

(Va)

or stereoisomers, tautomers, pharmaceutically acceptable salts, solvates, or prodrugs thereof, wherein:

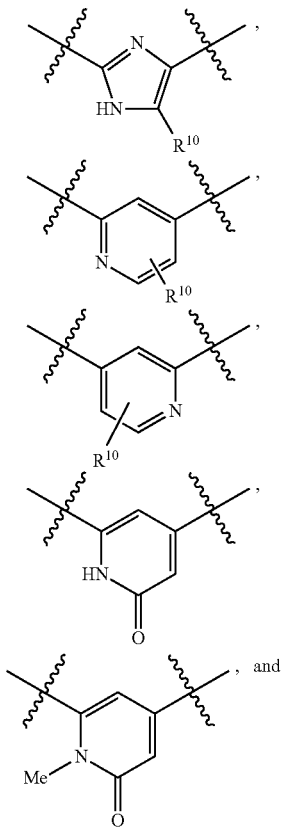

is independently selected from

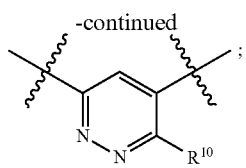

Q is selected from N and CR$^2$;

R$^{1a}$ is selected from H and F;

R$^{1b}$ is Cl;

R$^2$ is selected from H, OH, NH$_2$, F, Cl, and methyl;

R$^4$ is selected from H, OH, methyl, ethyl, and isopropyl;

R$^5$ is H and F;

R$^8$ is, independently at each occurrence, selected from H, NR$^{12}$R$^{12}$, C(O)OH, —NHC(O)OR$^{12}$, and —(CH$_2$)$_n$-4-10-membered heterocycle optionally substituted with R$^{13}$;

R$^{10}$ is selected from H, halogen, methyl, ethyl, methoxy, ethoxy, and CN;

R$^{12}$ is selected from H, C$_{1-4}$ alkyl (optionally substituted with F, OH, —O(C$_{1-4}$ alkyl), —C(O)OH, —C(O)O(C$_{1-4}$ alkyl)), —(CH$_2$)$_n$—C$_{3-10}$ carbocycle, and —(CH$_2$)$_n$-4-10-membered heterocycle, wherein said carbocycle and heterocycle are optionally substituted with R$^{13}$;

R$^{13}$ is selected from OH, halogen, C$_{1-6}$ alkyl, C$_{3-6}$ cycloalkyl, —(CH$_2$)$_n$—C(═O)OH, —(CH$_2$)$_n$—C(═O)OC$_{1-4}$ alkyl, —(CH$_2$)$_n$—OC$_{1-4}$ alkyl, and ═O; and n is, independently at each occurrence, selected from 0, 1, 2, and 3.

In another aspect, the present invention provides compounds of Formula (Vab):

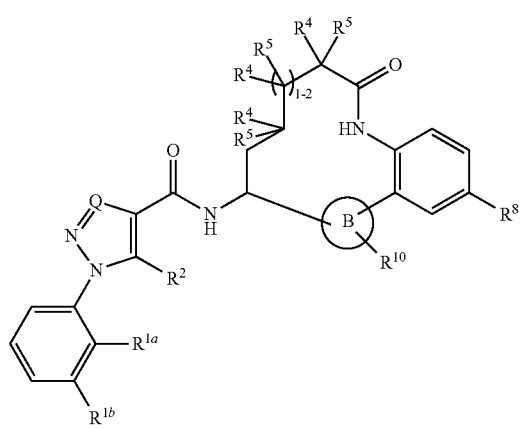

(Vab)

or stereoisomers, tautomers, pharmaceutically acceptable salts, solvates, or prodrugs thereof, wherein:

R$^8$ is selected from C(O)OH and a 4-10-membered heterocycle optionally substituted with R$^{13}$.

In another aspect, the present invention provides compounds of Formula (VIa):

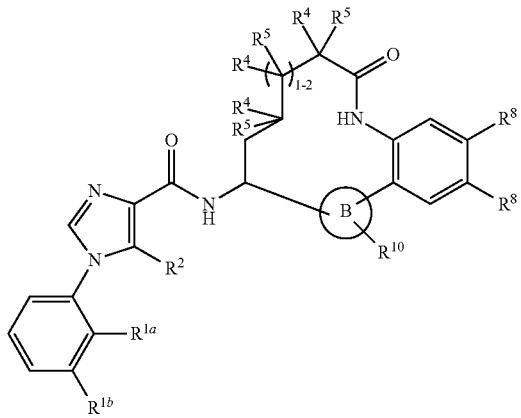

(VIa)

or stereoisomers, tautomers, pharmaceutically acceptable salts, solvates, or prodrugs thereof, wherein:

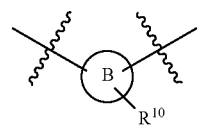

is independently selected from

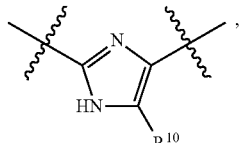

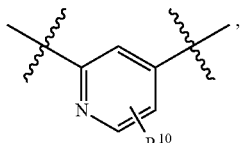

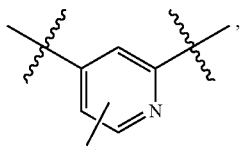

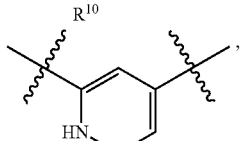

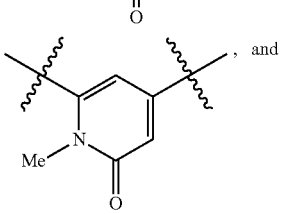

-continued

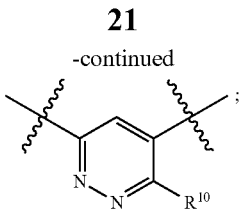

R$^{1a}$ is selected from H and F;

R$^{1b}$ is Cl;

R$^2$ is selected from H, OH, NH$_2$, F, Cl, and methyl;

R$^4$ is selected from H, OH, methyl, ethyl, and isopropyl;

R$^5$ is H and F;

R$^8$ is, independently at each occurrence, selected from H, NR$^{12}$R$^{12}$, C(O)OH, and —NHC(O)OR$^{12}$;

R$^{10}$ is selected from H, halogen, methyl, ethyl, methoxy, ethoxy, and CN;

R$^{12}$ is selected from H, C$_{1-4}$ alkyl (optionally substituted with F, OH, —O(C$_{1-4}$ alkyl), —C(O)OH, —C(O)O(C$_{1-4}$ alkyl)), —(CH$_2$)$_n$—C$_{3-10}$ carbocycle and —(CH$_2$)$_n$-4-10-membered heterocycle, wherein said carbocycle and heterocycle are optionally substituted with R$^{13}$;

R$^{13}$ is selected from OH, halogen, C$_{1-6}$ alkyl, C$_{3-6}$ cycloalkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, and =O; and n is, independently at each occurrence, selected from 0, 1, 2, and 3.

In another aspect, the present invention provides compounds of Formula (VIIa):

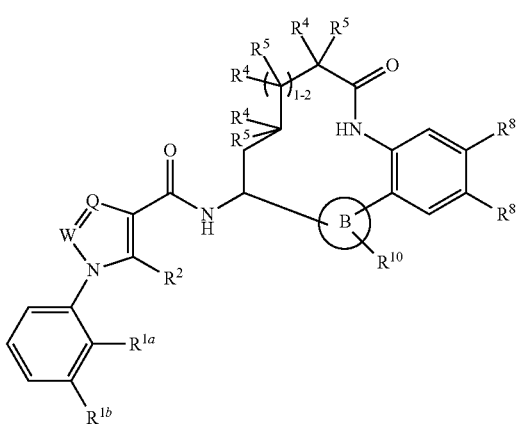

(VIIa)

or stereoisomers, tautomers, pharmaceutically acceptable salts, solvates, or prodrugs thereof, wherein:

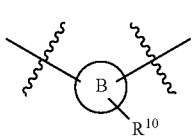

is independently selected from

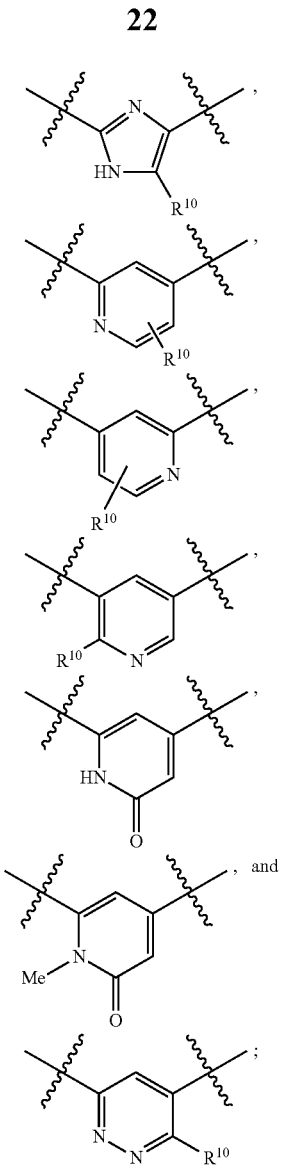

W is selected from N and CR$^2$;

Q is selected from N and CR$^2$;

R$^{1a}$ is selected from H and F;

R$^{1b}$ is Cl;

R$^2$ is selected from H, Cl, NH$_2$, and methyl;

R$^4$ is selected from H, F, methyl, ethyl, OH;

R$^5$ is selected from H and F;

R$^8$ is selected from H, NHR$^{12}$, —(CH$_2$)$_n$OH, —NHC(N=CN)NHR$^{12}$, —C(O)OH, and —NHC(O)OR$^{12}$, and —(CH$_2$)$_n$-4-10-membered heterocycle optionally substituted with R$^{13}$;

R$^{10}$ is selected from H, F, Cl, C$_{1-2}$ alkyl, methoxy, ethoxy, and CN;

R$^{12}$ is selected from H, C$_{1-4}$ alkyl (optionally substituted with F, OH, —OC$_{1-4}$ alkyl, —C(O)OH, —C(O)OC$_{1-4}$ alkyl, —O-arylalkyl), —(CH$_2$)$_n$—C$_{3-6}$ cycloalkyl and —(CH$_2$)$_n$-4-6-membered heterocycle comprising carbon atoms and 1-4 heteroatoms selected from N, NH, N(C$_{1-4}$ alkyl), and O wherein said heterocycle is optionally substituted with R$^{13}$;

R$^{13}$ is selected from OH, OC$_{1-4}$ alkyl, C$_{1-6}$ alkyl (optionally substituted with alkoxy), C$_{3-6}$ cycloalkyl, and =O; and n is, independently at each occurrence, selected from 0, 1, 2, and 3.

In another aspect, the present invention provides compounds of Formula (VIIa) or a stereoisomer, a tautomer, a pharmaceutically acceptable salt, a solvate thereof, wherein:

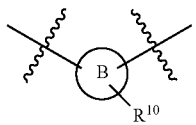

is independently selected from

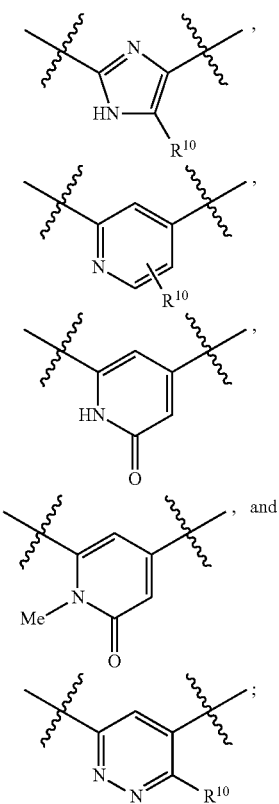

W is selected from N and $CR^2$;
Q is selected from N and $CR^2$;
$R^{1a}$ is selected from H and F;
$R^{1b}$ is Cl;
$R^2$ is selected from H, Cl, $NH_2$, and methyl;
$R^4$ is selected from H, F, methyl, ethyl, OH;
$R^5$ is selected from H and F;
$R^8$ is selected from H, $NHR^{12}$, —C(O)OH, and —NHC(O)$R^{12}$;
$R^{10}$ is selected from H, F, Cl, methyl methoxy, ethoxy, and CN;
$R^{12}$ is selected from H, $C_{1-4}$ alkyl (optionally substituted with F, OH, —O$C_{1-4}$ alkyl, —C(O)OH, —C(O)O$C_{1-4}$ alkyl), —(CH$_2$)$_n$—$C_{3-6}$ cycloalkyl and —(CH$_2$)$_n$-4-6-membered heterocycle comprising carbon atoms and 1-4 heteroatoms selected from N, NH, N($C_{1-4}$ alkyl), and O wherein said heterocycle is optionally substituted with $R^{13}$;
$R^{13}$ is selected from OH, O$C_{1-4}$ alkyl, $C_{1-6}$ alkyl (optionally substituted with alkoxy), $C_{3-6}$ cycloalkyl, and =O; and
n is, independently at each occurrence, selected from 0, 1, 2, and 3.

In another aspect, the present invention provides compounds of Formula (VIIIa):

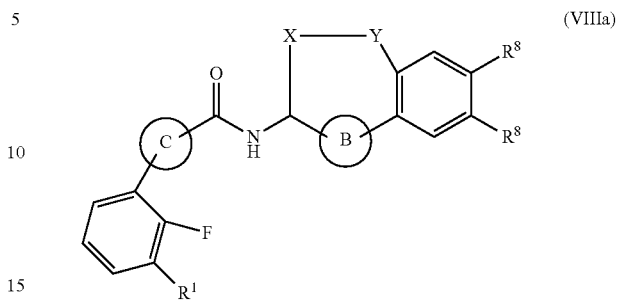

or stereoisomers, tautomers, pharmaceutically acceptable salts, solvates, or prodrugs thereof, wherein:
ring B is a 5- to 6-membered heterocycle comprising: carbon atoms and 1-4 heteroatoms selected from N, NH, S(O)$_p$, and O, wherein said heterocycle is optionally substituted with $R^{10}$;
ring C is a 4- to 6-membered heterocycle comprising: carbon atoms and 1-4 heteroatoms selected from N, $NR^9$, S(O)$_p$, and O, wherein said heterocycle is optionally substituted with $R^2$;
X is selected from $C_{4-8}$ alkylene and $C_{4-8}$ alkenylene, wherein said alkylene and alkenylene are substituted with $R^4$ and $R^5$; alternatively one or more of the carbon atoms of said alkylene and alkenylene may be replaced by O, C=O, S(O)$_p$, NH, and N($C_{1-4}$ alkyl);
Y is selected from —$CR^6R^7$—NH— and —NH—$CR^6R^7$—;
$R^{1b}$ is selected from H and Cl;
$R^2$ is selected from H, =O, OH, $NH_2$, $CF_3$, halogen, $C_{1-4}$ alkyl (optionally substituted with OH), $C_{1-3}$ alkoxy, and C(O)$C_{1-3}$ alkyl;
$R^3$ is selected from H and $C_{1-4}$ alkyl;
$R^4$ and $R^5$ are independently selected from H, halogen, $C_{1-6}$ alkyl, OH, $NH_2$, —$CH_2NH_2$, $C_{1-4}$ haloalkyl, —OCH$_2$F, —OCHF$_2$, —OCF$_3$, NH($C_{1-4}$ alkyl), N($C_{1-4}$ alkyl)$_2$, $C_{1-4}$ alkoxy, —$CH_2$OH, and —$CH_2$O($C_{1-4}$ alkyl); when $R^4$ and $R^5$ are not attached to the same carbon atom, they may be taken together with the carbon atoms to which they are attached to form a carbocycle;
$R^6$ is selected from H, halogen, C(O)OH, and C(O)O($C_{1-4}$ alkyl);
$R^7$ is selected from H, $C_{1-4}$ alkyl, and $CF_3$;
alternatively, $R^6$ and $R^7$ together are =O;
$R^8$ is, independently at each occurrence, selected from H, halogen, haloalkyl, CN, —(CH$_2$)$_n$OH, $NR^{12}R^{12}$, —$CH_2NH_2$, C(O)OH, —(CH$_2$)$_n$—NHC(O)O$R^{12}$, —NHC(O)$R^{12}$, —NHC(O)C(O)$R^{12}$, —NHC(=N—CN)NHR$^{12}$, —NHC(=N—CN)NHR$^{12}$, —N=CHNR$^{12}R^{12}$, —NHC(O)NR$^{12}R^{12}$, —NHS(O)$_2C_{1-4}$ alkyl, —(CH$_2$)$_n$—CONR$^{12}$R', —(CH$_2$)$_n$C(O)O($C_{1-4}$ alkyl), —(CH$_2$)$_n$—$C_{3-10}$ carbocycle, and —(CH$_2$)$_n$-4-10-membered heterocycle wherein said carbocycle and heterocycle are optionally substituted with $R^{13}$;
$R^9$ is selected from H and $C_{1-4}$ alkyl;
$R^{10}$ is selected from H, halogen, CN, =O, OH, $NH_2$, $C_{3-6}$ cycloalkyl, $C_{1-4}$ alkyl, $C_{1-4}$ alkoxy, $C_{1-4}$ haloalkyl, $CH_2$OH, C(O)OH, C(O)O($C_{1-4}$ alkyl), and CONH;
$R^{11}$ is selected from H, halogen, and methyl;
$R^{12}$ is selected from H, $C_{1-4}$ alkyl (optionally substituted with halogen, hydroxy, alkoxy, carboxy, alkoxycarbonyl), —(CH$_2$)$_n$—$C_{3-10}$ carbocycle and —(CH$_2$)$_n$-4-10-membered heterocycle, wherein said carbocycle and heterocycle are optionally substituted with $R^{13}$;

$R^{13}$ is selected from OH, halogen, $C_{1-6}$ alkyl, $C_{3-6}$ cycloalkyl, $-(CH_2)_n-C(=O)OH$, $-(CH_2)_n-C(=O)OC_{1-4}$ alkyl, $-(CH_2)_n-OC_{1-4}$ alkyl, and $=O$;

n is, independently at each occurrence, selected from 0, 1, 2, 3, and 4;

p is, independently at each occurrence, selected from 0, 1, and 2.

In another aspect, the present invention provides compounds of Formula (IIa) or stereoisomers, tautomers, pharmaceutically acceptable salts, solvates, or prodrugs thereof, wherein ring A is

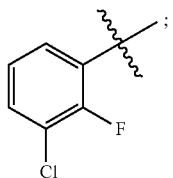 [SMILES: *c1cccc(Cl)c1F]

$X^{1a}$ is selected from $-CR^4R^5-CR^4R^5-$, $-CR^4R^5-CR^4R^5-CR^4R^5-$, and $-CR^4=CR^5CR^4R^5-$, wherein one or more $-CR^4R^5-$ may be replaced by O or C=O. All other variables have the meanings as defined in Formula (IIa).

In another aspect, the present invention provides compounds of Formula (IXa):

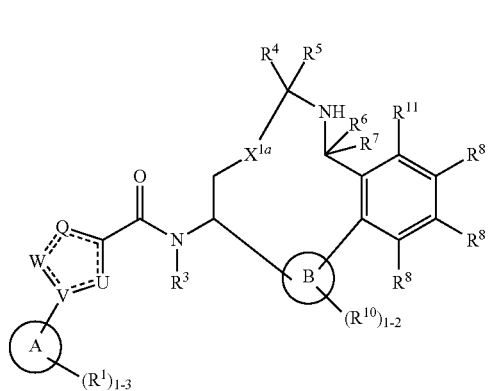

(IXa)

or stereoisomers, tautomers, pharmaceutically acceptable salts, solvates, or prodrugs thereof, wherein the variables have the meanings as defined in Formula (IIa).

In one embodiment, the present invention provides compounds of Formula (I) or (II), or stereoisomers, tautomers, pharmaceutically acceptable salts, solvates, or prodrugs thereof, wherein:

ring A is selected from piperidine and phenyl optionally substituted with $R^1$;

$R^1$ is, independently at each occurrence, selected from H, halogen, haloalkyl, $NO_2$, $CO(C_{1-4}$ alkyl), $C_{1-6}$ alkyl, OH, OMe, and CN.

In another embodiment, ring A is selected from

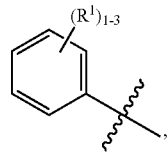

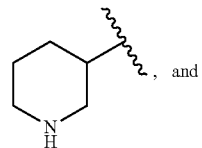, and

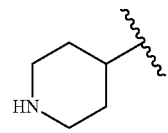

wherein $R^1$ is, independently at each occurrence, selected from H, halogen, and $C_{1-6}$ alkyl.

In another embodiment, ring A is

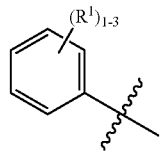

and is selected from

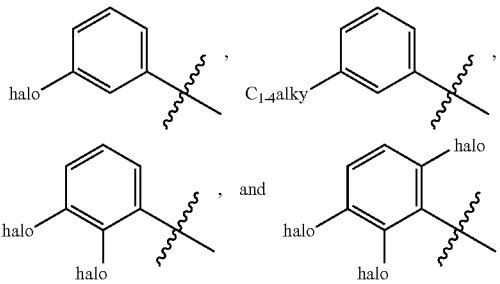

In another embodiment, ring A is

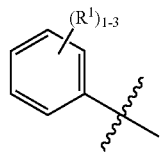

and is selected from

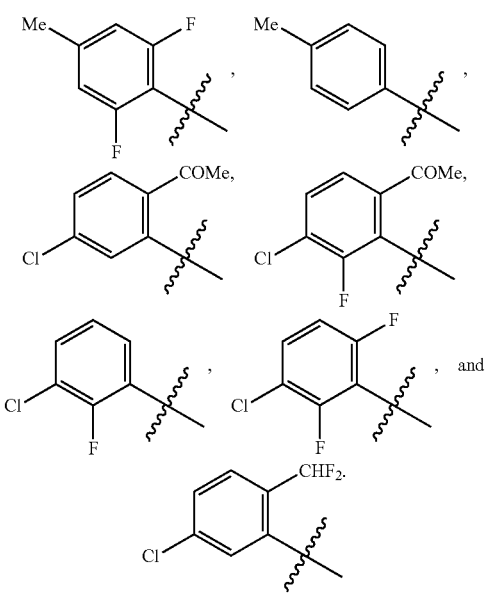

In another embodiment, ring A is

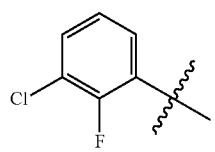

In yet another embodiment, the present invention provides compounds of Formula (I), (II), or (III), or stereoisomers, tautomers, pharmaceutically acceptable salts, solvates, or prodrugs thereof, wherein ring B is selected from imidazole, oxadiazole, pyridine, pyridinone, pyridazine, pyridazinone, and phenyl.

In another embodiment,

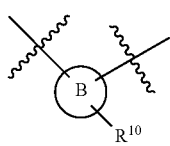

is selected from

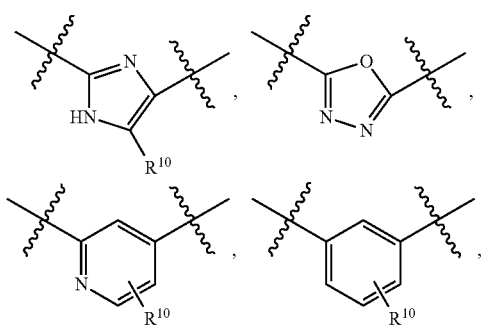

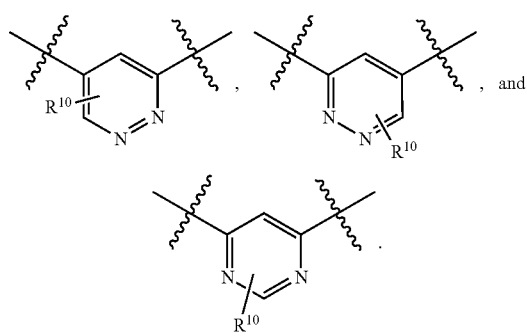

In another embodiment,

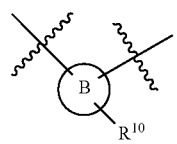

is selected from

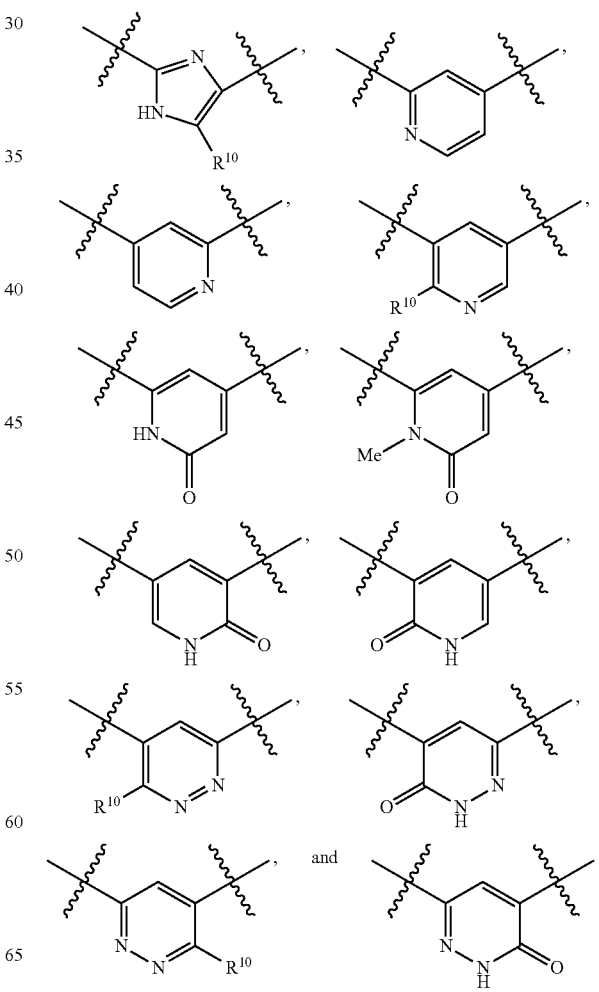

-continued

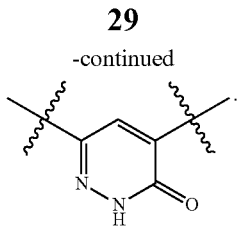

In another embodiment,

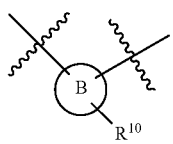

is selected from

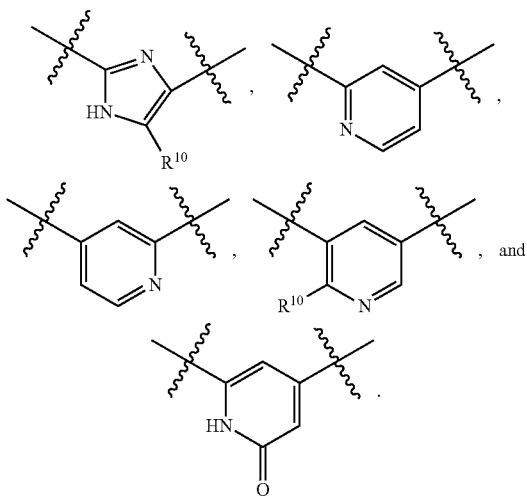

In still another embodiment,

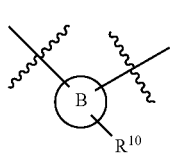

is selected from

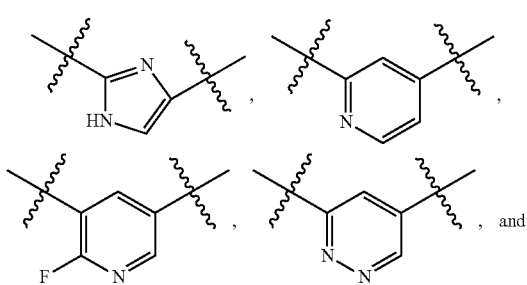

-continued

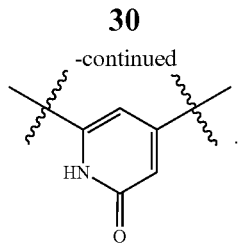

In another embodiment,

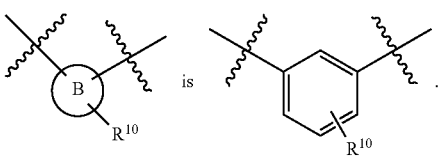

In another embodiment,

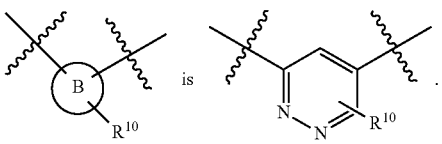

In another embodiment,

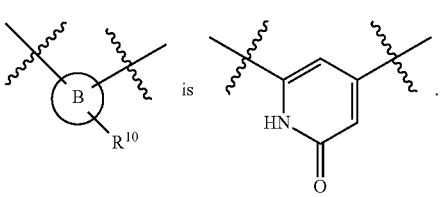

In another embodiment,

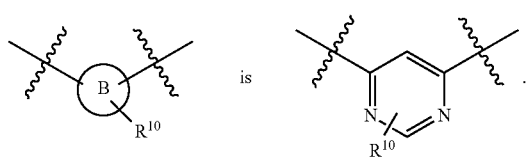

In another embodiment, ring C is a 4-membered heterocycle comprising: carbon atoms and 1-4 heteroatoms selected from N, $NR^9$, $S(O)_p$, and O.

In another embodiment, ring C is

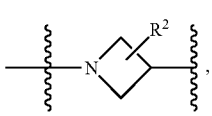

wherein the nitrogen in the azetidine ring is attached to ring A.

In another embodiment, ring C is a 5-membered heterocycle comprising: carbon atoms and 1-4 heteroatoms selected from N, $NR^9$, $S(O)_p$, and O.

In another embodiment, ring C is

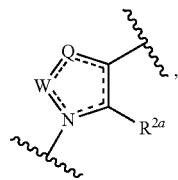, wherein W and Q are each independently selected from C, N, O, and S, whereby carbon is tetravalent, nitrogen is trivalent, and sulfur and oxygen are divalent; and ----- is a single or double bond.

In another embodiment, ring C is

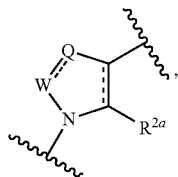, wherein W and Q are each independently selected from N, NR$^9$, CR$^2$, and CHR$^2$;

In another embodiment, ring C is a 5-membered heterocycle comprising: carbon atoms and 1-4 heteroatoms selected from N, NR$^9$, S(O)$_p$, and O.

In another embodiment, ring C is

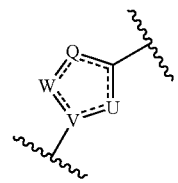

wherein U, V, W, and Q are each independently selected from the group consisting of C, N, O, and S, whereby carbon is tetravalent, nitrogen is trivalent, and sulfur and oxygen are divalent; and ----- is a single or double bond.

In another wherein U, V, W, and Q are each independently selected from N, NR$^9$, S, O, C, CR$^2$, and CHR$^2$.

In another embodiment, ring C is

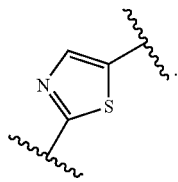 [SMILES: *c1cnc(*)s1].

In another embodiment, ring C is

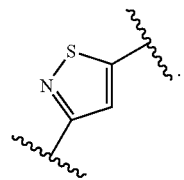 [SMILES: *c1cc(*)sn1].

In another embodiment, ring C is

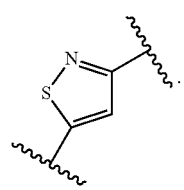 [SMILES: *c1cc(*)sn1].

In another embodiment, ring C is

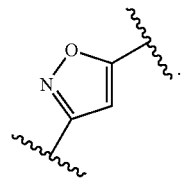 [SMILES: *c1cc(*)on1].

In another embodiment, ring C is

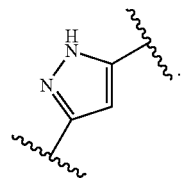 [SMILES: *c1cc(*)[nH]n1].

In another embodiment, ring C is

In another embodiment, ring C is

In another embodiment, ring C is

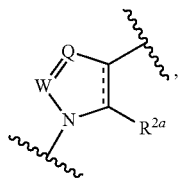

wherein W and Q are each independently selected from N, NR$^9$, CR$^2$, and CHR$^2$;
R$^{2a}$ is selected from H, =O, OH, NH$_2$, CF$_3$, halogen, and C$_{1-4}$ alkyl optionally substituted with OH.

In another embodiment, ring C is

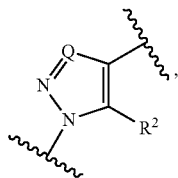

wherein Q is selected from N and CR$^2$;
R$^2$ is selected from H, NH$_2$, and C$_{1-4}$ alkyl substituted with OH.

In another embodiment, ring C is

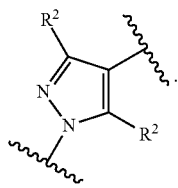

In another embodiment, ring C is

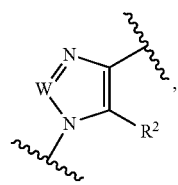

W is selected from N and CR$^2$.

In another embodiment, ring C is

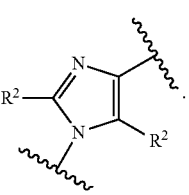

In another embodiment, ring C is

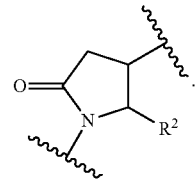

In another embodiment, ring C is

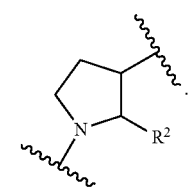

In another embodiment, ring C is 6-membered heterocycle comprising: carbon atoms and 1-4 heteroatoms selected from N, NR$^9$, S(O)$_p$, and O.

In another embodiment, ring C is

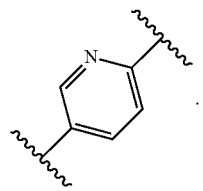 [SMILES: *c1ccc(*)nc1]

In one embodiment, X$^{1a}$ is selected from C$_{2-3}$ alkylene and C$_{2-4}$ alkenylene; wherein said alkylene and alkenylene are optionally substituted with F, OH and C$_{1-4}$ alkyl; alternatively, one or two of the carbon atoms of said alkylene and alkenylene may be replaced by O, NH, and N(C$_{1-4}$ alkyl).

In another embodiment, X$^{1a}$ is selected from —CH$_2$CH$_2$—, —CHFCH$_2$—, —CH$_2$CHF—, —CH=CHCH$_2$—, —CH=C(C$_{1-4}$ alkyl)CH$_2$—, —C(C$_{1-4}$ alkyl)=CHCH$_2$—, —CH$_2$OCH$_2$—, —CH$_2$CH$_2$O—, —OCH$_2$CH$_2$—, —CH$_2$CF$_2$—, —(CH$_2$)$_4$CH(CF$_3$)—, —CH$_2$CH$_2$NHCO—, —CH$_2$NHCH$_2$—, —CH$_2$N(C$_{1-4}$ alkyl)CH$_2$—, —CH$_2$CONH—, —CH$_2$—CONH—CH$_2$—, and —CH$_2$—CON(C$_{1-4}$ alkyl).

In another embodiment, X$^{1a}$ is selected from —CH$_2$CH$_2$—, —CH=CHCH$_2$—, —C(Me)=CHCH$_2$—, and —CH$_2$NHCH$_2$—.

In another embodiment, X$^{1a}$ is selected from —CH$_2$CH$_2$—, —CH=CHCH$_2$—, —CHFCH$_2$—, and —CH$_2$CHF—.

In another embodiment, X$^{1a}$ is selected from —CH$_2$CH$_2$— and —CH=CHCH$_2$—.

In another embodiment, X$^{1a}$ is —CH$_2$CH$_2$—.

In one embodiment, X$^1$ is selected from C$_{1-3}$ alkylene and C$_{2-4}$ alkenylene; wherein said alkylene and alkenylene are optionally substituted with OH and C$_{1-4}$ alkyl; alternatively, one or two of the carbon atoms of said alkylene and alkenylene may be replaced by O, S(O)$_p$, NH, N(C$_{1-4}$ alkyl), CONH, or CON(C$_{1-4}$ alkyl).

In another embodiment, X$^1$ is selected from —CH$_2$—, —CH(C$_{1-4}$ alkyl), —CH$_2$—CH$_2$—, —CH=CH—, —CH=C(C$_{1-4}$ alkyl)-, —C(C$_{1-4}$ alkyl)=CH—, —OCH$_2$—, —CH$_2$O—, —CF$_2$—, —(CH$_2$)$_4$CH(CF$_3$)—, —CH$_2$NHCO—, —CH$_2$NHCH$_2$—, —CH 2N(C$_{1-4}$ alkyl)CH$_2$—, —CH$_2$CONH—, —CH$_2$—CONH—CH$_2$—, and —CH$_2$—CON(C$_{1-4}$ alkyl).

In another embodiment, X$^1$ is selected from —CH$_2$—, —CH═CH—, —C(Me)═CH—, —C≡C—, and —CH$_2$NH—.

In another embodiment, X$^1$ is selected from —CH$_2$—, —CH═CH—, and —C(Me)═CH—.

In another embodiment, X$^1$ is selected from —CH$_2$— and —CH═CH—.

In another embodiment, X$^1$ is —CH$_2$—.

In one embodiment, R$^1$ is, independently at each occurrence, selected from H, halogen, NO$_2$, C$_{1-6}$ alkyl, C$_{1-4}$ alkoxy, CO(C$_{1-4}$ alkyl), C$_{1-4}$ alkylthio, OH, CH$_2$F, CHF$_2$, CF$_3$, OCH$_2$F, OCHF$_2$, OCF$_3$, CN, and NH$_2$.

In another embodiment, R$^1$ is, independently at each occurrence, selected from H, halogen, NO$_2$, C$_{1-6}$ alkyl, OH, OMe, and CN.

In another embodiment, R$^1$ is, independently at each occurrence, selected from H and halogen.

In another embodiment, ring A is

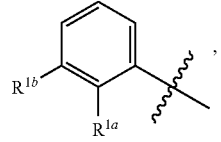

wherein R$^{1a}$ and R$^{1b}$ are each independently selected from H and halogen.

In another embodiment, R$^{1a}$ is selected from H, F and Cl.
In another embodiment, R$^{1a}$ is selected from H and F.
In another embodiment, R$^{1a}$ is F and R$^{1b}$ is Cl.
In another embodiment, R$^3$ is selected from H, and C$_{1-4}$ alkyl.
In another embodiment, R$^3$ is H.
In another embodiment, R$^4$ is selected from H, C$_{1-4}$ alkyl, and hydroxyl.
In another embodiment, R$^4$ is selected from H and C$_{1-4}$ alkyl.
In another embodiment, R$^4$ is selected from H and methyl, ethyl, isopropyl, and C$_{3-6}$ cycloalkyl.
In another embodiment, R$^5$ is selected from H and C$_{1-4}$ alkyl.
In another embodiment, R$^5$ is selected from H and methyl.
In another embodiment, R$^6$ is selected from H, halogen, haloalkyl, C(O)OH, C(O)O—R$^a$, C(O)NR$^b$R$^c$, wherein:

R$^a$ is selected from C$_{1-4}$ alkyl, C$_{3-6}$ cycloalkyl, 5- to 6-membered heteroaryl, 4- to 7-membered heterocycle, and benzyl, said groups being optionally substituted with OH, OMe, and halogen;
R$^b$ is selected from H and C$_{1-6}$ alkyl;
R$^c$ is selected from H and C$_{1-6}$ alkyl;
alternatively, R$^b$ and R$^c$ are taken together with the nitrogen atom to which they are attached to form a 4- to 7-membered heterocycle optionally substituted with OH, OMe, and halogen.

In another embodiment, R$^6$ is selected from H, halogen, C(O)OH, and C(O)O(C$_{1-4}$ alkyl).

In another embodiment, R$^7$ is selected from H, C$_{1-4}$ alkyl, and CF$_3$.

In another embodiment, R$^6$ and R$^7$ are taken together to be ═O.

In another embodiment, R$^8$ is selected from H, halogen, haloalkyl, CN, OH, NR$^{12}$R$^{12}$, —CH$_2$NH$_2$, C(O)OH, —(CH$_2$)$_n$—NHC(O)OR$^{12}$, —NHC(O)R$^{12}$, —NHC(O)NR$^{12}$R$^{12}$, —NHS(O)$_2$C$_{1-4}$ alkyl, —(CH$_2$)$_n$—CONR$^{12}$R$^{12}$, —(CH$_2$)$_n$C(O)O(C$_{1-4}$ alkyl), —(CH$_2$)$_n$—C$_{3-10}$ carbocycle, and —(CH$_2$)$_n$-4-10-membered heterocycle wherein said carbocycle and heterocycle are optionally substituted with R$^{13}$.

In another embodiment, R$^8$ is selected from H, CN, OH, NR$^{12}$R$^{12}$, C(O)OH, —(CH$_2$)$_n$—NHC(O)OR$^{12}$, —NHS(O)$_2$C$_{1-4}$ alkyl, —(CH$_2$)$_n$—CONR$^{12}$R$^{12}$, —(CH$_2$)$_n$C(O)O(C$_{1-4}$ alkyl), —(CH$_2$)$_n$—C$_{3-10}$ carbocycle, and —(CH$_2$)$_n$-4-10-membered heterocycle optionally substituted with R$^{13}$.

In another embodiment, R$^8$ is selected from H, NR$^{12}$R$^{12}$, C(O)OH, and NHC(O)O—C$_{1-4}$ alkyl.

In another embodiment, R$^8$ is NH$_2$, C(O)OH, and NHC(O)OR$^{12}$.

In another embodiment, R$^{12}$ is selected from H, C$_{1-4}$ alkyl (optionally substituted with halogen, hydroxy, alkoxy, carboxy, alkoxycarbonyl), —(CH$_2$)$_n$—C$_{3-10}$ carbocycle and —(CH$_2$)$_n$-4-10-membered heterocycle, wherein said carbocycle and heterocycle are optionally substituted with R$^{13}$.

In another embodiment, R$^{12}$ is selected from H, C$_{1-4}$ alkyl (optionally substituted with F, OH, —O(C$_{1-4}$ alkyl), —C(O)OH, —C(O)O(C$_{1-4}$ alkyl)), —(CH$_2$)$_n$—C$_{3-10}$ carbocycle and —(CH$_2$)$_n$-4-10-membered heterocycle, wherein said carbocycle and heterocycle are optionally substituted with R$^{13}$.

In another embodiment, R$^{12}$ is selected from methyl, —(CH$_2$)$_n$—OC$_{1-4}$ alkyl, —(CH$_2$)$_n$—OH, —(CH$_2$)$_n$—C$_{3-6}$ cycloalkyl, and —(CH$_2$)$^n$-5-membered heterocycle optionally substituted with R$^{13}$ and selected from

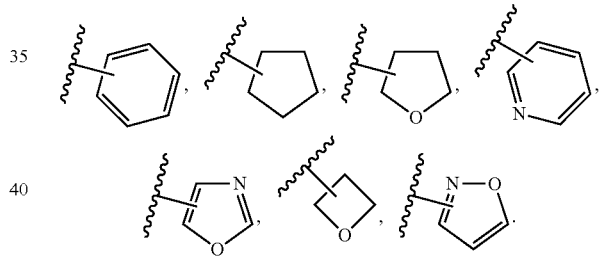

R$^{13}$ is selected from OH, halogen, C$_{1-6}$ alkyl, C$_{3-6}$ cycloalkyl, —(CH$_2$)$_n$—C(═O)OH, —(CH$_2$)$_n$—C(═O)OC$_{1-4}$ alkyl, —(CH$_2$)$_n$—OC$_{1-4}$ alkyl, and ═O.

In another embodiment, R$^8$ is selected from H, halogen, NHC(O)O—C$_{1-4}$ alkyl, CN, OH, O—C$_{1-4}$ alkyl; CF$_3$, CO$_2$H, CO$_2$(C$_{1-4}$ alkyl), —CH$_2$CO$_2$H, —(CH$_2$)$_2$CO$_2$H, —CH$_2$CO$_2$(C$_{1-4}$ alkyl), —(CH$_2$)$_2$CO$_2$(C$_{1-4}$ alkyl), NH$_2$, —CH$_2$NH$_2$, —NHCO(C$_{1-4}$ alkyl), —NHCO$_2$(CH$_2$)$_{1-2}$O(C$_{1-4}$ alkyl), —NHCO$_2$(CH$_2$)$_{1-3}$O(C$_{1-4}$ alkyl), NHCO$_2$CH$_2$CH(C$_{1-4}$ alkyl)O(C$_{1-4}$ alkyl), —NHCO$_2$(CH$_2$)$_{1-2}$OH, —NHCO$_2$CH$_2$CO$_2$H, —CH$_2$NHCO$_2$(C$_{1-4}$ alkyl), —NHC(O)NH(C$_{1-4}$ alkyl), —NHC(O)N(C$_{1-4}$ alkyl)$_2$, NHC(O)NH(C$_{1-4}$ alkyl)N[5- to 6-membered heterocycle)], —NHSO$_2$(C$_{1-4}$ alkyl), —CONH$_2$, —CONH(C$_{1-4}$ alkyl), —CON(C$_{1-4}$ alkyl)$_2$, and —CH$_2$CONH$_2$.

In another embodiment, R$^8$ is selected from H, halogen, NHC(O)O—C$_{1-4}$ alkyl, NHC(O)(CH$_2$)$_2$OMe, CN, OH, and O—C$_{1-4}$ alkyl.

In another embodiment, R$^8$ is NHC(O)O—C$_{1-4}$ alkyl.

In another embodiment, the present invention provides compounds of Formula (I), or stereoisomers, tautomers, pharmaceutically acceptable salts, solvates, or prodrugs thereof, wherein:

ring A is a 6-membered aryl or piperidine, said ring moieties are optionally substituted with $R^1$;

ring B is selected from imidazole, oxadiazole, pyridine, pyridinone, pyridazine, pyridazinone, pyrimidine, and phenyl, said ring moieties are optionally substituted with $R^{10}$; and ring C is selected from imidazole, pyrazole, pyrrole, and triazole, said ring moieties are optionally substituted with $R^2$.

In one embodiment, the present invention provides compounds of Formula (VII):

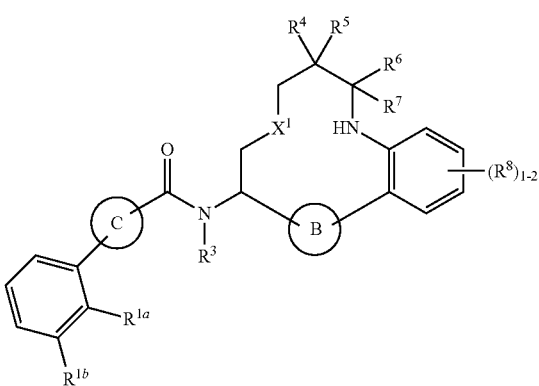

(VII)

or stereoisomers, tautomers, pharmaceutically acceptable salts, solvates, or prodrugs thereof, wherein:

ring B is a 5- to 6-membered heterocycle comprising: carbon atoms and 1-4 heteroatoms selected from N, NH, $S(O)_p$, and O, wherein said heterocycle are optionally substituted with one or more $R^{10}$ as valence allows;

ring C is a 4- to 5-membered heterocycle comprising: carbon atoms and 1-4 heteroatoms selected from N, $NR^9$, $S(O)_p$, and O, wherein said heterocycle are optionally substituted with one or more $R^2$ as valence allows;

$X^1$ is selected from $C_{1-4}$ alkylene, and $C_{2-4}$ alkenylene wherein said alkylene and alkenylene are optionally substituted with OH and $C_{1-4}$ alkyl; alternatively one or more of the carbon atoms of said alkylene and alkenylene may be replaced by O, $S(O)_p$, NH, and $N(C_{1-4}$ alkyl);

$R^{1a}$ and $R^{1b}$ are each independently selected from H and halogen;

$R^2$ is selected from H, =O, OH, $NH_2$, $CF_3$, halogen, and $C_{1-4}$ alkyl optionally substituted with OH;

$R^3$ is selected from H and $C_{1-4}$ alkyl;

alternatively, $R^2$ and $R^3$, together with the atoms to which they are directly or indirectly attached, form a ring wherein said ring is optionally substituted with =O;

$R^4$ is selected from H, $C_{1-4}$ alkyl, hydroxyl, and $C_{3-6}$ cycloalkyl;

$R^5$ is selected from H and $C_{1-4}$ alkyl;

$R^6$ is selected from H, halogen, haloalkyl, C(O)OH, C(O)O—$R^{11}$, and C(O)$NR^{12}R^{13}$;

$R^7$ is selected from H, $C_{1-4}$ alkyl, and $CF_3$;

alternatively, $R^6$ and $R^7$ together are =O;

$R^8$ is selected from H, halogen, NHC(O)O—$C_{1-4}$ alkyl, CN, OH, O—$C_{1-4}$ alkyl; $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —NHC(O)($C_{1-4}$ alkyl), —$NHCO_2(CH_2)_{1-2}O(C_{1-4}$ alkyl), —$NHCO_2(CH_2)_{1-3}O(C_{1-4}$ alkyl), $NHCO_2CH_2CH(C_{1-4}$ alkyl)O($C_{1-4}$ alkyl), —$NHCO_2(CH_2)_{1-2}OH$, —$NHCO_2CH_2CO_2H$, —$CH_2NHCO_2(C_{1-4}$ alkyl), —NHC(O)NH($C_{1-4}$ alkyl), —NHC(O)N($C_{1-4}$ alkyl)$_2$, NHC(O)NH($C_{1-4}$ alkyl)N[5- to 6-membered heterocycle)], —$NHSO_2(C_{1-4}$ alkyl), —$CONH_2$, —CONH($C_{1-4}$ alkyl), —CON($C_{1-4}$ alkyl)$_2$, and —$CH_2CONH_2$;

$R^9$ is selected from H and $C_{1-4}$ alkyl;

$R^{10}$ is, independently at each occurrence, selected from H, halogen, CN, OH, =O, $NH_2$, $C_{3-6}$ cycloalkyl, $C_{1-4}$ alkoxy, $CF_3$, $CH_2OH$, $CO_2H$, $CO_2(C_{1-4}$ alkyl), and CONH;

$R^{11}$ is selected from $C_{1-4}$ alkyl, $C_{3-6}$ cycloalkyl, 5- to 6-membered heteroaryl, 4- to 7-membered heterocycle, and benzyl, said groups being optionally substituted with OH, OMe, and halogen;

$R^{12}$ is selected from H and $C_{1-6}$ alkyl;

$R^{13}$ is selected from H and $C_{1-6}$ alkyl;

alternatively, $R^{12}$ and $R^{13}$ are taken together with the nitrogen atom to which they are attached to form a 4- to 7-membered heterocycle, optionally substituted with OH, OMe, and halogen; and p is, independently at each occurrence, selected from 0, 1, and 2.

In another embodiment, the present invention provides compounds of Formula (VII), or stereoisomers, tautomers, pharmaceutically acceptable salts, solvates, or prodrugs thereof, wherein:

is selected from

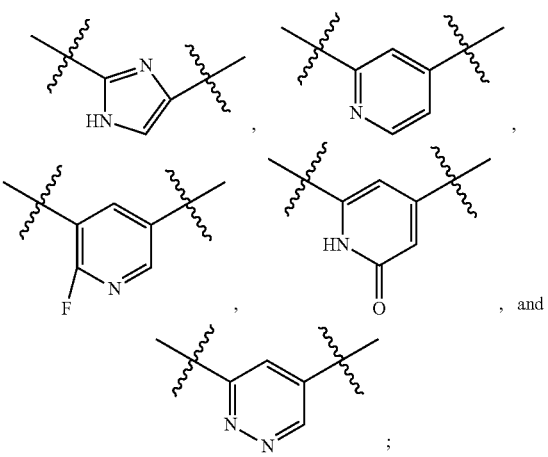

;

ring C is

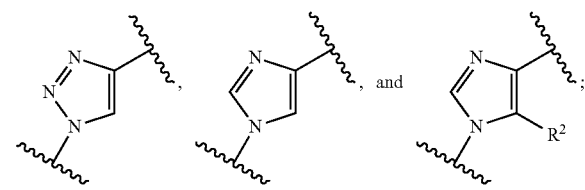

;

$R^2$ is selected from H and $NH_2$; and
$R^4$ is selected from H, methyl, and ethyl; and
$R^6$ and $R^7$ together are =O; and
$R^8$ is $NHC(O)O$—$C_{1-4}$ alkyl.

In another embodiment, the present invention provides compounds of Formula (VIII):

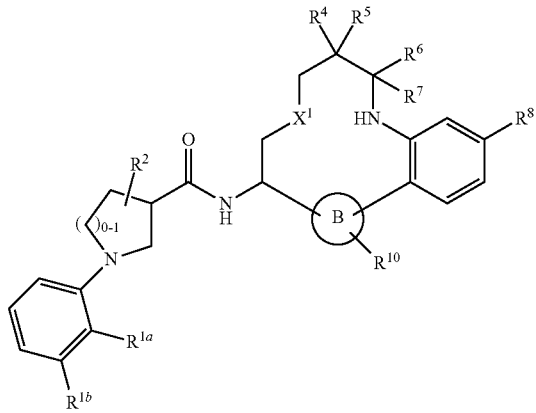

(VIII)

or stereoisomers, tautomers, pharmaceutically acceptable salts, solvates, or prodrugs thereof, wherein the variables have the meanings as defined in Formula (VII).

In another embodiment, the present invention provides compounds of Formula (IX):

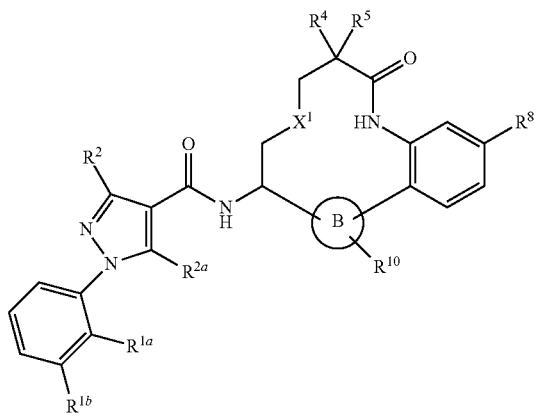

(IX)

or stereoisomers, tautomers, pharmaceutically acceptable salts, solvates, or prodrugs thereof, wherein the variables have the meanings as defined in Formula (VII).

In another embodiment, the present invention provides compounds of Formula (IXa):

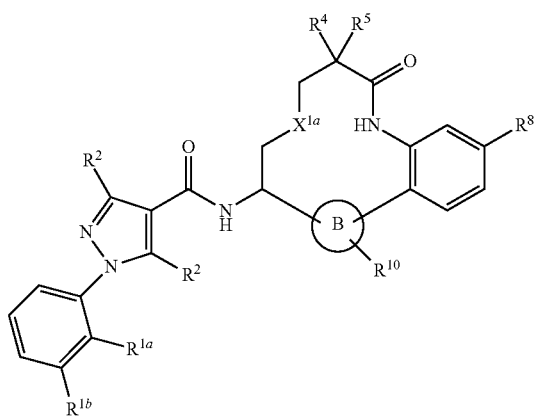

(IXa)

or stereoisomers, tautomers, pharmaceutically acceptable salts, solvates, or prodrugs thereof, wherein the variables have the meanings as defined in Formula (IVa).

In another embodiment, the present invention provides compounds of Formula (X):

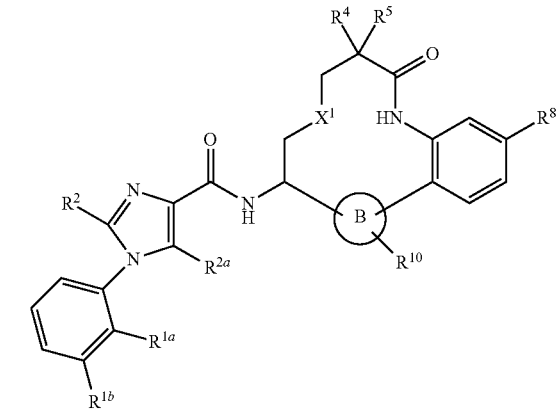

(X)

or stereoisomers, tautomers, pharmaceutically acceptable salts, solvates, or prodrugs thereof, wherein the variables have the meanings as defined in Formula (VII).

In another embodiment, the present invention provides compounds of Formula (XI):

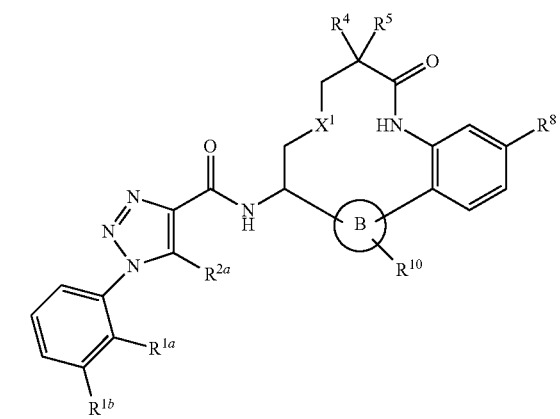

(XI)

or stereoisomers, tautomers, pharmaceutically acceptable salts, solvates, or prodrugs thereof, wherein the variables have the meanings as defined in Formula (VII).

In another embodiment, the present invention provides compounds of Formula (XIa):

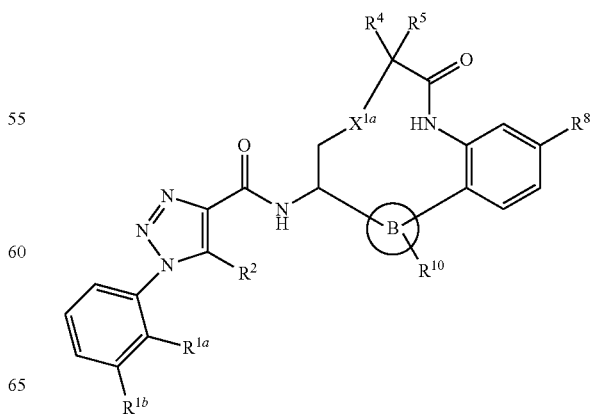

(XIa)

or stereoisomers, tautomers, pharmaceutically acceptable salts, solvates, or prodrugs thereof, wherein the variables have the meanings as defined in Formula (IVa).

In another aspect, the present invention provides a compound selected from any subset list of compounds exemplified in the present application.

In another embodiment, the compounds of the present invention have Factor XIa Ki values ≤10 µM.

In another embodiment, the compounds of the present invention have Factor XIa Ki values ≤1 µM.

In another embodiment, the compounds of the present invention have Factor XIa Ki values ≤0.5 µM.

In another embodiment, the compounds of the present invention have Factor XIa Ki values ≤0.1 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second factor Xa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic Pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "carboxy" refers to the group —C(=O)OH.

The term "alkoxycarbonyl" refers to the group —C(=O)OR$^w$ where R$^w$ is an alkyl, substituted alkyl, cycloalkyl or substituted cycloalkyl.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "arylalkyloxy" refers to an arylalkyl bonded through an oxygen linkage (—O-arylalkyl).

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of Formula (I) may have prodrug forms. Any compound that will be converted in vivo to provide the bioactive agent (i.e., a compound of Formula (I)) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, $C_{1-6}$alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_{1-6}$ alkoxycarbonyloxy-$C_{1-6}$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl Ph Phenyl
Bn Benzyl
Boc tert-butyloxycarbonyl
AcOH or HOAc acetic acid
AlCl₃ aluminum chloride
AIBN Azobisisobutyronitrile
BBr₃ boron tribromide
BCl₃ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
CH₂Cl₂ Dichloromethane
CH₃CN or ACN Acetonitrile
CDCl₃ deutero-chloroform
CHCl₃ Chloroform
mCPBA or m-CPBA meta-chloroperbenzoic acid
Cs₂CO₃ cesium carbonate
Cu(OAc)₂ copper (II) acetate
Cy₂NMe N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et₃N or TEA triethylamine
EtOAc ethyl acetate
Et₂O diethyl ether
EtOH ethanol
GMF glass microfiber filter
Grubbs (II) (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
H₂SO₄ sulfuric acid
K₂CO₃ potassium carbonate
KOAc potassium acetate
K₃PO₄ potassium phosphate
LAH lithium aluminum hydride
LG leaving group
LiOH lithium hydroxide
MeOH methanol
MgSO₄ magnesium sulfate
MsOH or MSA methylsulfonic acid
NaCl sodium chloride
NaH sodium hydride
NaHCO₃ sodium bicarbonate
Na₂CO₃ sodium carbonate
NaOH sodium hydroxide
Na₂SO₃ sodium sulfite
Na₂SO₄ sodium sulfate
NBS N-bromosuccinimide
NCS N-chlorosuccinimide
NH₃ ammonia
NH₄Cl ammonium chloride
NH₄OH ammonium hydroxide
OTf triflate or trifluoromethanesulfonate
Pd₂(dba)₃ tris(dibenzylideneacetone)dipalladium(0)
Pd(OAc)₂ palladium(II) acetate
Pd/C palladium on carbon Pd(dppf)Cl₂ [1,1'-bis(diphenylphosphino)-ferrocene]dichloropalladium(II)
Ph₃PCl₂ triphenylphosphine dichloride
PG protecting group
POCl₃ phosphorus oxychloride
i-PrOH or IPA isopropanol
PS polystyrene
SEM-Cl 2-(trimethysilyl)ethoxymethyl chloride
SiO₂ silica oxide
SnCl₂ tin(II) chloride
TBAI tetra-n-butylammonium iodide
TEA triethylamine
TFA trifluoroacetic acid
THF tetrahydrofuran
TMSCHN₂ trimethylsilyldiazomethane
T₃P propane phosphonic acid anhydride
TRIS tris(hydroxymethyl)aminomethane The compounds of the present invention can be prepared in a number of ways known to one skilled in the art of organic synthesis.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice*, 5th Edition, p. 853, Lippincott Williams & Wilkins (2006))

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000))

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterial-venous shunt thrombosis (Gruber et al., *Blood*, 102:953-955 (2003)). Evidence for an antithrombotic effect of small molecule inhibitors of factor XIa is also disclosed in published U.S. Patent Application No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis*, pp. 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the enzyme; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, 3(Suppl. 1):P 1228 (2005); Schumacher, W. A. et al., *European Journal of Pharmacology*, pp. 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N Engl. J. Med.,* 334(11):677-681 (1996); Blom, J. W. et al., *JAMA,* 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. or 37° C. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o - v_s)/v_s = I/(K_i(1+S/K_m))$$

for a competitive inhibitor with one binding site; or $$v_s/v_o = A + ((B-A)/(1+((IC_{50}/(I))^n)));$$

and $$K_i = IC_{50}/(1+S/K_m)$$

for a competitive inhibitor,
where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;

S is the concentration of substrate; and $K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Ill.) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or INNOVIN®, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 μM (10000 nM) was observed. Table 1 below lists Factor XIa Ki values measured for the following examples.

TABLE 1

| Example No. | Factor XIa Ki (nM) |
| --- | --- |
| 3 | <5.00 |
| 5 | 5.52 |
| 11 | 69.44 |
| 15 | <5.00 |
| 18 | 98.71 |
| 21 | 9.08 |
| 24 | <5.00 |
| 26 | 177.50 |

TABLE 1-continued

| Example No. | Factor XIa Ki (nM) |
| --- | --- |
| 32 | 11.43 |
| 39 | 10.82 |
| 40 | <5.00 |
| 41 | 12.77 |
| 52 | 216.90 |
| 58 | 934.60 |
| 71 | 32.83 |
| 72 | 10.38 |
| 75 | 36.48 |
| 78 | <5.00 |
| 88 | 52.61 |
| 113 | <5.00 |
| 120 | <5.00 |
| 127 | <5.00 |
| 131 | <5.00 |
| 133 | <5.00 |
| 134 | <5.00 |
| 137 | 546.60 |
| 139 | 5.49 |
| 151 | 17.26 |
| 156 | 16.81 |
| 158 | <5.00 |
| 159 | 9.94 |
| 165 | 5079.00 |
| 177 | 54.93 |
| 190 | 6.65 |
| 193 | 2983.00 |
| 207 | 153.00 |
| 221 | 311.60 |
| 227 | <5.00 |
| 232 | 4287.00 |
| 234 | <5.00 |
| 246 | <5.00 |
| 251 | <5.00 |
| 256 | <5.00 |
| 257 | <5.00 |
| 262 | 13.61 |
| 263 | 33.25 |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid Em. equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid Em. equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of anti-platelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an antiarrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic Pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic Pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

Certain 2-bromoacetophenone analogs (1b) that are not commercially available but used in the current invention may be synthesized from commercially available starting materials as described in Scheme 1. Acetophenone derivatives 1a can be treated with a brominating reagent such as bromine in a solvent such as $CHCl_3$ to give 1b. Alternatively, acetophenone derivatives 1a can be treated with either copper (II) bromide in a solvent such as EtOAc at elevated temperature or phenyltrimethylammonium tribromide in a solvent such as THF at low temperature to provide 1b. Benzoic acid derivatives 1c can be treated sequentially with oxalyl chloride in a suitable solvent, such as DCM, containing a few drops of DMF, and then treated with trimethylsilyldiazomethane in a suitable solvent or solvent combination, such as ACN and hexane. The intermediate diazoketone is isolated and treated with aqueous hydrobromic acid and DCM to provide 1b. Alternatively the benzoic acid derivatives 1c can be converted to the acetophenone derivatives 1a in three steps as described in Scheme 1. Alternatively, Stille coupling between a suitably substituted aryl halide or triflate and tributyl-(1-ethoxyvinyl) stannane with a palladium catalyst, such as bis-(triphenylphosphine) palladium dichloride, in a suitable solvent, such as toluene, at elevated temperature yields the enol ether 1e, which can then be converted to 1b with N-bromosuccinimide.

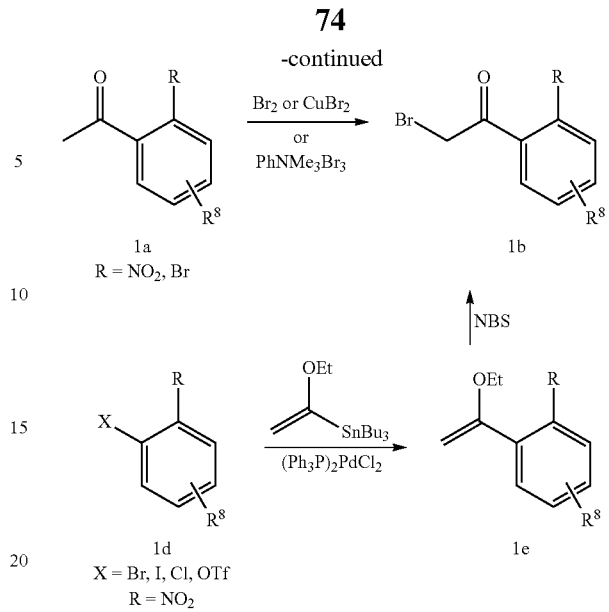

Scheme 1

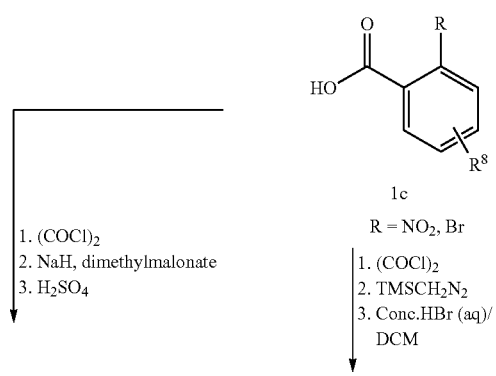

Triazole acids of this invention such as 2c, 2d, 2e, 2f can be easily prepared from readily accessible anilines in a three step process outlined in Scheme 2. Formation of the arylazide (2b) intermediate via diazotization and displacement with sodium azide followed by condensation with appropriate acetylenic compounds and removal of the protecting groups known to those in the art should afford intermediates such as 2c. Condensation of the arylazides with either malonates or ketoesters followed by hydrolysis should afford intermediates of this invention such as 2d, 2e and 2f. In cases wherein the anilines are not available, the corresponding arylcarboxylic acids can be used which are then converted to the anilines via the Curtius rearrangement. Alternatively haloaryl intermediates can be lithiated via BuLi and reacted with $CO_2$ to afford the corresponding carboxylic acids which can then be converted to the anilines as outlined below.

Scheme 2

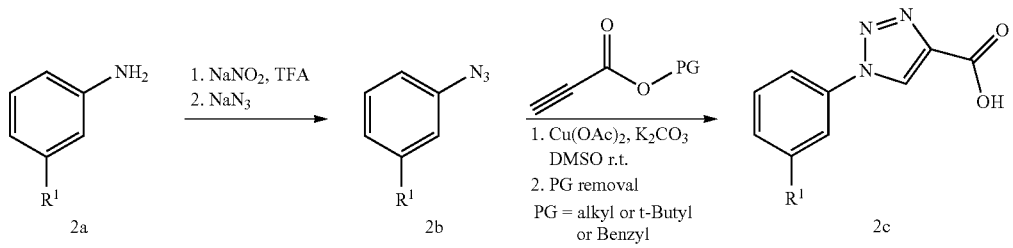

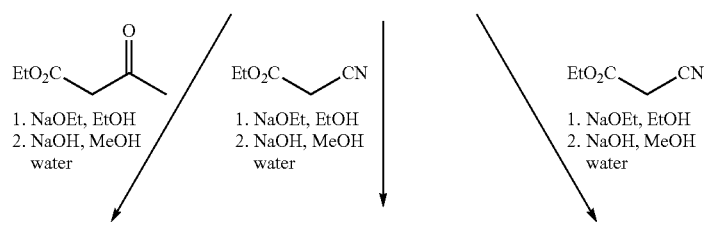

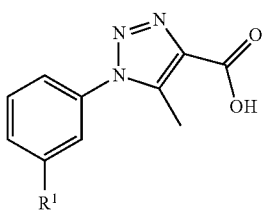
2d

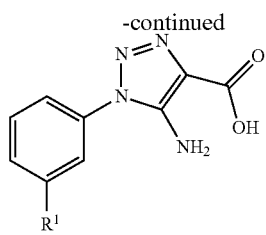
2e

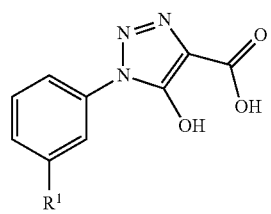
2f

Substituted hydrazine (3a) of this invention can be obtained from commercial sources or can be made from the corresponding anilines via diazotization followed by reduction with tin chloride. These can be reacted either directly or after isolation with an appropriate malononitrile to afford aminopyrazole such as compound 3b. Treatment of 3b with isoamylnitrite in THF under elevated temperatures should provide the requisite pyrazole intermediate which is hydrolyzed to afford pyrazole acid intermediates of this invention such as 3c. Furthermore amino pyrazole intermediates of this invention can be obtained by hydrolysis of the ester will give 3d. Diazotization of the amino moiety as in 3b in fluoroboric acid followed by heating at high temperature should then provide fluoropyrazole intermediates such as 3e. Appropriately substituted hydrazines can be condensed with (E)-ethyl 2-((dimethylamino)methylene)-3-oxobutanoate to give, after hydrolysis, the methyl pyrazole derivatives 3f.

Scheme 3

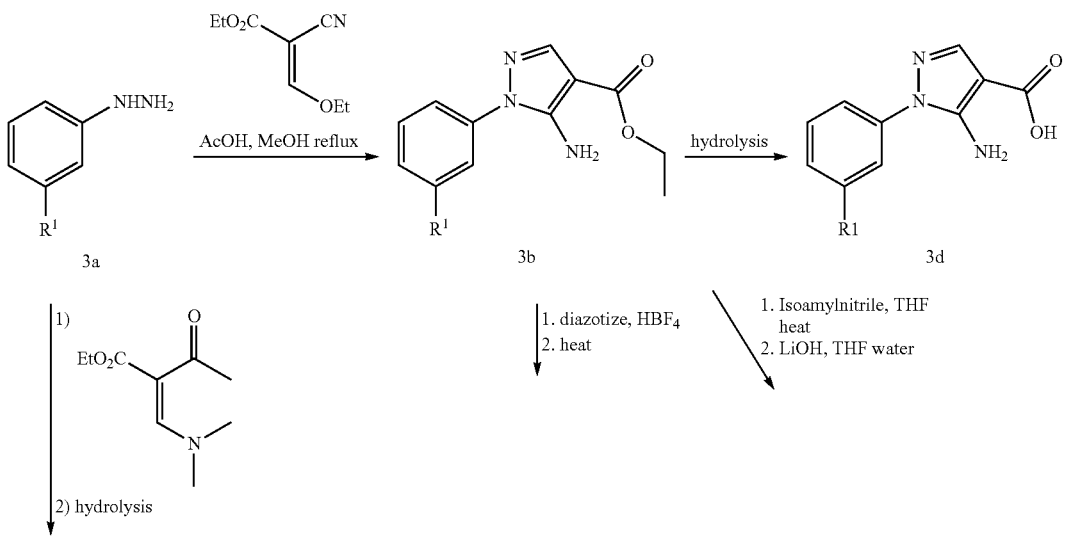

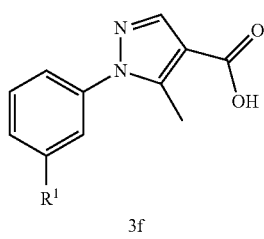
3f

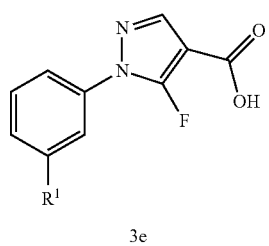
3e

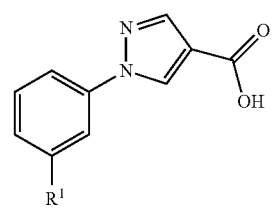
3c

Alternative approaches to pyrazoles can also be obtained via the Chan-Lam coupling as shown in Scheme 4. The requisite pyrazole (4b) and appropriately substituted boronic acids (4a) are commercially available. Alternatively these entities could be coupled via the Ullman coupling methodology with CuI, $K_2CO_3$ in DMSO at 130° C. In these cases the boronic acid derivatives would be substituted with the arylbromides or iodides.

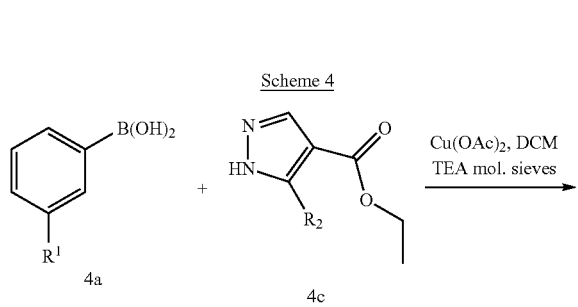

Scheme 4

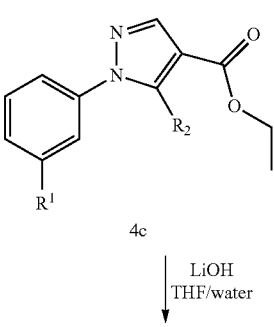

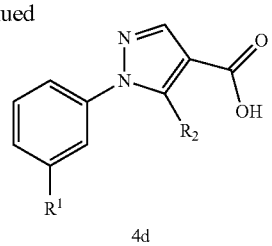

4d

Imidazole acids of this invention such as 4af and 4ag can be prepared as outlined in Scheme 4a. Ullman coupling between an appropriately substituted imidazole 4aa and an appropriately substituted arylhalide 4ab can provide the imidazole derivatives 4ad and 4ae in one step. Hydrolysis of the ester will generate the imidazole acids 4af and 4ag. Alternatively, an appropriately substituted imidazole 4aa can be coupled to an appropriately substituted arylboronic acid 4ac using a modified procedure described by Sreedhar (*Synthesis,* 5:795 (2008)). Alternative approaches to the imidazole derivatives 4ad and 4ae can be achieved using a modified procedure described by Gomez-Sanchez (*J. Heterocyclic Chem.,* 24:1757 (1987)). Condensation of the ethyl nitroacetate, triethyl orthoformate, and an appropriately substituted aniline (4ah) can provide ethyl 3-arylamino-2-nitroacrylate 4ai. The ethyl 3-arylamino-2-nitrocrotonate derivatives 4aj can be prepared by reacting ethyl 3-ethoxy-2-nitrocrotonate with an appropriately substituted aniline 4ah. Reacting compounds 4ai and 4aj with triethyl orthoformate and platinum on carbon under a hydrogen atmosphere at elevated temperature can yield the imidazole derivatives 4ad and 4ae. Hydrolysis of the ester will generate the imidazole acids 4af and 4ag.

Scheme 4a

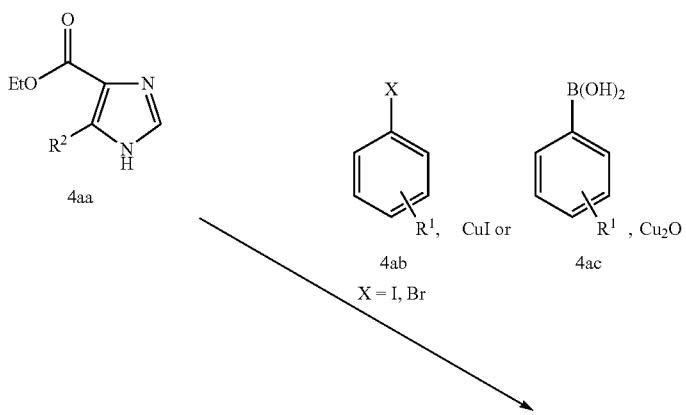

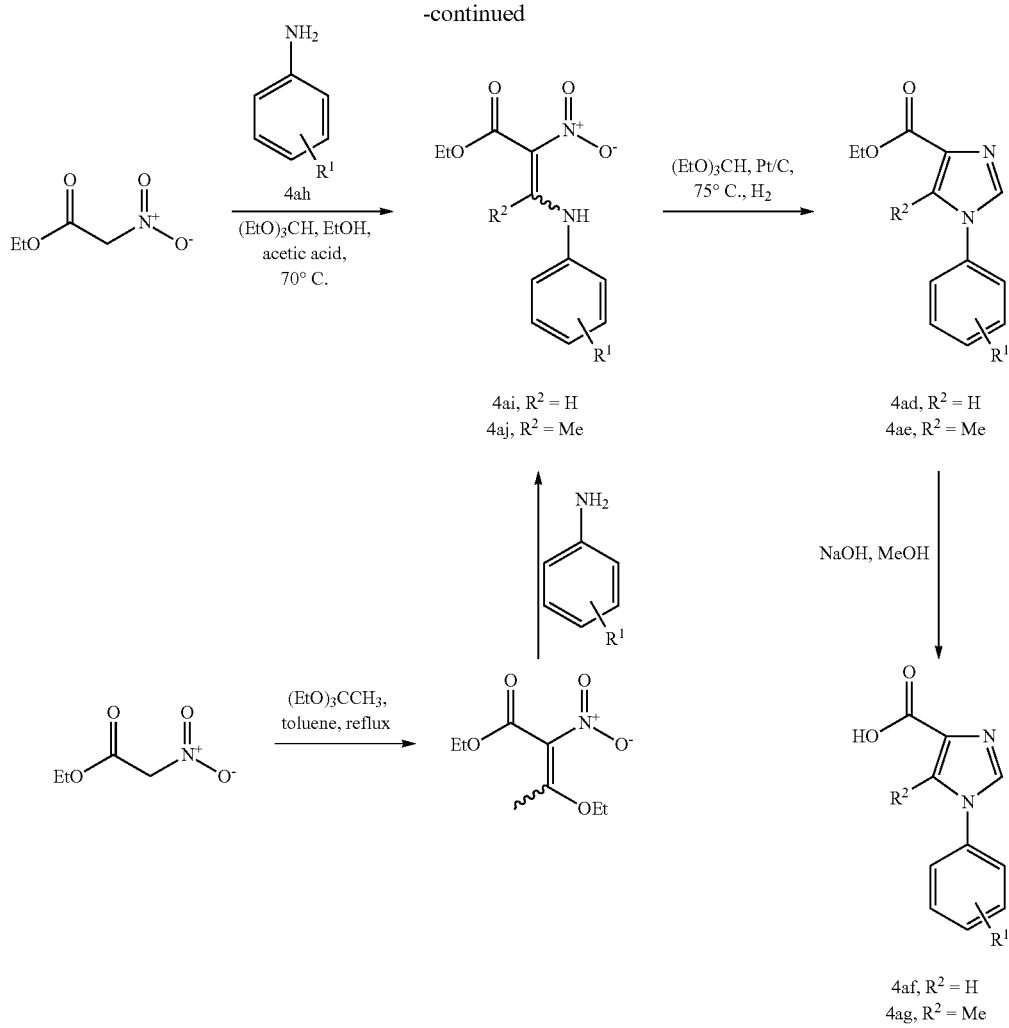

4ai, R² = H
4aj, R² = Me

4ad, R² = H
4ae, R² = Me

4af, R² = H
4ag, R² = Me

Bicyclic pyrazole intermediates of this invention can be constructed via the methodology outline in Scheme 5. Reaction of the hydrazine (3a) with an appropriate aldehyde should afford the hydrazone 5a which on chlorination with NCS followed by condensation with an appropriate malonate should lead to pyrazole such as 5b. Coupling of the requisite acid with macrocyclic amines of this invention should lead to carboxamide pyrazole 5c which can be converted to the compounds of this invention via methods outlined or known to those in the art.

Scheme 5

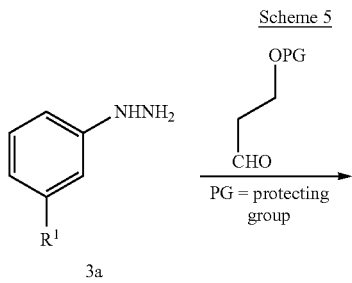

3a

PG = protecting group

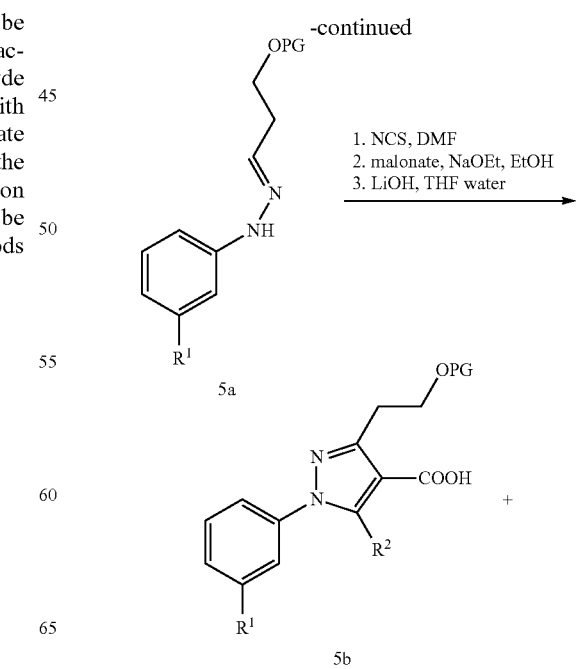

5a

5b

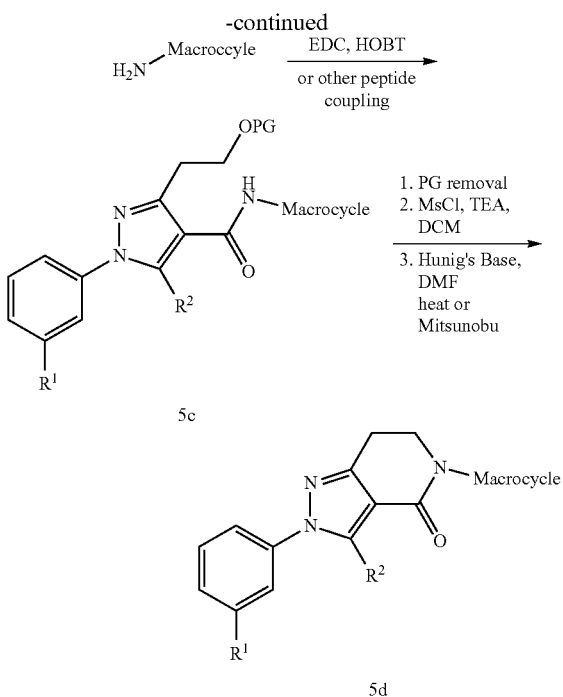

Intermediates for preparation of compounds of this invention wherein ring B is an imidazole ring, can be prepared from an appropriately N-protected allylglycine (6a) according to the general method outlined in Scheme 6 (Contour-Galcera et al., *Bioorg. Med. Chem. Lett.*, 11(5):741-745 (2001)). Condensation of 6a with a suitably substituted bromoacetophenone (1b) in the presence of a suitable base such as potassium bicarbonate, $K_2CO_3$ or $Cs_2CO_3$ in a suitable solvent such as DMF provides a keto ester intermediate which can be cyclized to afford an imidazole (6c) by heating in the presence of excess ammonium acetate in a solvent such as toluene or xylene. This latter transformation can be conveniently carried out on small scale at 160° C. in a microwave reactor or on larger scale by refluxing the mixture while removing water via a Dean-Stark trap. The resulting imidazole intermediate (6c) is then protected by treatment with SEM-Cl in the presence of a base such as sodium hydride or dicyclohexylmethylamine in a solvent such as THF or DCM. The aryl bromide (6d) is then converted to the corresponding aniline (6e) by heating in a sealed vessel with excess ammonium hydroxide, in the presence of copper iodide, a base such as $Cs_2CO_3$ and a catalytic amount of proline in DMSO as solvent. Acylation of 6e with the appropriate alkenoic acid and a coupling agent such as T3P or BOP reagent, or alternately, by treatment with an alkenoic acid chloride in the presence of a base such as TEA or DIEA provides diene 6f, which undergoes ring closing metathesis by heating in dilute solution in the presence of p-toluene sulfonic acid and Grubbs II catalyst in a suitable solvent such as DCM or DCE to provide the corresponding macrocycle (6g) (*Tetrahedron Letters*, 44:1379 (2003)). Alternately, the RCM can be run in a microwave at elevated temperatures without pTsOH. Chlorination on the imidazole ring with NCS, or initial reduction of the double bond followed by chlorination, and deprotection provides intermediates 6h and 6i, respectively. Alternately, for compounds wherein $R_{10}=CN$, catalytic hydrogenation of 6g followed by bromination with NBS at room temperature and subsequent palladium-catalyzed cyanation and deprotection provides intermediate 6j. Intermediates 6h-j can be converted to compounds of this invention following the steps described in Scheme 15.

Scheme 6

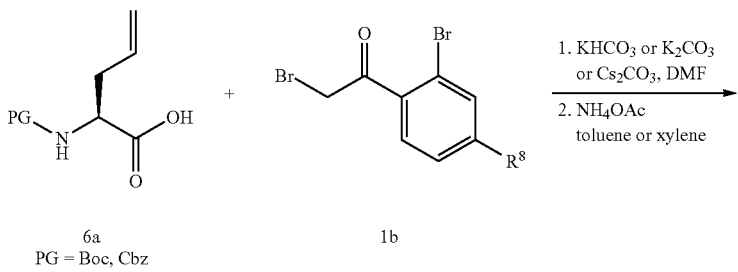

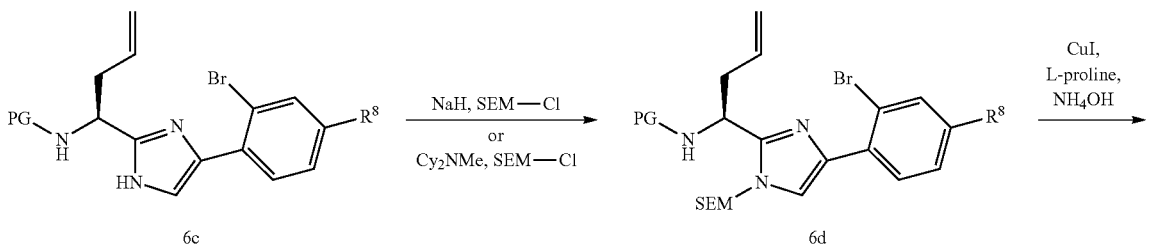

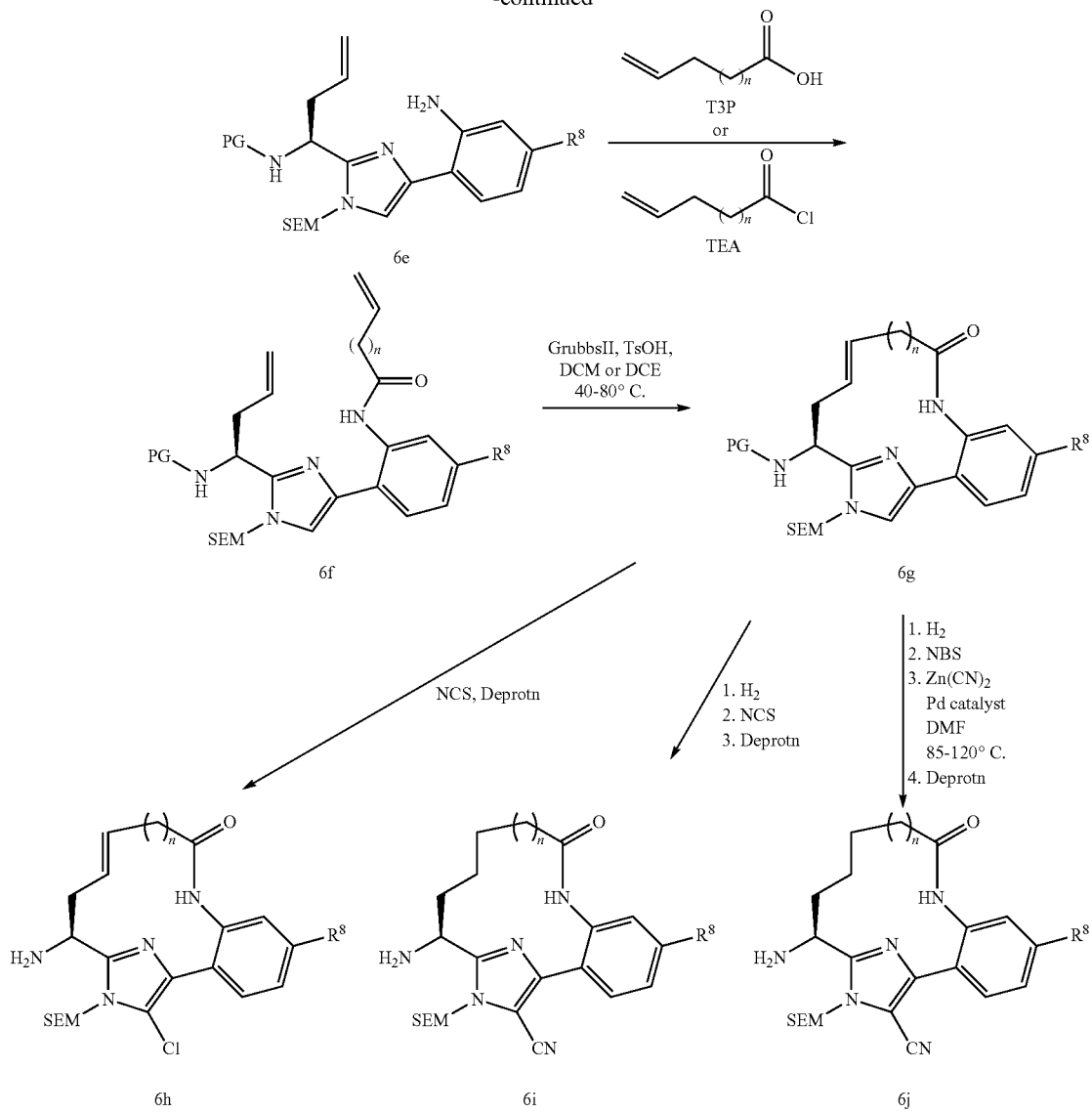

Representative imidazole containing amide macrocycle intermediates useful for the synthesis of compounds of this invention are described in Scheme 7. The aniline 6e can be coupled with an appropriately substituted carboxylic acid 7a using propane phosphonic acid anhydride (T3P) to give the amide 7b (n=0) and 7c (n=1). Using a modified procedure described by Lovely (*Tetrahedron Letters*, 44:1379 (2003)), 7b and 7c, following pretreatment with p-TsOH to form the imidazolinium ion, can be cyclized via ring-closing metathesis using a catalyst, such as Grubbs (II), in a suitable solvent, such as DCM, DCE, or toluene at elevated temperature, to give the imidazole-containing macrocycles 7d (n=0) and 7e (n=1). The alkene can then be reduced with hydrogen over either palladium on carbon or platinum oxide and subsequent deprotection with TFA in DCM provides amine 7f and 7g. Compounds of the formulae 7f and 7g can be converted to compounds in this invention according to Scheme 15.

Scheme 7

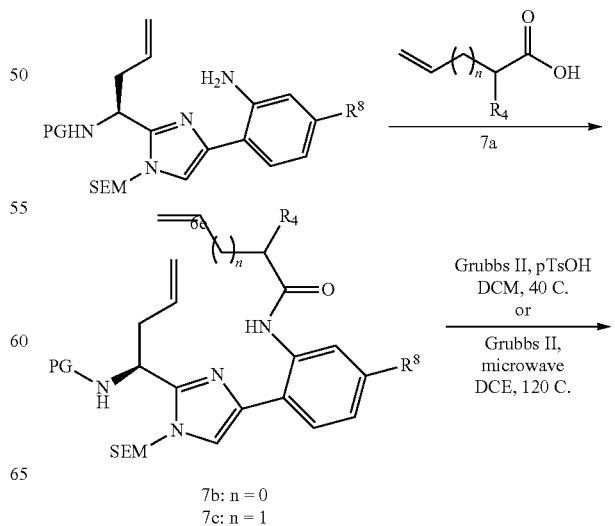

7b: n = 0
7c: n = 1

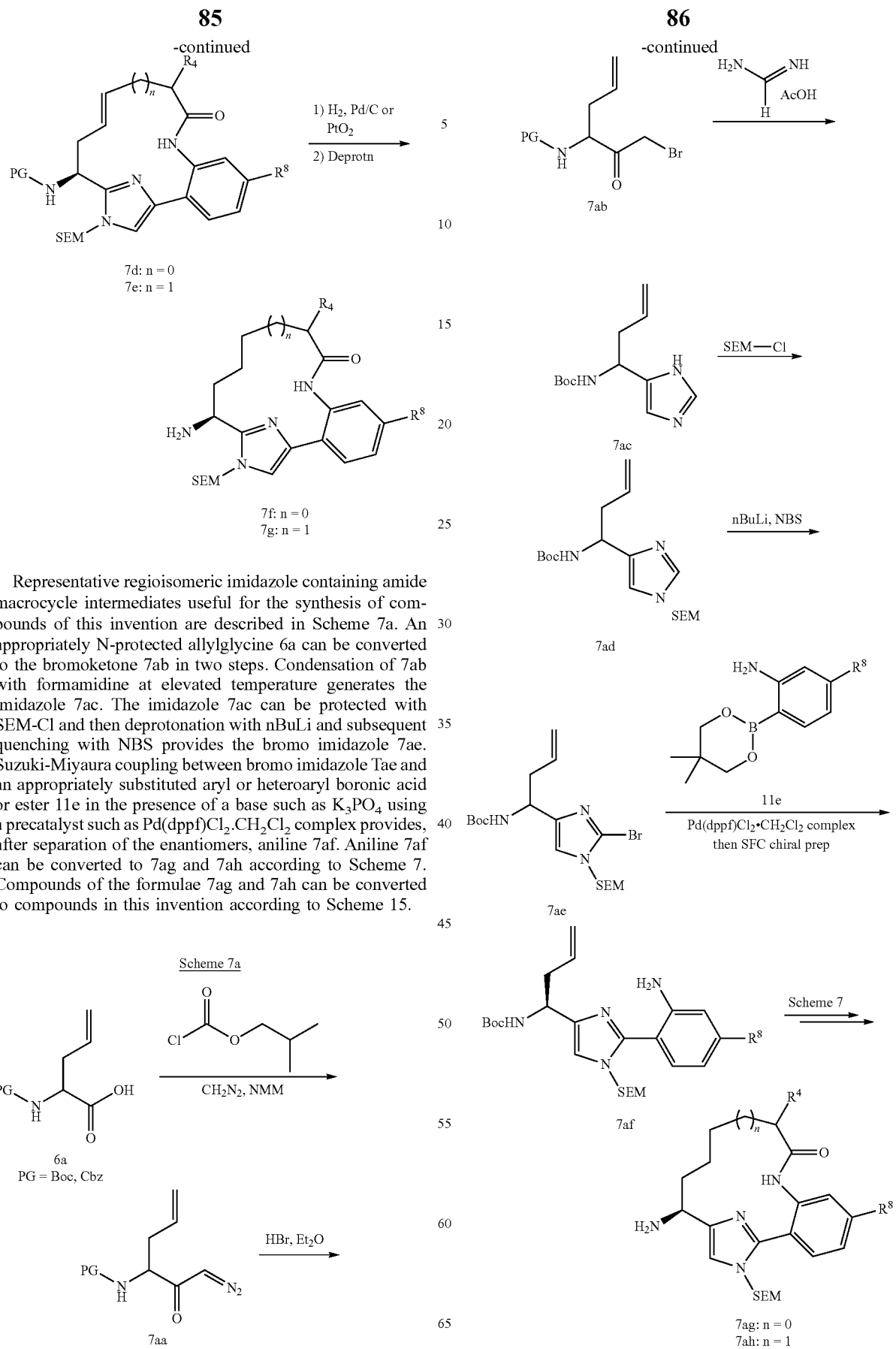

Representative regioisomeric imidazole containing amide macrocycle intermediates useful for the synthesis of compounds of this invention are described in Scheme 7a. An appropriately N-protected allylglycine 6a can be converted to the bromoketone 7ab in two steps. Condensation of 7ab with formamidine at elevated temperature generates the imidazole 7ac. The imidazole 7ac can be protected with SEM-Cl and then deprotonation with nBuLi and subsequent quenching with NBS provides the bromo imidazole 7ae. Suzuki-Miyaura coupling between bromo imidazole 7ae and an appropriately substituted aryl or heteroaryl boronic acid or ester 11e in the presence of a base such as $K_3PO_4$ using a precatalyst such as $Pd(dppf)Cl_2 \cdot CH_2Cl_2$ complex provides, after separation of the enantiomers, aniline 7af. Aniline 7af can be converted to 7ag and 7ah according to Scheme 7. Compounds of the formulae 7ag and 7ah can be converted to compounds in this invention according to Scheme 15.

Alternatively, imidazole containing macrocycles of this invention can be derived from intermediate 8e according to Scheme 8. Ullmann type coupling reaction of compound 6d and allyl glycine, followed by methylation of the acid would provide the extended aniline analog 8b. Ring closing metathesis of the diene 8b using Grubb II catalyst would provide the macrocyclic olefin 8c. Then, the macrocyclic olefin 8c may be converted to the key intermediate 8e via hydrogenation and selective deprotection of the amine protecting group from compound 8d. The amine 8e may be converted to the corresponding cyclic carbamate or other analogs following the procedures described in Scheme 15. The other diastereomer at the methyl ester position can also be made in the same way as described above.

The cyano or chloro imidazole analog of intermediate 8e may be obtained by a slightly modified sequence of Scheme 9. The aniline nitrogen in compound 8b may be protected with a trifluoroacetyl group (TFA) in order to suppress bromination/chlorination on the phenyl group during conversion of compound 9b to 9c. Following the same sequence as outlined in Scheme 8, the resulting protected aniline 9a may be converted to macrocyclic compound 9b. Bromination or chlorination of 9b with NBS or NCS respectively provides intermediates 9c. For compounds wherein $R^{10}$ is CN, bromide 9c is converted to cyanoimidazole 9d by palladium-catalyzed cyanation as described in Scheme 6 above. Selective removal of the amine protecting group from compound 9d provides amine intermediates 9e. For example a Boc protecting group can be selectively removed either under mild acidic conditions or thermally by heating in trifluoroethanol in a microwave at 150° C. Intermediate 9e can be converted to the final compounds described in this invention according to Scheme 15.

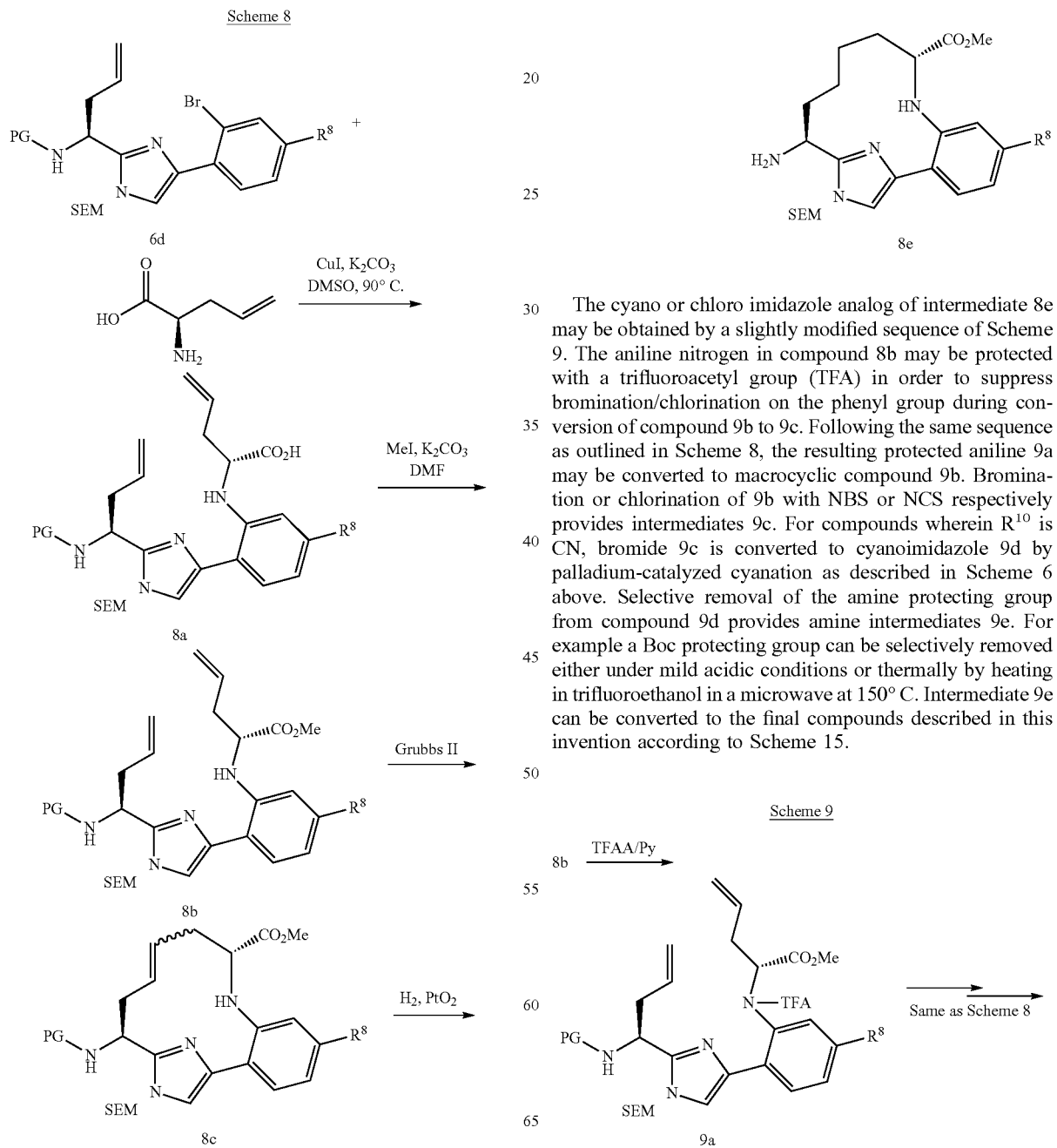

Scheme 8

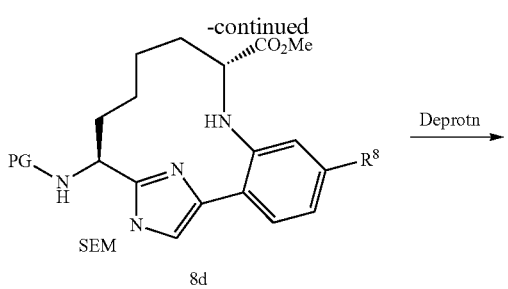

Scheme 9

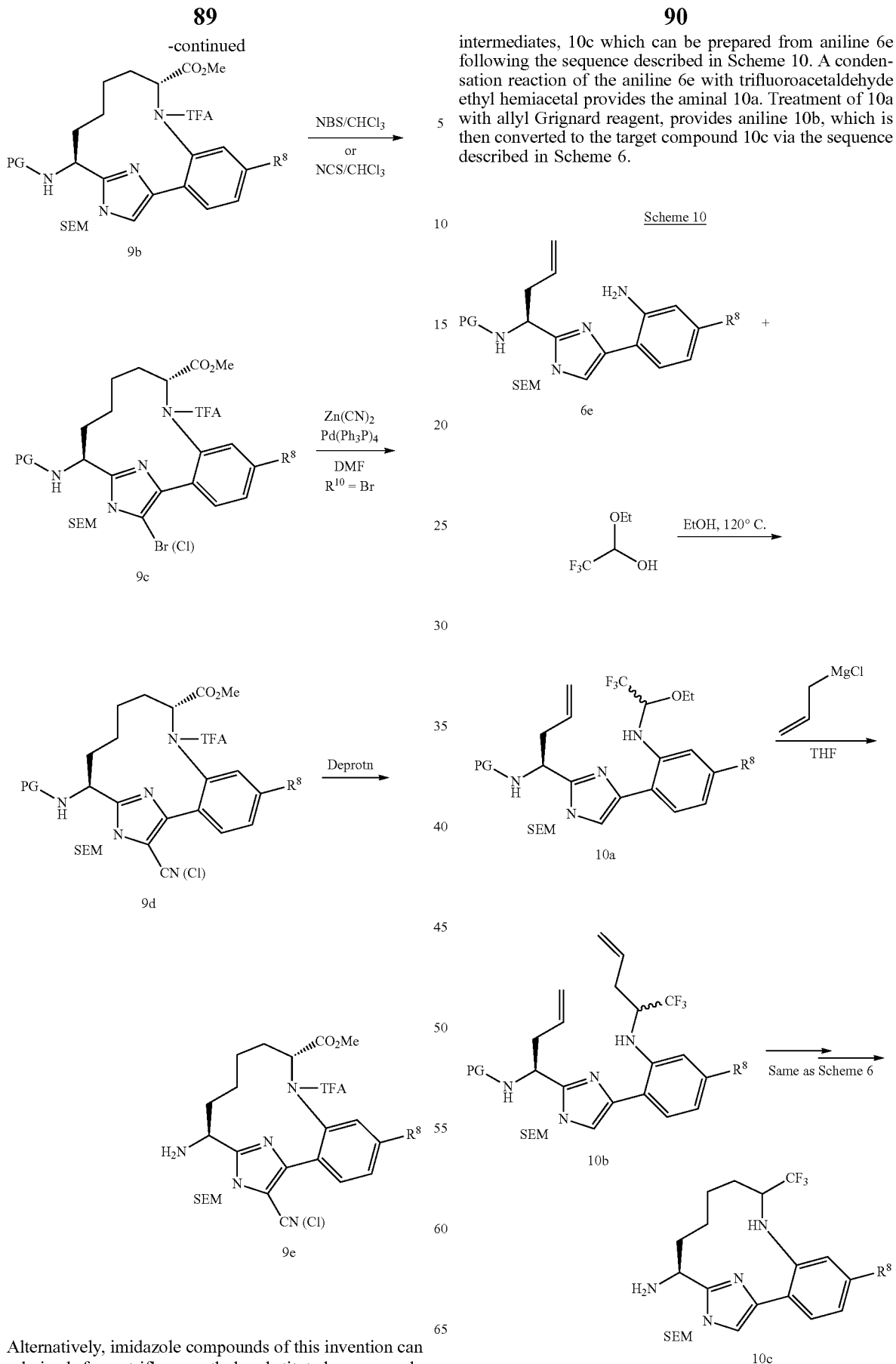

intermediates, 10c which can be prepared from aniline 6e following the sequence described in Scheme 10. A condensation reaction of the aniline 6e with trifluoroacetaldehyde ethyl hemiacetal provides the aminal 10a. Treatment of 10a with allyl Grignard reagent, provides aniline 10b, which is then converted to the target compound 10c via the sequence described in Scheme 6.

Alternatively, imidazole compounds of this invention can be derived from trifluoromethyl substituted macrocycle Scheme 11
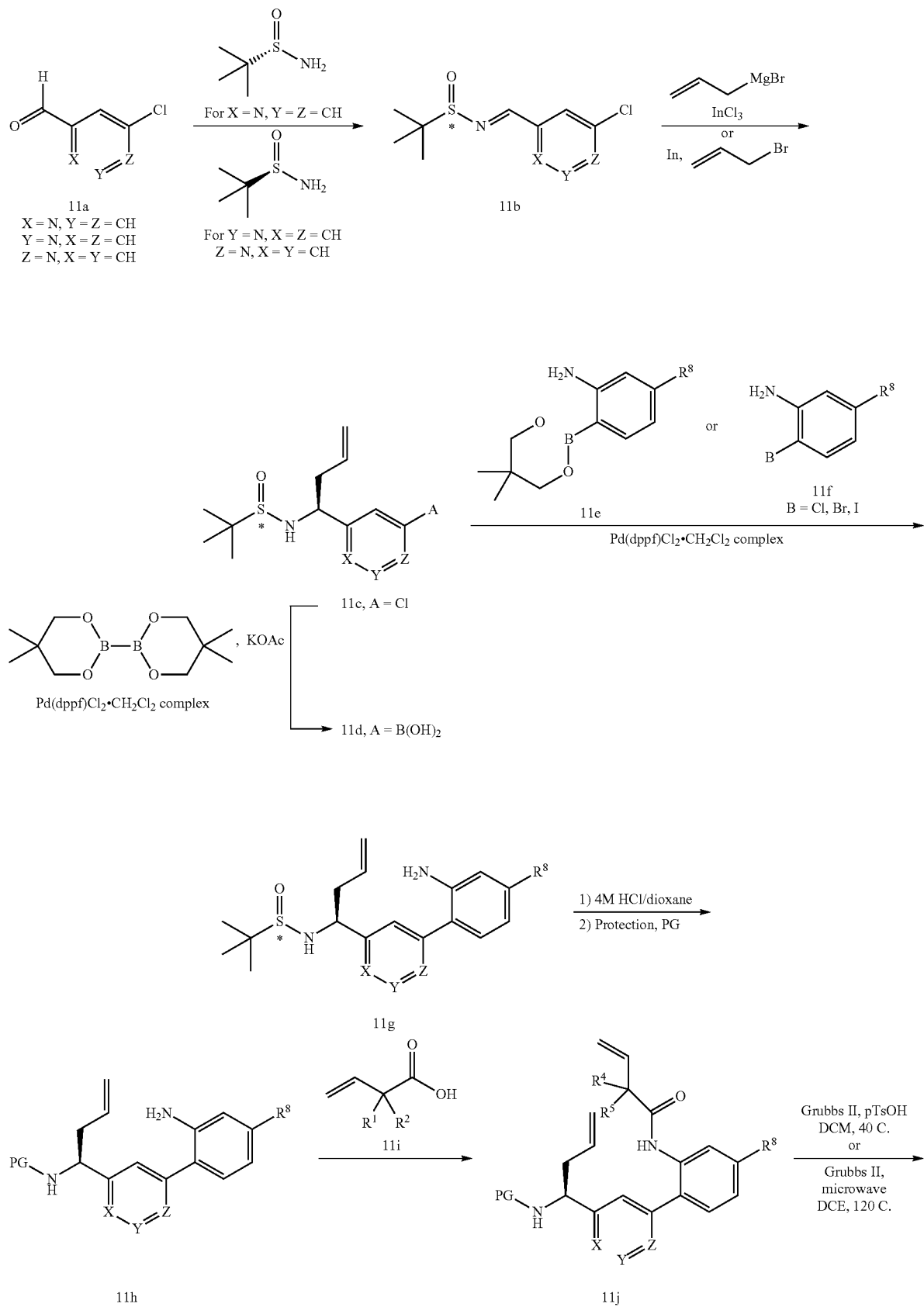

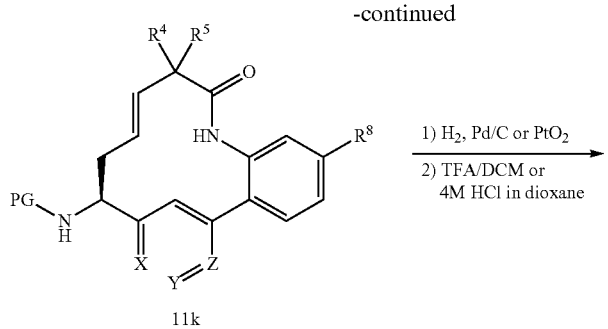 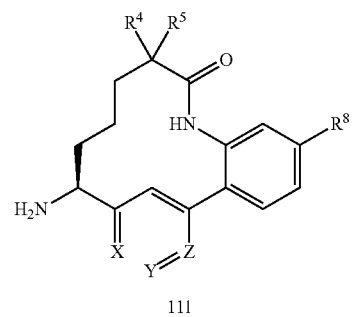

Representative compounds of this invention where ring B is a six-membered heterocycle (example—pyridine) can be derived from intermediates 11l, the synthesis of which is described in Scheme 11. Condensation of aldehyde 11a (X=N) prepared according to a modified procedure described by Negi (*Synthesis,* 991 (1996)), with (S)-2-methylpropane-2-sulfinamide in the presence of anhydrous copper sulfate in a solvent such as DCM gives the sulfinimine 11b (Ellman, J., *J. Org. Chem.,* 64:1278 (1999)). Using a modified procedure described by Kuduk (*Tetrahedron Letters,* 45:6641 (2004)), suitably substituted Grignard reagents, for example allylmagnesium bromide, can be added to sulfinimine 11b to give a sulfinamide 11c, as a mixture of diastereomers which can be separated at various stages of the sequence. The diastereoselectivity for the addition of allylmagnesium bromide to sulfinimine 11b can be improved by employing indium(III) chloride according to a modified procedure of Xu (Xu, M-H, *Organic Letters,* 10(6):1259 (2008)). Suzuki-Miyaura coupling between 4-chloropyridine 1c and an appropriately substituted aryl or heteroaryl boronic acid or ester 11e in the presence of a base such as potassium phosphate, in a solvent mixture, such as DMSO and H$_2$O, or DMF, using a precatalyst such as Pd(dppf)Cl$_2$·CH$_2$Cl$_2$ complex provides 11g. Alternatively, the Suzuki-Miyaura coupling between boronic acid 11d and an appropriately substituted aryl or heteroaryl halide 11f can be used to prepared 11g. Protecting group interconversion can be accomplished in two steps to give 11h. Alternatively, the protecting group interconversion can take place initially on 11c followed by the Suzuki-Miyaura coupling. The aniline 11h can then be coupled with an appropriately substituted carboxylic acid 11i using T3P and a base, such as pyridine, to give the amide 11j. Using a modified procedure described by Lovely (*Tetrahedron Letters,* 44:1379 (2003)), 11j, following pretreatment with p-toluenesulfonic acid to form the pyridinium ion, can be cyclized via ring-closing metathesis using a catalyst, such as Grubbs (II), in a suitable solvent, such as DCM, DCE, or toluene at elevated temperature, to give the pyridine-containing macrocycle 11k. The alkene can be reduced with hydrogen over either palladium on carbon or platinum oxide, and subsequent deprotection with TFA in DCM or 4M HCl in dioxane provides amine 11l. Compounds of the formulae 11l can be converted to compounds in this invention according to Scheme 15.

Additional pyridine containing macrocycles useful for the synthesis of compounds of this invention can also be prepared according to Scheme 11. In cases where the pyridine core is a 4-pyridine (Z=N) rather than the 2-pyridine (X=N), conversion of 11h to 11j can be easily accomplished by using an acid chloride of 11i. Intermediates of formulae 11g where R$^8$=NO$_2$ may be modified further to give intermediates where R$^8$=NH CO$_2$—C$_{1-4}$ alkyl either before coupling with acid 11i or after coupling with acid. Reduction of the nitro group to an amino group may be accomplished with a reducing agent (e.g., Zn—NH$_4$Cl) in an inert solvent (e.g., MeOH) to give an intermediate of formula 11g where R$^8$=NH$_2$. These anilino derivatives may be coupled with chloroalkanoates of the formula ClCO$_2$—C$_{1-4}$ alkyl in the presence of a base (e.g., DIEA) in an inert solvent (e.g., DCM) to give intermediates where R$^8$=NH CO$_2$—C$_{1-4}$ alkyl.

Scheme 12

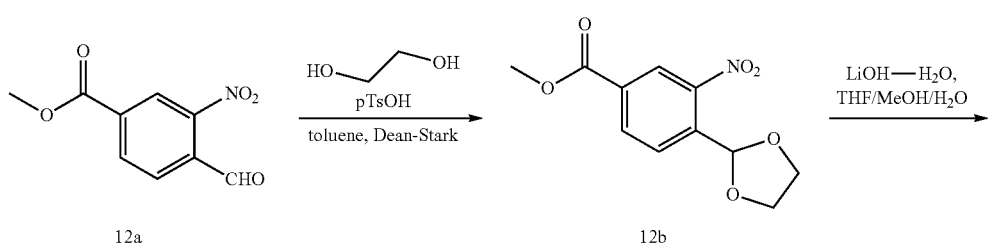

-continued
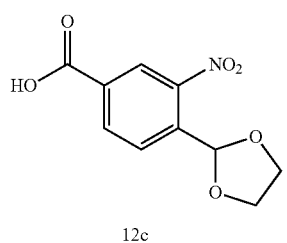
12c
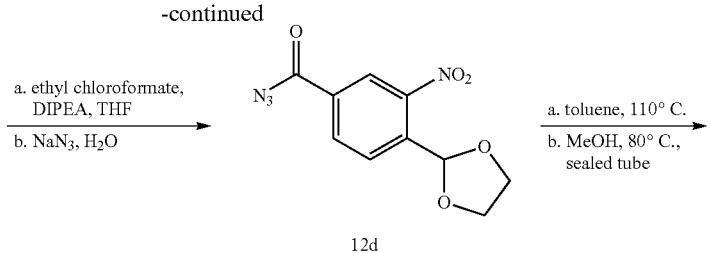
12d
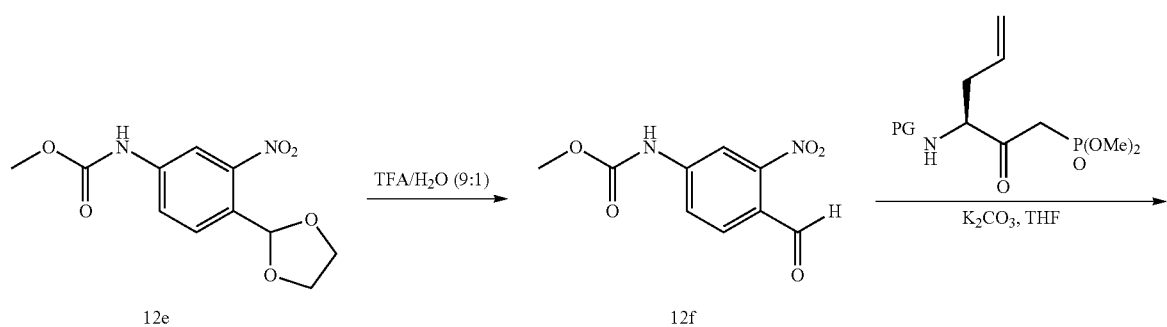
12e 12f
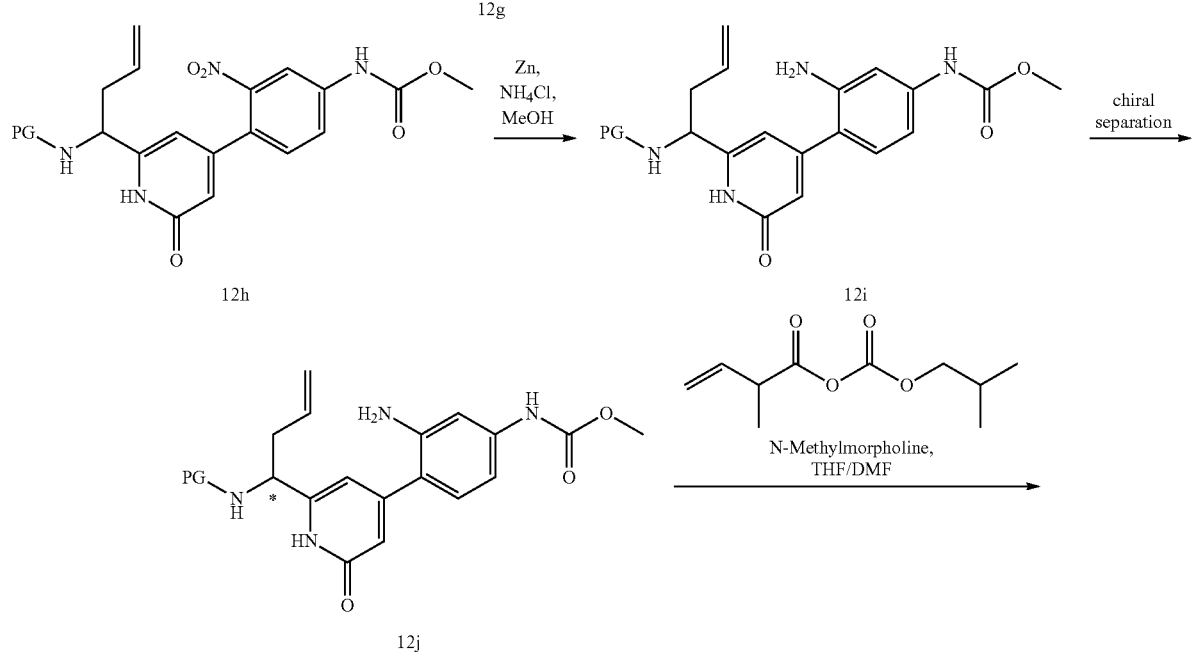
12g
12h 12i
12j -continued
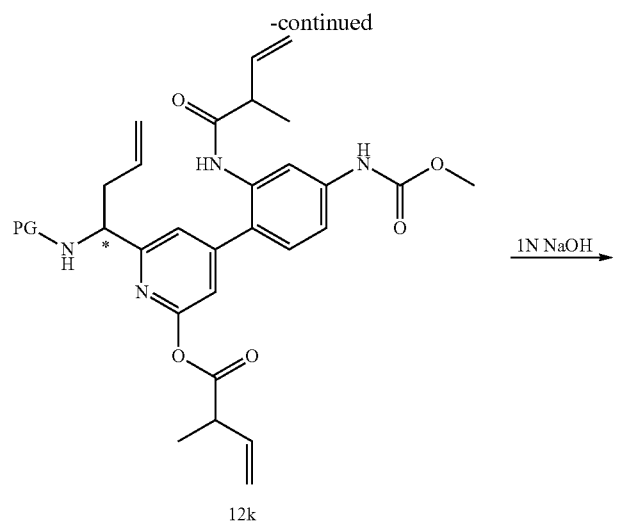
12k
1N NaOH →
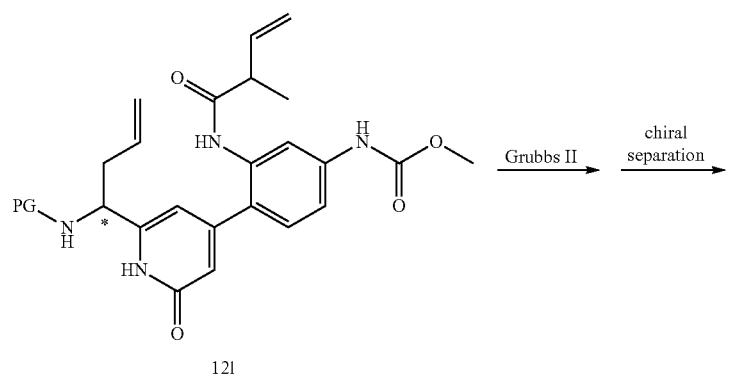
12l
Grubbs II → chiral separation →
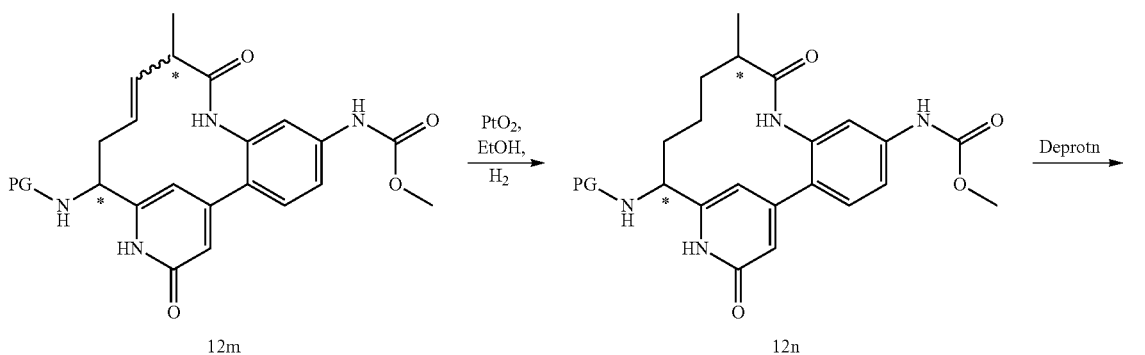
12m          12n
PtO₂, EtOH, H₂ →
Deprotn →
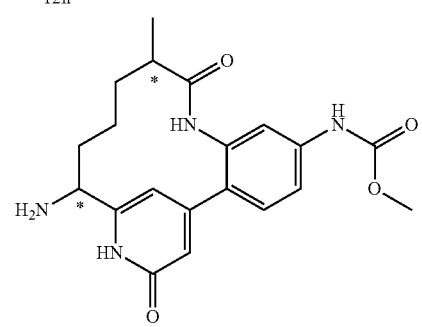
12o The amino ester analog 13e was obtained from key intermediate 12j following the sequence described in Scheme 13. Step-wise imine formation of 12j with ethyl 2,3-dioxopropanoate followed by addition of allyltributyltin under tin (IV) chloride conditions afforded RCM precursor 13a. Following the same sequence in Scheme 12, 13a can be converted into critical intermediate 13e over several steps. Other macrocyclic intermediates such as 13e wherein the ester is replaced with a variety of substituents can also be similarly constructed and following the sequence of reactions outlined above can be converted to compounds of this invention according to Scheme 15.

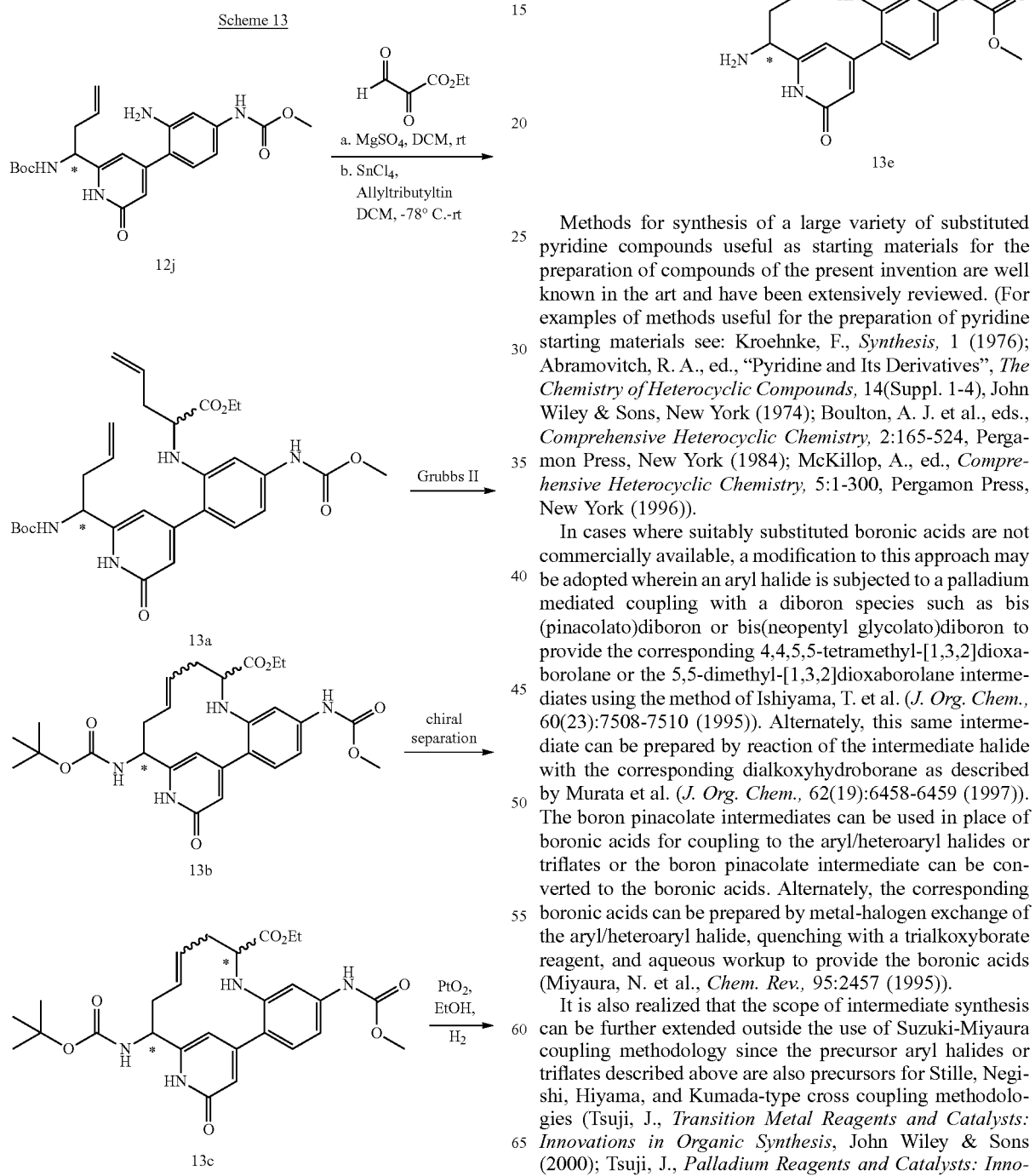

Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., *Synthesis*, 1 (1976); Abramovitch, R. A., ed., "Pyridine and Its Derivatives", *The Chemistry of Heterocyclic Compounds*, 14(Suppl. 1-4), John Wiley & Sons, New York (1974); Boulton, A. J. et al., eds., *Comprehensive Heterocyclic Chemistry*, 2:165-524, Pergamon Press, New York (1984); McKillop, A., ed., *Comprehensive Heterocyclic Chemistry*, 5:1-300, Pergamon Press, New York (1996)).

In cases where suitably substituted boronic acids are not commercially available, a modification to this approach may be adopted wherein an aryl halide is subjected to a palladium mediated coupling with a diboron species such as bis(pinacolato)diboron or bis(neopentyl glycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (*J. Org. Chem.*, 60(23):7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons (2000); Tsuji, J., *Palladium Reagents and Catalysts: Innovations in Organic Synthesis*, John Wiley & Sons (1996)).

Additional pyridazine and pyridazinone containing macrocycles can be prepared according to Scheme 14. Condensation of the potassium salt of 14a with a suitably substituted α-ketoester 14b, which is either commercially available or prepared using a modified procedure described by Domagala (*Tetrahedron Lett.*, 21:4997-5000), in a solvent such as THF generates the α,β-unsaturated ketone derivative which can then be condensed with a suitably substituted hydrazine derivative to give pyridazinone 14c. The nitro group can then be reduced to the aniline 14f with zinc and $NH_4Cl$ in methanol. The pyridazinone 14c can be converted to chloropyridazine 14d by deprotection of the amine protecting group, followed by treatment with $POCl_3$, then reprotection. The nitro group can be reduced to the aniline 14e with iron and AcOH. The anilines 14e and 14f can then be coupled with an appropriately substituted carboxylic acid 7a using T3P to give the amide 14g ($R_{10}$=Cl) and 14h ($R_{10}$=OH), respectively. 14g and 14h can then be cyclized via ring-closing metathesis using a catalyst, such as Grubbs (II), in a suitable solvent, such as DCM, DCE, or toluene at elevated temperature, to give the macrocycle 14i ($R_{10}$=Cl) and 14j ($R_{10}$=OH), respectively. The resulting alkenes can then be reduced with hydrogen over either palladium on carbon or platinum oxide to give 14k and 14l. 14k can be reduced with ammonium acetate and palladium on carbon to reduce the chlorine to give 14m. Subsequent deprotection of 14m and 14l provides amines 14n ($R_{10}$=H) and 14o ($R_{10}$=OH). Compounds of the formulae 14n and 14o can be converted to compounds in this invention according to Scheme 15.

Scheme 14

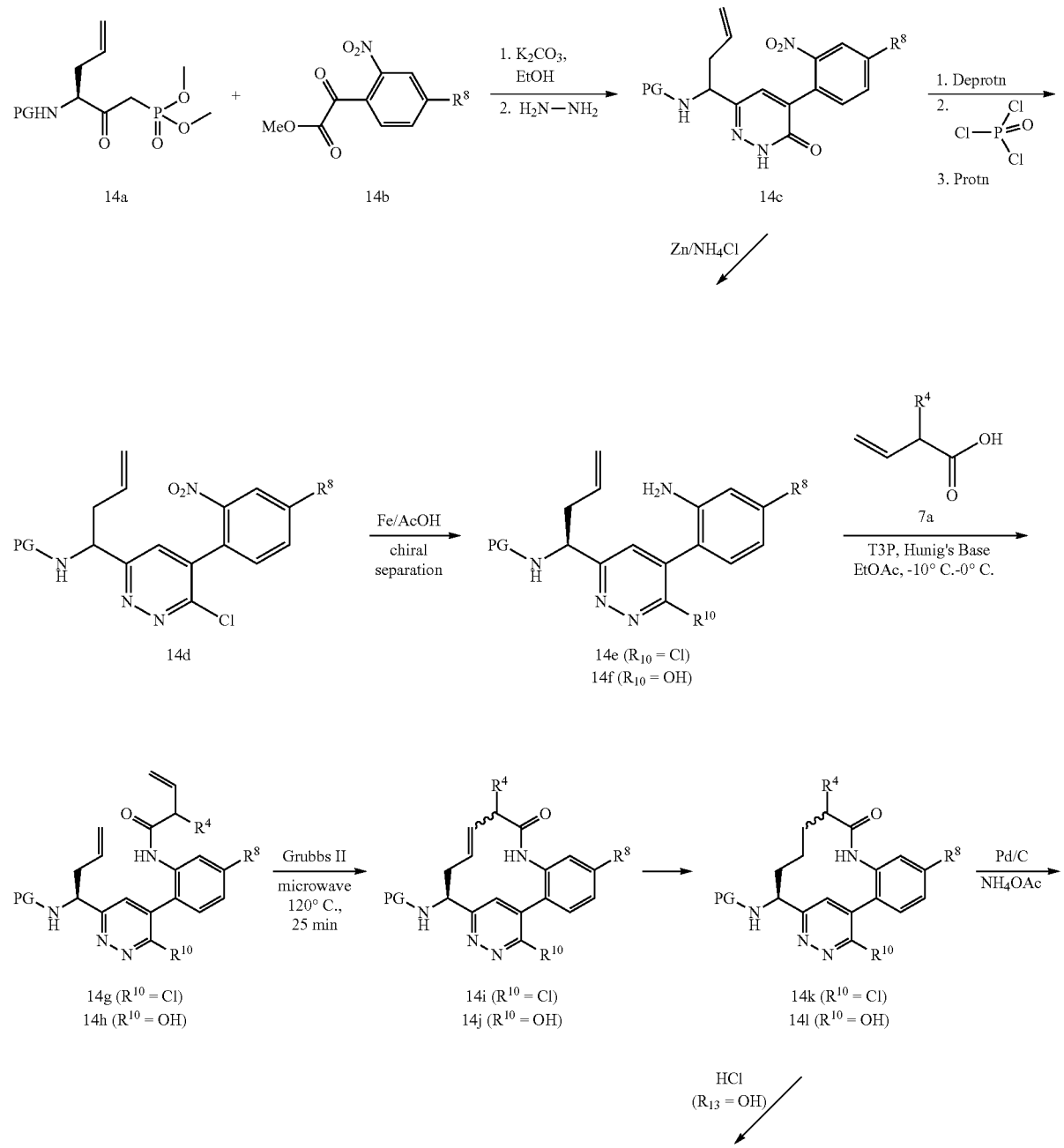

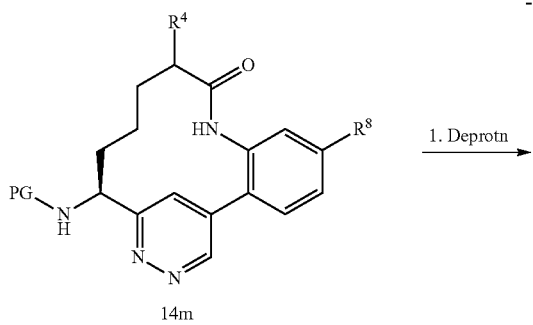

14m

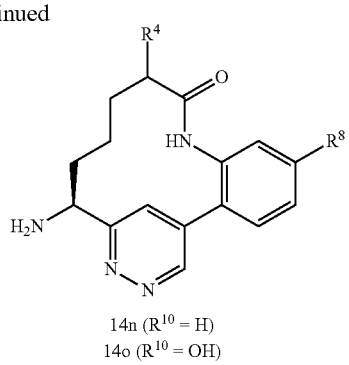

14n (R[10] = H)
14o (R[10] = OH)

Representative regioisomeric pyridazine containing amide macrocycle intermediates useful for the synthesis of compounds of this invention are described in Scheme 14a. Using a modification of the Minisci reaction described by Cowden (*Org. Leu.*, 5:4497-4499 (2003)), an appropriately protected glycine 14aa and 3,6-dichloropyridazine can be coupled at elevated temperature in the presence of silver nitrate, ammonium persulfate, and an acid, such as ammonium formate, in a solvent, such as water or a water/dimethylformamide mixture, to give compounds of the formulae 14ab. Compound 14ab can be further functionalized by deprotonation with nBuLi and subsequent alkylation with an appropriately substituted alkyl halide, for instance allyl bromide, to give compound 14ac. Suzuki-Miyaura coupling between chloropyridazine 14ac and an appropriately substituted aryl or heteroaryl boronic acid or ester 11e in the presence of a base such as sodium carbonate using a precatalyst such as (Ph₃P)₄Pd provides, after separation of the enantiomers, aniline 14ad. Aniline 14ad can be converted to 14ae and 14af according to Scheme 7. Hydrogenolysis of the chloro under transfer hydrogenation conditions and Boc-deprotection will give compounds 14ag and 14ah. Compounds of the formulae 14ag and 14ah can be converted to compounds in this invention according to Scheme 15.

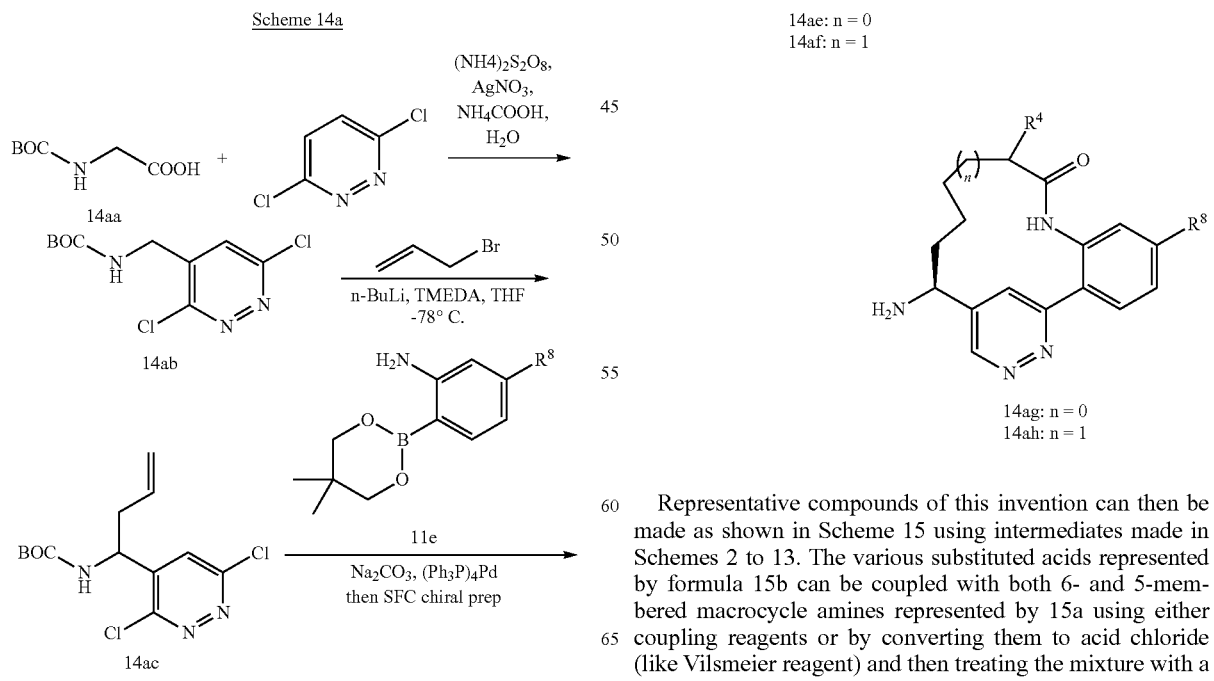

Representative compounds of this invention can then be made as shown in Scheme 15 using intermediates made in Schemes 2 to 13. The various substituted acids represented by formula 15b can be coupled with both 6- and 5-membered macrocycle amines represented by 15a using either coupling reagents or by converting them to acid chloride (like Vilsmeier reagent) and then treating the mixture with a base to afford the desired macrocycles of this invention.

Scheme 15

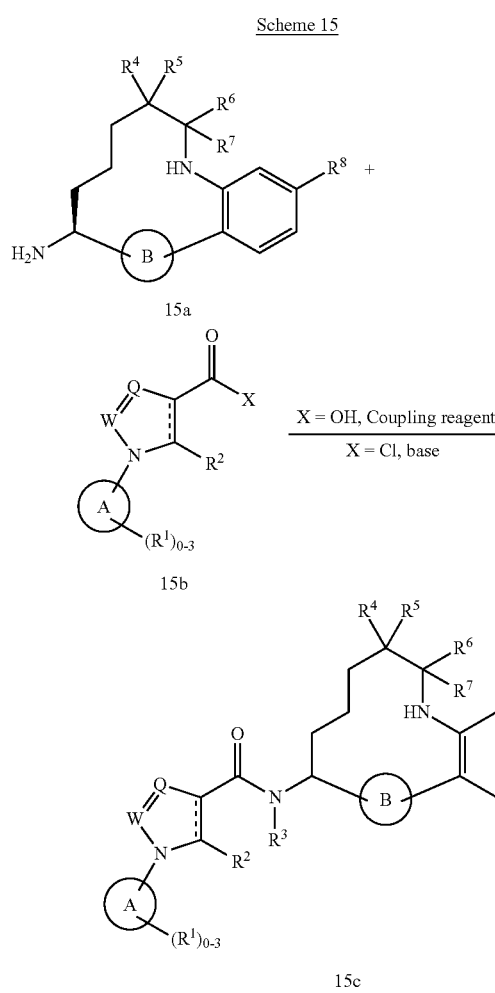

Purification of intermediates and final products was carried out via either normal or reverse phase chromatography. Normal phase chromatography was carried out using prepacked SiO₂ cartridges eluting with either gradients of hexanes and EtOAc or DCM and MeOH unless otherwise indicated. Reverse phase preparative HPLC was carried out using C18 columns eluting with gradients of Solvent A (90% H₂O, 10% MeOH, 0.1% TFA) and Solvent B (10% H₂O, 90% MeOH, 0.1% TFA, UV 220 nm) or with gradients of Solvent A (90% H₂O, 10% ACN, 0.1% TFA) and Solvent B (10% H₂O, 90% ACN, 0.1% TFA, UV 220 nm) or with gradients of Solvent A (98% H₂O, 2% ACN, 0.05% TFA) and Solvent B (98% ACN, 2% H₂O, 0.05% TFA, UV 220 nm) (or) Sunfire Prep C18 OBD 5u 30×100 mm, 25 min gradient from 0-100% B. A=H₂O/ACN/TFA 90:10:0.1. B=ACN/H₂O/TFA 90:10:0.1.

Unless otherwise stated, analysis of final products was carried out by reverse phase analytical HPLC.

Method A: A majority of analytical HPLC runs were: SunFire (3.0×150 mm) (15 min gradient—95:5 H₂O/ACN- to 95:5 ACN/H₂O—0.05% TFA).

Method B: ZORBAX® (4.6×75 mm) (8 min gradient—10:90 MeOH/H₂O to 90:10 MeOH/H₂O, 0.2% H₃PO₄)

Method C: PHENOMENEX® Luna 5μ 4.6×50 mm (4 min gradient—10:90 ACN/H₂O to 90:10 ACN/H₂O—0.1% TFA)

Method D: SunFire column (3.5 μm C18, 3.0×150 mm) Gradient elution (1.0 mL/min) from 10-100% Solvent B for 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method E: SunFire column (3.5 μm C18, 3.0×150 mm) Gradient elution (1.0 mL/min) from 10-100% Solvent B for 12 min and then 100% Solvent B for 3 min was used. Solvent A is (95% water, 5% acetonitrile, 0.05% TFA) and Solvent B is (5% water, 95% acetonitrile, 0.05% TFA, UV 254 nm).

A majority of mass spectra runs were: LCMS(ESI) m/z: [M+H]⁺ PHENOMENEX® Luna C18 (2×30 mm) (2 min gradient 90% H₂O/10% MeOH/0.1% TFA to 90% MeOH/10% H₂O/0.1% TFA) (or) BEH C18 2.1×50 mm—2 min gradient from 0-100% B. (A: 90/10/0.1 H₂O/ACN/TFA; B: 90/10/0.1 ACN/H₂O/TFA).

Intermediate 1

1-(3-Chloro-2-fluorophenyl)-1H-1,2,3-triazole-4-carboxylic acid

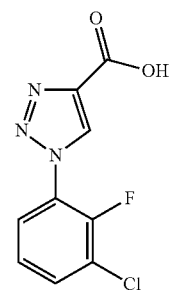

Intermediate 1. 1-(3-Chloro-2-fluorophenyl)-1H-1,2,3-triazole-4-carboxylic acid: 3-chloro-2-fluoro aniline was dissolved in TFA (4 mL) and H₂O (2 mL) was added to the above solution. The mixture was then cooled to 0° C. and to this was added a predissolved aqueous solution (2 mL) of NaNO₂ dropwise to ensure the temperature did not rise above 5° C. The reaction mixture was stirred at this temperature for 0.5 h followed by the addition of solid NaN₃ portionwise. The reaction mixture was stirred cold and then allowed to warm up to rt overnight. The reaction mixture was quenched with H₂O (100 mL) and extracted the azide with EtOAc (2×50 mL), dried and evaporated to a solid mass (1.1 g). The product obtained was dissolved in DMSO (5 mL) in a microwave flask and to this was added L-proline (0.02 g), Cu(OAc)₂ (0.1 g), K₂CO₃ (1.5 g) and sodium ascorbate (0.1 g) and excess t-butyl propiolate (3 mL). The flask was sealed and heated at 75° C. overnight. Aliquot LCMS showed the reaction to be complete. The reaction mixture was quenched with H₂O (100 mL) and extracted the organic layer with EtOAc (2×100 mL), washed with brine (50 mL) and dried (MgSO₄). The crude product was then purified using silica gel chromatography. The desired ester was isolated and concentrated, evaporated to a brown solid (0.98 g). The ester (0.2 g) was dissolved in DCM (2 mL) and to this was added TFA (1 mL) and stirred at rt overnight.

Aliquot LCMS showed the reaction to be complete. The reaction mixture was then quenched with $H_2O$ (50 mL) and the organic layer was extracted with EtOAc (2×100 mL), dried and evaporated to a brown solid mass. MS(ESI) m/z: 342.1 (M+H)+. $^1$H NMR (500 MHz, CDCl$_3$) δ 8.20 (s, 1H), 7.60-7.55 (dt, 1H), 7.42-7.37 (dt, 1H), 7.28-7.23 (dt, 1H) ppm.

Intermediate 2

1-(3-Chloro-2-fluorophenyl)-1H-pyrazole-4-carboxylic acid

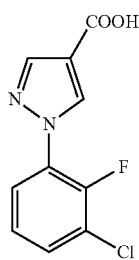 [SMILES: O=C(O)c1cnn(-c2cccc(Cl)c2F)c1]

Intermediate 2A. Ethyl 5-amino-1-(3-chloro-2-fluorophenyl)-1H-pyrazole-4-carboxylate: To a mixture of (3-chloro-2-fluorophenyl)hydrazine hydrochloride (0.67 g, 3.40 mmol), (E)-ethyl 2-cyano-3-ethoxyacrylate (0.633 g, 3.72 mmol) and sodium acetate (0.586 g, 7.12 mmol) at rt was added AcOH and $H_2O$ to form a slurry. The reaction mixture was continued to stir at rt for 0.25 h and then heated at 100° C. for overnight. After overnight stirring, the reaction mixture was quenched with $H_2O$ (200 mL) and a yellowish brown solid separated. The solids were filtered and washed thoroughly with $H_2O$. Re-dissolved the residue in DCM, dried and evaporated to a brown solid as the desired product (0.76 g, 78%). MS(ESI) m/z: 284.2 (M+H)+. $^1$H NMR (400 MHz, CDCl$_3$) δ 7.76 (s, 1H), 7.51-7.29 (m, 2H), 7.27-7.03 (m, 1H), 5.30-5.06 (m, 2H), 4.24 (q, J=7.2 Hz, 2H), 1.38-1.04 (m, 3H) ppm.

Intermediate 2. 1-(3-Chloro-2-fluorophenyl)-1H-pyrazole-4-carboxylic acid: A mixture of Intermediate 2A (0.317 g, 1.117 mmol), isoamylnitrite (1.304 g, 11.14 mmol) in THF (20 mL) was heated at 100° C. After 2 h, the reaction mixture was concentrated in vacuo to yield the crude product. To the crude product was added NaOH (0.610 g, 10 Eq), MeOH and $H_2O$. The reaction mixture was stirred at rt for 2 h. The reaction mixture was then quenched with $H_2O$ (100 mL) and extracted the unreacted starting material with EtOAc (2×100 mL). The aqueous layer was then acidified with HCl (1 N) and then extracted the organics with EtOAc (2×100 mL). The combined organic layers were dried over sodium sulfate, filtered, and concentrated to give Intermediate 2 as a brown solid mass. MS(ESI) m/z: 240.9 (M+H)+. $^1$H NMR (400 MHz, CDCl$_3$) δ 8.49 (d, J=2.5 Hz, 1H), 8.12 (s, 1H), 7.77 (ddd, J=8.3, 6.9, 1.8 Hz, 1H), 7.41-7.28 (m, 1H), 7.23-7.10 (m, 1H) ppm.

Intermediate 3

5-Amino-1-(3-chlorophenyl)-1H-pyrazole-4-carboxylic acid

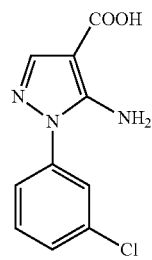 [SMILES: Nc1c(C(=O)O)cnn1-c1cccc(Cl)c1]

Intermediate 3A. Ethyl-5-amino-1-(3-chlorophenyl)-1H-pyrazole-4-carboxylate: (Ref: *J. Heterocyclic Chem.*, 267 (1987)) To a mixture of (3-chlorophenyl)hydrazine hydrochloride (2.328 g, 13 mmol), (E)-ethyl 2-cyano-3-ethoxyacrylate (2.199 g, 13.00 mmol) and $K_2CO_3$ (1.797 g, 13.00 mmol) was added EtOH (20 mL). The suspension was then warmed to reflux and stirred at refluxing temperatures for overnight. After 20 h, the reaction mixture was poured into ice-$H_2O$. The suspension was then filtered and the solid collected by filtration was dried in vacuo (50° C.) for overnight to yield a brown solid (2.93 g). MS(ESI) m/z: 266.1 (M+H)+.

Intermediate 3. 5-Amino-1-(3-chlorophenyl)-1H-pyrazole-4-carboxylic acid: (Reference: *J. Heterocyclic Chem.*, 773 (2003)) A solution of Intermediate 3A (0.652 g, 2.454 mmol) and NaOH (0.613 g, 15.34 mmol) in EtOH (1.534 mL) and $H_2O$ (13.80 mL) was refluxed until the reaction mixture became homogeneous. After 24 h, the reaction mixture was cooled to rt and filtered. The filtrate was acidified with concentrated HCl to give a suspension which was subjected to filtration. The solid collected by filtration was washed with $H_2O$ and dried in vacuo (50° C.) for 4 h to give a yellow solid (0.51 g) as the desired product. MS(ESI) m/z: 238.1 (M+H)+. $^1$H NMR (500 MHz, MeOD) δ 7.77 (s, 1H), 7.64-7.61 (m, 1H), 7.58-7.51 (m, 2H), 7.50-7.46 (m, 1H) ppm.

Intermediate 4

5-Amino-1-(3-chloro-2-fluorophenyl)-1H-pyrazole-4-carboxylic acid

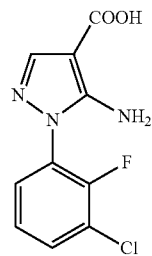 [SMILES: Nc1c(C(=O)O)cnn1-c1cccc(Cl)c1F]

Intermediate 4A. Ethyl 5-amino-1-(3-chloro-2-fluorophenyl)-1H-pyrazole-4-carboxylate: A brown suspension of (3-chloro-2-fluorophenyl)hydrazine hydrochloride (0.500 g, 2.54 mmol) and (E)-ethyl 2-cyano-3-ethoxyacrylate (0.472 g, 2.79 mmol) in EtOH (2.54 mL) and triethylamine (0.707 mL, 5.08 mmol) was warmed to 85° C. After 4.5 h, the reaction was stopped and cooled to rt. The reaction was concentrated to give a brown solid. Purification by normal phase chromatography gave Intermediate 4A (0.185 g, 26%) as an off-white solid. MS(ESI) m/z: 284.0 (M+H)+.

Intermediate 4. 5-Amino-1-(3-chloro-2-fluorophenyl)-1H-pyrazole-4-carboxylic acid: A clear, dull yellow solution of Intermediate 4A (0.184 g, 0.649 mmol) in MeOH (3.24 mL) and 1.0 N NaOH (1.946 mL, 1.946 mmol) was stirred at rt. After 1 h, the reaction was warmed to 50° C. After 8 h, the reaction was stopped and cooled to rt. The clear, yellow orange solution was concentrated to give a white solid. The white solid was partitioned between EtOAc, water, and 1.0 N NaOH and the layers were separated. The aqueous layer was extracted with EtOAc. The aqueous layer was acidified with 1.0 N HCl and then extracted with EtOAc (2×). The combined organic layers, following acidification, were washed with brine, dried over sodium sulfate, filtered and concentrated to give Intermediate 4 (0.153 g, 92%) as an off-white solid. MS(ESI) m/z: 256.0 (M+H)+ and 258.0 (M+2+H)+. $^1$H NMR (500 MHz, DMSO-d$_6$) δ 12.02 (br. s., 1H), 7.74 (ddd, J=8.1, 6.7, 1.7 Hz, 1H), 7.69 (s, 1H), 7.50 (td, J=7.4, 1.7 Hz, 1H), 7.37 (td, J=8.0, 1.2 Hz, 1H), 6.43 (s, 2H).

Intermediate 5

1-(3-Chloro-2,6-difluorophenyl)-1H-1,2,3-triazole-4-carboxylic acid

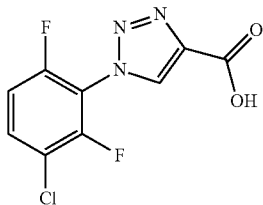 [SMILES: O=C(O)c1cn(-c2c(F)ccc(Cl)c2F)nn1]

Intermediate 5A: tert-Butyl (3-chloro-2,6-difluorophenyl) carbamate: 3-chloro-2,6-difluorobenzoic acid (4.85 g, 25.2 mmol) was dissolved in THF (50 mL) and cooled to 0° C. To this solution was then added ethylchloroformate (3.01 g, 27.7 mmol) followed by TEA (3.86 mL, 27.7 mmol) and stirred at the same temperature for 1 h. To the slurry that developed was then added NaN$_3$ in H$_2$O (5 mL) dropwise and stirred the reaction mixture at 0° C. for 1.25 h. Solids separated out from the reaction mixture and allowed the solids to decant followed by separation of the decantant. The residue was dissolved in H$_2$O (50 mL) and extracted with DCM (2×). The above organic layer was then combined with the decantant, dried (MgSO$_4$) and concentrated to yield a residue. The residue was re-dissolved in toluene (50 mL) and heated at 110° C. To the above solution was added t-BuOH (1.5 g) and refluxed for overnight. The reaction mixture was concentrated and purified by silica gel chromatography to yield the desired product (2.86 g, 43%). MS(ESI) m/z: 286.0 (M+Na)+. $^1$H NMR (400 MHz, CDCl$_3$) δ 7.28 (s, 1H), 7.03-6.72 (m, 1H), 6.10-5.83 (m, 1H), 1.57-1.37 (m, 9H) ppm.

Intermediate 5B. tert-Butyl 1-(3-chloro-2,6-difluorophenyl)-1H-1,2,3-triazole-4-carboxylate: To a solution of Intermediate 5A in DCM (5 mL) was added TFA (1 mL) and stirred at rt for 1 h. The reaction mixture was then concentrated to yield a brown oil which was redissolved in TFA (5 mL) and cooled to 0° C. To this cooled solution was then added NaNO$_2$ (0.209 g, 3.03 mmol) in H$_2$O (1 mL) dropwise. The reaction mixture was allowed to stir at 0° C. for 0.5 h followed by the addition of NaN$_3$ (0.394 g, 6.07 mmol) in H$_2$O (1 mL). The reaction mixture was continued to stir for 2 h at the same temperature and then quenched with H$_2$O (100 mL) and extracted the aqueous layer with EtOAc (2×). The combined organic layers were dried and evaporated to a brown oil. The azide from the above reaction was then dissolved in DMSO (5 mL) and to this solution was added t-butylpropiolate (1.5 mL, 1.517 mmol), Cu(OAc)$_2$ (0.055 g, 0.303 mmol) and K$_2$CO$_3$ (0.839 g, 6.07 mmol). The reaction was stirred at rt for overnight. The reaction mixture was then quenched with H$_2$O and solid mass separated. The reaction mixture was extracted with EtOAc (2×). The organic layer was dried and evaporated to a dark brownish-black oil. The crude product was then purified using silica gel chromatography. The desired product was isolated as reddish oil (0.3 g, 62%). MS(ESI) m/z: 316.0 (M+H)+.

Intermediate 5. 1-(3-Chloro-2,6-difluorophenyl)-1H-1,2,3-triazole-4-carboxylic acid: To a solution of Intermediate 5B (0.3 g, 0.950 mmol) in DCM (5 mL) was added TFA (1 mL) and the reaction mixture was stirred at rt for 1 h. The reaction mixture was then concentrated to yield the crude product which was purified using reverse phase HPLC. MS(ESI) m/z: 260.0 (M+H)+. $^1$H NMR (400 MHz, MeOD) δ 8.94 (s, 1H), 7.85 (ddd, J=9.3, 8.1, 5.3 Hz, 1H), 7.40 (td, J=9.2, 2.0 Hz, 1H) ppm.

Intermediate 6

1-(3-Chlorophenyl)-1H-1,2,3-triazole-4-carboxylic acid

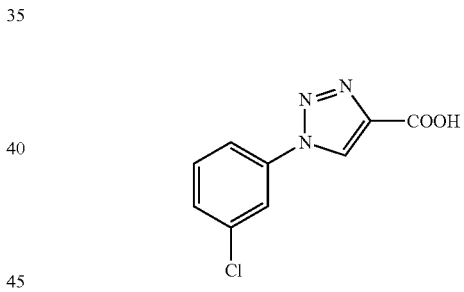

Intermediate 6A. Ethyl 1-(3-chlorophenyl)-1H-1,2,3-triazole-4-carboxylate: Sodium nitrite (1.947 g, 28.2 mmol) dissolved in H$_2$O (5 mL) was added to a cold (<5° C.) TFA (20 mL) solution of 3-chloro aniline (3.6 g, 28.2 mmol). After 0.5 h, sodium azide (1.835 g, 28.2 mmol) dissolved in H$_2$O (1 mL) was added dropwise to the above reaction mixture. The reaction mixture was then stirred cold for 2 h and then quenched with H$_2$O (100 mL) and extracted the organics with EtOAc (2×100 mL). The organic layers were then dried over MgSO$_4$ and concentrated to a brown oil (3.5 g). Approximately 1 g of the azide from the above crude product was taken in a microwave flask. To this was added ethyl propiolate (1.5 mL), DMSO (4 mL), sodium carbonate (0.1 g) and L-proline (0.1 g) and the reaction mixture was heated at 75° C. overnight. The reaction was then quenched with H$_2$O to precipitated out the solids. Filtered the solids and washed with excess H$_2$O followed by drying under vacuum to afford 1.3 g of the desired triazole ester. MS(ESI) m/z: 252.1 (M+H)+.

Intermediate 6. 1-(3-Chlorophenyl)-1H-1,2,3-triazole-4-carboxylic acid: To a solution for Intermediate 6A (0.3 g, 1.192 mmol) in a mixture of THF and H₂O (1:1) was added LiOH and stirred at rt for 1 h. After 1 h, the reaction mixture was quenched with H₂O (50 mL) and extracted the unreacted starting material with EtOAc. The aqueous layer was then acidified and extracted the acid with EtOAc (2×100 mL). The organic layers were then dried over MgSO₄ and evaporated to a brown oil which solidified at rt. MS(ESI) m/z: 224.0 (M+H)⁺. ¹H NMR (400 MHz, MeOD) δ 9.13 (s, 1H), 8.03 (s, 1H), 7.89 (dd, J=2.2 & 8.4 Hz, 2H), 7.61-7.56 (m, 2H) ppm.

Intermediate 7

1-(3-Chlorophenyl)-1H-pyrazole-4 carboxylic acid

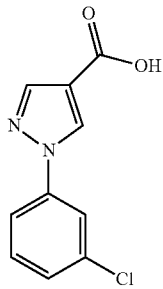

Intermediate 7. 1-(3-Chlorophenyl)-1H-pyrazole-4 carboxylic acid: 1-(1-(3-Chlorophenyl)-1H-pyrazol-4-yl)ethanone was dissolved in a solution of MeOH and DMSO (5:1). To this solution was then added a solution of NaOMe (2 N, 10 mL) followed by bleach (20 mL) and stirred at rt for overnight. After overnight stirring, the reaction mixture was quenched with H₂O (200 mL) and acidified with concentrated HCl. Extracted the organics with EtOAc (2×100 mL) and concentrated to yield a brown solid as the desired product. MS(ESI) m/z: 223.1 (M+H)⁺. ¹H NMR (400 MHz, CD₃OD) δ 7.36-7.38 (m, 1H), 7.47-7.51 (m, 1H), 7.74-7.77 (m, 1H), 7.89-7.90 (m, 1H), 8.04 (s, 1H), 8.65 (s, 1H) ppm.

Intermediate 8

5-Amino-1-(3-chlorophenyl)-1H-1,2,3-triazole-4-carboxylic acid

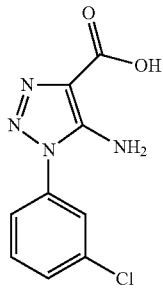

Intermediate 8. 5-Amino-1-(3-chlorophenyl)-1H-1,2,3-triazole-4-carboxylic acid: The azide was made as previously described (Intermediate 6) starting with 3-chloroaniline. The azide was then treated with tert-butyl 2-cyanoacetate under refluxing conditions for overnight. After overnight stirring, the reaction mixture was quenched with H₂O (100 mL) and extracted with EtOAc (2×100 mL). The organic layers were then dried (MgSO₄) and evaporated to a brown solid. The brown solid was then re-dissolved in DCM (2 mL) and to this solution was added TFA (2 mL) and stirred at rt for overnight. The reaction mixture was then concentrated and quenched with H₂O to precipitate out a brown solid. The solids were filtered, washed with excess MeOH and dried to afford brownish white solid. MS(ESI) m/z: 238.9 (M+H)⁺. ¹H NMR (400 MHz, MeOD) δ 7.75 (bs, 1H), 7.37-7.34 (dd, J=1.7 & 8.3 Hz, 1H), 7.25-7.21 (t, 1H), 6.91-6.89 (bd, 1H) ppm.

Intermediate 9

1-(3-Chlorophenyl)-3-(2-hydroxyethyl)-1H-pyrazole-4-carboxylic acid

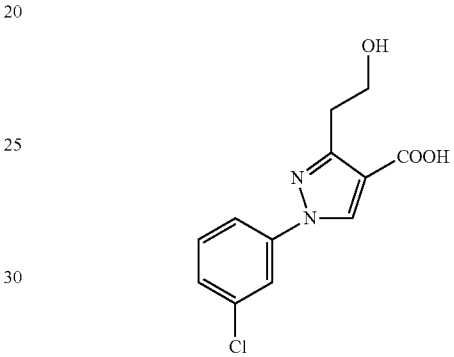

Intermediate 9A: 3-((tert-Butyldiphenylsilyl)oxy)propanal: To a solution of tert-butyldiphehenylsilylchloride (2.20 g, 8.0 mmol) in DCM/DMF (95:1) was added 1,3 propanediol (2.010 g, 26.4 mmol) followed by TEA (1.053 g, 10.43 mmol) and catalytic DMAP (0.049 g, 0.4 mmol) and the reaction mixture was stirred at rt overnight. The reaction mixture was then quenched with H₂O (200 mL) and extracted the organics with EtOAc (3×). The crude product in a solution of DCM (5 mL) was added slowly to a cooled solution (−78° C.) of oxalyl chloride (5.75 mL, 11.59 mmol) in DCM (20 mL). The reaction mixture was continued to stir at −78° C. for 20 min and then treated with TEA (5.34 mL, 38.3 mmol) and then raised to rt slowly. The reaction mixture was then diluted with ether, washed with 10% aqueous citric acid followed by brine. The organic layers were then dried and concentrated to give the desired product. ¹H NMR (400 MHz, CDCl₃) δ 7.90-7.56 (m, 4H), 7.49-7.28 (m, 6H), 3.96-3.61 (m, 2H), 2.27 (br. s., 1H), 1.88-1.72 (m, 2H), 1.16-0.96 (m, 9H) ppm.

Intermediate 9B: (E)-1-(3-((tert-Butyldiphenylsilyl)oxy)propylidene)-2-(3-chlorophenyl)hydrazine: A solution of (3-chlorophenyl)hydrazine hydrochloride and TEA (3 mL, 21.5 mmol) and 3-(tert-butyldiphenylsilyloxy)propanal (21.5 mmol) in toluene was stirred at rt overnight. The reaction mixture was then quenched with H₂O (100 mL) and extracted with EtOAc (2×). The organic layers were dried (MgSO₄) and evaporated to a reddish oil. The crude product was then purified using silica gel chromatography. The desired product was isolated as a red oil. MS(ESI) m/z: 437.1 (M-Boc)⁺. ¹H NMR (400 MHz, CDCl₃) δ 7.84-7.59 (m, 4H), 7.50-7.29 (m, 6H), 7.18-6.90 (m, 1H), 6.77 (dt, J=8.1, 2.0 Hz, 1H), 3.98-3.68 (m, 2H), 2.63-2.38 (m, 2H), 1.12-0.90 (m, 9H) ppm.

Intermediate 9B. Ethyl 5-amino-3-(2-((tert-butyldiphenylsilyl)oxy)ethyl)-1-(3-chlorophenyl)-1H-pyrazole-4-carboxylate: To a solution of Intermediate 9A (1.34 g, 3.1 mmol) in DMF (5 mL) was added NCS (0.455, 3.41 mmol) and stirred at rt. After 4 h, the reaction mixture was quenched with $H_2O$ (100 mL) and extracted with EtOAc (2×). The organic layers were dried ($MgSO_4$) and evaporated to a reddish oil. Separately ethylcyanoacetate (0.351 g, 3.10 mmol) was dissolved in EtOH (5 mL) and to this solution was added NaOEt (21%) (1.16 mL, 3.10 mmol) and the reaction was stirred at rt for 0.5 h followed by the introduction of the iminochloride crude mixture. The above mixture was then stirred at rt. After 2 h, the reaction was quenched with $H_2O$ and extracted with EtOAc (2×). The organic layers were dried ($MgSO_4$) and evaporated to yield orange-red oil. The crude product was then purified using silica gel chromatography. Two peaks were isolated—one is the desired product and the other is the chlorinated pyrazoline compound and the two products were taken to the next step as a crude mixture. MS(ESI) m/z: 548.1 $(M+H)^+$.

Intermediate 9C. Ethyl 3-(2-((tert-butyldiphenylsilyl)oxy)ethyl)-1-(3-chlorophenyl)-1H-pyrazole-4-carboxylate: Isoamylnitride (1 mL) was added to a THF solution of Intermediate 9B (crude mixture) and stirred at 70° C. overnight. The reaction mixture was concentrated and taken to the next step as a crude mixture. MS(ESI) m/z: 555.3 $(M+Na)^+$.

Intermediate 9. 1-(3-Chlorophenyl)-3-(2-hydroxyethyl)-1H-pyrazole-4-carboxylic acid: To a stirring THF solution of Intermediate 9C (0.5 g, 0.938 mmol) was added 1 M $nBu_4NF$ (2.81 mL, 2.81 mmol) in THF and the reaction mixture was stirred vigorously at rt overnight. The reaction mixture was then quenched with $H_2O$ (100 mL) and extracted with EtOAc (2×). The combined organic layers were dried ($MgSO_4$) and concentrated to an oil. The crude product was then purified using reverse phase HPLC to yield the desired product (0.045 g, 16%) as oil. MS(ESI) m/z: 295.1 $(M+H)^+$. $^1$H NMR (400 MHz, $CDCl_3$) δ 8.35 (s, 1H), 7.83 (s, 1H), 7.59-7.42 (m, 2H), 7.31-7.18 (m, 1H), 5.42 (br. s., 1H), 4.80-4.65 (m, 1H), 4.42-4.26 (m, 2H), 4.14-3.93 (m, 2H), 3.51-3.38 (m, 1H), 3.26 (t, J=5.8 Hz, 3H) ppm.

Intermediate 10

1-(3-Chlorophenyl)-5-oxopyrrolidine-3-carboxylic acid

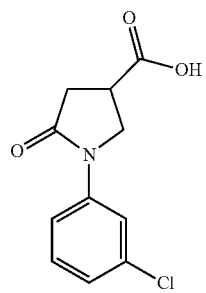 [SMILES: O=C(O)C1CC(=O)N(c2cccc(Cl)c2)C1]

Intermediate 10. 1-(3-Chlorophenyl)-5-oxopyrrolidine-3-carboxylic acid: (Reference: *J. Med. Chem.*, 30:400-405 (1987)) A mixture of 3-chloroaniline (2.55 g, 20 mmol) and 2-methylenesuccinic acid (2.60 g, 20.00 mmol) was heated at 120° C. (open flash). After 20 min, the reaction was cooled to rt. Next, water was added and the reaction mixture was warmed to 110° C. (sealed tube) to give a yellow suspension. After cooling to rt, the yellow oil slowly solidifies to which was added MeOH (20 mL) to give a yellow solution. After 1 h, the mixture was filtered and the solid rinsed with a small amount of MeOH and air-dried to yield an off-white solid as Intermediate 10 (2.5 g, 52%). MS(ESI) m/z: 240.0 $(M+H)^+$. $^1$H NMR (500 MHz, MeOD) δ 7.80 (t, J=2.1 Hz, 1H), 7.49-7.46 (m, 1H), 7.36 (t, J=8.1 Hz, 1H), 7.18 (ddd, J=8.0, 2.1, 1.0 Hz, 1H), 4.16-4.07 (m, 2H), 3.46-3.38 (m, 1H), 2.88 (dd, J=8.3, 1.1 Hz, 2H).

Intermediate 11

1-(3-Chlorophenyl)pyrrolidine-3-carboxylic acid

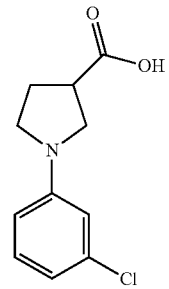 [SMILES: O=C(O)C1CCN(c2cccc(Cl)c2)C1]

Intermediate 11A. Methyl 1-(3-chlorophenyl)-5-oxopyrrolidine-3-carboxylate (Ref: *Tetrahedron*, 62:4011-4017 (2006)). To a cold solution of MeOH (8.35 mL) (0° C.) was added thionyl chloride (0.335 mL, 4.59 mmol) dropwise. After 30 min, Intermediate 10 (1 g, 4.17 mmol) was added, and the reaction mixture was warmed to rt. The reaction mixture was then concentrated and the residue dissolved in EtOAc, washed with saturated $NaHCO_3$, $H_2O$ and brine. The organic layers were dried over $Na_2SO_4$, filtered and concentrated to yield the desired product (1.04 g, 98%) as yellow oil. MS(ESI) m/z: 254.0 $(M+H)^+$.

Intermediate 11B. Methyl 1-(3-chlorophenyl)pyrrolidine-3-carboxylate: To a solution of Intermediate 11A (0.27 g, 1.064 mmol) in THF (3 mL) was added $BH_3$-THF complex (1.596 mL, 1.596 mmol) (1 M in THF). The reaction mixture was stirred at rt. After 17 h, the reaction mixture was quenched by adding 1 mL MeOH, then $H_2O$. The above mixture was then extracted with EtOAc and the organic layers were washed with $H_2O$, brine, dried over $Na_2SO_4$, filtered and concentrated. The crude product was then purified using silica gel chromatography to afford a colorless oil as the desired product (0.175 g, 68.6%). MS(ESI) m/z: 240.1 $(M+H)^+$.

Intermediate 11. 1-(3-Chlorophenyl)pyrrolidine-3-carboxylic acid: To a solution of methyl 1-(3-chlorophenyl)pyrrolidine-3-carboxylate (0.175 g, 0.730 mmol) in MeOH (5 mL) was added 1N NaOH (1.460 mL, 1.460 mmol). The reaction mixture was stirred at rt for 2 h. After 2 h, the reaction mixture was then concentrated to remove MeOH. The residue was then neutralized with 1 N HCl (2 mL) and extracted with EtOAc. The organic layer was washed with brine, dried over $Na_2SO_4$, filtered, and concentrated. A white solid was obtained as the desired product (0.15 g, 91%). MS(ESI) m/z: 226.1 $(M+H)^+$. $^1$H NMR (500 MHz, $CDCl_3$) δ 10.34 (br. s., 1H), 7.16 (t, J=8.1 Hz, 1H), 6.72-6.68 (m, 1H), 6.57 (t, J=2.2 Hz, 1H), 6.49-6.43 (m, 1H), 3.64-3.52 (m, 2H), 3.48-3.25 (m, 3H), 2.43-2.29 (m, 2H) ppm.

Intermediate 12

1-(3-Chlorophenyl)-1H-imidazole-4-carboxylic acid, HCl

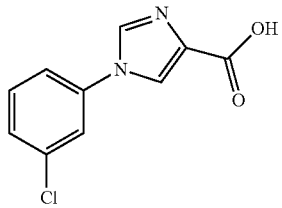 [SMILES: O=C(O)c1cn(-c2cccc(Cl)c2)cn1]

Intermediate 12A. Ethyl 1-(3-chlorophenyl)-1H-imidazole-4-carboxylate, 1

TFA: A mixture of 1-chloro-3-iodobenzene (0.170 g, 0.714 mmol), ethyl 1H-imidazole-4-carboxylate (0.1 g, 0.714 mmol), copper(I) iodide (0.027 g, 0.143 mmol), and $K_2CO_3$ (0.296 g, 2.141 mmol) in DMSO (1.427 mL) was vacuumed and back-filled with argon for three times, then capped and heated at 110° C. After 16 h, the reaction was cooled to rt and was then diluted with EtOAc, washed with $H_2O$ followed by brine. The organic layer was then dried over $Na_2SO_4$, filtered, and concentrated. The crude product was purified using silica gel chromatography to afford a white solid as the desired product (0.118 g, 66%). MS(ESI) m/z: 251.0 (M+H)$^+$.

Intermediate 12. 1-(3-Chlorophenyl)-1H-imidazole-4-carboxylic acid: To a solution of Intermediate 12A (0.118 g, 0.471 mmol) in MeOH (4.71 mL) was added 1 N NaOH (0.941 mL, 0.941 mmol) and the reaction mixture was stirred at rt. After 2 h, the reaction mixture was concentrated and the residue was dissolved in MeOH/$H_2O$. To the above solution was then added 1 N HCl (1.5 mL) to afford a white suspension which was filtered to isolate the solid. The solid was rinsed with $H_2O$ and then dried in a vacuum oven (50° C.) for 4 h to yield a white solid as Intermediate 12 (0.09 g, 74%). MS(ESI) m/z: 223.0 (M+H)$^+$. $^1$H NMR (400 MHz, MeOD) δ 8.44-8.23 (m, 2H), 7.77 (t, J=1.9 Hz, 1H), 7.63-7.45 (m, 3H) ppm.

Intermediate 13

1-(3-Chloro-2-fluorophenyl)-1H-imidazole-4-carboxylic acid, 1 TFA

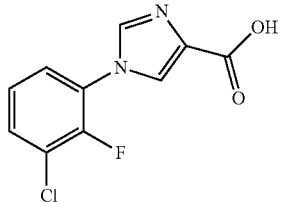 [SMILES: O=C(O)c1cn(-c2cccc(Cl)c2F)cn1]

Intermediate 13A. Ethyl 1-(3-chloro-2-fluorophenyl)-1H-imidazole-4-carboxylate, 1 TFA: A mixture of 1-chloro-2-fluoro-3-iodobenzene (0.549 g, 2.141 mmol), ethyl 1H-imidazole-4-carboxylate (0.3 g, 2.141 mmol), copper(I) iodide (0.082 g, 0.428 mmol), L-proline (0.099 g, 0.856 mmol), and $K_2CO_3$ (0.888 g, 6.42 mmol) in DMSO (4.28 mL) was vacuumed and back-filled with argon for three times, then capped and heated at 110° C. After 20 h, the reaction mixture was cooled to rt and diluted with EtOAc. The organic layer was washed with $H_2O$, brine, dried over $Na_2SO_4$, filtered, and concentrated. The crude product was then purified using reverse phase HPLC chromatography to yield the desired product (0.01 g, 1.2%) as a colorless oil. MS(ESI) m/z: 269.0 (M+H)$^+$.

Intermediate 13. 1-(3-Chloro-2-fluorophenyl)-1H-imidazole-4-carboxylic acid: Intermediate 13 was made in the same way as Intermediate 12 by replacing Intermediate 12A with Intermediate 13A. MS(ESI) m/z: 241.0 (M+H)$^+$.

Intermediate 14

1-(1-(tert-Butoxycarbonyl)piperidin-3-yl)-1H-pyrazole-4-carboxylic acid

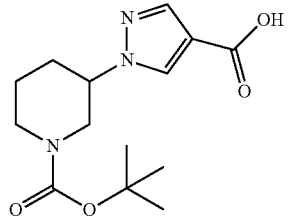 [SMILES: CC(C)(C)OC(=O)N1CCCC(n2cc(C(=O)O)cn2)C1]

Intermediate 14A. tert-Butyl 3-(4-(ethoxycarbonyl)-1H-pyrazol-1-yl)piperidine-1-carboxylate: To a clear, colorless solution of 1-Boc-3-hydroxypiperidine (0.250 g, 1.242 mmol), 4-ethoxycarbonyl-pyrazole (0.174 g, 1.242 mmol), and triphenylphosphine (0.391 g, 1.491 mmol) in THF (4.97 mL) was added in portions over 5 min di-tert-butylazodicarboxylate (0.372 g, 1.615 mmol). The resulting pale yellow solution was stirred at rt overnight. The reaction mixture was then concentrated and purified by silica gel chromatography to yield Intermediate 14A (0.0646 g, 16%) as a clear, colorless residue. MS(ESI) m/z: 268.1 (M-$C_4H_8$+H)$^+$.

Intermediate 14. 1-(1-(tert-Butoxycarbonyl)piperidin-3-yl)-1H-pyrazole-4-carboxylic acid: To a clear, colorless solution of Intermediate 14A (0.0646 g, 0.200 mmol) in MeOH (0.666 ml) was added dropwise 1.0 M sodium hydroxide (0.599 ml, 0.599 mmol). The resulting slightly cloudy reaction mixture was stirred at rt. After 6 h, the reaction was cooled to 0° C. and neutralized with 1.0 N HCl. The mixture was then concentrated to give a white solid. The solid was partitioned between EtOAc and 0.5 N HCl and the layers were separated. The aqueous layer was extracted with EtOAc (2×). The combined organic layers were washed with brine, dried over sodium sulfate, filtered and concentrated to give Intermediate 14 (0.0616 g, 104%) as a white foam. MS(ESI) m/z: 240.1 (M-$C_4H_8$+H)$^+$.

Intermediate 15

1-(3-Chlorophenyl)-5-methyl-1H-pyrazole-4-carboxylic acid

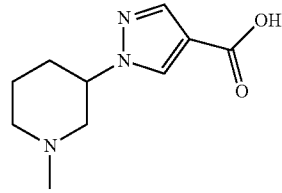

Intermediate 15 was prepared in the same way as Intermediate 14. MS(ESI) m/z: 210.1 (M+H)⁺.

Intermediate 16

Methyl 4-(2-bromoacetyl)-3-nitrophenylcarbamate

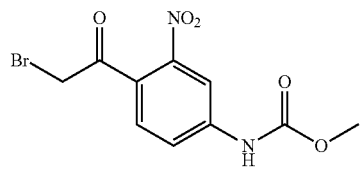 [SMILES: COC(=O)Nc1ccc(C(=O)CBr)c([N+](=O)[O-])c1]

Intermediate 16A. Methyl 4-iodo-3-nitrophenylcarbamate: To a cooled (0° C.), yellow suspension of 4-iodo-3-nitroaniline (8.46 g, 32.0 mmol) in DCM (320 mL) and pyridine (2.85 mL, 35.2 mmol) was added dropwise methyl chloroformate (2.61 mL, 33.6 mmol) and the reaction was stirred for 1.5 h. The reaction mixture was diluted with DCM and washed with saturated NaHCO₃ solution followed by brine. The organic layer was then dried over MgSO₄, filtered and concentrated. The residue was dissolved in minimal DCM (~100 mL), then hexane (600 mL) was added to give a yellow suspension. The above suspension was then filtered and the solid was rinsed with hexane and air-dried to yield the desired product as a yellow solid (10.3 g, 100%). MS(ESI) m/z: 321.3 (M−H).

Intermediate 16B. Methyl 4-acetyl-3-nitrophenylcarbamate: A solution of Intermediate 16A (1 g, 3.11 mmol), tributyl(1-ethoxyvinyl)stannane (2.098 mL, 6.21 mmol), and bis(triphenylphosphine) palladium(II)chloride (0.218 g, 0.311 mmol) in toluene (6.21 mL) was heated at 110° C. in a sealed tube. After 3 h, the reaction mixture was cooled to rt and concentrated to dryness. The residue was then dissolved in THF (5 mL), added 1 N HCl solution (15.53 mL, 15.53 mmol), and the reaction was stirred at rt for 1 h. The reaction mixture was diluted with EtOAc, washed with brine, dried over Na₂SO₄, filtered and concentrated. The crude product was then purified by silica gel chromatography to yield the desired product as a brown solid (0.544 g, 74%). MS(ESI) m/z: 239.3 (M+H)⁺.

Intermediate 16. Methyl 4-(2-bromoacetyl)-3-nitrophenylcarbamate: To a yellow solution of Intermediate 16B (0.544 g, 2.284 mmol) in EtOAc (18.27 mL) was added copper (II) bromide (1.020 g, 4.57 mmol). The flask was equipped with a reflux condenser and then the reaction was warmed to 70° C. After 3 h, the reaction was stopped and cooled to rt. The reaction mixture was then filtered through a sintered glass funnel eluting with EtOAc. The green filtrate was washed with H₂O (3×), brine, dried over Na₂SO₄, filtered and concentrated to yield the desired product as a brown foam (0.724 g, 100%). MS(ESI) m/z: 317.4 (M+H)⁺, 319.4 (M+2+H)⁺. The crude product was carried forward without any further purification.

An alternative procedure for Intermediate 16 is highlighted here.

Alternative Intermediate 16B. Methyl 4-(1-ethoxyvinyl)-3-nitrophenylcarbamate: A solution of Intermediate 16A (1 g, 3.11 mmol), tributyl(1-ethoxyvinyl)stannane (1.574 mL, 4.66 mmol) and bis(triphenylphosphine)palladium(II) chloride (0.109 g, 0.155 mmol) in toluene (6.21 mL) in a round bottom flask equipped with a condenser was heated at 110° C. After 2 h, the reaction was cooled to rt, filtered through a 0.45μ GMF filter and rinsed with EtOAc. The filtrate concentrated to dryness and purified by silica gel chromatography to obtain the desired product as a brown solid (0.56 g, 68%). MS(ESI) m/z: 267.3 (M+H)⁺.

Alternative Intermediate 16. (Reference: *J. Med. Chem.*, 45:2127-2130 (2002)) To a solution of alternative intermediate 16B (0.56 g, 2.103 mmol) in THF (3.12 mL) and H₂O (1.091 mL) was added NBS (0.374 g, 2.103 mmol). After stirring at rt for 20 min, the reaction mixture was partitioned between EtOAc and brine. The organic layer was then dried over Na₂SO₄, filtered, and concentrated to yield the desired product as a yellow oil (0.667 g, 100%). MS(ESI) m/z: 317.2 (M+H)⁺, 319.2 (M+2+H)⁺.

Intermediate 17

Benzyl 2-methylbut-3-enoate

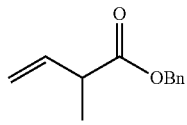

Intermediate 17. Benzyl 2-methylbut-3-enoate: To a solution of 2-methylbut-3-enoic acid (9.5 g, 95 mmol) in DCM (80 mL) was added phenylmethanol (10.26 g, 95 mmol), N,N'-methanediylidenedicyclohexanamine (19.58 g, 95 mmol) and DMAP (1.159 g, 9.49 mmol) (exothermic reaction) and the reaction was stirred at rt over weekend. The reaction mixture was filtered through a pad of CELITE® to remove the solids and the filtrate was concentrated. The residue was purified by silica gel chromatography to yield the desired product as a colorless oil.

Intermediate 18

[3-Bromo-4-(2-bromo-acetyl)-phenyl]-carbamic acid methyl ester

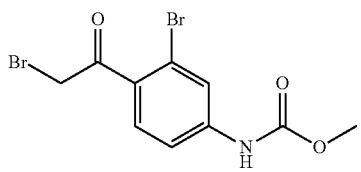 [SMILES: COC(=O)Nc1ccc(C(=O)CBr)c(Br)c1]

Intermediate 18A. 2-Bromo-4-nitro-benzoic acid: To a warm (80° C.) solution of pyridine (500 mL) and water (1 L) was added 4-nitro-2-bromo toluene (100 g, 0.46 mol). The resulting suspension was stirred until it became a clear solution. To the above reaction mixture was then added KMnO₄ (600 g, 3.8 mol) in portions over 1.5 h and stirring was continued overnight. The reaction mixture was then cooled to rt and then 10% aqueous NaOH (200 mL) was added. After 15 min, the reaction was filtered and the solid was rinsed with 10% aqueous NaOH (5×100 mL). The filtrate was extracted with MTBE (3×250 mL). The clear aqueous layer was cooled to 10° C. and then it was acidified with concentrated HCl. The aqueous layer was again extracted with MTBE (4×500 mL). The combined organic layers were dried over sodium sulfate, filtered, and concentrated to afford 72 g of Intermediate 18A. $^1$H NMR (400 MHz, DMSO-d$_6$) δ 7.96 (d, J=8 Hz, 1H), 8.28-8.48 (m, 1H), 8.49 (d, J=2.4 Hz, 1H), 14.1 (br. s, 1H) ppm.

Intermediate 18B. 2-(2-Bromo-4-nitro-benzoyl)-malonic acid diethyl ester: To a solution of Intermediate 18A (50 g, 0.2 mol) in toluene (500 mL) was added TEA (24.6 g, 0.24 mol). The reaction was cooled to 15° C. and ethyl chloroformate (24 g, 0.22 mol) was added. After 45 min, the mixed anhydride solution was cooled to 0° C. In a separate flask: To a suspension of Mg turnings (5.4 g) in dry ether (300 mL) was added EtOH (3.0 mL), CCl$_4$ (2.0 mL), and diethyl malonate (34 mL, 0.22 mol). The mixture was stirred at 40° C. for an hour to ensure that the magnesium dissolved completely. After the reaction became a clear solution, it was added to the cooled solution of the mixed anhydride. After 2 h, the reaction was quenched with 2 N sulfuric acid (200 mL) and then extracted with EtOAc (4×100 mL). The combined organic layers were dried over sodium sulfate, filtered, and concentrated to afford 80 g of Intermediate 18B. This was used in the next step without further purification.

Intermediate 18C. 1-(2-Bromo-4-nitro-phenyl)-ethanone: A mixture of Intermediate 18B (80 g, 0.2 mol) in acetic acid (400 mL) and sulfuric acid (400 mL) was stirred at 105° C. After 3 h, the reaction mixture was cooled to rt and then extracted with ethyl acetate (2×500 mL). The combined organic layers were washed with 20% aqueous NaOH solution, dried over sodium sulfate, filtered and concentrated to give 43.0 g of Intermediate 18C. $^1$H NMR (400 MHz, CDCl$_3$) δ 2.66 (s, 3H), 7.57 (d, J=8 Hz, 1H), 8.21-8.24 (dd, 1H), 8.48 (d, J=2.0 Hz, 1H) ppm.

Intermediate 18D. 1-(4-Amino-2-bromophenyl)ethanone: To a solution of Intermediate 18C (19 g, 0.077 mol) in EtOH (400 mL) was added in portions tin(II) chloride (74 g, 0.39 mol). Following the addition, the reaction was heated to refluxing temperature overnight. The reaction mixture was then concentrated and the residue was dissolved in 10% aqueous NaOH (200 mL). The aqueous solution was extracted with ethyl acetate (2×200 mL). The combined organic layers were washed with brine and concentrated to afford an oil. Petroleum ether (25 mL) was added to the oil to afford a suspension that was decanted and the solid was suspended in 20% ethyl acetate/petroleum ether. The organic layer was filtered and the solids were collected to afford 14 g of Intermediate 18D.

Intermediate 18E. (4-Acetyl-3-bromo-phenyl)-carbamic acid methyl ester: To a cooled (10° C.) mixture of Intermediate 18D (14 g, 0.065 mol) and Hunig's base (12.7 g, 0.098 mol) in dry dioxane (140 mL) was added methyl chloroformate (7.4 g, 0.078 m) dropwise. After 3 h, the reaction mixture was quenched with water (100 mL) and then extracted with ethyl acetate (2×150 mL). The combined organic layers were washed with brine, dried over sodium sulfate, filtered, and concentrated. Purification by trituration from isopropanol provided 14 g of Intermediate 18E. MS(ESI): 271.7 (M+H)$^+$. $^1$H NMR (400 MHz, DMSO-d$_6$) 2.50 (s, 3H), 3.71 (s, 3H), 7.53-7.56 (m, 1H), 7.78 (d, J=8.8 Hz, 1H), 7.86 (d, J=2.0 Hz, 1H), 10.14 (s, 1H) ppm.

Intermediate 18. [3-Bromo-4-(2-bromo-acetyl)-phenyl]-carbamic acid methyl ester: To a cooled (10° C.) solution of Intermediate 18E (90 g, 0.33 mol) in dry dioxane (900 mL) was added a solution of bromine (52.9 g, 0.33 mol) in dioxane (430 mL) dropwise over 1 h. After 2 h, ice cold water (500 mL) was added and the reaction was extracted with ethyl acetate (2×500 mL). The combined organic layers were washed with brine, dried over sodium sulfate, filtered, and concentrated to afford 110 g of crude product. A suspension of the crude product in EtOH (1 L) was warmed to 50° C. After a clear solution had formed, water (1.0 L) was added dropwise and the mixture was gradually cooled to 35° C. The precipitated solid was collected by filtration, washed with EtOH (200 mL), air-dried, and then dried at 50° C. under vacuum for 30 min to yield 70 g of Intermediate 18.

Intermediate 19

5-Amino-1-(2,3-dichlorophenyl)-1H-pyrazole-4-carboxylic acid

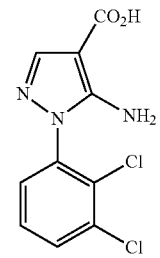

Intermediate 19A. Ethyl 5-amino-1-(2,3-dichlorophenyl)-1H-pyrazole-4-carboxylate: A mixture of (2,3-dichlorophenyl)hydrazine, HCl (1 g, 4.68 mmol), (E)-ethyl 2-cyano-3-ethoxyacrylate (0.792 g, 4.68 mmol), and K$_2$CO$_3$ (0.647 g, 4.68 mmol) in EtOH (10 mL) was added to a microwave vial and was heated at 85° C. for 20 h. The reaction mixture was then cooled to rt and then poured into ice-water. The suspension formed was then filtered and the solid was rinsed with water and dried in a vacuum oven (50° C.) for 4 h to afford a brown solid. The crude product was then purified by silica gel chromatography to yield a brown solid as ethyl 5-amino-1-(2,3-dichlorophenyl)-1H-pyrazole-4-carboxylate (0.93 g, 66% yield). MS(ESI) m/z: 300.0 (M+H)$^+$.

Intermediate 19. 5-Amino-1-(2,3-dichlorophenyl)-1H-pyrazole-4-carboxylic acid: A clear yellow solution of Intermediate 19A (0.026 g, 0.087 mmol) in MeOH (2 mL) and 1.0 N NaOH (0.260 mL, 0.260 mmol) was stirred at rt followed by heating to 70° C. for 24 h. To the mixture was added additional 1 N NaOH (0.260 ml, 0.260 mmol), and the reaction mixture was warmed to 90° C. for 7 h. The reaction mixture was cooled to rt, and 1 N HCl (0.75 mL) was added and the reaction mixture was concentrated to afford a yellow solid as 5-amino-1-(2,3-dichlorophenyl)-1H-pyrazole-4-carboxylic acid (0.065 g, 99%). MS(ESI) m/z: 271.9 (M+H)$^+$.

Intermediate 20

1-(2,3-Dichlorophenyl)-1H-pyrazole-4-carboxylic acid

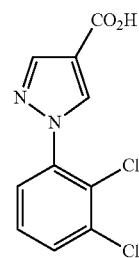 [SMILES: O=C(O)c1cnn(-c2cccc(Cl)c2Cl)c1]

Intermediate 20A. Ethyl 1-(2,3-dichlorophenyl)-1H-pyrazole-4-carboxylate: To a solution of Intermediate 19A (0.23 g, 0.766 mmol) in THF (8 mL) was added isoamyl nitrite (0.206 mL, 1.533 mmol) and the reaction was heated in a microwave vial at 80° C. After 16 h, the reaction mixture was cooled to rt and concentrated. The crude product was then purified by silica gel chromatography to afford a yellow gummy oil as ethyl 1-(2,3-dichlorophenyl)-1H-pyrazole-4-carboxylate (0.187 g, 86%). MS(ESI) m/z: 285.0 (M+H)+.

Intermediate 20. 1-(2,3-Dichlorophenyl)-1H-pyrazole-4-carboxylic acid: To a clear yellow solution of Intermediate 20A (0.187 g, 0.656 mmol) in MeOH (8 mL) was added 1.0 N NaOH (1.968 mL, 1.968 mmol) and the reaction mixture was stirred at rt. After 18 h, the reaction mixture was concentrated to remove MeOH. To the above crude product was then added water to afford a yellow solution. To this solution was then added 1 N HCl (2.5 mL) to afford a white suspension which was filtered and the solid was rinsed with water, and then dried in a vacuum oven (50° C.) for 4 h. A yellow solid was obtained as 1-(2,3-dichlorophenyl)-1H-pyrazole-4-carboxylic acid (0.16 g, 95%). MS(ESI) m/z: 257.0 (M+H)+. $^1$H NMR (500 MHz, MeOD) δ 8.51 (s, 1H), 8.13 (s, 1H), 7.75 (dd, J=8.3, 1.7 Hz, 1H), 7.61-7.56 (m, 1H), 7.54-7.49 (m, 1H) ppm.

Intermediate 21

1-(3-Chloro-2-fluorophenyl)-5-methyl-1H-1,2,3-triazole-4-carboxylic acid

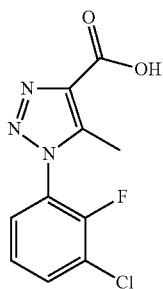

Intermediate 21. 1-(3-Chloro-2-fluorophenyl)-5-methyl-1H-1,2,3-triazole-4-carboxylic acid: To a solution of 3-chloro-2-fluoroaniline (1.7 g, 11.68 mmol) in TFA (10 mL) was added water (2 mL) and the reaction mixture was cooled to 0° C. To the above solution was then added sodium nitrite (0.806 g, 11.68 mmol) over 0.5 h. To the above mixture was then added slowly a solution of sodium azide (1.928 g, 29.7 mmol) in water. The reaction mixture was then stirred at 0° C. for 10 min, and then allowed to warm to rt. After 2 h, the reaction mixture was quenched by addition of water (100 mL) and the insoluble solids from the reaction mixture were filtered and dried under suction in the presence of nitrogen. To the azide was then added methyl acetoacetate (1.492 g, 12.85 mmol) in MeOH (12 mL) and methanol, sodium derivative (2.78 g, 12.85 mmol) and the mixture was heated at 65° C. in a sealed tube overnight. The reaction mixture was cooled to rt and then to 0° C. followed by addition of THF (50 mL). To the above mixture was then added NaOH (58.4 mL, 58.4 mmol), and the reaction was warmed to 50° C. After 2 h, the organics were concentrated and the remaining aqueous layer was acidified with 1.0 M HCl solution. The resulting suspension was filtered and the solids were washed with water followed by a small amount of cold MeOH and dried in an oven overnight (50° C.) to give 1-(3-chloro-2-fluorophenyl)-5-methyl-1H-1,2,3-triazole-4-carboxylic acid (1.86 g, 62%) as an off-white solid. MS(ESI) m/z: 256.0 (M+H)+. $^1$H NMR (400 MHz, DMSO-$d_6$) δ 7.99-7.89 (m, 1H), 7.80-7.71 (m, 1H), 7.53 (td, J=8.2, 1.3 Hz, 1H), 2.44 (s, 3H) ppm.

Intermediate 22

2-(3-Chloro-2,6-difluorophenyl)-1H-imidazole-4-carboxylic acid

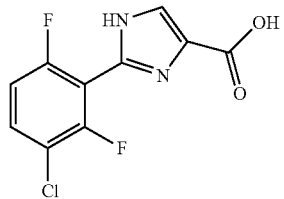 [SMILES: O=C(O)c1c[nH]c(-c2c(F)ccc(Cl)c2F)n1]

Intermediate 22A. 2-(3-Chloro-2,6-difluorophenyl)-4-(trifluoromethyl)-1H-imidazole: (Reference: WO 2008/050244) To a solution of potassium acetate (0.872 g, 8.88 mmol) in H$_2$O (3 mL) was added 3,3-dibromo-1,1,1-trifluoropropan-2-one (1.098 g, 4.07 mmol). The above reaction mixture was then heated at 100° C. for 0.5 h. The reaction mixture was then cooled to rt and to the mixture was then added a solution of 3-chloro-2,6-difluorobenzaldehyde (0.653 g, 3.7 mmol) in MeOH (4 mL) and THF (4 mL), followed by concentrated NH$_4$OH (8 mL). The mixture was stirred overnight at rt. The reaction mixture was extracted with EtOAc. The organic layer was washed with brine, dried over Na$_2$SO$_4$ and concentrated in vacuo to yield 2-(3-chloro-2,6-difluorophenyl)-4-(trifluoromethyl)-1H-imidazole (0.95 g, 91%). MS(ESI) m/z: 283.0 (M+H)+.

Intermediate 22. 2-(3-Chloro-2,6-difluorophenyl)-1H-imidazole-4-carboxylic acid: A solution of Intermediate 22A (0.95 g, 3.36 mmol) in 5 N aqueous NaOH (10 mL) solution was heated at 90° C. for 2 h. The reaction mixture was then cooled to rt, neutralized carefully to pH=6-7 and extracted with 1-butanol (3×30 mL) to provide 2-(3-chloro-2,6-difluorophenyl)-1H-imidazole-4-carboxylic acid (0.57 g, 66%). MS(ESI) m/z: 259.0 (M+H)+. $^1$H NMR (400 MHz, MeOD) δ 7.66-7.55 (m, H), 7.60 (s, 1H), 7.16 (td, J=9.2, 1.8 Hz, 1H) ppm.

Intermediate 23

5-Amino-1-(5-chloro-2-fluorophenyl)-1H-pyrazole-4-carboxylic acid

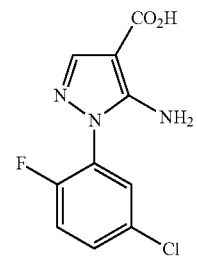

Intermediate 23A. Ethyl 5-amino-1-(5-chloro-2-fluorophenyl)-1H-pyrazole-4-carboxylate: A brown suspension of (5-chloro-2-fluorophenyl)hydrazine hydrochloride (0.500 g, 2.54 mmol), (E)-ethyl 2-cyano-3-ethoxyacrylate (0.472 g, 2.79 mmol) in EtOH (2.54 mL) and TEA (0.707 mL, 5.08 mmol) was warmed to 85° C. After 5 h, the reaction was stopped, cooled to rt, and concentrated to give a brown solid. Purification by normal phase chromatography provided Intermediate 23A (0.244 g, 34%) as a thick, viscous orange oil. MS(ESI) m/z: 284.0 (M+H)$^+$.

Intermediate 23. 5-Amino-1-(5-chloro-2-fluorophenyl)-1H-pyrazole-4-carboxylic acid: A cloudy, yellow suspension of Intermediate 23A (0.125 g, 0.441 mmol) in MeOH (2.203 mL) and 1.0 N NaOH (1.763 mL, 1.763 mmol) was warmed to 50° C. After 8 h, the reaction mixture was cooled to rt and the clear, yellow orange solution was concentrated to give a yellow solid. The yellow solid was dissolved in water and 1.0 N HCl was added to give a white suspension (pH 3-4). The mixture was then extracted with EtOAc (2×). The combined organic layers were washed with brine, dried over $Na_2SO_4$, filtered, and concentrated to give Intermediate 23 (0.096 g, 85%) as an off-white solid. MS(ESI) m/z: 256.0 (M+H)$^+$ and 258.0 (M+2+H)$^+$.

Intermediate 24

1-(3-Chloro-2-fluorophenyl)-5-methyl-1H-imidazole-4-carboxylic acid, HCl

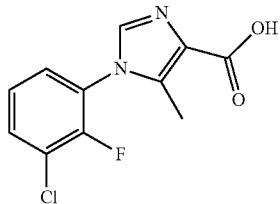 [SMILES: Cc1c(C(=O)O)ncn1-c1cccc(Cl)c1F]

Intermediate 24A. Ethyl 1-(3-chloro-2-fluorophenyl)-5-methyl-1H-imidazole-4-carboxylate: Using a modified procedure of Sreedhar. (Reference: Sreedhar, B., *Synthesis*, 795 (2008)). To a suspension of ethyl 4-methyl-1H-imidazole-5-carboxylate (0.530 g, 3.44 mmol) and (3-chloro-2-fluorophenyl)boronic acid (0.500 g, 2.87 mmol) in MeOH (5.74 mL) was added cuprous oxide (0.041 g, 0.287 mmol). The resulting purple suspension was stirred vigorously under an atmosphere of air (drying tube used). After 20 h, the reaction mixture was filtered to remove the solids and the clear blue filtrate was concentrated to give a blue solid. The blue solid was suspended in DCM and filtered to remove the solids and the blue filtrate was concentrated to give a pale blue solid weighing 0.187 g. Purification by normal phase chromatography gave ethyl 1-(3-chloro-2-fluorophenyl)-4-methyl-1H-imidazole-5-carboxylate (0.0187 g, 2%) as a clear, colorless residue and ethyl 1-(3-chloro-2-fluorophenyl)-5-methyl-1H-imidazole-4-carboxylate (Intermediate 24A) (0.0079 g, 1%) as a clear, colorless residue. MS(ESI) m/z: 283.1 (M+H)$^+$.

Intermediate 24A can also be synthesized in three steps according to the following sequence:

Intermediate 24A1. Ethyl 3-(3-chloro-2-fluorophenyl)amino)-2-nitrobut-2-enoate: Using a modified procedure described by Gomez-Sanchez. (Reference: Gomez-Sanchez, A. et al., *Anales De Quimica*, 81(2):139 (1985).) A clear, faint yellow solution of ethyl nitroacetate (4.17 ml, 37.6 mmol) and triethylorthoacetate (6.93 mL, 37.6 mmol) in toluene (9.39 mL) was heated to 110° C. A Dean-Stark trap was used to azeotrope the ethanol. Approximately every 30 min, the solvent was removed from the Dean-Stark and additional toluene (6 mL) was added to the reaction flask. Over the course of the reaction the color became a clear, dull yellow color. After 7.5 h, the reaction was stopped and it was cooled to rt. Excess solvent and starting materials were removed by distillation (5 mm Hg at 100° C.) leaving ethyl 3-ethoxy-2-nitrobut-2-enoate (5.46 g) as an orange liquid. An orange solution of 3-chloro-2-fluoroaniline (5.86 g, 40.2 mmol) and ethyl 3-ethoxy-2-nitrobut-2-enoate (5.45 g, 26.8 mmol) in ethanol (13.41 mL) was stirred at rt. After 7 h, the reaction was stopped and concentrated to give an orange oil. The orange oil was diluted with EtOAc and washed with 1.0 N HCl (2×), saturated $NaHCO_3$, brine, dried over sodium sulfate, filtered and concentrated to give an orange oil. Purification by normal phase chromatography gave Intermediate 24A1 (2.90 g, 36%) as a viscous orange-yellow oil. $^1$H NMR indicated a 1:1 E:Z mixture. MS(ESI) m/z: 325.0 (M+H)$^+$. $^1$H NMR (500 MHz, $CDCl_3$) δ 11.54 (br. s., 1H), 10.77 (br. s., 1H), 7.50-7.45 (m, 1H), 7.44-7.38 (m, 1H), 7.24-7.12 (m, 4H), 4.39 (q, J=7.2 Hz, 2H), 4.34 (q, J=7.2 Hz, 2H), 2.15 (d, J=1.4 Hz, 3H), 2.12 (d, J=1.4 Hz, 3H), 1.39 (t, J=7.2 Hz, 3H), 1.36 (t, J=7.0 Hz, 3H).

Intermediate 24A (Alternative). Ethyl 1-(3-chloro-2-fluorophenyl)-5-methyl-1H-imidazole-4-carboxylate: Using a modified procedure described by Gomez-Sanchez. (Reference: Gomez-Sanchez, A. et al., *J. Heterocyclic Chem.*, 24:1757 (1987).) A clear, yellow solution of Intermediate 24A1 (2.90 g, 9.58 mmol) in triethylorthoformate (96 mL) was degassed with argon for 20 min. Next, platinum on carbon (0.935 g, 0.479 mmol) was added. The flask was equipped with a reflux condenser and the reaction was purged with hydrogen (balloon) for several minutes. The reaction was stirred under a hydrogen atmosphere and the reaction was warmed to 75° C. After a total of 4 h, the reaction was cooled to rt. The reaction was placed under vacuum for several minutes and then backfilled with argon. The process was repeated a total of 5 times. Next, CELITE® was added and the reaction was filtered, washing with ethanol. The filtrate was concentrated to give a clear, yellow-brown oil weighing 3.17 g. Purification by normal phase chromatography provided Intermediate 24A (Alternative) (1.64 g, 61%) as a white solid. MS(ESI) m/z: 283.0 (M+H)$^+$. $^1$H NMR (500 MHz, methanol-$d_4$) δ 7.82 (d, J=0.8 Hz, 1H), 7.73 (ddd, J=8.3, 6.7, 1.8 Hz, 1H), 7.48 (ddd, J=8.0, 6.5, 1.7 Hz, 1H), 7.43-7.38 (m, 1H), 4.36 (q, J=7.2 Hz, 2H), 2.39 (d, J=1.1 Hz, 3H), 1.39 (t, J=7.2 Hz, 3H).

Intermediate 24. 1-(3-Chloro-2-fluorophenyl)-5-methyl-1H-imidazole-4-carboxylic acid, 1 HCl: To a clear, colorless solution Intermediate 24A (Alternative) (1.64 g, 5.80 mmol) in methanol (29.0 ml) was added 1.0 M NaOH (17.40 mL, 17.40 mmol). The reaction was stirred at rt. After 20 h, the reaction was concentrated under high vacuum with minimal heating to give a white solid. The solid was suspended in water and 1.0 N HCl was added until the mixture was at a pH=1-2. The solid was collected by filtration and rinsed with water, air-dried, and dried under high vacuum to give Intermediate 24 (1.44 g, 81%) as a white solid. $^1$H NMR (500 MHz, DMSO-$d_6$) δ 7.91 (d, J=0.5 Hz, 1H), 7.83 (ddd, J=8.3, 6.9, 1.7 Hz, 1H), 7.63 (td, J=7.5, 1.5 Hz, 1H), 7.46 (td, J=8.1, 1.4 Hz, 1H), 2.32 (s, 3H). MS(ESI) m/z: 255.0 (M+H)$^+$ and 257.0 (M+2+H)$^+$.

Intermediate 25

1-(3-Chloro-2-fluorophenyl)-5-methyl-1H-pyrazole-4-carboxylic acid

Intermediate 25A. Ethyl 1-(3-chloro-2-fluorophenyl)-5-methyl-1H-pyrazole-4-carboxylate: (Reference: Herold, P. et al., *Tetrahedron*, 56:6497-6499 (2000)) A solution of ethyl 2-((dimethylamino)methylene)-3-oxobutanoate (0.517 g, 2.79 mmol), (3-chloro-2-fluorophenyl)hydrazine hydrochloride (0.500 g, 2.54 mmol) in EtOH (2.54 mL) and TEA (0.707 mL, 5.08 mmol) was stirred at rt. After 10 min, the reaction mixture was concentrated and purified by silica gel chromatography. The desired product, ethyl 1-(3-chloro-2-fluorophenyl)-5-methyl-1H-pyrazole-4-carboxylate (200 mg, 28%), was obtained as an off white solid. MS(ESI) m/z: 283.1 (M+H)$^+$.

Intermediate 25. 1-(3-Chloro-2-fluorophenyl)-5-methyl-1H-pyrazole-4-carboxylic acid: To a solution of Intermediate 25A (50 mg, 0.177 mmol) in MeOH (0.884 mL) was added 1 N NaOH (aqueous) (1.061 mL, 1.061 mmol) and the reaction was stirred at 50° C. in a sealed vial for 3 h. The reaction mixture was then cooled to rt and concentrated. The residue was then partitioned between 1 N HCl (aqueous) and EtOAc. The layers were separated and the aqueous layer was extracted with EtOAc. The organic layers were combined, washed with brine, and concentrated to give Intermediate 25 as an off-white solid (48 mg, 107%). MS(ESI) m/z: 255.0 (M+H)$^+$.

Intermediate 26

1-(3-Chloro-2,6-difluorophenyl)-5-methyl-1H-1,2,3-triazole-4-carboxylic acid

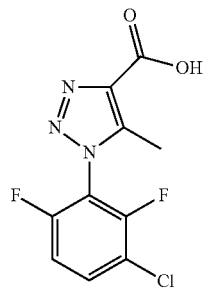 [SMILES: Cc1c(C(=O)O)nnn1-c1c(F)ccc(Cl)c1F]

Intermediate 26A. 2-Azido-4-chloro-1,3-difluorobenzene: To a solution of 3-chloro-2,6-difluoroaniline (1.7 g, 10.39 mmol) in TFA (10 mL) and water (2 mL) at 0° C. was added sodium nitrite (0.717 g, 10.39 mmol) over a period of 0.5 h. After completion of addition, sodium azide (1.716 g, 26.4 mmol) in water (5 mL) was added dropwise. The reaction mixture was stirred at 0° C. for 10 min and then allowed to warm to rt. The reaction was diluted with water (75 mL) and extracted with EtOAc. The organic layer was dried and concentrated to give the desired product (1.16 g, 56%) as a brown solid.

Intermediate 26B. Methyl 1-(3-chloro-2,6-difluorophenyl)-5-methyl-1H-1,2,3-triazole-4-carboxylate: The mixture of Intermediate 26A (1.16 g, 6.12 mmol), methyl 3-oxobutanoate (0.729 mL, 6.73 mmol), NaOMe (1.539 mL, 6.73 mmol), and MeOH (12 mL) in a microwave vial was stirred at 65° C. overnight. The reaction was concentrated and purified by silica gel chromatography to isolate the desired product (46 mg, 2%) as a yellow solid. MS(ESI) m/z: 287.8 (M+H)$^+$.

Intermediate 26. 1-(3-Chloro-2,6-difluorophenyl)-5-methyl-1H-1,2,3-triazole-4-carboxylic acid: To a solution of Intermediate 26B (46 mg, 0.160 mmol) was added LiOH (0.320 mL, 0.320 mmol). The reaction was stirred at rt overnight and acidified with 1 N HCl. The mixture was extracted with EtOAc. The organic layer was dried and concentrated to yield the desired product (40 mg, 82%). MS(ESI) m/z: 274.0 (M+H)$^+$.

Intermediate 27

5-Amino-1-(3-chloro-2-fluorophenyl)-1H-1,2,3-triazole-4-carboxylic acid

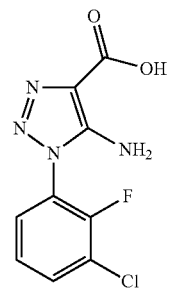

Intermediate 27A. Ethyl 5-amino-1-(3-chloro-2-fluorophenyl)-1H-1,2,3-triazole-4-carboxylate: (PCT International Application No. 2006/047516 (2006)) To a solution of NaOEt (4.99 g, 15.39 mmol) in EtOH (10 mL) at 0° C. was added ethyl 2-cyanoacetate (1.501 ml, 14.11 mmol). The reaction was stirred at 0° C. for 10 min and added 1-azido-3-chloro-2-fluorobenzene (2.2 g, 12.82 mmol). The reaction was allowed to slowly warm up to rt and stirred for 14 h. The mixture was treated with water (3 mL) and extracted with EtOAc (3×30 mL). The combined extracts were concentrated and purified by silica gel chromatography to yield the desired product (2.1 g, 58%). MS(ESI) m/z: 285.1 (M+H)$^+$.

Intermediate 27. 5-Amino-1-(3-chloro-2-fluorophenyl)-1H-1,2,3-triazole-4-carboxylic acid: To a solution of Intermediate 27A (100 mg, 0.351 mmol) in THF (15 mL) and MeOH (15.0 mL) was added NaOH (70 mg, 1.756 mmol). The reaction was stirred at 50° C. for 2 h and then concentrated. The mixture was acidified to pH~5 with 1 N HCl. The resulting solid was filtered and dried to yield the desired product (69 mg, 77%). MS(ESI) m/z: 257.0 (M+H)$^+$.

Intermediate 28

5-Chloro-1-(3-chloro-2-fluorophenyl)-1H-1,2,3-triazole-4-carboxylic acid

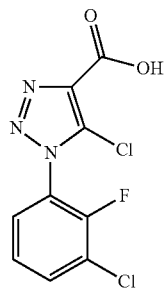

Intermediate 28A. Ethyl 5-chloro-1-(3-chloro-2-fluorophenyl)-1H-1,2,3-triazole-4-carboxylate: (*Can. J. Chem.*, 37:118-119 (1959)). To a solution of Intermediate 27A (1.1 g, 3.86 mmol) in EtOH (30 mL) at 0° C. was passed HCl gas until all of the solid dissolved. To the solution was added isoamyl nitrite (0.520 mL, 3.86 mmol) in one portion and the resulting solution was kept at 0-5° C. for 48 h. The reaction mixture was diluted in EtOAc and washed with aq NaHCO$_3$ and brine. The organic layer was concentrated and purified by reverse phase HPLC to yield the desired product. MS(ESI) m/z: 304.0 (M+H)$^+$.

Intermediate 28. 1-(3-Chloro-2,6-difluorophenyl)-5-methyl-1H-1,2,3-triazole-4-carboxylic acid: To a solution of Intermediate 28A (50 mg, 0.164 mmol) in THF (6 mL) and MeOH (3.00 mL) was added LiOH (39.4 mg, 1.644 mmol). The reaction was stirred at rt for 1 h and concentrated. The residue was purified by reverse phase HPLC to yield Intermediate 28 (23 mg, 51%). MS(ESI) m/z: 276.0 (M+H)$^+$.

Intermediate 29

1-(3-Chloro-2-fluorophenyl)-5-methoxy-1H-1,2,3-triazole-4-carboxylic acid

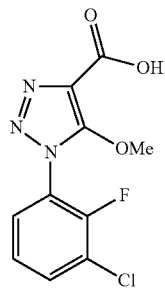

Intermediate 29. 1-(3-Chloro-2-fluorophenyl)-5-methoxy-1H-1,2,3-triazole-4-carboxylic acid: To a solution of Intermediate 28A (50 mg, 0.164 mmol) in THF (6 mL) and MeOH (3.00 mL) was added LiOH (39.4 mg, 1.644 mmol). The reaction was stirred at rt for 1 h and concentrated. The residue was purified by reverse phase HPLC to yield Intermediate 29 (12 mg, 27%). MS(ESI) m/z: 272.0 (M+H)$^+$.

Intermediate 30

1-(2-Fluoro-3-methoxyphenyl)-5-methoxy-1H-1,2,3-triazole-4-carboxylic acid

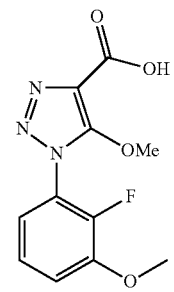

Intermediate 30. 1-(3-Chloro-2-fluorophenyl)-5-methoxy-1H-1,2,3-triazole-4-carboxylic acid: To a solution of 2-fluoro-3-methoxyaniline (1 g, 7.09 mmol) in TFA (10 mL) and water (5 mL) at 0° C. was added an aq. solution of NaNO$_2$ (0.733 g, 10.63 mmol) dropwise. The resulting mixture was stirred at 0° C. for 0.5 h and NaN$_3$ (0.921 g, 14.17 mmol) was added portionwise. The reaction mixture was gradually warmed to rt and stirred for 4 h. The reaction was quenched with water (150 mL) and extracted with EtOAc (2×100 mL). The organic layer was washed with sodium phosphate solution (10%) and brine (50 mL), dried, and concentrated. The resulting brown oil was re-dissolved in DMSO (20 mL) and added t-butylpropiolate (1 mL) followed by K$_2$CO$_3$ (1 g), Cu(OAc)$_2$ (0.2 g), and sodium ascorbate (100 mg). The resulting mixture was stirred at rt overnight. The reaction was quenched with water (200 mL) and extracted with EtOAc (2×100 mL). The organic layer was dried and concentrated. The residue was purified by silica gel chromatography to yield the desired product as brown oil. $^1$H NMR (400 MHz, CDCl$_3$) δ 13.19 (br. s., 1H), 7.36-7.20 (m, 2H), 7.17-6.95 (m, 1H), 6.76 (td, J=8.1, 1.3 Hz, 1H), 3.91 (s, 3H), 1.74-1.49 (m, 10H). MS(ESI) m/z: 238.0 (M+H)$^+$.

Intermediate 31

1-(Thiazol-2-yl)-1H-1,2,3-triazole-4-carboxylic acid

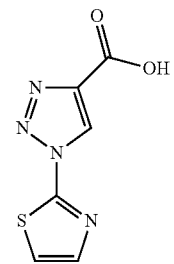 [SMILES: O=C(O)c1cn(-c2nccs2)nn1]

Intermediate 31. 1-(Thiazol-2-yl)-1H-1,2,3-triazole-4-carboxylic acid: To a suspension of methyl 1-(thiazol-2-yl)-1H-1,2,3-triazole-4-carboxylate (7.4 mg, 0.035 mmol) (prepared as in *J. Heterocyclic Chem.*, 42:1167 (2005)) in MeOH (352 µL) was added 1 N NaOH (141 µL, 0.141 mmol). The reaction became clear within 5 min. The reaction was concentrated. The resulting residue was partitioned between 1 N HCl and EtOAc. The layers were separated and the aqueous layer was extracted with EtOAc (2×). The organic layers were combined, washed with brine, dried over MgSO$_4$, filtered and concentrated to yield the desired product (5 mg, 72%) as a white solid. MS(ESI) m/z: 169.9 (M+H)$^+$.

Intermediate 32

3-Acetyl-1-(3-chloro-2-fluorophenyl)-5-methyl-1H-pyrazole-4-carboxylic acid

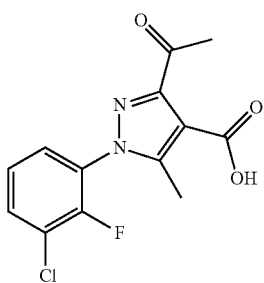 [SMILES: CC(=O)c1nn(-c2cccc(Cl)c2F)c(C)c1C(=O)O]

Intermediate 32A. (E)-N'-(3-Chloro-2-fluorophenyl)-2-oxopropanehydrazonoyl chloride: To a solution of 3-chloro-2-fluoroaniline (1.511 mL, 13.74 mmol) in HCl (116 mL, 116 mmol) at 0° C. was added a solution of sodium nitrite (1.896 g, 27.5 mmol) in water (12 mL) dropwise while maintaining the temperature at 0° C. After completion of addition, the reaction was stirred at the same temperature for additional 30 mins. The pH of the reaction mixture was adjusted to 4.5 using solid sodium acetate. The resultant mixture was then treated dropwise with 3-chloropentane-2,4-dione (2.129 mL, 17.86 mmol) in methanol (12 mL). After completion of addition, the reaction mixture was allowed to warm to room temperature and stirred at room temperature overnight. The reaction mixture was diluted with water and then extracted with ether. The crude product was then purified by silica gel chromatography to isolate the desired product. MS(ESI) m/z: 249.0 (M+2H)$^+$.

Intermediate 32B. Ethyl 3-acetyl-1-(3-chloro-2-fluorophenyl)-5-methyl-1H-pyrazole-4-carboxylate: To a solution (E)-ethyl 3-(pyrrolidin-1-yl)but-2-enoate (36.8 mg, 0.201 mmol) in DCM (2 mL) was added DIEA (0.168 mL, 1.204 mmol) followed by 32A (50 mg, 0.201 mmol) and the reaction was stirred at refluxing temperatures overnight. The reaction mixture was diluted with water and extracted with ethyl acetate. The organic layer was dried over MgSO$_4$ and concentrated to give the crude product. The crude product was then purified using an ISCO normal phase system. MS(ESI) m/z: 325.0 (M+H)$^+$.

Intermediate 32. 3-Acetyl-1-(3-chloro-2-fluorophenyl)-5-methyl-1H-pyrazole-4-carboxylic acid: To a solution of 32B (67 mg, 0.206 mmol) in THF (2 mL) was added LiOH (0.227 mL, 0.227 mmol) and the reaction was stirred at room temperature overnight. The reaction mixture was acidified with 1 N HCl and extracted with EtOAc. The crude product was taken to the next step without further purification. MS(ESI) m/z: 297.0 (M+H)$^+$.

Intermediate 33

1-(3-Chloro-2-fluorophenyl)-3-hydroxy-1H-pyrazole-4-carboxylic acid

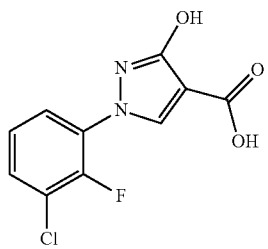 [SMILES: O=C(O)c1cn(-c2cccc(Cl)c2F)nc1O]

Intermediate 33A. N'-(3-Chloro-2-fluorophenyl)acetohydrazide: To a solution of (3-chloro-2-fluorophenyl)hydrazine, HCl (450 mg, 2.284 mmol) in ether (10 mL) and THF (1 mL) at 0° C. was added sodium hydroxide (0.228 mL, 2.284 mmol) and stirred at room temperature for 1 h. The reaction mixture was concentrated, diluted with EtOAc and washed with brine. The crude product was then dried under vacuum and taken to the next step. To a solution of the above obtained oil in ether (10 mL) at 0° C. was added dropwise a solution of acetic anhydride (0.215 mL, 2.284 mmol) in ether (5 mL) and stirred at 0° C. for 30 min. The reaction mixture was concentrated, diluted with ethyl acetate and washed with brine. The organic layer was dried over MgSO$_4$ and concentrated to yield the crude product. The crude product was then taken to the next step without further purification. MS(ESI) m/z: 203.1 (M+H)$^+$.

Intermediate 33B. Ethyl 1-(3-chloro-2-fluorophenyl)-3-hydroxy-1H-pyrazole-4-carboxylate: To Intermediate 33A (261 mg, 1.288 mmol) was added phosphoryl trichloride (973 μL, 10.43 mmol) followed by diethyl 2-(ethoxymethylene)malonate (351 μL, 1.739 mmol) and the resulting solution was heated at 70° C. for overnight. To the reaction mixture was added water slowly (Caution: lot of heat generated) and allowed to stir until the reaction mixture cooled back to room temperature. The crude product was then diluted with ethyl acetate and washed with brine. The organic layer was dried over MgSO$_4$ and concentrated to yield the crude product which was then purified using silica gel chromatography. MS(ESI) m/z: 285.0 (M+H)$^+$.

Intermediate 33. 1-(3-Chloro-2-fluorophenyl)-3-hydroxy-1H-pyrazole-4-carboxylic acid: To a solution of Intermediate 33B (52 mg, 0.183 mmol) in THF (2 mL) was added LiOH (0.183 mL, 0.183 mmol) and stirred at room temperature overnight. The reaction mixture was acidified using 1 N HCl and then extracted with EtOAc. The organic layer was dried over MgSO$_4$ and concentrated to yield the crude product. The crude product was taken further without any further purification. MS(ESI) m/z: 257.0 (M+H)$^+$.

Intermediate 34

1-(5-Chloro-2-cyanophenyl)-5-methyl-1H-1,2,3-triazole-4-carboxylic acid

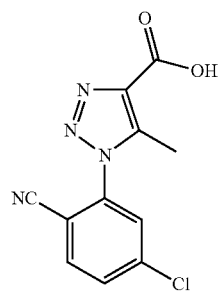 [SMILES: Cc1c(C(=O)O)nnn1-c1cc(Cl)ccc1C#N]

Intermediate 34A. 2-Azido-4-chlorobenzonitrile: To a solution of 2-amino-4-chlorobenzonitrile (2.0 g, 13.11 mmol) in TFA (12 mL) was added water (2.4 mL). After cooling to 0° C., sodium nitrite (0.904 g, 13.11 mmol) was added over a period of 0.5 h. After this addition, sodium azide (2.164 g, 33.3 mmol) in water (5 mL) was gradually added dropwise. The reaction was stirred at 0° C. for 10 min, and then allowed to warm to room temperature. After 2 h, quenched the reaction with water (100 mL) and insoluble solid was filtered and dried under suction and nitrogen. Aliquot LCMS analysis indicated starting material disappeared and a new peak formed which was not ionizing.

Intermediate 34. 1-(5-Chloro-2-cyanophenyl)-5-methyl-1H-1,2,3-triazole-4-carboxylic acid: To a mixture of Intermediate 34A (400 mg, 2.035 mmol) and methyl acetoacetate (0.241 mL, 2.238 mmol) in MeOH (12 mL) was added NaOMe (121 mg, 2.238 mmol). The mixture was heated at 65° C. in a sealed tube overnight. The reaction mixture was quenched with brine and extracted to give the ester product. The aqueous layer was acidified and then extracted with ethyl acetate to yield the desired hydrolyzed product which was used in the next step without further purification. MS(ESI) m/z: 262.9 (M+H)+.

Intermediate 35

1-(3-Chloro-2,6-difluorophenyl)-1H-imidazole-4-carboxylic acid

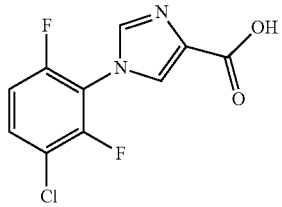 [SMILES: O=C(O)c1cn(-c2c(F)ccc(Cl)c2F)cn1]

Intermediate 35A. Ethyl 3-((3-chloro-2,6-difluorophenyl)amino)-2-nitroacrylate: A sealed, high pressure vial containing a clear, colorless solution of ethyl nitroacetate (0.170 ml, 1.529 mmol), triethylorthoformate (0.255 ml, 1.529 mmol), 3-chloro-2,6-difluoroaniline (0.250 g, 1.529 mmol), acetic acid (0.026 ml, 0.459 mmol), and EtOH (1.529 ml) was heated to 70° C. After 92 h, the clear, dark yellow solution was concentrated to give an orange oil. Purification by normal phase chromatography gave Intermediate 35A (0.0721 g, 15%) as a yellow solid. MS(ESI) m/z: 307.0 (M+H)+.

Intermediate 35B. Ethyl 1-(3-chloro-2,6-difluorophenyl)-1H-imidazole-4-carboxylate: Intermediate 35B (0.029 g, 43%) was prepared according to the procedure described for Intermediate 24A (Alternative), by replacing Intermediate 24A1 with Intermediate 35A. MS(ESI) m/z: 287.1 (M+H)+.

Intermediate 35. 1-(3-Chloro-2,6-difluorophenyl)-1H-imidazole-4-carboxylic acid: Intermediate 35 (0.0246 g, 94%) was prepared according to the procedure described for Intermediate 24, by replacing Intermediate 24A (Alternative) with Intermediate 35B. MS(ESI) m/z: 259.0 (M+H)+.

Intermediate 36

3-(3-Chloro-2-fluorophenyl)-4,5-dihydroisoxazole-5-carboxylic acid

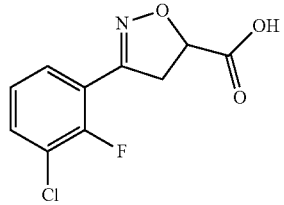 [SMILES: O=C(O)C1CC(c2cccc(Cl)c2F)=NO1]

$^1$H NMR (500 MHz, MeOD) δ 7.72 (ddd, J=8.0, 6.5, 1.7 Hz, 1H), 7.60-7.56 (m, 1H), 7.24 (td, J=8.0, 1.1 Hz, 1H), 5.22 (dd, J=11.8, 6.9 Hz, 1H), 3.84-3.76 (m, 1H), 3.71-3.64 (m, 1H).

Intermediate 37

1-(3-Chloro-2-fluorophenyl)-2-methyl-1H-imidazole-4-carboxylic acid, HCl

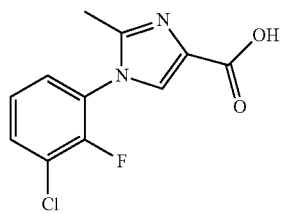 [SMILES: Cc1nc(C(=O)O)cn1-c1cccc(Cl)c1F]

Intermediate 37A. Ethyl 3-((3-chloro-2-fluorophenyl)amino)-2-nitroacrylate: Intermediate 37A (0.563 g, 52%) was prepared according to the procedure described for Intermediate 35A, by replacing 3-chloro-2,6-difluoroaniline with 3-chloro-2-fluoroaniline. MS(ESI) m/z: 289.0 (M+H)+.

Intermediate 37B. Ethyl 1-(3-chloro-2-fluorophenyl)-2-methyl-1H-imidazole-4-carboxylate, TFA: Intermediate 37B was prepared according to the procedure described for Intermediate 24A (Alternative), by replacing Intermediate 24A1 with Intermediate 37A, by replacing triethylorthoformate with triethylorthoacetate, and by running the reaction for 45 min. Purification by reverse phase chromatography gave Intermediate 37B (0.027 g, 17%). MS(ESI) m/z: 283.1 (M+H)+.

Intermediate 37. 1-(3-Chloro-2-fluorophenyl)-2-methyl-1H-imidazole-4-carboxylic acid, HCl: Intermediate 37 (0.0175 g, 88%) was prepared according to the procedure described for Intermediate 24, by replacing Intermediate 24A (Alternative) with Intermediate 37B. MS(ESI) m/z: 254.9 (M+H)+.

Intermediate 38

1-(5-Chloro-2-methoxyphenyl)-5-methyl-1H-pyrazole-4-carboxylic acid

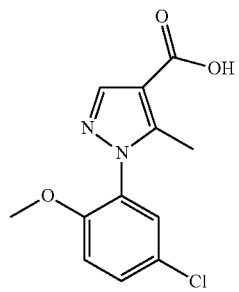 [SMILES: COc1ccc(Cl)cc1-n1ncc(C(=O)O)c1C]

Intermediate 38A. Ethyl 1-(5-chloro-2-methoxyphenyl)-5-methyl-1H-pyrazole-4-carboxylate: Intermediate 38A (0.472 g, 67%) was prepared according to the procedure described for Intermediate 25, by replacing (3-chloro-2-fluorophenyl)hydrazine hydrochloride with (5-chloro-2-methoxyphenyl)hydrazine hydrochloride. MS(ESI) m/z: 295.1 (M+H)+.

Intermediate 38. 1-(5-Chloro-2-methoxyphenyl)-5-methyl-1H-pyrazole-4-carboxylic acid: Intermediate 38 (0.075 g, 73%) was prepared according to the procedure described for Intermediate 24, by replacing Intermediate 24A (Alternative) with Intermediate 38A. MS(ESI) m/z: 267.0 (M+H)+ and 269.0 (M+2+H)+.

Intermediate 39

1-(5-Chloro-2-hydroxyphenyl)-5-methyl-1H-pyrazole-4-carboxylic acid

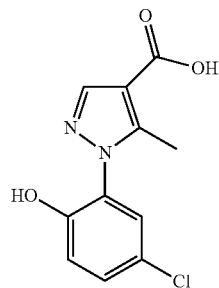

Intermediate 39. 1-(5-Chloro-2-hydroxyphenyl)-5-methyl-1H-pyrazole-4-carboxylic acid: To a cooled (0° C.), clear yellow solution of Intermediate 38A (0.100 g, 0.339 mmol) in DCM (3.39 mL) was added dropwise boron tribromide (0.321 ml, 3.39 mmol). The resulting clear light green solution was stirred at 0° C. for 30 min and then the reaction was allowed to warm to rt. After 45 min, the reaction was added dropwise to a vigorously stirred mixture of cold EtOAc and NaHCO3. After the addition, the mixture was stirred vigorously for 10 min. Then, the layers were separated and the aqueous layer was extracted with EtOAc. The organic layers were combined, washed with brine, dried over sodium sulfate, filtered and concentrated to give the phenol (0.105 g) as an orange residue. MS(ESI) m/z: 281.0 (M+H)+ and 283.0 (M+2H)+. To a clear, yellow orange solution of the phenol in methanol (2 mL) was added 1.0 M NaOH (2.036 mL, 2.036 mmol). The resulting clear, burgundy solution was stirred overnight at RT. The reaction was warmed to 50° C. for 2.5 h. The reaction was cooled to rt and concentrated. The residue was partitioned between water and EtOAc and the layers were separated. The aqueous layer was extracted with EtOAc. The aqueous layer was acidified with 1.0 M HCl and then this was extracted with EtOAc (2×). The organic layers, following acidification, were combined and washed with brine, dried over sodium sulfate, filtered and concentrated to give Intermediate 39 (0.0657 g, 77%) as an orange-brown solid. MS(ESI) m/z: 253.0 (M+H)+ and 254.9 (M+2H)+.

Intermediate 40

3-Amino-1-(3-chloro-2-fluorophenyl)-1H-pyrazole-4-carboxylic acid

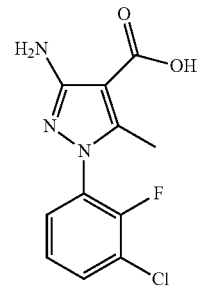 [SMILES: Cc1c(C(=O)O)c(N)nn1-c1cccc(Cl)c1F]

Intermediate 40A. (E)-1-Benzylidene-2-(3-chloro-2-fluorophenyl)hydrazine: Using a modified procedure described by Deprez-Poulain. (Deprez-Poulain, R. et al., *European Journal of Medicinal Chemistry*, 46:3867 (2011).) To a clear, orange brown solution of (3-chloro-2-fluorophenyl)hydrazine, HCl (3 g, 15.23 mmol) in methanol (60.9 ml) was added benzaldehyde (1.543 mL, 15.23 mmol) followed by the slow addition of 1.0 M NaOH (15.23 mL, 15.23 mmol). The resulting dark brown solution was stirred at rt. Over time, a precipitate formed. After 2.5 h, the reaction was stopped and the solid was collected by filtration. The solid was washed with water, air-dried, and dried under vacuum overnight to give Intermediate 40A (1.01 g, 27%) as an off-white solid. MS(ESI) m/z: 249.0 (M+H)+.

Intermediate 40B. Ethyl 3-amino-1-(3-chloro-2-fluorophenyl)-1H-pyrazole-4-carboxylate: A dark brown mixture of Intermediate 40A (1.10 g, 4.42 mmol) and 2-cyano-3-ethoxy-2-propenoic acid ethyl ester (0.786 g, 4.64 mmol) in xylene (5.90 ml) was warmed to 160° C. After 72 h, the reaction was stopped and cooled to rt. The reaction was concentrated to give a brown residue. Next, 30 mL of a solution of 37% HCl/EtOH (1:2) was added to give a suspension. The suspension was warmed to 100° C. At elevated temperature a brown solution formed. After 20 min., the reaction was cooled to rt and the solvent was removed to give a brown residue. The residue was partitioned between sat. NaHCO₃ and EtOAc and the layers were separated. The aqueous layer was extracted with EtOAc (2×). The combined organic layers were washed with brine, dried over sodium sulfate, filtered and concentrated to give a brown liquid weighing 1.3 g. Purification by normal phase chromatography gave an off-white solid weighing 0.269 g. Purification by reverse phase chromatography gave Intermediate 40B (0.080 g, 6%) as a fluffy, white solid. MS(ESI) m/z: 284.0 (M+H)⁺ and 286.0 (M+2+H)⁺.

Intermediate 40. 3-Amino-1-(3-chloro-2-fluorophenyl)-1H-pyrazole-4-carboxylic acid: To a white suspension of Intermediate 40B (0.075 g, 0.264 mmol) in methanol (2.64 mL) was added 1.0 M NaOH (1.058 mL, 1.058 mmol). The suspension was warmed to 50° C. After 3 h, the resulting clear, colorless solution was cooled to rt. Then, the reaction was concentrated to give a white solid. The solid was dissolved in water and acidified to pH 3-4 with 1.0 N HCl to give a white suspension. The suspension was extracted with EtOAc (3×). The combined organic layers were washed with brine, dried over sodium sulfate, filtered and concentrated to give Intermediate 40 (0.0708 g, 105%) as a white solid. MS(ESI) m/z: 256.0 (M+H)⁺ and 258.0 (M+2+H)⁺.

Intermediate 41

1-(4-Chloro-3-fluoropyridin-2-yl)-5-methyl-1H-pyrazole-4-carboxylic acid

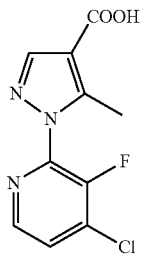 [SMILES: Cc1c(C(=O)O)cnn1-c1nccc(Cl)c1F]

Intermediate 101A. 2-Bromo-4-chloro-3-fluoropyridine: To a solution of 2,2,6,6-tetramethylpiperidine (1.54 mL, 9.12 mmol) in THF (40 mL) was added 1.6 M n-BuLi in hexanes (5.23 mL, 8.36 mmol) dropwise at −78° C. The resulting solution was stirred for 0.5 h at 0° C. It was then cooled to −78° C. and 4-chloro-3-fluoropyridine (0.769 mL, 7.60 mmol) in 5 mL THF was added dropwise over 30 min. The resulting solution was stirred at −78° C. for 30 min. To the solution was added NBS (1.624 g, 9.12 mmol) in THF (25 mL) dropwise and the resulting solution was stirred for 1 h at −78° C., then at ambient temperature for 12 h. The reaction mixture was then diluted with EtOAc and water. The organic layer was washed with brine, concentrated and purified on silica gel chromatography to give the desired product (0.541 g, 34%) as orange oil (volatile). ¹H NMR (400 MHz, CDCl₃) δ 8.13 (d, J=5.0 Hz, 1H), 7.35 (t, J=5.1 Hz, 1H).

Intermediate 41B. 4-Chloro-3-fluoro-2-hydrazinylpyridine, 2HCl: In microwave vial was added toluene (3 mL) and purged with N₂ for 5 min. tert-Butyl carbazate (128 mg, 0.950 mmol), Intermediate 101A (200 mg, 0.950 mmol), Cs₂CO₃ (310 mg, 0.950 mmol), DPPF (20 mg, 0.036 mmol), and Pd₂(dba)₃ (25 mg, 0.027 mmol) were added sequentially into the solution. The sealed tube was heated at 100° C. for 12 h. The reaction was diluted with brine, and extracted with EtOAc (2×). The combined organic layer was concentrated in vacuo, yielding oily residue, which was purified by silica gel chromatography to provide tert-butyl 2-(4-chloro-3-fluoropyridin-2-yl)hydrazinecarboxylate (41 mg, 16%) as orange solid. MS(ESI) m/z: 262.1 (M+H)⁺. To the solid was added EtOH (1 mL) and 4 N HCl in dioxane (4 mL) and the reaction mixture was stirred for 2 h at rt. The mixture was concentrated to dryness to the desired product. MS(ESI) m/z: 162.1 (M+H)⁺.

Intermediate 41. 1-(4-Chloro-3-fluoropyridin-2-yl)-5-methyl-1H-pyrazole-4-carboxylic acid: To a solution of tert-butyl 2-((dimethylamino)methylene)-3-oxobutanoate (0.045 g, 0.211 mmol) in acetonitrile (2 mL) was added TEA (0.030 mL, 0.215 mmol) followed by Intermediate 41B (0.038 g, 0.19 mmol). The dark brown solution was stirred for 1 h at 85° C. The reaction was concentrated, and water (1 mL) and CH₂Cl₂ (1 mL) were added. The organic layer was concentrated and purified by silica gel chromatography to provide tert-butyl 1-(4-chloro-3-fluoro-pyridin-2-yl)-5-methyl-1H-pyrazole-4-carboxylate as brown oil. MS(ESI) m/z: 312.1 (M+H). ¹H NMR (400 MHz, CDCl₃) δ 8.39-8.25 (m, 1H), 8.04 (s, 1H), 7.51 (t, J=5.0 Hz, 1H), 2.57 (s, 3H), 1.48 (s, 9H). The oil was stirred with 4 N HCl in dioxane (2 mL) for 12 h at rt. The solution was evaporated to dryness followed by coevaporation with toluene (2×) to give the desired product (12 mg, 22%). MS(ESI) m/z: 256.1 (M+H)⁺.

Intermediate 42

1-(4-Chloropyridin-2-yl)-5-methyl-1H-pyrazole-4-carboxylic acid

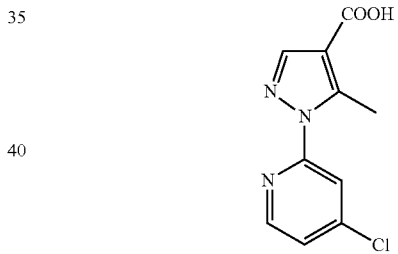

Intermediate 42A. 4-Chloro-2-hydrazinylpyridine, 2HCl: In microwave vial was added toluene (4 mL) and purged with N₂ for 5 min. tert-Butyl carbazate (66.6 mg, 0.494 mmol), 2-bromo-4-chloropyridine (95 mg, 0.494 mmol), Cs₂CO₃ (161 mg, 0.494 mmol), and PdCl₂(dppf)-CH₂Cl₂ adduct (4.03 mg, 4.94 μmol) were added. The sealed tube was heated at 100° C. for 5 h. To the reaction mixture was added water, brine and the mixture was extracted with EtOAc (2×). The combined organic layer was concentrated and purified by silica gel chromatography to provide tert-butyl 2-(4-chloropyridin-2-yl)hydrazinecarboxylate (42 mg, 35%) as red oil. MS(ESI) m/z: 244.2 (M+H)⁺. To the above oil was added 4 N HCl in dioxane (2 mL) and the reaction was stirred at rt for 2 h. The mixture was concentrated to dryness to give the desired (36 mg, 34%) as a white solid. MS(ESI) m/z: 144.0 (M+H)⁺.

Intermediate 42. 1-(4-Chloropyridin-2-yl)-5-methyl-1H-pyrazole-4-carboxylic acid: To a solution of tert-butyl 2-((dimethylamino)methylene)-3-oxobutanoate (0.032 g, 0.148 mmol) in acetonitrile (2 mL) was added TEA (0.021 mL, 0.148 mmol) and Intermediate 42A (0.024 g, 0.133 mmol). The dark brown solution was heated to 85° C. for 1 h. The reaction mixture was concentrated, and water (1 mL) and CH₂Cl₂ (1 mL) were added. The organic layer was concentrated and purified by silica gel chromatography to give tert-butyl 1-(4-chloropyridin-2-yl)-5-methyl-1H-pyrazole-4-carboxylate (12 mg, 27%) as yellow oil. MS(ESI) m/z: 294.2 (M+H)⁺. To the oil was added 4 N HCl in dioxane (2 mL). The reaction was stirred at rt for 4 h, and the clear orange solution was evaporated to dryness followed by coevaporation with toluene (2×) to give the desired product as sticky pink solid. MS(ESI) m/z: 238.2 (M+H)⁺.

Intermediate 43

1-(3-Fluoro-4-methylpyridin-2-yl)-5-methyl-1H-pyrazole-4-carboxylic acid

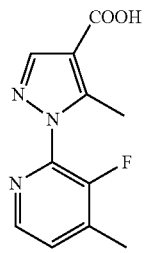

Intermediate 43A. 3-Fluoro-2-hydrazinyl-4-methylpyridine: In a microwave vial, a solution of hydrazine monohydrate (0.051 mL, 1.053 mmol), 2-bromo-3-fluoro-4-methylpyridine (200 mg, 1.053 mmol), DIEA (0.551 mL, 3.16 mmol) in isopropanol (2 mL) was heated at 50° C. overnight. Additional hydrazine monohydrate (0.100 mL) was added and the reaction was heated at 100° C. for 30 min, then 120° C. for 30 min in a microwave reactor. Additional hydrazine monohydrate (0.100 mL) was added and the reaction was heated at 120° C. overnight. The volatile organics were removed in vacuo and the residue was washed with CH₂Cl₂. The resulting solid was filtered to provide the desired product. MS(ESI) m/z: 142.0 (M+H)⁺.

Intermediate 43. 1-(3-Fluoro-4-methylpyridin-2-yl)-5-methyl-1H-pyrazole-4-carboxylic acid: To a solution of tert-butyl 2-((dimethylamino)methylene)-3-oxobutanoate (0.123 g, 0.575 mmol) in acetonitrile (2 mL) was added TEA (0.080 mL, 0.575 mmol) and Intermediate 43A (0.073 g, 0.517 mmol). The orange solution was heated to 85° C. for 1 h. Additional tert-butyl 2-((dimethylamino)methylene)-3-oxobutanoate (0.160 mL) and Et₃N (0.080 mL) were added into the solution and the reaction was heated at 85° C. for 1 h. The reaction mixture was concentrated and purified by silica gel chromatography to give tert-butyl 1-(3-fluoro-4-methylpyridin-2-yl)-5-methyl-1H-pyrazole-4-carboxylate as yellow oil. MS(ESI) m/z: 292.1 (M+H)⁺. ¹H NMR (400 MHz, CDCl₃) δ 8.26 (d, J=4.8 Hz, 1H), 8.02 (s, 1H), 7.29 (t, J=4.8 Hz, 1H), 2.54 (s, 3H), 2.43 (d, J=1.5 Hz, 3H), 1.58 (s, 9H). To the oil was added 4 N HCl in dioxane (2 mL) and the reaction was stirred at rt for 4 h. The clear orange solution was evaporated to dryness followed by coevaporation with toluene (2×) to give the desired product (15 mg, 11%) as sticky pink solid. MS(ESI) m/z: 236.1 (M+H)⁺.

Intermediate 44

1-(3-Fluoro-4-methylpyridin-2-yl)-1H-imidazole-4-carboxylic acid

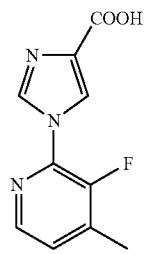 [SMILES: Cc1ccnc(-n2cnc(C(=O)O)c2)c1F]

Intermediate 44A. Methyl 1-(3-fluoro-4-methylpyridin-2-yl)-1H-imidazole-4-carboxylate: A suspension of methyl 1H-imidazole-4-carboxylate (83 mg, 0.658 mmol), 2-bromo-3-fluoro-4-methylpyridine (200 mg, 1.053 mmol), copper (I) iodide (125 mg, 0.658 mmol) and potassium carbonate (546 mg, 3.95 mmol) in DMSO (2 mL) was heated at 120° for 90 min under microwave conditions. The reaction mixture was quenched with H₂O, and the solid was suspended in EtOAc and MeOH. The combined organic layer was concentrated in vacuo, yielding oily residue, which was purified by reverse phase HPLC to give the desired product (5 mg, 3%). MS(ESI) m/z: 236.1 (M+H)⁺.

Intermediate 44. 1-(3-Fluoro-4-methylpyridin-2-yl)-1H-imidazole-4-carboxylic acid: To a solution of Intermediate 44A (5 mg, 0.021 mmol) in THF (0.6 mL) and H₂O (0.3 mL) was added LiOH (5 mg). The reaction was stirred for 12 h at rt. The THF was removed in vacuo and 1 N HCl aq. solution was added until the solution became acidic. The mixture was extracted with EtOAc (2×). The combined organic layer was concentrated to dryness to give the desired product (4 mg, 3%) as a white solid. MS(ESI) m/z: 222.1 (M+H)⁺.

Intermediate 45

(R)-2-Methylbut-3-enoic acid

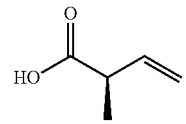

Intermediate 45A. (R)-4-Benzyl-3-((R)-2-methylbut-3-enoyl)oxazolidin-2-one: To the solution of 2-methylbut-3-enoic acid (5.59 g, 55.9 mmol) and N-methylmorpholine (6.14 ml, 55.9 mmol) in THF (62 mL) at 0° C. was added pivaloyl chloride (6.87 ml, 55.9 mmol) dropwise. The reaction mixture was cooled down to −78° C., and stirred for ~2 h. In a separate flask: To the solution of (R)-4-benzyloxazolidin-2-one (8.25 g, 46.6 mmol) in THF (126 mL) at −78° C. was added dropwise N-butyllithium (2.5 M in hexane) (20.49 mL, 51.2 mmol). After 35 min, this reaction was transferred via cannula to the first reaction. The reaction mixture was stirred at −78° C. for 2 h, then the cold bath was removed, and the reaction was quenched with saturated NH₄Cl. The reaction was diluted with water and extracted with EtOAc (3×). The combined organic layers were washed with brine, dried over Na$_2$SO$_4$, filtered, and concentrated to give a yellow oil (15 g). Purification by silica gel chromatography afforded the desired product (6.59 g, 55%) as a colorless oil. MS(ESI) m/z: 282.1 (M+Na)$^+$. $^1$H NMR (500 MHz, CDCl$_3$) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J=13.5, 3.3 Hz, 1H), 2.79 (dd, J=13.5, 9.6 Hz, 1H), 1.35 (d, J=6.9 Hz, 3H) ppm. The other diastereomer (R)-4-benzyl-3-((S)-2-methylbut-3-enoyl)oxazolidin-2-one (4.6 g, 38%) also obtained as a white solid. MS(ESI) m/z: 260.1 (M+H)$^+$.

Intermediate 45. (R)-2-Methylbut-3-enoic acid: To a clear colorless solution of Intermediate 45A (6.05 g, 23.33 mmol) in THF (146 mL) at 0° C. was added dropwise hydrogen peroxide (9.53 mL, 93 mmol) (30% aqueous) followed by 2 N lithium hydroxide (23.33 mL, 46.7 mmol). After 30 min, the reaction was quenched with 25 mL of saturated Na$_2$SO$_3$ and 25 mL of saturated NaHCO$_3$. The reaction was then concentrated to remove the THF. The residue was diluted with water and extracted with CHCl$_3$ (3×). The aqueous layer was acidified with conc. HCl to pH~3 and then it was extracted with EtOAc (3×). The EtOAc layers were combined, washed with brine, dried over MgSO$_4$, filtered and concentrated to afford the desired product (2.15 g, 92%) as a colorless oil. $^1$H NMR (500 MHz, CDCl$_3$) δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H) ppm.

Intermediate 46

3-(3-Chloro-2-fluorophenyl)-4-methylisoxazole-5-carboxylic acid

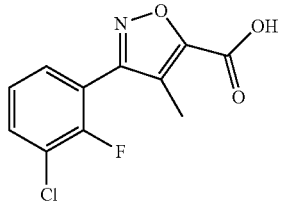 [SMILES: Cc1c(-c2cccc(Cl)c2F)noc1C(=O)O]

Intermediate 46A. (E)-3-Chloro-2-fluorobenzaldehyde oxime: To the solution of 3-chloro-2-fluorobenzaldehyde (1.3 g, 8.20 mmol) and hydroxylamine hydrochloride (0.695 g, 10.00 mmol) in EtOH (6.83 mL)/water (6.83 mL) was added 1 N NaOH (10.00 mL, 10.00 mmol). The reaction was stirred at rt for 4 h, then it was acidified to pH 6 with 1 N HCl which gave a white suspension. The reaction mixture was filtered, and the solid was rinsed with water, and air-dried to afford the desired product (1.31 g, 92%) as a white solid. MS(ESI) m/z: 174.0 (M+H)$^+$. $^1$H NMR (500 MHz, CDCl$_3$) δ 8.36 (s, 1H), 7.74 (s, 1H), 7.66 (ddd, J=7.8, 6.3, 1.7 Hz, 1H), 7.42 (ddd, J=8.0, 7.2, 1.7 Hz, 1H), 7.13-7.07 (m, 1H) ppm.

Intermediate 46B. Ethyl 3-(3-chloro-2-fluorophenyl)-4-methylisoxazole-5-carboxylate: Ethyl but-2-ynoate (0.725 ml, 6.22 mmol) and Intermediate 46A (0.36 g, 2.074 mmol) were dissolved in acetonitrile (10.37 mL). Magtrieve (1.742 g, 20.74 mmol) was added and the reaction mixture was stirred in a sealed tube at 80° C. After 2 h, the reaction was cooled to rt and then it was filtered through CELITE®, rinsing with EtOAc. The filtrate was concentrated and purified by reverse phase HPLC to afford the desired product (0.009 g, 2% yield) as a white solid. MS(ESI) m/z: 284.0 (M+H)$^+$. $^1$H NMR (500 MHz, MeOD) δ 7.70 (ddd, J=8.0, 7.2, 1.7 Hz, 1H), 7.49 (ddd, J=7.8, 6.3, 1.7 Hz, 1H), 7.35 (td, J=7.8, 1.1 Hz, 1H), 4.46 (q, J=7.2 Hz, 2H), 2.25 (d, J=1.9 Hz, 3H), 1.42 (t, J=7.2 Hz, 3H) ppm. The other regioisomer, ethyl 3-(3-chloro-2-fluorophenyl)-5-methylisoxazole-4-carboxylate (0.083 g, 14%) was also obtained as a colorless oil. MS(ESI) m/z: 284.0 (M+H)$^+$.

Intermediate 46. 3-(3-Chloro-2-fluorophenyl)-4-methylisoxazole-5-carboxylic acid: To the solution of Intermediate 46B (0.011 g, 0.039 mmol) in MeOH (1 mL) was added 1 N NaOH (0.078 mL, 0.078 mmol). After 18 h, the reaction was quenched with 1 N HCl (0.1 mL) and then it was concentrated to give the desired product (10 mg, 100% yield) as a white solid. MS(ESI) m/z: 255.9 (M+H)$^+$. The material was carried onto the next step without further purification.

Intermediate 47

5-(3-Chloro-2-fluorophenyl)-4-methylisoxazole-3-carboxylic acid

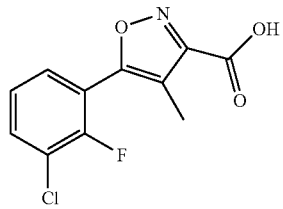 [SMILES: Cc1c(C(=O)O)noc1-c1cccc(Cl)c1F]

Intermediate 47A. 1-(3-Chloro-2-fluorophenyl)propan-1-ol: To the solution of 3-chloro-2-fluorobenzaldehyde (2.8 g, 17.66 mmol) in THF (88 mL) at −78° C. was added dropwise ethylmagnesium bromide (1 M in THF) (21.19 mL, 21.19 mmol). After 2 h, the reaction was warmed to 0° C. and it was carefully quenched with saturated NH$_4$Cl solution. The reaction mixture was diluted with water and extracted with EtOAc (3×). The organic layers were combined and washed with water, brine, dried over MgSO$_4$, filtered and concentrated. Purification by silica gel chromatography yielded the desired product (2.04 g, 61%) as a colorless oil. MS(ESI) m/z: 211.0 (M+Na)$^+$. $^1$H NMR (500 MHz, CDCl$_3$) δ 7.37 (td, J=7.0, 1.7 Hz, 1H), 7.33-7.28 (m, 1H), 7.09 (td, J=7.8, 1.1 Hz, 1H), 4.99-4.94 (m, 1H), 1.92 (d, J=4.4 Hz, 1H), 1.85-1.77 (m, 2H), 0.95 (t, J=7.4 Hz, 3H) ppm.

Intermediate 47B. 1-(3-Chloro-2-fluorophenyl)propan-1-one: To the solution of Intermediate 47A (1.9 g, 10.07 mmol) in DCM (40.3 ml) was added PDC (11.37 g, 30.2 mmol) and 4 Å MS (2 g) (powdered). The reaction was stirred at rt for 24 h, then it was filtered through CELITE® washing with DCM. The filtrate was concentrated. Purification by silica gel chromatography yielded the desired product (1.6 g, 85%) as a colorless oil. MS(ESI) m/z: 187.0 (M+H)$^+$. $^1$H NMR (500 MHz, CDCl$_3$) δ 7.74 (ddd, J=7.9, 6.3, 1.8 Hz, 1H), 7.58-7.53 (m, 1H), 7.17 (td, J=7.8, 0.8 Hz, 1H), 3.00 (qd, J=7.2, 3.3 Hz, 2H), 1.21 (td, J=7.2, 0.7 Hz, 3H) ppm.

Intermediate 47C. Ethyl 4-(3-chloro-2-fluorophenyl)-3-methyl-2,4-dioxobutanoate: To the solution of LiHMDS (1 M in THF) (3.19 mL, 3.19 mmol) in ether (12 mL) at −78° C. was added dropwise a solution of Intermediate 47B (0.59 g, 3.16 mmol) in ether (2 mL). After 45 min., diethyl oxalate (0.492 mL, 3.60 mmol) was added in one portion, and the reaction was warmed to rt. After 18 h, the reaction mixture was filtered, washing with ether. The filtrate was diluted with EtOAc, washed with 1 N HCl, brine, dried over Na$_2$SO$_4$, filtered and concentrated. Purification by silica gel chromatography yielded the desired product (0.057 g, 6%) as a yellow oil. MS(ESI) m/z: 241.0 (M-OEt)$^+$. $^1$H NMR (500 MHz, CDCl$_3$) δ 7.80 (ddd, J=8.0, 6.3, 1.7 Hz, 1H), 7.65 (ddd, J=7.8, 7.0, 1.9 Hz, 1H), 7.23 (td, J=8.0, 0.8 Hz, 1H), 4.91 (q, J=7.2 Hz, 1H), 4.31 (qd, J=7.2, 0.8 Hz, 2H), 1.46 (dd, J=7.2, 0.8 Hz, 3H), 1.34 (t, J=7.2 Hz, 3H) ppm.

Intermediate 47D. Ethyl 5-(3-chloro-2-fluorophenyl)-4-methylisoxazole-3-carboxylate: The mixture of Intermediate 47C (0.057 g, 0.199 mmol) and hydroxylamine hydrochloride (0.017 g, 0.239 mmol) in EtOH (1 mL) was heated in a sealed tube at 90° C. After 5 h, the reaction was cooled to rt and then it was concentrated. Purification by reverse phase HPLC afforded the desired product (0.022 g, 39%) as a white solid. MS(ESI) m/z: 284.0 (M+H)$^+$. $^1$H NMR (500 MHz, MeOD) δ 7.73-7.68 (m, 1H), 7.56 (ddd, J=7.8, 6.2, 1.7 Hz, 1H), 7.37 (td, J=8.0, 1.1 Hz, 1H), 4.45 (q, J=7.0 Hz, 2H), 2.24 (d, J=2.2 Hz, 3H), 1.42 (t, J=7.2 Hz, 3H) ppm.

Intermediate 47. 5-(3-Chloro-2-fluorophenyl)-4-methylisoxazole-3-carboxylic acid: To the solution of Intermediate 47D (0.009 g, 0.032 mmol) in MeOH (1 mL) was added 1 N NaOH (0.063 mL, 0.063 mmol). After 3 h, the reaction was quenched with 1 N HCl (0.1 mL) and then it was concentrated to give the desired product (8.1 mg, 100% yield) as a white solid. MS(ESI) m/z: 255.9 (M+H)$^+$. The material was carried onto the next step without further purification.

Intermediate 48

(R)-2-Methylbut-3-enoyl chloride

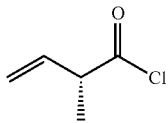

Intermediate 48. (R)-2-Methylbut-3-enoyl chloride: To a cooled (0° C.) solution of (R)-2-methylbut-3-enoic acid (0.450 g, 4.49 mmol) in DCM was added dropwise oxalyl chloride (0.393 mL, 4.49 mmol). The reaction mixture was stirred at 0° C. for 30 min and then it was allowed to stir at rt for 80 min. The resulting solution of (R)-2-methylbut-3-enoyl chloride was used directly.

Intermediate 49

2-(5,5-Dimethyl-1,3,2-dioxaborinan-2-yl)-5-nitrophenylamine

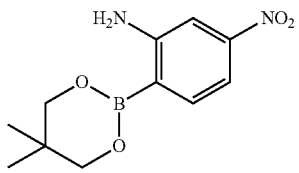 [SMILES: CC1(C)COB(c2ccc([N+](=O)[O-])cc2N)OC1]

To a flame-dried flask, equipped with a reflux condenser, containing 2-bromo-5-nitroaniline (10.0 g, 46.1 mmol), bis(neopentyl glycolato)diboron (13.01 g, 57.6 mmol), potassium acetate (13.57 g, 138 mmol), and PdCl$_2$(dppf)-CH$_2$Cl$_2$ adduct (0.941 g, 1.152 mmol) was added DMSO (132 mL). The resulting dark red-brown suspension was degassed with argon for 30 min and then the reaction was warmed to 80° C. After 4 h, the reaction was stopped and cooled to rt. The reaction was poured slowly into vigorously stirred ice-cold water (300 mL) to give a brown suspension. After stirring for 10 min, the suspension was filtered to collect the solid. The solid was rinsed with water (3×125 mL), air-dried, and then dried under a vacuum to give a brown solid. Purification by normal phase chromatography gave 4.36 g of Intermediate 49 as an orange solid. MS(ESI) m/z: 183.1 (M-C$_5$H$_8$+H)$^+$.

Intermediate 50

4-Chloro-5-(3-chloro-2-fluorophenyl)isothiazole-3-carboxylic acid

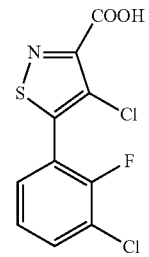 [SMILES: O=C(O)c1nsc(-c2cccc(Cl)c2F)c1Cl]

Intermediate 50A. Methyl 4,5-dichloroisothiazole-3-carboxylate: To a solution of 4,5-dichloroisothiazole-3-carboxylic acid (211 mg, 1.07 mmol) in toluene (3 mL)) and MeOH (1 mL) was added trimethylsilyldiazomethane (2 M in hexane) (0.7 mL, 1.400 mmol) solution dropwise. The pale yellow solution was stirred at rt for 0.5 h. The solution was concentrated under vacuum to give yellow solid, which was subjected to the following reaction without further purification. MS(ESI) m/z: 212.1 (M+H)$^+$.

Intermediate 50B. Methyl 4-chloro-5-(3-chloro-2-fluorophenyl)isothiazole-3-carboxylate: To a solution of Intermediate 50A (0.100 g, 0.472 mmol) and Cs$_2$CO$_3$ (0.461 g, 1.415 mmol) in DME (3.02 mL) and water (0.605 mL) was added methyl 4,5-dichloroisothiazole-3-carboxylate (0.100 g, 0.472 mmol). The solution was purged with Ar for 0.5 h. To the solution was added Pd(PPh$_3$)$_4$ (0.054 g, 0.047 mmol). The reaction mixture was then sealed and heated in microwave for 0.5 h at 100° C. The reaction mixture was then diluted with EtOAc and aqueous layer was decanted. The organic layer was concentrated in vacuo, yielding an oily residue which was purified by silica gel column chromatography to provide the desired product (53 mg, 37%) as a white solid. MS(ESI) m/z: 360.0 (M+H)$^+$.

Intermediate 50. 4-Chloro-5-(3-chloro-2-fluorophenyl)isothiazole-3-carboxylic acid: To a solution of Intermediate 50B (53 mg, 0.173 mmol) in THF (2 mL) and water (1 mL) was added lithium hydroxide monohydrate (0.014 mL, 0.519 mmol). The resulting solution was stirred for 2 h at rt.

143

The reaction mixture was concentrated in vacuo. The aqueous solution was acidified with 1 N HCl (pH=2-3) and extracted with EtOAc (2×). The organic solution was dried over $Na_2SO_4$, filtered and concentrated in vacuo to provide the desired product as a white solid (47 mg, 93%). MS(ESI) m/z: 291.1 $(M+H)^+$.

Intermediate 51

5-(3-Chloro-2-fluorophenyl)nicotinic acid, HCl

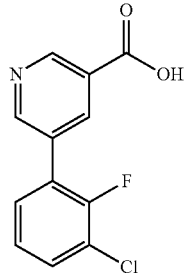 [SMILES: O=C(O)c1cncc(-c2cccc(Cl)c2F)c1]

Intermediate 51A. Ethyl 5-(3-chloro-2-fluorophenyl) nicotinate: To a solution of (3-chloro-2-fluorophenyl)boronic acid (148 mg, 0.848 mmol), ethyl 5-bromonicotinate (150 mg, 0.652 mmol), tetrabutylammonium bromide (315 mg, 0.978 mmol) and $Cs_2CO_3$ (637 mg, 1.956 mmol) in dimethoxyethane (9 mL) and water (1 mL) was added $Pd(Ph_3P)_4$ (113 mg, 0.098 mmol) and the resulting heterogeneous solution was purged with $N_2$. It was then sealed and heated at 120° C. for 0.5 h in a microwave reactor. The reaction mixture was diluted with DCM and washed with brine (2×). The organic solution was dried over $Na_2SO_4$, filtered and concentrated in vacuo, yielding oily residue which was purified by silica gel column chromatography to provide the desired product (100 mg, 55%). MS(ESI) m/z: 280.1 $(M+H)^+$.

Intermediate 51. 5-(3-Chloro-2-fluorophenyl)nicotinic acid: To a solution of Intermediate 51 A (100 mg, 0.358 mmol) in THF (4 mL) and water (3 mL) was added lithium hydroxide monohydrate (0.030 mL, 1.073 mmol) and the resulting solution was stirred for 2 h at rt. The reaction mixture was concentrated in vacuo. The aqueous solution was acidified with 1 N HCl (pH=2-3). At this point, a white solid was precipitated from the solution. The solid was collected by filtration and dried under vacuum to provide Intermediate 51 (102 mg, 99%) as a white solid. MS(ESI) m/z: 252.1 $(M+H)^+$.

144

Example 1

Methyl N-[(14S)-14-[1-(3-chlorophenyl)-3-(2-hydroxyethyl)-1H-pyrazole-4-amido]-16-fluoro-10-methyl-9-oxo-8,17-diazatricyclo[13.3.1.0$^{2,7}$]nonadeca-1(19),2,4,6,15,17-hexaen-5-yl]carbamate, TFA salt

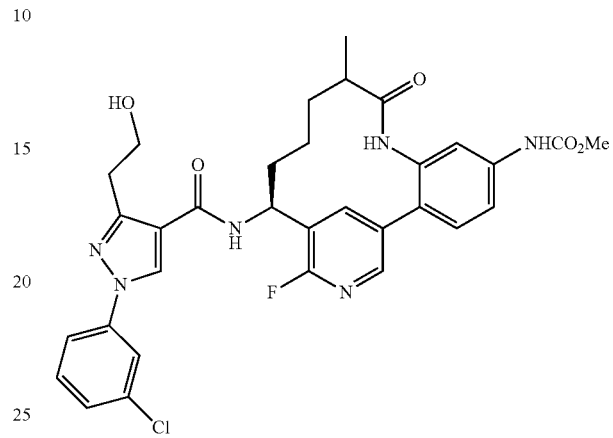

1A. (R,E)-N-((5-Bromo-2-fluoropyridin-3-yl)methylene)-2-methylpropane-2-sulfinamide: To the solution of 5-bromo-2-fluoronicotinaldehyde (5 g, 24.51 mmol), titanium (IV) ethoxide (15.42 ml, 73.5 mmol) in DCM (49.0 ml) was added (R)-2-methylpropane-2-sulfinamide (3.12 g, 25.7 mmol) and the reaction mixture was stirred at rt. After 48 h, the reaction mixture was poured into brine while rapidly stirring to form a suspension. The resulting suspension was filtered through a plug of CELITE®, and the filter cake was washed several times with DCM. The filtrate phases were separated, and the organic phase was washed with brine and dried over $MgSO_4$. The organic layers were then concentrated to give 7.6 g crude product which was further purified using silica gel chromatography to yield the desired product (6.97 g, 93%) as an off white solid. MS(ESI) m/z: 330.8 $(M+Na)^+$.

1B. (R)—N—((S)-1-(5-Bromo-2-fluoropyridin-3-yl)but-3-en-1-yl)-2-methylpropane-2-sulfinamide: To a saturated aqueous solution of sodium bromide (420 g, 4084 mmol) (app. 420 g in 450 ml $H_2O$) was added 1A (6.97 g, 22.69 mmol) and indium (10.42 g, 91 mmol). To this mixture was then added 3-bromoprop-1-ene (7.85 ml, 91 mmol) dropwise, and the resulting cloudy white suspension was allowed to stir at rt for 10 h. The reaction was then quenched with saturated aqueous $NaHCO_3$ solution followed by extraction with EtOAc. The organic layer was dried over anhydrous $MgSO_4$ and concentrated to yield the crude product. The crude product was then purified using silica gel chromatography to give the desired product (8.8 g, 98%) as an off white solid. MS(ESI) m/z: 350.8 $(M+H)^+$.

1C. (S)-1-(5-Bromo-2-fluoropyridin-3-yl)but-3-en-1-amine, 2 HCl: To a solution of 1B (8.8 g, 25.2 mmol) in MeOH (100 mL) was added HCl (31.5 mL, 126 mmol) (4 M in dioxane). The reaction mixture was stirred at rt for 1 h and then concentrated to near dryness. $Et_2O$ was added to give a yellow suspension which was then filtered and the filtered solid was further washed with $Et_2O$. The filtrate was concentrated and re-filtered with $Et_2O$. The collected solid was then dried on the vacuum pump to give 1C (6.45 g, 80%) as a white solid. MS(ESI) m/z: 246.9 $(M+H)^+$.

1D. (S)-tert-Butyl (1-(5-bromo-2-fluoropyridin-3-yl)but-3-en-1-yl)carbamate: To a solution of 1C (6.55 g, 20.60 mmol) in DCM (68.7 ml) at 0° C. was added TEA (11.48 ml, 82 mmol) and Boc$_2$O (4.50 g, 20.60 mmol). The reaction mixture was stirred at 0° C. for 2 h, and then allowed to warm to rt. After stirring for 2 h, the reaction mixture was diluted with DCM and washed with saturated NaHCO$_3$ solution. The aqueous layer was re-extracted with DCM (2×). The combined organic layers were then washed with brine, dried over MgSO$_4$ to yield the crude product. The crude product was then purified using silica gel chromatography to yield the desired product (6.64 g, 87%) as a white solid. MS(ESI) m/z: 368.9 (M+Na)$^+$.

1E. (S)-tert-Butyl (1-(5-(2-amino-4-nitrophenyl)-2-fluoropyridin-3-yl)but-3-en-1-yl)carbamate: To a RBF was added 1D (4.5 g, 13.04 mmol), 2-(5,5-dimethyl-1,3,2-dioxaborinan-2-yl)-5-nitroaniline (6.52 g, 26.1 mmol), PdCl$_2$ (dppf)-DCM adduct (1.065 g, 1.304 mmol), and potassium phosphate, tribasic (5.53 g, 26.1 mmol). The RBF was equipped with a reflux condenser and the apparatus was vacuumed and back-filled with argon. Degassed DMSO (65.2 mL) was added followed by degassed H$_2$O (1.174 mL, 65.2 mmol). The dark red reaction mixture was warmed to 90° C. for 1 h, and then allowed to cool to rt. The reaction mixture was then partitioned between EtOAc and brine, and the layers were separated. The aqueous layer was re-extracted with EtOAc. The combined organic layers were dried over MgSO$_4$, filtered and concentrated to give the crude product as thick black oil which was subjected to silica gel chromatography to yield the desired product (5.90 g, 100%) as yellow foam. MS(ESI) m/z: 403.0 (M+H)$^+$.

1F. Methyl (3-amino-4-(5-((1S)-1-((tert-butoxycarbonyl)amino)but-3-en-1-yl)-6-fluoropyridin-3-yl)phenyl)carbamate: To a clear, orange solution of 1E (4.4 g, 9.95 mmol) in MeOH (100 mL) was added sequentially zinc (6.51 g, 99 mmol) and ammonium chloride (5.32 g, 99 mmol). The resulting yellow-orange suspension turned clear after a few minutes and was stirred at rt. After 2 h, the reaction mixture was filtered off to remove solid and concentrated to give a residue. The residue was diluted with EtOAc and washed with saturated NaHCO$_3$ solution. The organic layer was then dried over MgSO$_4$ and purified by silica gel chromatography to yield the desired bis amine product as peach colored foam. To a −78° C. clear, orange solution of the above bis amine product (5.08 g, 13.64 mmol) and pyridine (1.103 ml, 13.64 mmol) in DCM (136 mL) was added dropwise methyl chlorocarbonate (0.949 ml, 12.28 mmol) and the reaction mixture was stirred at −78° C. for 1.5 h. The reaction was then quenched with saturated NH$_4$Cl solution and allowed to slowly warm to rt. The reaction mixture was diluted with DCM and the aqueous layer was re-extracted with DCM. The combined organic layers were washed with saturated NaHCO$_3$ solution followed by brine. The organic layer was then dried over MgSO$_4$, filtered and concentrated to give the crude product as peach-colored foam which was then purified using silica gel chromatography. COSY and NOE analysis confirmed the site of addition. The desired product (4.77 g, 81%) was isolated as beige foam. MS(ESI) m/z: 431.1 (M+H)$^+$.

1G. Methyl (4-(5-((1S)-1-((tert-butoxycarbonyl)amino)but-3-en-1-yl)-6-fluoropyridin-3-yl)-3-((2-methylbut-3-enoyl)amino)phenyl)carbamate: To a solution of 2-methylbut-3-enoic acid (0.216 mL, 2.091 mmol) and 1F (0.900 g, 2.091 mmol) in EtOAc (59.7 mL) was added DIEA (1.095 mL, 6.27 mmol) and the reaction was allowed to cool to −10° C. under argon. To this mixture was then added T3P (2.464 mL, 4.18 mmol) and the reaction was allowed to stir for 5 min at the same temperature and then allowed to warm to 0° C. followed by to rt slowly while stirring under argon at rt. After overnight stirring, the reaction mixture was concentrated and purified by silica gel chromatography to give 1G (887 mg, 83%) as a white solid. MS(ESI) m/z: 513.1 (M+H)$^+$.

1H. tert-Butyl N-[(11E)-16-fluoro-9-hydroxy-5-[(methoxycarbonyl)amino]-10-methyl-8,17-diazatricyclo[13.3.1.0$^{2,7}$]nonadec-11-en-14-yl]carbamate: A clear, colorless solution of 11G (887 mg, 1.730 mmol) in DCE (100 mL) was degassed with argon, then split into 5 microwave vials. To the above mixture was then added Grubbs II (588 mg, 0.692 mmol) (118 mg to each vial) and heated each vial in the microwave at 120° C. for 25 min. The reaction mixture was then combined and washed with saturated NaHCO$_3$ followed by brine. The organic layer was then dried over MgSO$_4$, filtered and concentrated to give the crude product which was purified by silica gel chromatography. Desired fractions were collected and concentrated to give 1H (568 mg, 68%) as a brown solid. MS(ESI) m/z: 485.1 (M+H)$^+$.

1I. tert-Butyl N-[(14S)-16-fluoro-5-[(methoxycarbonyl)amino]-10-methyl-9-oxo-8,17-diazatricyclo[13.3.1.0$^{2,7}$]nonadeca-1(19),2,4,6,15,17-hexaen-14-yl]carbamate: To a solution of 1H (0.568 g, 1.172 mmol) in MeOH (39.1 mL) was added platinum (IV) oxide (0.027 g, 0.117 mmol). The reaction mixture was then charged with H$_2$ gas using a H$_2$ balloon and vacuumed with H$_2$ several times. The reaction was then stirred at rt under H$_2$ for 40 h. After stirring for 40 h, the reaction mixture was filtered through a pad of CELITE® and the filtrate was concentrated to yield the crude product. The crude product was then purified by silica gel chromatography to yield the Diastereomer A (Ha) (178 mg, 25%) and Diastereomer-B (95 mg, 14%, 1Ib) as white solids. Diastereomer A—MS(ESI) m/z: 487.1 (M+H)$^+$.

1J. Methyl N-[(14S)-14-amino-16-fluoro-10-methyl-9-oxo-8,17-diazatricyclo[13.3.1.0$^{2,7}$]nonadeca-1(19),2,4,6,15,17-hexaen-5-yl]carbamate: A solution of hydrogen chloride in dioxane (5932 μL, 23.73 mmol) was added to 1Ia (95 mg, 0.158 mmol) and the reaction mixture was stirred at rt. After 1 h of stirring, the reaction mixture was concentrated to give the desired product (73 mg, 100%). MS(ESI) m/z: 387.1 (M+H)$^+$.

Example 1. Methyl N-[(14S)-14-[1-(3-chlorophenyl)-3-(2-hydroxyethyl)-1H-pyrazole-4-amido]-16-fluoro-10-methyl-9-oxo-8,17-diazatricyclo[13.3.1.0$^{2,7}$]nonadeca-1(19),2,4,6,15,17-hexaen-5-yl]carbamate, TFA salt: A mixture of Intermediate 9 (0.030 g, 0.112 mmol), 1J (0.043 g, 0.112 mmol), DIEA (0.60 mL, 0.334 mmol) and T3P (0.115 mmol) in DMF (2 mL) was stirred at rt overnight. The reaction mixture was concentrated and purified directly by reverse phase HPLC to isolate the desired product as a homochiral compound. $^1$H NMR (400 MHz, MeOD) δ 8.59 (s, 1H), 8.01-7.99 (m, 1H), 7.96-7.95 (dd, J=8.3 & 1.3 Hz, 1H), 7.67-7.49 (m, 3H), 7.48-7.39 (m, 1H), 7.38-6.37 (m, 2H), 7.26-7.24 (m, 1H), 5.17-4.93 (m, 1H), 3.82-3.57 (t, J=6.3 Hz, 2H), 3.02 (t, J=6.3 Hz, 2H), 2.23-2.00 (m, 1H), 1.96 (m, 1H), 1.82 (m, 1H), 1.51-1.49 (m, 1H), 1.36 (m, 2H), 1.12-1.10 (d, 2H), 0.92 (m, 1H) ppm. MS(ESI) m/z: 635.1 (M+H)$^+$. Analytical HPLC RT=6.44 min (Method B).

Example 2

Methyl N-[(10R,14S)-14-[1-(3-chlorophenyl)pyrrolidine-3-amido]-10-methyl-9-oxo-8,16-diazatricyclo[13.3.1.0²,⁷]nonadeca-1(19),2(7),3,5,15,17-hexaen-5-yl]carbamate, 2TFA

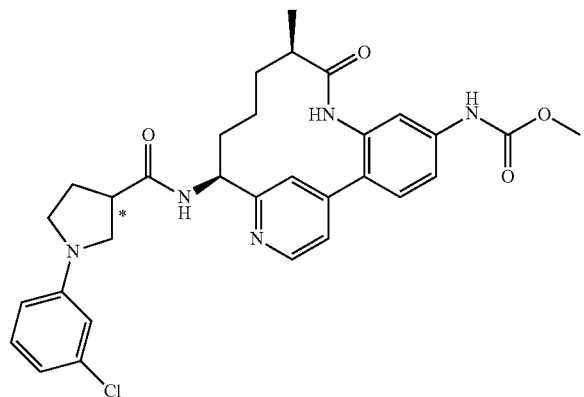 [SMILES: COC(=O)Nc1ccc2c(c1)NC(=O)[C@H](C)CCC[C@H](NC(=O)C1CCN(c3cccc(Cl)c3)C1)c1cc-2ccn1]

2A. (S,E)-N-((4-Chloropyridin-2-yl)methylene)-2-methylpropane-2-sulfinamide: Liu, G. et al., *J. Org. Chem.*, 64:1278 (1999). To a solution of S-(–)-t-butyl-sulfinamide (0.856 g, 7.06 mmol) in dichloromethane (14.13 mL) was added sequentially copper(II) sulfate (2.481 g, 15.54 mmol) and 4-chloropicolinaldehyde [1.0 g, 7.06 mmol, prepared according to a modified described by Negi (*Synthesis*, 991 (1996))]. The white suspension was stirred at rt. After 3 h, the brown suspension was filtered through CELITE®, eluting with DCM, to give a clear brown filtrate. Concentration gave a brown oil weighing 1.85 g. Purification by normal phase chromatography gave 1.31 g of 2A as a clear, yellow oil. MS(ESI) m/z: 245.0 (M+H)⁺.

2B. (S)—N—((S)-1-(4-Chloropyridin-2-yl)but-3-enyl)-2-methylpropane-2-sulfinamide: To a cooled solution (–78° C.) of 2A (10 g, 40.9 mmol) in THF (204 mL) was added dropwise allyl magnesium bromide (44.9 mL, 44.9 mmol, 1M in Et₂O). The reaction mixture was stirred at –78° C. After 2 h, the reaction mixture was quenched with the addition of saturated NH₄Cl (25 mL) and then the reaction mixture was allowed to warm to rt. The reaction mixture was then diluted with EtOAc and water and the layers were separated. The aqueous layer was extracted with EtOAc. The combined organic layers were washed with brine, dried over Na₂SO₄, filtered, and concentrated. Purification by normal phase chromatography gave 2B (9.23 g, 79%) as a clear, orange oil. ¹H NMR indicated a 4.7:1 mixture of diastereomers whereby the major diastereomer corresponds to the title compound. MS(ESI) m/z: 287.1 (M+H)⁺.

2C. (S)—N—((S)-1-(4-(2-Amino-4-nitrophenyl)pyridin-2-yl)but-3-enyl)-2-methylpropane-2-sulfinamide, Diastereomer A and 2D. (S)—N—((R)-1-(4-(2-amino-4-nitrophenyl)pyridin-2-yl)but-3-enyl)-2-methylpropane-2-sulfinamide, Diastereomer B: To a RBF was added 2B (9.23 g, 32.2 mmol), 2-(5,5-dimethyl-1,3,2-dioxaborinan-2-yl)-5-nitroaniline (16.09 g, 64.4 mmol), potassium phosphate, tribasic (13.66 g, 64.4 mmol), DMSO (161 mL), and water (2.90 mL, 161 mmol). The RBF was equipped with a reflux condenser and then the apparatus was purged with argon for 30 minutes. Next, Pd(dppf)Cl₂—CH₂Cl₂ adduct (2.63 g, 3.22 mmol) was added and the reaction mixture was warmed to 90° C. After 4 h, the reaction was cooled to rt and then it was poured into water (1000 mL) to give a suspension. The solid was collected by filtration and then it was dissolved in EtOAc. The filtrate was extracted with EtOAc (1×). The organic layers were combined and washed with brine, dried over sodium sulfate, filtered, and concentrated. Purification by normal phase chromatography gave 2C (3.9 g) as an orange foam. An additional 3.84 g of material was obtained as a mixture of diastereomers 2C and 2D. The diastereomers were separated by chiral SFC prep HPLC (CHIRALCEL® OD-H; 20% methanol/80% carbon dioxide) which gave 2C (2.0 g) as an orange foam and 2D (0.90 g) as an orange foam. The total amount of 2C isolated was (5.9 g, 47%) as an orange foam. MS(ESI) m/z: 389.2 (M+H)⁺.

2E. (S)—N—((S)-1-(4-(2,4-Diaminophenyl)pyridin-2-yl)but-3-enyl)-2-methylpropane-2-sulfinamide: To a clear, orange solution of 2C (2 g, 5.15 mmol) in methanol (51.5 mL) was added sequentially zinc (3.37 g, 51.5 mmol) and ammonium chloride (2.75 g, 51.5 mmol). The resulting suspension was stirred vigorously. After 3 h, the reaction was stopped and it was filtered through a 0.45 micron GMF eluting with methanol to give a yellow filtrate. The filtrate was concentrated, then the residue was partitioned between EtOAc and water, and the layers were separated. The aqueous layer was extracted with EtOAc. The combined organic layers were washed with saturated sodium bicarbonate, brine, dried over sodium sulfate, filtered, and concentrated to give 2E (1.86 g, 101%) as a yellow foam. This material was used in the next step without further purification. MS(ESI) m/z: 359.1 (M+H)⁺.

2F. Methyl 3-amino-4-(2-((S)-1-((S)-1,1-dimethylethylsulfinamido)but-3-enyl)pyridin-4-yl)phenylcarbamate: To a cooled (–78° C.) clear, yellow solution of 2E (1.86 g, 5.19 mmol) and pyridine (0.420 mL, 5.19 mmol) in DCM (52 mL) was added dropwise methyl chlorocarbonate (0.361 mL, 4.67 mmol). The reaction mixture was stirred at –78° C. After 2 h, the reaction was quenched with saturated NH₄Cl and the reaction was allowed to warm to rt. The reaction mixture was then diluted with DCM and water and the layers were separated. The aqueous layer was extracted with DCM. The combined organic layers were washed with saturated NaHCO₃, brine, dried over sodium sulfate, filtered and concentrated to give 2F (2.3 g, 106%) as a yellow foam. This material was used in the next step without further purification. MS(ESI) m/z: 417.1 (M+H)⁺.

2G. (S)-Methyl 3-amino-4-(2-(1-aminobut-3-enyl)pyridin-4-yl)phenylcarbamate, 3 HCl: To a clear, yellow solution of 2F (2.3 g, 5.52 mmol) in MeOH (55.2 mL) was added 4 M HCl in dioxane (13.80 mL, 55.2 mmol). The reaction mixture was stirred at rt. After 2 h, the reaction was concentrated to give a yellow residue. The residue was suspended in DCM and then it was concentrated. This was repeated one more time to give 2G (2.329 g, 100%) as a yellow solid. This material was used in the next step without further purification. MS(ESI) m/z: 313.1 (M+H)⁺.

2H. Methyl N-(3-amino-4-{2-[(1S)-1-{[(tert-butoxy)carbonyl]amino}but-3-en-1-yl]pyridin-4-yl}phenyl)carbamate: To a yellow suspension of 2G (2.328 g, 5.52 mmol) in DCM (18.40 mL) was added Boc₂O (1.282 mL, 5.52 mmol) followed by TEA (3.08 mL, 22.08 mmol). The resulting orange-brown solution was stirred at rt. After 3 h, the reaction was diluted with DCM and then washed with saturated NaHCO₃, brine, dried over MgSO₄, filtered, and concentrated. Purification by normal phase chromatography gave 2H (1.91 g, 84%) as an off-white solid. MS(ESI) m/z: 413.0 (M+H)⁺.

2I. Methyl N-(4-{2-[(1S)-1-{[(tert-butoxy)carbonyl] amino}but-3-en-1-yl]pyridin-4-yl}-3-(2-methylbut-3-enamido)phenyl)carbamate (Diastereomers): To a cooled solution (−10° C.) of 2-methylbut-3-enoic acid (0.456 mL, 4.41 mmol) and 2H (1.82 g, 4.41 mmol) in EtOAc (126 mL) and DIEA (2.312 mL, 13.24 mmol) was added dropwise a solution of 1-propanephosphonic acid cyclic anhydride in EtOAc (5.20 mL, 8.82 mmol). After 5 min, the reaction was allowed to warm to 0° C. After 7 h, the reaction was stopped and concentrated. Purification by normal phase chromatography gave 2I (1.57 g, 72%) as a mixture of diastereomers and as a yellow solid. MS(ESI) m/z: 495.1 (M+H)$^+$.

2J. ((E)-(10R,14S)-5-Methoxycarbonylamino-10-methyl-9-oxo-8,16-diaza-tricyclo[13.3.1.0$^{2,7}$]nonadeca-1(19),2(7),3,5,11,15,17-heptaen-14-yl)-carbamic acid tert-butyl ester, Diastereomer A and 2K. ((E)-(10S,14S)-5-Methoxycarbonylamino-10-methyl-9-oxo-8,16-diaza-tricyclo[13.3.1.0$^{2,7}$] nonadeca-1(19),2(7),3,5,11,15,17-heptaen-14-yl)-carbamic acid tert-butyl ester, Diastereomer B: To a RBF was added 2I (1.57 g, 3.17 mmol), pTsOH (0.664 g, 3.49 mmol), and DCM (794 mL). The flask was then equipped with a reflux condenser and the clear yellow solution was degassed with argon for 30 min. The reaction mixture was then warmed to 40° C. for 1 h. Then a solution of Grubbs II (0.269 g, 0.317 mmol) in DCM (2 mL) was added dropwise to the reaction mixture. The reaction mixture was then stirred at 40° C. After 6 h, the reaction was cooled to rt. The reaction was washed with saturated sodium carbonate, brine, dried over magnesium sulfate, filtered, and concentrated to give the crude product as a dark brown solid. Purification by normal phase chromatography gave 2J, Diastereomer A (0.374 g, 25%) as a brown solid and a mixture of 2J, Diastereomer A and 2K, Diastereomer B (0.44 g, 30%) as a brown solid. MS(ESI) m/z: 466.9 (M+H)$^+$.

2L. Methyl N-[(10R,14S)-14-{[(tert-butoxy)carbonyl] amino}-10-methyl-9-oxo-8,16-diazatricyclo[13.3.1.0$^{2,7}$] nonadeca-1(19),2(7),3,5,15,17-hexaen-5-yl]carbamate: A 500-mL hydrogenation flask was charged with 10% palladium on carbon (0.372 g, 0.349 mmol). The flask was purged with argon and then degassed methanol (72 mL) was added slowly to the flask. Next, a clear, light brown solution 2J (1.63 g, 3.49 mmol) in methanol (5 mL) was added. The flask was pressurized to 50 psi of hydrogen and the reaction was stirred overnight. After 20 h, the reaction was stopped, diluted with methanol (100 mL) and then the reaction was filtered through CELITE®, rinsing with methanol to give a clear, light brown filtrate. The filtrate was concentrated to give an off-white solid weighing 1.37 g. The off-white solid was suspended in methanol (10 mL) and sonicated. The solid was collected by filtration, rinsed with methanol (8 mL), air-dried, and dried under vacuum to give 2L (1.13 g, 69.0%) as a white solid. MS(ESI) m/z: 469.1 (M+H)$^+$.

2M. Methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, 2TFA salt: To a white suspension of 2L (0.45 g, 0.960 mmol) in DCM (5 mL) was added TFA (3 mL, 38.9 mmol). The resulting clear solution was stirred at rt. After 1 h, the reaction was concentrated to give a solid. Lyophilization gave 2M (0.52 g, 91%) as a yellow solid. MS(ESI) m/z: 369.0 (M+H)$^+$.

2M (Alternative, 2HCl): To a flask containing 2L (0.880 g, 1.878 mmol) was added 4.0 M HCl in dioxane (21.13 ml, 85 mmol). The resulting suspension was sonicated to give a clear, yellow solution. After 5 to 10 min, a precipitate formed. After 1 h, the reaction was stopped and the precipitate was collected by filtration. The solid was rinsed with dioxane and air-dried to give a hygroscopic, yellow solid. The solid was dissolved in methanol, concentrated, and lyophilized to give 2M (Alternative, 2HCl) (0.7171 g, 87%) as a yellow solid. MS(ESI) m/z: 369.3 (M+H)$^+$.

Example 2. Methyl N-[(10R,14S)-14-[1-(3-chlorophenyl) pyrrolidine-3-amido]-10-methyl-9-oxo-8,16-diazatricyclo [13.3.1.0$^{2,7}$]nonadeca-1(19),2(7),3,5,15,17-hexaen-5-yl] carbamate, 2TFA: A solution of 2M (0.02 g, 0.034 mmol), Intermediate 11 (0.011 g, 0.050 mmol), EDC (0.013 g, 0.067 mmol), HOBT (10.27 mg, 0.067 mmol) and TEA (0.023 mL, 0.168 mmol) in DMF (1 mL) was stirred at 50° C. After 2 h, the reaction was cooled to rt and then concentrated. Purification by reverse phase chromatography gave Example 2 (0.012 g, 44%) as a mixture of diastereomers and as a yellow solid. $^1$H NMR (500 MHz, CD$_3$OD) δ 8.80-8.72 (m, 1H), 8.20 (s, 1H), 7.99-7.91 (m, 1H), 7.68-7.48 (m, 3H), 7.15-7.07 (m, 1H), 6.65-6.43 (m, 3H), 5.11 (dd, J=10.6, 5.9 Hz, 1H), 3.79 (s, 3H), 3.59-3.47 (m, 1H), 3.43-3.26 (m, 4H), 2.82-2.73 (m, 1H), 2.37-2.09 (m, 3H), 1.99-1.84 (m, 2H), 1.69-1.47 (m, 2H), 0.97 (d, J=6.9 Hz, 3H), 0.55-0.41 (m, 1H) ppm. MS(ESI) m/z: 576.3 (M+H)$^+$. Analytical HPLC RT=6.70 min.

The preferred sequence for the preparation of compound 2J is described below:

2B (Alternative). (S)—N—((S)-1-(4-Chloropyridin-2-yl) but-3-enyl)-2-methylpropane-2-sulfinamide: To a cooled (0-5° C.) mixture of indium(III) chloride (13.56 g, 61.3 mmol) in tetrahydrofuran (170 mL) was added dropwise over 30 min. Allylmagnesium bromide (1 M in diethylether) (62 mL, 61.3 mmol). The reaction was allowed to warm to rt. After 1 h at rt, a solution of 2A (10 g, 40.9 mmol) in ethanol (170 mL) was added. After 2-3 h, the reaction was concentrated under vacuum at 50-55° C. The crude material was partitioned between ethyl acetate (200 mL) and water (50 mL) and the layers were separated. The aqueous layer was extracted with ethyl acetate (2×50 mL). The organic layers were combined and washed with brine (100 mL), dried over sodium sulfate, filtered and concentrated to give 2B (Alternative) (13.5 g, 106%) as a yellow oil. MS(ESI) m/z: 287.2 (M+H)$^+$. This material was used in the next step without further purification.

2N. (S)-tert-Butyl 1-(4-Chloropyridin-2-yl)but-3-enylcarbamate: Compound 2B (Alternative) was converted to 2N in two steps by removal of the chiral auxiliary according to the procedure in step 2G and Boc-protection according to the procedure in step 2H. MS(ESI) 227.3 (M-C$_4$H$_8$+H)$^+$ and 305.4 (M+Na)$^+$.

2O. (S)-tert-Butyl 1-(4-(2-amino-4-nitrophenyl)pyridin-2-yl)but-3-enylcarbamate: Compound 2O was prepared by following the procedure described in step 2C, by replacing 2B with 2N. MS(ESI) 385.1 (M+H)$^+$.

2P. (S)-tert-Butyl 1-(4-(2,4-diaminophenyl)pyridin-2-yl) but-3-enylcarbamate: To a clear, orange solution of 2O (2.9 g, 7.54 mmol) in methanol (75 mL) was added sequentially zinc dust (4.93 g, 75 mmol) and ammonium chloride (4.04 g, 75 mmol). The resulting suspension was stirred vigorously for 4 h. The reaction was stopped and filtered through a 0.45 micron GMF eluting with methanol to give a clear, yellow filtrate. Concentration of the filtrate gave a yellow-black residue. The residue was partitioned between EtOAc and 0.25 M HCl (50 mL) and the layers were separated. The organic layer was extracted with 0.25 M HCl (50 mL). The combined aqueous layers were basified with 1.5 M K$_2$HPO$_4$ and then extracted with EtOAc (3×). The combined organic layers were washed with brine, dried over Na$_2$SO$_4$, filtered and concentrated to give 2P (2.63 g, 98%) as a brown foam. MS(ESI) m/z: 355.2 (M+H)$^+$.

2Q. {3-Amino-4-[2-((S)-1-tert-butoxycarbonylamino-but-3-enyl)-pyridin-4-yl]-phenyl}-carbamic acid methyl ester: To a cooled (−78° C.) clear, brown solution of 2P (2.63 g, 7.42 mmol) and pyridine (0.600 ml, 7.42 mmol) in dichloromethane (74.2 ml) was added dropwise over 30 min methyl chloroformate (0.516 ml, 6.68 mmol). The reaction was stirred at −78° C. After 1.5 h, the reaction was quenched with sat. NH₄Cl and allowed to warm to rt. The reaction was diluted with DCM and water and the layers were separated. The aqueous layer was extracted with DCM. The combined organic layers were washed with saturated NaHCO₃, brine, dried over Na₂SO₄, filtered and concentrated. The residue dissolved in DCM (~10 mL) and then hexane (~300 mL) was added to give a brown suspension with brown gummy sticky substance at the bottom. The mixture was sonicated to give a mostly clear solution with the brown substance at the bottom. The solution decanted and the bottom substance rinsed with hexane, dried to give 2Q (2.7 g, 88%) as a slightly brown foam. MS(ESI) m/z: 413.2 (M+H)⁺.

2I (Alternative). Methyl N-(4-{2-[(1S)-1-{[(tert-butoxy)carbonyl]amino}but-3-en-1-yl]pyridin-4-yl}-3-[(2R)-2-methylbut-3-enamido]phenyl)carbamate: Intermediate 45 (1.201 g, 12.00 mmol), 2Q (3.3 g, 8.00 mmol), pyridine (1.937 ml, 24.00 mmol) in EtOAc (40.0 mL) was cooled down to −10° C. under Ar, T3P (50 wt % in EtOAc) (9.52 mL, 16.00 mmol) was added dropwise and stirred at −10° C., then gradually warmed up to rt over night. The reaction mixture was washed with saturated NaHCO₃ twice. The combined aqueous layer was extracted with EtOAc. The combined EtOAc phase washed with brine, dried over MgSO₄, filtered, concentrated. The crude product was then purified using silica gel chromatography to give the desired the desired product (4.06 g, 97%) as a white solid. ¹H NMR (500 MHz, MeOD) δ 8.46 (d, J=5.0 Hz, 1H), 7.64 (s, 1H), 7.47 (dd, J=8.4, 2.1 Hz, 1H), 7.35 (s, 1H), 7.29 (d, J=8.3 Hz, 1H), 7.25 (m, 1H), 5.87-5.73 (m, 2H), 5.16-5.02 (m, 4H), 4.79-4.71 (m, 1H), 3.75 (s, 3H), 3.14-3.05 (m, 1H), 2.64-2.55 (m, 1H), 2.52-2.43 (m, 1H), 1.42 (s, 9H), 1.16 (d, J=6.9 Hz, 3H). MS(ESI) m/z: 495.1 (M+H)⁺.

2J (Alternative). Methyl N-[(10R,11E,14S)-14-{[(tert-butoxy)carbonyl]amino}-10-methyl-9-oxo-8,16-diazatricyclo[13.3.1.0²,⁷]nonadeca-1(19),2(7),3,5,11,15,17-heptaen-5-yl]carbamate: To a RBF was added 2I (Alternative) (0.5 g, 1.011 mmol), pTsOH monohydrate (0.212 g, 1.112 mmol), and dichloromethane (84 ml). The flask was equipped with a reflux condenser and the clear yellow solution was degassed with argon for 30 min. The reaction was then warmed to reflux for 1 h. Then a solution of Grubbs II (0.172 g, 0.202 mmol) in DCM (2 mL) was added dropwise to the reaction mixture. After 4 h at reflux, the reaction was cooled to rt, washed with saturated Na₂CO₃, brine, dried over MgSO₄, filtered, and concentrated to give brown solid. The crude product was then purified using silica gel chromatography to give the desired product (0.336 g, 71%) as a yellow solid. ¹H NMR (500 MHz, MeOD) δ 8.52 (d, J=5.2 Hz, 1H), 7.54 (d, J=1.4 Hz, 1H), 7.48-7.43 (m, 1H), 7.38 (d, J=8.3 Hz, 1H), 7.24 (dd, J=5.1, 1.5 Hz, 1H), 6.89 (s, 1H), 5.75-5.65 (m, 1H), 4.60 (dd, J=11.3, 3.6 Hz, 1H), 4.39 (dd, J=15.1, 9.6 Hz, 1H), 3.75 (s, 3H), 3.14-3.06 (m, 1H), 2.75-2.68 (m, 1H), 2.04-1.94 (m, 1H), 1.44 (s, 9H), 1.30 (br. s., 1H), 1.04 (d, J=6.6 Hz, 3H). MS(ESI) m/z: 467.2 (M+H)⁺.

The following Examples in Table 2 were made by using the same procedure as shown in Example 2. The acids used in the final step are as indicated in the below table in the Intermediate section. Various coupling reagents could be used other than the one described in Example 2 such as BOP, PyBop, EDC/HOBt or HATU. If needed, the coupled products are subjected to TFA deprotection condition to remove the tert-Butyl protecting group.

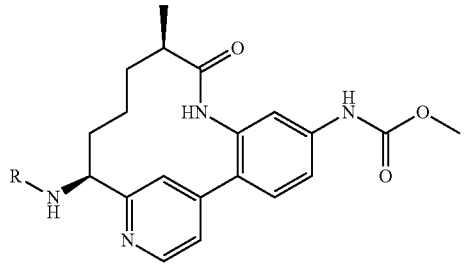

TABLE 2

| Example # | Stereochemistry | R | M + H | RT, min Method |
|---|---|---|---|---|
| 3 | Homochiral | (structure: triazole-C(O)- linked to 2-fluoro-3-chlorophenyl) | 592.0 | 7.47 A |

TABLE 2-continued
| Example # | Stereochemistry | R | M + H | RT, min Method |
|---|---|---|---|---|
| 4 | Homochiral | 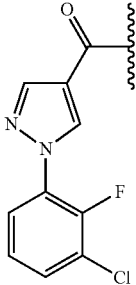 [SMILES: *C(=O)c1cnn(-c2cccc(Cl)c2F)c1] | 591.1 | 6.93 A |
| 5 | Homochiral | 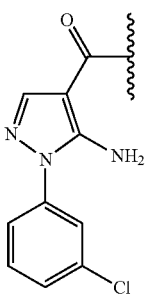 | 588.0 | 6.32 A |
| 6 | Homochiral | 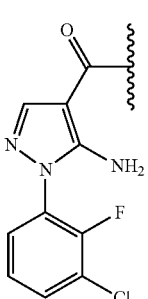 | 606.4 | 4.94 D |
| 7 | Homochiral | 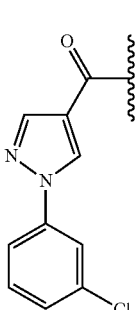 | 573.0 | 7.05 A |
| 8 | Homochiral | 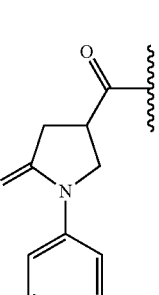 | 590.3 | 5.69 A |

TABLE 2-continued
| Example # | Stereochemistry | R | M + H | RT, min Method |
|---|---|---|---|---|
| 9 | Homochiral | 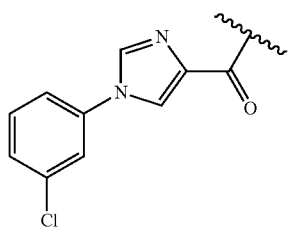 [SMILES: *C(=O)c1cn(-c2cccc(Cl)c2)cn1] | 573.4 | 5.64 A |
| 10 | Homochiral | 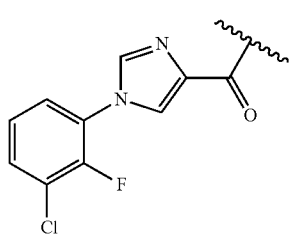 [SMILES: *C(=O)c1cn(-c2cccc(Cl)c2F)cn1] | 591.4 | 5.72 A |
| 11 | Diastereomer | 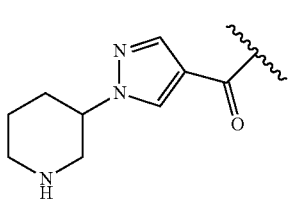 [SMILES: *C(=O)c1cnn(C2CCCNC2)c1] | 546.4 | 2.77 D |
| 12 | Homochiral | 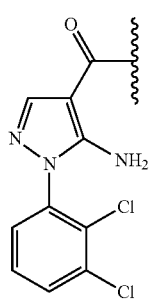 | 622.3 | 5.50 A |
| 13 | Homochiral | 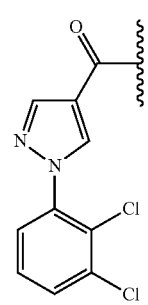 [SMILES: *C(=O)c1cnn(-c2cccc(Cl)c2Cl)c1] | 607.3 | 6.00 A |

TABLE 2-continued
| Example # | Stereochemistry | R | M + H | RT, min Method |
|---|---|---|---|---|
| 14 | Homochiral | 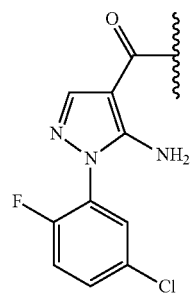 [SMILES: *C(=O)c1cnn(-c2cc(Cl)ccc2F)c1N] | 606.3 | 4.79 D |
| 15 | Homochiral | 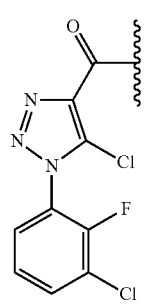 [SMILES: *C(=O)c1nnn(-c2cccc(Cl)c2F)c1Cl] | 626.0 | 5.72 A |
| 16 | Homochiral | 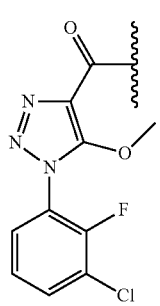 | 622.1 | 5.64 A |
| 17 | Homochiral | 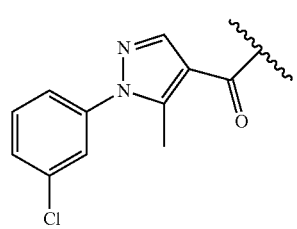 [SMILES: *C(=O)c1cnn(-c2cccc(Cl)c2)c1C] | 587.3 | 5.18 D |
| 18 | Homochiral | 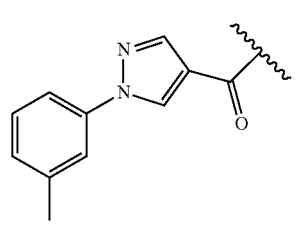 [SMILES: *C(=O)c1cnn(-c2cccc(C)c2)c1] | 553.4 | 4.82 D |

TABLE 2-continued

| Example # | Stereochemistry | R | M + H | RT, min Method |
|---|---|---|---|---|
| 19 | Homochiral | (structure: 4-chloro-2-nitrophenyl azetidine ketone) | 607.4 | 6.16 A |
| 20 | Homochiral | (structure: 3-(3-chlorophenyl)-1H-pyrazole ketone) | 573.3 | 5.22 D |

*Subjected to TFA deprotection

Example 21

Methyl N-[(14S)-14-[1-(3-chloro-2-fluorophenyl)-1H-pyrazole-4-amido]-9-oxo-8,16-diazatricyclo[13.3.1.0²,⁷]nonadeca-1(19),2(7),3,5,15,17-hexaen-5-yl]carbamate, TFA salt

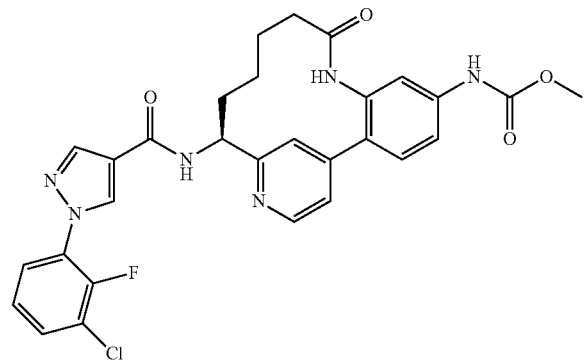 [SMILES: COC(=O)Nc1ccc2c(c1)NC(=O)CCCC[C@H](NC(=O)c1cnn(-c3cccc(Cl)c3F)c1)c1cc-2ccn1]

21A. Methyl (3-(but-3-enoylamino)-4-(2-((1S)-1-((tert-butoxycarbonyl)amino)but-3-en-1-yl)pyridin-4-yl)phenyl)carbamate: To a solution of but-3-enoic acid (0.412 mL, 4.85 mmol) in EtOAc (100 mL) was added DIEA (2.54 mL, 14.55 mmol) and 2G (2 g, 4.85 mmol) and the reaction mixture was allowed to cooled to −78° C. under argon. To this mixture was then added T3P (5.71 mL, 9.70 mmol) and the reaction was allowed to stir for 15 min at the same temperature and the reaction temperature was gradually warmed to rt and stirred at rt for overnight. After stirring for overnight at rt, the reaction mixture was concentrated to yield dark brown oil which was purified using silica gel chromatography to yield the desired product (1.88 g, 81%) as a white solid. MS(ESI) m/z: 481.2 (M+H)⁺.

21B. tert-Butyl methyl ((4E,7S)-2-oxo-2,3,6,7-tetrahydro-1H-8,12-(metheno)-1,9-benzodiazacyclotetradecine-7,15-diyl)biscarbamate: To a RBF was added 21A (1.57 g, 3.27 mmol), pTsOH (0.684 g, 3.59 mmol) and DCM (817 mL). The flask was then equipped with a reflux condenser and the clear yellow solution was degassed with argon for 70 min. The reaction was then warmed to 40° C. for 1 h. In a separate RBF was added Grubbs II (1.109 g, 1.307 mmol) and the flask was purged with argon for several minutes. Degassed DCM (2 mL) was added to give a clear, burgundy solution. The solution was then added dropwise over 15 min via a syringe to the above reaction. The reaction mixture was stirred at 40-45° C. After stirring for 3 h, the reaction was gradually allowed to cool to rt and stirred at rt overnight. The reaction mixture was then washed with saturated Na₂CO₃ solution followed by brine. The organic layers were then dried over MgSO₄, filtered, and concentrated to give dark brown oil. The crude product was purified using silica gel chromatography to give the desired product (395 mg, 26%) as light brown gray solid. MS(ESI) m/z: 453.1 (M+H)⁺.

21C. tert-Butyl methyl ((7S)-2-oxo-2,3,4,5,6,7-hexahydro-1H-8,12-(metheno)-1,9-benzodiazacyclotetradecine-7,15-diyl)biscarbamate: A mixture of 21B (395 mg, 0.873 mmol) and palladium(II) carbon (93 mg, 0.087 mmol) in MeOH (5 mL) was stirred under a hydrogen atmosphere (50-55 psi). After stirring for 8 h, the reaction mixture was filtered through microfilter to yield the desired product (350 mg, 88%) as red brown solid. MS(ESI) m/z: 455.2 (M+H)⁺.

21D. Methyl ((7S)-7-amino-2-oxo-2,3,4,5,6,7-hexahydro-1H-8,12-(metheno)-1,9-benzodiazacyclotetradecin-15-yl)carbamate: A mixture of 21C (20 mg, 0.044 mmol) and HCl (550 µL, 2.200 mmol) (4 N in dioxane) was stirred at rt. After stirring for 2 h, the reaction mixture was concentrated to yield a tan yellow powder as the desired product (18 mg, 99%). MS(ESI) m/z: 355.2 (M+H)⁺.

Example 21. Methyl N-[(14S)-14-[1-(3-chloro-2-fluorophenyl)-1H-pyrazole-4-amido]-9-oxo-8,16-diazatricyclo[13.3.1.0²,⁷]nonadeca-1(19),2(7),3,5,15,17-hexaen-5-yl]carbamate, TFA salt: A mixture of Intermediate 2 (5.57 mg, 0.023 mmol), HOBT (6.45 mg, 0.042 mmol), EDC (8.07 mg, 0.042 mmol) and DIEA (0.037 mL, 0.211 mmol) in DMF (0.2 mL) was stirred at rt for 15 min. To this mixture was then added 21D (9 mg, 0.021 mmol) and stirred at rt for overnight. The reaction mixture was concentrated and purified by reverse phase HPLC to isolate the desired product (7.2 mg, 48%) as an off white solid. $^1$H NMR (500 MHz, CD$_3$CN) δ 8.82 (d, J=5.78 Hz, 1H), 8.55 (d, J=6.05 Hz, 1H), 8.49 (d, J=2.20 Hz, 1H), 8.31 (s, 1H), 8.07 (s, 1H), 8.05 (d, J=J=16, 2H), 7.98 (s, 1H), 7.68 (t, J=1.38 Hz, 1H), 7.64 (dd, J=1.65, 6.05 Hz, 1H), 7.43 (m, 2H), 7.37 (m, 2H), 7.22 (dt, J=1.51, 8.18 Hz, 1H), 5.31 (m, 1H), 3.63 (s, 3H), 2.40 (m, 2H), 2.00 (m, 2H), 1.71 (m, 2H), 1.55 (m, 1H), 1.38 (dd, J=3.85, 11.00 Hz, 1H), 0.43 (m, 1H) ppm. MS(ESI) m/z: 577.2 (M+H)$^+$. Analytical HPLC (Method E) RT=5.79 min.

Example 22

Methyl N-[(14S)-14-[1-(3-chloro-2-fluorophenyl)-1H-pyrazole-4-amido]-10-methyl-9-oxo-8,16,17-triazatricyclo[13.3.1.0$^{2,7}$]nonadeca-1(19),2(7),3,5,15,17-hexaen-5-yl]carbamate, TFA salt

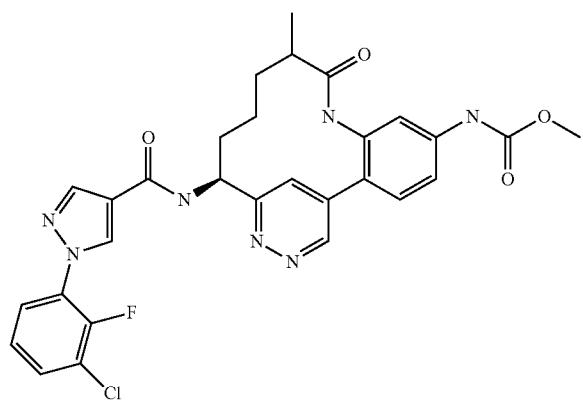 [SMILES: COC(=O)Nc1ccc2c(c1)NC(=O)C(C)CCC[C@H](NC(=O)c1cnn(-c3cccc(Cl)c3F)c1)c1cc-2cnn1]

22A. (S)-tert-Butyl 1-(dimethoxyphosphoryl)-2-oxohex-5-en-3-ylcarbamate: To a solution of dimethyl methylphosphonate (15.85 ml, 148 mmol) in THF (99 mL) at −78° C. was added n-butyllithium (93 mL, 148 mmol) dropwise. After completion of addition, the reaction was stirred at the same temperature for 30 min and then a solution of (S)-methyl 2-(tert-butoxycarbonylamino)pent-4-enoate (6.8 g, 29.7 mmol) in THF (15 mL) was added dropwise. The reaction mixture was then stirred for another 40 min at −78° C. The reaction was then quenched by adding H$_2$O and diluted with EtOAc. The organic layer was washed with 1 M HCl, saturated NaHCO$_3$ solution and brine. The organic phase was dried over MgSO$_4$, filtered and concentrated to give clear oil. The crude product was then purified by silica gel chromatography to give the desired product (9.3 g, 98%) as colorless oil. MS(ESI) m/z: 599.0 (M+Na)$^+$.

22B. Methyl 4-iodo-3-nitrophenylcarbamate: To a cooled (0° C.), yellow suspension of 4-iodo-3-nitroaniline (1.320 g, 5 mmol) in DCM (50.0 mL) and pyridine (0.445 mL, 5.50 mmol) was added dropwise methyl chloroformate (0.407 mL, 5.25 mmol) and stirred for 3 h. The reaction was then diluted with DCM, washed with brine, dried over MgSO$_4$, filtered and concentrated. The crude product was then dissolved in minimal DCM (~20 mL) and then hexane (200 mL) was added to give a yellow suspension. The yellow suspension was then filtered and the filtered solid was rinsed with hexane and air-dried to obtain a yellow solid as the desired product (1.51 g, 94%). MS(ESI) m/z: 322.9 (M+H)$^+$.

22C. Methyl 4-acetyl-3-nitrophenylcarbamate: A solution of 22B (0.5 g, 1.553 mmol), tributyl(1-ethoxyvinyl)stannane (1.049 mL, 3.11 mmol), and bis(triphenylphosphine)palladium(II) chloride (0.109 g, 0.155 mmol) in toluene (3 mL) in a sealed tube was heated at 110° C. After 3 h, the reaction was cooled to rt and concentrated to yield a residue. The residue was dissolved in THF (3 mL), followed by addition of 1 N HCl solution (5 mmol). The above mixture was then stirred at rt for 1 h and then diluted with EtOAc. The EtOAc mixture was then washed with brine, dried over Na$_2$SO$_4$, filtered and concentrated to give the crude product which was purified by silica gel chromatography to obtain the desired product (0.254 g, 69%) as a yellow solid. MS(ESI) m/z: 239.3 (M+H)$^+$.

22D. 2-(4-((Methoxycarbonyl)amino)-2-nitrophenyl)-2-oxoacetic acid: To a solution of 22C (11.5 g, 48.3 mmol) in pyridine (48.3 mL) was added selenium dioxide (8.04 g, 72.4 mmol) in portions. The reaction mixture was then stirred under argon at 60° C. overnight and concentrated. The residue was pumped for several hours to make sure most pyridine was removed. To the solid was then added 1.0 N HCl (80 mL) and filtered to obtain a grayish solid which was dried in a vacuum-oven at 45° C. overnight. The grayish solid was then mixed with MeOH (200 mL) to yield a suspension which was then filtered and the filtrate was concentrated to give brownish foam (11.8 g, 79%) with still some residual pyridine in it. MS(ESI) m/z: 269.0 (M+H)$^+$.

22E. Methyl 2-(4-((methoxycarbonyl)amino)-2-nitrophenyl)-2-oxoacetate: To a red oil of 22D (11.8 g, 38.3 mmol) in DCM (150 mL) at 0° C. was added TEA (7.47 mL, 53.6 mmol) and the mixture was subjected to sonication to form a red-colored solution. To this mixture was then added methyl carbonochloridate (4.15 mL, 53.6 mmol) at 0° C. After 20 min, the reaction mixture was diluted with DCM (300 mL), washed with 1 M HCl, saturated NaHCO$_3$ solution and brine. The organic phase was dried over MgSO$_4$, filtered and concentrated to give a red colored solid. The crude product was then purified by silica gel chromatography to yield the desired product (8.6 g, 80%) as light grayish powder. MS(ESI) m/z: 283.0 (M+H)$^+$.

22F. Methyl (4-(6-((1S)-1-((tert-butoxycarbonyl)amino)but-3-en-1-yl)-3-oxo-2,3-dihydropyridazin-4-yl)-3-nitrophenyl)carbamate: To a clear solution of 22A (1.16 g, 3.61 mmol) in EtOH (38.4 mL) at rt was added K$_2$CO$_3$ (0.748 g, 5.42 mmol). The reaction mixture was stirred for 2 h and then concentrated to yield a residue which was dried under vacuum for 1 h. To the residue was then added THF (30 mL) followed by addition of a suspension of 22E (1.121 g, 3.97 mmol) in 8 mL of THF dropwise via an addition funnel After 3 h, hydrazine (0.567 mL, 18.05 mmol) was added and the reaction was stirred at rt for 4 days. The reaction mixture was then diluted with EtOAc, washed with 1 N HCl and brine. The organic layer was then dried over MgSO$_4$, filtered, and concentrated to give the crude product that was purified by silica gel chromatography to give the desired product (0.48 g, 29%) as a light orange solid. MS(ESI) m/z: 460.0 (M+H)$^+$.

22G. (S)-Methyl (4-(6-(1-aminobut-3-en-1-yl)-3-chloropyridazin-4-yl)-3-nitrophenyl)carbamate: To a solution of 22F (2.2 g, 4.79 mmol) in MeOH (23.94 mL) was added HCl (4 M in Dioxane) (5.186 mL, 20.74 mmol) and stirred at rt for 6 h. The reaction mixture was then concentrated to yield a brownish solid. To the brownish solid was added ACN (23.94 mL) and phosphoryl trichloride (13.39 mL, 144 mmol), and the reaction mixture was heated at 80° C.

overnight. After overnight stirring, the reaction mixture was concentrated and dried under vacuum overnight. The crude mixture was then cooled down to 0° C., followed by addition of 1 N HCl (20 mL) to quench the reaction. Neutralized the mixture with 1 N NaOH and extracted with EtOAc (2×). The organic layers were then combined, washed with brine, dried and concentrated to give a brownish solid as the desired product (1.03 g, 57%). MS(ESI) m/z: 377.9 (M+H)+.

22H. Methyl (4-(6-(1-((tert-butoxycarbonyl)amino)but-3-en-1-yl)-3-chloropyridazin-4-yl)-3-nitrophenyl)carbamate: To a solution of 22G (1.03 g, 2.73 mmol) in DCM (27.3 mL) at 0° C. was added TEA (1.140 mL, 8.18 mmol) and Boc₂O (0.760 mL, 3.27 mmol). The reaction was then stirred at 0° C. for 10 min and then was slowly allowed to warm to rt and stirred overnight. The crude product was concentrated and purified by silica gel chromatography to isolate the desired product (414 mg, 36%) as orange colored foam. MS(ESI) m/z: 477.9 (M+H)+.

22I. Methyl (3-amino-4-(6-((1S)-1-((tert-butoxycarbonyl)amino)but-3-en-1-yl)-3-chloropyridazin-4-yl)phenyl) carbamate: To a mixture of 22H (472 mg, 0.988 mmol) and iron powder (276 mg, 4.94 mmol) in acetic acid (7.407 mL) was added H₂O (2.469 mL) and heated at 70° C. for 1 h. The reaction mixture was then cooled down using an ice-H₂O bath, followed by neutralization with 10 N NaOH (aq), and at final stage concentrated NaHCO₃ solution was used to adjusted pH to 7-8. The reaction mixture was then extracted with EtOAc (3×) and the combined EtOAc layers were further washed with brine, dried over MgSO₄, filtered, concentrated and purified by silica gel chromatography. The purified product was then subjected to chiral HPLC separation using CHIRALPAK® AD column and 40% isopropanol/60% heptane) mixture as mobile phase. Two peaks were seen eluting and peak 1 was designated as Diastereomer A (22Ia) and peak 2 was designated as Diastereomer B (22IB) (144 mg, 32%). MS(ESI) m/z: 447.8 (M+H)+.

Example 22. Methyl N-[(14S)-14-[1-(3-chloro-2-fluorophenyl)-1H-pyrazole-4-amido]-10-methyl-9-oxo-8,16,17-triazatricyclo[13.3.1.0²,⁷]nonadeca-1(19),2(7),3,5,15,17-hexaen-5-yl]carbamate, TFA salt: Example 22 was made in the same way as Example 1 by replacing 1F with 22I followed by substituting Intermediate 2 for Intermediate 14 at the last coupling step. The coupling reagent used in the last step was EDC/HOBt and the desired product was isolated as a homochiral compound. ¹H NMR (400 MHz, MeOD) δ 9.56 (br. s., 1H), 9.22 (br. s., 1H), 7.82 (d, J=1.8 Hz, 1H), 7.62 (d, J=8.6 Hz, 4H), 7.11-7.01 (m, 1H), 5.81 (dd, J=11.9, 2.8 Hz, 1H), 5.40 (dd, J=12.3, 5.4 Hz, 1H), 4.45-4.36 (m, 1H), 3.85-3.74 (m, 4H), 2.90-2.48 (m, 2H), 2.39-2.21 (m, 2H), 2.12-1.99 (m, 1H), 1.94-1.78 (m, 1H), 1.56-1.20 (m, 2H), 0.97 (d, J=6.8 Hz, 3H), 0.67 (br. s., 1H) ppm. MS(ESI) m/z: 592.1 (M+H)+. Analytical HPLC (Method A) RT=8.25 min.

Example 23

Methyl N-[(14S)-14-[1-(3-chloro-2-fluorophenyl)-1H-pyrazole-4-amido]-10-methyl-9-oxo-8,16,17-triazatricyclo[13.3.1.0²,⁷]nonadeca-1(19),2(7),3,5,15,17-hexaen-5-yl]carbamate, TFA salt
(Diastereomer A)

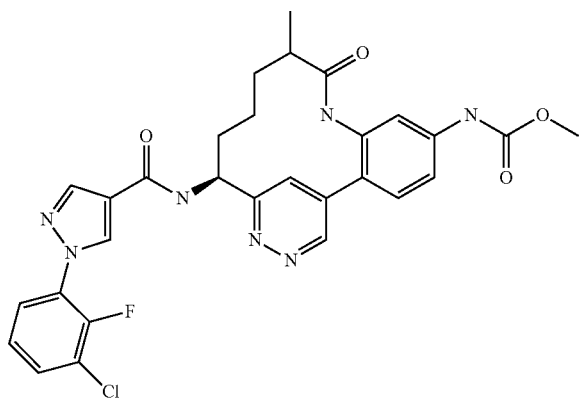 [SMILES: COC(=O)Nc1ccc2c(c1)NC(=O)C(C)CCC[C@H](NC(=O)c1cnn(-c3cccc(Cl)c3F)c1)c1cc-2cnn1]

Example 23. Methyl N-[(14S)-14-[1-(3-chloro-2-fluorophenyl)-1H-pyrazole-4-amido]-10-methyl-9-oxo-8,16,17-triazatricyclo[13.3.1.0²,⁷]nonadeca-1(19),2(7),3,5,15,17-hexaen-5-yl]carbamate, TFA salt: Example 23 was made in the same way as Example 22 by replacing 22IB with 22IA. ¹H NMR (500 MHz, MeOD) δ 9.67 (s, 1H), 9.43 (br. s., 1H), 8.75-8.70 (m, 1H), 8.27-8.18 (m, 2H), 7.82 (ddd, J=8.3, 6.8, 1.7 Hz, 1H), 7.67 (d, J=8.5 Hz, 1H), 7.63-7.49 (m, 4H), 7.37 (td, J=8.2, 1.5 Hz, 1H), 5.43-5.29 (m, 1H), 3.84-3.77 (m, 1H), 2.82-2.69 (m, 1H), 2.26-2.00 (m, 2H), 1.96-1.83 (m, 1H), 1.66-1.42 (m, 2H), 0.98 (d, J=6.9 Hz, 3H), 0.50 (d, J=11.8 Hz, 1H) ppm. MS(ESI) m/z: 592.0 (M+H)+. Analytical HPLC (Method A) RT=8.27 min.

Example 24

Methyl N-[(14S)-14-[1-(3-chloro-2-fluorophenyl)-1H-1,2,3-triazole-4-amido]-10-ethyl-9-oxo-8,16-diazatricyclo[13.3.1.0²,⁷]nonadeca-1(19),2(7),3,5,15,17-hexaen-5-yl]carbamate, TFA salt

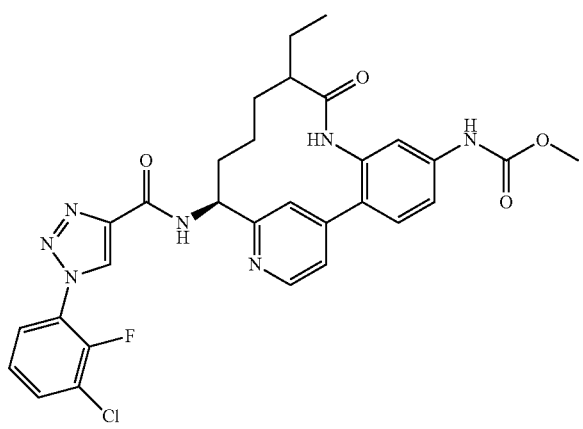 [SMILES: CCC1CCC[C@H](NC(=O)c2cn(-c3cccc(Cl)c3F)nn2)c2cc(ccn2)-c2ccc(NC(=O)OC)cc2NC1=O]

24A. Methyl (4-(2-((1S)-1-((tert-butoxycarbonyl)amino) but-3-en-1-yl)pyridin-4-yl)-3-(2-ethylbut-3-enoyl)amino) phenyl)carbamate: Compound 24A was prepared following the procedure described in 2I by replacing 2-methylbut-3-enoic acid with 2-ethylbut-3-enoic acid. Purification by normal phase chromatography gave 24A (0.412 g, 74%) as a yellow foam. MS(ESI) m/z: 509.3 (M+H)$^+$.

24B. tert-Butyl methyl ((4E,7S)-3-ethyl-2-oxo-2,3,6,7-tetrahydro-1H-8,12-(metheno)-1,9-benzodiazacyclotetradecine-7,15-diyl)biscarbamate (Diastereomer A) and 24C. tert-Butyl methyl ((4E,7S)-3-ethyl-2-oxo-2,3,6,7-tetrahydro-1H-8,12-(metheno)-1,9-benzodiazacyclotetradecine-7,15-diyl)biscarbamate (Diastereomer B): Compounds 24B and 24C were prepared following the procedure described in 1H, by replacing 1G with 24A. Purification by normal phase chromatography gave 24C (peak 1, designated as Diastereomer B) [0.05 g, 16%, MS(ESI) m/z: 481.2 (M+H)$^+$] and 24B (peak 2, designated as Diastereomer A) [0.03 g, 10%, MS(ESI) m/z: 481.2 (M+H)$^+$].

24D. tert-Butyl methyl ((3R,7S)-3-ethyl-2-oxo-2,3,4,5,6,7-hexahydro-1H-8,12-(metheno)-1,9-benzodiazacyclotetradecine-7,15-diyl)biscarbamate (Diastereomer C): To a degassed solution of 24C (0.05 g, 0.104 mmol) in MeOH (5 mL) was added 10% palladium on carbon (0.011 g, 10.40 µmol). The reaction mixture was then stirred under H$_2$-balloon for 72 h. The reaction mixture was then filtered through a pad of CELITE® rinsing with MeOH and DCM. The filtrate was concentrated to give 24D (0.045 g, 90%) as a brown solid. This material was used in the next step without further purification. MS(ESI) m/z: 483.3 (M+H)$^+$.

Example 24. Methyl N-[(14S)-14-[1-(3-chloro-2-fluorophenyl)-1H-1,2,3-triazole-4-amido]-10-ethyl-9-oxo-8,16-diazatricyclo[13.3.1.0$^{2,7}$]nonadeca-1(19),2(7),3,5,15,17-hexaen-5-yl]carbamate, TFA salt: Example 24 (0.006 g, 49%, yellow solid) was prepared following the procedures described in step 2M, by replacing 2L with 24D; followed by step 2N, by replacing Intermediate 11 with Intermediate 1. $^1$H NMR (500 MHz, CD$_3$OD) δ 8.91 (d, J=2.2 Hz, 1H), 8.76 (d, J=6.1 Hz, 1H), 8.26 (d, J=1.4 Hz, 1H), 7.93 (dd, J=6.1, 1.7 Hz, 1H), 7.86 (ddd, J=8.2, 6.7, 1.4 Hz, 1H), 7.75 (ddd, J=8.2, 6.8, 1.5 Hz, 1H), 7.66 (d, J=8.5 Hz, 1H), 7.61 (d, J=2.2 Hz, 1H), 7.53 (dd, J=8.5, 2.2 Hz, 1H), 7.45 (td, J=8.3, 1.4 Hz, 1H), 5.40 (dd, J=11.4, 5.9 Hz, 1H), 3.80 (s, 3H), 2.56-2.50 (m, 1H), 2.33-2.24 (m, 1H), 2.09-2.01 (m, 1H), 1.96-1.88 (m, 1H), 1.73-1.46 (m, 3H), 1.36-1.25 (m, 1H), 0.89 (t, J=7.4 Hz, 3H), 0.70-0.59 (m, 1H) ppm. MS(ESI) m/z: 606.3 (M+H)$^+$. Analytical HPLC (Method A) RT=6.32 min.

Example 25

Methyl N-[(14S)-14-[1-(3-chloro-2-fluorophenyl)-1H-1,2,3-triazole-4-amido]-10-ethyl-9-oxo-8,16-diazatricyclo[13.3.1.0$^{2,7}$]nonadeca-1(19),2(7),3,5,15,17-hexaen-5-yl]carbamate, TFA salt

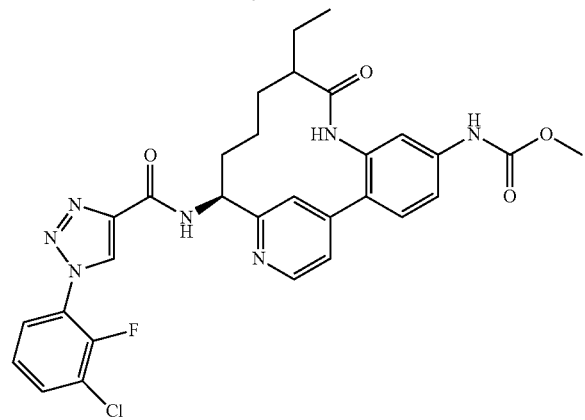 [SMILES: CCC1CCC[C@H](NC(=O)c2cn(-c3cccc(Cl)c3F)nn2)c2cc(ccn2)-c2ccc(NC(=O)OC)cc2NC1=O]

Example 25. Methyl N-[(14S)-14-[1-(3-chloro-2-fluorophenyl)-1H-1,2,3-triazole-4-amido]-10-ethyl-9-oxo-8,16-diazatricyclo[13.3.1.0$^{2,7}$]nonadeca-1(19),2(7),3,5,15,17-hexaen-5-yl]carbamate, TFA salt: Example 25 (0.013 g, 60%, yellow solid) was prepared following the procedures described in Example 24, by replacing 24C (Diastereomer B) with 24B (Diastereomer A) in step 24D. $^1$H NMR (500 MHz, CD$_3$OD) δ 8.87 (d, J=2.2 Hz, 1H), 8.69 (d, J=5.2 Hz, 1H), 7.87 (ddd, J=8.1, 6.6, 1.5 Hz, 1H), 7.77-7.70 (m, 2H), 7.62-7.51 (m, 4H), 7.45 (td, J=8.2, 1.5 Hz, 1H), 5.29 (dd, J=11.0, 5.0 Hz, 1H), 3.79 (s, 3H), 2.22-2.04 (m, 2H), 1.92-1.76 (m, 3H), 1.61-1.38 (m, 3H), 1.03 (t, J=7.3 Hz, 3H), 0.91-0.78 (m, 1H) ppm. MS(ESI) m/z: 606.2 (M+H)$^+$. Analytical HPLC (Method A) RT=7.09 min.

Example 26

Ethyl (9R,14S)-14-[1-(3-chloro-2-fluorophenyl)-1H-pyrazole-4-amido]-5-[(methoxycarbonyl)amino]-8,16-diazatricyclo[13.3.1.0$^{2,7}$]nonadeca-1(19),2(7),3,5,15,17-hexaene-9-carboxylate, 2 TFA salt

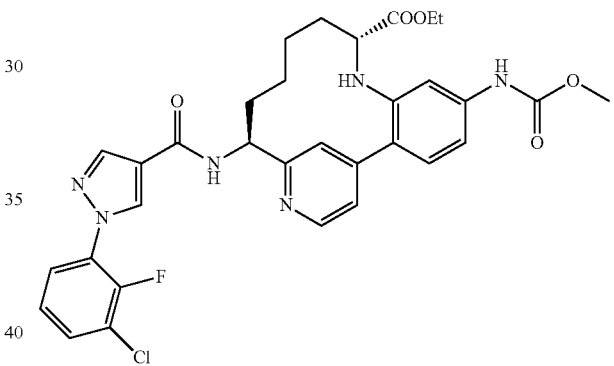

26A. Ethyl 2-((2-(2-((S)-1-((tert-butoxycarbonyl)amino) but-3-en-1-yl)pyridin-4-yl)-5-((methoxycarbonyl)amino) phenyl)amino)pent-4-enoate: A mixture of 2G (954 mg, 2.313 mmol) and maleic acid (537 mg, 4.63 mmol) in ACN (20 mL) was stirred at rt under argon. To this mixture was then added ethyl 2-oxoacetate (0.458 mL, 2.313 mmol) (50% in toluene) and stirring was continued for 5 min. Next, allyltributylstannane (0.860 mL, 2.78 mmol) was added to the above mixture and stirring was continued for overnight. After overnight stirring, the reaction mixture was concentrated in vacuo and diluted with EtOAc. The organic layer was then washed with 1 N NaOH (2×) solution and dried over MgSO$_4$. The organic layer was then concentrated in vacuo to give the crude product which was purified using silica gel chromatography to give the desired product (344 mg, 28%) as pale yellow oil. MS(ESI) m/z: 539.0 (M+H)$^+$.

26B. Ethyl (4E,7S)-7-((tert-butoxycarbonyl)amino)-15-((methoxycarbonyl)amino)-2,3,6,7-tetrahydro-1H-8,12-(metheno)-1,9-benzodiazacyclotetradecine-2-carboxylate: Grubbs chemistry was performed as described before on 26A to yield the desired product (0.315 g, 47%) as brown oil. MS(ESI) m/z: 510.9 (M+H)$^+$.

26C. Ethyl (2R,7S)-7-((tert-butoxycarbonyl)amino)-15-((methoxycarbonyl)amino)-2,3,4,5,6,7-hexahydro-1H-8,12-(metheno)-1,9-benzodiazacyclotetradecine-2-carboxylate:
A mixture of 26B (315 mg, 0.617 mmol), palladium (II) on carbon (131 mg, 0.123 mmol) (10% on carbon), trifluoroacetic acid (0.047 mL, 0.617 mmol) and EtOH (7 mL) was stirred vigorously under a hydrogen balloon for 4 h. The reaction mixture was then filtered through a pad of CELITE® and the solvent was removed in vacuo to give brown oil. The oil was diluted with EtOAc and washed with saturated $Na_2CO_3$ (2×) solution. The combined organics were dried over $MgSO_4$ and then concentrated to give the crude product. The crude product was then purified using silica gel chromatography to give 26Ca (132 mg, 42%, Diastereomer A) as pale yellow oil and 26Cb was designated as Diastereomer B. MS(ESI) m/z: 513.1 $(M+H)^+$.

26D. Ethyl (2R,7S)-7-amino-15-((methoxycarbonyl)amino)-2,3,4,5,6,7-hexahydro-1H-8,12-(metheno)-1,9-benzodiazacyclotetradecine-2-carboxylate: A mixture of 26Ca (132 mg, 0.258 mmol), HCl (1288 µL, 5.15 mmol) (4 M in dioxane) and EtOAc (2 mL) was stirred at rt. After stirring for 4.5 h, the solvent was removed in vacuo to give a light tan yellow solid as the desired product (125 mg, 100%).

Example 26. Ethyl (9R,14S)-14-[1-(3-chloro-2-fluorophenyl)-1H-pyrazole-4-amido]-5-[(methoxycarbonyl)amino]-8,16-diazatricyclo[13.3.1.0$^{2,7}$]nonadeca-1(19),2(7),3,5,15,17-hexaene-9-carboxylate, 2 TFA salt (Diastereomer A): A mixture of 1-(3-chloro-2-fluorophenyl)-1H-pyrazole-4-carboxylic acid (3.82 mg, 0.016 mmol), HOBT (4.42 mg, 0.029 mmol), EDC (5.53 mg, 0.029 mmol) and DIEA (0.025 mL, 0.144 mmol) in DMF (0.2 mL) was stirred at rt for 5 min. To the above mixture was then added 26D (7 mg, 0.014 mmol) and stirring was continued for overnight. The reaction mixture was diluted with MeOH and purified by reverse phase HPLC to isolate the desired product (4.2 mg, 33%) as light yellow solid. $^1$H NMR (400 MHz, $CD_3CN$) δ 8.86 (br. s., 1H), 8.67 (s, 1H), 8.56 (d, J=6.0 Hz, 1H), 8.51 (d, J=2.7 Hz, 1H), 8.07 (s, 1H), 7.88 (s, 1H), 7.69 (td, 1H, J=8, 2), 7.62 (dd, J=6.0, 1.6 Hz, 1H), 7.44 (ddd, J=8.1, 6.7, 1.6 Hz, 1H), 7.35 (d, 1H, J=8), 7.30 (d, J=1.6 Hz, 1H), 7.22 (td, J=8.2, 1.6 Hz, 1H), 7.12 (dd, J=8.2, 2.2 Hz, 1H), 5.35 (m, 1H), 3.85 (m, 2H), 3.62 (s, 3H), 2.93 (d, J=11.0 Hz, 1H), 2.08 (m, 4H), 1.63 (m, 2H), 1.29 (m, 4H), 0.97 (t, J=7.1 Hz, 3H), 0.20 (m, 1H) ppm. MS(ESI) m/z: 635.1 $(M+H)^+$. Analytical HPLC (Method E) RT=7.39 min.

27A. 2-(1-(3-Chlorophenyl)-4-(((7S)-9-fluoro-15-((methoxycarbonyl)amino)-3-methyl-2-oxo-2,3,4,5,6,7-hexahydro-1H-8,12-(metheno)-1,10-benzodiazacyclotetradecin-7-yl)carbamoyl)-1H-pyrazol-3-yl)ethyl methanesulfonate: To a solution of Example 1 (0.01 g, 0.016 mmol) in pyridine (0.274 mL, 3.39 mmol) and DCM (0.5 mL) was added methane sulfonylchloride (1.23 µL, 0.016 mmol) and the reaction mixture was stirred at rt overnight. The reaction mixture was then concentrated and taken to the next step without further workup or purification. MS(ESI) m/z: 713.5 $(M+H)^+$.

27B. Methyl ((7S)-7-(((3-(2-chloroethyl)-1-(3-chlorophenyl)-1H-pyrazol-4-yl)carbonyl)amino)-9-fluoro-3-methyl-2-oxo-2,3,4,5,6,7-hexahydro-1H-8,12-(metheno)-1,10-benzodiazacyclotetradecin-15-yl)carbamate: The crude product from step 27A (0.014 g, 0.020 mmol) was dissolved in DCM (1 mL) and transferred to a sealed tube where the DCM was evaporated. To the above solid was then added DIEA (0.2 mL) and toluene (1 mL). The reaction flask was sealed and heated to 110° C. for 18 h. Aliquot LCMS shows no ring closure product but only the chloroethyl product was observed. MS(ESI) m/z: 653.4 $(M+H)^+$.

Example 27. Methyl N-[(14S)-14-[2-(3-chlorophenyl)-4-oxo-2H,4H,5H,6H,7H-pyrazolo[4,3-c]pyridin-5-yl]-16-fluoro-10-methyl-9-oxo-8,17-diazatricyclo[13.3.1.0$^{2,7}$]nonadeca-1(19),2,4,6,15,17-hexaen-5-yl]carbamate, TFA salt: NaH (0.147 mg, 6.12 µmol) was added to a THF solution of 27B (4 mg, 6.12 µmol) and to this was added excess NaI and stirred at rt overnight. The reaction mixture was quenched with $H_2O$ (0.1 mL), concentrated and purified directly on reverse phase HPLC. $^1$H NMR (500 MHz, MeOD) δ 8.61 (s, 1H), 8.38 (dd, J=9.3, 2.1 Hz, 1H), 8.23 (d, J=1.4 Hz, 1H), 7.90 (s, 1H), 7.99 (m, 1H), 7.73 (dd, 1H), 7.72 (m, 1H), 7.55 (m, 3H), 7.35 (dd, 1H), 5.75-5.71 (m, 1H), 3.77 (m, 1H), 3.76 (s, 3H), 3.70 (m, 1H), 2.65 (m, 1H), 2.29 (m, 1H), 2.28 (m, 1H), 1.99 (m, 1H), 1.85 (m, 1H), 1.65 (m, 1H), 1.40 (m, 1H), (d, J=6.9 Hz, 3H), 1.05 (m, 1H) ppm. MS(ESI) m/z: 617.2 $(M+H)^+$. Analytical HPLC (Method B) RT=11.7 min.

Example 27

Methyl N-[(14S)-14-[2-(3-chlorophenyl)-4-oxo-2H,4H,5H,6H,7H-pyrazolo[4,3-c]pyridin-5-yl]-16-fluoro-10-methyl-9-oxo-8,17-diazatricyclo[13.3.1.0$^{2,7}$]nonadeca-1(19),2,4,6,15,17-hexaen-5-yl]carbamate, TFA salt

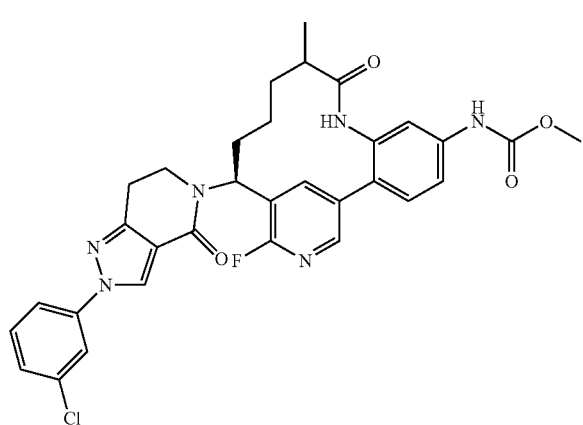 [SMILES: COC(=O)Nc1ccc2c(c1)NC(=O)C(C)CCC[C@H](N1CCc3nn(-c4cccc(Cl)c4)cc3C1=O)c1cc-2cnc1F]

Example 28

Methyl N-[(14S)-14-[1-(3-chloro-2-fluorophenyl)-1H-pyrazole-4-amido]-16-fluoro-10-methyl-9-oxo-8,17-diazatricyclo[13.3.1.0$^{2,7}$]nonadeca-1(19),2(7),3,5,15,17-hexaen-5-yl]carbamate, TFA salt

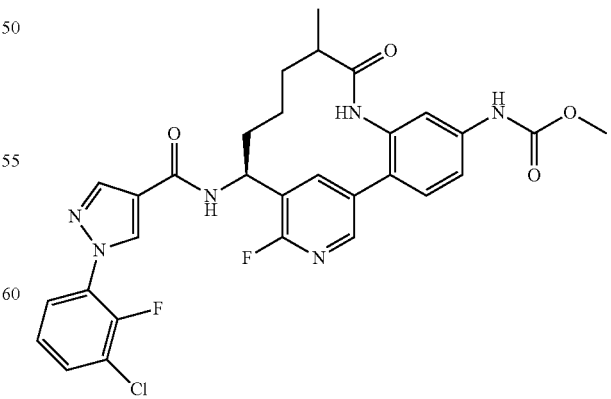

Example 28. Methyl N-[(14S)-14-[1-(3-chloro-2-fluorophenyl)-1H-pyrazole-4-amido]-16-fluoro-10-methyl-9-oxo- 8,17-diazatricyclo[13.3.1.0²,⁷]nonadeca-1(19),2(7),3,5,15, 17-hexaen-5-yl]carbamate, TFA salt: Example 28 was made in the same way as Example 1 using 1Ib and replacing Intermediate 9 with Intermediate 2. ¹H NMR (400 MHz, MeOD) δ 9.47 (s, 1H), 8.75 (d, J=7.2 Hz, 1H), 8.67 (d, J=2.2 Hz, 1H), 8.21 (s, 1H), 8.05-8.18 (m, 2H), 7.81 (ddd, J=8.3, 6.8, 1.7 Hz, 1H), 7.58 (ddd, J=8.2, 6.7, 1.4 Hz, 1H), 7.45-7.54 (m, 3H), 7.35 (td, J=8.3, 1.7 Hz, 1H), 5.18-5.31 (m, 1H), 3.78 (s, 3H), 2.55-2.68 (m, 1H), 2.09-2.23 (m, 1H), 1.94-2.09 (m, 1H), 1.71-1.87 (m, 1H), 1.51-1.63 (m, 1H), 1.29-1.43 (m, 1H), 1.06 (d, J=6.9 Hz, 4H) ppm. MS(ESI) m/z: 609.0 (M+H)⁺. Analytical HPLC RT=9.71 min (Method A).

Example 29

Methyl N-[(14S)-14-[1-(3-chloro-2-fluorophenyl)-1H-1,2,3-triazole-4-amido]-10-methyl-9,17-dioxo-8,16-diazatricyclo[13.3.1.0²,⁷]nonadeca-1(18),2,4,6,15(19)-pentaen-5-yl]carbamate

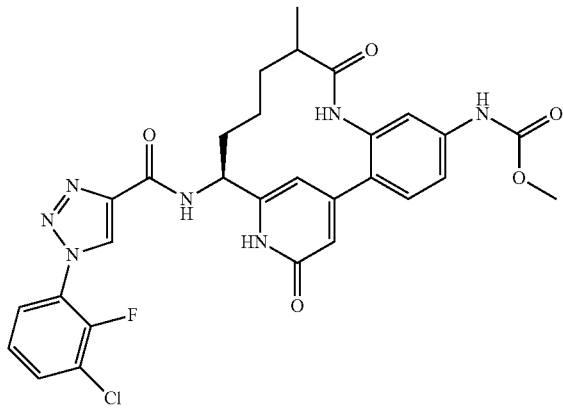 [SMILES: COC(=O)Nc1ccc2c(c1)NC(=O)C(C)CCC[C@H](NC(=O)c1cn(-c3cccc(Cl)c3F)nn1)c1cc-2cc(=O)[nH]1]

29A. Methyl 4-(1,3-dioxolan-2-yl)-3-nitrobenzoate: To a solution of methyl 4-formyl-3-nitrobenzoate (9.0 g, 43.0 mmol) in toluene (150 mL) was added ethylene glycol (7.20 mL, 129 mmol) followed by p-TsOH (0.409 g, 2.152 mmol) and the reaction mixture was heated at reflux temperatures with azeotropic removal of H₂O using a Dean-Stark trap for 4 h. The reaction mixture was then cooled and diluted with DCM. The DCM layers were then washed with saturated NaHCO₃ solution. The organic layer was dried (MgSO₄), filtered, and concentrated to yield a residue. The residue was dissolved in minimal quantity of DCM and purified by silica gel chromatography to yield the desired product (8.53 g, 78%) as a white solid. ¹H NMR (400 MHz, DMSO-d₆) δ 8.39 (s, 1H), 8.27 (d, J=8.2 Hz, 1H), 7.90 (d, J=8.2 Hz, 1H), 6.38 (s, 1H), 4.00 (dt, J=3.8, 1.9 Hz, 2H), 3.94 (dt, J=3.8, 1.9 Hz, 2H), 3.91 (s, 3H) ppm.

29B. 4-(1,3-Dioxolan-2-yl)-3-nitrobenzoic acid: Lithium hydroxide monohydrate (5.67 g, 135 mmol) was added to a solution of 29A (11.4 g, 45.0 mmol) in THF (120 mL), MeOH (120 mL) and H₂O (40.0 mL). The above mixture was then heated to 50° C. After 1 h, the heating was reduced to rt and stirring was continued for overnight. To the reaction mixture was then added H₂O (50 mL) and the organics were concentrated. The remaining aqueous layer was made acidic with 1.0 N HCl solution to precipitate out the solids. The solids were collected by filtration, washed with H₂O and dried under vacuum overnight. ¹H NMR (400 MHz, DMSO-d₆) δ 13.68 (br. s., 1H), 8.36 (d, J=1.5 Hz, 1H), 8.25 (dd, J=8.1, 1.3 Hz, 1H), 7.88 (d, J=8.1 Hz, 1H), 6.38 (s, 1H), 4.05-3.89 (m, 4H) ppm.

29C. Methyl (4-(1,3-dioxolan-2-yl)-3-nitrophenyl)carbamate: To a solution of 29B (6.77 g, 28.3 mmol) in THF (100 mL) was added TEA (7.89 mL, 56.6 mmol) dropwise in THF (25 mL) at −5° C. in a ice-salt bath. The temperature was maintained at −5° C., and a solution of ethyl chloroformate (3.25 mL, 34.0 mmol) in THF (30 mL) was added dropwise over 10 minutes. After stirring for an additional 30 minutes, a cold solution of sodium azide (3.68 g, 56.6 mmol) in H₂O (12.5 mL) was added dropwise. After stirring for additional 1 hour, the reaction mixture was concentrated in vacuo (without heating). The oily residue was dissolved in the Et₂O (100 mL), washed with H₂O, brine, and dried over sodium sulfate, filtered, and concentrated (without heating) to give the acyl azide. This material was dissolved in toluene (100 mL) and heated to 110° C. After 1 h, the temperature was lowered to 80° C., MeOH (60 mL) was added, and heating was continued for overnight. The reaction mixture was concentrated and purified by silica gel chromatography to yield the desired product (5.01 g, 66%) as amber solid. ¹H NMR (400 MHz, DMSO-d₆) δ 10.21 (s, 1H), 8.10 (d, J=1.6 Hz, 1H), 7.74-7.62 (m, 2H), 6.22 (s, 1H), 3.95-3.90 (m, 4H), 3.69 (s, 3H) ppm.

29D. Methyl (4-formyl-3-nitrophenyl)carbamate: 29C (5.00 g, 18.64 mmol) was added to a solution of TFA (27 mL) and H₂O (3 mL) and stirred at rt. After 3 h, the reaction mixture was concentrated and the residue was partitioned between H₂O and EtOAc. The organic layer was then washed with saturated sodium bicarbonate solution, brine, dried over sodium sulfate, filtered, and concentrated to give a light yellow solid as the desired product (3.83 g, 92%). ¹H NMR (400 MHz, DMSO-d₆) δ 10.59 (s, 1H), 10.09 (s, 1H), 8.23 (d, J=1.6 Hz, 1H), 7.92 (d, J=8.2 Hz, 1H), 7.86-7.81 (m, 1H), 3.74 (s, 3H) ppm.

29E. (S)-tert-Butyl 1-(dimethoxyphosphoryl)-2-oxohex-5-en-3-ylcarbamate: To a solution of dimethyl methylphosphonate (13.98 mL, 131 mmol) in THF (87 mL) at −78° C. was added n-BuLi (82 mL, 131 mmol) slowly. After completion of addition, the reaction was stirred for 40 min and then a solution of (S)-methyl 2-(tert-butoxycarbonylamino)pent-4-enoate (6.0 g, 26.2 mmol) in THF (30 mL) was added slowly. Stirring was continued for another 40 min at −78° C. The reaction mixture was then quenched by adding H₂O (2.357 mL, 131 mmol). The reaction mixture was diluted with EtOAc (100 mL) and the layers were separated. The organic layer was washed with 1 M HCl, saturated NaHCO₃ solution, brine, dried over MgSO₄, filtered, and concentrated to give a clear oil. The crude product was finally purified using silica gel chromatography to give the desired product (7.46 g, 89%) as a colorless oil. MS(ESI) m/z: 343.9 (M+Na)⁺. ¹H NMR (500 MHz, CDCl₃) δ 5.63-5.76 (1H, m), 5.08-5.17 (2H, m), 4.33-4.43 (1H, m), 3.80 (3H, d, J=2.20 Hz), 3.77 (3H, d, J=2.20 Hz), 3.28-3.37 (1H, m), 3.05-3.16 (1H, m), 2.58-2.69 (1H, m), 2.42 (1H, dt, J=14.58, 7.29 Hz), 1.43 (9H, s) ppm.

29F. Methyl (4-((1E,4S)-4-((tert-butoxycarbonyl)amino)-3-oxohepta-1,6-dien-1-yl)-3-nitrophenyl)carbamate: To a vigorously stirred solution of 29E (4.47 g, 13.92 mmol) and 29D (2.6 g, 11.60 mmol) in THF (anhydrous) (115 mL) and EtOH (absolute) (1.148 mL) under nitrogen was added portion wise K₂CO₃ (anhydrous) (2.56 g, 18.56 mmol) at 0° C. The reaction mixture was allowed to warm to rt and then the mixture was heated at 55° C. The reaction mixture was then filtered with the aid of EtOAc and the filtrate evaporated to a residue which was dissolved in a small amount of methylene chloride and purified by normal phase chromatography to give the desired product (4.38 g, 90%) as a yellow solid. MS(ESI) m/z: 420.2 (M+H)⁺. ¹H NMR (400 MHz, DMSO-d₆) δ 10.36 (s, 1H), 8.22 (d, J=2.2 Hz, 1H), 7.89 (d, J=8.8 Hz, 1H), 7.83-7.73 (m, 2H), 7.21 (d, J=7.7 Hz, 1H), 7.02 (d, J=15.9 Hz, 1H), 5.77 (ddt, J=17.0, 10.2, 6.7 Hz, 1H), 5.16-5.01 (m, 2H), 4.32 (td, J=8.5, 4.9 Hz, 1H), 3.71 (s, 3H), 2.34-2.23 (m, 1H), 1.36 (s, 9H) ppm.

29G. Methyl (4-(6-(1-((tert-butoxycarbonyl)amino)but-3-en-1-yl)-2-oxo-1,2-dihydropyridin-4-yl)-3-nitrophenyl)carbamate: To a solution of 29F (3.0 g, 7.15 mmol) and 1-(2-ethoxy-2-oxoethyl)pyridinium bromide (1.189 g, 7.15 mmol) in EtOH (130 mL), was added ammonium acetate (11.03 g, 143 mmol) portionwise. After 15 min, the mixture was stirred at 75° C. The reaction mixture was then concentrated and dissolved in EtOAc. The organic layer was then washed with 1.0 N HCl, H₂O, saturated sodium bicarbonate solution and finally by brine. The organic phase was dried over sodium sulfate, filtered and concentrated to yield a residue which was purified by normal phase chromatography to isolate the desired product (2.2 g, 67%) as a brown solid. MS(ESI) m/z: 459.3 (M+H)⁺.

29H. Methyl (3-amino-4-(6-((1S)-1-((tert-butoxycarbonyl)amino)but-3-en-1-yl)-2-oxo-1,2-dihydropyridin-4-yl) phenyl)carbamate: To a solution of 29G (2.9 g, 6.33 mmol) in MeOH (120 mL) was added ammonium chloride (0.677 g, 12.65 mmol) and zinc (4.14 g, 63.3 mmol). The suspension was stirred for 1 hour at rt and then at 65° C. for overnight. The suspension was filtered hot through a plug of CELITE® and the filter cake was washed with hot MeOH. The filtrate was concentrated and dried under vacuum to give a yellowish brown solid. This residue was re-dissolved in EtOAc (with 10% MeOH), washed with saturated sodium bicarbonate solution and brine. The organic layer was then dried over sodium sulfate, filtered and concentrated. The crude product was then subjected to chiral separation using chiral AD-H 21×250 mm, using a mixture of 35% (50/50 EtOH, i-PrOH and 0.1% DEA) and 65% CO₂ with a flow rate of 70 mL/min and 150 bar at 40° C. Each separated enantiomer was concentrated separately and the resulting solid placed under vacuum overnight. Analytical data corresponds to the desired product (1.12 g, 41%, 29Ha). MS(ESI) m/z: 429.2 (M+H)⁺. ¹H NMR: (400 MHz, MeOD) δ 7.03 (d, J=8.6 Hz, 2H), 6.79 (dd, J=8.3, 2.0 Hz, 1H), 6.48 (d, J=5.6 Hz, 2H), 5.91-5.74 (m, 1H), 5.22-5.09 (m, 2H), 4.58-4.48 (m, 1H), 3.75 (s, 3H), 2.55 (t, J=5.9 Hz, 1H), 2.53-2.43 (m, 1H), 1.45 (br. s., 9H) ppm. The other isomer (29Hb) is also separately isolated.

29I. Methyl (4-(6-((1S)-1-((tert-butoxycarbonyl)amino)but-3-en-1-yl)-2-oxo-1,2-dihydropyridin-4-yl)-3-((2-methylbut-3-enoyl)amino)phenyl)carbamate: Isobutyl chloroformate (0.956 g, 7.00 mmol) was added to 2-methylbut-3-enoic acid (0.701 g, 7.00 mmol) and 4-methylmorpholine (0.770 mL, 7.00 mmol) in THF (33.3 mL) at 0° C. under a nitrogen atmosphere and stirred for 3 h. The resulting solids were filtered off and the filtrate was used directly for next step. To a round bottom flask containing the mixed anhydride, 29H (0.200 g, 0.467 mmol) and 4-methylmorpholine (0.770 ml, 7.00 mmol) in DMF (6 mL) was added portionwise (1 mL) every ten minutes over 1 h. The reaction mixture was then stirred at rt. After 3 d, the reaction mixture was partitioned between EtOAc and 1.0 NaOH (20 mL). The organic layer was washed with 1.0 N NaOH, H₂O, 1.0 N HCl solution, H₂O, and brine. The organic layer was dried, filtered and concentrated. The crude product was again dissolved in THF (20 mL) and treated with NaOH (10 mL, 10.00 mmol). After stirring for 1 h, the reaction mixture was concentrated and purified using reverse phase HPLC to give the desired product (0.09 g, 38%). MS(ESI) m/z: 511.4 (M+H)⁺.

29J. tert-Butyl methyl ((7S)-3-methyl-2,10-dioxo-2,3,4,5,6,7,9,10-octahydro-1H-12,8-(metheno)-1,9-benzodiazacyclotetradecine-7,15-diyl)biscarbamate: A solution of 29I (90 mg, 0.176 mmol) in DCE (anhydrous) (9793 µL) in a microwave vial was degassed for 15 minutes. To this solution was then added tricyclohexylphosphine[1,3-bis(2,4,6-trimethylphenyl)-4,5-dihydroimidazol-2-ylidene][benzylidine]ruthenium(IV)dichloride (60.0 mg, 0.071 mmol) and the mixture was heated to 120° C. for 30 min under microwave conditions. The reaction mixture was then concentrated and purified by reverse phase HPLC. Fractions for diastereomer 29J1 (minor; Peak 1; more polar RT (by ACN PREP)=3.776 minutes) and diastereomer 29J2 (major; Peak 2; less polar RT (by ACN PREP)=3.978 minutes) were concentrated. Recovered 29J1 (8.2 mg, 19%) and 29J2 (14.8 mg, 35%) after Grubbs macrocyclization. Each diastereomer was taken on to PtO₂ reduction by dissolution with EtOH (10 mL) in two separate hydrogenation vessels, treatment to each with equal amount of platinum(IV) oxide (12.01 mg, 0.053 mmol), and exposed to hydrogen gas (55 psi) overnight. The reactions were filtered, concentrated, and carried forward to the next reaction without further purification. Final saturated analogs 29J3 (8.4 mg, 20%) and 29J4 (13.8 mg, 32%) were recovered as brown films. MS(ESI) m/z: 485.3 (M+H)⁺ for both diastereomers.

Example 29. Methyl N-[(14S)-14-[1-(3-chloro-2-fluorophenyl)-1H-1,2,3-triazole-4-amido]-10-methyl-9,17-dioxo-8,16-diazatricyclo[13.3.1.0²,⁷]nonadeca-1(18),2,4,6,15(19)-pentaen-5-yl]carbamate: Example 21 was prepared in the same way as Example 1 by subjecting 29J4 to Boc deprotection followed by T3P coupling using the free amine and Intermediate 1. The crude reaction mixture was purified by reverse phase HPLC. ¹H NMR (500 MHz, MeOD) δ 8.88 (d, J=2.2 Hz, 1H), 7.86 (ddd, J=8.1, 6.6, 1.5 Hz, 1H), 7.76-7.71 (m, 1H), 7.52-7.40 (m, 4H), 6.67 (d, J=1.1 Hz, 1H), 6.52 (d, J=1.1 Hz, 1H), 5.17 (dd, J=10.7, 6.6 Hz, 1H), 3.78 (s, 3H), 2.79 (d, J=5.5 Hz, 1H), 2.05-1.94 (m, 2H), 1.79-1.58 (m, 3H), 1.37-1.25 (m, 1H), 1.11-1.05 (m, 3H), 1.04 (d, J=7.2 Hz, 3H), 0.96-0.88 (m, 1H) ppm. MS(ESI) m/z: 608.4 (M+H)⁺. Analytical HPLC (Method A) RT=6.27 min.

Example 30

Methyl N-[(14S)-14-[1-(3-chloro-2-fluorophenyl)-1H-1,2,3-triazole-4-amido]-10-methyl-9,17-dioxo-8,16-diazatricyclo[13.3.1.0²,⁷]nonadeca-1(18),2,4,6,15(19)-pentaen-5-yl]carbamate

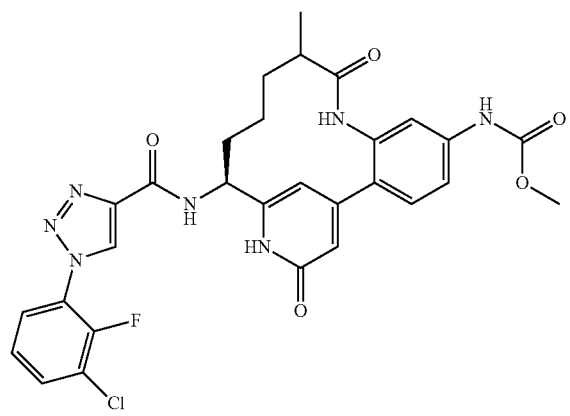 [SMILES: COC(=O)Nc1ccc2c(c1)NC(=O)C(C)CCC[C@H](NC(=O)c1cn(-c3cccc(Cl)c3F)nn1)c1cc-2cc(=O)[nH]1]

Methyl N-[(14S)-14-[1-(3-chloro-2-fluorophenyl)-1H-1,2,3-triazole-4-amido]-10-methyl-9,17-dioxo-8,16-diazatricyclo[13.3.1.0$^{2,7}$]nonadeca-1(18),2,4,6,15(19)-pentaen-5-yl]carbamate: Example 30 is made the same way as with Example 29 by replacing 29J4 with 29J3. $^1$H NMR (500 MHz, MeOD) δ 8.90 (d, J=2.2 Hz, 1H), 7.88 (ddd, J=8.3, 6.6, 1.7 Hz, 2H), 7.76 (ddd, J=8.2, 6.8, 1.5 Hz, 1H), 7.54-7.44 (m, 5H), 6.57 (s, 1H), 6.47 (s, 1H), 5.11 (dd, J=10.6, 6.2 Hz, 1H), 3.80 (s, 3H), 2.41-2.30 (m, 1H), 2.10-1.93 (m, 3H), 1.87-1.78 (m, 1H), 1.58-1.49 (m, 1H), 1.39-1.32 (m, 1H), 1.31-1.28 (m, 3H), 1.21-1.04 (m, 1H) ppm. MS(ESI) m/z: 608.4 (M+H)$^+$. Analytical HPLC (Method A) RT=6.23 min.

Example 31

Methyl N-[(14S)-14-[1-(3-chloro-2-fluorophenyl)-1H-pyrazole-4-amido]-10-methyl-9-oxo-8,18-diazatricyclo[13.3.1.0$^{2,7}$]nonadeca-1(19),2(7),3,5,15,17-hexaen-5-yl]carbamate, TFA salt

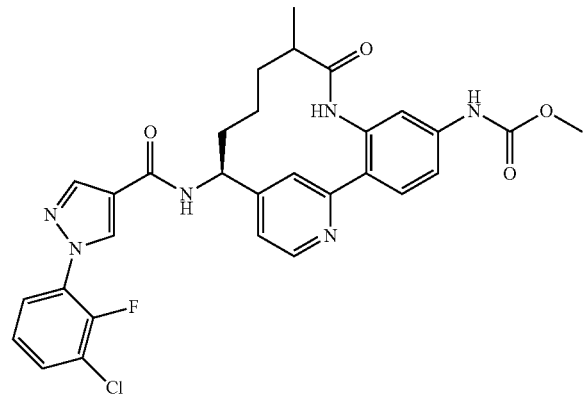 [SMILES: COC(=O)Nc1ccc2c(c1)NC(=O)C(C)CCC[C@H](NC(=O)c1cnn(-c3cccc(Cl)c3F)c1)c1ccnc-2c1]

Example 31. Methyl N-[(14S)-14-[1-(3-chloro-2-fluorophenyl)-1H-pyrazole-4-amido]-10-methyl-9-oxo-8,18-diazatricyclo[13.3.1.0$^{2,7}$]nonadeca-1(19),2(7),3,5,15,17-hexaen-5-yl]carbamate, TFA salt: Example 31 was prepared the same way as Example 2 by replacing 4-bromopicolinaldehyde with 2-bromoisonicotinaldehyde and substituting Intermediate 11 with Intermediate 2. Also, the acid chloride was used in step 2H instead of the acid in the coupling step. Unfortunately with Example 31, chiral resolution was not achieved as with Example 1 at step 1I and hence the final compound was a diastereomeric mixture. $^1$H NMR (500 MHz, CD$_3$CN) δ 8.60 (m, 1H), 8.42 (m, 1H), 8.22 (s, 1H), 8.02 (m, 1H), 7.91 (m, 1H), 7.70 (ddd, J=8.4, 7.0, 1.7 Hz, 1H), 7.62 (m, 1H), 7.37 (m, 2H), 7.23 (td, J=8.2, 1.5 Hz, 1H), 4.98 (m, 1H), 3.64, 3.66 (2s, 3H), 2.55 (m, 2H), 1.98 (m, 1H), 1.71 (m, 4H), 1.33 (m, 5H), 1.08 (d, J=6.9 Hz, 0.3H), 0.81 (d, J=6.9 Hz, 2.7H), 0.49 (m, 1H) ppm. MS(ESI) m/z: 591.1 (M+H)$^+$. Analytical HPLC (Method E) RT=6.00 min.

Example 32

Methyl N-[(14S)-14-[1-(3-chloro-2-fluorophenyl)-1H-pyrazole-4-amido]-16-fluoro-9-oxo-8,17-diazatricyclo[13.3.1.0$^{2,7}$]nonadeca-1(19),2(7),3,5,15,17-hexaen-5-yl]carbamate, TFA salt

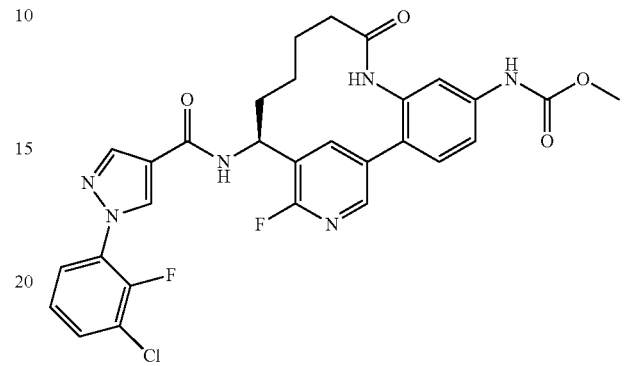

Example 32. Methyl N-[(14S)-14-[1-(3-chloro-2-fluorophenyl)-1H-pyrazole-4-amido]-16-fluoro-9-oxo-8,17-diazatricyclo[13.3.1.0$^{2,7}$]nonadeca-1(19),2(7),3,5,15,17-hexaen-5-yl]carbamate, TFA salt: Example 32 was made in the same way as Example 21 by using 1F instead of starting with 21A. $^1$H NMR (400 MHz, MeOD) δ 8.68 (d, J=1.9 Hz, 1H), 8.22 (s, 1H), 8.14 (d, J=1.7 Hz, 1H), 8.07 (dd, J=9.4, 2.2 Hz, 1H), 7.81 (ddd, J=8.3, 6.8, 1.7 Hz, 1H), 7.58 (ddd, J=8.2, 6.7, 1.7 Hz, 1H), 7.45-7.55 (m, 3H), 7.36 (td, J=8.2, 1.5 Hz, 1H), 5.23 (dd, J=11.0, 5.5 Hz, 1H), 3.78 (s, 3H), 2.39-2.55 (m, 1H), 2.08-2.23 (m, 1H), 1.94-2.08 (m, 2H), 1.60-1.84 (m, 2H), 1.35-1.50 (m, 1H), 0.99-1.21 (m, 1H) ppm. MS(ESI) m/z: 594.9 (M+H)$^+$. Analytical HPLC RT=9.18 min (Method A).

Example 33

Methyl N-[(12E,15S)-15-[1-(3-chloro-2-fluorophenyl)-1H-1,2,3-triazole-4-amido]-9,18-dioxo-8,17-diazatricyclo[14.3.1.0$^{2,7}$]icosa-1(19),2,4,6,12,16(20)-hexaen-5-yl]carbamate, TFA salt

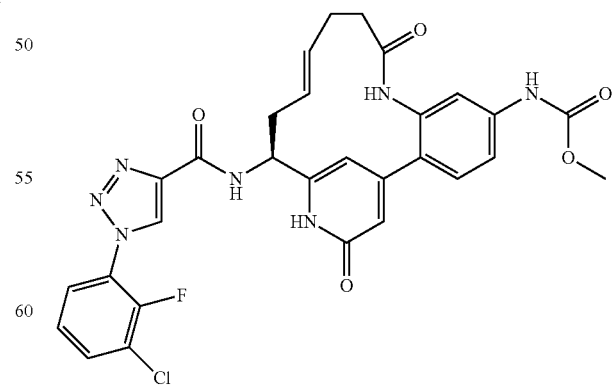

33A. Methyl (4-(6-(((1S)-1-((tert-butoxycarbonyl)amino)but-3-en-1-yl)-2-oxo-1,2-dihydropyridin-4-yl)-3-(pent-4-enoylamino)phenyl)carbamate: To a solution of 29H (115.4 mg, 0.269 mmol) in DCM (40 mL) was added pyridine (0.109 mL, 1.347 mmol). The flask was placed under nitrogen and the mixture cooled to 0° C. To this mixture was then added pent-4-enoyl chloride (0.104 mL, 0.943 mmol) and the mixture was stirred for 10 minutes at the same temperature and the reaction mixture was slowly allowed to warm to rt and stirred at rt. After stirring for overnight, the reaction mixture was concentrated under reduced pressure and the resulting yellow residue was taken up in THF and 1 N NaOH (5:2, 7 mL) and stirred at 30° C. for 1.5 h to effect hydrolysis of o-acylated intermediate to desired product. The reaction mixture was diluted with EtOAc and 1 N HCl was added to adjust the pH to 5-6 and the two phases were separated. The aqueous layer was further extracted with EtOAc (2×) and the combined organics washed with brine, dried ($Na_2SO_4$), filtered and evaporated to a residue. The crude product was then purified using silica gel chromatography to yield the desired product (97 mg, 70%) as a tan solid. MS(ESI) m/z: 511.1 $(M+H)^+$.

33B. tert-Butyl methyl ((5E,8S)-2,11-dioxo-1,2,3,4,7,8, 10,11-octahydro-13,9-(metheno)-1,10-benzodiazacyclopentadecine-8,16-diyl)biscarbamate: To a microwave vial was charged with 33A (96.6 mg, 0.189 mmol) and tricyclohexylphosphine[1,3-bis(2,4,6-trimethylphenyl)-4,5-dihydroimidazol-2-ylidene][benzylidine]ruthenium(IV)dichloride (64.4 mg, 0.076 mmol). The vial was then capped, purged with argon and DCE (anhydrous—degassed) (10 mL) was added. The reaction mixture was then heated to 120° C. for 30 min in the microwave. The mixture was then cooled to rt and washed with saturated $NaHCO_3$ followed by brine. The organic layers were then dried over $Na_2SO_4$, filtered and evaporated to give a dark solid. The crude product was then purified using reverse phase HPLC to yield the desired product (24 mg, 26%) as a brown solid. MS(ESI) m/z: 483.0 $(M+H)^+$.

Example 33. Methyl N-[(12E,15S)-15-[1-(3-chloro-2-fluorophenyl)-1H-1,2,3-triazole-4-amido]-9,18-dioxo-8,17-diazatricyclo[14.3.1.0$^{2,7}$]icosa-1(19),2,4,6,12,16(20)-hexaen-5-yl]carbamate, TFA salt: To a RBF containing 33B (4.1 mg, 8.50 μmol) was added HCl (4 M in dioxane) (2 mL, 8.00 mmol) and the reaction mixture was stirred under nitrogen at ambient temperature. After 1 h, the reaction mixture was concentrated and the crude product was taken to the next step without further purification. To a solution of the Boc deprotected product (3.59 mg, 8.57 μmol) and DIEA (0.015 mL, 0.086 mmol) in DMF (anhydrous) (1.5 mL) under nitrogen was added Intermediate 1(2.485 mg, 10.28 μmol) followed by T3P (7.65 μL, 0.013 mmol). The reaction mixture was stirred for 20 min at ambient temperature. After 20 min, the reaction mixture was diluted with MeOH to 2 mL and purified by reverse phase HPLC to yield the final desired product (2.4 mg, 43%) as a white solid. $^1$H NMR (400 MHz, MeOD) δ 8.85 (d, J=2.2 Hz, 1H), 7.85-7.80 (m, 1H), 7.74-7.69 (m, 1H), 7.55-7.52 (m, 1H), 7.44-7.39 (m, 2H), 7.30-7.27 (m, 1H), 6.40 (d, J=1.4 Hz, 1H), 6.23 (d, J=1.1 Hz, 1H), 5.56-5.49 (m, 2H), 5.03-4.97 (m, 2H), 3.74 (s, 3H), 2.69-2.60 (m, 3H), 2.51-2.38 (m, 5H). MS(ESI) m/z: 606.0 $(M+H)^+$. Analytical HPLC RT=8.75 min.

Example 34

Methyl N-[(10R,14S)-10-methyl-9-oxo-14-[1-(piperidin-4-yl)-1H-1,2,3-triazole-4-amido]-8,16,18-triazatricyclo[13.2.1.0$^{2,7}$]octadeca-1(17),2,4,6,15(18)-pentaen-5-yl]carbamate, bis TFA salt

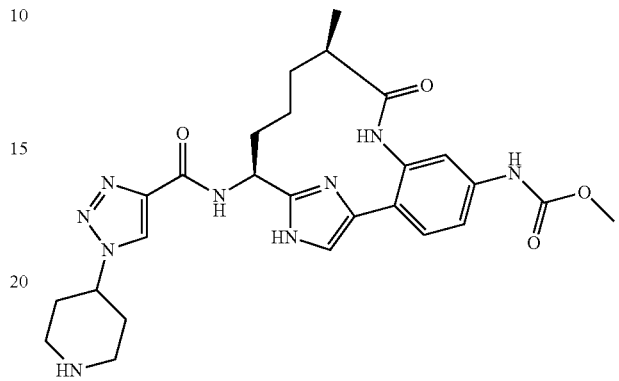

34A. (S)-2-(4-(Methoxycarbonylamino)-2-nitrophenyl)-2-oxoethyl 2-(tert-butoxycarbonylamino)pent-4-enoate: To a clear, colorless solution of (S)-2-(tert-butoxycarbonylamino)pent-4-enoic acid (2.91 g, 13.50 mmol) in DMF (33.7 mL) was added potassium hydrogen carbonate (1.622 g, 16.20 mmol). The reaction mixture was stirred for 20 min at rt and then cooled to 0° C. To the above reaction mixture was added a solution of Intermediate 16 (4.28 g, 13.50 mmol) in DMF (33.7 mL) dropwise and the reaction mixture was allowed to warm to rt and then stirred at rt. After 18 h, the reaction was cooled to 0° C. and poured into ice-cold water. The aqueous layer was then extracted with EtOAc (3×) and the combined organic layers were washed with $H_2O$ and brine. The organic layer was then dried over $Na_2SO_4$, filtered and concentrated to yield a yellow foam as (S)-2-(4-(methoxycarbonylamino)-2-nitrophenyl)-2-oxoethyl 2-(tert-butoxycarbonylamino)pent-4-enoate (6.09 g, 100%). MS(ESI) m/z: 450.5 $(M-H)^+$.

34B. Methyl (4-(2-((1S)-1-((tert-butoxycarbonyl)amino) but-3-en-1-yl)-1H-imidazol-5-yl)-3-nitrophenyl)carbamate: To a 1000-mL RBF containing 34A (6.09 g, 13.49 mmol) was added xylene (135 mL) and the above mixture was sonicated to obtain a clear yellow solution. To this solution was then added ammonium acetate (10.40 g, 135 mmol) and the flask was equipped with a dean-stark trap and reflux condenser. The reaction was warmed to 110° C. for 2 h and then raised to 140° C. for 2 h. After a total of 4 h stirring, the reaction was stopped and cooled to rt. The reaction mixture was then diluted with EtOAc and washed with saturated $NaHCO_3$ (2×) solution and brine. The organic layer was then dried over $Na_2SO_4$, filtered and concentrated to yield a brown gum which was purified using silica gel chromatography to isolate a brown foam as the desired product (0.91 g, 16%). MS(ESI) m/z: 432.5 $(M+H)^+$.

34C. Methyl (4-(2-((1S)-1-((tert-butoxycarbonyl)amino) but-3-en-1-yl)-1-((2-(trimethylsilyl)ethoxy)methyl)-1H-imidazol-4-yl)-3-nitrophenyl)carbamate: A flame-dried 25 mL RBF was charged with NaH (0.092 g, 2.295 mmol) and then THF (4.17 mL) was added to give a gray suspension. The above suspension was then cooled to 0° C. and then a clear, yellow solution of 34B (0.9 g, 2.086 mmol) in THF (4.17 mL) was added dropwise. The reaction mixture was then stirred at 0° C. for 30 min and then allowed to warm to rt and stirred for 0.5 h. The yellow suspension was again cooled to 0° C. and then SEM-Cl (0.370 mL, 2.086 mmol) was added dropwise. The resulting cloudy reaction mixture was stirred at 0° C. After 1 h, the reaction was stopped by quenching with saturated NH$_4$Cl followed by dilution with EtOAc. The layers were then separated and the aqueous layer was extracted with EtOAc. The combined organic layers were washed with saturated NaHCO$_3$, brine, dried over Na$_2$SO$_4$, filtered, and concentrated to obtain a yellow oil which was purified by silica gel chromatography to yield the desired product as yellow foam (0.424 g, 36%). MS(ESI) m/z: 562.0 (M+H)$^+$. 1D NOE confirmed the regioisomeric position of SEM on the imidazole ring.

34D. (S)-Methyl 4-(2-(1-Boc-aminobut-3-enyl)-1-((2-(trimethylsilyl)ethoxy)methyl)-1H-imidazol-4-yl)-3-aminophenylcarbamate: To a solution of 34C (0.424 g, 0.755 mmol) in MeOH (5 mL) was added zinc (0.494 g, 7.55 mmol) and ammonium chloride (0.404 g, 7.55 mmol). The mixture was then stirred at 60° C. in a sealed tube. After 4 h, the reaction mixture was cooled to rt and the yellow suspension was diluted with DCM and washed with H$_2$O. The aqueous layer was extracted with 15% IPA in CHCl$_3$. The combined organic layers were washed with brine, dried over MgSO$_4$, filtered and concentrated. The crude product was then purified using silica gel chromatography to give an orange solid as the desired product (0.31 g, 77%). MS(ESI) m/z: 532.4 (M+H)$^+$.

34E. Methyl (4-(2-((1S)-1-((tert-butoxycarbonyl)amino)but-3-en-1-yl)-1-((2-(trimethylsilyl)ethoxy)methyl)-1H-imidazol-4-yl)-3-((trifluoroacetyl)amino)phenyl)carbamate: A solution of 34D (10.2 g, 19.18 mmol) and TEA (3.19 mL, 23.02 mmol) in EtOAc (50 mL) was cooled down to 0° C. under argon. To this solution was added 2,2,2-trifluoroacetic anhydride (2.97 mL, 21.10 mmol) dropwise via a syringe pump. After completion of addition, the reaction mixture was stirred for another 30 min at 0° C. The reaction mixture was then diluted with EtOAc, washed with H$_2$O, brine and dried over MgSO$_4$. The crude product was then filtered to remove the solids and the organic layer was concentrated and purified by silica gel chromatography to yield the desired product (10.69 g, 89%) as a yellow solid. MS(ESI) m/z: 627.9 (M+H)$^+$.

34F. (6S,E)-Benzyl 6-((tert-butoxycarbonyl)amino)-6-(4-(4-((methoxycarbonyl)amino)-2-(2,2,2-trifluoroacetamido)phenyl)-1-((2-(trimethylsilyl)ethoxy)methyl)-1H-imidazol-2-yl)-2-methylhex-3-enoate: To a solution of 34E (3.3 g, 5.26 mmol) and Intermediate 17 (5.91 g, 31.1 mmol) in DCM (80 mL) was added pTsOH (0.905 g, 5.26 mmol). The above solution was then bubbled with argon for 30 min. The reaction mixture was sealed, heated to 40° C. under argon for 10 min, and added Grubbs II (1.5 g, 1.767 mmol) in 20 mL argon degassed DCM dropwise via syringe pump over 3 h while maintaining the reaction temperature at 40° C. After overnight stirring, the reaction mixture was washed with concentrated NaHCO$_3$ (aq) and brine. The organic layer was dried over MgSO$_4$, filtered and concentrated. The crude product was then purified by silica gel chromatography to yield the desired product (1.93 g, 46%) as a yellow solid. MS(ESI) m/z: 790.4 (M+H)$^+$.

34G. (6S)-6-((tert-Butoxycarbonyl)amino)-6-(4-(4-((methoxycarbonyl)amino)-2-(2,2,2-trifluoroacetamido)phenyl)-1-((2-(trimethylsilyl)ethoxy)methyl)-1H-imidazol-2-yl)-2-methylhexanoic acid: A solution of 34F (1.76 g, 2.228 mmol) in MeOH (40 mL) was vacuumed and refilled with argon. To this solution under argon was added palladium on carbon (10%) (500 mg, 0.470 mmol), vacuumed and refilled with H$_2$ gas (3×). The reaction mixture was then stirred at rt under H$_2$ balloon. After overnight stirring, the reaction mixture was filtered through CELITE®. The filtrate was concentrated and purified by silica gel chromatography to isolate the desired product (1.23 g, 79%) as a beige solid. MS(ESI) m/z: 702.1 (M+H)$^+$.

34H. (6S)-6-(4-(2-Amino-4-((methoxycarbonyl)amino)phenyl)-1-((2-(trimethylsilyl)ethoxy)methyl)-1H-imidazol-2-yl)-6-((tert-butoxycarbonyl)amino)-2-methylhexanoic acid: To a solution of 34G (1.656 g, 2.360 mmol) in MeOH (14 mL) was added LiOH (2 N aq) (7 mL, 14.00 mmol). The reaction mixture was sealed and heated at 60° C. After 1 h, the reaction mixture was cooled down on an ice H$_2$O bath, 1 N HCl (aq) was added to adjust pH to 6. The aqueous layer was extracted with EtOAc (2×60 mL). The combined EtOAc layers were washed with brine, dried over MgSO$_4$, filtered, and concentrated to yield the desired product (1.43 g, 100%) as a grayish solid. MS(ESI) m/z: 606.3 (M+H)$^+$.

34I. tert-Butyl methyl ((3R,7S)-3-methyl-2-oxo-9-((2-(trimethylsilyl)ethoxy)methyl)-1,2,3,4,5,6,7,9-octahydro-11,8-(azeno)-1,9-benzodiazacyclotridecine-7,14-diyl)biscarbamate: To a mixture of BOP (1141 mg, 2.58 mmol), DMAP (529 mg, 4.33 mmol) and DIEA (1.261 mL, 7.22 mmol) in DCM (300 mL) was added 34H (625 mg, 1.032 mmol) in DMF (5 mL) dropwise via syringe pump. The reaction mixture was stirred at rt for 2 days before transferred to a sealed vessel. The reaction was heated at 50° C. for 48 h before cooling down to rt. The reaction mixture was concentrated to small volume and to the residue was added EtOAc. The EtOAc layer was washed with 10% LiCl solution to remove DMF and the organic layers were dried over MgSO$_4$. The organic layer was then concentrated and purified by silica gel chromatography followed by reverse phase HPLC. Two major peaks were seen on HPLC and the first peak was identified as the desired product (second peak is the other isomer) based on previous X-ray studies and stereochemistry is assigned based on previous compounds. Isolated 132 mg (22%) of the desired product as a white solid. MS(ESI) m/z: 588.1 (M+H)$^+$.

34J. Methyl ((3R,7S)-7-amino-3-methyl-2-oxo-9-((2-(trimethylsilyl)ethoxy)methyl)-1,2,3,4,5,6,7,9-octahydro-11,8-(azeno)-1,9-benzodiazacyclotridecin-14-yl)carbamate: To a solution of 34I (120 mg, 0.204 mmol) in DCM (4 mL) was added TFA (0.8 mL, 10.38 mmol) and stirred at rt for 1 h. The reaction was quenched with concentrated Na$_2$CO$_3$ aqueous solution followed by extraction with DCM and EtOAc. The organic layers were washed with brine, dried over MgSO$_4$ and concentrated under vacuo to yield the desired product (71 mg, 71%) as a yellow gum. MS(ESI) m/z: 488.3 (M+H)$^+$.

Example 34. Methyl N-[(10R,14S)-10-methyl-9-oxo-14-[1-(piperidin-4-yl)-1H-1,2,3-triazole-4-amido]-8,16,18-triazatricyclo[13.2.1.0$^{2,7}$]octadeca-1(17),2,4,6,15(18)-pentaen-5-yl]carbamate, bis TFA salt: To a solution of 34J (23 mg, 0.047 mmol) in DMF (1 mL) was added 1-[1-(tert-butoxycarbonyl)piperidin-4-yl]-1H-1,2,3-triazole-4-carboxylic acid (15.37 mg, 0.052 mmol), EDC (18.08 mg, 0.094 mmol), HOBT (14.45 mg, 0.094 mmol) and TEA (0.066 mL, 0.472 mmol) and the reaction mixture was stirred at rt overnight. The reaction mixture was concentrated and purified on reverse phase HPLC to give the Boc protected product (29 mg, 70%) as a white solid. To the above white solid (29.2 mg, 0.033 mmol) in a vial was added HCl (4 N in dioxane) (0.8 mL, 3.20 mmol) and the reaction mixture was heated at 75° C. for 1 h. The reaction mixture was cooled down to rt and concentrated. The crude product was then subjected to reverse phase HPLC purification to yield the desired product (22 mg, 81%) as a white solid. $^1$H NMR (400 MHz, MeOD) δ 9.57 (s, 1H), 8.52 (s, 1H), 7.57 (d, J=2.0 Hz, 1H), 7.52-7.38 (m, 2H), 5.38 (dd, J=10.4, 6.8 Hz, 1H), 4.99-4.89 (m, 1H), 3.76 (s, 3H), 3.63-3.55 (m, 2H), 3.28-3.21 (m, 1H), 2.77 (br. s., 1H), 2.51-2.19 (m, 4H), 2.17-2.02 (m, 1H), 1.84-1.51 (m, 3H), 1.03 (d, J=7.1 Hz, 3H), 0.70 (d, J=12.1 Hz, 1H) ppm. MS(ESI) m/z: 536.4 (M+H)$^+$. Analytical HPLC RT=5.02 min (Method A).

The following Examples in Table 3 were made by using the same procedure as shown in Example 34. The acids used in the final step are as indicated in the below table in the Intermediate section. Various coupling reagents could be used other than the one described in Example 34 like BOP, PyBop, EDC/HOBt, HATU or T3P. Boc and SEM deprotection was achieved prior to the final coupling unlike with Example 34 where the Boc group alone was removed in step 34J.

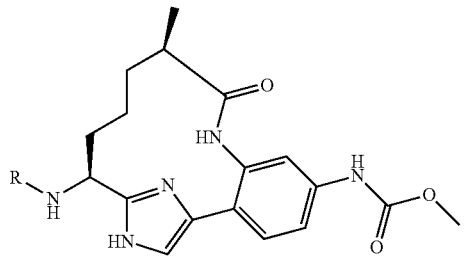

TABLE 3

| Example # | Stereochemistry | R | M + H | RT, min Method A |
|---|---|---|---|---|
| 35 | Homochiral | | 581.0 | 6.74 |
| 36 | Homochiral | | 580.2 | 6.79 |
| 37 | Homochiral | | 595.3 | 5.81 |
| 38 | Homochiral | | 599.1 | 6.99 |

TABLE 3-continued

| Example # | Stereochemistry | R | M + H | RT, min Method A |
|---|---|---|---|---|
| 39 | Homochiral | (1-(2-fluoro-3-chlorophenyl)-5-methyl-1H-1,2,3-triazol-4-yl)carbonyl | 595.3 | 5.68 |
| 40 | Homochiral | (1-(2-fluoro-3-chlorophenyl)-5-methyl-1H-pyrazol-4-yl)carbonyl | 594.4 | 5.59 |
| 41 | Homochiral | (1-(3-chlorophenyl)-5-methyl-1H-pyrazol-4-yl)carbonyl | 576.3 | 5.54 |

The following Examples in Table 4 were made by using the same procedure as shown in Example 34 using the second isomer at step 34I. The acids used in the final step are as indicated in the below table in the Intermediate section. Various coupling reagents could be used other than the one described in Example 34 such as BOP, PyBop, EDC/HOBt, HATU or T3P. Boc and SEM deprotection was achieved prior to the final coupling unlike with Example 34 where the Boc group alone was removed in step 34J.

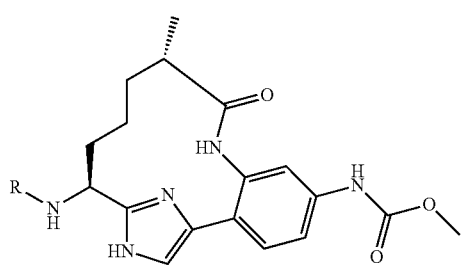

TABLE 4

| Example # | Stereochemistry | R (Acid used) | M + H | RT, min Method A |
|---|---|---|---|---|
| 42 | Homochiral | (1-(3-chlorophenyl)-5-methyl-1H-pyrazole-4-carbonyl) | 576.3 | 6.15 |
| 43 | Homochiral | (5-amino-1-(3-chloro-2-fluorophenyl)-1H-pyrazole-4-carbonyl) | 595.2 | 5.08 |
| 44 | Homochiral | (1-(3-chloro-2-fluorophenyl)-5-methyl-1H-1,2,3-triazole-4-carbonyl) | 595.2 | 5.64 |

Example 45

Methyl (9R,14S)-14-[5-amino-1-(3-chlorophenyl)-1H-1,2,3-triazole-4-amido]-5-[(methoxycarbonyl)amino]-8,16,18-triazatricyclo[13.2.1.0$^{2,7}$]octadeca-1(17),2,4,6,15(18)-pentaene-9-carboxylate, TFA salt

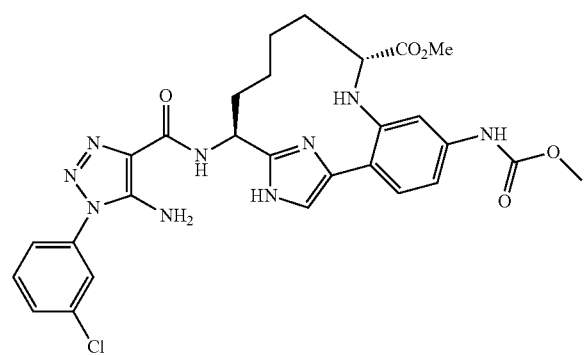 [SMILES: COC(=O)Nc1ccc2c(c1)N[C@@H](C(=O)OC)CCCC[C@H](NC(=O)c1nnn(-c3cccc(Cl)c3)c1N)c1nc-2c[nH]1]

45A. Methyl (3-bromo-4-(2-((1S)-1-((tert-butoxycarbonyl)amino)but-3-en-1-yl)-1-((2-(trimethylsilyl)ethoxy)methyl)-1H-imidazol-4-yl)phenyl)carbamate: 45A was prepared following the procedures described in step 34A, by replacing Intermediate 16 with Intermediate 18; followed by step 34B and 34C. MS(ESI) m/z: 597.1 (M+2+H)$^+$.

45B: (R)-2-(2-(2-((S)-1-(tert-Butoxycarbonylamino)but-3-enyl)-1-((2-(trimethylsilyl) ethoxy)methyl)-1H-imidazol-4-yl)-5-(methoxycarbonylamino)phenylamino)pent-4-enoic acid: To a mixture of 45A (2 g, 3.36 mmol), copper(I) iodide (0.064 g, 0.336 mmol) and K$_2$CO$_3$ (1.160 g, 8.39 mmol) in a sealable tube were added (R)-2-aminopent-4-enoic acid (0.464 g, 4.03 mmol) and DMSO (6.72 mL). The reaction mixture was vacuumed and back-filled with argon for three times, then capped and heated at 90° C. for 18 h. The reaction mixture was then cooled to rt and then diluted with EtOAc and H$_2$O. The aqueous layer was extracted with EtOAc (2×). The combined organic layers were washed with brine, dried over Na$_2$SO$_4$, filtered, and concentrated to give the crude residue. A small amount of DCM (~5 mL) was added to give a brown solution followed by addition of hexanes (~300 mL) to result in a yellow suspension which was filtered. The solid was rinsed with hexane and air-dried to yield the desired product as a yellow solid (1.8 g, 85%). MS(ESI) m/z: 630.4 (M+H)$^+$.

45C. (R)-Methyl 2-(2-(2-((S)-1-(tert-butoxycarbonylamino)but-3-enyl)-1-((2-(trimethylsilyl)ethoxy)methyl)-1H-imidazol-4-yl)-5-(methoxycarbonylamino)phenylamino)pent-4-enoate: To the solution of 45B (1.8 g, 2.86 mmol) in DMF (25 mL) was added K$_2$CO$_3$ (0.395 g, 2.86 mmol) and MeI (0.179 mL, 2.86 mmol). The reaction mixture was stirred at rt. After 20 h, the reaction mixture was diluted with EtOAc and H₂O. The aqueous layer was extracted with EtOAc and the combined organic layers were washed with H₂O and brine. The organic layer was then dried over Na₂SO₄, filtered and concentrated. The crude product was then purified by silica gel chromatography to give brown foam as the desired product (0.58 g, 32%). MS(ESI) m/z: 644.3 (M+H)⁺.

45D. Methyl (2R,7S)-7-((tert-butoxycarbonyl)amino)-14-((methoxycarbonyl)amino)-9-((2-(trimethylsilyl)ethoxy)methyl)-1,2,3,4,5,6,7,9-octahydro-11,8-(azeno)-1,9-benzodiazacyclotridecine-2-carboxylate: A solution of 45C (0.58 g, 0.901 mmol) and Grubbs (II) (0.306 g, 0.360 mmol) in DCE (22.52 mL) was heated at 120° C. under microwave conditions for 20 min and then cooled to rt. The reaction mixture was diluted with EtOAc and then washed with saturated NaHCO₃ solution and brine. The organic layer was then dried over MgSO₄, filtered, and concentrated. The crude product was then purified using silica gel chromatography to give a yellow solid as the desired product (0.128 g, 23%). MS(ESI) m/z: 616.4 (M+H)⁺.

45E. Methyl (2R,7S)-7-((tert-butoxycarbonyl)amino)-14-((methoxycarbonyl)amino)-9-((2-(trimethylsilyl)ethoxy)methyl)-1,2,3,4,5,6,7,9-octahydro-11,8-(azeno)-1,9-benzodiazacyclotridecine-2-carboxylate: To a solution of 45D (0.128 g, 0.208 mmol) in EtOAc (5 mL) was added TFA (0.032 mL, 0.416 mmol) and 10% palladium on carbon (0.022 g, 0.021 mmol). Hydrogen was bubbled through the reaction mixture for 5 min, and the reaction was stirred under H₂-balloon. After 17 h, EtOH (1 mL) was added to the reaction mixture, and the reaction was filtered through a 0.45 μM GMF rinsing with MeOH (filtered twice) and concentrated. The crude product was then purified by reverse phase HPLC and isolated the desired product as a solid (0.113 g, 64%). MS(ESI) m/z: 618.4 (M+H)⁺.

Example 45. Methyl (9R,14S)-14-[5-amino-1-(3-chlorophenyl)-1H-1,2,3-triazole-4-amido]-5-[(methoxycarbonyl)amino]-8,16,18-triazatricyclo[13.2.1.0²,⁷]octadeca-1(17),2,4,6,15(18)-pentaene-9-carboxylate, TFA salt: To a RBF was charged 45E (0.01 g, 0.016 mmol) followed by addition of HCl (4 N in dioxane) (2 mL) and the reaction mixture was heated at 50° C. with small amount of cysteine for overnight. The reaction mixture was then concentrated to a solid mass. In a separate flask, to Intermediate 8 (3.86 mg, 0.016 mmol) in DCM (1 mL) was added Vilsmeier reagent (0.1 mL) and the reaction was stirred at rt for 2 h. The above dried deprotected macrolide was stirred in DCM (1 mL) and to this was cannulated the triazole acid chloride crude followed by the addition of pyridine (0.4 mL) and stirring was continued for 2 h at rt. The reaction mixture was concentrated and purified via reverse phase HPLC to yield the desired product (3 mg, 27%). ¹H NMR (400 MHz, MeOD) δ 7.57-7.46 (m, 4H), 7.45-7.32 (m, 2H), 7.13 (m, 2H), 5.40-5.37 (dd, J=10.9, 7.1 Hz, 1H), 3.66 (s, 3H), 3.49 (s, 3H), 3.03-2.94 (m, 2H), 2.28 (m, J=6.8 Hz, 1H), 1.75-1.66 (m, 4H), 1.23-1.14 (m, 2H), 0.32 (d, J=11.9 Hz, 1H) ppm. MS(ESI) m/z: 608.2 (M+H)⁺. Analytical HPLC (Method A): RT=6.96 min.

The following Examples in Table 5 were made by using the same procedure as shown in Example 45. The acids used in the final step are as indicated in the below table in the Intermediate section. Various coupling reagents could be used other than the one described in Example 45 like BOP, PyBop, EDC/HOBt, HATU or T3P.

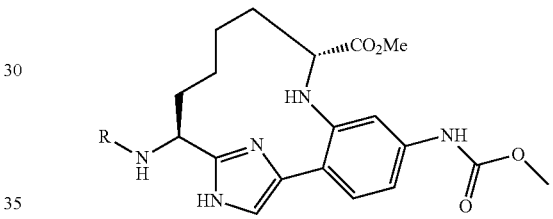

TABLE 5

| Example # | Stereochemistry | R | M + H | RT, min Method A |
|---|---|---|---|---|
| 46 | Homochiral | ![structure with triazole, 2-F-3-Cl-phenyl] | 611.0 | 7.32 |
| 47 | Homochiral | ![structure with pyrazole, 2-F-3-Cl-phenyl] | 610.0 | 7.49 |

TABLE 5-continued

| Example # | Stereochemistry | R | M + H | RT, min Method A |
|---|---|---|---|---|
| 48 | Homochiral | ![structure with pyrazole, NH2, 3-chlorophenyl, ketone] | 607.0 | 6.67 |
| 49 | Homochiral | ![structure with pyrazole, NH2, 2-fluoro-3-chlorophenyl, ketone] | 625.0 | 6.96 |
| 50 | Homochiral | ![structure with triazole, 2,6-difluoro-3-chlorophenyl, ketone] | 629.0 | 7.57 |

Example 51

Methyl N-[(14S)-14-[1-(3-chloro-2-fluorophenyl)-1H-1,2,3-triazole-4-amido]-9-oxo-8,16,18-triazatricyclo[13.0.2.1.0$^{2,7}$]octadeca-1(17),2,4,6,15(18)-pentaen-5-yl]carbamate, TFA salt

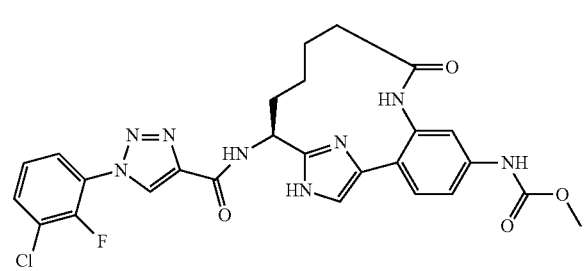 [SMILES: COC(=O)Nc1ccc2c(c1)NC(=O)CCCC[C@H](NC(=O)c1cn(-c3cccc(Cl)c3F)nn1)c1nc-2c[nH]1]

51A. (S)-2-(4-(Methoxycarbonylamino)-2-nitrophenyl)-2-oxoethyl 2-(tert-butoxycarbonylamino)pent-4-enoate: To a clear, colorless solution of (S)-2-(tert-butoxycarbonylamino)pent-4-enoic acid (2.91 g, 13.50 mmol) in DMF (33.7 mL) was added potassium hydrogen carbonate (1.622 g, 16.20 mmol). The reaction mixture was then stirred for 20 min at rt and then cooled to 0° C. To the above cooled solution was then added a solution of Intermediate 16 (4.28 g, 13.50 mmol) in DMF (33.7 mL) dropwise and the reaction mixture was allowed to warm to rt and continued to stir at rt. After 18 h, the reaction was cooled to 0° C. and poured into ice-cold H$_2$O. The aqueous layer was then extracted with EtOAc (3×) and the combined organic layers were washed with H$_2$O, brine, dried over Na$_2$SO$_4$, filtered, and concentrated to yield the desired product as a yellow foam (6.09 g, 100%). MS(ESI) m/z: 450.5 (M−H)$^−$.

51B. Methyl (4-(2-((1S)-1-((tert-butoxycarbonyl)amino)but-3-en-1-yl)-1H-imidazol-5-yl)-3-nitrophenyl)carbamate: To a 1000-mL RBF containing 51A (6.09 g, 13.49 mmol) was added xylene (135 mL) and the reaction mixture was sonicated to obtain a clear yellow solution. To the clear solution was then added ammonium acetate (10.40 g, 135 mmol) and the flask was equipped with a dean-stark trap and reflux condenser. The reaction mixture was then heated 110° C. for 2 h and then at 140° C. for additional 2 h. The reaction was cooled to rt and diluted with EtOAc. The mixture was then washed with saturated NaHCO$_3$ (2×) solution followed by brine. The organic layer was dried over Na$_2$SO$_4$, filtered, and concentrated. The residue was purified by silica gel chromatography to yield the desired product as a brown foam (0.91 g, 16%). MS(ESI) m/z: 432.5 (M+H)$^+$.

51C. Methyl (4-(2-((1S)-1-((tert-butoxycarbonyl)amino)but-3-en-1-yl)-1-((2-(trimethylsilyl)ethoxy)methyl)-1H-imidazol-4-yl)-3-nitrophenyl)carbamate: A flame-dried 25 mL RBF was charged with NaH (0.092 g, 2.295 mmol) and then THF (4.17 mL) was added to give a gray suspension.

The suspension was cooled to 0° C. and then a clear, yellow solution of 51B (0.9 g, 2.086 mmol) in THF (4.17 mL) was added dropwise. The reaction mixture was stirred at 0° C. for 30 min and then allowed to warm to rt and stirred for 0.5 h. The yellow suspension was cooled to 0° C. and then SEM-Cl (0.370 mL, 2.086 mmol) was added dropwise. The resulting cloudy reaction mixture was stirred at 0° C. After 1 h, the reaction was stopped and quenched with saturated NH$_4$Cl solution followed by dilution with EtOAc. The layers were separated and the aqueous layer was extracted with EtOAc. The combined organic layers were washed with saturated NaHCO$_3$, brine, dried over Na$_2$SO$_4$, filtered, and concentrated. The residue was then purified by silica gel chromatography to obtain the desired product as a yellow foam (0.424 g, 36%). MS(ESI) m/z: 562.0 (M+H)$^+$. 1D NOE confirmed the regioisomeric position of SEM on the imidazole ring.

51D. (S)-Methyl 4-(2-(1-Boc-aminobut-3-enyl)-1-((2-(trimethylsilyl)ethoxy)methyl)-1H-imidazol-4-yl)-3-aminophenylcarbamate: To a solution of 51C (0.424 g, 0.755 mmol) in MeOH (5 mL) was added zinc (0.494 g, 7.55 mmol) and ammonium chloride (0.404 g, 7.55 mmol). The combined reaction mixture was stirred at 60° C. in a sealed tube for 4 h and then cooled to rt. The yellow suspension was diluted with DCM and washed with H$_2$O. The aqueous layer was extracted with 15% IPA/CHCl$_3$ and the combined organic layers were washed with brine, dried over MgSO$_4$, filtered and concentrated. The crude product was then purified using silica gel chromatography to give an orange solid as the desired product (0.31 g, 77%). MS(ESI) m/z: 532.4 (M+H)$^+$.

51E. (S)-Methyl 4-(2-(1-Boc-aminobut-3-enyl)-1-((2-(trimethylsilyl)ethoxy)methyl)-1H-imidazol-4-yl)-3-(but-4-enamido)-phenylcarbamate: To a solution of but-3-enoic acid (0.024 g, 0.282 mmol) and 51D (0.15 g, 0.282 mmol) in EtOAc (8.06 mL) was added DIEA (0.148 mL, 0.846 mmol). The reaction mixture was allowed to cool to −10° C. under argon. Next, T3P (0.332 mL, 0.564 mmol) was added and the reaction was allowed to stir for 5 min. The reaction mixture was then warmed to rt while stirring under argon for 1 h. The crude product was then purified by silica gel chromatography to yield a yellow solid (0.130 g, 77%). MS(ESI) m/z: 600.4 (M+H)$^+$.

51F. tert-Butyl methyl ((7S)-2-oxo-9-((2-(trimethylsilyl)ethoxy)methyl)-1,2,3,4,5,6,7,9-octahydro-11,8-(azeno)-1,9-benzodiazacyclotridecine-7,14-diyl)biscarbamate: 51E was subjected to the macrocyclization protocol as described previously to obtain the unsaturated macrocyclized product. The purified product was then subjected to hydrogenation using palladium on carbon (10%) (83 mg, 0.042 mmol). The flask was purged with nitrogen and to the flask was added EtOH (absolute) (10 mL) and EtOAc (10 mL). The flask was again purged with nitrogen (3×), evacuated and an atmosphere of hydrogen (approx. 55 psi) was introduced and the reaction was stirred at ambient temperature. The reaction mixture was then filtered through a pad of CELITE® with the aid of additional EtOAc and the solvent was evaporated. The desired product was obtained as a colorless solid (113 mg, 93%) which was used without further purification. MS(ESI) m/z: 574.5 (M+H)$^+$.

Example 51. Methyl N-[(14S)-14-[1-(3-chloro-2-fluorophenyl)-1H-1,2,3-triazole-4-amido]-9-oxo-8,16,18-triazatricyclo[13.2.1.0$^{2,7}$]octadeca-1(17),2,4,6,15(18)-pentaen-5-yl]carbamate, TFA salt: To a RBF charged with 51F (0.02 g, 0.035 mmol) was added 4 N HCl in dioxane (2 mL) and stirred at 70° C. for 2 h. The reaction mixture was then concentrated and dried under vacuum. The crude product was then dissolved in DMF (2 mL) and to the above solution was added Intermediate 1 (8.42 mg, 0.035 mmol) and T3P (0.040 mmol). The reaction mixture was again stirred at rt. After 2 h, the reaction mixture was then concentrated and purified via reverse phase HPLC to isolate the desired product as a yellow solid (1.4 mg, 5%). $^1$H NMR (400 MHz, MeOD) δ 8.84 (dd, J=17.0, 2.2 Hz, 1H), 7.75 (td, J=7.3, 1.4 Hz, 1H), 7.68-7.55 (m, 1H), 7.50 (d, J=1.6 Hz, 1H), 7.44-7.23 (m, 5H), 5.27 (dd, J=10.7, 6.3 Hz, 3H), 4.49-4.29 (m, 3H), 3.72-3.59 (m, 3H), 2.47-2.34 (m, 2H), 2.32-2.12 (m, 3H), 2.09-1.89 (m, 4H), 1.69-1.08 (m, 13H), 1.31-1.08 (m, 4H), 0.93 (s, 3H) ppm. MS(ESI) m/z: 567.0 (M+H)$^+$. Analytical HPLC: RT=4.76 min (Method B).

Example 52

Methyl N-[(14S)-14-[1-(3-chlorophenyl)-1H-1,2,3-triazole-4-amido]-9-oxo-8,16,18-triazatricyclo[13.2.1.0$^{2,7}$]octadeca-1(17),2,4,6,15(18)-pentaen-5-yl]carbamate, TFA salt

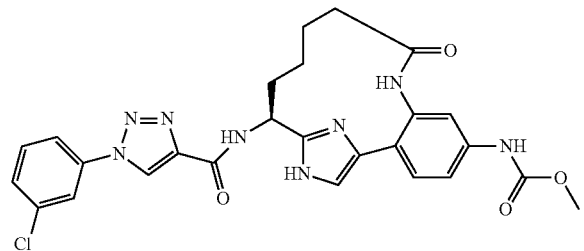 [SMILES: COC(=O)Nc1ccc2c(c1)NC(=O)CCCC[C@H](NC(=O)c1cn(-c3cccc(Cl)c3)nn1)c1nc-2c[nH]1]

Example 52. Methyl N-[(14S)-14-[1-(3-chlorophenyl)-1H-1,2,3-triazole-4-amido]-9-oxo-8,16,18-triazatricyclo[13.2.1.0$^{2,7}$]octadeca-1(17),2,4,6,15(18)-pentaen-5-yl]carbamate, TFA salt: Example 52 was made in the same way as Example 51 except the final coupling step where it used the Vilsmeier protocol as described with Example 45. $^1$H NMR (400 MHz, MeOD) δ 8.96 (s, 1H), 7.91 (t, 1H), 7.78 (dd, 1H), 7.51-7.45 (m, 3H), 7.42-7.403 (m, 2H), 7.34 (dd, 1H), 5.26 (m, 1H), 3.66 (s, 3H), 2.40 (m, 1H), 2.24 (m, 1H), 2.04-1.98 (m, 2H), 1.65-1.53 (m, 2H), 1.38 (m, 1H), 0.98 (bm, 1H) ppm. MS(ESI) m/z: 549.2 (M+H)$^+$. Analytical HPLC: RT=4.90 min (Method B).

Example 53

Methyl N-[(10S,14S)-14-[1-(3-chloro-2-fluorophenyl)-1H-1,2,3-triazole-4-amido]-10-ethyl-9-oxo-8,16,18-triazatricyclo[13.2.1.0$^{2,7}$]octadeca-1(17),2(7),3,5,15(18)-pentaen-5-yl]carbamate, TFA salt

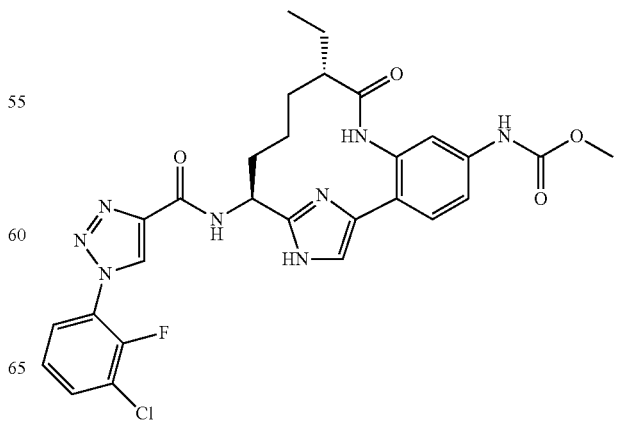

Example 53. Methyl N-[(10S,14S)-14-[1-(3-chloro-2-fluorophenyl)-1H-1,2,3-triazole-4-amido]-10-ethyl-9-oxo-8,16,18-triazatricyclo[13.2.1.0$^{2,7}$]octadeca-1(17),2(7),3,5,15(18)-pentaen-5-yl]carbamate, TFA salt: Example 53 was prepared in the same way as Example 24 by substituting 24A with 51D and using 4 N HCl in dioxane to deprotect Boc and SEM group at the same time before the final coupling step. Example 53 was isolated as one of the early eluting diastereomers during the reduction of the macrocycle on prep HPLC. $^1$H NMR (400 MHz, MeOD) δ 8.86 (d, J=2.3 Hz, 1H), 7.93 (dd, J=8.2, 1.6 Hz, 1H), 7.78-7.90 (m, 1H), 7.68-7.76 (m, 1H), 7.52 (d, J=1.8 Hz, 1H), 7.28-7.48 (m, 3H), 7.09 (s, 1H), 5.40-5.51 (m, 1H), 3.74 (s, 3H), 2.34-2.47 (m, 1H), 2.08-2.24 (m, 1H), 1.86-2.02 (m, 2H), 1.50-1.79 (m, 2H), 1.33-1.50 (m, 2H), 1.23-1.32 (m, 1H), 0.93 (t, J=7.5 Hz, 3H) ppm. MS(ESI) m/z: 595.2 (M+H)$^+$. Analytical HPLC: RT=5.55 min (Method A).

Example 54

Methyl N-[(10R,14S)-14-[1-(3-chloro-2-fluorophenyl)-1H-1,2,3-triazole-4-amido]-10-ethyl-9-oxo-8,16,18-triazatricyclo[13.2.1.0$^{2,7}$]octadeca-1(17),2(7),3,5,15(18)-pentaen-5-yl]carbamate, TFA salt

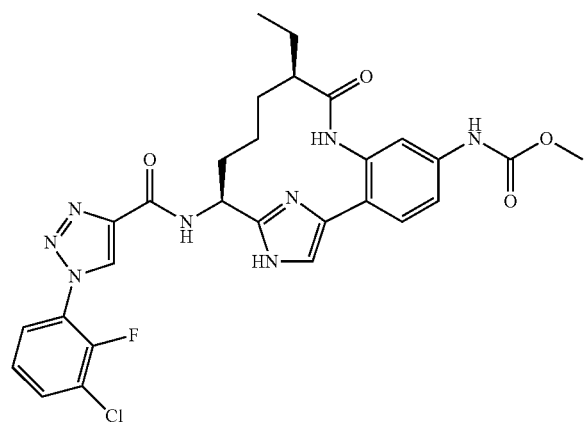 [SMILES: CC[C@@H]1CCC[C@H](NC(=O)c2cn(-c3cccc(Cl)c3F)nn2)c2nc(c[nH]2)-c2ccc(NC(=O)OC)cc2NC1=O]

Example 54. Methyl N-[(10R,14S)-14-[1-(3-chloro-2-fluorophenyl)-1H-1,2,3-triazole-4-amido]-10-ethyl-9-oxo-8,16,18-triazatricyclo[13.2.1.0$^{2,7}$]octadeca-1(17),2(7),3,5,15(18)-pentaen-5-yl]carbamate, TFA salt: Example 54 was made in the same way as Example 53 and isolated as the late eluting diastereomer during the reduction of the macrocycle on prep HPLC. $^1$H NMR (400 MHz, MeOD) δ 9.62 (s, 1H), 8.93 (d, J=2.2 Hz, 1H), 7.80-7.94 (m, 1H), 7.76 (ddd, J=8.3, 6.7, 1.5 Hz, 1H), 7.41-7.64 (m, 5H), 5.31 (dd, J=10.3, 5.9 Hz, 1H), 3.78 (s, 3H), 2.25-2.45 (m, 2H), 1.99-2.16 (m, 1H), 1.71-1.85 (m, 1H), 1.58-1.71 (m, 1H), 1.45-1.58 (m, 1H), 1.18-1.41 (m, 3H), 1.02 (t, J=7.3 Hz, 3H) ppm. MS(ESI) m/z: 595.3 (M+H)$^+$. Analytical HPLC: RT=5.91 min (Method A).

Example 55

Methyl N-[(14S)-14-[1-(3-chloro-2-fluorophenyl)-1H-1,2,3-triazole-4-amido]-9-oxo-10-(propan-2-yl)-8,16,18-triazatricyclo[13.2.1.0$^{2,7}$]octadeca-1(17),2,4,6,15(18)-pentaen-5-yl]carbamate, TFA salt

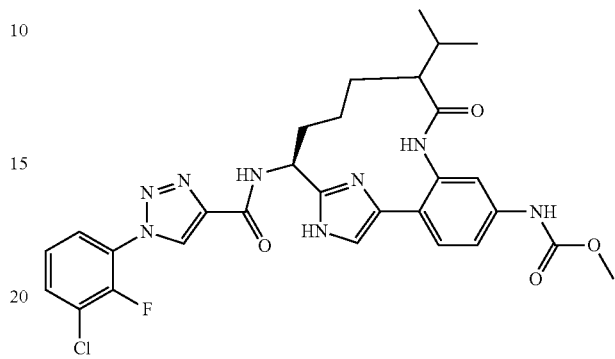

55A. tert-Butyl N-[(1S)-1-(4-{4-[(methoxycarbonyl)amino]-2-[2-(propan-2-yl)but-3-enamido]phenyl}-1-{[2-(trimethylsilyl)ethoxy]methyl}-1H-imidazol-2-yl)but-3-en-1-yl]carbamate, TFA salt: 55A was prepared in the same way as 21B by substituting but-3-enoic acid with 2-isopropylbut-3-enoic acid and 21A with 51D. The desired product was isolated as a greenish oil. MS(ESI) m/z: 642.6 (M+H)$^+$.

Example 55. Methyl N-[(14S)-14-[1-(3-chloro-2-fluorophenyl)-1H-1,2,3-triazole-4-amido]-9-oxo-10-(propan-2-yl)-8,16,18-triazatricyclo[13.2.1.0$^{2,7}$]octadeca-1(17),2,4,6,15(18)-pentaen-5-yl]carbamate, TFA salt: Example 55 is prepared the same way as Example 24 by substituting 24A with 55A and using 4 N HCl in dioxane to deprotect Boc and SEM group at the same time before the final coupling step. Example 55 was isolated as a diastereomeric mixture and so the final compound is a diastereomeric mixture. $^1$H NMR (500 MHz, MeOD) δ 8.90 (m, 1H), 7.85-7.84 (m, 1H), 7.71-7.69 (m, 1H), 7.60 (s, 1H), 7.55-7.41 (m, 4H), 5.39 (dd, J=10.8, 6.9 Hz, 1H), 3.76 (s, 2H), 2.42 (m, 1H), 2.24-2.10 (m, 2H), 1.81-1.47 (m, 4H), 0.98 (d, 3H), 0.90 (d, 3H) ppm. MS(ESI) m/z: 609.2 (M+H)$^+$. Analytical HPLC: RT=5.51 min (Method B).

Example 56

Methyl N-[(14S)-14-[1-(3-chloro-2-fluorophenyl)-1H-1,2,3-triazole-4-amido]-9-oxo-10-(propan-2-yl)-8,16,18-triazatricyclo[13.2.1.0$^{2,7}$]octadeca-1(17),2,4,6,15(18)-pentaen-5-yl]carbamate, TFA salt

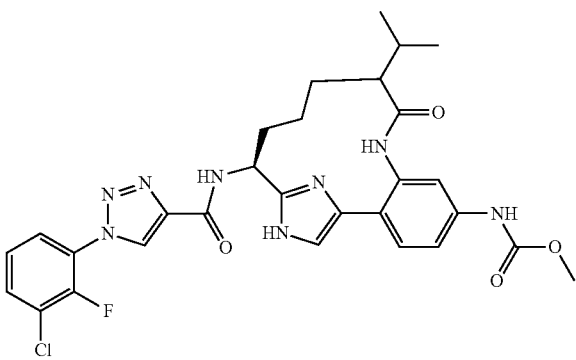 [SMILES: COC(=O)Nc1ccc2c(c1)NC(=O)C(C(C)C)CCC[C@H](NC(=O)c1cn(-c3cccc(Cl)c3F)nn1)c1nc-2c[nH]1]

Example 56. Methyl N-[(14S)-14-[1-(3-chloro-2-fluorophenyl)-1H-1,2,3-triazole-4-amido]-9-oxo-10-(propan-2-yl)-8,16,18-triazatricyclo[13.2.1.0$^{2,7}$]octadeca-1(17),2,4,6,15(18)-pentaen-5-yl]carbamate, TFA salt: Example 56 was made in the same way as Example 55 and was isolated as a single diastereomer during Grubbs macrocyclization protocol. It was isolated as the second peak following macrocyclization and the final compound was homochiral. MS(ESI) m/z: 609.3 (M+H)$^+$. Analytical HPLC (Method A) RT=7.34 min.

Example 57

Methyl N-[(12E,15 S)-15-[1-(3-chloro-2-fluorophenyl)-1H-pyrazole-4-amido]-18-cyano-9-oxo-8,17,19-triazatricyclo[14.2.1.0$^{2,7}$]nonadeca-1(18),2,4,6,12,16(19)-hexaen-5-yl]carbamate, TFA salt

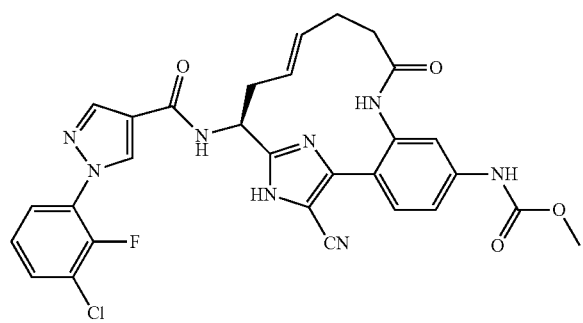 [SMILES: COC(=O)Nc1ccc2c(c1)NC(=O)CC/C=C/C[C@H](NC(=O)c1cnn(-c3cccc(Cl)c3F)c1)c1nc-2c(C#N)[nH]1]

57A. (S)-2-(4-(Methoxycarbonylamino)-2-nitrophenyl)-2-oxoethyl 2-(tert-butoxycarbonylamino)pent-4-enoate: To a clear, colorless solution of (S)-2-(tert-butoxycarbonylamino)pent-4-enoic acid (2.91 g, 13.50 mmol) in DMF (33.7 mL) was added potassium hydrogen carbonate (1.622 g, 16.20 mmol) and the reaction mixture was stirred for 20 min at rt and then cooled to 0° C. To the above mixture was then added a solution of Intermediate 16 (4.28 g, 13.50 mmol) in DMF (33.7 mL) dropwise and the reaction was allowed to warm to rt and stirring was continued. After 18 h, the reaction was stopped, cooled to 0° C. and poured into ice-cold H$_2$O. The aqueous layer was then extracted with EtOAc (3×) and the combined organic layers were washed with H$_2$O and brine. The organic layers were then dried over Na$_2$SO$_4$, filtered and concentrated to give the desired product as a yellow foam (6.09 g, 100%). MS(ESI) m/z: 450.5 (M-H)$^-$.

57B. Methyl (4-(2-(((1S)-1-((tert-butoxycarbonyl)amino)but-3-en-1-yl)-1H-imidazol-5-yl)-3-nitrophenyl)carbamate: To a 1000-mL RBF containing 57A (6.09 g, 13.49 mmol) was added xylene (135 mL) and sonicated to obtain a clear yellow solution. To the above clear solution was then added ammonium acetate (10.40 g, 135 mmol) and the flask was equipped with a dean-stark trap and reflux condenser. The reaction mixture was then warmed to 110° C. for 2 h, then 140° C. for additional 2 h. The reaction was cooled to rt and diluted with EtOAc. The mixture was then washed with saturated NaHCO$_3$ (2×) and brine. The organic layer was dried over Na$_2$SO$_4$, filtered, and concentrated. The crude product was purified by silica gel chromatography to yield a brown foam as the desired product (0.91 g, 16%). MS(ESI) m/z: 432.5 (M+H)$^+$.

57C. Methyl (4-(2-(((1S)-1-((tert-butoxycarbonyl)amino)but-3-en-1-yl)-1-((2-(trimethylsilyl)ethoxy)methyl)-1H-imidazol-4-yl)-3-nitrophenyl)carbamate: A flame-dried 25 mL RBF was charged with NaH (0.092 g, 2.295 mmol) and then THF (4.17 mL) was added to give a gray suspension. The suspension was cooled to 0° C. and then a clear, yellow solution of 57B (0.9 g, 2.086 mmol) in THF (4.17 mL) was added dropwise. The reaction mixture was stirred at 0° C. for 30 min and then allowed to warm to rt and stirred for 0.5 h. The yellow suspension was cooled to 0° C. and then SEM-Cl (0.370 mL, 2.086 mmol) was added dropwise. The resulting cloudy reaction mixture was then stirred at 0° C. After 1 h, the reaction mixture was quenched with saturated NH$_4$Cl solution followed by dilution with EtOAc. The layers were separated and the aqueous layer was extracted with EtOAc. The combined organic layers were washed with saturated NaHCO$_3$, brine, dried over Na$_2$SO$_4$, filtered, and concentrated. The crude product was purified by silica gel chromatography to yield the desired product as a yellow foam (0.424 g, 36%). MS(ESI) m/z: 562.0 (M+H)$^+$. 1D NOE confirmed the regioisomeric position of SEM on the imidazole ring.

57D. (S)-Methyl 4-(2-(1-Boc-aminobut-3-enyl)-1-((2-(trimethylsilyl)ethoxy)methyl)-1H-imidazol-4-yl)-3-aminophenylcarbamate: To a solution of 57C (0.424 g, 0.755 mmol) in MeOH (5 mL) was added zinc (0.494 g, 7.55 mmol) and ammonium chloride (0.404 g, 7.55 mmol). The mixture was stirred at 60° C. in a sealed tube for 4 h and then cooled to rt. The yellow suspension was diluted with DCM and then washed with H$_2$O. The aqueous layer was extracted with 15% IPA/CHCl$_3$. The combined organic layers were washed with brine, dried over MgSO$_4$, filtered and concentrated. The crude product was purified using silica gel chromatography to give an orange solid as the desired product (0.31 g, 77%). MS(ESI) m/z: 532.4 (M+H)$^+$.

57E. (S)-Methyl 4-(2-(1-Boc-aminobut-3-enyl)-1-((2-(trimethylsilyl)ethoxy)methyl)-1H-imidazol-4-yl)-3-(pent-4-enamido)-phenylcarbamate: To a solution of pent-4-enoic acid (0.028 g, 0.282 mmol) and 57D (0.15 g, 0.282 mmol) in EtOAc (8.06 mL) was added DIEA (0.148 mL, 0.846 mmol). The reaction mixture was allowed to cool to −10° C. under argon. To the above mixture was then added 1-propanephosphonic acid cyclic anhydride in EtOAc (0.332 mL, 0.564 mmol) and the reaction was allowed to stir for 5 min. The reaction mixture was then warmed to rt while stirring under argon for additional 1 h and then it was concentrated. The crude product was purified by silica gel chromatography to obtain a yellow solid (0.092 g, 53%). MS(ESI) m/z: 614.1 (M+H)$^+$.

57F. tert-Butyl methyl ((5E,8S)-2-oxo-10-((2-(trimethylsilyl)ethoxy)methyl)-1,3,4,7,8,10-hexahydro-2H-12,9-(azeno)-1,10-benzodiazacyclotetradecine-8,15-diyl)biscarbamate: To a round bottom flask equipped with an argon bubbler was charged with finely powdered 57E (1.0165 g, 1.656 mmol) and p-TsOH monohydrate (0.299 g, 1.739 mmol). The flask was then purged with argon and DCM (anhydrous—degassed) (78 mL) was added followed by heating of the colorless mixture at 40° C. The mixture was rapidly stirred at this temperature until the reactants went into solution (~5 min) after which a solution of tricyclohexylphosphine[1,3-bis(2,4,6-trimethylphenyl)-4,5-dihydroimidazol-2-ylidene][benzylidene]ruthenium(IV)dichloride (0.070 g, 0.083 mmol) in DCM (anhydrous—degassed) (5.0 mL) was added at the rate of ~1 drop per second. Stirring was continued at 40° C. for 90 minutes at which time an aliquot was removed. The mixture was then cooled to rt and washed with saturated NaHCO$_3$ solution and brine.

The organic layer was then dried over Na₂SO₄, filtered, and concentrated to give a dark solid. The residue was purified using silica gel chromatography to give the desired product, as a mixture of the cis- and trans-olefin isomers. The crude product was purified by reverse phase HPLC to give two fractions, fraction 1 (trans-olefin isomer) and fraction 2 (cis-olefin isomer). Appropriate trans fractions were evaporated to obtain the desired product as a colorless solid (404 mg, 42%). MS(ESI) m/z: 586.5 (M+H)⁺.

57G. (5E,8S)-11-Bromo-10,15-dimethyl-8-(methylamino)-1,3,4,7,8,10-hexahydro-2H-12,9-(azeno)-1,10-benzodiazacyclotetradecin-2-one: To a solution of 57F (0.225 g, 0.384 mmol) in CHCl₃ (5 mL) and ACN (5 mL) was added NBS (0.082 g, 0.461 mmol) in a portion and the resulting solution was stirred for 0.5 h at rt. The mixture was concentrated and purified using silica gel chromatography to isolate the desired product (0.178 g, 70%). MS(ESI) m/z: 666.3 (M+H)⁺.

57H. tert-Butyl methyl ((5E,8S)-11-cyano-2-oxo-10-((2-(trimethylsilyl)ethoxy)methyl)-1,3,4,7,8,10-hexahydro-2H-12,9-(azeno)-1,10-benzodiazacyclotetradecine-8,15-diyl)biscarbamate: A solution of 57G (0.18 g, 0.271 mmol), zinc cyanide (0.019 g, 0.162 mmol), DPPF (0.018 g, 0.032 mmol) and Pd₂(dba)₃-CHCl₃ (0.012 g, 0.014 mmol) in DMF (2 mL) was degassed for 0.5 h under argon bubbling. The solution was then stirred at 130° C. for 0.5 h under microwave conditions. The reaction mixture was then diluted with EtOAc and washed with NaHCO₃ solution followed by brine. The organic layer was then dried over MgSO₄ and concentrated to give the crude product which was purified using reverse phase HPLC to isolate the desired product (0.145 g, 88%). MS(ESI) m/z: 611.3 (M+H)⁺.

57I. Methyl ((5E,8S)-8-amino-11-cyano-2-oxo-1,3,4,7,8,10-hexahydro-2H-12,9-(azeno)-1,10-benzodiazacyclotetradecin-15-yl)carbamate: To a solution of 57H (145 mg, 0.237 mmol) in DCM (3 mL) was added TFA (0.500 mL) and the reaction was stirred at rt. After 2 h, the reaction mixture was concentrated to dryness. To the solid was added EtOAc and enough saturated NaHCO₃ (to make it basic). The aqueous layer was then extracted with EtOAc (3×) and the combined organic layers were washed with brine, dried over MgSO₄, filtered, and concentrated to give 421 (90 mg, 100%) as a reddish solid. MS(ESI) m/z: 381.1 (M+H)⁺.

Example 57. Methyl N-[(12E,15S)-15-[1-(3-chloro-2-fluorophenyl)-1H-pyrazole-4-amido]-18-cyano-9-oxo-8,17,19-triazatricyclo[14.2.1.0²,⁷]nonadeca-1(18),2,4,6,12,16(19)-hexaen-5-yl]carbamate, TFA salt: 57I (0.017 g, 0.045 mmol) was coupled with Intermediate 2 (10.75 mg, 0.045 mmol) under the T3P (0.034 g, 0.045 mmol)/DIEA (7.81 µL, 0.045 mmol) and DMF conditions as previously described. After 2 h the reaction was concentrated and purified via reverse phase HPLC to yield the desired product as a white solid (6 mg, 22%). MS(ESI) m/z: 603.1 (M+H)⁺. Analytical HPLC: RT=6.16 min (Method B).

Example 58

Methyl ((12E,15S)-15-(((2-(3-chloro-2,6-difluorophenyl)-1H-imidazol-4-yl)carbonyl)amino)-9-oxo-8,17,19-triazatricyclo[14.2.1.0²,⁷]nonadeca-1(18),2,4,6,12,16(19)-hexaen-5-yl)carbamate, 2 TFA salt

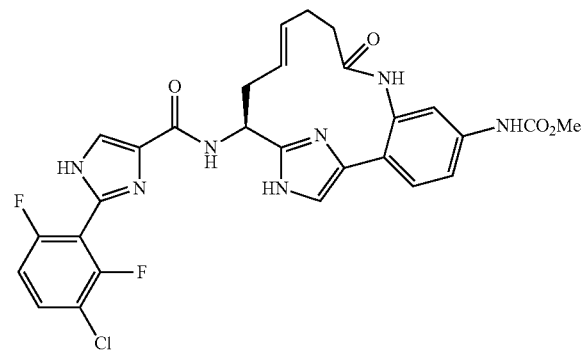

Example 58. Methyl ((12E,15S)-15-(((2-(3-chloro-2,6-difluorophenyl)-1H-imidazol-4-yl)carbonyl)amino)-9-oxo-8,17,19-triazatricyclo[14.2.1.0²,⁷]nonadeca-1(18),2,4,6,12,16(19)-hexaen-5-yl)carbamate, 2 TFA salt: Example 58 was made in the same way as Example 57 by replacing Intermediate 2 with Intermediate 22. ¹H NMR (400 MHz, CDCl₃) δ 7.95 (s, 1H), 7.73 (td, J=8.7, 5.5 Hz, 1H), 7.46 (s, 3H), 7.34-7.21 (m, 1H), 5.73-5.58 (m, 1H), 5.51 (br. s., 1H), 5.31 (dd, J=10.3, 4.8 Hz, 1H), 3.80 (s, 3H), 3.31-3.24 (m, 1H), 2.94 (d, J=13.8 Hz, 1H), 2.76-2.64 (m, 1H), 2.61-2.38 (m, 3H) ppm. MS(ESI) m/z: 596.1 (M+H)⁺. Analytical HPLC: RT=4.24 min.

Example 59

Methyl ((10R,14S)-14-(((1-(3-chloro-2-fluorophenyl)-1H-1,2,3-triazol-4-yl)carbonyl)amino)-10-methyl-9-oxo-8,18-diazatricyclo[13.3.1.0²,⁷]nonadeca-1(19),2,4,6,15,17-hexaen-5-yl)carbamate, TFA salt

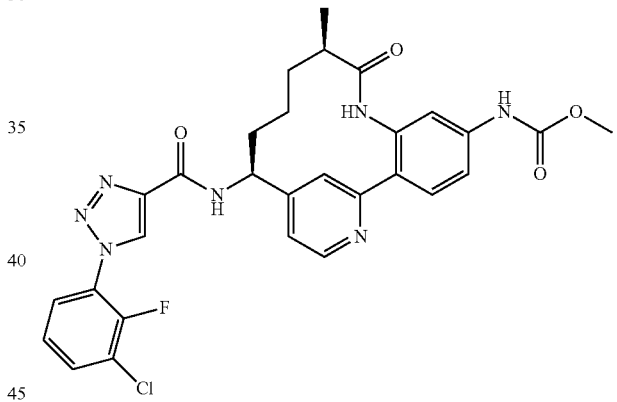

Example 59. Methyl ((10R,14S)-14-(((1-(3-chloro-2-fluorophenyl)-1H-1,2,3-triazol-4-yl)carbonyl)amino)-10-methyl-9-oxo-8,18-diazatricyclo[13.3.1.0²,⁷]nonadeca-1(19),2,4,6,15,17-hexaen-5-yl)carbamate, TFA salt: Example 59 was made in the same way as Example 31 by replacing intermediate 2 with intermediate 1. ¹H NMR (500 MHz, acetonitrile-d₃) δ 8.63 (d, J=5.8 Hz, 1H), 8.50 (d, J=2.2 Hz, 1H), 8.21 (s, 1H), 7.91 (s, 1H), 7.87 (d, J=6.9 Hz, 1H), 7.83 (s, 1H), 7.70 (ddd, J=8.2, 6.7, 1.7 Hz, 1H), 7.66 (d, J=8.5 Hz, 1H), 7.60 (ddd, J=8.3, 6.8, 1.7 Hz, 1H), 7.42-7.38 (m, 2H), 7.34-7.27 (m, 2H), 5.11-5.02 (m, 1H), 3.64 (s, 3H), 2.55 (td, J=6.4, 2.6 Hz, 2H), 1.99 (td, J=4.7, 2.3 Hz, 1H), 1.72-1.69 (m, 1H), 1.47-1.39 (m, 2H), 1.36-1.30 (m, 2H), 0.83 (d, J=6.9 Hz, 3H). MS(ESI) m/z: 592.3 (M+H)⁺. Analytical HPLC (Method E) RT=5.97 min.

Example 60

Methyl ((10S,14S)-14-(((1-(3-chloro-2-fluorophenyl)-1H-1,2,3-triazol-4-yl)carbonyl)amino)-10-methyl-9-oxo-8,18-diazatricyclo[13.3.1.0²,⁷]nonadeca-1(19),2,4,6,15,17-hexaen-5-yl)carbamate, TFA salt

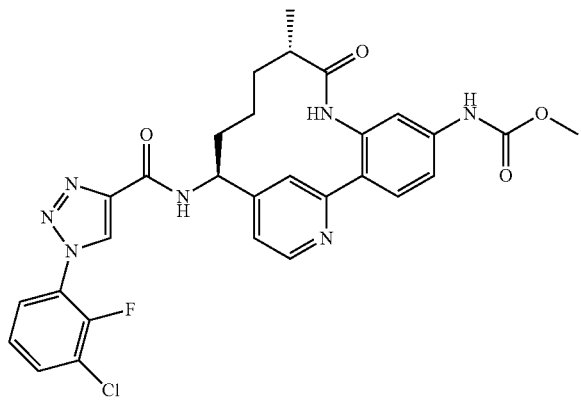 [SMILES: COC(=O)Nc1ccc2c(c1)NC(=O)[C@@H](C)CCC[C@H](NC(=O)c1cn(-c3cccc(Cl)c3F)nn1)c1ccnc-2c1]

Example 60. Methyl ((10S,14S)-14-(((1-(3-chloro-2-fluorophenyl)-1H-1,2,3-triazol-4-yl)carbonyl)amino)-10-methyl-9-oxo-8,18-diazatricyclo[13.3.1.0²,⁷]nonadeca-1(19),2,4,6,15,17-hexaen-5-yl)carbamate, TFA salt: Example 60 is prepared the same way as Example 59 using the other isomer. ¹H NMR (500 MHz, CD₃CN) δ 8.46-8.52 (m, 1H), 7.86 (s, 1H), 7.80 (br. s., 2H), 7.69 (d, J=8.25 Hz, 2H), 7.60 (ddd, J=1.51, 6.81, 8.18 Hz, 1H), 7.48 (s, 1H), 7.26-7.38 (m, 4H), 7.14 (dd, J=1.65, 5.23 Hz, 1H), 4.92-5.00 (m, 1H), 3.97 (q, J=7.15 Hz, 1H), 3.63 (s, 3H), 2.11-2.18 (m, 1H), 1.91-1.96 (m, 1H), 1.62-1.76 (m, 2H), 1.07-1.13 (m, 3H), 0.91-0.97 (m, 1H), 0.76-0.81 (m, 1H) ppm. MS(ESI) m/z: 592.2 (M+H)⁺. Analytical HPLC (Method E) RT=6.00 min.

Example 61

Methyl N-[(10R,14S)-14-[1-(3-chloro-2-fluorophenyl)-5-methyl-1H-pyrazole-4-amido]-10-methyl-9-oxo-8,16-diazatricyclo[13.3.1.0²,⁷]nonadeca-1(19),2(7),3,5,15,17-hexaen-5-yl]carbamate, TFA salt

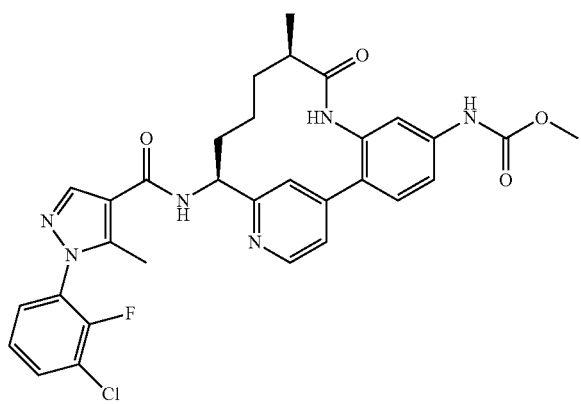

Example 61. Methyl N-[(10R,14S)-14-[1-(3-chloro-2-fluorophenyl)-5-methyl-1H-pyrazole-4-amido]-10-methyl-9-oxo-8,16-diazatricyclo[13.3.1.0²,⁷]nonadeca-1(19),2(7),3,5,15,17-hexaen-5-yl]carbamate, TFA salt: To a vial containing Intermediate 25 (0.085 g, 0.335 mmol), 2M (0.2 g, 0.335 mmol), EDC (0.096 g, 0.503 mmol), HOBT (0.077 g, 0.503 mmol), and DMF (4 mL) was added Hunig's base (0.293 mL, 1.677 mmol). The reaction was stirred at rt overnight and then concentrated. The residue was purified by reverse phase HPLC to yield the desired product (0.073 g, 30%) as an off-white solid. ¹H NMR (500 MHz, MeOD) δ 8.69 (d, J=6.1 Hz, 1H), 8.30 (s, 1H), 8.11 (d, J=1.1 Hz, 1H), 7.81 (dd, J=5.9, 1.8 Hz, 1H), 7.71 (ddd, J=8.1, 6.7, 1.7 Hz, 1H), 7.62 (d, J=8.5 Hz, 1H), 7.57 (d, J=1.9 Hz, 1H), 7.50 (dd, J=8.5, 2.2 Hz, 1H), 7.46 (ddd, J=8.0, 6.5, 1.7 Hz, 1H), 7.40-7.36 (m, 1H), 5.24 (dd, J=11.4, 5.9 Hz, 1H), 3.77 (s, 3H), 2.80-2.73 (m, 1H), 2.35 (d, J=1.1 Hz, 3H), 2.23-2.13 (m, 1H), 2.02-1.90 (m, 2H), 1.65-1.46 (m, 2H), 0.97 (d, J=6.9 Hz, 3H), 0.55-0.44 (m, 1H) ppm. MS(ESI) m/z: 605.2 (M+H)⁺. Analytical HPLC RT=5.96 min (Method A).

Example 62

Methyl N-[(10R,14S)-14-[1-(3-chloro-2-fluorophenyl)-5-methyl-1H-imidazole-4-amido]-10-methyl-9-oxo-8,16-diazatricyclo[13.3.1.0²,⁷]nonadeca-1(19),2(7),3,5,15,17-hexaen-5-yl]carbamate, 2 TFA salt

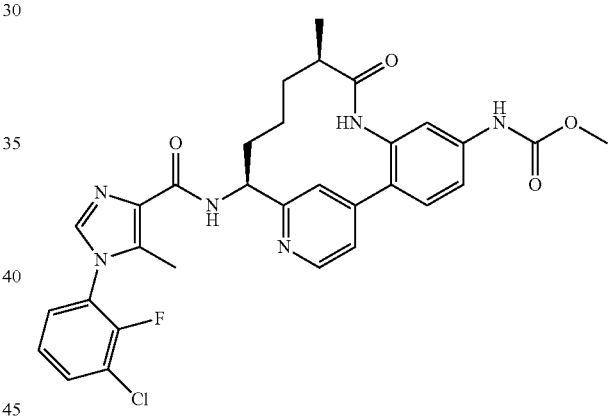

Example 62. Methyl N-[(10R,14S)-14-[1-(3-chloro-2-fluorophenyl)-5-methyl-1H-imidazole-4-amido]-10-methyl-9-oxo-8,16-diazatricyclo[13.3.1.0²,⁷]nonadeca-1(19),2(7),3,5,15,17-hexaen-5-yl]carbamate, 2 TFA salt: A clear, colorless solution of Intermediate 24 (0.012 g, 0.045 mmol), 2M (Alternative, 2 HCl) (0.020 g, 0.045 mmol), EDC (0.013 g, 0.068 mmol), HOBT (10.41 mg, 0.068 mmol), and Hunig's base (0.040 ml, 0.227 mmol) in DMF (0.453 mL) was stirred at rt overnight. The reaction was diluted with MeOH and purified by reverse phase HPLC to yield the desired product (0.0172 g, 44%) as an off-white granular solid. ¹H NMR (500 MHz, MeOD) δ 8.71 (d, J=5.8 Hz, 1H), 8.14 (d, J=1.7 Hz, 1H), 7.84 (dd, J=5.9, 1.8 Hz, 1H), 7.81 (s, 1H), 7.72 (ddd, J=8.2, 6.7, 1.7 Hz, 1H), 7.63 (d, J=8.5 Hz, 1H), 7.57 (d, J=1.9 Hz, 1H), 7.50 (dd, J=8.4, 2.1 Hz, 1H), 7.47-7.43 (m, 1H), 7.41-7.37 (m, 1H), 5.29 (dd, J=11.3, 6.1 Hz, 1H), 3.77 (s, 3H), 2.81-2.73 (m, 1H), 2.32 (d, J=0.6 Hz, 3H), 2.25-2.17 (m, 1H), 2.01-1.90 (m, 2H), 1.66-1.48 (m, 2H), 0.96 (d, J=7.2 Hz, 3H), 0.53-0.42 (m, 1H) ppm. MS(ESI) m/z: 605.4 (M+H)⁺. Analytical HPLC RT=5.20 min (Method D).

Example 63

Methyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate, TFA salt

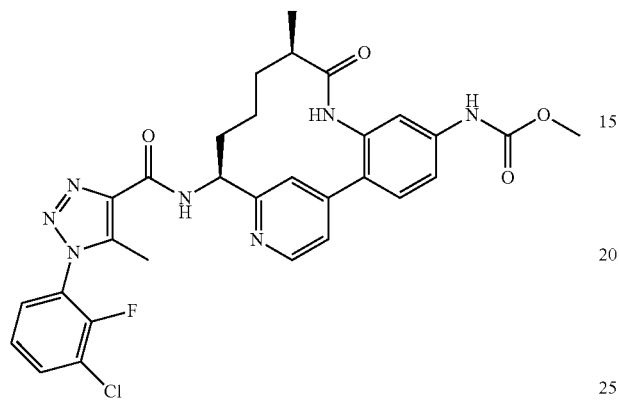

Example 63. Methyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate, TFA salt: To a vial containing Intermediate 21 (10.7 mg, 0.042 mmol), 2M (0.025 g, 0.042 mmol), EDC (0.012 g, 0.063 mmol), and HOBT (9.6 mg, 0.063 mmol) in DMF (0.5 mL) was added Hunig's base (0.037 mL, 0.210 mmol). The reaction was heated at 55° C. for 2 h and then cooled to rt. The reaction mixture was diluted with MeOH and filtered. The filtrate was concentrated and purified by reverse phase HPLC to yield the desired product (0.014 g, 46%) as a white solid. $^1$H NMR (500 MHz, MeOD) δ 8.70 (d, J=5.5 Hz, 1H), 7.92 (ddd, J=8.3, 6.9, 1.7 Hz, 1H), 7.81 (s, 1H), 7.70 (td, J=7.4, 1.7 Hz, 1H), 7.58-7.45 (m, 4H), 7.39 (d, J=1.9 Hz, 1H), 5.25 (dd, J=10.7, 5.8 Hz, 1H), 3.69 (s, 3H), 2.71-2.63 (m, 1H), 2.40 (s, 3H), 2.05-1.96 (m, 1H), 1.90-1.77 (m, 2H), 1.46-1.24 (m, 2H), 0.83 (d, J=6.9 Hz, 3H), 0.31-0.19 (m, 1H) ppm. MS(ESI) m/z: 606.3 (M+H)$^+$. Analytical HPLC RT=6.46 min (Method A).

The following Examples in Table 6 were made by using the same procedure as shown in Example 63. The acids used in the final step are as indicated in the below table in the Intermediate section. Various coupling reagents could be used other than the one described in Example 63 such as BOP, PyBop, EDC/HOBt or HATU.

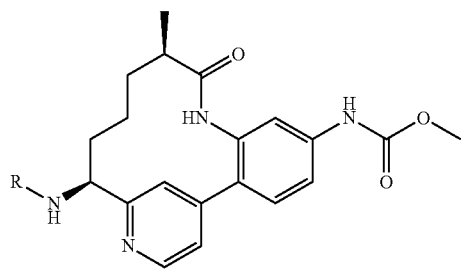

TABLE 6

| Example # | Stereochemistry | R | M + H | RT, min | Method |
|---|---|---|---|---|---|
| 64 | Homochiral | ![structure with triazole, NH2, F, Cl] | 606.9 | 5.94 | A |
| 65 | Homochiral | ![structure with pyrazole, HO, Cl] | 603.2 | 4.87 | D |
| 66 | Homochiral | ![structure with pyrazole, OMe, Cl] | 617.2 | 5.23 | D |
| 67 | Homochiral | ![structure with pyrazole, H2N, F, Cl] | 606.2 | 5.08 | D |
| 68 | Homochiral | ![structure with pyrazole, pyridine, F, Cl] | 606.1 | 4.81 | A |

TABLE 6-continued
| Example # | Stereochemistry | R | M + H | RT, min Method |
|---|---|---|---|---|
| 69 | Homochiral | 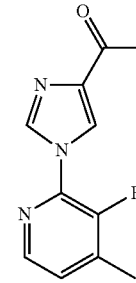 | 588.1 | 4.80 A |
| 70 | Homochiral | | 586.0 | 4.14 A |
| 71 | Homochiral | | 601.4 | 6.23 A |
| 72 | Homochiral | | 609.3 | 4.87 D |
| 73 | Homochiral | | 605.3 | 4.83 D |
| 74 | Homochiral | 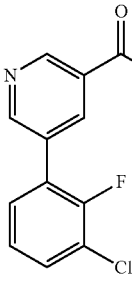 | 572.1 | 4.65 A |
| 75 | Homochiral | | 602.3 | 5.33 A |
| 76 | Homochiral | | 642.0 | 6.35 A |
Example 77
Methyl N-[(10R,14S)-14-[1-(2-fluoro-3-methoxyphenyl)-1H-1,2,3-triazole-4-amido]-10-methyl-9-oxo-8,16,18-triazatricyclo[13.2.1.0$^{2,7}$]octadeca-1(17),2,4,6,15(18)-pentaen-5-yl]carbamate, TFA salt
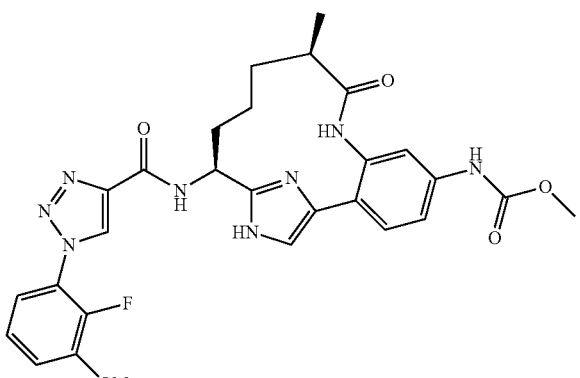

Example 77. Methyl N-[(10R,14S)-14-[1-(2-fluoro-3-methoxyphenyl)-1H-1,2,3-triazole-4-amido]-10-methyl-9-oxo-8,16,18-triazatricyclo[13.2.1.0$^{2,7}$]octadeca-1(17),2,4,6,15(18)-pentaen-5-yl]carbamate, TFA salt: Example 77 was made in the same way as Example 63 by using Intermediate 30. $^1$H NMR (400 MHz, MeOD) δ 8.85 (s, 1H), 7.61 (d, J=2.0 Hz, 1H), 7.56-7.52 (m, 2H), 7.47-7.36 (m, 4H), 5.55-5.39 (m, 1H), 4.06-3.92 (m, 3H), 3.99 (s, 3H), 3.79 (s, 3H), 2.79-2.77 (bm, J=10.6 Hz, 2H), 2.69-2.64 (bm, 1H), 2.32 (m, 1H), 1.75 (m, 1H), 1.66 (bm, 2H), 1.08 (d, 3H), 0.99 (bm, 1H). MS(ESI) m/z: 577.3 (M+H)$^+$. Analytical HPLC RT=5.74 min (Method A).

The following Examples in Table 7 were made by using the same procedure as shown in Example 31. The acids used in the final step are as indicated in the below table in the Intermediate section. Various coupling reagents could be used other than the one described in Example 2 like BOP, PyBop, EDC/HOBt or HATU. In step 2F methyl chloroformate can be replaced with 3-methoxypropanoyl chloride.

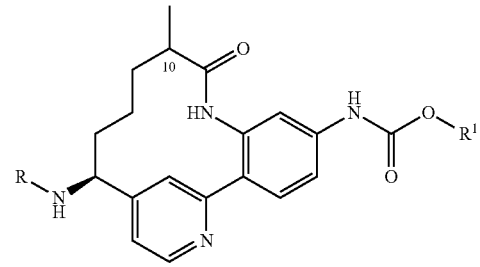

TABLE 7

| Example # | Stereochemistry | R | R$^1$ | M + H | RT, min Method A |
|---|---|---|---|---|---|
| 78 | Homochiral 10R | 5-methyl-1-(2-fluoro-3-chlorophenyl)-1H-pyrazole-4-carbonyl | Me | 606.6 | 6.39 |
| 79 | Homochiral 10R | 5-methyl-1-(2,6-difluoro-3-chlorophenyl)-1H-1,2,3-triazole-4-carbonyl | Me | 624.6 | 6.07 |
| 80 | Homochiral 10R | 5-methyl-1-(2,6-difluoro-3-chlorophenyl)-1H-1,2,3-triazole-4-carbonyl | 2-methoxyethyl | 668.7 | 6.04 |

TABLE 7-continued

| Example # | Stereochemistry | R | R¹ | M + H | RT, min Method A |
|---|---|---|---|---|---|
| 81 | Homochiral 10R | (1-(2-fluoro-3-chlorophenyl)-5-methyl-1H-pyrazol-4-yl)carbonyl | Me | 605.6 | 5.95 |
| 82 | Homochiral 10S | (1-(2-fluoro-3-chlorophenyl)-5-methyl-1H-pyrazol-4-yl)carbonyl | -CH₂CH₂OCH₃ | 649.6 | 5.80 |
| 83 | Homochiral 10R | (1-(2-fluoro-3-chlorophenyl)-5-methyl-1H-pyrazol-4-yl)carbonyl | -CH₂CH₂OCH₃ | 649.7 | 5.83 |
| 84 | Homochiral 10R | (1-(2-fluoro-3-chlorophenyl)-5-methyl-1H-imidazol-4-yl)carbonyl | Me | 605.6 | 4.98 |
| 85 | Homochiral 10R | (1-(2,6-difluoro-3-chlorophenyl)-5-methyl-1H-imidazol-4-yl)carbonyl | Me | 609.6 | 5.48 |

Example 86

Methyl N-[(10R,14S)-14-[1-(3-chloro-2-fluorophenyl)-5-methyl-1H-1,2,3-triazole-4-amido]-16-fluoro-10-methyl-9-oxo-8,18-diazatricyclo[13.3.1.0$^{2,7}$]non-adeca-1(19),2(7),3,5,15,17-hexaen-5-yl]carbamate, TFA salt

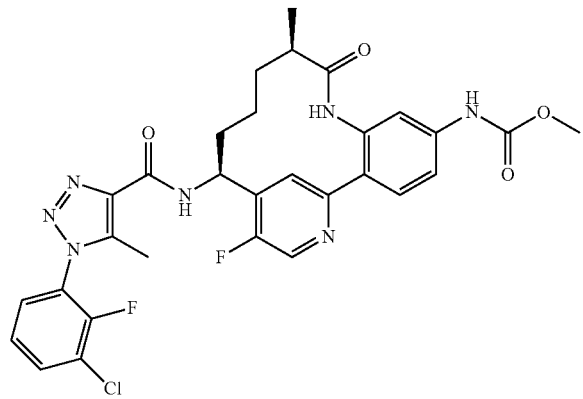 [SMILES: COC(=O)Nc1ccc2c(c1)NC(=O)[C@H](C)CCC[C@H](NC(=O)c1nnn(-c3cccc(Cl)c3F)c1C)c1cc-2ncc1F]

Example 86. Methyl N-[(10R,14S)-14-[1-(3-chloro-2-fluorophenyl)-5-methyl-1H-1,2,3-triazole-4-amido]-16-fluoro-10-methyl-9-oxo-8,18-diazatricyclo[13.3.1.0$^{2,7}$]nonadeca-1(19),2(7),3,5,15,17-hexaen-5-yl]carbamate, TFA salt: Example 86 was prepared the same way as Example 2 by replacing 4-bromopicolinaldehyde with 2-bromo-5-fluoroisonicotinaldehyde and substituting Intermediate 11 with Intermediate 21. $^{1}$H NMR (500 MHz, MeOD) δ 8.65 (d, J=2.8 Hz, 1H), 7.95 (d, J=6.3 Hz, 1H), 7.82 (ddd, J=8.2, 6.8, 1.5 Hz, 1H), 7.68 (d, J=8.5 Hz, 1H), 7.61-7.52 (m, 2H), 7.50-7.43 (m, 2H), 5.35 (dd, J=11.3, 5.8 Hz, 1H), 3.78 (s, 3H), 3.32 (m, 3H), 2.71 (td, J=6.7, 2.5 Hz, 1H), 2.45 (d, J=0.6 Hz, 3H), 2.24-2.16 (m, 1H), 2.14-2.05 (m, 1H), 1.97-1.86 (m, 1H), 1.74-1.62 (m, 1H), 1.55-1.43 (m, 1H), 1.01 (d, J=7.2 Hz, 3H), 0.97-0.86 (m, 1H) ppm. MS(ESI) m/z: 623.9 (M+H)$^{+}$. Analytical HPLC RT=8.73 min (Method A).

Example 87

Methyl N-[(10R,14S)-14-[1-(3-chloro-2-fluorophenyl)-5-methyl-1H-1,2,3-triazole-4-amido]-6-fluoro-10-methyl-9-oxo-8,16-diazatricyclo[13.3.1.0$^{2,7}$]nonadeca-1(19),2(7),3,5,15,17-hexaen-5-yl]carbamate, TFA salt

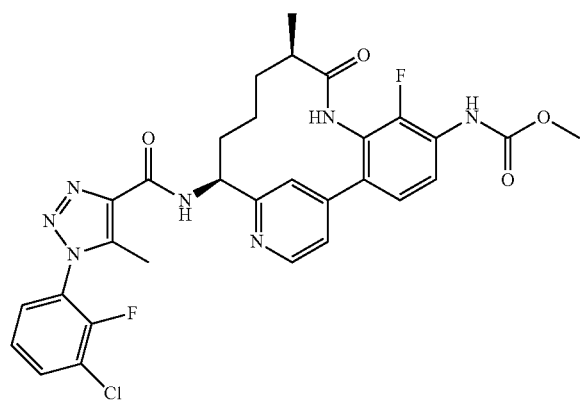 [SMILES: COC(=O)Nc1ccc2c(c1F)NC(=O)[C@H](C)CCC[C@H](NC(=O)c1nnn(-c3cccc(Cl)c3F)c1C)c1cc-2ccn1]

87A. Methyl N-{3-amino-4-[2-(1-{[(tert-butoxy)carbonyl]amino}but-3-en-1-yl)pyridin-4-yl]-2-fluorophenyl}carbamate: To a solution of 2H (50 mg, 0.121 mmol) in DMF (0.5 mL) was added Na$_2$CO$_3$ (22 mg, 0.208 mmol), followed by Accufluor (50% in alumina) (143 mg, 0.222 mmol). The reaction was stirred at rt for 40 min and concentrated. The residue was purified by reverse phase HPLC to isolate the desired product (10 mg, 19%). MS(ESI) m/z: 431.1 (M+H)$^{+}$.

87B. Methyl N-[(10R,11E,14S)-14-{[(tert-butoxy)carbonyl]amino}-6-fluoro-10-methyl-9-oxo-8,16-diazatricyclo[13.3.1.0$^{2,7}$]nonadeca-1(19),2(7),3,5,11,15,17-heptaen-5-yl]carbamate (diastereomer mixture): 87B was made in the same way as 2J by replacing 2H with 87A. MS(ESI) m/z: 485.1 (M+H)$^{+}$.

87C. Methyl N-[(10R,14S)-14-amino-6-fluoro-10-methyl-9-oxo-8,16-diazatricyclo[13.3.1.0$^{2,7}$]nonadeca-1(19),2(7),3,5,15,17-hexaen-5-yl]carbamate, HCl salt: To a solution of 87B (3.5 mg, 7.22 µmol) in ethyl acetate (5 mL) was added platinum(IV) oxide (1.8 mg, 7.93 µmol). The reaction was degassed, purged with argon (3×), and charged with a H$_2$ balloon overnight. The mixture was filtered and washed with MeOH. The filtrate was concentrated. The residue was treated 1 mL HCl (4 N in dioxane) for 1 h and then concentrated to yield the desired product (3.5 mg, 100%) as a brown solid (diastereomer mixture). MS(ESI) m/z: 387.2 (M+H)$^{+}$.

Example 87. Methyl N-[(10R,14S)-14-[1-(3-chloro-2-fluorophenyl)-5-methyl-1H-1,2,3-triazole-4-amido]-6-fluoro-10-methyl-9-oxo-8,16-diazatricyclo[13.3.1.0$^{2,7}$]nonadeca-1(19),2(7),3,5,15,17-hexaen-5-yl]carbamate, TFA salt (diastereomer mixture): Example 87 was made in the same way as Example 2 by replacing 2M with 87C. $^{1}$H NMR (500 MHz, MeOD) δ 8.75 (d, J=5.8 Hz, 1H), 8.28-8.00 (m, 2H), 7.93-7.74 (m, 2H), 7.67-7.41 (m, 3H), 5.35 (d, J=5.3 Hz, 1H), 3.80 (s, 3H), 2.83 (br. s., 1H), 2.44 (d, J=1.0 Hz, 3H), 2.23 (br. s., 1H), 2.09-1.85 (m, 1H), 1.81-1.42 (m, 3H), 1.26 (d, J=18.1 Hz, 1H), 0.99 (d, J=7.0 Hz, 3H), 0.62-0.42 (m, 1H) ppm. MS(ESI) m/z: 624.2 (M+H)$^{+}$. Analytical HPLC RT=5.79 min (Method A).

Example 88

Methyl N-[(14S)-14-[1-(3-chloro-2-fluorophenyl)-5-methyl-1H-1,2,3-triazole-4-amido]-13-methyl-9-oxo-8,16-diazatricyclo[13.3.1.0$^{2,7}$]nonadeca-1(19),2(7),3,5,15,17-hexaen-5-yl]carbamate, TFA salt

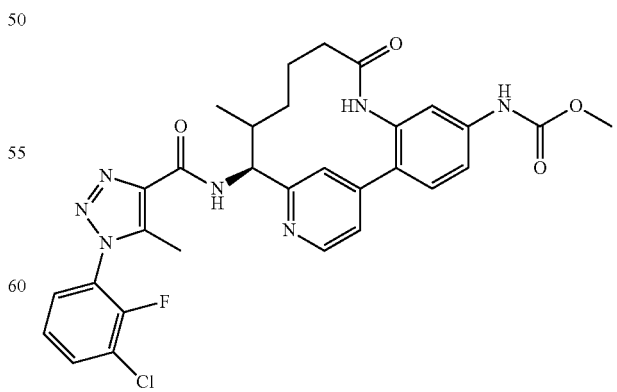

88A. (S,E)-N-((4-Chloropyridin-2-yl)methylene)-2-methylpropane-2-sulfinamide: *Angew. Chem. Int. Ed.*, 48:914-917 (2009). To a stirred suspension of (S)-2-methylpropane-2-sulfinamide (5 g, 41.3 mmol) and Cs$_2$CO$_3$ (20.16 g, 61.9 mmol) in DCM (100 mL) was added a solution of 4-chloropicolinaldehyde (5.84 g, 41.3 mmol) in DCM (50 mL) dropwise over a period of 10 min. The solution was then stirred for 2 h at rt. The reaction mixture was diluted with EtOAc (50 mL) and washed with brine (20 mL×3). The organic layer was dried over MgSO$_4$ and concentrated to give the desired product (9.56 g, 95%) as brown thick oil. MS(ESI) m/z: 246.9 (M+H)$^+$.

88B. (S)—N-((1S,2R)-1-(4-Chloropyridin-2-yl)-2-methylbut-3-enyl)-2-methylpropane-2-sulfinamide: To a solution of 88A (1.7 g, 6.95 mmol) in THF (50 mL) at −78° C. was added 1-methyl-2-propenylmagnesium chloride (0.5 M in THF) (13.89 mL, 6.95 mmol) dropwise over a period of 1 h. The resulting solution was stirred at −78° C. for 0.5 h and at rt overnight. The reaction was cooled to 0° C. and quenched with saturated NH$_4$Cl. The mixture was extracted with EtOAc (3×). The combined organic layer was concentrated and purified by silica gel chromatography to give the desired product (1.27 g, 61%) as a crude beige oil. $^1$H NMR indicated a ~4:1 mixture of diastereomers whereby the major diastereomer corresponds to the title compound. MS(ESI) m/z: 301.1 (M+H)$^+$.

88C. tert-Butyl (1S,2R)-1-(4-chloropyridin-2-yl)-2-methylbut-3-enylcarbamate: To a solution of 88B (1.27 g, 4.22 mmol) in MeOH (20 mL) at 0° C. was added HCl (5.28 mL, 21.11 mmol) (4 M in dioxane). The reaction was warmed to rt and stirred for 1 h. The mixture was concentrated and added Et$_2$O. The yellow suspension was filtered, washed Et$_2$O and dried. The above solid was dissolved in DCM (20 mL) and Et$_3$N (2.354 mL, 16.89 mmol) and cooled to 0° C. BOC$_2$O (0.980 mL, 4.22 mmol) was added and the reaction was stirred at rt for 2 h. The reaction was diluted with saturated NaHCO$_3$ and extracted with DCM (2×). The combined organic layer was washed with brine, dried over MgSO$_4$, filtered, and concentrated. The residue was purified by silica gel chromatography to give the desired product (1 g, 80% yield) as a white solid. MS(ESI) m/z: 297.1 (M+H)$^+$.

88D. tert-Butyl (1S,2R)-1-(4-(2-amino-4-nitrophenyl)pyridin-2-yl)-2-methylbut-3-enylcarbamate: To a 20 mL microwave vial was added 88C (0.25 g, 0.842 mmol), 2-(5,5-dimethyl-1,3,2-dioxaborinan-2-yl)-5-nitroaniline (0.253 g, 1.011 mmol), potassium phosphate, tribasic (0.358 g, 1.685 mmol), water (0.076 mL, 4.21 mmol) and DMSO (4.21 mL). The mixture was bubbled with N$_2$ for 5 min and added PdCl$_2$(dppf)-CH$_2$Cl$_2$ adduct (0.069 g, 0.084 mmol). The vial was sealed and heated at 90° C. for 3 h and then stirred at rt for 2 d. The mixture was partitioned between EtOAc and brine. The aqueous layer was extracted with EtOAc. The combined organic layer was concentrated and purified by silica gel chromatography to yield the desired product (0.27 g, 80%) as a yellow foam. MS(ESI) m/z: 399.1 (M+H)$^+$.

88E. tert-Butyl ((1S,2R)-1-(4-(2,4-diaminophenyl)pyridin-2-yl)-2-methylbut-3-en-1-yl)carbamate: To a clear orange solution of 88D (0.27 g, 0.678 mmol) in methanol (6.78 mL) was added zinc (0.443 g, 6.78 mmol) and NH$_4$Cl (0.362 g, 6.78 mmol). The resulting yellow-orange suspension turned clear after a few minutes and was stirred at rt for 1 h. The reaction was filtered and washed with MeOH. The filtrate was concentrated. The residue was diluted with EtOAc and washed with saturated aq. NaHCO$_3$, brine, dried over MgSO$_4$, filtered, and concentrated to give the desired product (0.25, 100%) as a brownish foam. MS(ESI) m/z: 369.2 (M+H)$^+$.

88F. tert-Butyl N-[(1S)-1-(4-{2-amino-4-[(methoxycarbonyl)amino]phenyl}pyridin-2-yl)-2-methylbut-3-en-1-yl]carbamate: To a clear orange solution of 88E (0.25 g, 0.678 mmol) and pyridine (0.055 mL, 0.678 mmol) in DCM (6.78 ml) at −78° C. was added methyl chlorocarbonate (0.047 mL, 0.611 mmol) dropwise. The reaction was stirred at −78° C. for 1 h and quenched with saturated NH$_4$Cl. The reaction was diluted with EtOAc and water. The aqueous layer was extracted with EtOAc. The combined organic layer was washed with brine, dried over MgSO$_4$, filtered and concentrated to give the desired product (0.3 g, 100%) as a brown glass. MS(ESI) m/z: 427.1 (M+H)$^+$.

88G. tert-Butyl N-[(1S)-1-{4-[2-(but-3-enamido)-4-[(methoxycarbonyl)amino]phenyl]pyridin-2-yl}-2-methylbut-3-en-1-yl]carbamate: To a solution of 88F (100 mg, 0.234 mmol) and but-3-enoic acid (0.020 mL, 0.234 mmol) in pyridine (1 mL) at 0° C. was added POCl$_3$ (0.044 mL, 0.469 mmol). The resulting orange solution was stirred at 0° C. for 10 min and diluted with DCM. The mixture was washed with aq. NaHCO$_3$, brine, and concentrated. The residue was purified by silica gel chromatography to give the desired product (52 mg, 45%) as a beige foam. MS(ESI) m/z: 495.1 (M+H)$^+$.

88H. tert-Butyl N-[(11E,14S)-5-[(methoxycarbonyl)amino]-13-methyl-9-oxo-8,16-diazatricyclo[13.3.1.0$^{2,7}$]nonadeca-1(19),2,4,6,11,15,17-heptaen-14-yl]carbamate: A solution of 88G (89 mg, 0.180 mmol) in toluene (20 mL) was bubbled with N$_2$ for 10 min. Grubbs II (61.1 mg, 0.072 mmol) was added and the reaction mixture was heated at 160° C. under microwave conditions for 20 min. The reaction was concentrated and purified by reverse phase HPLC to isolate the desired product (10 mg, 12%). MS(ESI) m/z: 467.1 (M+H)$^+$.

88I. Methyl N-[(14S)-14-amino-13-methyl-9-oxo-8,16-diazatricyclo[13.3.1.0$^{2,7}$]nonadeca-1(19),2,4,6,15,17-hexaen-5-yl]carbamate, HCl salt: To a solution of 88H (10 mg, 0.021 mmol) in MeOH was added platinum(IV) oxide (9 mg, 0.040 mmol). The mixture was evacuated, purged with H$_2$ (3×), and then charged with 50 psi H$_2$ overnight. The mixture was filtered and the filtrate was concentrated. The residue was treated with 1 mL HCl (4 N in dioxane) and stirred at rt for 1 h. The mixture was concentrated to yield the desired product (10 mg, 23%). MS(ESI) m/z: 369.2 (M+H)$^+$.

Example 88. Methyl N-[(14S)-14-[1-(3-chloro-2-fluorophenyl)-5-methyl-1H-1,2,3-triazole-4-amido]-13-methyl-9-oxo-8,16-diazatricyclo[13.3.1.0$^{2,7}$]nonadeca-1(19),2(7),3,5,15,17-hexaen-5-yl]carbamate, TFA salt: To a solution of 88I (10 mg, 0.023 mmol), Intermediate 21 (6.95 mg, 0.027 mmol), HOBT (5.20 mg, 0.034 mmol) and EDC (6.52 mg, 0.034 mmol) in DMF (1 mL) was added DIEA (0.040 mL, 0.227 mmol). The resulting solution was stirred at rt overnight. The reaction was quenched with aq. NaHCO$_3$ and then extracted with DCM (2×30 mL). The combined organic layer was concentrated and purified by reverse phase HPLC to yield the desired product (2.5 mg, 18%) as a white solid. $^1$H NMR (400 MHz, MeOD) δ 8.61 (d, J=5.0 Hz, 1H), 7.81 (td, J=7.5, 1.5 Hz, 1H), 7.65-7.32 (m, 7H), 5.48 (s, 1H), 5.04 (d, J=10.8 Hz, 1H), 3.76 (s, 3H), 2.64-2.54 (m, 1H), 2.52-2.42 (m, 3H), 2.18-2.03 (m, 1H), 1.82 (d, J=11.3 Hz, 3H), 1.43-1.26 (m, 3H), 1.21 (d, J=7.0 Hz, 2H), 1.07 (d, J=7.0 Hz, 1H), 0.90 (d, J=6.8 Hz, 1H), 0.72 (br. s., 1H) ppm. MS(ESI) m/z: 606.2 (M+H)$^+$. Analytical HPLC RT=5.40 min (Method A).

Example 89

N-[(10R,14S)-5-Amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-1,2,3-triazole-4-carboxamide, 2 TFA salt

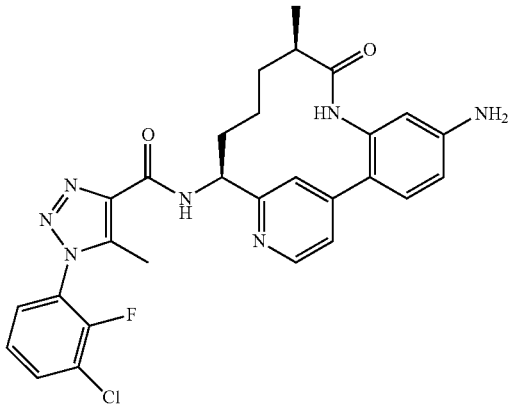 [SMILES: Cc1c(C(=O)N[C@H]2CCC[C@@H](C)C(=O)Nc3cc(N)ccc3-c3ccnc2c3)nnn1-c1cccc(Cl)c1F]

89A. tert-Butyl N-[(10R,14S)-5-amino-10-methyl-9-oxo-8,16-diazatricyclo[13.3.1.0$^{2,7}$]nonadeca-1(19),2(7),3,5,15,17-hexaen-14-yl]carbamate: To the suspension of 2L (0.9 g, 1.921 mmol) in MeOH (29.6 ml) was added 1 N NaOH (11.53 ml, 11.53 mmol). The reaction was stirred in a sealed tube at 75° C. overnight. The reaction was cooled to rt and concentrated. The residue was partitioned between 15% IPA/CHCl$_3$ and water. The organic layer was washed with brine, dried over Na$_2$SO$_4$, filtered, and concentrated to give the desired product (0.79 g, 100%) as a brown solid. MS(ESI) m/z: 411.1 (M+H)$^+$.

89B. (10R,14S)-5,14-Diamino-10-methyl-8,16-diazatricyclo[13.3.1.0$^{2,7}$]nonadeca-1(19),2(7),3,5,15,17-hexaen-9-one: 89A (0.75 g, 1.827 mmol) was treated with HCl (4 M in 1,4-dioxane) (10 mL, 40.0 mmol) and the reaction was stirred at rt for 1 h. The yellow suspension was filtered, rinsed with hexane and dried to give the desired product (0.87 g, 100%). MS(ESI) m/z: 311.1 (M+H)$^+$.

Example 89. N-[(10R,14S)-5-Amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-1,2,3-triazole-4-carboxamide, 2 TFA salt: A yellow solution of Intermediate 21 (0.229 g, 0.896 mmol), 89B (0.45 g, 0.943 mmol), EDC (0.362 g, 1.887 mmol), HOBT (0.289 g, 1.887 mmol), and Hunig's base (0.824 mL, 4.72 mmol) in DMF (6.29 mL) was stirred at rt overnight. The reaction was quenched with water. The resulting yellow suspension was filtered, dried and purified by reverse phase HPLC to isolate the desired product (0.454 g, 62%) as a yellow foam. $^1$H NMR (500 MHz, MeOD) δ 8.62 (d, J=6.3 Hz, 1H), 8.22 (d, J=1.9 Hz, 1H), 7.87 (dd, J=6.2, 1.8 Hz, 1H), 7.82 (ddd, J=8.3, 6.8, 1.7 Hz, 1H), 7.56 (ddd, J=8.0, 6.5, 1.7 Hz, 1H), 7.51 (d, J=8.5 Hz, 1H), 7.48-7.44 (m, 1H), 6.80 (dd, J=8.5, 2.2 Hz, 1H), 6.61 (d, J=2.2 Hz, 1H), 5.35 (dd, J=11.3, 6.1 Hz, 1H), 2.83-2.75 (m, 1H), 2.43 (d, J=0.8 Hz, 3H), 2.29-2.19 (m, 1H), 2.09-1.96 (m, 2H), 1.73-1.52 (m, 2H), 0.98 (d, J=6.9 Hz, 3H), 0.60-0.49 (m, 1H) ppm. MS(ESI) m/z: 548.1 (M+H)$^+$. Analytical HPLC RT=3.99 min (Method A).

Example 89 (Alternative, 2 HCl salt): Example 89 (0.067 g, 0.086 mmol) was dissolved in 1.25 M HCl in MeOH (1 mL, 1.250 mmol) and then concentrated. The process was repeated one more time to give the desired product (55 mg, 100%) as a yellow solid.

Example 90

N-[(10R,14S)-5-Amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide, 2 TFA salt

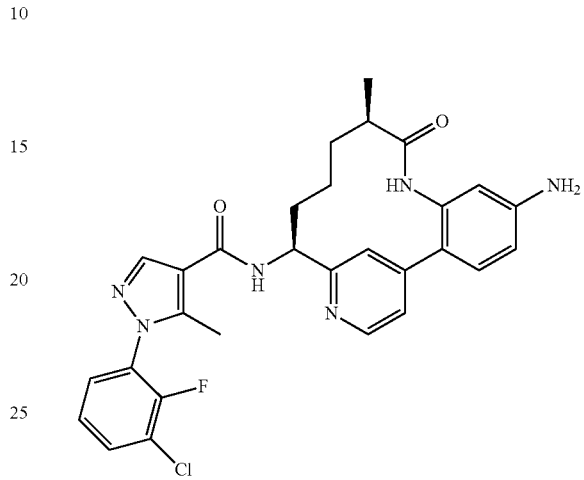

Example 90. N-[(10R,14S)-5-Amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide, 2 TFA salt: Example 90 was made in the same way as Example 89 by replacing Intermediate 21 with Intermediate 25. $^1$H NMR (500 MHz, MeOD) δ 8.58 (d, J=6.3 Hz, 1H), 8.31 (s, 1H), 8.19 (d, J=1.9 Hz, 1H), 7.85 (dd, J=6.2, 1.8 Hz, 1H), 7.72 (ddd, J=8.3, 6.8, 1.7 Hz, 1H), 7.49 (d, J=8.5 Hz, 1H), 7.46 (ddd, J=8.0, 6.5, 1.7 Hz, 1H), 7.41-7.36 (m, 1H), 6.77 (dd, J=8.5, 2.2 Hz, 1H), 6.58 (d, J=2.2 Hz, 1H), 5.22 (dd, J=11.4, 5.9 Hz, 1H), 2.81-2.74 (m, 1H), 2.35 (d, J=1.1 Hz, 3H), 2.25-2.16 (m, 1H), 2.04-1.95 (m, 2H), 1.71-1.61 (m, 1H), 1.61-1.50 (m, 1H), 0.98 (d, J=6.9 Hz, 3H), 0.61-0.51 (m, 1H) ppm. MS(ESI) m/z: 547.3 (M+H)$^+$. Analytical HPLC RT=4.57 min (Method D).

Example 91

N-[(10S,14S)-5-Amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide, 2 TFA

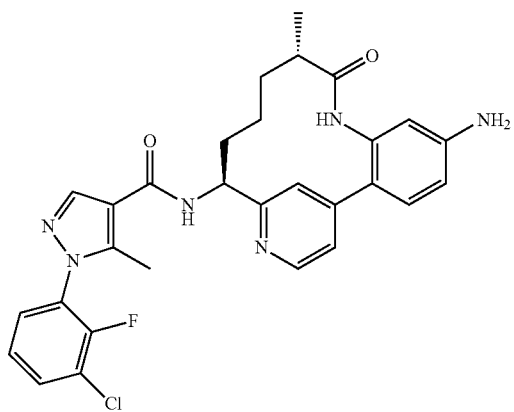 [SMILES: Cc1c(C(=O)N[C@H]2CCC[C@H](C)C(=O)Nc3cc(N)ccc3-c3ccnc2c3)cnn1-c1cccc(Cl)c1F]

213

Example 91. N-[(10S,14S)-5-Amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide, 2 TFA: Example 91 was made in the same way as Example 90 by using the other isomer. $^1$H NMR (500 MHz, MeOD) δ 8.58 (d, J=6.1 Hz, 1H), 8.29 (s, 1H), 8.09 (s, 1H), 7.83 (dd, J=6.2, 1.8 Hz, 1H), 7.71 (ddd, J=8.2, 6.7, 1.7 Hz, 1H), 7.52 (d, J=8.5 Hz, 1H), 7.45 (ddd, J=8.0, 6.5, 1.7 Hz, 1H), 7.40-7.35 (m, 1H), 6.79 (dd, J=8.5, 2.2 Hz, 1H), 6.60 (d, J=2.2 Hz, 1H), 5.13 (dd, J=11.3, 5.2 Hz, 1H), 2.46-2.38 (m, 1H), 2.36 (d, J=0.8 Hz, 3H), 2.23-2.14 (m, 1H), 2.07-1.98 (m, 1H), 1.80-1.70 (m, 1H), 1.66-1.56 (m, 1H), 1.31-1.22 (m, 4H), 1.06-0.95 (m, 1H) ppm. MS(ESI) m/z: 547.3 (M+H)$^+$. Analytical HPLC RT=4.45 min (Method D).

Example 92

N-[(10R,14S)-5-Amino-10-methyl-9-oxo-8,18-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide, TFA salt

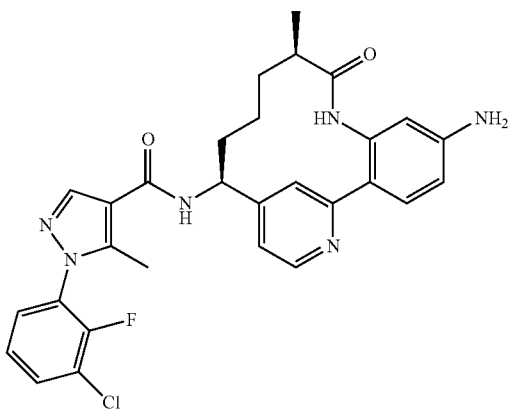 [SMILES: Cc1c(C(=O)N[C@H]2CCC[C@@H](C)C(=O)Nc3cc(N)ccc3-c3cc2ccn3)cnn1-c1cccc(Cl)c1F]

Example 92. N-[(10R,14S)-5-Amino-10-methyl-9-oxo-8,18-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide, TFA salt: Example 92 was made in the same way as Example 89 by replacing 4-chloropicolinaldehyde with 2-bromoisonicotinaldehyde in step 2A and replacing Intermediate 21 with Intermediate 25. $^1$H NMR (500 MHz, acetonitrile-d$_3$) δ 8.68 (d, J=6.33 Hz, 1H), 8.29 (s, 1H), 8.14 (s, 1H), 8.12 (d, J=1.65 Hz, 1H), 7.65-7.73 (m, 1H), 7.51 (s, 1H), 7.49 (s, 1H), 7.45 (ddd, J=1.79, 6.60, 8.12 Hz, 1H), 7.34-7.40 (m, 1H), 7.31 (d, J=5.78 Hz, 1H), 6.72 (dd, J=2.20, 8.53 Hz, 1H), 6.53 (d, J=2.20 Hz, 1H), 5.16 (td, J=5.95, 11.49 Hz, 1H), 2.61-2.72 (m, 1H), 2.35 (d, J=1.10 Hz, 3H), 2.07-2.15 (m, 1H), 1.93-1.98 (m, 2H), 1.88-1.93 (m, 1H), 1.42-1.62 (m, 2H), 0.93 (d, J=6.88 Hz, 3H), 0.55-0.65 (m, 1H) ppm. MS(ESI) m/z: 547.5 (M+H)$^+$. Analytical HPLC RT=5.43 min (Method A).

214

Example 93

N-[(10R,14S)-5-Amino-10-methyl-9-oxo-8,18-diazatricyclo[13.3.1.0$^{2,7}$]nonadeca-1(19),2(7),3,5,15,17-hexaen-14-yl]-1-(3-chloro-2-fluorophenyl)-5-methyl-1H-imidazole-4-carboxamide, TFA salt

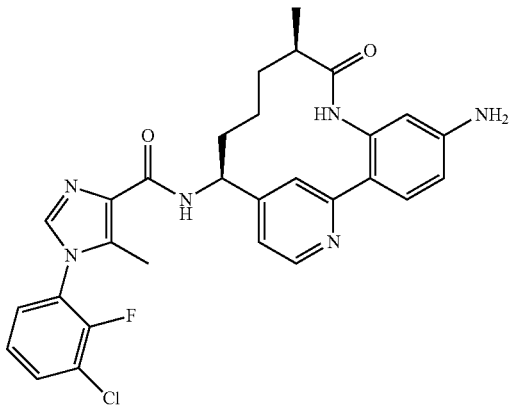 [SMILES: Cc1c(C(=O)N[C@H]2CCC[C@@H](C)C(=O)Nc3cc(N)ccc3-c3cc2ccn3)ncn1-c1cccc(Cl)c1F]

Example 93. N-[(10R,14S)-5-Amino-10-methyl-9-oxo-8,18-diazatricyclo[13.3.1.0$^{2,7}$]nonadeca-1(19),2(7),3,5,15,17-hexaen-14-yl]-1-(3-chloro-2-fluorophenyl)-5-methyl-1H-imidazole-4-carboxamide, TFA salt: Example 93 was made in the same way as Example 92 by replacing Intermediate 25 with Intermediate 24. $^1$H NMR (500 MHz, MeOD) δ 8.61 (d, J=6.3 Hz, 1H), 8.21 (d, J=1.9 Hz, 1H), 7.86 (dd, J=6.3, 1.9 Hz, 1H), 7.83 (s, 1H), 7.73 (ddd, J=8.3, 6.7, 1.8 Hz, 1H), 7.50 (d, J=8.3 Hz, 1H), 7.47-7.43 (m, 1H), 7.42-7.37 (m, 1H), 6.78 (dd, J=8.5, 2.2 Hz, 1H), 6.59 (d, J=2.2 Hz, 1H), 5.28 (dd, J=11.3, 6.1 Hz, 1H), 2.82-2.75 (m, 1H), 2.32 (br. s, 3H), 2.27-2.17 (m, 1H), 2.04-1.95 (m, 2H), 1.73-1.63 (m, 1H), 1.63-1.52 (m, 1H), 0.98 (d, J=7.2 Hz, 3H), 0.58-0.48 (m, 1H) ppm. MS(ESI) m/z: 547.3 (M+H)$^+$. Analytical HPLC RT=4.66 min (Method D).

Example 94

1-(3-Chloro-2-fluorophenyl)-5-methyl-N-[(10R,14S)-10-methyl-5-[(methylcarbamoyl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide, TFA salt

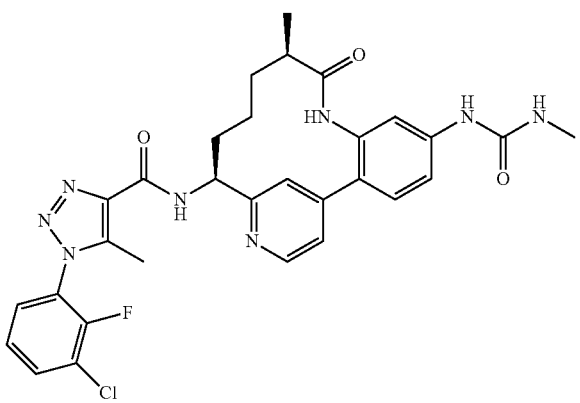 [SMILES: CNC(=O)Nc1ccc2c(c1)NC(=O)[C@H](C)CCC[C@H](NC(=O)c1nnn(-c3cccc(Cl)c3F)c1C)c1cc-2ccn1]

Example 94. 1-(3-Chloro-2-fluorophenyl)-5-methyl-N-[(10R,14S)-10-methyl-5-[(methylcarbamoyl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide, TFA salt: To a solution of Example 89 (0.02 g, 0.026 mmol) in DCM (1 mL) and acetonitrile (1 mL) was added sodium bicarbonate (6.49 mg, 0.077 mmol). The mixture was cooled to 0° C. under argon, and then added phosgene solution (20% in toluene) (0.041 mL, 0.077 mmol). The mixture was stirred at 0° C. for 30 min and concentrated. The residue was dissolved in acetonitrile (1 mL) and DCM (1 mL) under argon and cooled to 0° C. Methanamine, HCl salt (5.22 mg, 0.077 mmol) and TEA (7.18 µL, 0.052 mmol) were added. The resulting cloudy mixture was stirred at 0° C. for 30 min, and then at rt overnight. The reaction was concentrated and the residue was purified by reverse phase HPLC to yield the desired product (8 mg, 43%) as a yellow solid. $^1$H NMR (500 MHz, MeOD) δ 8.73 (d, J=6.3 Hz, 1H), 8.26 (d, J=1.7 Hz, 1H), 7.92 (dd, J=6.2, 1.8 Hz, 1H), 7.82 (ddd, J=8.3, 6.8, 1.7 Hz, 1H), 7.62 (d, J=8.5 Hz, 1H), 7.58-7.53 (m, 2H), 7.49-7.41 (m, 2H), 5.37 (dd, J=11.3, 6.1 Hz, 1H), 2.83-2.75 (m, 4H), 2.43 (d, J=0.8 Hz, 3H), 2.30-2.21 (m, 1H), 2.08-1.92 (m, 2H), 1.70-1.50 (m, 2H), 0.97 (d, J=7.2 Hz, 3H), 0.57-0.45 (m, 1H) ppm. MS(ESI) m/z: 605.1 (M+H)$^+$. Analytical HPLC RT=5.50 min (Method A).

Example 95

Propan-2-yl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate, TFA salt Example 95. Propan-2-yl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate, TFA salt: To the solution of Example 89 (0.025 g, 0.032 mmol), pyridine (0.013 mL, 0.161 mmol) in DCM (1 mL) at 0° C. was added isopropyl carbonochloridate (1 M in toluene) (0.097 mL, 0.097 mmol). The reaction was stirred at rt for 1 h and quenched with MeOH. The mixture was concentrated and purified by reverse phase HPLC to yield the desired product (0.015 g, 61%) as a white solid. $^1$H NMR (500 MHz, MeOD) δ 8.75 (d, J=6.1 Hz, 1H), 8.27 (d, J=1.4 Hz, 1H), 7.94 (dd, J=6.1, 1.9 Hz, 1H), 7.81 (ddd, J=8.2, 6.8, 1.5 Hz, 1H), 7.64 (d, J=8.5 Hz, 1H), 7.59-7.50 (m, 3H), 7.48-7.43 (m, 1H), 5.37 (dd, J=11.3, 6.1 Hz, 1H), 4.99 (spt, J=6.2 Hz, 1H), 2.82-2.75 (m, 1H), 2.42 (d, J=0.8 Hz, 3H), 2.31-2.21 (m, 1H), 2.10-1.92 (m, 2H), 1.70-1.51 (m, 2H), 1.32 (d, J=6.3 Hz, 6H), 0.97 (d, J=6.9 Hz, 3H), 0.57-0.45 (m, 1H) ppm. MS(ESI) m/z: 634.2 (M+H)$^+$. Analytical HPLC RT=6.86 min (Method A).

The following Examples in Table 8 were made in the same way as shown in Example 95. Carbonochloridates can be either from commercial source or generated by corresponding alcohol with various reagents such as phosgene, triphosgene. Carbonochloridates can also be replaced with activated alcohols by treating alcohols with 4-nitrophenyl carbonochloridate.

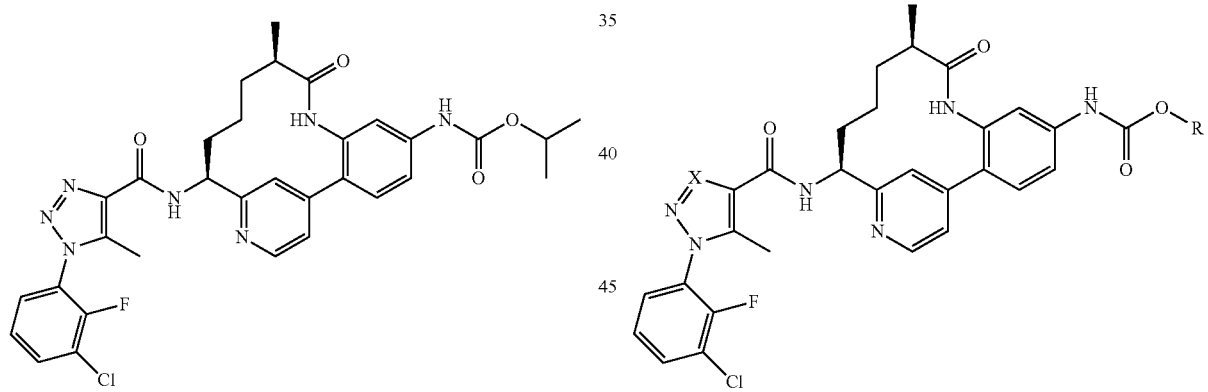

TABLE 8

| Example # | Stereochemistry | X | R | M + H | RT, min Method A |
|---|---|---|---|---|---|
| 96 | Homochiral | N | ⤳⟋⟍O⟋ | 650.3 | 6.18 |
| 97 | Homochiral | N | ⤳⟋⟨tetrahydrofuran-2-yl⟩ | 676.2 | 6.37 |

TABLE 8-continued
| Example # | Stereochemistry | X | R | M + H | RT, min Method A |
|---|---|---|---|---|---|
| 98 | Homochiral | N | 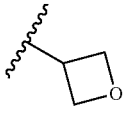 | 648.4 | 5.92 |
| 99 | Homochiral | N | 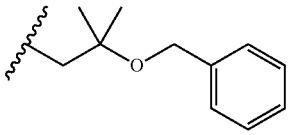 [SMILES: *CC(C)(C)OCc1ccccc1] | 754.4 | 8.21 |
| 100 | Homochiral | N | 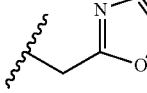 | 673.2 | 6.15 |
| 101 | Diastereomer mixture | N | 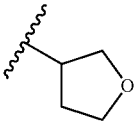 [SMILES: *C1CCOC1] | 662.2 | 6.10 |
| 102 | Diastereomer mixture | N | 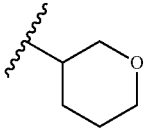 [SMILES: *C1CCCOC1] | 676.2 | 6.41 |
| 103 | Homochiral | N | 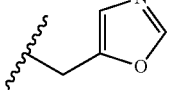 | 673.1 | 6.07 |
| 104 | Homochiral | N | 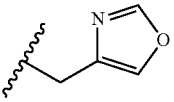 [SMILES: *Cc1cocn1] | 673.1 | 6.11 |
| 105 | Diastereomer mixture | N | 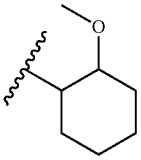 [SMILES: *C1CCCCC1OC] | 704.2 | 7.22 |
| 106 | Homochiral from cis diol | N | 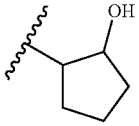 [SMILES: *C1CCCC1O] | 676.2 | 6.15 |
| 107 | Homochiral from cis diol | N | 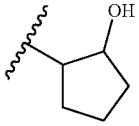 [SMILES: *C1CCCC1O] | 676.2 | 6.15 |
| 108 | Homochiral from trans diol | N | 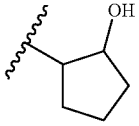 [SMILES: *C1CCCC1O] | 676.2 | 4.09 |

TABLE 8-continued

| Example # | Stereochemistry | X | R | M + H | RT, min Method A |
|---|---|---|---|---|---|
| 109 | Homochiral from trans diol | N | 2-hydroxycyclopentyl | 676.3 | 4.10 |
| 110 | Diastereomer mixture | N | 2-hydroxycyclohexyl | 690.3 | 4.07 |
| 111 | Homochiral | N | isoxazol-4-ylmethyl | 673.2 | 6.46 |
| 112 | Homochiral | N | isoxazol-5-ylmethyl | 673.1 | 6.48 |
| 113 | Homochiral | N | isoxazol-3-ylmethyl | 673.3 | 6.49 |
| 114 | Homochiral | N | 3-methoxypropyl | 664.2 | 4.09 |
| 115 | Homochiral | N | 2-hydroxy-2-methylpropyl | 664.2 | 5.94 |
| 116 | Homochiral | N | 2-methoxy-2-methylpropyl | 678.2 | 7.18 |
| 117 | Diastereomer mixture | N | 3-methoxycyclohexyl | 704.2 | 7.70 |
| 118 | Homochiral | N | (S)-2-methoxypropyl | 664.2 | 6.32 |
| 119 | Homochiral | CH | 3-methoxypropyl | 649.3 | 6.11 |
| 120 | Homochiral | CH | propyl | 619.3 | 6.52 |
| 121 | Homochiral | CH | 3-hydroxypropyl | 635.3 | 5.92 |

TABLE 8-continued
| Example # | Stereochemistry | X | R | M + H | RT, min Method A |
|---|---|---|---|---|---|
| 122 | Homochiral | CH | 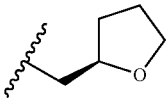 [SMILES: *C[C@H]1CCCO1] | 675.3 | 6.11 |
| 123 | Diastereomer mixture | CH | 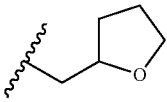 [SMILES: *CC1CCCO1] | 675.3 | 6.10 |
| 124 | Homochiral | CH | 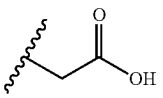 [SMILES: *CC(=O)O] | 649.2 | 5.41 |
| 125 | Homochiral | CH | 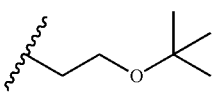 [SMILES: *CCOC(C)(C)C] | 691.4 | 6.54 |
| 126 | Diastereomer mixture | CH | 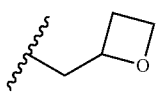 [SMILES: *CC1CCO1] | 661.2 | 5.80 |
| 127 | Homochiral | CH | 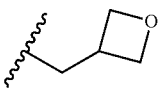 [SMILES: *CC1COC1] | 661.3 | 5.73 |
| 128 | Homochiral | CH | 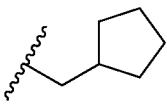 [SMILES: *CC1CCCC1] | 673.3 | 8.07 |
| 129 | Homochiral | CH | 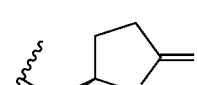 | 689.3 | 6.20 |
| 130 | Homochiral | CH | 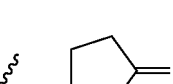 | 689.3 | 6.20 |
| 131 | Homochiral | CH | 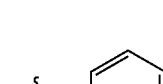 | 682.2 | 5.46 |
| 132 | Homochiral | CH | 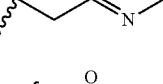 | 663.2 | 6.57 |
| 133 | Homochiral | CH | 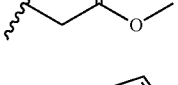 | 671.2 | 7.05 |
| 134 | Homochiral | CH | 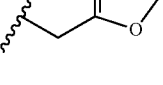 | 675.2 | 6.05 |

Example 135

1-(3-Chloro-2-fluorophenyl)-N-[(10R,14S)-5-[(dimethylcarbamoyl)amino]-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt

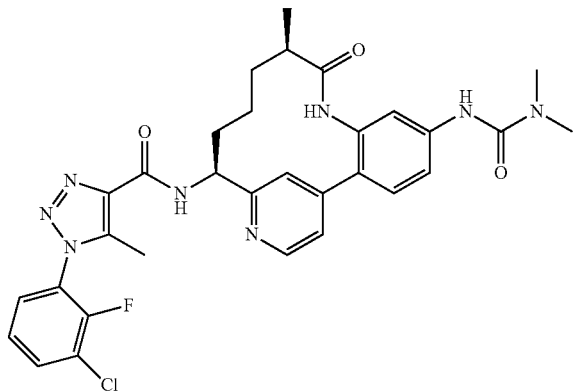 [SMILES: Cc1c(C(=O)N[C@H]2CCC[C@@H](C)C(=O)Nc3cc(NC(=O)N(C)C)ccc3-c3ccnc2c3)nnn1-c1cccc(Cl)c1F]

Example 135. 1-(3-Chloro-2-fluorophenyl)-N-[(10R,14S)-5-[(dimethylcarbamoyl)amino]-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt: Example 135 was made the same way as with Example 94 by replacing methanamine, HCl salt with dimethylamine, HCl salt. ¹H NMR (500 MHz, MeOD) δ 8.74 (d, J=6.1 Hz, 1H), 8.27 (d, J=1.7 Hz, 1H), 7.94 (dd, J=6.2, 1.8 Hz, 1H), 7.82 (ddd, J=8.1, 6.7, 1.7 Hz, 1H), 7.64 (d, J=8.5 Hz, 1H), 7.58-7.51 (m, 3H), 7.48-7.44 (m, 1H), 5.37 (dd, J=11.4, 6.2 Hz, 1H), 3.06 (s, 6H), 2.83-2.75 (m, 1H), 2.43 (d, J=1.1 Hz, 3H), 2.26 (m, 1H), 2.10-1.92 (m, 2H), 1.70-1.51 (m, 2H), 0.97 (d, J=6.9 Hz, 3H), 0.58-0.46 (m, 1H) ppm. MS(ESI) m/z: 619.1 (M+H)⁺. Analytical HPLC RT=5.64 min (Method A).

Example 136

1-(3-Chloro-2-fluorophenyl)-N-[(10R,14S)-5-methanesulfonamido-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt

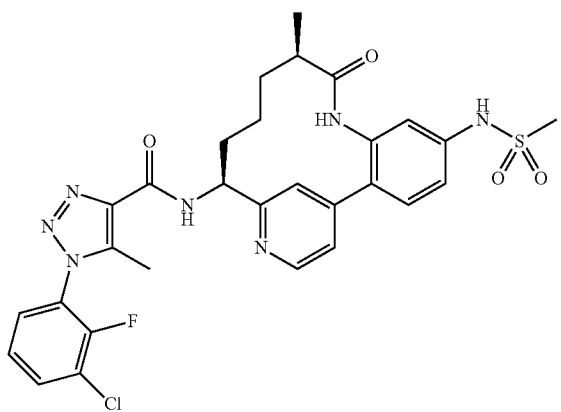 [SMILES: Cc1c(C(=O)N[C@H]2CCC[C@@H](C)C(=O)Nc3cc(NS(C)(=O)=O)ccc3-c3ccnc2c3)nnn1-c1cccc(Cl)c1F]

Example 136. 1-(3-Chloro-2-fluorophenyl)-N-[(10R,14S)-5-methanesulfonamido-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt: To the solution of Example 89 (Alternative, HCl salt) (0.012 g, 0.019 mmol) in pyridine (0.5 mL, 6.18 mmol) and DCM (1 mL) at 0° C. was added methanesulfonyl chloride (2.3 μL, 0.029 mmol). The reaction was stirred at 0° C. for 1 h and concentrated. The residue was purified by reverse phase HPLC to yield the desired product (10 mg, 69% yield) as a white solid. ¹H NMR (500 MHz, MeOD) δ 8.74 (d, J=5.8 Hz, 1H), 8.07 (d, J=1.4 Hz, 1H), 7.84-7.76 (m, 2H), 7.66 (d, J=8.5 Hz, 1H), 7.56 (ddd, J=8.0, 6.5, 1.7 Hz, 1H), 7.48-7.43 (m, 1H), 7.32 (dd, J=8.4, 2.3 Hz, 1H), 7.23 (d, J=2.5 Hz, 1H), 5.34 (dd, J=11.1, 5.9 Hz, 1H), 3.08 (s, 3H), 2.79-2.72 (m, 1H), 2.44 (d, J=0.8 Hz, 3H), 2.27-2.17 (m, 1H), 2.02-1.89 (m, 2H), 1.64-1.47 (m, 2H), 0.96 (d, J=6.9 Hz, 3H), 0.54-0.43 (m, 1H) ppm. MS(ESI) m/z: 626.1 (M+H)⁺. Analytical HPLC RT=6.02 min (Method A).

Example 137

1-(3-Chloro-2-fluorophenyl)-5-methyl-N-[(10R,14S)-10-methyl-9-oxo-5-(trifluoroacetamido)-8,16-diazatricyclo[13.3.1.0²,⁷]nonadeca-1(19),2(7),3,5,15,17-hexaen-14-yl]-1H-1,2,3-triazole-4-carboxamide, TFA salt

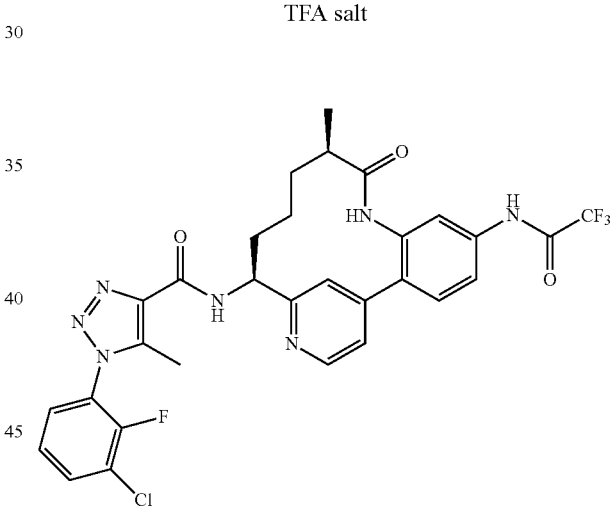

Example 137. 1-(3-Chloro-2-fluorophenyl)-5-methyl-N-[(10R,14S)-10-methyl-9-oxo-5-(trifluoroacetamido)-8,16-diazatricyclo[13.3.1.0²,⁷]nonadeca-1(19),2(7),3,5,15,17-hexaen-14-yl]-1H-1,2,3-triazole-4-carboxamide, TFA salt: Example 137 was made in the same way as Example 136 by using Example 89. ¹H NMR (500 MHz, MeOD) δ 8.74 (d, J=5.8 Hz, 1H), 8.02 (s, 1H), 7.82 (ddd, J=8.1, 6.7, 1.7 Hz, 1H), 7.78-7.69 (m, 4H), 7.56 (ddd, J=8.1, 6.5, 1.7 Hz, 1H), 7.48-7.43 (m, 1H), 5.34 (dd, J=11.1, 5.9 Hz, 1H), 2.79-2.72 (m, 1H), 2.44 (d, J=0.8 Hz, 3H), 2.25-2.16 (m, 1H), 2.00-1.89 (m, 2H), 1.62-1.45 (m, 2H), 0.96 (d, J=6.9 Hz, 3H), 0.54-0.43 (m, 1H) ppm. MS(ESI) m/z: 644.2 (M+H)⁺. Analytical HPLC RT=7.07 min (Method A).

Example 138

1-(3-Chloro-2-fluorophenyl)-N-[(10R,14S)-5-acetamido-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt

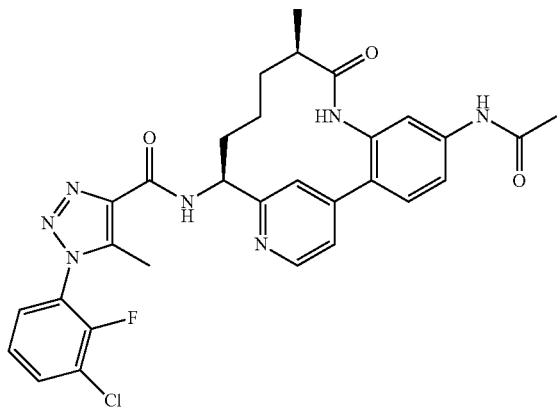 [SMILES: CC(=O)Nc1ccc2c(c1)NC(=O)[C@H](C)CCC[C@H](NC(=O)c1nnn(-c3cccc(Cl)c3F)c1C)c1cc-2ccn1]

Example 138. 1-(3-Chloro-2-fluorophenyl)-N-[(10R,14S)-5-acetamido-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt: Example 138 was made in the same way as Example 136 by replacing methanesulfonyl chloride with acetyl chloride. $^1$H NMR (500 MHz, MeOD) δ 8.75 (d, J=6.1 Hz, 1H), 8.22 (d, J=1.4 Hz, 1H), 7.91 (dd, J=6.1, 1.7 Hz, 1H), 7.82 (ddd, J=8.3, 6.8, 1.7 Hz, 1H), 7.76 (d, J=1.9 Hz, 1H), 7.69-7.65 (m, 1H), 7.60 (dd, J=8.5, 2.2 Hz, 1H), 7.56 (ddd, J=8.1, 6.5, 1.7 Hz, 1H), 7.46 (td, J=8.2, 1.5 Hz, 1H), 5.36 (dd, J=11.3, 6.1 Hz, 1H), 2.81-2.74 (m, 1H), 2.43 (d, J=1.1 Hz, 3H), 2.31-2.20 (m, 1H), 2.17 (s, 3H), 2.07-1.90 (m, 2H), 1.67-1.50 (m, 2H), 0.97 (d, J=7.2 Hz, 3H), 0.56-0.45 (m, 1H) ppm. MS(ESI) m/z: 590.2 (M+H)$^+$. Analytical HPLC RT=5.63 min (Method A).

Example 139

Fluoromethyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate, TFA salt

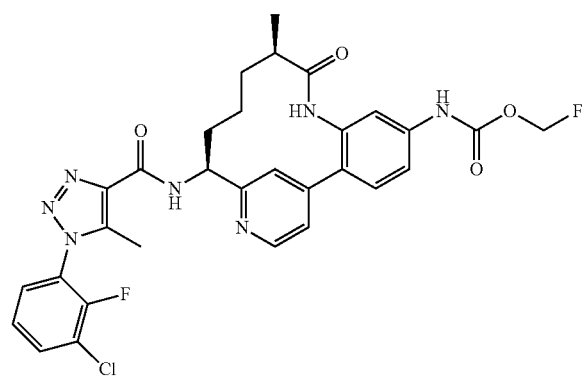 [SMILES: Cc1c(C(=O)N[C@H]2CCC[C@@H](C)C(=O)Nc3cc(NC(=O)OCF)ccc3-c3ccnc2c3)nnn1-c1cccc(Cl)c1F]

139A. Fluoromethyl carbonofluoridate: A mixture of chloromethyl carbonochloridate (0.16 g, 1.241 mmol), potassium fluoride (0.29 g, 4.99 mmol), and 18-crown-6 (0.1 g, 0.378 mmol) in acetonitrile (2.5 mL) in a sealed tube was stirred at rt overnight. The mixture was used in the next step without further purification as a 0.5 M solution.

Example 139. Fluoromethyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate, TFA salt: Example 139 was made in the same way as Example 136 by replacing methanesulfonyl chloride with 139A. $^1$H NMR (500 MHz, MeOD) δ 8.77 (d, J=6.3 Hz, 1H), 8.28 (d, J=1.7 Hz, 1H), 7.95 (dd, J=6.1, 1.9 Hz, 1H), 7.82 (ddd, J=8.3, 6.9, 1.7 Hz, 1H), 7.69 (d, J=8.5 Hz, 1H), 7.62 (s, 1H), 7.59-7.54 (m, 2H), 7.46 (td, J=8.1, 1.4 Hz, 1H), 5.86-5.83 (m, 1H), 5.76-5.72 (m, 1H), 5.37 (dd, J=11.3, 6.1 Hz, 1H), 2.83-2.75 (m, 1H), 2.42 (d, J=0.8 Hz, 3H), 2.30-2.21 (m, 1H), 2.10-1.91 (m, 2H), 1.70-1.51 (m, 2H), 0.97 (d, J=6.9 Hz, 3H), 0.54-0.43 (m, 1H) ppm. MS(ESI) m/z: 624.2 (M+H)$^+$. Analytical HPLC RT=6.44 min (Method A).

Example 140

Fluoromethyl N-[(10R,14S)-14-[1-(3-chloro-2-fluorophenyl)-5-methyl-1H-pyrazole-4-amido]-10-methyl-9-oxo-8,18-diazatricyclo[13.3.1.0$^{2,7}$]nonadeca-1(19),2(7),3,5,15,17-hexaen-5-yl]carbamate, TFA salt

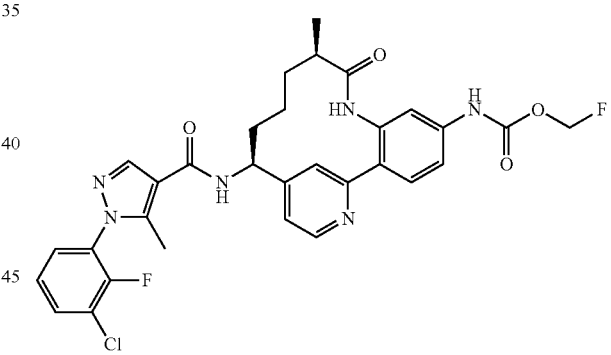

Example 140. Fluoromethyl N-[(10R,14S)-14-[1-(3-chloro-2-fluorophenyl)-5-methyl-1H-pyrazole-4-amido]-10-methyl-9-oxo-8,18-diazatricyclo[13.3.1.0$^{2,7}$]nonadeca-1(19),2(7),3,5,15,17-hexaen-5-yl]carbamate, TFA salt: Example 140 was made in the same way as Example 139 by replacing Example 89 with Example 92. $^1$H NMR (500 MHz, acetonitrile-d$_3$) δ 8.62 (d, J=5.78 Hz, 1H), 8.22 (s, 1H), 8.02 (s, 1H), 8.00 (s, 1H), 7.84 (s, 1H), 7.66 (d, J=8.53 Hz, 1H), 7.57 (ddd, J=1.79, 6.74, 8.25 Hz, 1H), 7.38-7.41 (m, 2H), 7.30-7.35 (m, 2H), 7.21-7.28 (m, 1H), 7.14 (d, J=6.05 Hz, 1H), 5.00 (td, J=5.88, 11.62 Hz, 1H), 4.58-4.61 (m, 1H), 4.48-4.51 (m, 1H), 4.30-4.33 (m, 1H), 4.25-4.28 (m, 1H), 2.55 (dt, J=2.75, 6.46 Hz, 1H), 2.24 (d, J=1.10 Hz, 3H), 1.91-2.01 (m, 2H), 1.68-1.80 (m, 3H), 1.41 (dt, J=6.33, 12.79 Hz, 1H), 1.27-1.36 (m, 1H), 0.82 (d, J=6.88 Hz, 2H), 0.46-0.59 (m, 1H) ppm. MS(ESI) m/z: 637.6 (M+H)$^+$. Analytical HPLC RT=6.09 min (Method A).

Example 141

1-(3-Chloro-2-fluorophenyl)-N-[(10R,14S)-5-(2-methoxyacetamido)-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt

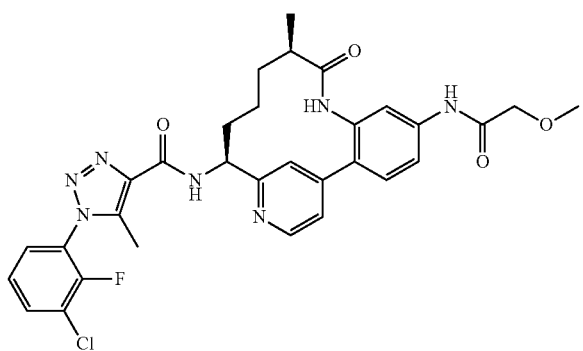 [SMILES: COCC(=O)Nc1ccc2c(c1)NC(=O)[C@H](C)CCC[C@H](NC(=O)c1nnn(-c3cccc(Cl)c3F)c1C)c1cc-2ccn1]

Example 141. 1-(3-Chloro-2-fluorophenyl)-N-[(10R,14S)-5-(2-methoxyacetamido)-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt: Example 141 was made in the same way as Example 136 by replacing methanesulfonyl chloride with 2-methoxyacetyl chloride. $^1$H NMR (500 MHz, acetonitrile-d₃) δ 8.63-8.69 (m, 1H), 8.60 (d, J=5.78 Hz, 1H), 8.36 (d, J=7.15 Hz, 1H), 8.17 (s, 1H), 7.85 (s, 1H), 7.67 (ddd, J=1.65, 6.88, 8.25 Hz, 1H), 7.64 (s, 1H), 7.46-7.53 (m, 3H), 7.38-7.44 (m, 1H), 7.29-7.35 (m, 1H), 5.24 (td, J=6.53, 10.87 Hz, 1H), 3.91 (s, 3H), 3.38 (s, 3H), 2.51-2.58 (m, 2H), 2.33 (s, 3H), 1.97-2.09 (m, 2H), 1.30-1.44 (m, 2H), 0.81 (d, J=6.88 Hz, 3H), 0.30-0.35 (m, 1H) ppm. MS(ESI) m/z: 620.6 (M+H)⁺. Analytical HPLC RT=6.06 min (Method A).

Example 142

1-(3-Chloro-2-fluorophenyl)-N-[(10S,14S)-5-(2-methoxyacetamido)-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt

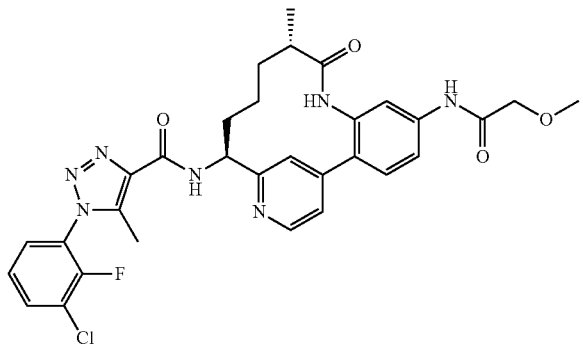 [SMILES: COCC(=O)Nc1ccc2c(c1)NC(=O)[C@@H](C)CCC[C@H](NC(=O)c1nnn(-c3cccc(Cl)c3F)c1C)c1cc-2ccn1]

Example 142. 1-(3-Chloro-2-fluorophenyl)-N-[(10S,14S)-5-(2-methoxyacetamido)-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt: Example 142 was made in the same way as Example 141 by using the other isomer. $^1$H NMR (500 MHz, acetonitrile-d₃) δ 8.66 (s, 1H), 8.61 (d, J=5.50 Hz, 1H), 8.35 (d, J=6.60 Hz, 1H), 7.93 (s, 1H), 7.65-7.69 (m, 2H), 7.64 (d, J=2.20 Hz, 1H), 7.56 (dd, J=2.20, 8.53 Hz, 1H), 7.46-7.50 (m, 2H), 7.41 (ddd, J=1.65, 6.53, 8.05 Hz, 1H), 7.33 (dt, J=1.51, 8.18 Hz, 1H), 5.18 (td, J=5.61, 11.62 Hz, 1H), 3.90 (s, 3H), 3.36 (s, 3H), 2.34 (d, J=1.10 Hz, 3H), 2.02-2.17 (m, 2H), 1.74-1.81 (m, 1H), 1.56-1.67 (m, 1H), 1.25-1.37 (m, 2H), 1.09 (d, J=7.15 Hz, 3H), 0.74-0.87 (m, 1H) ppm. MS(ESI) m/z: 620.6 (M+H)⁺. Analytical HPLC RT=6.11 min (Method A).

Example 143

1-(3-Chloro-2-fluorophenyl)-5-methyl-N-[(10R,14S)-10-methyl-9-oxo-5-(2-oxopropanamido)-8,16-diazatricyclo[13.3.1.0²,⁷]nonadeca-1(19),2(7),3,5,15,17-hexaen-14-yl]-1H-1,2,3-triazole-4-carboxamide, TFA salt

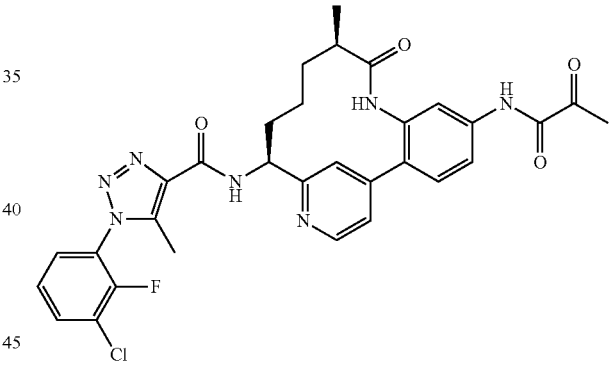

Example 143. 1-(3-Chloro-2-fluorophenyl)-5-methyl-N-[(10R,14S)-10-methyl-9-oxo-5-(2-oxopropanamido)-8,16-diazatricyclo[13.3.1.0²,⁷]nonadeca-1(19),2(7),3,5,15,17-hexaen-14-yl]-1H-1,2,3-triazole-4-carboxamide, TFA salt: Example 143 was made in the same way as Example 136 by replacing methanesulfonyl chloride with 2-oxopropanoyl chloride. $^1$H NMR (500 MHz, MeOD) δ 8.72 (d, J=5.2 Hz, 1H), 7.91 (td, J=7.6, 1.5 Hz, 1H), 7.85 (s, 1H), 7.82-7.77 (m, 2H), 7.72-7.67 (m, 1H), 7.64-7.57 (m, 2H), 7.51 (td, J=8.3, 1.4 Hz, 1H), 5.25 (dd, J=10.6, 5.6 Hz, 1H), 2.71-2.62 (m, 1H), 2.44 (s, 3H), 2.40 (s, 3H), 2.05-1.96 (m, 1H), 1.89-1.78 (m, 2H), 1.47-1.24 (m, 2H), 0.82 (d, J=6.9 Hz, 3H), 0.31-0.20 (m, 1H) ppm. MS(ESI) m/z: 618.1 (M+H)⁺. Analytical HPLC RT=6.34 min (Method A).

Example 144

1-(3-Chloro-2-fluorophenyl)-N-[(10R,14S)-5-(2-hydroxypropanamido)-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt

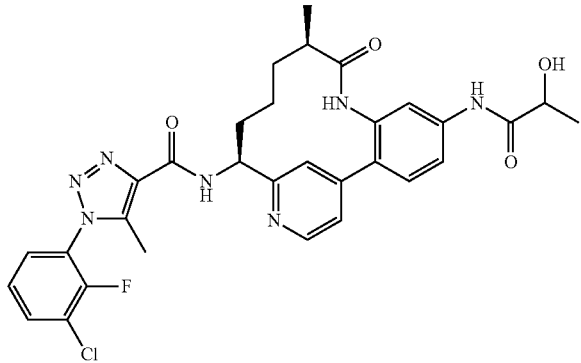 [SMILES: Cc1c(C(=O)N[C@H]2CCC[C@@H](C)C(=O)Nc3cc(NC(=O)C(C)O)ccc3-c3ccnc2c3)nnn1-c1cccc(Cl)c1F]

Example 144. 1-(3-Chloro-2-fluorophenyl)-N-[(10R,14S)-5-(2-hydroxypropanamido)-10-methyl-9-oxo-8,16-diazatricyclo[13.3.1.0²,⁷]nonadeca-1(19),2(7),3,5,15,17-hexaen-14-yl]-5-methyl-1H-1,2,3-triazole-4-carboxamide, TFA salt: To the solution of Example 143 (0.019 g, 0.026 mmol) in MeOH (1 mL) was added sodium borohydride (2 mg, 0.052 mmol). The reaction mixture was stirred at rt for 1 h and concentrated. The residue was purified by reverse phase HPLC to yield the desired product (8 mg, 40%) as a yellow solid. $^1$H NMR (500 MHz, MeOD) δ 8.75 (d, J=5.8 Hz, 1H), 8.17 (s, 1H), 7.86 (dd, J=5.9, 1.8 Hz, 1H), 7.84-7.79 (m, 2H), 7.73-7.65 (m, 2H), 7.56 (ddd, J=8.1, 6.5, 1.7 Hz, 1H), 7.46 (td, J=8.1, 1.4 Hz, 1H), 5.36 (dd, J=11.1, 5.9 Hz, 1H), 4.29 (q, J=6.9 Hz, 1H), 2.81-2.74 (m, 1H), 2.43 (d, J=0.8 Hz, 3H), 2.28-2.19 (m, 1H), 2.05-1.91 (m, 2H), 1.66-1.49 (m, 2H), 1.45 (d, J=6.9 Hz, 3H), 0.97 (d, J=7.2 Hz, 3H), 0.56-0.44 (m, 1H) ppm. MS(ESI) m/z: 620.2 (M+H)⁺. Analytical HPLC RT=5.62 min (Method A).

Example 145

2-Hydroxypropyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0²,⁷]nonadeca-1(19),2(7),3,5,15,17-hexaen-5-yl]carbamate, TFA salt

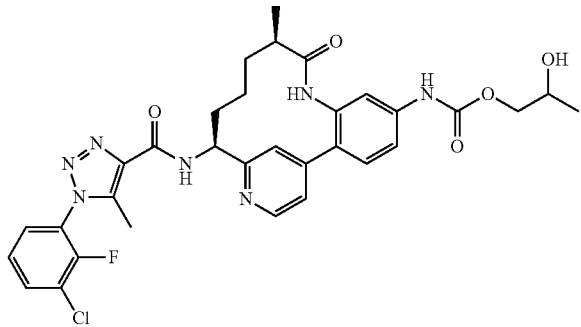 [SMILES: Cc1c(C(=O)N[C@H]2CCC[C@@H](C)C(=O)Nc3cc(NC(=O)OCC(C)O)ccc3-c3ccnc2c3)nnn1-c1cccc(Cl)c1F]

145A. 2-Oxopropyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0²,⁷]nonadeca-1(19),2(7),3,5,15,17-hexaen-5-yl]carbamate: To a solution of Example 89 (0.02 g, 0.032 mmol) in DCM (1 mL) and acetonitrile (1 mL) was added sodium bicarbonate (8.12 mg, 0.097 mmol). The mixture was cooled to 0° C. under argon, and then added phosgene solution (20% in toluene) (0.051 mL, 0.097 mmol). After another 2 h, the reaction was concentrated. The residue was dissolved in acetonitrile (1 mL) and DCM (1 mL) and cooled to 0° C. under argon. 1-Hydroxypropan-2-one (7.2 mg, 0.097 mmol) and TEA (9 μL, 0.064 mmol) were added and the resulting cloudy mixture was stirred at 0° C. for 30 min, then at rt overnight. The reaction was concentrated and purified by reverse phase HPLC to isolate the desired product as a yellow solid (11 mg, 18%). MS(ESI) m/z: 648.2 (M+H)⁺.

Example 145. 2-Hydroxypropyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0²,⁷]nonadeca-1(19),2(7),3,5,15,17-hexaen-5-yl]carbamate, TFA salt: To the solution of 145A (0.011 g, 5.77 μmol) in MeOH (1 mL) was added NaBH₄ (0.655 mg, 0.017 mmol). The reaction was stirred at rt for 1 h and concentrated. The residue was purified by reverse phase HPLC to yield the desired product as a yellow solid (2 mg, 44% yield). $^1$H NMR (500 MHz, MeOD) δ 8.71 (d, J=5.8 Hz, 1H), 8.05 (s, 1H), 7.82 (ddd, J=8.3, 6.8, 1.7 Hz, 1H), 7.75 (dd, J=5.8, 1.7 Hz, 1H), 7.61 (d, J=8.5 Hz, 1H), 7.58-7.54 (m, 2H), 7.51 (dt, J=8.5, 2.1 Hz, 1H), 7.46 (td, J=8.2, 1.5 Hz, 1H), 5.34 (dd, J=11.3, 5.8 Hz, 1H), 4.12-3.99 (m, 3H), 2.80-2.72 (m, 1H), 2.44 (d, J=0.8 Hz, 3H), 2.25-2.16 (m, 1H), 2.01-1.91 (m, 2H), 1.65-1.46 (m, 2H), 1.23 (d, J=6.3 Hz, 3H), 0.97 (d, J=7.2 Hz, 3H), 0.54-0.43 (m, 1H) ppm. MS(ESI) m/z: 650.2 (M+H)⁺. Analytical HPLC RT=5.77 min (Method A).

Example 146 tert-Butyl 2-{[(10R,14S)-14-[1-(3-chloro-2-fluorophenyl)-5-methyl-1H-1,2,3-triazole-4-amido]-10-methyl-9-oxo-8,16-diazatricyclo[13.3.1.0²,⁷]nonadeca-1(19),2(7),3,5,15,17-hexaen-5-yl]carbamoyl}acetate, TFA salt

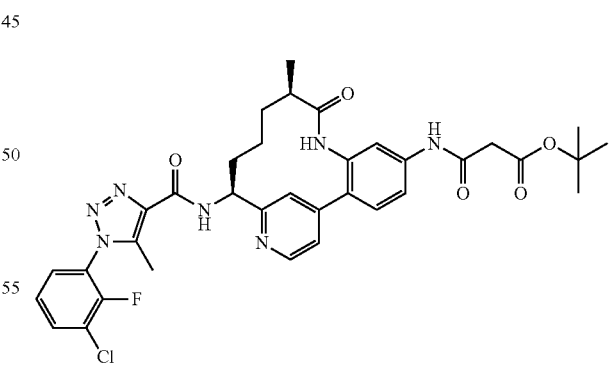

Example 146. tert-Butyl 2-{[(10R,14S)-14-[1-(3-chloro-2-fluorophenyl)-5-methyl-1H-1,2,3-triazole-4-amido]-10-methyl-9-oxo-8,16-diazatricyclo[13.3.1.0²,⁷]nonadeca-1(19),2(7),3,5,15,17-hexaen-5-yl]carbamoyl}acetate, TFA salt: To a solution of Example 89 (0.02 g, 0.026 mmol) in DMF (1 mL) was added 3-(tert-butoxy)-3-oxopropanoic acid (0.012 g, 0.077 mmol), EDC (9.88 mg, 0.052 mmol), HOBT (7.89 mg, 0.052 mmol), and DIPEA (0.023 mL, 0.129 mmol). The reaction was stirred at rt overnight and at 55° C. for 2 h. The mixture was cooled to rt and concentrated. The residue was purified by reverse phase to yield the desired product (12 mg, 57%) as a white solid. $^1$H NMR (500 MHz, MeOD) δ 8.76 (d, J=6.1 Hz, 1H), 8.25 (d, J=1.7 Hz, 1H), 7.93 (dd, J=6.1, 1.9 Hz, 1H), 7.81 (ddd, J=8.3, 6.8, 1.7 Hz, 1H), 7.76 (d, J=1.9 Hz, 1H), 7.69 (d, J=8.3 Hz, 1H), 7.62 (dd, J=8.4, 2.1 Hz, 1H), 7.56 (ddd, J=8.1, 6.5, 1.7 Hz, 1H), 7.46 (td, J=8.1, 1.4 Hz, 1H), 5.37 (dd, J=11.3, 6.1 Hz, 1H), 3.43 (s, 2H), 2.82-2.74 (m, 1H), 2.43 (d, J=0.8 Hz, 3H), 2.30-2.20 (m, 1H), 2.08-1.90 (m, 2H), 1.68-1.43 (m, 11H), 0.97 (d, J=6.9 Hz, 3H), 0.56-0.45 (m, 1H) ppm. MS(ESI) m/z: 690.3 (M+H)$^+$. Analytical HPLC RT=7.03 min (Method A).

Example 147

1-(3-Chloro-2-fluorophenyl)-N-[(10R,14S)-5-[(E)-2-cyano-1-methylcarbamimidamido]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt

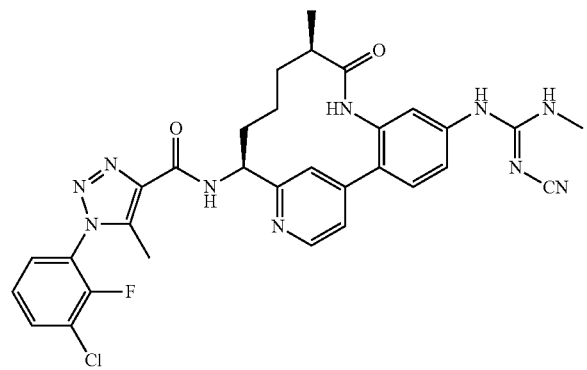 [SMILES: CN/C(=N\C#N)Nc1ccc2c(c1)NC(=O)[C@H](C)CCC[C@H](NC(=O)c1nnn(-c3cccc(Cl)c3F)c1C)c1cc-2ccn1]

147A. 1-(3-Chloro-2-fluorophenyl)-N-[(10R,14S)-5-{[(1Z)-(cyanoimino)(phenoxy)methyl]amino}-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide: A mixture of Example 89 (Alternative, HCl salt) (10 mg, 0.016 mmol), pyridine (10.42 μl, 0.129 mmol) and diphenyl cyanocarbonimidate (7.67 mg, 0.032 mmol) in 2-propanol (0.15 mL) was stirred in a pressure-tested vial at room temperature for 2 h. The reaction mixture was concentrated to give the product (11 mg, 99%) as an oily solid. MS(ESI) m/z: 692.7 (M+H)$^+$.

Example 147. 1-(3-Chloro-2-fluorophenyl)-N-[(10R,14S)-5-[(E)-2-cyano-1-methylcarbamimidamido]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt: A mixture of 147A (11 mg, 0.016 mmol) and monomethylamine (0.795 mL, 1.589 mmol) in 2-propanol (0.2 mL) was stirred in a pressure-tested vial at room temperature for 1 h. Monomethylamine (0.795 mL, 1.589 mmol) was added again and the reaction was stirred at rt for another hour. The reaction was concentrated and purified by reverse phase HPLC to yield the desired product (6.2 mg, 95%) as a white solid. $^1$H NMR (500 MHz, acetonitrile-d$_3$) δ 8.62 (d, J=5.78 Hz, 1H), 8.39 (d, J=6.88 Hz, 1H), 8.25 (s, 1H), 7.90 (s, 1H), 7.67 (ddd, J=1.51, 6.88, 8.12 Hz, 1H), 7.56 (dd, J=1.38, 5.78 Hz, 1H), 7.51 (d, J=8.53 Hz, 1H), 7.46 (br. s., 1H), 7.42 (ddd, J=1.65, 6.53, 8.05 Hz, 1H), 7.33 (dt, J=1.38, 8.12 Hz, 1H), 7.28 (dd, J=1.79, 8.39 Hz, 1H), 7.23 (br. s., 1H), 5.96 (d, J=3.58 Hz, 1H), 5.26 (td, J=6.57, 11.07 Hz, 1H), 2.80 (d, J=4.68 Hz, 3H), 2.52-2.60 (m, 2H), 2.33 (s, 2H), 2.01-2.09 (m, 2H), 1.90-1.99 (m, 2H), 1.77 (t, J=12.10 Hz, 1H), 1.33-1.46 (m, 2H), 0.81 (d, J=6.88 Hz, 3H), 0.24-0.36 (m, 1H) ppm. MS(ESI) m/z: 629.6 (M+H)$^+$. Analytical HPLC RT=5.92 min (Method A).

Example 148

1-(3-Chloro-2-fluorophenyl)-N-[(10S,14S)-5-[(E)-2-cyano-1-methylcarbamimidamido]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt

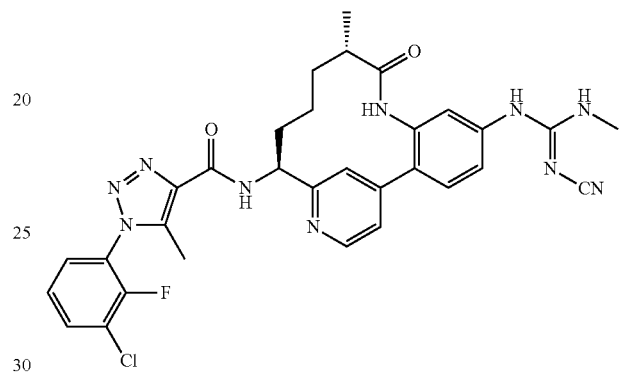

Example 148. 1-(3-Chloro-2-fluorophenyl)-N-[(10S,14S)-5-[(E)-2-cyano-1-methylcarbamimidamido]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt: Example 148 was made in the same way as Example 147 by using the other isomer. $^1$H NMR (500 MHz, acetonitrile-d$_3$) δ 8.62 (d, J=5.50 Hz, 1H), 8.33 (d, J=6.88 Hz, 1H), 7.88 (s, 1H), 7.64-7.70 (m, 1H), 7.61 (s, 1H), 7.50 (d, J=8.25 Hz, 1H), 7.39-7.46 (m, 2H), 7.30-7.36 (m, 2H), 7.26 (br. s., 1H), 5.90 (br. s., 1H), 5.13-5.20 (m, 1H), 2.80 (d, J=4.95 Hz, 3H), 2.42 (d, J=6.05 Hz, 1H), 2.35 (d, J=0.55 Hz, 3H), 2.03-2.18 (m, 2H), 1.67-1.78 (m, 2H), 1.66-1.60 (m, 1H), 1.25-1.35 (m, 4H), 1.08 (d, J=7.15 Hz, 3H), 0.88-83 (m, 1H) ppm. MS(ESI) m/z: 629.6 (M+H)$^+$. Analytical HPLC RT=5.90 min (Method A).

Example 149

1-(3-Chloro-2-fluorophenyl)-N-[(10R,14S)-5-{[6-(methoxymethyl)pyrimidin-4-yl]amino}-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt

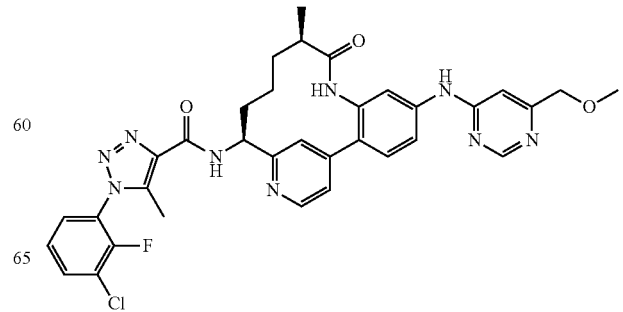

233

Example 149. 1-(3-Chloro-2-fluorophenyl)-N-[(10R,14S)-5-{[6-(methoxymethyl)pyrimidin-4-yl]amino}-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt: The solution of Example 89 (Alternative, HCl salt) (0.01 g, 0.016 mmol), 4-chloro-6-(methoxymethyl)pyrimidine (7.66 mg, 0.048 mmol), and DIPEA (0.014 mL, 0.081 mmol) in IPA (0.5 mL) was heated at 150° C. for 30 min under microwave conditions. The reaction was cooled to rt and concentrated. The residue was purified by reverse phase to yield the desired product (5 mg, 33%) as a yellow solid. $^1$H NMR (500 MHz, MeOD) δ 8.80 (d, J=0.8 Hz, 1H), 8.76 (d, J=5.8 Hz, 1H), 8.06 (d, J=1.1 Hz, 1H), 7.84-7.73 (m, 5H), 7.56 (ddd, J=8.0, 6.5, 1.7 Hz, 1H), 7.46 (td, J=8.1, 1.4 Hz, 1H), 7.04 (d, J=0.8 Hz, 1H), 5.35 (dd, J=11.1, 5.9 Hz, 1H), 4.58 (d, J=0.6 Hz, 2H), 3.53 (s, 3H), 2.80-2.73 (m, 1H), 2.44 (d, J=0.8 Hz, 3H), 2.26-2.17 (m, 1H), 2.02-1.90 (m, 2H), 1.64-1.47 (m, 2H), 0.97 (d, J=6.9 Hz, 3H), 0.55-0.45 (m, 1H) ppm. MS(ESI) m/z: 670.3 (M+H)$^+$. Analytical HPLC RT=4.94 min (Method A).

Example 150

1-(3-Chloro-2-fluorophenyl)-N-[(10R,14S)-5-[(E)-[(dimethylamino)methylidene]amino]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt

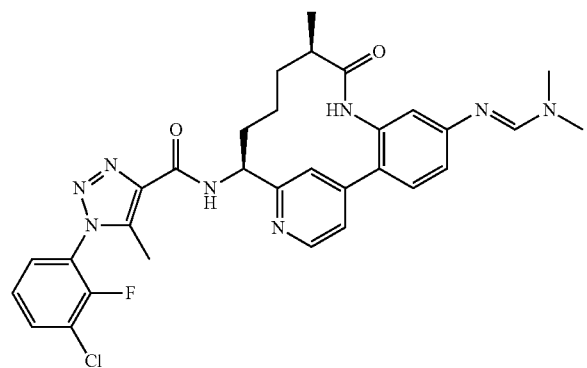 [SMILES: Cc1c(C(=O)N[C@H]2CCC[C@@H](C)C(=O)Nc3cc(/N=C/N(C)C)ccc3-c3ccnc2c3)nnn1-c1cccc(Cl)c1F]

Example 150. 1-(3-Chloro-2-fluorophenyl)-N-[(10R,14S)-5-[(E)-[(dimethylamino)methylidene]amino]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide, TFA salt: The solution of Example 89 (Alternative, HCl salt) (0.01 g, 0.016 mmol), ethyl 2-bromopropanoate (4.37 mg, 0.024 mmol), KI (0.802 mg, 4.83 μmol), and K$_2$CO$_3$ (6.68 mg, 0.048 mmol) in DMF (0.5 mL) was stirred at 120° C. for 5 h. The reaction was cooled to rt and purified by reverse phase HPLC to isolate the product (3.5 mg, 26%) as a yellow solid. $^1$H NMR (500 MHz, MeOD) δ 8.80-8.70 (m, 2H), 8.00 (br. s., 1H), 7.85-7.72 (m, 3H), 7.60-7.50 (m, 2H), 7.49-7.43 (m, 1H), 7.35 (d, J=2.5 Hz, 1H), 5.33 (dd, J=10.7, 5.8 Hz, 1H), 3.48 (s, 3H), 3.34 (s, 3H), 2.78-2.71 (m, 1H), 2.44 (d, J=0.8 Hz, 3H), 2.26-2.16 (m, 1H), 2.01-1.86 (m, 2H), 1.62-1.44 (m, 2H), 0.97 (d, J=7.2 Hz, 3H), 0.60-0.47 (m, 1H) ppm. MS(ESI) m/z: 603.2 (M+H)$^+$. Analytical HPLC RT=3.93 min (Method A).

The following Examples in Table 9 were synthesized using methods similar as those described in Example 149.

234

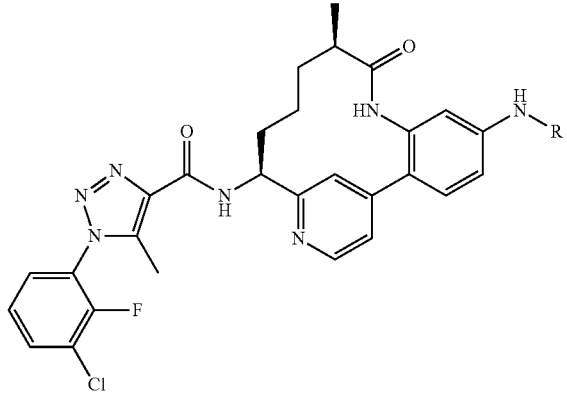

TABLE 9

| Example # | Stereo-chemistry | R | M + H | RT, min Method A |
|---|---|---|---|---|
| 151 | Homochiral | pyrimidin-4-yl | 626.2 | 5.83 |
| 152 | Homochiral | pyrimidin-2-yl | 626.2 | 6.08 |
| 153 | Homochiral Early eluting diastereomer | ethyl 2-methylpropanoate | 648.1 | 6.58 |
| 154 | Homochiral Late eluting diastereomer | ethyl 2-methylpropanoate | 648.2 | 6.65 |
| 155 | Homochiral | CH$_2$C(O)OH | 606.1 | 4.00 |

Example 156

Ethyl 2-{[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]amino}acetate, TFA salt

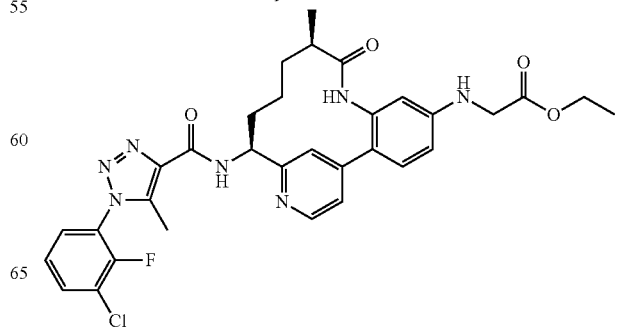

Example 156. Ethyl 2-{[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]amino}acetate, TFA salt: To the solution of Example 89 (Alternative, HCl salt) (0.013 g, 0.021 mmol) and ethyl 2-oxoacetate (6.23 µl, 0.031 mmol) in MeOH (0.5 mL) was added acetic acid (1.2 µL, 0.021 mmol), followed by sodium cyanoborohydride (1.3 mg, 0.021 mmol). The reaction was stirred at rt for 2 h and concentrated. The residue was purified by reverse phase HPLC to yield the desired product (11 mg, 59%) as a yellow solid. $^1$H NMR (500 MHz, MeOD) δ 8.63 (d, J=6.3 Hz, 1H), 8.24 (d, J=1.9 Hz, 1H), 7.88 (dd, J=6.2, 1.8 Hz, 1H), 7.82 (ddd, J=8.1, 6.7, 1.7 Hz, 1H), 7.58-7.52 (m, 2H), 7.46 (td, J=8.1, 1.4 Hz, 1H), 6.72 (dd, J=8.7, 2.3 Hz, 1H), 6.51 (d, J=2.5 Hz, 1H), 5.36 (dd, J=11.6, 6.1 Hz, 1H), 4.22 (q, J=7.0 Hz, 2H), 4.02 (s, 2H), 2.84-2.75 (m, 1H), 2.43 (d, J=0.8 Hz, 3H), 2.30-2.19 (m, 1H), 2.09-1.95 (m, 2H), 1.74-1.52 (m, 2H), 1.28 (t, J=7.2 Hz, 3H), 0.98 (d, J=6.9 Hz, 3H), 0.59-0.47 (m, 1H) ppm. MS(ESI) m/z: 634.2 (M+H)$^+$. Analytical HPLC RT=6.31 min (Method A).

Example 157

Methyl (10R,14S)-5-amino-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaene-4-carboxylate, 2 TFA salt

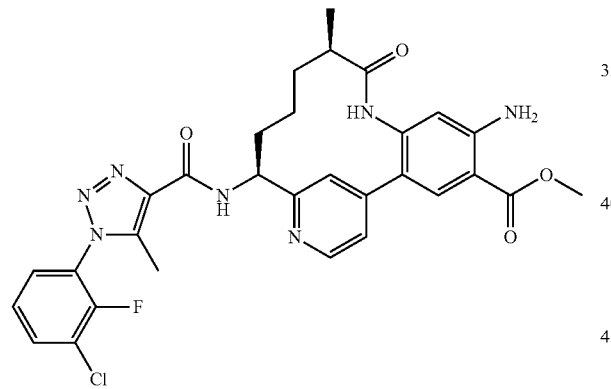

157A. tert-Butyl N-[(10R,14S)-5-amino-4-iodo-10-methyl-9-oxo-8,16-diazatricyclo[13.3.1.0$^{2,7}$]nonadeca-1(19),2(7),3,5,15,17-hexaen-14-yl]carbamate: To a solution of Example 89A (0.05 g, 0.122 mmol) in MeOH (2.5 mL) at 0° C. was added iodine monochloride (0.030 g, 0.183 mmol) in DCM (1.0 mL). The reaction was stirred at rt for 2 h and concentrated. The residue was re-dissolved in EtOAc, washed with saturated NaHCO$_3$, brine, dried over Na$_2$SO$_4$, filtered, and concentrated. The residue was purified by silica gel chromatography to yield the desired product (0.061 g, 93%) as a yellow solid. MS(ESI) m/z: 537.2 (M+H)$^+$.

157B. Methyl (10R,14S)-5-amino-14-{[(tert-butoxy)carbonyl]amino}-10-methyl-9-oxo-8,16-diazatricyclo[13.3.1.0$^{2,7}$]nonadeca-1(19),2(7),3,5,15,17-hexaene-4-carboxylate: The mixture of Pd(OAc)$_2$ (0.8 mg, 3.73 µmol), DPPF (2 mg, 3.73 µmol), K$_2$CO$_3$ (0.015 g, 0.112 mmol), TEA (5.2 µL, 0.037 mmol), and 157A (0.02 g, 0.037 mmol) in acetonitrile (2 mL) and MeOH (1 mL) was vacuumed and backfilled with argon for three times. CO was bubbled through a needle into the solution for 3 min, and the mixture was heated under a CO balloon at 70° C. for 3 h. The reaction was cooled to rt, diluted with EtOAc, washed with water, brine, dried over Na$_2$SO$_4$, filtered, and concentrated. The residue was purified by silica gel chromatography to yield the desired product (0.012 g, 69%) as a yellow solid. MS(ESI) m/z: 469.3 (M+H)$^+$.

Example 157. Methyl (10R,14S)-5-amino-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaene-4-carboxylate, 2 TFA salt: Example 157 was made in the same way as Example 89 by replacing Example 89A with 157B. $^1$H NMR (500 MHz, MeOD) δ 8.68 (d, J=6.3 Hz, 1H), 8.22 (d, J=1.9 Hz, 1H), 8.16 (s, 1H), 7.92 (dd, J=6.2, 1.8 Hz, 1H), 7.81 (ddd, J=8.3, 6.8, 1.7 Hz, 1H), 7.56 (ddd, J=8.1, 6.5, 1.4 Hz, 1H), 7.46 (td, J=8.1, 1.4 Hz, 1H), 6.67 (s, 1H), 5.37 (dd, J=11.6, 6.1 Hz, 1H), 3.90 (s, 3H), 2.84-2.75 (m, 1H), 2.43 (d, J=0.8 Hz, 3H), 2.30-2.20 (m, 1H), 2.10-1.94 (m, 2H), 1.74-1.53 (m, 2H), 0.96 (d, J=7.2 Hz, 3H), 0.55-0.43 (m, 1H) ppm. MS(ESI) m/z: 606.2 (M+H)$^+$. Analytical HPLC RT=6.19 min (Method A).

Example 158

(10R,14S)-5-Amino-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaene-4-carboxylic acid, 2 TFA salt

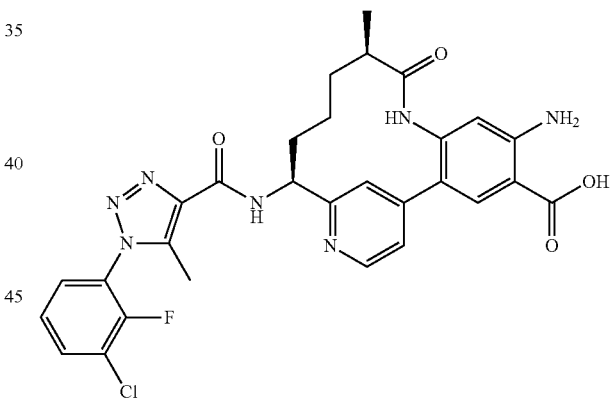

Example 158. (10R,14S)-5-Amino-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaene-4-carboxylic acid, 2 TFA salt: To the solution of Example 157 (0.009 g, 10.79 µmol) in MeOH (1 mL) was added 1 N NaOH (0.108 mL, 0.108 mmol). The reaction was stirred at 50° C. for 24 h. The reaction was quenched with TFA and purified by reverse phase HPLC to isolate the desired product (6 mg, 65% yield) as a yellow solid. $^1$H NMR (500 MHz, MeOD) δ 8.65 (d, J=5.8 Hz, 1H), 8.18 (s, 1H), 8.11 (s, 1H), 7.85-7.79 (m, 2H), 7.59-7.53 (m, 1H), 7.49-7.43 (m, 1H), 6.65 (s, 1H), 5.35 (dd, J=11.3, 6.1 Hz, 1H), 2.82-2.74 (m, 1H), 2.44 (s, 3H), 2.27-2.17 (m, 1H), 2.05-1.94 (m, 2H), 1.71-1.49 (m, 2H), 0.96 (d, J=6.9 Hz, 3H), 0.55-0.44 (m, 1H) ppm. MS(ESI) m/z: 592.3 (M+H)$^+$. Analytical HPLC RT=5.59 min (Method A).

Example 159

1-(3-Chloro-2-fluorophenyl)-5-methyl-N-[(10R,14S)-10-methyl-5-[(5-methyl-1,3,4-oxadiazol-2-yl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide, TFA salt

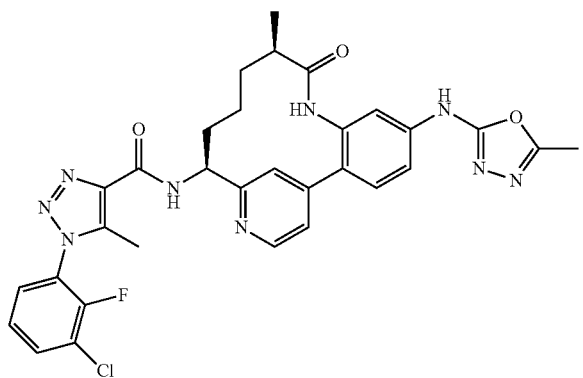 [SMILES: Cc1nnc(Nc2ccc3c(c2)NC(=O)[C@H](C)CCC[C@H](NC(=O)c2nnn(-c4cccc(Cl)c4F)c2C)c2cc-3ccn2)o1]

159A. 1-(3-Chloro-2-fluorophenyl)-N-[(10R,14S)-5-isothiocyanato-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide: To a solution of Example 89 (Alternative, patent) (36 mg, 0.066 mmol) in DCM (1 mL) at 0° C. was added 1,1'-thiocarbonylbis(pyridin-2(1H)-one) (15.26 mg, 0.066 mmol) in dichloromethane (0.5 mL) dropwise. The reaction mixture was slowly warm to rt and stirred overnight. The reaction was concentrated and purified by silica gel chromatography to yield the desired product (10 mg, 25%). MS(ESI) m/z: 592.3 (M+H)$^+$.

Example 159. 1-(3-Chloro-2-fluorophenyl)-5-methyl-N-[(10R,14S)-10-methyl-5-[(5-methyl-1,3,4-oxadiazol-2-yl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide, TFA salt: The mixture of 159A (10 mg, 0.017 mmol) and acetohydrazide (1.255 mg, 0.017 mmol) in THF (1 mL) was stirred at rt overnight. The mixture was concentrated. The residue was taken up with DMF (1 mL) and added EDC (13.00 mg, 0.068 mmol) and TEA (0.014 mL, 0.102 mmol). The resulting mixture was stirred at rt overnight. The reaction mixture was diluted with MeOH and purified by reverse phase HPLC to yield the desired product (4.5 mg, 34%) as a yellow solid. $^1$H NMR (500 MHz, MeOD) δ 8.78 (d, J=6.1 Hz, 1H), 8.29 (d, J=1.7 Hz, 1H), 7.96 (dd, J=6.1, 1.7 Hz, 1H), 7.85 (ddd, J=8.1, 6.7, 1.7 Hz, 1H), 7.75 (d, J=8.8 Hz, 1H), 7.69 (d, J=2.2 Hz, 1H), 7.63-7.56 (m, 2H), 7.49 (td, J=8.1, 1.4 Hz, 1H), 5.40 (dd, J=11.3, 6.1 Hz, 1H), 3.31 (m, 3H), 2.88-2.80 (m, 1H), 2.51 (s, 3H), 2.46 (d, J=0.8 Hz, 3H), 2.34-2.23 (m, 1H), 2.12-1.96 (m, 2H), 1.77-1.52 (m, 2H), 1.01 (d, J=7.2 Hz, 3H), 0.54 (d, J=11.6 Hz, 1H) ppm. MS(ESI) m/z: 629.9 (M+H)$^+$. Analytical HPLC RT=5.85 min (Method A).

Example 160

N-[(10R,14S)-5-Carbamimidamido-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-1,2,3-triazole-4-carboxamide, TFA salt

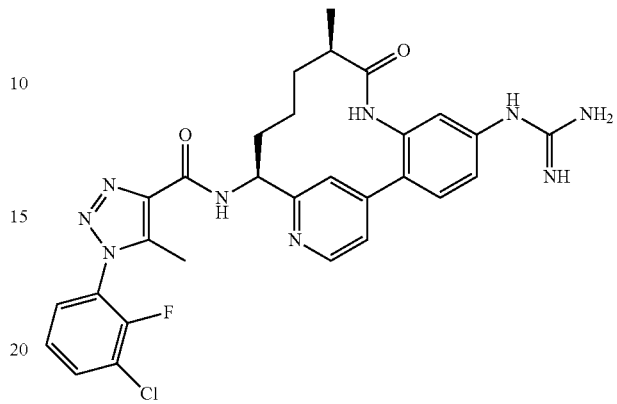

Example 160. N-[(10R,14S)-5-Carbamimidamido-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-1,2,3-triazole-4-carboxamide, TFA salt: To a mixture of 159A (31 mg, 0.053 mmol) and acetohydrazide (3.89 mg, 0.053 mmol) was added THF (1 mL) and the reaction was stirred at rt overnight. The reaction was concentrated. The residue was taken up in DCM (1.4 mL), cooled to 0° C. and added TFA (0.6 mL, 7.79 mmol). The reaction was stirred at 0° C. for 30 min. The reaction was concentrated and purified by reverse phase HPLC to yield the desired product (11 mg, 78%). $^1$H NMR (500 MHz, MeOD) δ 8.81 (d, J=5.5 Hz, 1H), 8.03 (d, J=1.1 Hz, 1H), 7.88-7.79 (m, 2H), 7.77 (dd, J=5.6, 1.8 Hz, 1H), 7.59 (ddd, J=8.0, 6.5, 1.7 Hz, 1H), 7.53-7.42 (m, 2H), 7.26 (d, J=2.2 Hz, 1H), 5.37 (dd, J=11.0, 5.8 Hz, 1H), 3.36 (m, 6H), 2.81-2.71 (m, 1H), 2.48 (d, J=1.1 Hz, 3H), 2.29-2.19 (m, 1H), 2.05-1.88 (m, 2H), 1.65-1.49 (m, 2H), 1.01 (d, J=6.9 Hz, 3H), 0.57 (d, J=12.7 Hz, 1H) ppm. MS(ESI) m/z: 590.0 (M+H)$^+$. Analytical HPLC RT=4.82 min (Method A).

Example 161

1-(2-Fluorophenyl)-5-methyl-N-[(10S,14S)-10-methyl-5-[(5-methyl-1,3,4-oxadiazol-2-yl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide, TFA salt

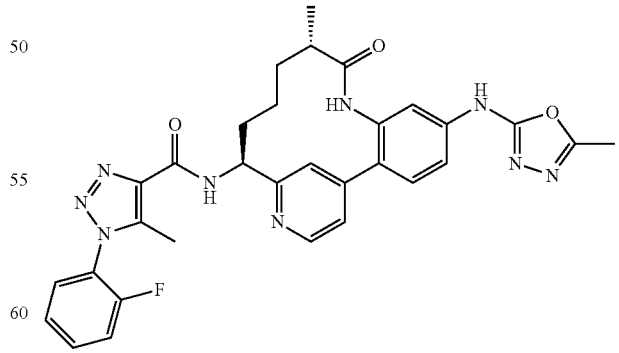

Example 161. 1-(3-Chloro-2-fluorophenyl)-5-methyl-N-[(10S,14S)-10-methyl-5-[(5-methyl-1,3,4-oxadiazol-2-yl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide, TFA salt: Example 161 was made in the same way as Example 159 by using corresponding amine intermediate. ¹H NMR (500 MHz, MeOD) δ 8.77 (d, J=5.8 Hz, 1H), 8.12 (d, J=1.4 Hz, 1H), 7.89 (dd, J=5.8, 1.7 Hz, 1H), 7.79-7.70 (m, 2H), 7.69-7.54 (m, 4H), 7.53-7.45 (m, 2H), 5.29 (dd, J=10.7, 5.2 Hz, 1H), 3.32 (m, 3H), 2.56-2.42 (m, 7H), 2.35-2.20 (m, 1H), 2.16-2.00 (m, 1H), 1.87-1.72 (m, 1H), 1.70-1.57 (m, 1H), 1.30-1.26 (m, 3H), 1.13-0.98 (m, 1H) ppm. MS(ESI) m/z: 596.0 (M+H)⁺. Analytical HPLC RT=5.16 min (Method A).

Example 162

1-(3-Chloro-2-fluorophenyl)-5-methyl-N-[(10R,14S)-10-methyl-5-[(1,3,4-oxadiazol-2-yl)amino]-9-oxo-8,16-diazatricyclo[13.3.1.0²,⁷]nonadeca-1(19),2(7),3,5,15,17-hexaen-14-yl]-1H-1,2,3-triazole-4-carboxamide, TFA salt

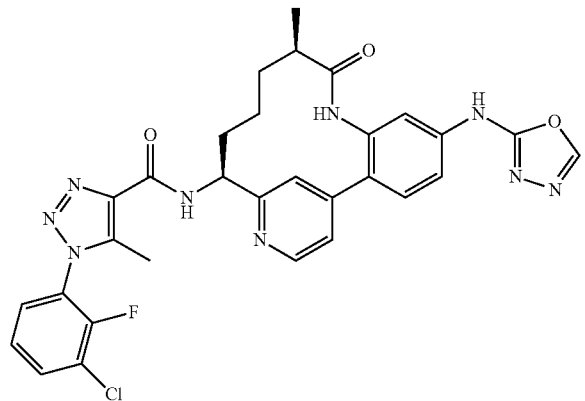 [SMILES: Cc1c(C(=O)N[C@H]2CCC[C@@H](C)C(=O)Nc3cc(Nc4nnco4)ccc3-c3ccnc2c3)nnn1-c1cccc(Cl)c1F]

Example 162. 1-(3-Chloro-2-fluorophenyl)-5-methyl-N-[(10R,14S)-10-methyl-5-[(1,3,4-oxadiazol-2-yl)amino]-9-oxo-8,16-diazatricyclo[13.3.1.0²,⁷]nonadeca-1(19),2(7),3,5,15,17-hexaen-14-yl]-1H-1,2,3-triazole-4-carboxamide, TFA salt: Example 162 was made in the same way as Example 159 by replacing acetohydrazide with formohydrazide. ¹H NMR (500 MHz, acetonitrile-d₃) δ 8.60 (d, J=5.50 Hz, 1H), 8.53 (br. s., 1H), 8.34 (d, J=6.88 Hz, 1H), 8.13 (s, 1H), 7.88 (s, 1H), 7.67 (ddd, J=1.65, 6.74, 8.12 Hz, 1H), 7.56 (d, J=1.93 Hz, 1H), 7.48-7.54 (m, 1H), 7.37-7.44 (m, 1H), 7.29-7.35 (m, 2H), 5.09-5.22 (m, 1H), 3.03 (dq, J=4.95, 7.24 Hz, 1H), 2.35 (d, J=1.10 Hz, 3H), 2.30-2.10 (m, 3H), 1.60-1.73 (m, 2H), 1.25-1.37 (m, 3H), 1.11 (d, J=7.15 Hz, 3H), 0.85 (dd, J=3.44, 11.69 Hz, 1H) ppm. MS(ESI) m/z: 616.6 (M+H)⁺. Analytical HPLC RT=5.80 min (Method A).

Example 163

N-[(10R,14S)-5-Bromo-10-methyl-9-oxo-8,16-diazatricyclo[13.3.1.0²,⁷]nonadeca-1(19),2(7),3,5,15,17-hexaen-14-yl]-1-(3-chloro-2 fluorophenyl)-5-methyl-1H-1,2,3-triazole-4 carboxamide, TFA salt

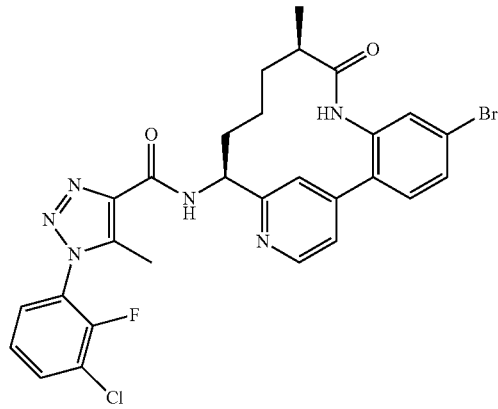 [SMILES: Cc1c(C(=O)N[C@H]2CCC[C@@H](C)C(=O)Nc3cc(Br)ccc3-c3ccnc2c3)nnn1-c1cccc(Cl)c1F]

Example 163. N-[(10R,14S)-5-Bromo-10-methyl-9-oxo-8,16-diazatricyclo[13.3.1.0²,⁷]nonadeca-1(19),2(7),3,5,15,17-hexaen-14-yl]-1-(3-chloro-2 fluorophenyl)-5-methyl-1H-1,2,3-triazole-4 carboxamide, TFA salt: To a mixture of copper (II) bromide (58.3 mg, 0.261 mmol) and tert-butyl nitrite (0.034 mL, 0.290 mmol) in acetonitrile (1 mL) at 0° C. was added to a solution of Example 89 (Alternative, parent) (159 mg, 0.290 mmol) in acetonitrile (1 mL). The reaction was allowed to slowly warm to rt and stirred overnight. The reaction was quenched with 1 N HCL (2.0 mL) and extracted with EtOAc. The organic layer was washed with brine, dried over MgSO₄, filtered, and concentrated. The residue was purified by reverse phase HPLC to yield the desired product (90 mg, 41%) as a white solid. ¹H NMR (500 MHz, MeOD) δ 8.78 (d, J=5.5 Hz, 1H), 7.95 (s, 1H), 7.85 (ddd, J=8.3, 6.8, 1.7 Hz, 1H), 7.73-7.66 (m, 2H), 7.64-7.57 (m, 2H), 7.54-7.44 (m, 2H), 5.35 (dd, J=11.0, 5.8 Hz, 1H), 3.31 (m, 2H), 2.80-2.69 (m, 1H), 2.49 (d, J=1.1 Hz, 3H), 2.22 (br. s., 1H), 2.04-1.84 (m, 2H), 1.65-1.45 (m, 2H), 0.99 (d, J=6.9 Hz, 3H), 0.51 (d, J=12.1 Hz, 1H) ppm. MS(ESI) m/z: 612.8 (M+H)⁺. Analytical HPLC RT=7.73 min (Method A).

Example 164

1-(3-Chloro-2-fluorophenyl)-5-methyl-N-[(10R,14S)-10-methyl-9-oxo-5-(1H-pyrazol-5-yl)-8,16-diazatricyclo[13.3.1.0²,⁷]nonadeca-1(19),2(7),3,5,15,17-hexaen-14-yl]-1H-1,2,3-triazole-4-carboxamide, TFA salt

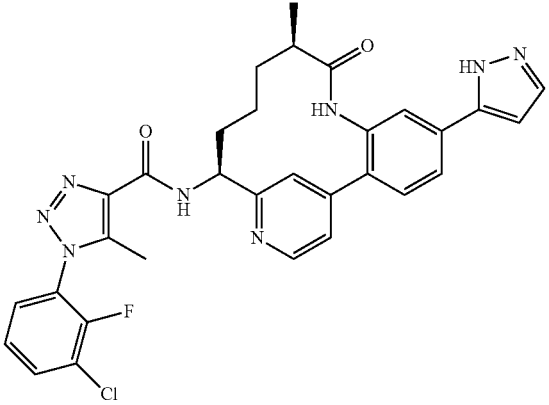 [SMILES: Cc1c(C(=O)N[C@H]2CCC[C@@H](C)C(=O)Nc3cc(-c4ccn[nH]4)ccc3-c3ccnc2c3)nnn1-c1cccc(Cl)c1F]

Example 164. 1-(3-Chloro-2-fluorophenyl)-5-methyl-N-[(10R,14S)-10-methyl-9-oxo-5-(1H-pyrazol-5-yl)-8,16-diazatricyclo[13.3.1.0²,⁷]nonadeca-1(19),2(7),3,5,15,17-hexaen-14-yl]-1H-1,2,3-triazole-4-carboxamide, TFA salt: A mixture of Example 163 (10 mg, 0.016 mmol), (1H-pyrazol-5-yl)boronic acid (3.66 mg, 0.033 mmol) and Cs₂CO₃ (16 mg, 0.049 mmol) in 1,2-dimethoxyethane (1 mL) and water (0.2 mL) was degassed for 15 min. To this mixture was then added palladium tetrakis (2 mg, 1.63 μmol). The reaction was heated at 120° C. under microwave conditions for 20 min. The mixture was concentrated and purified by reverse phase HPLC to yield the desired product (2.3 mg, 19%) as a yellow solid. ¹H NMR (500 MHz, MeOD) δ 8.76 (d, J=5.5 Hz, 1H), 8.07 (s, 1H), 7.91 (dd, J=8.0, 1.7 Hz, 1H), 7.85-7.78 (m, 3H), 7.76-7.69 (m, 3H), 7.61-7.53 (m, 1H), 7.46 (td, J=8.2, 1.5 Hz, 1H), 6.80 (d, J=2.5 Hz, 1H), 5.36 (dd, J=11.0, 6.1 Hz, 1H), 3.21 (m, 2H), 2.83-2.70 (m, 1H), 2.48-2.44 (m, 3H), 2.29-2.14 (m, 1H), 2.05-1.89 (m, 2H), 1.66-1.43 (m, 2H), 1.03-0.96 (m, 3H), 0.53 (d, J=12.1 Hz, 1H) ppm. MS(ESI) m/z: 598.9 (M+H)⁺. Analytical HPLC RT=1.37 min (Method C).

Example 165

1-(3-Chloro-2-fluorophenyl)-5-methyl-N-[(10S,14S)-10-methyl-9-oxo-5-(1H-pyrazol-5-yl)-8,16-diazatricyclo[13.3.1.0²,⁷]nonadeca-1(19),2(7),3,5,15,17-hexaen-14-yl]-1H-1,2,3-triazole-4-carboxamide, TFA salt

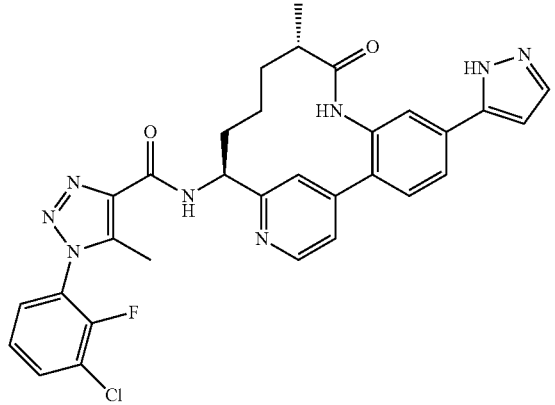 [SMILES: Cc1c(C(=O)N[C@H]2CCC[C@H](C)C(=O)Nc3cc(-c4ccn[nH]4)ccc3-c3ccnc2c3)nnn1-c1cccc(Cl)c1F]

Example 165. 1-(3-Chloro-2-fluorophenyl)-5-methyl-N-[(10S,14S)-10-methyl-9-oxo-5-(1H-pyrazol-5-yl)-8,16-diazatricyclo[13.3.1.0²,⁷]nonadeca-1(19),2(7),3,5,15,17-hexaen-14-yl]-1H-1,2,3-triazole-4-carboxamide, TFA salt: Example 165 was made in the same way as Example 164 by using the other isomer. ¹H NMR (500 MHz, MeOD) δ 8.76 (d, J=5.5 Hz, 1H), 8.07 (s, 1H), 7.91 (dd, J=8.0, 1.7 Hz, 1H), 7.85-7.78 (m, 3H), 7.76-7.69 (m, 3H), 7.61-7.53 (m, 1H), 7.46 (td, J=8.2, 1.5 Hz, 1H), 6.80 (d, J=2.5 Hz, 1H), 5.36 (dd, J=11.0, 6.1 Hz, 1H), 3.21 (m, 2H), 2.83-2.70 (m, 1H), 2.48-2.44 (m, 3H), 2.29-2.14 (m, 1H), 2.05-1.89 (m, 2H), 1.66-1.43 (m, 2H), 1.03-0.96 (m, 3H), 0.53 (d, J=12.1 Hz, 1H) ppm. MS(ESI) m/z: 598.9 (M+H)⁺. Analytical HPLC RT=6.27 min (Method A).

Example 166

1-(3-Chloro-2-fluorophenyl)-5-methyl-N-[(10R,14S)-10-methyl-9-oxo-5-[(1,3-thiazol-2-yl)amino]-8,16-diazatricyclo[13.3.1.0²,⁷]nonadeca-1(19),2(7),3,5,15,17-hexaen-14-yl]-1H-1,2,3-triazole-4-carboxamide, TFA salt

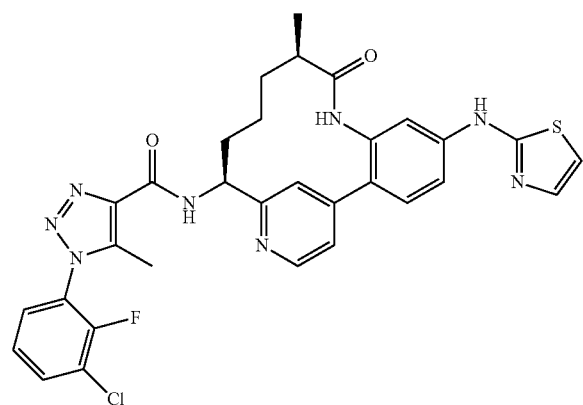 [SMILES: Cc1c(C(=O)N[C@H]2CCC[C@@H](C)C(=O)Nc3cc(Nc4nccs4)ccc3-c3ccnc2c3)nnn1-c1cccc(Cl)c1F]

Example 166. 1-(3-Chloro-2-fluorophenyl)-5-methyl-N-[(10R,14S)-10-methyl-9-oxo-5-[(1,3-thiazol-2-yl)amino]-8,16-diazatricyclo[13.3.1.0²,⁷]nonadeca-1(19),2(7),3,5,15,17-hexaen-14-yl]-1H-1,2,3-triazole-4-carboxamide, TFA salt: A vial containing potassium carbonate (16.94 mg, 0.123 mmol), thiazol-2-amine (2.455 mg, 0.025 mmol), di-tert-butyl(2',4',6'-triisopropyl-3,6-dimethoxy-[1,1'-biphenyl]-2-yl)phosphine (2.376 mg, 4.90 µmol) and tris(dibenzylideneacetone)dipalladium(0) (1.122 mg, 1.226 µmol) was purged with a stream of argon and sealed with a cap. A separate pressure-tested vial containing a magnetic stirrer, Example 163 (15 mg, 0.025 mmol), t-butanol (0.3 mL), acetic acid (1 drop) and (1 drop) was purged by bubbling argon through the liquid for 10 min. The contents of the first vial were added quickly and the second vial was sealed. The reaction was heated at 110° C. for 4.5 h and then cooled to rt. The reaction was concentrated and purified by reverse phase HPLC to yield the desired product (2.5 mg, 12%) as a light yellow solid. ¹H NMR (500 MHz, acetonitrile-d₃) δ 8.58 (d, J=5.50 Hz, 1H), 8.42 (d, J=7.15 Hz, 1H), 8.22 (s, 1H), 7.89 (s, 1H), 7.67 (ddd, J=1.65, 6.88, 8.25 Hz, 1H), 7.46-7.54 (m, 4H), 7.42 (ddd, J=1.65, 6.53, 8.05 Hz, 1H), 7.33 (dt, J=1.38, 8.12 Hz, 1H), 7.25 (d, J=3.85 Hz, 1H), 6.79 (d, J=3.85 Hz, 1H), 5.22-5.31 (m, 1H), 2.56-2.62 (m, 1H), 2.33 (s, 3H), 1.92-2.08 (m, 2H), 1.77-1.81 (m, 2H), 1.32-1.48 (m, 3H), 0.82 (d, J=6.88 Hz, 3H), 0.26-0.36 (m, 1H) ppm. MS(ESI) m/z: 631.6 (M+H)⁺. Analytical HPLC RT=6.13 min (Method A).

Example 167

1-(3-Chloro-2-fluorophenyl)-5-methyl-N-[(10S,14S)-10-methyl-9-oxo-5-[(1,3-thiazol-2-yl)amino]-8,16-diazatricyclo[13.3.1.0²,⁷]nonadeca-1(19),2(7),3,5,15,17-hexaen-14-yl]-1H-1,2,3-triazole-4-carboxamide, TFA salt

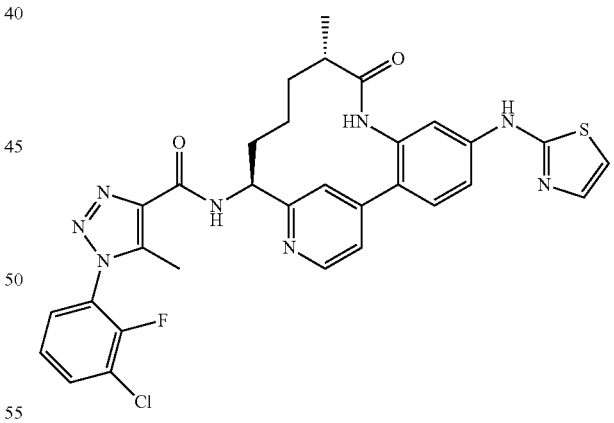

Example 167. 1-(3-Chloro-2-fluorophenyl)-5-methyl-N-[(10S,14S)-10-methyl-9-oxo-5-[(1,3-thiazol-2-yl)amino]-8,16-diazatricyclo[13.3.1.0²,⁷]nonadeca-1(19),2(7),3,5,15,17-hexaen-14-yl]-1H-1,2,3-triazole-4-carboxamide, TFA salt: Example 167 was made in the same way as Example 166 by using the other isomer. ¹H NMR (500 MHz, acetonitrile-d₃) δ 8.59 (d, J=5.50 Hz, 1H), 8.38 (d, J=7.15 Hz, 1H), 7.83 (s, 1H), 7.68 (ddd, J=1.65, 6.81, 8.32 Hz, 1H), 7.50-7.55 (m, 2H), 7.46-7.49 (m, 1H), 7.42 (ddd, J=1.51, 6.53, 8.18 Hz, 1H), 7.30-7.36 (m, 2H), 7.23 (d, J=3.58 Hz, 1H), 6.76 (d, J=3.85 Hz, 1H), 5.09-5.19 (m, 1H), 2.36 (d, J=0.83 Hz, 3H), 2.02-2.17 (m, 4H), 1.97-2.00 (m, 1H), 1.60-1.73 (m, 3H), 1.25-1.37 (m, 2H), 1.10 (d, J=7.15 Hz, 3H), 0.88-0.82 (m, 1H) ppm. MS(ESI) m/z: 631.6 (M+H)⁺. Analytical HPLC RT=6.11 min (Method A).

The following Examples in Table 10 were synthesized using procedures similar to those shown in Example 164. Example 171 was a common by-product of the coupling reaction.

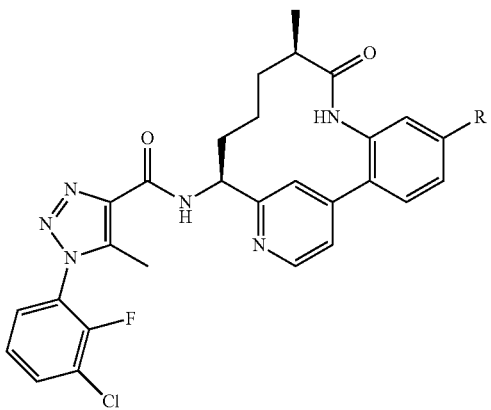

TABLE 10

| Example # | Stereo-chemistry | R | M + H | RT, min Method A |
|---|---|---|---|---|
| 168 | Homochiral | 2,6-dimethoxypyridin-3-yl | 670.0 | 8.34 |
| 169 | Homochiral | 1H-pyrazol-4-yl | 598.9 | 6.06 |
| 170 | Homochiral | 2-methoxypyridin-3-yl | 639.9 | 7.45 |
| 171 | Homochiral | H | 532.9 | 6.55 |

Example 172

1-(3-Chloro-2-fluorophenyl)-5-methyl-N-[(10R,14S)-10-methyl-9-oxo-5-(2-oxo-1,2-dihydropyridin-3-yl)-8,16-diazatricyclo[13.3.1.0²,⁷]nonadeca-1(19),2(7),3,5,15,17-hexaen-14-yl]-1H-1,2,3-triazole-4-carboxamide, TFA salt

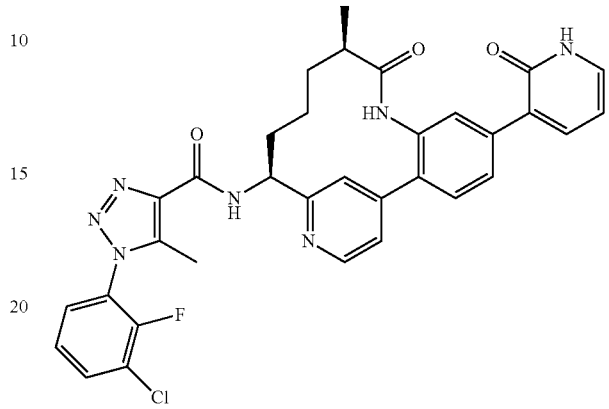

Example 172. 1-(3-Chloro-2-fluorophenyl)-5-methyl-N-[(10R,14S)-10-methyl-9-oxo-5-(2-oxo-1,2-dihydropyridin-3-yl)-8,16-diazatricyclo[13.3.1.0²,⁷]nonadeca-1(19),2(7),3,5,15,17-hexaen-14-yl]-1H-1,2,3-triazole-4-carboxamide, TFA salt: To a solution of Example 170 (4 mg, 6.25 μmol) in water (0.50 mL) and dioxane (0.2 mL) was added concentrated HCl (0.011 mL, 0.375 mmol). The reaction was stirred at 100° C. for 1 h. The reaction mixture was concentrated and purified by reverse phase HPLC to yield the desired product (1.4 mg, 29%) as an off white solid. ¹H NMR (500 MHz, MeOD) δ 8.78 (d, J=5.5 Hz, 1H), 8.06 (s, 1H), 7.92-7.82 (m, 3H), 7.79 (dd, J=5.5, 1.7 Hz, 1H), 7.77-7.73 (m, 2H), 7.60 (ddd, J=8.0, 6.4, 1.5 Hz, 1H), 7.54-7.47 (m, 2H), 6.60-6.52 (m, 1H), 5.39 (dd, J=11.0, 5.8 Hz, 1H), 3.32 (m, 3H), 2.84-2.75 (m, 1H), 2.49 (d, J=0.8 Hz, 3H), 2.30-2.15 (m, 1H), 2.06-1.92 (m, 2H), 1.66-1.49 (m, 2H), 1.00 (d, J=7.2 Hz, 3H), 0.55 (d, J=12.1 Hz, 1H) ppm. MS(ESI) m/z: 625.9 (M+H)⁺. Analytical HPLC RT=5.87 min (Method A).

Example 173

Methyl N-[(10R,14S)-14-[1-(3-chloro-2-fluorophenyl)-5-methyl-1H-1,2,3-triazole-4-amido]-10-methyl-9,11-dioxo-8,16-diazatricyclo[13.3.1.0²,⁷]nonadeca-1(19),2(7),3,5,15,17-hexaen-5-yl]carbamate, TFA salt

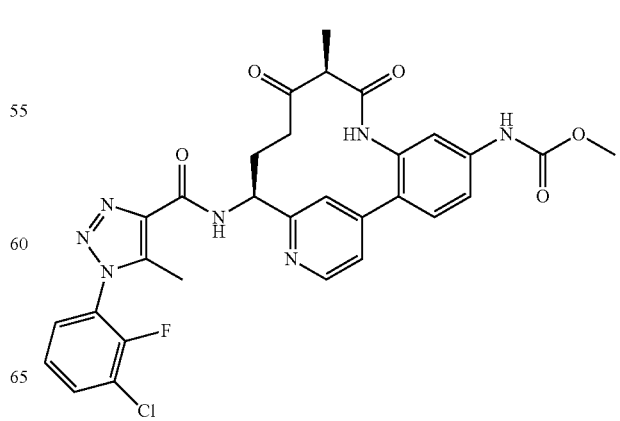

173A. tert-Butyl N-[(10R,14S)-11-hydroxy-5-[(methoxy-carbonyl)amino]-10-methyl-9-oxo-8,16-diazatricyclo[13.3.1.0$^{2,7}$]nonadeca-1(18),2,4,6,15(19),16-hexaen-14-yl]carbamate and tert-butyl N-[(10R,14S)-12-hydroxy-5-[(methoxycarbonyl)amino]-10-methyl-9-oxo-8,16-diazatricyclo[13.3.1.0$^{2,7}$]nonadeca-1(18),2,4,6,15(19),16-hexaen-14-yl]carbamate (1:1 mixture): To a solution of 2J (634 mg, 1.36 mmol) in THF (13.6 mL) at 0° C. was added borane tetrahydrofuran complex (4.08 mL, 4.08 mmol) dropwise. The reaction was allowed to warm up to rt and stirred for 2.5 h. The reaction mixture was cooled to 0° C. and added sodium acetate (9.06 ml, 27.2 mmol), followed by hydrogen peroxide (4.16 mL, 40.8 mmol) dropwise. The reaction was warmed up to rt and stirred at for 8 h. The mixture was diluted with H$_2$O and extracted with EtOAc (2×). The combined organic layer was washed with brine, dried over MgSO$_4$, filtered, and concentrated. The residue was purified by silica gel chromatography (0-10% MeOH/DCM) to yield a mixture of two products (323 mg, 49%) as a light grey solid. MS(ESI) m/z: 485.1 (M+H)$^+$.

173B. tert-Butyl N-[(10R,14S)-5-[(methoxycarbonyl)amino]-10-methyl-9,11-dioxo-8,16-diazatricyclo[13.3.1.0$^{2,7}$]nonadeca-1(18),2,4,6,15(19),16-hexaen-14-yl]carbamate and tert-butyl N-[(10R,14S)-5-[(methoxycarbonyl)amino]-10-methyl-9,12-dioxo-8,16-diazatricyclo[13.3.1.0$^{2,7}$]nonadeca-1(18),2,4,6,15(19),16-hexaen-14-yl]carbamate (1:1 mixture): 173A (1:1 mixture of diastereomers) (116 mg, 0.239 mmol) was dissolved in DCM (2.4 mL) and added Martin's reagent (132 mg, 0.311 mmol) at rt. The reaction was stirred at rt for 1.5 h. The mixture was diluted with DCM, washed with H$_2$O, brine, dried over MgSO$_4$, filtered, and concentrated. The residue was purified by silica gel chromatography to yield a 1:1 mixture of regioisomers (78 mg, 68%) as a white solid. MS(ESI) m/z: 483.1 (M+H)$^+$.

173C. Methyl N-[(10R,14S)-14-amino-10-methyl-9,11-dioxo-8,16-diazatricyclo[13.3.1.0$^{2,7}$]nonadeca-1(18),2,4,6,15(19),16-hexaen-5-yl]carbamate and 173D, methyl N-[(10R,14S)-14-amino-10-methyl-9,12-dioxo-8,16-diazatricyclo[13.3.1.0$^{2,7}$]nonadeca-1(18),2,4,6,15(19),16-hexaen-5-yl]carbamate: 173B (1:1 mixture of regioisomers) (78 mg, 0.162 mmol) was suspended in DCM (3 mL) and added TFA (0.623 mL, 8.08 mmol). The reaction became a clear light brownish solution and was stirred at rt for 1 h. The reaction was concentrated and purified by reverse phase HPLC to yield 173C, early eluting regioisomer (40 mg, 38%) as brownish oil and 173D, late eluting regioisomer (27 mg, 26%) as brownish oil. MS(ESI) m/z: 383.1 (M+H)$^+$.

Example 173. Methyl N-[(10R,14S)-14-[1-(3-chloro-2-fluorophenyl)-5-methyl-1H-1,2,3-triazole-4-amido]-10-methyl-9,11-dioxo-8,16-diazatricyclo[13.3.1.0$^{2,7}$]nonadeca-1(19),2(7),3,5,15,17-hexaen-5-yl]carbamate, TFA salt: Example 173 was made in the same way as Example 63 by replacing 2M with 173C. $^1$H NMR (500 MHz, MeOD) δ 9.69 (s, 1H), 8.76 (d, J=6.1 Hz, 1H), 7.90-7.77 (m, 2H), 7.70-7.40 (m, 6H), 5.30 (dd, J=10.0, 6.5 Hz, 1H), 3.80 (s, 3H), 3.75 (d, J=6.6 Hz, 1H), 3.06-2.95 (m, 1H), 2.72-2.58 (m, 1H), 2.52-2.36 (m, 5H), 1.24 (d, J=6.6 Hz, 3H) ppm. MS(ESI) m/z: 619.9 (M+H)$^+$. Analytical HPLC RT=6.98 min (Method A).

Example 174

Methyl N-[(10R,14S)-14-[1-(3-chloro-2-fluorophenyl)-5-methyl-1H-1,2,3-triazole-4-amido]-10-methyl-9,12-dioxo-8,16-diazatricyclo[13.3.1.0$^{2,7}$]nonadeca-1(19),2(7),3,5,15,17-hexaen-5-yl]carbamate, TFA salt

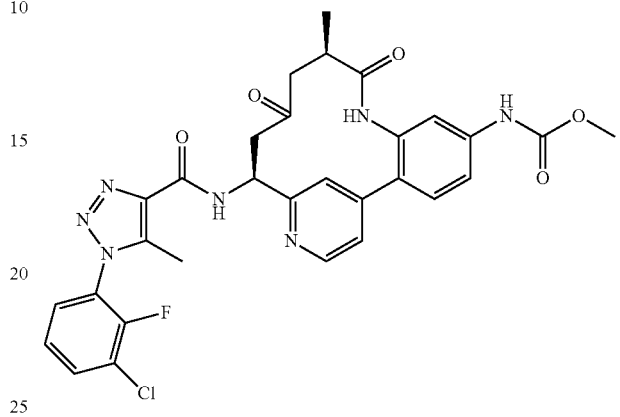

Example 174. Methyl N-[(10R,14S)-14-[1-(3-chloro-2-fluorophenyl)-5-methyl-1H-1,2,3-triazole-4-amido]-10-methyl-9,12-dioxo-8,16-diazatricyclo[13.3.1.0$^{2,7}$]nonadeca-1(19),2(7),3,5,15,17-hexaen-5-yl]carbamate, TFA salt: Example 174 was made in the same way as Example 173 by replacing 173C with 173D. $^1$H NMR (500 MHz, MeOD) δ 8.78 (d, J=5.5 Hz, 1H), 8.06 (s, 1H), 7.92-7.82 (m, 3H), 7.79 (dd, J=5.5, 1.7 Hz, 1H), 7.77-7.73 (m, 2H), 7.60 (ddd, J=8.0, 6.4, 1.5 Hz, 1H), 7.54-7.47 (m, 2H), 6.60-6.52 (m, 1H), 5.39 (dd, J=11.0, 5.8 Hz, 1H), 3.32 (m, 3H), 2.84-2.75 (m, 1H), 2.49 (d, J=0.8 Hz, 3H), 2.30-2.15 (m, 1H), 2.06-1.92 (m, 2H), 1.66-1.49 (m, 2H), 1.00 (d, J=7.2 Hz, 3H), 0.55 (d, J=12.1 Hz, 1H) ppm. MS(ESI) m/z: 620.1 (M+H)$^+$. Analytical HPLC RT=7.86 min (Method A).

Example 175

Methyl N-[(10R,12R,14S)-14-[1-(3-chloro-2-fluorophenyl)-5-methyl-1H-pyrazole-4-amido]-12-hydroxy-10-methyl-9-oxo-8,16-diazatricyclo[13.3.1.0$^{2,7}$]nonadeca-1(19),2(7),3,5,15,17-hexaen-5-yl]carbamate, TFA salt

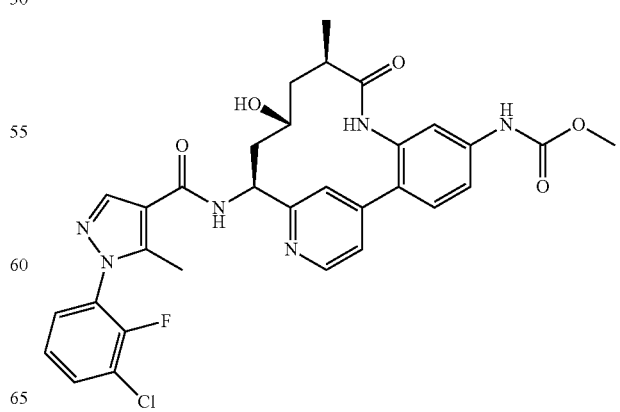

175A. To a solution of 2J (68.9 mg, 0.148 mmol) in THF (1477 µL) at 0° C. was added borane tetrahydrofuran complex (443 µL, 0.443 mmol) dropwise. The reaction was allowed to warm up to rt and stirred for 4 h. 3 M NaOAc (985 µL, 2.95 mmol) and $H_2O_2$ (453 µL, 4.43 mmol) were added dropwise. The reaction was stirred at rt for 2 h and diluted with $H_2O$. The mixture was extracted with EtOAc. The organic layer was washed with brine, dried over $Na_2SO_4$, filtered, and concentrated. The residue was purified by silica gel chromatography. Further purification was carried out by using Chiral OD column (mobile phase: 50% MeOH/EtOH:50% Heptane) to give 175A (the second peak) as diastereomer mixture (7 mg, 10%). The other regioisomers, 175B (the first peak) (5 mg, 6%) and 175C (the third peak) (3 mg, 4%), were separated as methyl N-[(10R,14S)-14-{[(tert-butoxy)carbonyl]amino}-11-hydroxy-10-methyl-9-oxo-8,16-diazatricyclo[13.3.1.0$^{2,7}$]nonadeca-1(19),2(7),3,5,15,17-hexaen-5-yl]carbamate as homochiral compounds. MS(ESI) m/z: 485.1 (M+H)$^+$.

Example 175. Methyl N-[(10R,12R,14S)-14-[1-(3-chloro-2-fluorophenyl)-5-methyl-1H-pyrazole-4-amido]-12-hydroxy-10-methyl-9-oxo-8,16-diazatricyclo[13.3.1.0$^{2,7}$]nonadeca-1(19),2(7),3,5,15,17-hexaen-5-yl]carbamate, TFA salt, TFA salt: To a solution of 175A (7.1 mg, 0.015 mmol) in $CH_2Cl_2$ (0.5 mL) was added TFA (0.034 mL, 0.440 mmol). The reaction was stirred at rt for 40 min and concentrated. The residue redissolved in DMF (0.3 mL), and added Intermediate 25 (3.73 mg, 0.015 mmol), followed by EDC (4.21 mg, 0.022 mmol), HOBT (3.37 mg, 0.022 mmol), and Hunig's base (0.026 mL, 0.147 mmol). The reaction was stirred at rt overnight. The reaction was concentrated and purified by reverse phase HPLC to yield the desired product, the late eluting isomer, as a white solid (2 mg, 18%). The stereochemistry was determined by X-ray crystallography. $^1$H NMR (500 MHz, MeOD) δ 8.78 (d, J=5.5 Hz, 1H), 8.06 (s, 1H), 7.92-7.82 (m, 3H), 7.79 (dd, J=5.5, 1.7 Hz, 1H), 7.77-7.73 (m, 2H), 7.60 (ddd, J=8.0, 6.4, 1.5 Hz, 1H), 7.54-7.47 (m, 2H), 6.60-6.52 (m, 1H), 5.39 (dd, J=11.0, 5.8 Hz, 1H), 3.32 (m, 3H), 2.84-2.75 (m, 1H), 2.49 (d, J=0.8 Hz, 3H), 2.30-2.15 (m, 1H), 2.06-1.92 (m, 2H), 1.66-1.49 (m, 2H), 1.00 (d, J=7.2 Hz, 3H), 0.55 (d, J=12.1 Hz, 1H) ppm. MS(ESI) m/z: 621.2 (M+H)$^+$. Analytical HPLC RT=5.13 min (Method A).

Example 176

Methyl N-[(10R,12S,14S)-14-[1-(3-chloro-2-fluorophenyl)-5-methyl-1H-pyrazole-4-amido]-12-hydroxy-10-methyl-9-oxo-8,16-diazatricyclo[13.3.1.0$^{2,7}$]nonadeca-1(19),2(7),3,5,15,17-hexaen-5-yl] carbamate, TFA salt

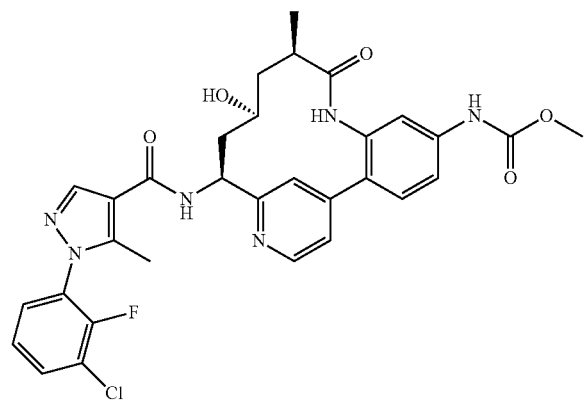 [SMILES: COC(=O)Nc1ccc2c(c1)NC(=O)[C@H](C)C[C@H](O)C[C@H](NC(=O)c1cnn(-c3cccc(Cl)c3F)c1C)c1cc-2ccn1]

Example 176. Methyl N-[(10R,12S,14S)-14-[1-(3-chloro-2-fluorophenyl)-5-methyl-1H-pyrazole-4-amido]-12-hydroxy-10-methyl-9-oxo-8,16-diazatricyclo[13.3.1.0$^{2,7}$]nonadeca-1(19),2(7),3,5,15,17-hexaen-5-yl]carbamate, TFA salt: Example 176 was made in the same way as Example 175 and isolated as the early eluting isomer at the final step. $^1$H NMR (500 MHz, MeOD) δ 9.63 (s, 1H), 8.71 (d, J=5.8 Hz, 1H), 8.23 (s, 1H), 7.83 (s, 1H), 7.76 (dd, J=5.9, 1.5 Hz, 1H), 7.71 (ddd, J=8.1, 6.7, 1.7 Hz, 1H), 7.58 (s, 1H), 7.55 (d, J=1.1 Hz, 2H), 7.45 (ddd, J=8.0, 6.4, 1.8 Hz, 1H), 7.41-7.36 (m, 1H), 5.32 (dd, J=11.1, 4.8 Hz, 1H), 3.77 (s, 3H), 3.63-3.55 (m, 1H), 2.60-2.52 (m, 1H), 2.37 (d, J=0.8 Hz, 3H), 2.33 (dt, J=14.0, 4.7 Hz, 1H), 2.18 (ddd, J=14.0, 11.2, 5.6 Hz, 1H), 1.47 (dd, J=12.8, 7.3 Hz, 1H), 1.33-1.25 (m, 1H), 1.12 (d, J=6.9 Hz, 3H) ppm. MS(ESI) m/z: 621.2 (M+H)$^+$. Analytical HPLC RT=5.10 min (Method A).

Example 177

Methyl N-[(10R,14S)-14-[1-(3-chloro-2-fluorophenyl)-5-methyl-1H-pyrazole-4-amido]-11-hydroxy-10-methyl-9-oxo-8,16-diazatricyclo[13.3.1.0$^{2,7}$]nonadeca-1(19),2(7),3,5,15,17-hexaen-5-yl]carbamate, TFA salt

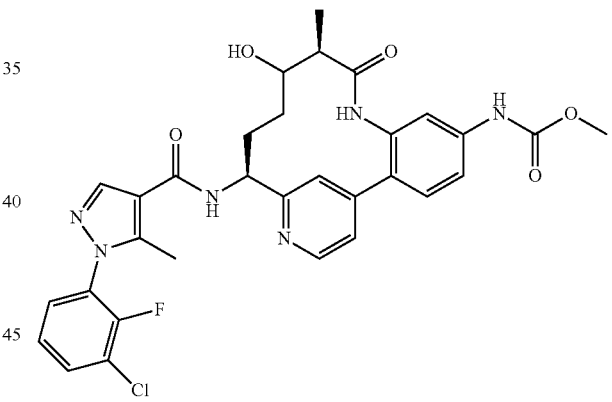

Example 177. Methyl N-[(10R,14S)-14-[1-(3-chloro-2-fluorophenyl)-5-methyl-1H-pyrazole-4-amido]-11-hydroxy-10-methyl-9-oxo-8,16-diazatricyclo[13.3.1.0$^{2,7}$]nonadeca-1(19),2(7),3,5,15,17-hexaen-5-yl]carbamate, TFA salt: Example 177 was made in the same way as Example 175 by replacing 175A with 175B. $^1$H NMR (500 MHz, MeOD) δ 9.70 (s, 1H), 8.70 (d, J=6.1 Hz, 1H), 8.24-8.21 (m, 1H), 8.17 (s, 1H), 7.89 (dd, J=6.1, 1.7 Hz, 1H), 7.78-7.68 (m, 2H), 7.63-7.46 (m, 3H), 7.45-7.36 (m, 1H), 5.46 (dd, J=7.3, 5.6 Hz, 1H), 3.83-3.78 (s, 3H), 2.94 (quin, J=6.5 Hz, 1H), 2.81-2.72 (m, 1H), 2.46-2.37 (m, 5H), 2.21-2.12 (m, 1H), 1.99-1.91 (m, 1H), 1.71 (dt, J=14.6, 7.6 Hz, 1H), 1.20 (d, J=6.9 Hz, 3H) ppm. MS(ESI) m/z: 621.2 (M+H)$^+$. Analytical HPLC RT=6.04 min (Method A).

Example 178

Methyl N-[(10R,14S)-14-[1-(3-chloro-2-fluorophenyl)-5-methyl-1H-pyrazole-4-amido]-11-hydroxy-10-methyl-9-oxo-8,16-diazatricyclo[13.3.1.0²,⁷]nonadeca-1(19),2(7),3,5,15,17-hexaen-5-yl]carbamate, TFA salt

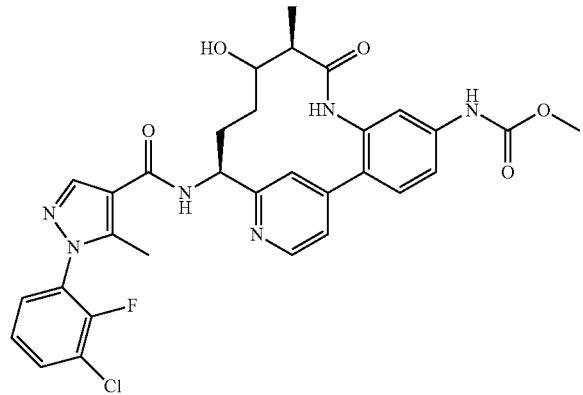 [SMILES: COC(=O)Nc1ccc2c(c1)NC(=O)[C@H](C)C(O)CC[C@H](NC(=O)c1cnn(-c3cccc(Cl)c3F)c1C)c1cc-2ccn1]

Example 178. Methyl N-[(10R,14S)-14-[1-(3-chloro-2-fluorophenyl)-5-methyl-1H-pyrazole-4-amido]-11-hydroxy-10-methyl-9-oxo-8,16-diazatricyclo[13.3.1.0²,⁷]nonadeca-1(19),2(7),3,5,15,17-hexaen-5-yl]carbamate, TFA salt: Example 178 was made in the same way as Example 175 by replacing 175A with 175C. ¹H NMR (500 MHz, MeOD) δ 9.70 (s, 1H), 8.70 (d, J=6.3 Hz, 1H), 8.38 (s, 1H), 8.35 (s, 1H), 7.94 (dd, J=6.2, 1.8 Hz, 1H), 7.78-7.72 (m, 1H), 7.68-7.62 (m, 2H), 7.55 (dd, J=8.4, 2.1 Hz, 1H), 7.49 (ddd, J=8.1, 6.5, 1.7 Hz, 1H), 7.44-7.39 (m, 1H), 5.47 (dd, J=10.2, 5.8 Hz, 1H), 3.80 (s, 3H), 3.54-3.46 (m, 1H), 3.24-3.09 (m, 1H), 2.66 (quin, J=6.9 Hz, 1H), 2.48-2.40 (m, 1H), 2.38 (s, 3H), 2.08-1.99 (m, 1H), 1.74-1.66 (m, 1H), 1.06 (d, J=7.2 Hz, 3H) ppm. MS(ESI) m/z: 621.2 (M+H)⁺. Analytical HPLC RT=6.09 min (Method A).

Example 179

Methyl N-[(10S,14S)-14-[1-(3-chloro-2-fluorophenyl)-5-methyl-1H-pyrazole-4-amido]-11-fluoro-10-methyl-9-oxo-8,16-diazatricyclo[13.3.1.0²,⁷]nonadeca-1(19),2(7),3,5,15,17-hexaen-5-yl]carbamate, TFA salt

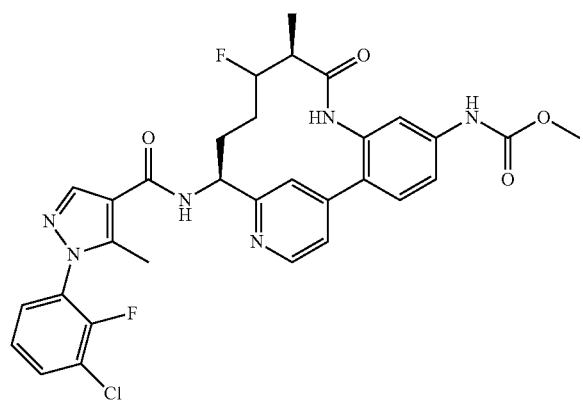 [SMILES: COC(=O)Nc1ccc2c(c1)NC(=O)[C@H](C)C(F)CC[C@H](NC(=O)c1cnn(-c3cccc(Cl)c3F)c1C)c1cc-2ccn1]

179A. Methyl N-[(10S,14S)-14-{[(tert-butoxy)carbonyl]amino}-11-fluoro-10-methyl-9-oxo-8,16-diazatricyclo[13.3.1.0²,⁷]nonadeca-1(19),2(7),3,5,15,17-hexaen-5-yl]carbamate: To a solution of 175B (25 mg, 0.052 mmol) in DCM (1 mL) at −78° C. was added DAST (10.76 µL, 0.077 mmol). The reaction was stirred at −78° C. for 10 min, and then warmed slowly to rt. The reaction was stirred at rt for 1 h and concentrated. The residue was purified by reverse phase HPLC to yield the product as a homochiral compound (2.3 mg, 7%). ¹H NMR (500 MHz, MeOD) δ 9.67 (s, 1H), 8.72 (d, J=5.8 Hz, 1H), 8.33 (s, 1H), 7.98 (s, 1H), 7.79-7.70 (m, 2H), 7.65-7.59 (m, 2H), 7.55-7.45 (m, 2H), 7.44-7.37 (m, 1H), 5.36 (dd, J=11.6, 6.1 Hz, 1H), 5.26-5.08 (m, 1H), 3.80 (s, 3H), 3.22-3.18 (m, 1H), 2.49-2.42 (m, 1H), 2.38 (s, 3H), 2.07-1.97 (m, 1H), 1.84-1.68 (m, 1H), 1.00 (d, J=6.9 Hz, 3H), 0.84-0.63 (m, 1H) ppm. MS(ESI) m/z: 487.0 (M+H)⁺. Analytical HPLC RT=6.97 min (Method A).

Example 180

Methyl N-[(14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0²,⁷]nonadeca-1(19),2(7),3,5,15,17-hexaen-5-yl]carbamate, TFA salt

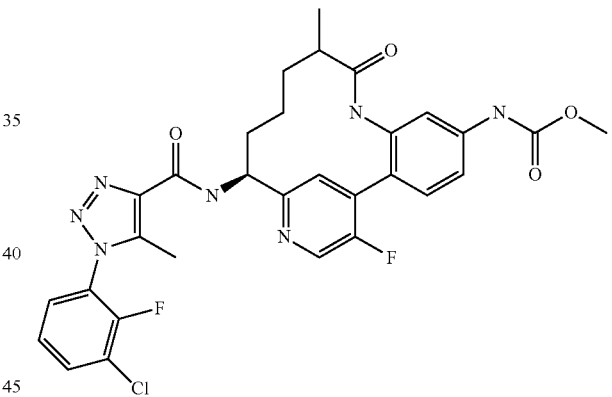

Example 180. Methyl N-[(14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0²,⁷]nonadeca-1(19),2(7),3,5,15,17-hexaen-5-yl]carbamate, TFA salt: Example 180 was made in the same way as Example 2 by using 4-bromo-5-fluoropicolinaldehyde as starting material and replacing Intermediate 11 with Intermediate 21. The intermediates were carried on as diastereomers to give Example 180 as a diastereomer mixture. ¹H NMR (500 MHz, MeOD) δ 8.90 (d, J=3.0 Hz, 1H), 8.09 (d, J=6.5 Hz, 1H), 7.88-7.76 (m, 1H), 7.71-7.60 (m, 2H), 7.59-7.52 (m, 1H), 7.52-7.40 (m, 2H), 5.32 (dd, J=11.3, 6.0 Hz, 1H), 3.78 (s, 3H), 3.66 (s, 2H), 2.70 (br. s., 1H), 2.44 (s, 3H), 2.26 (d, J=10.0 Hz, 1H), 2.05-1.88 (m, 1H), 1.87-1.70 (m, 1H), 1.50 (br. s., 2H), 0.96 (d, J=6.8 Hz, 3H), 0.66 (br. s., 1H) ppm. MS(ESI) m/z: 624.1 (M+H)⁺. Analytical HPLC RT=8.07 min (Method A).

Example 181

Methyl N-[(10S,14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0²,⁷]nonadeca-1(19),2(7),3,5,15,17-hexaen-5-yl]carbamate, TFA salt

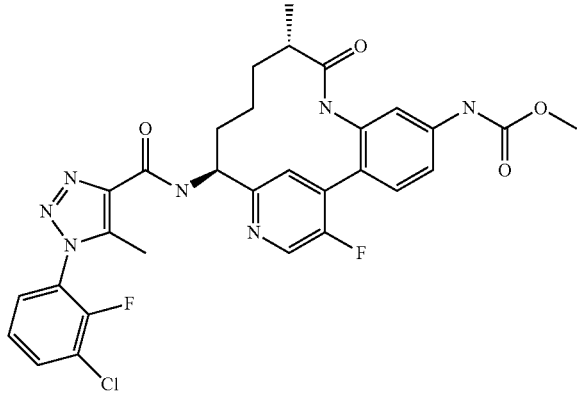 [SMILES: COC(=O)Nc1ccc2c(c1)NC(=O)[C@@H](C)CCC[C@H](NC(=O)c1nnn(-c3cccc(Cl)c3F)c1C)c1cc-2c(F)cn1]

Example 181. Methyl N-[(10S,14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0²,⁷]nonadeca-1(19),2(7),3,5,15,17-hexaen-5-yl]carbamate, TFA salt: Example 180 was subjected to chiral HPLC separation using CHIRALCEL® OJ-H column and 15% Methanol/85% CO$_2$ as mobile phase. Peak 1 was obtained as Example 181. $^1$H NMR (400 MHz, MeOD) δ 8.86 (d, J=3.0 Hz, 1H), 7.91 (d, J=6.3 Hz, 1H), 7.85-7.75 (m, 1H), 7.67-7.58 (m, 2H), 7.58-7.40 (m, 3H), 5.23 (dd, J=10.2, 5.1 Hz, 1H), 3.77 (s, 4H), 3.66 (s, 1H), 2.44 (s, 3H), 2.26-2.08 (m, 1H), 1.98 (br. s., 1H), 1.67-1.39 (m, 2H), 1.29 (d, J=5.0 Hz, 2H), 1.19 (d, J=7.0 Hz, 3H), 1.13-0.98 (m, 1H) ppm. MS(ESI) m/z: 624.2 (M+H)$^+$. Analytical HPLC RT=8.07 min (Method A).

Example 182

Methyl N-[(10R,14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0²,⁷]nonadeca-1(19),2(7),3,5,15,17-hexaen-5-yl]carbamate, TFA salt

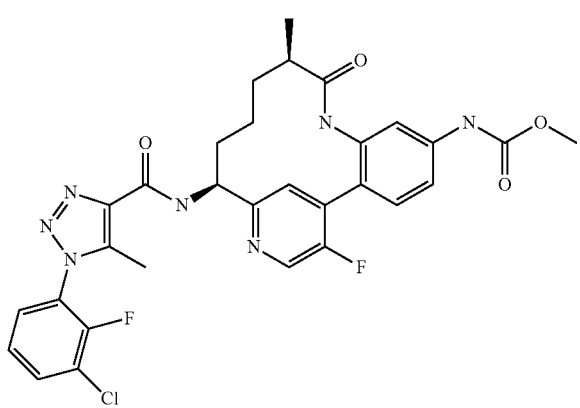 [SMILES: COC(=O)Nc1ccc2c(c1)NC(=O)[C@H](C)CCC[C@H](NC(=O)c1nnn(-c3cccc(Cl)c3F)c1C)c1cc-2c(F)cn1]

Example 182. Methyl N-[(10S,14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0²,⁷]nonadeca-1(19),2(7),3,5,15,17-hexaen-5-yl]carbamate, TFA salt: Example 180 was subjected to chiral HPLC separation using CHIRALCEL® OJ-H column and 15% Methanol/85% CO$_2$ as mobile phase. Peak 2 was obtained as Example 182. $^1$H NMR (400 MHz, MeOD) δ 8.90 (d, J=3.0 Hz, 1H), 8.09 (d, J=6.5 Hz, 1H), 7.88-7.76 (m, 1H), 7.71-7.60 (m, 2H), 7.59-7.52 (m, 1H), 7.52-7.40 (m, 2H), 5.32 (dd, J=11.3, 6.0 Hz, 1H), 3.78 (s, 3H), 3.66 (s, 2H), 2.70 (br. s., 1H), 2.44 (s, 3H), 2.26 (d, J=10.0 Hz, 1H), 2.05-1.88 (m, 1H), 1.87-1.70 (m, 1H), 1.50 (br. s., 2H), 0.96 (d, J=6.8 Hz, 3H), 0.66 (br. s., 1H) ppm. MS(ESI) m/z: 624.2 (M+H)$^+$. Analytical HPLC RT=8.07 min (Method A).

Example 183

Methyl N-[(14S)-14-[1-(3-chloro-2-fluorophenyl)-5-methyl-1H-1,2,3-triazole-4-amido]-10,18-dimethyl-9-oxo-8,16-diazatricyclo[13.3.1.0²,⁷]nonadeca-1(19),2(7),3,5,15,17-hexaen-5-yl]carbamate, TFA salt

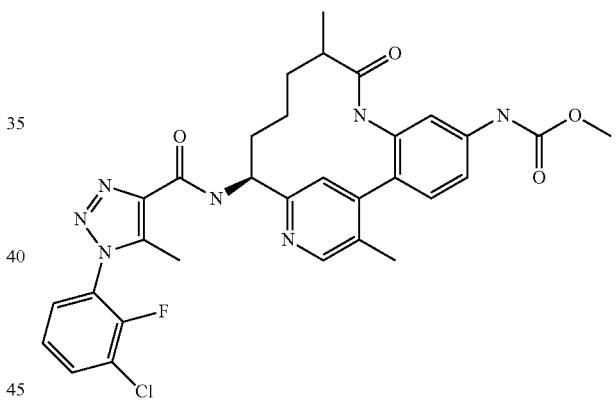

Example 183. Methyl N-[(14S)-14-[1-(3-chloro-2-fluorophenyl)-5-methyl-1H-1,2,3-triazole-4-amido]-10,18-dimethyl-9-oxo-8,16-diazatricyclo[13.3.1.0²,⁷]nonadeca-1(19),2(7),3,5,15,17-hexaen-5-yl]carbamate, TFA salt: Example 183 was made in the same way as Example 2 by using 4-bromo-5-methylpicolinaldehyde as starting material and replacing Intermediate 11 with Intermediate 21. The intermediates were carried on as diastereomers to give Example 183 as a diastereomer mixture. $^1$H NMR (400 MHz, MeOD) δ 8.67 (s, 1H), 7.87-7.77 (m, 2H), 7.63-7.41 (m, 5H), 5.32 (dd, J=11.3, 6.0 Hz, 1H), 3.78 (s, 3H), 3.66 (s, 2H), 2.70 (br. s., 1H), 2.50 (s, 3H), 2.44 (s, 3H), 2.26 (d, J=10.0 Hz, 1H), 2.05-1.88 (m, 1H), 1.87-1.70 (m, 1H), 1.50 (br. s., 2H), 0.96 (d, J=6.8 Hz, 3H), 0.66 (br. s., 1H) ppm. MS(ESI) m/z: 620.1 (M+H)$^+$. Analytical HPLC RT=5.53 min (Method A).

Example 184

Methyl (10R,14S)-14-[1-(3-chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylate, TFA salt

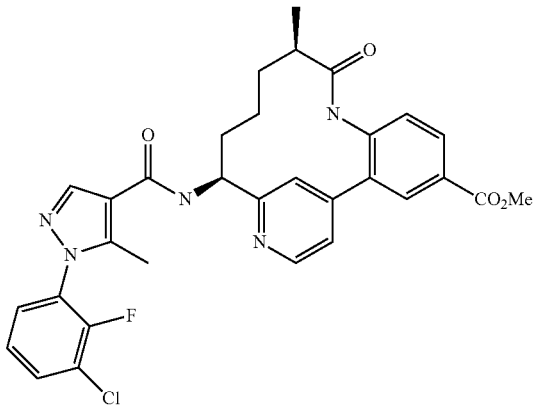 [SMILES: COC(=O)c1ccc2c(c1)-c1ccnc(c1)[C@@H](NC(=O)c1cnn(-c3cccc(Cl)c3F)c1C)CCC[C@@H](C)C(=O)N2]

Example 184. Methyl (10R,14S)-14-[1-(3-chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylate, TFA salt: Example 184 was made in the same way as Example 2 by replacing 2-amino-4-nitrophenylboronic acid with (2-amino-4-(methoxycarbonyl)phenyl)boronic acid in step 2C and replacing Intermediate 11 with Intermediate 25. The diastereomer mixture was separated during step 2J. Diastereomer A, the early eluting isomer on silica gel chromatography, was used to generate the homochiral final product. $^1$H NMR (500 MHz, MeOD) δ 8.84 (d, J=5.8 Hz, 1H), 8.40-8.30 (m, 2H), 8.27-8.12 (m, 2H), 7.99 (dd, J=5.9, 1.8 Hz, 1H), 7.74 (d, J=1.4 Hz, 1H), 7.53-7.30 (m, 3H), 5.28 (dd, J=11.4, 6.2 Hz, 1H), 3.98 (s, 3H), 2.84-2.73 (m, 1H), 2.37 (s, 3H), 2.28-2.17 (m, 1H), 2.08-1.97 (m, 1H), 1.96-1.83 (m, 1H), 1.68-1.49 (m, 2H), 0.98 (d, J=6.9 Hz, 3H), 0.62-0.46 (m, 1H) ppm. MS(ESI) m/z: 590.2 (M+H)$^+$. Analytical HPLC RT=5.53 min (Method A).

Example 185

(10R,14S)-14-[1-(3-Chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylic acid, TFA salt

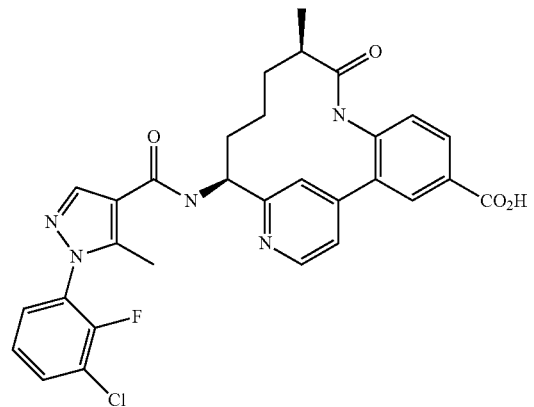 [SMILES: Cc1c(C(=O)N[C@H]2CCC[C@@H](C)C(=O)Nc3ccc(C(=O)O)cc3-c3ccnc2c3)cnn1-c1cccc(Cl)c1F]

Example 185. (10R,14S)-14-[1-(3-Chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylic acid: To a solution of Example 184 (12.15 mg, 0.017 mmol) in THF (173 μL) was added LiOH (34.5 μL, 0.069 mmol). The reaction was stirred at rt for 2 h. 0.1 mL of 1 N HCl was added and the mixture was concentrated. The residue was purified by reverse phase HPLC to give the desired product (8.8 mg, 73%) as a clear glass. $^1$H NMR (400 MHz, MeOD) δ 8.82 (d, J=6.1 Hz, 1H), 8.36-8.29 (m, 2H), 8.27-8.17 (m, 2H), 8.01 (d, J=5.8 Hz, 1H), 7.70 (t, J=7.5 Hz, 1H), 7.50-7.33 (m, 3H), 5.27 (dd, J=11.1, 6.1 Hz, 1H), 2.82-2.72 (m, J=6.6 Hz, 1H), 2.34 (s, 3H), 2.28-2.16 (m, 1H), 2.09-1.96 (m, 1H), 1.90 (t, J=12.1 Hz, 1H), 1.68-1.46 (m, 2H), 0.96 (d, J=6.8 Hz, 3H), 0.53 (d, J=11.4 Hz, 1H) ppm. MS(ESI) m/z: 576.1 (M+H)$^+$. Analytical HPLC RT=5.84 min (Method A).

Example 186

(10S,14S)-14-[1-(3-Chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylic acid, TFA salt

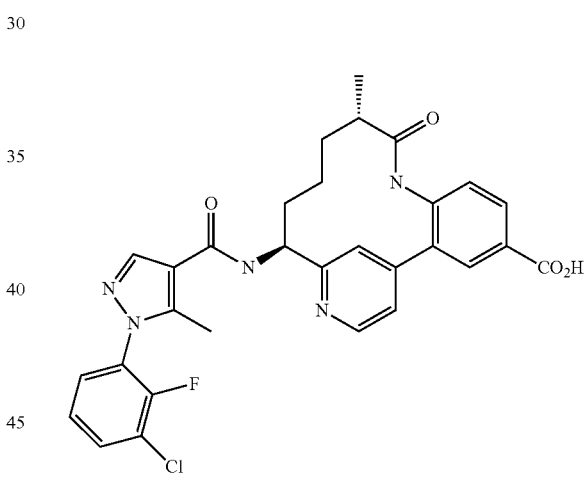

Example 186. (10S,14S)-14-[1-(3-Chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylic acid, TFA salt: Example 186 was made in the same way as Example 185 by using the other isomer. $^1$H NMR (500 MHz, MeOD) δ 8.82 (d, J=5.8 Hz, 1H), 8.35 (d, J=1.9 Hz, 1H), 8.29 (s, 1H), 8.24 (dd, J=8.3, 1.9 Hz, 1H), 8.04 (s, 1H), 7.91 (d, J=5.5 Hz, 1H), 7.74 (ddd, J=8.3, 6.7, 1.8 Hz, 1H), 7.51-7.45 (m, 2H), 7.41 (dd, J=8.1, 1.2 Hz, 1H), 5.20 (dd, J=10.5, 5.5 Hz, 1H), 2.47-2.34 (m, 4H), 2.26-2.14 (m, 1H), 2.07-1.96 (m, 1H), 1.76-1.63 (m, 1H), 1.57 (d, J=11.0 Hz, 1H), 1.35-1.21 (m, 4H), 1.10-0.96 (m, 1H) ppm. MS(ESI) m/z: 576.2 (M+H)$^+$. Analytical HPLC RT=5.44 min (Method A).

Example 187

(10R,14S)-14-[1-(3-Chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-5-carboxylic acid, TFA salt

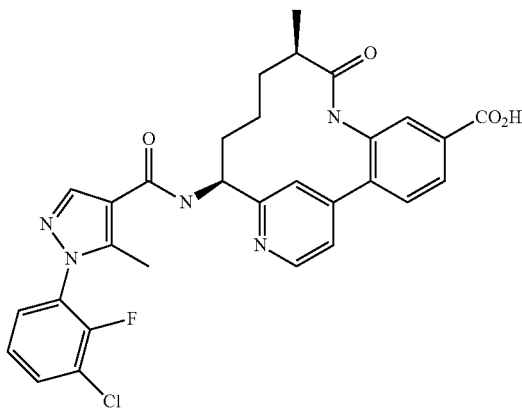 [SMILES: Cc1c(C(=O)N[C@H]2CCC[C@@H](C)C(=O)Nc3cc(C(=O)O)ccc3-c3ccnc2c3)cnn1-c1cccc(Cl)c1F]

Example 187. (10R,14S)-14-[1-(3-Chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-5-carboxylic acid, TFA salt: Example 187 was made in the same way as Example 185 by replacing (2-amino-4-(methoxycarbonyl)phenyl)boronic acid with 2-amino-5-(methoxycarbonyl)phenylboronic acid in step 2C. $^1$H NMR (500 MHz, MeOD) δ 8.81 (d, J=6.1 Hz, 1H), 8.30 (s, 1H), 8.17 (s, 1H), 8.12 (dd, J=8.0, 1.4 Hz, 1H), 7.95-7.87 (m, 2H), 7.81 (d, J=8.0 Hz, 1H), 7.75-7.67 (m, 1H), 7.49-7.42 (m, 1H), 7.41-7.34 (m, 1H), 5.26 (dd, J=11.1, 5.9 Hz, 1H), 2.81-2.70 (m, 1H), 2.35 (s, 3H), 2.26-2.14 (m, 1H), 2.06-1.94 (m, 1H), 1.93-1.83 (m, 1H), 1.63-1.44 (m, 2H), 0.97 (d, J=6.9 Hz, 3H), 0.53 (d, J=10.5 Hz, 1H) ppm. MS(ESI) m/z: 576.3 (M+H)$^+$. Analytical HPLC RT=5.84 min (Method A).

Example 188

(14S)-14-[1-(3-Chloro-2-fluorophenyl)-5-methyl-1H-pyrazole-4-amido]-9-oxo-8,16-diazatricyclo[13.3.1.0$^{2,7}$]nonadeca-1(19),2(7),3,5,15,17-hexaene-4-carboxylic acid, TFA salt

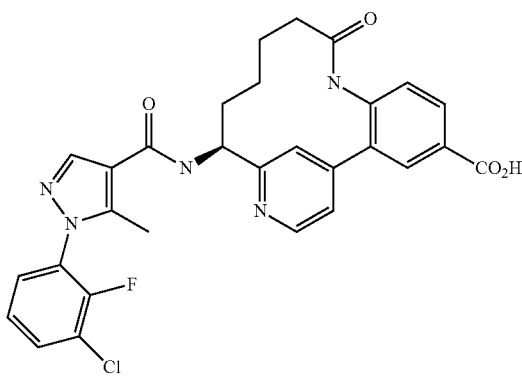 [SMILES: Cc1c(C(=O)N[C@H]2CCCCC(=O)Nc3ccc(C(=O)O)cc3-c3ccnc2c3)cnn1-c1cccc(Cl)c1F]

Example 188. (14S)-14-[1-(3-Chloro-2-fluorophenyl)-5-methyl-1H-pyrazole-4-amido]-9-oxo-8,16-diazatricyclo[13.3.1.0$^{2,7}$]nonadeca-1(19),2(7),3,5,15,17-hexaene-4-carboxylic acid, TFA salt: Example 188 was made in the same way as Example 21 by replacing 2-amino-4-nitrophenylboronic acid with 2-amino-5-(methoxycarbonyl)phenylboronic acid. Hydrolysis of the methyl ester to acid was carried out at the last step. $^1$H NMR (400 MHz, MeOD) δ 8.82 (d, J=6.1 Hz, 1H), 8.34-8.28 (m, 2H), 8.21 (dd, J=8.2, 1.9 Hz, 1H), 8.17 (d, J=1.3 Hz, 1H), 7.95 (dd, J=6.1, 1.8 Hz, 1H), 7.71 (ddd, J=8.2, 6.7, 1.8 Hz, 1H), 7.49-7.33 (m, 3H), 5.26 (dd, J=11.1, 5.8 Hz, 1H), 2.60-2.50 (m, 1H), 2.35 (d, J=0.8 Hz, 3H), 2.29-2.17 (m, 1H), 2.08-1.93 (m, 2H), 1.89-1.63 (m, 2H), 1.52-1.37 (m, 1H), 0.87-0.71 (m, 1H) ppm. MS(ESI) m/z: 562.2 (M+H)$^+$. Analytical HPLC RT=6.05 min (Method A).

Example 189

(10R,14S)-14-C-1-(3-Chloro-2-fluorophenyl)-5-methyl-1H-pyrazole-4-N,10-dimethyl-9-oxo-8,16-diazatricyclo[13.3.1.0$^{2,7}$]nonadeca-1(19),2(7),3,5,15,17-hexaene-4,14-diamido, TFA salt

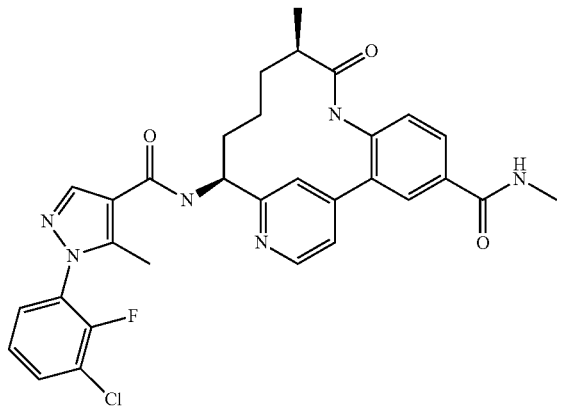 [SMILES: CNC(=O)c1ccc2c(c1)-c1ccnc(c1)[C@@H](NC(=O)c1cnn(-c3cccc(Cl)c3F)c1C)CCC[C@@H](C)C(=O)N2]

Example 189. (10R,14S)-14-C-1-(3-Chloro-2-fluorophenyl)-5-methyl-1H-pyrazole-4-N,10-dimethyl-9-oxo-8,16-diazatricyclo[13.3.1.0$^{2,7}$]nonadeca-1(19),2(7),3,5,15,17-hexaene-4,14-diamido, TFA salt: Example 185 (5.76 mg, 8.35 μmol), methanamine (29.2 μL, 0.058 mmol) (2 M in THF), EDC (3.20 mg, 0.017 mmol), and HOBT (2.56 mg, 0.017 mmol) were weighed into a 2 dram vial. DMF (167 μL) followed by Hunig's base (7.29 μL, 0.042 mmol) were added. The mixture was stirred at rt overnight. The reaction mixture was diluted with MeOH and purified by reverse phase HPLC to give the desired product (1.6 mg, 27%) as a white solid. $^1$H NMR (500 MHz, MeOD) δ 8.82 (d, J=6.1 Hz, 1H), 8.32 (s, 1H), 8.19-8.12 (m, 2H), 8.03 (dd, J=8.3, 2.2 Hz, 1H), 7.94 (dd, J=5.9, 1.8 Hz, 1H), 7.74 (td, J=7.5, 1.8 Hz, 1H), 7.52-7.45 (m, 1H), 7.44-7.37 (m, 2H), 5.27 (dd, J=11.1, 5.9 Hz, 1H), 2.98 (s, 3H), 2.82-2.74 (m, 1H), 2.38 (s, 3H), 2.27-2.16 (m, 1H), 2.06-1.86 (m, 2H), 1.66-1.48 (m, 2H), 0.98 (d, J=6.9 Hz, 3H), 0.54 (d, J=11.8 Hz, 1H) ppm. MS(ESI) m/z: 589.2 (M+H)$^+$. Analytical HPLC RT=5.25 min (Method A).

Example 190

(10R,14S)-14-C-1-(3-Chloro-2-fluorophenyl)-5-methyl-1H-pyrazole-4-10-methyl-9-oxo-8,16-diazatricyclo[13.3.1.0^{2,7}]nonadeca-1(19),2(7),3,5,15,17-hexaene-5,14-diamido, TFA salt

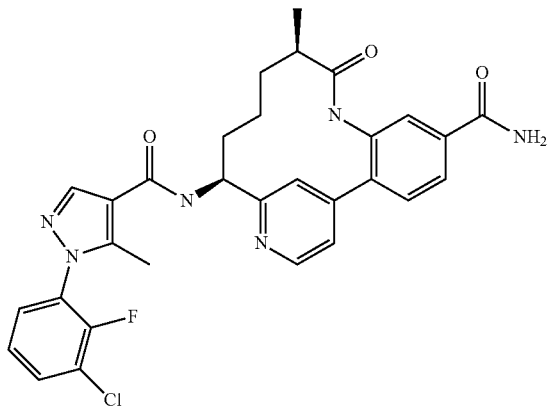 [SMILES: Cc1c(C(=O)N[C@H]2CCC[C@@H](C)C(=O)Nc3cc(C(N)=O)ccc3-c3ccnc2c3)cnn1-c1cccc(Cl)c1F]

Example 190. (10R,14S)-14-C-1-(3-Chloro-2-fluorophenyl)-5-methyl-1H-pyrazole-4-10-methyl-9-oxo-8,16-diazatricyclo[13.3.1.0^{2,7}]nonadeca-1(19),2(7),3,5,15,17-hexaene-5,14-diamido, TFA salt: Example 187 (12 mg, 0.021 mmol), NH$_4$Cl (7.80 mg, 0.146 mmol), EDC (7.99 mg, 0.042 mmol), and HOBT (6.38 mg, 0.042 mmol) were weighed into a 1 dram vial. DMF (208 µL) was added followed by Hunig's base (18.19 µL, 0.104 mmol). The resulting clear pale yellow solution was stirred at rt overnight. The mixture was diluted with MeOH and purified by reverse phase HPLC to yield the desired product (11.3 mg, 77%) as a white solid. $^1$H NMR (500 MHz, MeOD) δ 8.82 (d, J=6.1 Hz, 1H), 8.31 (s, 1H), 8.24 (s, 1H), 8.04-7.90 (m, 2H), 7.87-7.76 (m, 2H), 7.71 (ddd, J=8.2, 6.7, 1.7 Hz, 1H), 7.51-7.42 (m, 1H), 7.40-7.28 (m, 1H), 5.27 (dd, J=11.1, 5.9 Hz, 1H), 2.76 (t, J=6.5 Hz, 1H), 2.35 (d, J=0.6 Hz, 3H), 2.27-2.12 (m, 1H), 2.10-1.96 (m, 1H), 1.97-1.81 (m, 1H), 1.68-1.44 (m, 2H), 0.97 (d, J=6.9 Hz, 3H), 0.55 (d, J=10.7 Hz, 1H) ppm. MS(ESI) m/z: 575.3 (M+H)$^+$. Analytical HPLC RT=5.32 min (Method A).

Example 191

(10S,14S)-14-C-1-(3-Chloro-2-fluorophenyl)-5-methyl-1H-pyrazole-4-10-methyl-9-oxo-8,16-diazatricyclo[13.3.1.0^{2,7}]nonadeca-1(19),2(7),3,5,15,17-hexaene-5,14-diamido, TFA salt

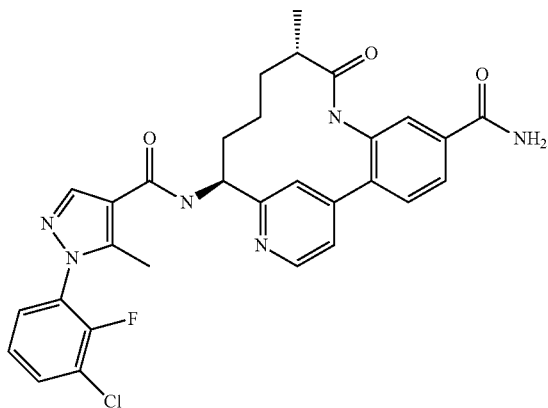 [SMILES: Cc1c(C(=O)N[C@H]2CCC[C@H](C)C(=O)Nc3cc(C(N)=O)ccc3-c3ccnc2c3)cnn1-c1cccc(Cl)c1F]

Example 191. (10S,14S)-14-C-1-(3-Chloro-2-fluorophenyl)-5-methyl-1H-pyrazole-4-10-methyl-9-oxo-8,16-diazatricyclo[13.3.1.0^{2,7}]nonadeca-1(19),2(7),3,5,15,17-hexaene-5,14-diamido, TFA salt: Example 191 was made in the same way as Example 190 by using the other isomer. $^1$H NMR (500 MHz, MeOD) δ 8.82 (d, J=5.8 Hz, 1H), 8.28 (s, 1H), 8.09 (s, 1H), 8.02 (dd, J=8.0, 1.7 Hz, 1H), 7.93 (d, J=5.2 Hz, 1H), 7.87-7.80 (m, 2H), 7.71 (ddd, J=8.3, 6.8, 1.7 Hz, 1H), 7.45 (ddd, J=8.0, 6.5, 1.7 Hz, 1H), 7.41-7.34 (m, 1H), 5.19 (dd, J=10.7, 5.2 Hz, 1H), 2.45-2.37 (m, 1H), 2.35 (d, J=0.6 Hz, 3H), 2.24-2.13 (m, 1H), 2.07-1.96 (m, 1H), 1.68 (q, J=10.8 Hz, 1H), 1.60-1.50 (m, 1H), 1.30 (dd, J=8.4, 4.3 Hz, 1H), 1.24 (d, J=6.9 Hz, 3H), 1.06-0.93 (m, 1H) ppm. MS(ESI) m/z: 575.3 (M+H)$^+$. Analytical HPLC RT=5.25 min (Method A).

Example 192

(14S)-14-C-1-(3-Chloro-2-fluorophenyl)-5-methyl-1H-pyrazole-4-9-oxo-8,16-diazatricyclo[13.3.1.0^{2,7}]nonadeca-1(19),2(7),3,5,15,17-hexaene-5,14-diamido, TFA salt

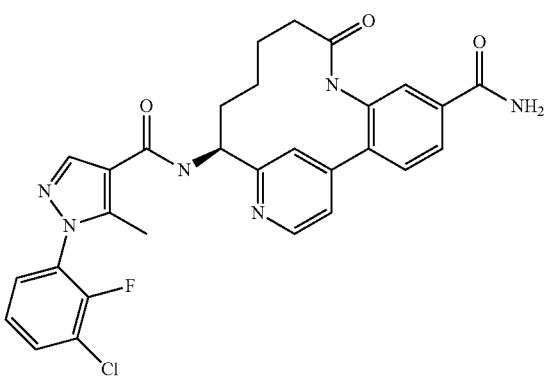 [SMILES: Cc1c(C(=O)N[C@H]2CCCCC(=O)Nc3cc(C(N)=O)ccc3-c3ccnc2c3)cnn1-c1cccc(Cl)c1F]

Example 192. (14S)-14-C-1-(3-Chloro-2-fluorophenyl)-5-methyl-1H-pyrazole-4-9-oxo-8,16-diazatricyclo[13.3.1.0^{2,7}]nonadeca-1(19),2(7),3,5,15,17-hexaene-5,14-diamido, TFA salt: Example 192 was made in the same way as Example 190 by replacing Example 187 with Example 188. $^1$H NMR (400 MHz, MeOD) δ 8.85 (d, J=6.0 Hz, 1H), 8.32 (s, 1H), 8.26 (s, 1H), 8.22 (d, J=2.2 Hz, 1H), 8.09 (dd, J=8.2, 2.2 Hz, 1H), 8.03 (dd, J=6.0, 1.6 Hz, 1H), 7.72 (ddd, J=8.2, 6.6, 1.6 Hz, 1H), 7.48-7.35 (m, 3H), 5.27 (dd, J=11.0, 6.0 Hz, 1H), 2.60-2.52 (m, 1H), 2.34 (s, 3H), 2.31-2.20 (m, 1H), 2.09-1.94 (m, 2H), 1.89-1.67 (m, 2H), 1.45 (dd, J=7.1, 3.8 Hz, 1H), 0.86-0.71 (m, 1H) ppm. MS(ESI) m/z: 561.2 (M+H)$^+$. Analytical HPLC RT=5.56 min (Method A).

Example 193

(14S)-14-C-1-(3-Chloro-2-fluorophenyl)-5-methyl-1H-pyrazole-4-5-N,5-N-dimethyl-9-oxo-8,16-diazatricyclo[13.3.1.0^{2,7}]nonadeca-1(19),2(7),3,5,15,17-hexaene-5,14-diamido, TFA salt

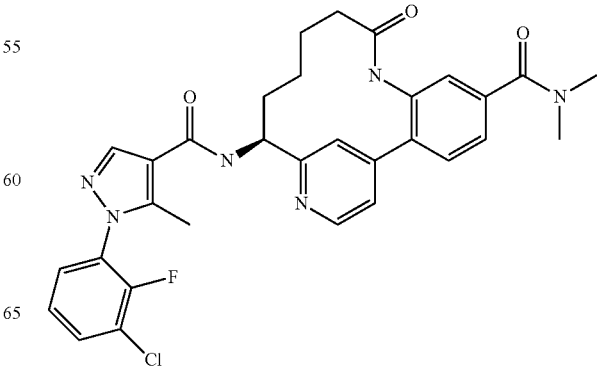

Example 193. (14S)-14-C-1-(3-Chloro-2-fluorophenyl)-5-methyl-1H-pyrazole-4-5-N,5-N-dimethyl-9-oxo-8,16-diazatricyclo[13.3.1.0$^{2,7}$]nonadeca-1(19),2(7),3,5,15,17-hexaene-5,14-diamido, TFA salt: Example 193 was made in the same way as Example 192 by replacing NH$_4$Cl with dimethylamine. $^1$H NMR (400 MHz, MeOD) δ 8.80 (d, J=6.0 Hz, 1H), 8.30 (s, 1H), 8.17 (d, J=1.1 Hz, 1H), 7.92 (dd, J=6.0, 1.6 Hz, 1H), 7.79 (d, J=1.6 Hz, 1H), 7.75-7.63 (m, 2H), 7.49-7.35 (m, 3H), 5.24 (dd, J=11.0, 5.5 Hz, 1H), 3.13 (s, 3H), 3.08 (s, 3H), 2.60-2.49 (m, 1H), 2.38-2.31 (s, 3H), 2.29-2.16 (m, 1H), 2.07-1.92 (m, 2H), 1.89-1.63 (m, 2H), 1.52-1.37 (m, 1H) ppm. MS(ESI) m/z: 589.3 (M+H)$^+$. Analytical HPLC RT=5.90 min (Method A).

Example 194

1-(3-Chloro-2-fluorophenyl)-5-methyl-N-[(10R,14S)-10-methyl-9-oxo-5-(1H-1,2,4-triazol-5-yl)-8,16-diazatricyclo[13.3.1.0$^{2,7}$]nonadeca-1(19),2(7),3,5,15,17-hexaen-14-yl]-1H-pyrazole-4-carboxamide, TFA salt

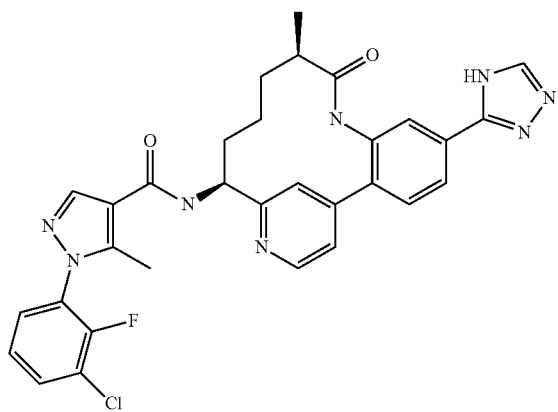 [SMILES: Cc1c(C(=O)N[C@H]2CCC[C@@H](C)C(=O)Nc3cc(-c4nnc[nH]4)ccc3-c3ccnc2c3)cnn1-c1cccc(Cl)c1F]

Example 194. 1-(3-Chloro-2-fluorophenyl)-5-methyl-N-[(10R,14S)-10-methyl-9-oxo-5-(1H-1,2,4-triazol-5-yl)-8,16-diazatricyclo[13.3.1.0$^{2,7}$]nonadeca-1(19),2(7),3,5,15,17-hexaen-14-yl]-1H-pyrazole-4-carboxamide, TFA salt: Example 190 (8.3 mg, 0.014 mmol) was stirred in N,N-dimethylformamide dimethyl acetal (0.5 mL, 3.73 mmol) at 75° C. for 3 h. The reaction mixture was concentrated. The residue was taken up in AcOH (0.1 mL, 1.747 mmol) and hydrazine monohydrate (0.025 mL, 0.510 mmol). The mixture was stirred at 75° C. for 1 h and concentrated. The residue was purified by reverse phase HPLC to yield the desired product (7.2 mg, 60%) as a pale yellow solid. $^1$H NMR (500 MHz, MeOD) δ 8.80 (d, J=5.8 Hz, 1H), 8.54 (s, 1H), 8.31 (s, 1H), 8.26 (s, 1H), 8.17 (dd, J=8.3, 1.7 Hz, 1H), 8.02-7.93 (m, 2H), 7.84 (d, J=8.3 Hz, 1H), 7.71 (ddd, J=8.1, 6.7, 1.7 Hz, 1H), 7.46 (ddd, J=8.0, 6.5, 1.7 Hz, 1H), 7.41-7.34 (m, 1H), 5.27 (dd, J=11.3, 6.1 Hz, 1H), 2.83-2.74 (m, 1H), 2.35 (d, J=0.8 Hz, 3H), 2.28-2.15 (m, 1H), 2.08-1.98 (m, 1H), 1.97-1.87 (m, 1H), 1.70-1.45 (m, 2H), 0.99 (d, J=6.9 Hz, 3H), 0.56 (d, J=11.6 Hz, 1H) ppm. MS(ESI) m/z: 599.3 (M+H)$^+$. Analytical HPLC RT=5.26 min (Method A).

Example 195

1-(3-Chloro-2-fluorophenyl)-5-methyl-N-[(10R,14S)-10-methyl-5-(5-methyl-4H-1,2,4-triazol-3-yl)-9-oxo-8,16-diazatricyclo[13.3.1.0$^{2,7}$]nonadeca-1(19),2(7),3,5,15,17-hexaen-14-yl]-1H-pyrazole-4-carboxamide, TFA salt

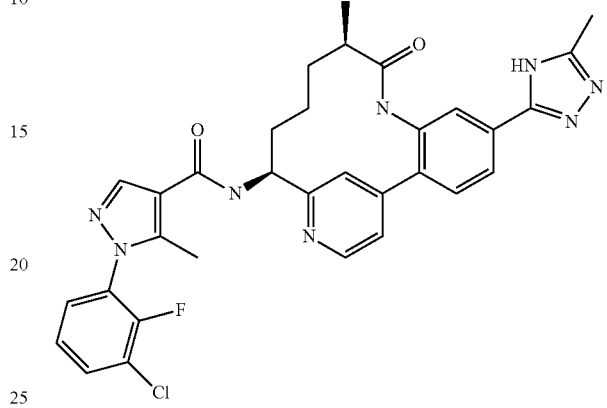

Example 195. 1-(3-Chloro-2-fluorophenyl)-5-methyl-N-[(10R,14S)-10-methyl-5-(5-methyl-4H-1,2,4-triazol-3-yl)-9-oxo-8,16-diazatricyclo[13.3.1.0$^{2,7}$]nonadeca-1(19),2(7),3,5,15,17-hexaen-14-yl]-1H-pyrazole-4-carboxamide, TFA salt: Example 195 was made in the same way as Example 194 by replacing N,N-dimethylformamide dimethyl acetal with 1,1-dimethoxy-N,N-dimethylethanamine. $^1$H NMR (500 MHz, MeOD) δ 8.80 (d, J=6.1 Hz, 1H), 8.31 (s, 1H), 8.29 (d, J=1.4 Hz, 1H), 8.13 (dd, J=8.1, 1.8 Hz, 1H), 8.01 (dd, J=6.1, 1.9 Hz, 1H), 7.94 (d, J=1.7 Hz, 1H), 7.84 (d, J=8.0 Hz, 1H), 7.72 (ddd, J=8.1, 6.7, 1.7 Hz, 1H), 7.46 (ddd, J=8.1, 6.5, 1.7 Hz, 1H), 7.42-7.34 (m, 1H), 5.27 (dd, J=11.3, 6.1 Hz, 1H), 2.83-2.74 (m, 1H), 2.55 (s, 3H), 2.35 (d, J=0.8 Hz, 3H), 2.29-2.18 (m, 1H), 2.03 (m, 1H), 1.97-1.86 (m, 1H), 1.68-1.48 (m, 2H), 0.99 (d, J=6.9 Hz, 3H), 0.57 (d, J=11.3 Hz, 1H) ppm. MS(ESI) m/z: 613.3 (M+H)$^+$. Analytical HPLC RT=5.16 min (Method A).

Example 196

1-(3-Chloro-2-fluorophenyl)-N-[(10R,14S)-5-(hydroxymethyl)-10-methyl-9-oxo-8,16-diazatricyclo[13.3.1.0$^{2,7}$]nonadeca-1(19),2(7),3,5,15,17-hexaen-14-yl]-5-methyl-1H-pyrazole-4-carboxamide

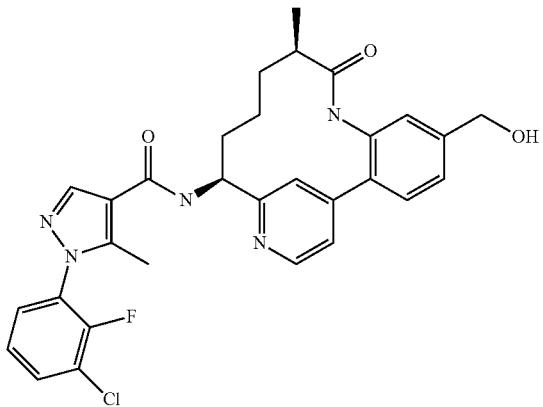 [SMILES: Cc1c(C(=O)N[C@H]2CCC[C@@H](C)C(=O)Nc3cc(CO)ccc3-c3ccnc2c3)cnn1-c1cccc(Cl)c1F]

Example 196. 1-(3-Chloro-2-fluorophenyl)-N-[(10R,14S)-5-(hydroxymethyl)-10-methyl-9-oxo-8,16-diazatricyclo[13.3.1.0²,⁷]nonadeca-1(19),2(7),3,5,15,17-hexaen-14-yl]-5-methyl-1H-pyrazole-4-carboxamide: To a suspension of Example 187 (35 mg, 0.061 mmol) and BOP (32.2 mg, 0.073 mmol) in THF (1 mL) was added DIPEA (0.032 mL, 0.182 mmol). The reaction was stirred at rt for 5 min and added NaBH₄ (9.20 mg, 0.243 mmol). The reaction was stirred for 1 h, quenched MeOH, and then concentrated. The residue was purified by reverse phase HPLC to yield the desired product (9 mg, 25% yield) as a white solid. ¹H NMR (500 MHz, MeOD) δ 8.63 (d, J=5.2 Hz, 1H), 8.25 (s, 1H), 7.78-7.68 (m, 1H), 7.65 (s, 1H), 7.57 (d, J=8.0 Hz, 1H), 7.52-7.33 (m, 4H), 7.25 (s, 1H), 5.21 (dd, J=11.1, 5.6 Hz, 1H), 4.67 (s, 2H), 2.70 (m, 1H), 2.38 (d, J=0.8 Hz, 3H), 2.00 (d, J=14.3 Hz, 1H), 1.96-1.80 (m, 2H), 1.51 (m, 1H), 1.40 (m, 1H), 0.95 (d, J=6.9 Hz, 3H), 0.44 (m, 1H) ppm. MS(ESI) m/z: 562.2 (M+H)⁺. Analytical HPLC RT=5.23 min (Method A).

Example 197

1-(3-Chloro-2-fluorophenyl)-5-methyl-N-[(14S)-10-methyl-5-(3-methyl-1,2,4-oxadiazol-5-yl)-9-oxo-8,16-diazatricyclo[13.3.1.0²,⁷]nonadeca-1(19),2(7),3,5,15,17-hexaen-14-yl]-1H-pyrazole-4-carboxamide, TFA salt

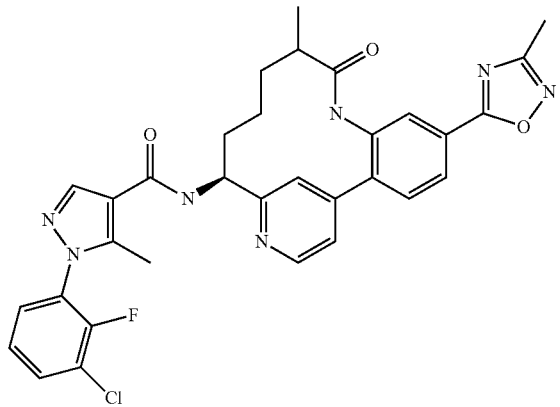 [SMILES: Cc1noc(-c2ccc3c(c2)NC(=O)C(C)CCC[C@H](NC(=O)c2cnn(-c4cccc(Cl)c4F)c2C)c2cc-3ccn2)n1]

197A. (14S)-14-C-1-(3-Chloro-2-fluorophenyl)-5-methyl-1H-pyrazole-4-10-methyl-9-oxo-8,16-diazatricyclo[13.3.1.0²,⁷]nonadeca-1(19),2(7),3,5,15,17-hexaene-5,14-diamido, TFA salt: 197A was made in the same way as Example 189 by replacing (2-amino-4-(methoxycarbonyl)phenyl)boronic acid with 2-amino-5-(methoxycarbonyl)phenylboronic acid in step 2C. The diastereomer mixture was not separated and carried on through the syntheses. MS(ESI) m/z: 575.6 (M+H)⁺.

Example 197. 1-(3-Chloro-2-fluorophenyl)-5-methyl-N-[(14S)-10-methyl-5-(3-methyl-1,2,4-oxadiazol-5-yl)-9-oxo-8,16-diazatricyclo[13.3.1.0²,⁷]nonadeca-1(19),2(7),3,5,15,17-hexaen-14-yl]-1H-pyrazole-4-carboxamide, TFA salt: 197A (8 mg, 0.012 mmol) was stirred in N,N-Dimethylacetamide dimethyl acetal (0.424 mL, 2.90 mmol) at 75° C. for 4 h. The reaction mixture was diluted with ether and mixed. The organic solution was decanted from the pale yellow-white solid. The solid was dried and treated with hydroxylamine hydrochloride (0.807 mg, 0.012 mmol), sodium hydroxide (0.017 mL, 0.017 mmol), acetic acid (1.329 μL, 0.023 mmol), and dioxane (0.5 mL). The mixture was stirred at rt for 1 h and stand at rt overnight. The reaction mixture was concentrated. The residue was purified by reverse phase HPLC to give the desired product (3.4 mg, 39%) as diastereomer mixture. ¹H NMR (500 MHz, MeOD) δ 8.64 (d, J=5.50 Hz, 1H), 8.26 (s, 1H), 8.02-8.09 (m, 1H), 8.01 (d, J=5.65 Hz, 1H), 7.96 (d, J=1.65 Hz, 1H), 7.91 (s, 0.5H), 7.86 (d, J=1.65 Hz, 1H), 7.81 (s, 0.5H), 7.69-7.72 (m, 1H), 7.56 (dt, J=1.51, 7.50 Hz, 1H), 7.51 (d, J=4.13 Hz, 0.5H), 7.41 (dd, J=1.38, 5.23 Hz, 0.5H), 7.31-7.35 (m, 1H), 7.22-7.27 (m, 1H), 5.18-5.24 (m, 1H), 5.08-5.15 (m, 1H), 2.53-2.58 (m, 1H), 2.34-2.36 (m, 1H), 2.35 (s, 3H), 2.27, 2.26 (2s, 3H), 2.12 (d, J=7.43 Hz, 1H), 1.98 (ddd, J=2.48, 4.95, 7.43 Hz, 1H), 1.69-1.72 (m, 1H), 1.56-1.63 (m, 1H), 1.28-1.42 (m, 1H), 1.11 (d, J=6.88 Hz, 1.2H), 0.81 (d, J=6.88 Hz, 1.8H), 0.28 (m, 1H) ppm. MS(ESI) m/z: 614.6 (M+H)⁺. Analytical HPLC RT=6.78 min (Method A).

Example 198

1-(3-Chloro-2-fluorophenyl)-5-methyl-N-[(14S)-9-oxo-4-(2H-1,2,3,4-tetrazol-5-yl)-8,16-diazatricyclo[13.3.1.0²,⁷]nonadeca-1(19),2(7),3,5,15,17-hexaen-14-yl]-1H-pyrazole-4-carboxamide, TFA salt

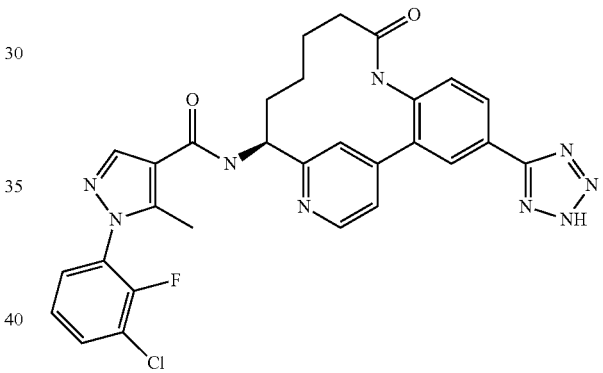

198A. tert-Butyl N-[(11E,14S)-4-cyano-9-oxo-8,16-diazatricyclo[13.3.1.0²,⁷]nonadeca-1(19),2(7),3,5,11,15,17-heptaen-14-yl]carbamate: 198A was made in the same way as 2J by replacing 2-amino-4-nitrophenylboronic acid with 2-amino-5-cyanophenylboronic acid in step 2C and replacing 2-methylbut-3-enoic acid with but-3-enoic acid in step 2I. MS(ESI) m/z: 405.3 (M+H)⁺.

Example 198B. tert-Butyl N-[(11E,14S)-9-oxo-4-(2H-1,2,3,4-tetrazol-5-yl)-8,16-diazatricyclo[13.3.1.0²,⁷]nonadeca-1(19),2(7),3,5,11,15,17-heptaen-14-yl]carbamate: To a solution of 198A (56 mg, 0.138 mmol) in DMF (1385 μL) was added NaN₃ (45 mg, 0.692 mmol) and NH₄Cl (44.4 mg, 0.831 mmol). The mixture was stirred at 90° C. overnight. The mixture was cooled to rt and purified by reverse phase HPLC to isolate the desired product (64 mg, 68%) as a yellow solid. MS(ESI) m/z: 448.2 (M+H)⁺.

Example 198. 1-(3-Chloro-2-fluorophenyl)-5-methyl-N-[(14S)-9-oxo-4-(2H-1,2,3,4-tetrazol-5-yl)-8,16-diazatricyclo[13.3.1.0²,⁷]nonadeca-1(19),2(7),3,5,15,17-hexaen-14-yl]-1H-pyrazole-4-carboxamide, TFA salt: Example 198 was made in the same way as Example 2 by replacing 2J with 198B and using Intermediate 25 in the final step. ¹H NMR (400 MHz, MeOD) δ 8.84 (d, J=6.0 Hz, 1H), 8.37 (d, J=2.2 Hz, 1H), 8.31 (s, 1H), 8.24 (dd, J=8.2, 1.6 Hz, 1H), 8.15 (s, 1H), 7.94 (dd, J=6.0, 1.6 Hz, 1H), 7.72 (ddd, J=8.2, 6.6, 1.6 Hz, 1H), 7.52 (d, J=8.2 Hz, 1H), 7.49-7.43 (m, 1H), 7.42-7.35 (m, 1H), 5.26 (dd, J=11.0, 6.0 Hz, 1H), 2.61-2.51 (m, 1H), 2.35 (s, 3H), 2.29-2.16 (m, 1H), 2.05-1.93 (m, 2H), 1.91-1.64 (m, 2H), 1.52-1.37 (m, 1H), 0.85-0.69 (m, 1H) ppm. MS(ESI) m/z: 586.2 (M+H)+. Analytical HPLC RT=6.14 min (Method A).

Example 199

Methyl N-[(10R,14S)-14-[1-(3-chloro-2-fluorophenyl)-5-methyl-1H-1,2,3-triazole-4-amido]-17-methoxy-10-methyl-9-oxo-8,16-diazatricyclo [13.3.1.0$^{2,7}$]nonadeca-1(18),2,4,6,15(19),16-hexaen-5-yl]carbamate, TFA salt

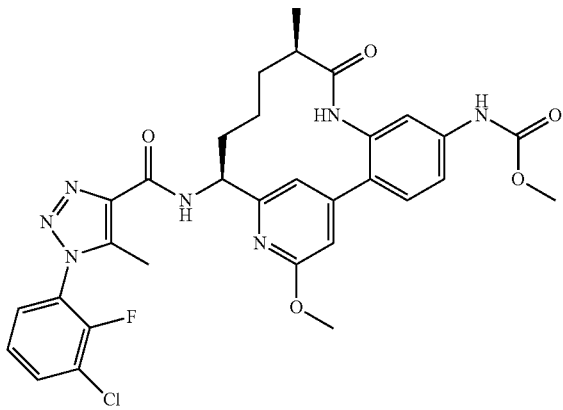 [SMILES: COC(=O)Nc1ccc2c(c1)NC(=O)[C@H](C)CCC[C@H](NC(=O)c1nnn(-c3cccc(Cl)c3F)c1C)c1cc-2cc(OC)n1]

199A. Methyl N-(4-{2-[(1S)-1-{[(tert-butoxy)carbonyl]amino}but-3-en-1-yl]-6-methoxypyridin-4-yl}-3-nitrophenyl)carbamate: To a stirred solution of 29G (3.0 g, 6.54 mmol; enriched by chiral SFC separation method similar to those used for 29H) in chloroform (131 mL) under an argon atmosphere was added silver (I) carbonate (50% on CELITE®) (3.61 g, 6.54 mmol) and iodomethane (1.22 mL, 19.63 mmol), respectively. The reaction mixture was heated at 65° C. After stirring for 14 hours, the reaction was filtered, concentrated, and purified by normal phase chromatography to give 199A (2.69 grams, 87%) as a tan solid. MS(ESI) m/z: 473 (M+H)+.

199B. Methyl N-(3-amino-4-{2-[(1S)-1-{[(tert-butoxy)carbonyl]amino}but-3-en-1-yl]-6-methoxy-pyridin-4-yl}phenyl)carbamate: 199A (2.69 g, 5.69 mmol) in MeOH (60 ml) was treated with zinc powder (3.86 g, 59.0 mmol) and ammonium chloride (0.632 g, 11.81 mmol) and heated at 65° C. overnight. The suspension was filtered hot through a plug of CELITE® and concentrated. This residue was re-dissolved in EtOAc (with 10% MeOH), washed with saturated sodium bicarbonate solution, brine, dried over sodium sulfate, filtered, and concentrated to give 199B. MS(ESI) m/z: 443 (M+H)+.

199C. Methyl N-(4-{2-[(1S)-1-{[(tert-butoxy)carbonyl]amino}but-3-en-1-yl]-6-methoxypyridin-4-yl}-3-(2-methylbut-3-enamido)phenyl)carbamate: DIPEA (3.02 mL, 17.29 mmol) was added to a solution of 2-methylbut-3-enoic acid (0.865 g, 8.64 mmol) and 199B (2.55 g, 5.76 mmol) in EtOAc (57.6 ml) at −10° C. under argon. Next, 1-propanephosphonic acid cyclic anhydride (6.79 ml, 11.53 mmol; 50% solution in EtOAc) was added dropwise and the reaction stirred for 1 h under set conditions and then allowed to come to rt. After 48 hours, the reaction was diluted with EtOAc, washed with saturated NaHCO$_3$, brine, dried over Na$_2$SO$_4$, filtered, and concentrated. Purification by normal phase chromatography gave 199C (2.52 g, 83%) as a white solid. MS(ESI) m/z: 525.1 (M+H)+.

199D. tert-Butyl N-[(14S)-17-methoxy-5-[(methoxycarbonyl)amino]-10-methyl-9-oxo-8,16-diazatricyclo [13.3.1.0$^{2,7}$]nonadeca-1(19),2,4,6,15,17-hexaen-14-yl]carbamate: A solution of 199C (1.50 g, 2.86 mmol) and Ts-OH (0.598 g, 3.15 mmol) in DCM (337 mL) was heated for 0.5 h. The solution was cooled down to room temperature and bubbled with argon for 0.5 h. To the solution was added tricyclohexylphosphine[1,3-bis(2,4,6-trimethylphenyl)-4,5-dihydroimidazol-2-ylidene][benzylidine]ruthenium(IV)dichloride (0.728 g, 0.858 mmol) and the resulting solution bubbled with argon for additional 0.5 h before heating at 45° C. for 12 hours. The reaction mixture was washed with aqueous saturated NaHCO$_3$ solution. Aqueous layer was further extracted with DCM (2×30 mL). The combined organic extract was dried over Na$_2$SO$_4$, concentrated, and purified by normal phase chromatography. The olefin double bond was reduced by dissolution in EtOH (50 mL), treatment with platinum oxide (0.065 gram, 0.286 mmol), and subjected to a hydrogen atmosphere (55 psi) overnight. The catalyst was filtered off through a plug of CELITE® and the filtrate concentrated to give 199D (720 mg, 51%) as a diastereomer mixture.

199E1. tert-Butyl N-[(10S,14S)-17-methoxy-5-[(methoxycarbonyl)amino]-10-methyl-9-oxo-8,16-diazatricyclo[13.3.1.0$^{2,7}$]nonadeca-1(19),2,4,6,15,17-hexaen-14-yl]carbamate and 199E2. tert-butyl N-[(10R,14S)-17-methoxy-5-[(methoxycarbonyl)amino]-10-methyl-9-oxo-8,16-diazatricyclo-[13.3.1.0$^{2,7}$]nonadeca-1(19),2,4,6,15,17-hexaen-14-yl]carbamate: Diastereomeric mixture 199D (720 mg, 1.44 mmol) was subjected to chiral SFC separation using chiral AD-H 30×250 mm column, with a mixture of 30% EtOH and 70% CO$_2$ with a flow rate of 85 mL/min and 100 bar at 40° C. Peak 1 was designated as enantiomer A (199E1; 280 mg, 74%) and peak 2 was designated as enantiomer B (199E2; 360 mg, 100%). MS(ESI) m/z: 499.1 (M+H)+ for both enantiomers.

Example 199. Methyl N-[(10R,14S)-14-[1-(3-chloro-2-fluorophenyl)-5-methyl-1H-1,2,3-triazole-4-amido]-17-methoxy-10-methyl-9-oxo-8,16-diazatricyclo[13.3.1.0$^{2,7}$] nonadeca-1(18),2,4,6,15(19),16-hexaen-5-yl]carbamate, TFA salt: 199E2 (0.020 g, 0.040 mmol) in MeOH (0.20 mL) was treated with HCl (0.501 mL, 2.006 mmol) for 1 hour and then concentrated to dryness. The crude residue was purified reverse phase preparative HPLC. The amine TFA salt was dissolved in DMF (1 mL) then Intermediate 21 (0.012 g, 0.048 mmol), EDC (0.015 g, 0.080 mmol), 1-hydroxybenzotriazole hydrate (0.012 g, 0.080 mmol), and DIPEA (0.070 mL, 0.401 mmol), added respectively. After 3 hours, reaction mixture was purified by reverse phase HPLC to give the desired product (11 mg, 35%) as a white solid. Chirality was assigned based on previous compounds. $^1$H NMR (500 MHz, MeOD) δ 7.87-7.84 (m, 1H), 7.64-7.60 (m, 1H), 7.52-7.46 (m, 4H), 7.19 (d, J=1.1 Hz, 1H), 6.79 (d, J=1.4 Hz, 1H), 5.25 (dd, J=10.5, 5.5 Hz, 1H), 4.07 (s, 3H), 3.80 (s, 3H), 2.75-2.72 (m, 1H), 2.54 (d, J=0.8 Hz, 3H), 2.17-2.12 (m, 1H), 1.98-1.93 (m, 1H), 1.85-1.79 (m, 1H), 1.51-1.45 (m, 2H), 1.01 (d, J=7.2 Hz, 3H), 0.64 (m, 1H) ppm. MS(ESI) m/z: 636 (M+H)+. Analytical HPLC RT=7.32 min (Method B).

Example 200

Methyl N-[(10R,14S)-14-[1-(3-chloro-2-fluorophenyl)-5-methyl-1H-1,2,3-triazole-4-amido]-17-ethoxy-10-methyl-9-oxo-8,16-diazatricyclo[13.3.1.0²,⁷]nonadeca-1(18),2,4,6,15(19),16-hexaen-5-yl]carbamate, TFA salt

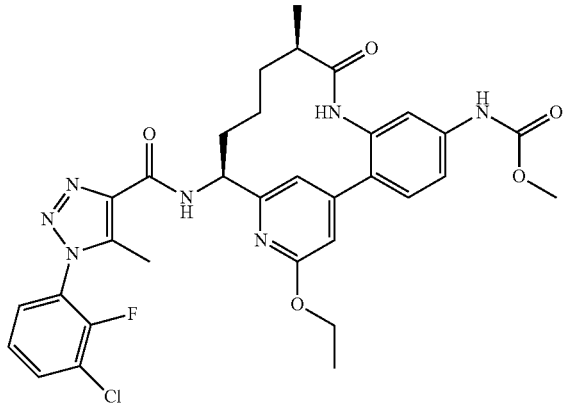 [SMILES: CCOc1cc2cc(n1)[C@@H](NC(=O)c1nnn(-c3cccc(Cl)c3F)c1C)CCC[C@@H](C)C(=O)Nc1cc(NC(=O)OC)ccc1-2]

Example 200. Methyl N-[(10R,14S)-14-[1-(3-chloro-2-fluorophenyl)-5-methyl-1H-1,2,3-triazole-4-amido]-17-ethoxy-10-methyl-9-oxo-8,16-diazatricyclo[13.3.1.0²,⁷]nonadeca-1(18),2,4,6,15(19),16-hexaen-5-yl]carbamate, TFA salt: Example 200 was prepared in a similar manner as Example 199 by replacing iodomethane with iodoethane in the o-alkylation step. Chirality was assigned based on previous compounds. $^1$H NMR (500 MHz, DMSO-$d_6$) δ 9.89 (s, 1H), 9.68 (s, 1H), 8.43 (d, J=8.0 Hz, 1H), 7.95 (ddd, J=8.3, 6.8, 1.7 Hz, 1H), 7.75 (ddd, J=8.1, 6.6, 1.5 Hz, 1H), 7.53 (td, J=8.3, 1.4 Hz, 1H), 7.51-7.47 (m, 1H), 7.46-7.42 (m, 1H), 7.35 (d, J=1.7 Hz, 1H), 7.16 (d, J=0.8 Hz, 1H), 6.66 (d, J=1.1 Hz, 1H), 5.19-5.05 (m, 1H), 4.40 (q, J=7.1 Hz, 2H), 3.70 (s, 3H), 2.69-2.63 (m, 1H), 2.49-2.43 (m, 3H), 2.00-1.83 (m, 2H), 1.77-1.65 (m, 1H), 1.43-1.35 (m, 4H), 1.33-1.23 (m, 1H), 0.85 (d, J=6.9 Hz, 3H), 0.37 (d, J=11.0 Hz, 1H) ppm. MS(ESI) m/z: 650 (M+H)⁺. Analytical HPLC RT=7.58 min (Method B).

Example 201

Methyl N-[(10R,14S)-14-[1-(3-chloro-2-fluorophenyl)-5-methyl-1H-1,2,3-triazole-4-amido]-10,16-dimethyl-9,17-dioxo-8,16-diazatricyclo[13.3.1.0²,⁷]nonadeca-1(18),2,4,6,15(19)-pentaen-5-yl]carbamate

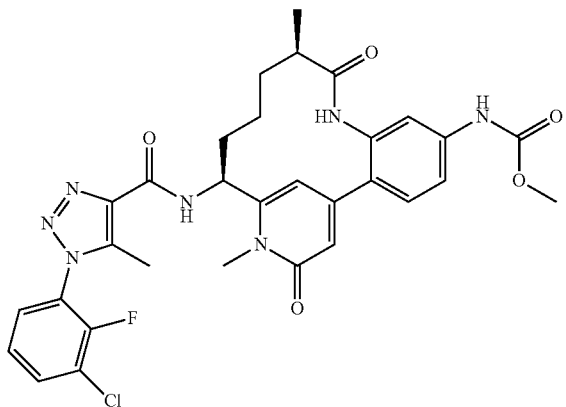 [SMILES: COC(=O)Nc1ccc2c(c1)NC(=O)[C@H](C)CCC[C@H](NC(=O)c1nnn(-c3cccc(Cl)c3F)c1C)c1cc-2cc(=O)n1C]

201A. Methyl N-(4-{6-[(1S)-1-{[(tert-butoxy)carbonyl]amino}but-3-en-1-yl]-1-methyl-2-oxo-1,2-dihydropyridin-4-yl}-3-nitrophenyl)carbamate: To a stirred solution of 29G (1.0 g, 2.181 mmol; enriched by SFC separation method similar to that used for 29H) in chloroform (43.6 mL) under an argon atmosphere was added $Cs_2CO_3$ (0.711 g, 2.181 mmol) and iodomethane (0.929 g, 6.54 mmol). The reaction mixture was heated at 65° C. After 14 hours, the reaction shows a 1:1 ratio of the desired N-methylated product (more polar by LC) and the O-methoxy (less polar by LC). The reaction mixture was filtered, concentrated, and purified by normal phase column chromatography. Both products were isolated with desired product (0.542 g, 53%) being carried forward to subsequent reaction and the O-methylated side-product (382 mg, 37%, analytical data corresponds that from an earlier alternative synthesis) being set aside. MS(ESI) m/z: 473 (M+H)⁺.

201B. Methyl N-(4-{6-[(1S)-1-{[(tert-butoxy)carbonyl]amino}but-3-en-1-yl]-1-methyl-2-oxo-1,2-dihydropyridin-4-yl}-3-(2-methylbut-3-enamido)phenyl)carbamate: Ammonium chloride (0.122 g, 2.286 mmol) was added to a suspension of 201A (0.540 g, 1.143 mmol) and zinc (0.747 g, 11.43 mmol) in MeOH (11.43 mL). The reaction mixture was heated at 65° C. overnight. The reaction mixture was through a plug of CELITE® and concentrated. This residue was re-dissolved in EtOAc, washed with saturated sodium bicarbonate solution, brine, dried over sodium sulfate, filtered, and concentrated. 1-Propanephosphonic acid cyclic anhydride (1.455 g, 2.286 mmol; 50% in EtOAc) was added to a solution of aniline intermediate, 2-methylbut-3-enoic acid (0.460 g, 4.58 mmol), and DIPEA (1.2 ml, 6.86 mmol) in EtOAc (30 mL). After stirring for 48 hours, the reaction mixture was washed with saturated sodium bicarbonate solution, brine, dried over sodium sulfate, filtered, and concentrated to give the desired product. MS(ESI) m/z: 525.2 (M+H)⁺.

201C. tert-Butyl N-[(14S)-5-[(methoxycarbonyl)amino]-10,16-dimethyl-9,17-dioxo-8,16-diazatricyclo-[13.3.1.0²,⁷]nonadeca-1(18),2,4,6,15(19)-pentaen-14-yl]carbamate: 201B (200 mg, 0.381 mmol) dissolved in DCE (anhydrous) (21.8 mL) was charged to two large microwave vials in equal portions. After degassing for 15 min, tricyclohexylphosphine[1,3-bis(2,4,6-trimethylphenyl)-4,5-dihydroimidazol-2-ylidene][benzylidine]ruthenium(IV)dichloride (130 mg, 0.152 mmol) was added in equal portions to each vial followed by irradiation at 120° C. for 30 min under microwave conditions. The reaction mixture was concentrated and purified by reverse phase preparative HPLC. The diastereomers were successfully separated under these conditions. Peak 1 was designated as Diastereomer A (201C1; minor; more polar RT by ACN prep.) and Peak 2 was designated as Diastereomer B (201C2, major; less polar RT by ACN prep). Each diastereomer was dissolved in EtOH (10 mL), treated with platinum(IV) oxide (13 mg, 0.057 mmol), and subjected to hydrogen gas (55 psi) overnight. The reactions were filtered, concentrated. 201C1 (42 mg, 44%) was set aside and 201C2 (51 mg, 54%) was carried forward to the next reaction without further purification. MS(ESI) m/z: 499 (M+H)⁺ for both diastereomers.

Example 201

Methyl N-[(10R,14S)-14-[1-(3-chloro-2-fluorophenyl)-5-methyl-1H-1,2,3-triazole-4-amido]-10,16-dimethyl-9,17-dioxo-8,16-diazatricyclo[13.3.1.0$^{2,7}$]nonadeca-1(18),2,4,6,15(19)-pentaen-5-yl]carbamate: 201C2 (0.022 g, 0.044 mmol) in MeOH (0.200 mL) was treated with HCl (0.552 ml, 2.206 mmol) for 1 hour and then concentrated to dryness. The amine HCl salt was dissolved in DMF (1 mL) then Intermediate 21 (0.014 g, 0.053 mmol), EDC (0.017 g, 0.088 mmol), 1-hydroxybenzotriazole hydrate (0.014 g, 0.088 mmol), DIPEA (0.077 ml, 0.441 mmol), added respectively. After 15 hours, the reaction mixture was purified by reverse phase preparative HPLC to give the desired product (10 mg, 33%) as a white solid. Chirality was assigned based on previous compounds. $^1$H NMR (500 MHz, MeOD) δ 7.83 (ddd, J=8.2, 6.8, 1.5 Hz, 1H), 7.57 (ddd, J=8.0, 6.5, 1.7 Hz, 1H), 7.53-7.45 (m, 4H), 6.74 (d, J=1.7 Hz, 1H), 6.60 (d, J=1.9 Hz, 1H), 5.26 (dd, J=11.0, 4.4 Hz, 1H), 3.77 (s, 3H), 3.66 (s, 3H), 2.58-2.53 (m, 1H), 2.52-2.49 (m, 3H), 2.19-2.14 (m, 1H), 2.11-2.06 (m, 1H), 1.67-1.61 (m, 2H), 1.46-1.40 (m, 1H), 1.35-1.29 (m, 1H), 1.19 (d, J=6.9 Hz, 3H) ppm. MS(ESI) m/z: 636 (M+H)$^+$. Analytical HPLC RT=6.28 min (Method B).

Example 202

Methyl N-[(10R,14S)-14-[1-(3-chloro-2-fluorophenyl)-5-methyl-1H-1,2,3-triazole-4-amido]-10-methyl-9-oxo-8,16,17-triazatricyclo[13.3.1.0$^{2,7}$]nonadeca-1(19),2(7),3,5,15,17-hexaen-5-yl]carbamate, TFA salt

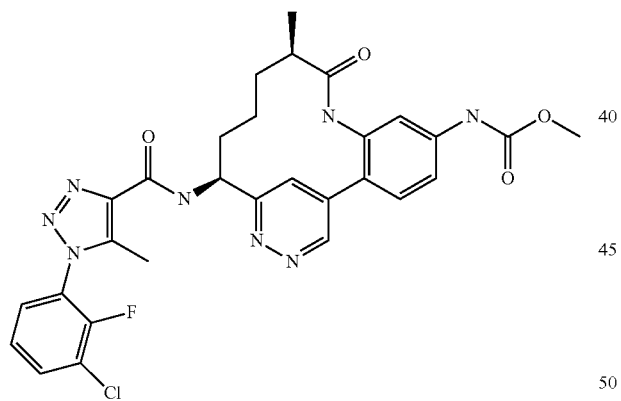

Example 202. Methyl N-[(10R,14S)-14-[1-(3-chloro-2-fluorophenyl)-5-methyl-1H-1,2,3-triazole-4-amido]-10-methyl-9-oxo-8,16,17-triazatricyclo[13.3.1.0$^{2,7}$]nonadeca-1(19),2(7),3,5,15,17-hexaen-5-yl]carbamate, TFA salt: Example 202 was made in the same way as Example 22 by using 22IA and replacing Intermediate 2 with Intermediate 21. $^1$H NMR (400 MHz, CDCl$_3$) δ 9.63 (br. s., 1H), 8.74-8.11 (m, 2H), 8.04-7.31 (m, 4H), 7.21-6.97 (m, 1H), 5.53 (br. s., 1H), 3.64-3.32 (m, 3H), 2.76 (br. s., 1H), 2.57-2.37 (s, 3H), 2.27 (br. s., 1H), 2.09 (d, J=9.3 Hz, 1H), 1.99-1.48 (m, 3H), 0.94 (d, J=6.6 Hz, 3H), 0.43 (br. s., 1H) ppm. MS(ESI) m/z: 607.2 (M+H)$^+$. Analytical HPLC RT=9.17 min (Method A).

Example 203

Methyl N-[(14S)-14-[1-(3-chloro-2-fluorophenyl)-5-methyl-1H-pyrazole-4-amido]-10,10-difluoro-9-oxo-8,16,18-triazatricyclo[13.2.1.0$^{2,7}$]octadeca-1(17),2,4,6,15(18)-pentaen-5-yl]carbamate, TFA salt

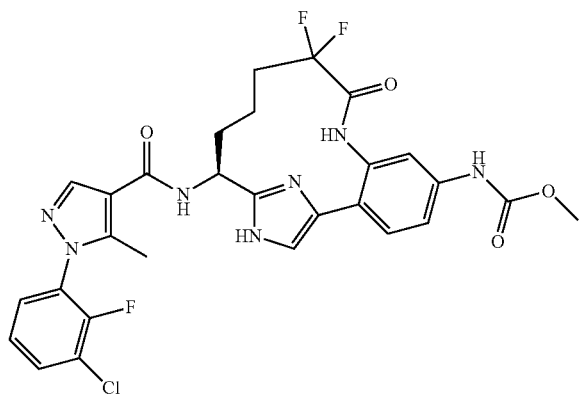 [SMILES: COC(=O)Nc1ccc2c(c1)NC(=O)C(F)(F)CCC[C@H](NC(=O)c1cnn(-c3cccc(Cl)c3F)c1C)c1nc-2c[nH]1]

Example 203. Methyl N-[(14S)-14-[1-(3-chloro-2-fluorophenyl)-5-methyl-1H-pyrazole-4-amido]-10,10-difluoro-9-oxo-8,16,18-triazatricyclo[13.2.1.0$^{2,7}$]octadeca-1(17),2,4,6,15(18)-pentaen-5-yl]carbamate, TFA salt: Example 203 was made in the same way as example 34 by replacing 2-methylbut-3-enoic acid with 2,2-difluoropent-4-enoic acid in step 21 and using Intermediate 25 in the final step. $^1$H NMR (400 MHz, MeOD) δ 9.69 (s, 1H), 8.28 (s, 1H), 7.73 (ddd, J=8.2, 6.6, 1.6 Hz, 1H), 7.65 (d, J=1.6 Hz, 1H), 7.60-7.44 (m, 4H), 7.43-7.35 (m, 1H), 5.23 (dd, J=10.4, 6.6 Hz, 1H), 3.77 (s, 3H), 2.45-2.29 (m, 4H), 2.20-2.04 (m, 3H), 1.63 (br. s., 1H), 1.05 (br. s., 1H) ppm. MS(ESI) m/z: 616.2 (M+H)$^+$. Analytical HPLC RT=6.89 min (Method A).

Example 204

Methyl N-[(15 S)-15-[1-(3-chloro-2-fluorophenyl)-5-methyl-1H-pyrazole-4-amido]-9-oxo-8,17,19-triazatetracyclo[14.2.1.0$^{2,7}$.0$^{11,13}$]nonadeca-1(18),2,4,6,16(19)-pentaen-5-yl]carbamate, TFA salt

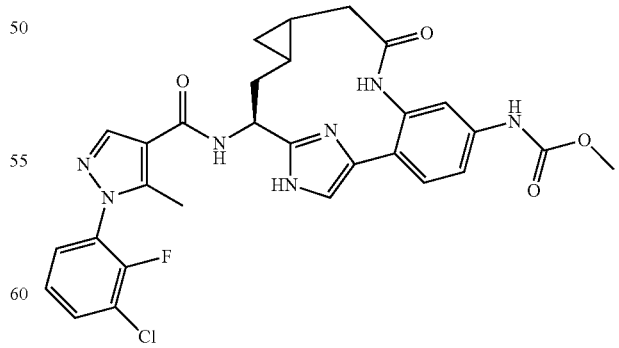

204A. tert-Butyl N-[(15S)-5-[(methoxycarbonyl)amino]-9-oxo-17-{[2-(trimethylsilyl)ethoxy]methyl}-8,17,19-triazatetracyclo[14.2.1.0$^{2,7}$.0$^{11,13}$]nonadeca-1(18),2,4,6,16(19)-pentaen-15-yl]carbamate: To a mixture of 34F (100 mg, 0.175 mmol) and diacetoxypalladium (1.963 mg, 8.75 μmol) in CH$_2$Cl$_2$ (20 mL) at 0° C. was added diazomethane (73.5 mg, 1.749 mmol) dropwise. The reaction was stirred for 2 h and quenched with 1 mL HOAc. The solution was neutralized with aq. Na$_2$CO$_3$ and extracted with ether. The organic layer was washed with brine, dried over MgSO$_4$, filtered, and concentrated. The residue was purified by reverse phase HPLC yield the product (29 mg, 28%) as white solid. NMR was shown to be a mixture a diastereomers. MS(ESI) m/z: 586.4 (M+H)$^+$.

Example 204. Methyl N-[(15S)-15-[1-(3-chloro-2-fluorophenyl)-5-methyl-1H-pyrazole-4-amido]-9-oxo-8,17,19-triazatetracyclo[14.2.1.0$^{2,7}$.0$^{11,13}$]nonadeca-1(18),2,4,6,16(19)-pentaen-5-yl]carbamate, TFA salt: Example 204 was made in the same way as Example 34 by replacing 34F with 204A. Example 204 was a mixture of diastereomers. $^1$H NMR (500 MHz, MeOD) δ 8.36 (s, 1H), 7.74 (ddd, J=8.3, 6.7, 1.8 Hz, 1H), 7.60 (d, J=1.7 Hz, 1H), 7.52-7.37 (m, 5H), 5.31 (dd, J=4.4, 3.6 Hz, 1H), 3.78 (s, 3H), 2.80-2.70 (m, 2H), 2.38 (d, J=0.8 Hz, 3H), 1.58-1.46 (m, 2H), 1.06 (tt, J=9.3, 4.7 Hz, 1H), 0.82 (ddd, J=11.1, 7.6, 3.9 Hz, 1H), 0.60-0.48 (m, 2H) ppm. MS(ESI) m/z: 592.0 (M+H)$^+$. Analytical HPLC RT=5.31 min (Method A).

Example 205

Methyl N-[(12E,15S)-15-[1-(3-chloro-2-fluorophenyl)-5-methyl-1H-pyrazole-4-amido]-9-oxo-8,17,19-triazatricyclo[14.2.1.0$^{2,7}$]nonadeca-1(18),2,4,6,12,16(19)-hexaen-5-yl]carbamate, TFA salt

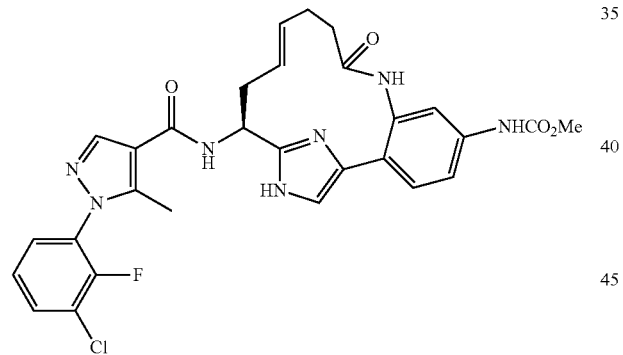

Example 205. Methyl N-[(12E,15S)-15-[1-(3-chloro-2-fluorophenyl)-5-methyl-1H-pyrazole-4-amido]-9-oxo-8,17,19-triazatricyclo[14.2.1.0$^{2,7}$]nonadeca-1(18),2,4,6,12,16(19)-hexaen-5-yl]carbamate, TFA salt: Example 205 was made in the same way as Example 58 by replacing Intermediate 22 with Intermediate 25. $^1$H NMR (500 MHz, MeOD) δ 8.30 (s, 1H), 7.72 (ddd, J=8.3, 6.8, 1.7 Hz, 1H), 7.58 (s, 1H), 7.50-7.37 (m, 6H), 5.60 (ddd, J=15.2, 9.1, 5.6 Hz, 1H), 5.48-5.40 (m, 1H), 5.20 (dd, J=10.5, 4.7 Hz, 1H), 3.76 (s, 3H), 2.91-2.85 (m, 1H), 2.67-2.60 (m, 1H), 2.55-2.36 (m, 7H) ppm. MS(ESI) m/z: 592.3 (M+H)$^+$. Analytical HPLC RT=5.84 min (Method A).

The following Examples in Table 11 were made by using the same procedure as shown in Example 34. The acids used in the final step are as indicated in the below table in the Intermediate section. Various coupling reagents could be used other than the one described in Example 34 like BOP, PyBop, EDC/HOBt, HATU or T3P. Boc and SEM deprotection was achieved prior to the final coupling unlike with Example 34 where the Boc group alone was removed in step 34J.

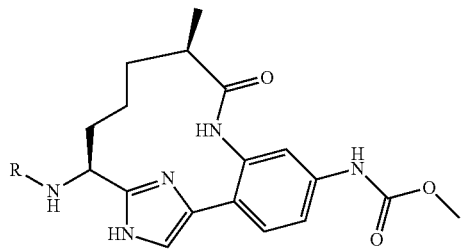

TABLE 11

| Example # | Stereochemistry | R | M + H | RT, min Method A |
|---|---|---|---|---|
| 206 | Homochiral | (triazole with ethyl and 3-chlorophenyl) | 591.3 | 6.49 |
| 207 | Homochiral | (triazole with methyl and 2,6-difluoro-3-chlorophenyl) | 612.9 | 5.99 |
| 208 | Homochiral | (triazole with methyl and 2-CN-5-Cl-phenyl) | 601.9 | 6.25 |
| 209 | Homochiral | (triazole with thiazole) | 536.1 | 5.02 |

TABLE 11-continued

| Example # | Stereochemistry | R | M + H | RT, min Method A |
|---|---|---|---|---|
| 210 | Homochiral |  | 595.2 | 4.29 |
| 211 | Homochiral | 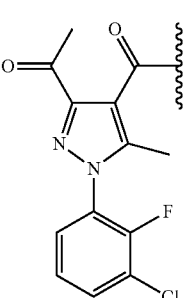 | 635.9 | 6.70 |
| 212 | Homochiral | 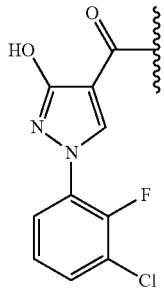 | 596.0 | 6.45 |
| 213 | Homochiral | 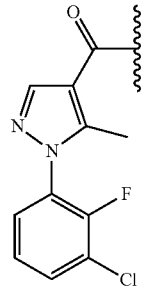 [SMILES: *C(=O)c1cnn(-c2cccc(Cl)c2F)c1C] | 594.2 | 5.75 |
| 214 | Homochiral | 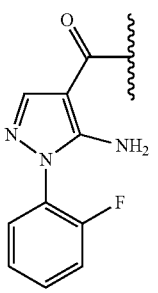 [SMILES: *C(=O)c1cnn(-c2ccccc2F)c1N] | 561.2 | 5.08 |

Example 215

2-Methoxyethyl N-[(10R,14S)-14-[1-(3-chloro-2-fluorophenyl)-1H-1,2,3-triazole-4-amido]-10-methyl-9-oxo-8,16,18-triazatricyclo[13.2.1.0$^{2,7}$]octadeca-1(17),2,4,6,15(18)-pentaen-5-yl]carbamate, TFA salt

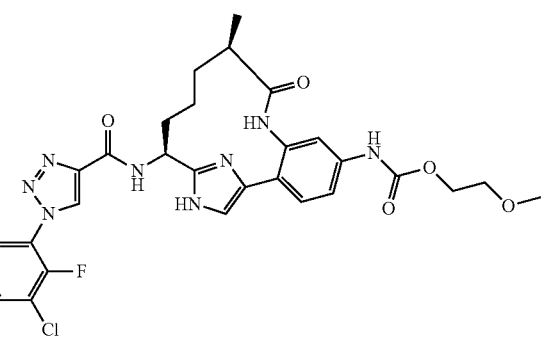

215A. {3-Bromo-4-[2-((S)-1-tert-butoxycarbonylamino-but-3-enyl)-3H-imidazol-4-yl]-phenyl}-carbamic acid methyl ester: This compound was prepared following the procedure described in step 34A, by replacing Intermediate 16 with Intermediate 18; followed by step 34B. MS(ESI) m/z: 467.1 (M+2+H)$^+$.

215B. {3-Bromo-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: To a cooled (0° C.) solution of 215A (15 g, 32.2 mmol) in THF (77 mL) was added N,N-dicyclohexylmethylamine (7.52 mL, 35.5 mmol) followed by the dropwise addition of SEM-Cl (6.29 mL, 35.5 mmol). The reaction was stirred at 0° C. for 2 h and then it was allowed to warm slowly to rt. After 18 h, the yellow suspension was diluted with EtOAc, washed with saturated sodium bicarbonate, brine, dried over MgSO$_4$, filtered and concentrated. Purification by normal phase chromatography gave 12.24 g (64%) of 215B as an off-white solid. MS(ESI) m/z: 595.1 (M+H)$^+$ and 597.2 (M+2+H)$^+$.

215C. {3-Amino-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: A thick-walled vial containing 215B (2 g, 3.36 mmol), copper(I) iodide (0.128 g, 0.672 mmol), L-proline (0.155 g, 1.343 mmol) and potassium carbonate (1.392 g, 10.07 mmol) in DMSO (6.72 mL) was vacuumed and back-filled with argon three times. Then 28% aq. ammonium hydroxide (0.607 mL, 4.37 mmol) was added. The vial was sealed with a Teflon-coated screw cap and the reaction was warmed to 85° C. After 20 h, the reaction was cooled to rt, diluted with EtOAc, washed with water, brine, dried over sodium sulfate, filtered and concentrated. Purification by normal phase chromatography afforded 1.05 g (58.8%) of 215C as a yellow solid. MS(ESI) m/z: 532.5 (M+H)$^+$.

215D. tert-Butyl N-[(1S)-1-(4-{4-[(methoxycarbonyl)amino]-2-[(2R)-2-methylbut-3-enamido]phenyl}-1-{[2-(trimethylsilyl)ethoxy]methyl}-1H-imidazol-2-yl)but-3-en-1-yl]carbamate: To a cooled (0° C.), clear yellow orange solution of 215C (4.83 g, 9.08 mmol) in ethyl acetate (91 mL) was added Intermediate 45 (1.0 g, 9.99 mmol) and Hunig's base (6.34 mL, 36.3 mmol). Next, 1-propanephosphonic acid cyclic anhydride (T3P) (50% in EtOAc) (13.38 mL, 22.70 mmol) was added dropwise over 20 min. and the reaction was stirred at 0° C. After 3 h, the reaction was diluted with EtOAc and washed with sat. NaHCO₃. The aqueous layer was extracted with EtOAc (2×). The organic layers were combined and washed with brine, dried over sodium sulfate, filtered and concentrated to give an orange foam. Purification by normal phase chromatography gave 215D (4.53 g, 81%) as a white foam. Proton NMR indicated a 3:1 mixture of diastereomers. MS(ESI) m/z: 614.4 (M+H)⁺.

215E. tert-Butyl N-[(10R,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-(17),2,4,6,11,15(18)-hexaen-14-yl]carbamate (Diastereomer A) and 215F. tert-butyl N-[(10S,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (Diastereomer B): To a solution of 215D (4.40 g, 7.17 mmol) in dichloromethane (717 mL) was added pTsOH monohydrate (1.523 g, 7.89 mmol) and the mixture was degassed with argon for 30 min. Next, the flask was equipped with a reflux condenser and the reaction was warmed to 40° C. for 1 h. Next, a burgundy solution of Grubbs catalyst 2nd generation (2.440 g, 2.87 mmol) in 20 mL of DCM (degassed with argon) was added dropwise via syringe over 35 to 40 min. After 21.5 h, the reaction was cooled to rt. The reaction mixture was washed with saturated NaHCO₃, brine, dried over MgSO₄, filtered and concentrated to give a brown foam. Purification by normal phase chromatography gave 215E, Diastereomer A (1.71 g, 41%) as an off-white solid and a mixture of 215E, Diastereomer A and 215F, Diastereomer B (1.4 g). MS(ESI) m/z: 586.3 (M+H)⁺.

215G. tert-Butyl N-[(10R,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate: A dark brown solution of 215E (1.71 g, 2.92 mmol) in EtOAc (97 mL) was degassed with argon for 30 minutes. Next, platinum(IV) oxide (0.066 g, 0.292 mmol) was added and hydrogen gas from a balloon was bubbled through the reaction mixture for several minutes. The reaction was stirred under a hydrogen atmosphere. After 24 h, an additional amount of platinum (IV) oxide (0.192 g, 0.876 mmol) was added and the reaction was stirred under a hydrogen atmosphere. After 21 h, the reaction was stopped. The vessel was purged with vacuum/argon three times, then CELITE® was added, and the reaction was filtered rinsing with EtOAc. The resulting clear, yellow brown filtrate was concentrated to give an off-white solid weighing 1.66 g. Recrystallization from methanol (30 mL) gave 215G (0.575 g, 34%) as a white solid. MS(ESI) m/z: 588.4 (M+H)⁺.

215H. tert-Butyl N-[(10R,14S)-5-amino-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate (Diastereomer A), 2 TFA and 215I. tert-butyl N-[(10S,14S)-5-amino-10-methyl-9-oxo-16-{[2-(trimethylsilyl)ethoxy]methyl}-8,16,18 triazatricyclo [13.2.1.0$^{2,7}$]octadeca-1(17),2,4,6,15(18)-pentaen-14-yl]carbamate (Diastereomer B), 2 TFA: A sealed tube containing a white suspension of 215G (0.100 g, 0.170 mmol) in MeOH (2.84 mL) and 1.0 M NaOH (1.021 mL, 1.021 mmol) was warmed to 75° C. After 2.5 h, additional MeOH (5.6 mL) and 1.0 M NaOH (1.021 mL, 1.021 mmol) were added and the reaction was heated at 75° C. After 16.5 h, additional 1.0 M NaOH (2 mL) was added and the reaction was heated at 75° C. After 21 h, the reaction was stopped and cooled to rt. The reaction was neutralized with 1.0 N HCl and concentrated. The solid was partitioned between EtOAc and saturated NaHCO₃ and the layers were separated. The aqueous layer was extracted with EtOAc. The combined organic layers were washed with brine, dried over sodium sulfate, filtered and concentrated to give a white solid weighing 0.107 g. Purification by reverse phase chromatography gave 215H (Diastereomer A) (0.082 g, 63.6% yield) and 215I (Diastereomer B) (0.025 g, 19%). MS(ESI) m/z: 530.4 (M+H)⁺.

215J. tert-Butyl N-[(10R,14S)-5-{[(2-methoxyethoxy)carbonyl]amino}-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate: To a cooled (0° C.), clear, slightly yellow solution of 215H (0.082 g, 0.108 mmol) in dichloromethane (1.082 mL) and pyridine (0.026 mL, 0.325 mmol) was added 2-methoxyethyl chloroformate (0.013 mL, 0.114 mmol). After 1.5 h, the reaction was diluted with EtOAc and washed with sat. NaHCO₃, brine, dried over sodium sulfate, filtered and concentrated to give 215J (0.062 g, 91% yield) as an off-white solid. MS(ESI) m/z: 632.4 (M+H)⁺. This material was used in the next step without further purification.

215K. 2-Methoxyethyl N-[(10R,14S)-14-amino-10-methyl-9-oxo-8,16,18-triazatricyclo[13.2.1.0$^{2,7}$]octadeca-1(17),2,4,6,15(18)-pentaen-5-yl]carbamate, 2 HCl: A sealed tube containing a clear, slightly yellow solution of 215J (0.062 g, 0.098 mmol) in 4.0 M HCl in dioxane (2.453 mL, 9.81 mmol) was heated at 75° C. After 1 h, the resulting suspension was concentrated to give 215K (0.057 g, 122%) as a dull, yellow solid. MS(ESI) m/z: 402.1 (M+H)⁺. This material was used in the next step without further purification.

Example 215. 2-Methoxyethyl N-[(10R,14S)-14-[1-(3-chloro-2-fluorophenyl)-1H-1,2,3-triazole-4-amido]-10-methyl-9-oxo-8,16,18-triazatricyclo[13.2.1.0$^{2,7}$]octadeca-1(17),2,4,6,15(18)-pentaen-5-yl]carbamate, TFA salt: Example 215 was prepared according to the procedure described in Example 2, by replacing 2M with 215K and by replacing Intermediate 11 with Intermediate 1. ¹H NMR (500 MHz, MeOD) δ 8.91 (d, J=2.2 Hz, 1H), 7.84 (ddd, J=8.1, 6.6, 1.5 Hz, 1H), 7.73 (ddd, J=8.3, 6.8, 1.7 Hz, 1H), 7.58 (d, J=1.9 Hz, 1H), 7.51 (d, J=8.3 Hz, 1H), 7.48 (s, 1H), 7.47-7.40 (m, 2H), 5.41 (dd, J=10.3, 6.7 Hz, 1H), 4.32-4.27 (m, 2H), 3.68-3.63 (m, 2H), 3.39 (s, 3H), 2.82-2.73 (m, 1H), 2.34-2.24 (m, 1H), 2.18-2.08 (m, 1H), 1.82-1.73 (m, 1H), 1.67-1.56 (m, 2H), 1.04 (d, J=7.2 Hz, 3H), 0.78-0.65 (m, 1H). MS(ESI) m/z: 625.1 (M+H)⁺. Analytical HPLC RT=4.92 min (Method D).

Example 216

Methyl N-[(12E,15S)-18-chloro-15-[1-(3-chloro-2-fluorophenyl)-1H-1,2,3-triazole-4-amido]-9-oxo-8,17,19-triazatricyclo[14.2.1.0$^{2,7}$]nonadeca-1(18),2,4,6,12,16(19)-hexaen-5-yl]carbamate, TFA salt

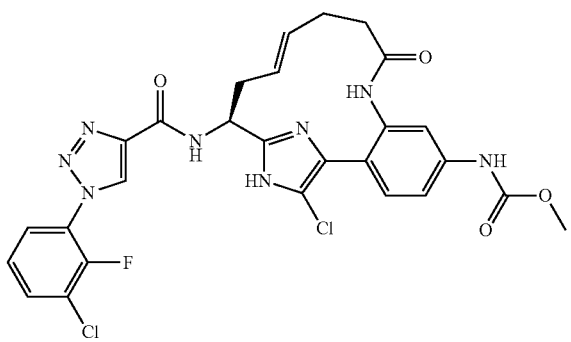 [SMILES: COC(=O)Nc1ccc2c(c1)NC(=O)CC/C=C/C[C@H](NC(=O)c1cn(-c3cccc(Cl)c3F)nn1)c1nc-2c(Cl)[nH]1]

216A. tert-Butyl N-[(12E,15S)-18-chloro-5-[(methoxycarbonyl)amino]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-15-yl]carbamate: A white suspension of 57F (2.56 g, 4.37 mmol) and NCS (0.700 g, 5.24 mmol) in CHCl$_3$ (18.36 mL) and ACN (18.36 mL) was heated to 65° C. After 10 h, the reaction mixture was cooled to rt and partitioned between DCM and water and the layers were separated. The aqueous layer was extracted with DCM (2×). The organic layers were combined, washed with saturated NaHCO$_3$, brine, dried over MgSO$_4$, filtered and concentrated to give a brown foam. The E- and Z-alkene isomers were separated by reverse phase chromatography. The fractions containing the E-alkene isomer were combined, neutralized with a solution of saturated NaHCO$_3$, and then concentrated to give a solid. The solid was partitioned between EtOAc and water and the layers were separated. The organic layer was washed with brine, dried over Na$_2$SO$_4$, filtered and concentrated to give the desired product (1.15 g, 42%) as yellow foam. MS(ESI) m/z: 620.1 (M+H)$^+$.

216B. Methyl N-[(12E,15S)-15-amino-18-chloro-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: To a solution of 216A (0.24 g, 0.387 mmol) in DCM (5 mL) was added TFA (1 mL, 12.98 mmol). The reaction was stirred at rt for 1 h and concentrated. Purification by reverse phase chromatography gave, after neutralization of the fractions with saturated NaHCO$_3$ and concentration, a solid. The solid was partitioned between EtOAc and water and the layers were separated. The organic layer was washed with brine, dried over Na$_2$SO$_4$, filtered and concentrated to give the desired product (0.095 g, 47%) as a white solid. MS(ESI) m/z: 520.1 (M+H)$^+$.

Example 216. Methyl N-[(12E,15S)-18-chloro-15-[1-(3-chloro-2-fluorophenyl)-1H-1,2,3-triazole-4-amido]-9-oxo-8,17,19-triazatricyclo[14.2.1.0$^{2,7}$]nonadeca-1(18),2,4,6,12,16(19)-hexaen-5-yl]carbamate, TFA salt: Example 216 was made in the same way as Example 57 by using 216B and Intermediate 1. $^1$H NMR (400 MHz, MeOD) δ 9.52 (br. s., 1H), 8.84 (dd, J=17.0, 2.2 Hz, 2H), 7.75 (td, J=7.3, 1.4 Hz, 1H), 7.68 (m, 1H), 7.41 (m, 1H), 7.35-7.31 (m, 2H), 5.27 (dd, J=10.7, 6.3 Hz, 1H), 4.51-4.20 (m, 1H), 3.67 (s, 3H), 2.51-2.33 (m, 1H), 2.30-1.92 (m, 2H), 1.67-1.42 (m, 2H), 1.45-1.07 (m, 2H), 0.93 (s, 1H) ppm. MS(ESI) m/z: 613.0 (M+H)$^+$. Analytical HPLC RT=8.53 min (Method A).

Example 217

Methyl N-[(14S)-14-[1-(3-chloro-2-fluorophenyl)-5-methyl-1H-pyrazole-4-amido]-9-oxo-11-oxa-8,16-diazatricyclo[13.3.1.0$^{2,7}$]nonadeca-1(19),2(7),3,5,15,17-hexaen-5-yl]carbamate, TFA salt

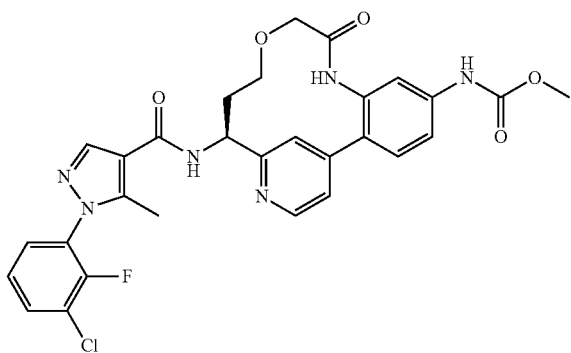 [SMILES: COC(=O)Nc1ccc2c(c1)NC(=O)COCC[C@H](NC(=O)c1cnn(-c3cccc(Cl)c3F)c1C)c1cc-2ccn1]

217A. (S)-1-(4-Chloropyridin-2-yl)but-3-en-1-amine: To (S)-tert-butyl (1-(4-chloropyridin-2-yl)but-3-en-1-yl)carbamate (3 g, 10.61 mmol) was added HCl in dioxane (15 mL, 60.0 mmol) and the reaction was stirred at room temperature for 1 h. The reaction mixture was then concentrated and taken to the next step without further purification. MS(ESI) m/z: 183.1 (M+H)$^+$.

217B. (S)-Benzyl (1-(4-chloropyridin-2-yl)but-3-en-1-yl)carbamate: To a solution of 217A (1.938 g, 10.61 mmol) in MeOH (40 mL) was added benzyl (2,5-dioxopyrrolidin-1-yl) carbonate (2.64 g, 10.61 mmol) followed by DIEA (3.71 mL, 21.22 mmol) and the reaction was stirred at room temperature over night. The mixture was concentrated. The residue was diluted with ethylacetate and washed with brine. The organic layer was dried over MgSO$_4$ and concentrated. The crude product was purified by silica gel chromatography to yield the desired product (3.3 g, 95%) as a yellow solid. MS(ESI) m/z: 317.0 (M+H)$^+$.

217C. (S)-Benzyl (1-(4-chloropyridin-2-yl)-3-oxopropyl)carbamate: (Reference: *J. Org. Chem.*, 58(4):860-866 (1993)) To a solution of 217B (1 g, 3.16 mmol) in MeOH (40 mL) and water (20 mL) was added OsO$_4$ 4 wt % in water (1.350 mL, 0.221 mmol). After 5 min of stirring, a clear tan yellow solution formed. To this solution was then added sodium periodate (2.026 g, 9.47 mmol) with vigorous stirring. The color discharged then gradually a white suspension formed. The reaction mixture was continued to stir at room temperature over night. The reaction mixture was diluted with water (~100 mL) and extracted with EtOAc (3×). The combined organic layers were dried over MgSO$_4$, filtered, and concentrated. The residue was purified by silica gel chromatography to yield the desired product (66%). MS(ESI) m/z: 319.0 (M+H)$^+$.

217D. (S)-Benzyl (1-(4-chloropyridin-2-yl)-3-hydroxypropyl)carbamate: To a solution of 217C (2.2 g, 6.90 mmol) in ethanol (50 mL) was added sodium borohydride (0.522 g, 13.80 mmol) and the reaction was stirred at rt over night. The reaction mixture was then quenched with brine and extracted with EtOAc. The organic layer was concentrated and the residue was purified by silica gel chromatography to yield the desired product (1.58 g, 68%). MS(ESI) m/z: 321.0 (M+H)$^+$.

217E. (S)-tert-Butyl 2-(3-(((benzyloxy)carbonyl)amino)-3-(4-chloropyridin-2-yl)propoxy)acetate: To a mixture of tert-butyl bromoacetate (0.415 mL, 2.81 mmol) and NaH (224 mg, 5.61 mmol) in THF (18 mL) at 0° C. was added a solution of 217D (900 mg, 2.81 mmol) in THF (9 mL) dropwise. The reaction mixture was stirred at 0° C. for additional 1 h and then quenched with saturated NH$_4$Cl. The mixture was extracted with ethylacetate. The organic layer was dried over MgSO$_4$ and concentrated. The residue was purified by silica gel chromatography to isolate the desired product (300 mg, 23%). MS(ESI) m/z: 435.0 (M+H)$^+$.

217F. (S)-tert-Butyl 2-(3-(4-(2-amino-4-nitrophenyl)pyridin-2-yl)-3-(((benzyloxy)carbonyl)amino)propoxy)acetate: Argon was bubbled through a solution of DMSO (8 mL) and water (0.062 mL, 3.45 mmol) for 30 min. Then this solvent mixture was added to a microwave vial containing 217E (300 mg, 0.690 mmol), 2-(5,5-dimethyl-1,3,2-dioxaborinan-2-yl)-5-nitroaniline (345 mg, 1.380 mmol) and phosphoric acid, potassium salt (293 mg, 1.380 mmol). Argon was again bubbled through the deep red solution for 15-20 min. Then 1,1'-bis(diphenylphosphino)ferrocenepalladium(II) dichloride, DCM (56.7 mg, 0.069 mmol) was added and the mixture was stirred at 90° C. for 5 h. The reaction mixture was diluted with ethyl acetate and washed with brine. The organic layer was dried over MgSO$_4$ and concentrated. The residue purified by silica gel chromatography to yield the desired product (170 mg, 43%). MS(ESI) m/z: 537.0 (M+H)$^+$.

217G. (S)-tert-Butyl 2-(3-(((benzyloxy)carbonyl)amino)-3-(4-(2,4-diaminophenyl)pyridin-2-yl)propoxy)acetate: To a solution of 217F (170 mg, 0.317 mmol) in MeOH (8 mL) was added zinc (207 mg, 3.17 mmol) and ammonium chloride (169 mg, 3.17 mmol). The reaction was stirred at rt for 5 h. The reaction mixture was filtered using a 0.45 micron filter and concentrated to give the crude product which was purified by silica gel chromatography to yield the desired product (70 mg, 41%). MS(ESI) m/z: 507.0 (M+H)$^+$.

217H. (S)-tert-Butyl 2-(3-(4-(2-amino-4-((methoxycarbonyl)amino)phenyl)pyridin-2-yl)-3-(((benzyloxy)carbonyl)amino)propoxy)acetate: To a solution of 217G (70 mg, 0.138 mmol) in DCM (5 mL) at −78° C. was added pyridine (0.011 mL, 0.138 mmol) followed by methyl chloroformate (10.70 µL, 0.138 mmol). The reaction was stirred at −78° C. for 1 h and then quenched with saturated ammonium chloride. The mixture was extracted with DCM and EtOAc. The combined organic layer was concentrated and purified by silica gel chromatography to yield the desired product (70 mg, 85%). MS(ESI) m/z: 565.1 (M+H)$^+$.

217I. (S)-2-(3-(4-(2-Amino-4-((methoxycarbonyl)amino)phenyl)pyridin-2-yl)-3-(((benzyloxy)carbonyl)amino)propoxy)acetic acid: 217H (70 mg, 0.124 mmol) was treated with HCl in dioxane (5 mL, 20.00 mmol) at rt under argon for 1 h. The reaction mixture was then concentrated and the crude product was taken to the next step without further purification (56 mg, 84%). MS(ESI) m/z: 509.0 (M+H)$^+$.

217J. Benzyl N-[(14S)-5-[(methoxycarbonyl)amino]-9-oxo-11-oxa-8,16-diazatricyclo[13.3.1.0$^{2,7}$]nonadeca-1(19),2,4,6,15,17-hexaen-14-yl]carbamate: To a round bottom flask was added BOP (41.3 mg, 0.093 mmol), DMAP (19.17 mg, 0.157 mmol) and DIEA (0.046 mL, 0.262 mmol) and DCM (11 mL). The above mixture was kept stirring at room temperature while in a separate round bottom containing 217I (19 mg, 0.037 mmol) was added DIEA (0.046 mL, 0.262 mmol) and DMF (2 mL). The DMF solution was then added to the DCM solution dropwise over a period of 6 h. The reaction was concentrated and the crude product was then purified by reverse phase HPLC to yield the desired product (5.2 mg, 27%). MS(ESI) m/z: 491.0 (M+H)$^+$.

217K. Methyl N-[(14S)-14-amino-9-oxo-11-oxa-8,16-diazatricyclo[13.3.1.0$^{2,7}$]nonadeca-1(19),2,4,6,15,17-hexaen-5-yl]carbamate: To a degassed solution of 217J (1.2 mg, 2.446 µmol) in ethanol (1 mL) was added Pd/C (2.60 mg, 2.446 µmol). The reaction vessel was purged with hydrogen 3 times and then allowed to stir under hydrogen balloon for 2 h. The reaction mixture was filtered through CELITE® eluting with MeOH. The filtrated was concentrated to yield the desired product (0.9 mg, 98%). MS(ESI) m/z: 357.2 (M+H)$^+$.

Example 217. Methyl N-[(14S)-14-[1-(3-chloro-2-fluorophenyl)-5-methyl-1H-pyrazole-4-amido]-9-oxo-11-oxa-8,16-diazatricyclo[13.3.1.0$^{2,7}$]nonadeca-1(19),2(7),3,5,15,17-hexaen-5-yl]carbamate, TFA salt: To a solution of Intermediate 25 (2.59 mg, 10.19 µmol) in DMF (0.5 mL) was added EDC (3.55 mg, 0.019 mmol), HOBT (4.5 mg, 0.019 mmol) and DIEA (0.016 mL, 0.093 mmol). The reaction was stirred at rt for 15 min and added 217K (3.3 mg, 9.26 µmol). The reaction was stirred at rt under argon overnight. The reaction mixture was concentrated and purified by reverse phase HPLC to yield the desired product. $^1$H NMR (50 0 MHz, acetonitrile-d$_3$) δ 8.65 (d, J=5.8 Hz, 1H), 8.60 (s, 1H), 8.20-8.13 (m, 3H), 8.05 (s, 1H), 7.85 (d, J=1.7 Hz, 1H), 7.72-7.64 (m, 2H), 7.61 (d, J=8.5 Hz, 1H), 7.48 (dd, J=8.5, 1.9 Hz, 1H), 7.45-7.39 (m, 1H), 7.37-7.31 (m, 1H), 5.41-5.29 (m, 1H), 4.00 (d, J=12.9 Hz, 1H), 3.77 (s, 1H), 3.68-3.58 (m, 1H), 3.37-3.25 (m, 2H), 2.51-2.38 (m, 3H), 2.36 (s, 3H), 2.25-2.18 (m, 1H) ppm. MS(ESI) m/z: 593.0 (M+H)$^+$. Analytical HPLC RT=6.18 min (Method A).

Example 218

Methyl N-[(14R)-14-[1-(3-chloro-2-fluorophenyl)-5-methyl-1H-pyrazole-4-amido]-9-oxo-12-oxa-8,16,18-triazatricyclo[13.2.1.0$^{2,7}$]octadeca-1(17),2,4,6,15(18)-pentaen-5-yl]carbamate, TFA salt

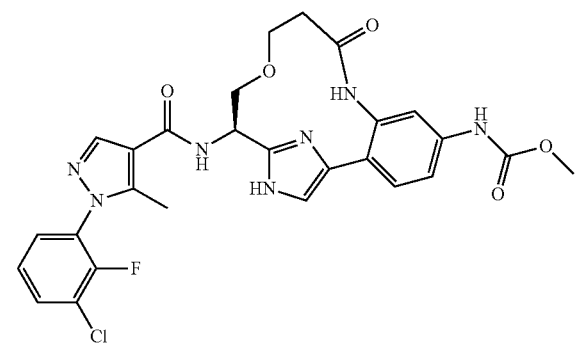 [SMILES: COC(=O)Nc1ccc2c(c1)NC(=O)CCOC[C@H](NC(=O)c1cnn(-c3cccc(Cl)c3F)c1C)c1nc-2c[nH]1]

218A. tert-Butyl N-[(1R)-1-(4-{2-amino-4-[(methoxycarbonyl)amino]phenyl}-1-{[2-(trimethylsilyl)ethoxy]methyl}-1H-imidazol-2-yl)-2-(benzyloxy)ethyl]carbamate: This compound was prepared following the literature procedure (WO 11/100401, Example 10, by replacing (S)-2-(tert-butoxycarbonylamino)pent-4-enoic acid with (S)-3-(benzyloxy)-2-((tert-butoxycarbonyl)amino)propanoic acid. Yellow solid. MS(ESI) m/z: 612.5 (M+H)$^+$.

218B. tert-Butyl N-[(1R)-2-(benzyloxy)-1-(4-{4-[(methoxycarbonyl)amino]-2-(trifluoroacetamido)phenyl}-1-{[2-(trimethylsilyl)ethoxy]methyl}-1H-imidazol-2-yl)ethyl]carbamate: To a solution of 218A (2.035 g, 3.33 mmol) in DCM (107 mL) at 0° C. was added pyridine (0.404 mL, 4.99 mmol), followed by TFAA (0.611 mL, 4.32 mmol). After 30 min, the reaction was stopped and it was washed with saturated NaHCO$_3$, 1 N HCl, brine, dried over magnesium sulfate, filtered and concentrated to give the desired product (2.3 g, 98% yield) as a yellow solid. The material was carried onto the next step without further purification.

218C. tert-Butyl N-[(1R)-2-hydroxy-1-(4-{4-[(methoxycarbonyl)amino]-2-(trifluoroacetamido)phenyl}-1-{[2-(trimethylsilyl)ethoxy]methyl}-1H-imidazol-2-yl)ethyl]carbamate: To the solution of 218B (2.07 g, 2.92 mmol) in EtOH (58.5 mL) was added TFA (0.338 mL, 4.39 mmol). The reaction was stirred at rt for 5 min, then 10% palladium on carbon (0.311 g, 0.292 mmol) was added. Hydrogen was bubbled in for a few minutes, and the reaction was then stirred under a hydrogen balloon for 24 h. The reaction was filtered through a 45 µm GMF filter, rinsing with MeOH. The filtrate was concentrated. The residue was dissolved in EtOAc, washed with saturated NaHCO$_3$, brine, dried over Na$_2$SO$_4$, filtered and concentrated. Purification by silica gel chromatography afforded the desired product (1.61 g, 89%) as a white solid. MS(ESI) m/z: 618.4 (M+H)$^+$. $^1$H NMR (500 MHz, MeOD) δ 8.58 (d, J=2.2 Hz, 1H), 7.68-7.62 (m, 2H), 7.43 (d, J=8.0 Hz, 1H), 5.58 (d, J=10.7 Hz, 1H), 5.46 (d, J=11.0 Hz, 1H), 5.04 (t, J=6.2 Hz, 1H), 3.92 (d, J=6.6 Hz, 2H), 3.77 (s, 3H), 3.65 (t, J=8.1 Hz, 2H), 1.46 (s, 9H), 1.04-0.92 (m, 2H), 0.02 (s, 9H) ppm.

218D. Benzyl 3-[(2R)-2-{[(tert-butoxy)carbonyl]amino}-2-(4-{4-[(methoxycarbonyl)amino]-2-(trifluoroacetamido)

phenyl}-1-{[2-(trimethylsilyl)ethoxy]methyl}-1H-imidazol-2-yl)ethoxy]propanoate, TFA salt: To the solution of 218C (0.054 g, 0.074 mmol), benzyl acrylate (0.575 mL, 3.69 mmol) in THF (0.922 mL) at rt was added benzyltrimethylammonium hydroxide (0.087 mL, 0.221 mmol) (40 wt % in water). The reaction was stirred at rt for 3 days, then it was concentrated. Purification by reverse phase HPLC afforded the desired product (0.013 g, 20%) as a white solid. MS(ESI) m/z: 780.4 (M+H)$^+$. $^1$H NMR (500 MHz, MeOD) δ 8.26 (br. s., 1H), 7.61-7.55 (m, 3H), 7.47 (d, J=7.4 Hz, 1H), 7.34-7.23 (m, 4H), 5.57-5.44 (m, 2H), 5.20-5.15 (m, 1H), 5.08-4.98 (m, 2H), 3.88-3.73 (m, 7H), 3.64 (t, J=8.3 Hz, 2H), 2.61 (t, J=5.9 Hz, 2H), 1.43 (s, 9H), 1.04-0.90 (m, 2H), 0.01 (s, 9H) ppm.

218E. 3-[(2R)-2-(4-{2-Amino-4-[(methoxycarbonyl)amino]phenyl}-1-{[2-(trimethylsilyl)ethoxy]methyl}-1H-imidazol-2-yl)-2-{[(ten-butoxy)carbonyl]amino}ethoxy]propanoic acid, 2 TFA salt: To the solution of 218D (0.013 g, 0.015 mmol) in MeOH (1 mL) was added 1 N NaOH (0.1 mL, 0.100 mmol). The reaction was stirred at 75° C. in a sealed tube. After 7 h, the reaction was cooled to rt and then it was concentrated. Purification by reverse phase HPLC afforded the desired product (0.008 g, 67%) as a yellow solid. MS(ESI) m/z: 594.4 (M+H)$^+$.

218F. tert-Butyl N-[(14R)-5-[(methoxycarbonyl)amino]-9-oxo-16-{[2-(trimethylsilyl)ethoxy]methyl}-12-oxa-8,16,18-triazatricyclo[13.2.1.0$^{2,7}$]octadeca-1(17),2,4,6,15(18)-pentaen-14-yl]carbamate, TFA salt: To the solution of 218E (0.008 g, 9.73 µmol) in DMF (9.73 mL) was added BOP (0.015 g, 0.034 mmol), DMAP (4.16 mg, 0.034 mmol), and DIPEA (8.50 µL, 0.049 mmol). The reaction was stirred at rt for 16 h and then it was concentrated. Purification by reverse phase HPLC afforded the desired product (0.005 g, 75%) as a yellow solid. MS(ESI) m/z: 576.3 (M+H)$^+$. $^1$H NMR (500 MHz, MeOD) δ 7.67 (s, 1H), 7.61 (d, J=1.9 Hz, 1H), 7.53 (d, J=8.5 Hz, 1H), 7.41 (dd, J=8.4, 2.1 Hz, 1H), 5.79 (d, J=11.0 Hz, 1H), 5.59 (d, J=11.0 Hz, 1H), 5.19 (t, J=2.6 Hz, 1H), 4.15 (dd, J=10.5, 2.5 Hz, 1H), 3.99 (dt, J=8.7, 3.5 Hz, 1H), 3.81-3.69 (m, 5H), 3.56-3.48 (m, 1H), 3.42 (dd, J=10.2, 3.0 Hz, 1H), 2.71 (ddd, J=14.5, 11.2, 3.7 Hz, 1H), 2.35 (dt, J=14.3, 2.8 Hz, 1H), 1.43 (s, 9H), 1.13-0.96 (m, 2H), 0.06 (s, 9H) ppm.

218G. Methyl N-[(14R)-14-amino-9-oxo-12-oxa-8,16,18-triazatricyclo[13.2.1.0$^{2,7}$]octadeca-1(17),2,4,6,15(18)-pentaen-5-yl]carbamate, 2 HCl salt: The solution of 218F (0.005 g, 7.25 µmol) in 4 M HCl in 1,4-dioxane (0.5 mL, 2.000 mmol) in a sealed vial was heated at 65° C. After 1 h, the reaction was cooled to rt and then it was concentrated to give the desired product (3 mg, 100% yield) as a yellow solid. MS(ESI) m/z: 346.2 (M+H)$^+$. The material was carried onto the next step without further purification.

Example 218. Methyl N-[(14R)-14-[1-(3-chloro-2-fluorophenyl)-5-methyl-1H-pyrazole-4-amido]-9-oxo-12-oxa-8,16,18-triazatricyclo[13.2.1.0$^{2,7}$]octadeca-1(17),2,4,6,15(18)-pentaen-5-yl]carbamate, TFA salt: Example 218 (0.0021 g, 41% yield, white solid) was prepared according to the procedures described in Example 2 by replacing 2M with 218G and by replacing Intermediate 11 with Intermediate 25. MS(ESI) m/z: 582.2 (M+H)$^+$. $^1$H NMR (500 MHz, MeOD) δ 8.30 (s, 1H), 7.75 (ddd, J=8.3, 6.8, 1.7 Hz, 1H), 7.62 (d, J=1.9 Hz, 1H), 7.56 (d, J=8.5 Hz, 1H), 7.51-7.47 (m, 2H), 7.44-7.39 (m, 2H), 5.34 (dd, J=7.2, 4.4 Hz, 1H), 3.96-3.85 (m, 2H), 3.84-3.77 (m, 5H), 2.67-2.61 (m, 1H), 2.55 (ddd, J=14.4, 6.3, 3.2 Hz, 1H), 2.42 (d, J=0.8 Hz, 3H) ppm. Analytical HPLC RT=5.54 min (Method A).

Example 219

Methyl N-[(14S)-14-[1-(3-chloro-2-fluorophenyl)-5-methyl-1H-pyrazole-4-amido]-9-oxo-10-oxa-8,16-diazatricyclo[13.3.1.0$^{2,7}$]nonadeca-1(19),2,4,6,15,17-hexaen-5-yl]carbamate, TFA salt

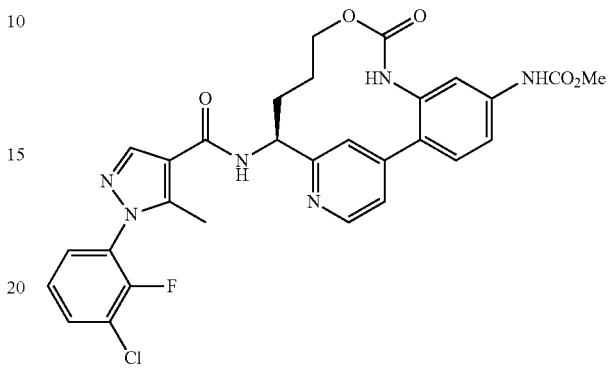

219A. tert-Butyl N-[(1S)-1-(4-{2-amino-4-[(methoxycarbonyl)amino]phenyl}pyridin-2-yl)-4-hydroxybutyl]carbamate: To a solution of 2H (0.110 g, 0.267 mmol) in THF (5 mL) was added 1.0 M borane in THF (0.533 mL, 0.533 mmol). After 3 h, the reaction mixture was cooled with an ice bath. Next, 6 N NaOH (0.089 mL, 0.533 mmol) was slowly added followed by slow addition of H$_2$O$_2$ (0.054 mL, 0.533 mmol). The reaction was allowed to warm to rt. After 1 h, the reaction was extracted with ethyl acetate (20 mL). The organic layer was washed with brine (50 mL), dried over Na$_2$SO$_4$, filtered and concentrated to give a pale yellow oil. Purification by normal phase chromatography gave the desired product (0.150 g, 27%) as a pale yellow semi-solid. MS(ESI) m/z: 431.2 (M+H)$^+$. $^1$H NMR (400 MHz, MeOD) δ 8.49-8.50 (m, 1H), 7.51 (s, 1H), 7.40 (d, J=5.02 Hz, 1H), 7.00-7.14 (m, 2H), 6.83 (dd, J=8.41, 2.13 Hz, 1H), 4.68 (br. s, 1H), 3.75 (s, 3H), 3.54-3.64 (m, 2H), 1.51-2.05 (m, 5H), 1.44 (s, 9H).

219B. To a cooled (0° C.) solution of 219A (0.050 g, 0.116 mol) in DCM (10 mL) and acetonitrile (10 mL) was added phosgene (20% toluene) (0.077 mL, 0.139 mmol). The reaction mixture was allowed to warm to rt. After 1 h, the reaction was concentrated by purging with nitrogen to give a residue. In a separate flask, a solution of TEA (0.113 mL, 0.813 mmol) and DMAP (0.004 g, 0.116 µmol) in DCM (25 mL) was prepared. The above residue was dissolved in DCM (10 mL) and this solution was slowly added over 2 h using a syringe pump to the TEA/DMAP solution. The reaction was concentrated. Purification by silica gel chromatography provided the desired product (0.03 g 57%) as an off white solid. MS(ESI) m/z: 457.2 (M+H)$^+$. $^1$H NMR (300 MHz, MeOD) δ 8.51 (d, J=5.6 Hz, 1H), 7.73 (s, 1H), 7.56-7.59 (m, 1H), 7.18-7.37 (m, 2H), 7.01 (dd, J=8.4, 2.50 Hz, 1H), 6.63 (d, J=8.3 Hz, 1H), 3.77 (s, 3H), 2.30-2.40 (m, 1H), 1.99-2.24 (m, 4H), 1.44 (d, J=42.4 Hz, 2H), 1.20-1.51 (m, 9H).

219C. Methyl N-[(14S)-14-amino-9-oxo-10-oxa-8,16-diazatricyclo[13.3.1.0$^{2,7}$]nonadeca-1(19),2,4,6,15,17-hexaen-5-yl]carbamate, 2TFA: To a stirred solution of 219B (0.026 g, 0.057 mmol) in DCM (5 mL) at 0° C. was added TFA (0.500 mL, 6.49 mmol). The reaction was allowed to warm to rt. After 2 h, the reaction was concentrated and the crude material was washed with diethyl ether (6 mL) and dried to give the desired product (0.015 g, 73%). MS(ESI) m/z: 357.2 (M+H)$^+$. $^1$H NMR (400 MHz, DMSO-d$_6$) δ 9.94 (s, 1H), 9.35 (s, 1H), 8.61 (d, J=5.27 Hz, 1H), 8.29 (br. s, 3H), 7.74 (s, 1H), 7.57-7.59 (m, 1H), 7.48-7.51 (m, 1H), 7.39-7.40 (m, 1H), 7.35 (d, J=1.76 Hz, 1H), 4.71 (br. s, 1H), 3.91-3.94 (m, 1H), 3.69 (s, 3H), 3.66 (s, 1H), 2.11-2.32 (m, 2H), 0.94-1.40 (m, 2H).

Example 219. Methyl N-[(14S)-14-[1-(3-chloro-2-fluorophenyl)-5-methyl-1H-pyrazole-4-amido]-9-oxo-10-oxa-8,16-diazatricyclo[13.3.1.0$^{2,7}$]nonadeca-1(19),2,4,6,15,17-hexaen-5-yl]carbamate, TFA salt: 219C was coupled with Intermediate 25 according to the procedure described in Example 2. An off-white solid (0.019 g, 48%) was obtained. $^1$H NMR (400 MHz, DMSO-d$_6$ with two drops of D$_2$O) δ 8.69 (d, J=5.77 Hz, 1H), 8.24 (s, 1H), 8.11 (s, 1H), 7.76-7.83 (dd, J=6.80 Hz, J=1.60 Hz, 1H), 7.72 (d, J=5.27 Hz, 1H), 7.66 (d, J=8.53 Hz, 1H), 7.48-7.55 (m, 2H), 7.38-7.46 (m, 2H), 5.13 (dd, J=9.20, 6.4 Hz, 1H), 3.96-4.01 (m, 1H), 3.76-3.80 (m, 1H), 3.68 (s, 3H), 2.33 (s, 3H), 2.23-2.26 (m, 2H), 1.42-1.53 (m, 1H), 1.05-1.12 (m 1H). MS(ESI) m/z: 593.2 (M+H)$^+$. Analytical HPLC RT=7.24 min (Method A).

Example 220

Methyl N-[(14S)-14-[1-(3-chloro-2-fluorophenyl)-5-methyl-1H-pyrazole-4-amido]-10-methyl-8-oxo-9,16-diazatricyclo[13.3.1.0$^{2,7}$]nonadeca-1(19),2(7),3,5,15,17-hexaen-5-yl]carbamate, TFA salt

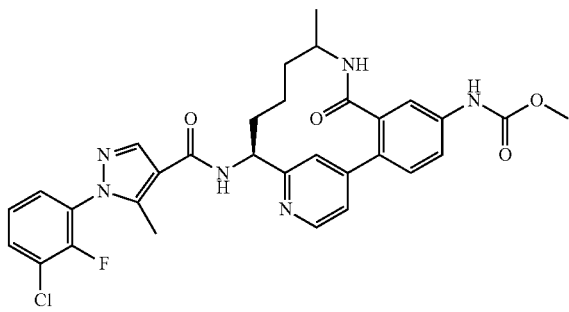 [SMILES: COC(=O)Nc1ccc2c(c1)C(=O)NC(C)CCC[C@H](NC(=O)c1cnn(-c3cccc(Cl)c3F)c1C)c1cc-2ccn1]

220A. (S)-(2-(1-((tert-Butoxycarbonyl)amino)but-3-en-1-yl)pyridin-4-yl)boronic acid, TFA salt: To a solution of 5,5,5',5'-tetramethyl-2,2'-bi(1,3,2-dioxaborinane) (1.198 g, 5.30 mmol) and (S)-tert-butyl (1-(4-chloropyridin-2-yl)but-3-en-1-yl)carbamate (1.0 g, 3.54 mmol) in DMSO (10 mL) was added potassium acetate (1.041 g, 10.61 mmol) and PdCl$_2$(dppf)-CH$_2$Cl$_2$ adduct (0.289 g, 0.354 mmol). The reaction was purged with argon for 10 min. The reaction mixture was then sealed and stirred for 12 h at 85° C. The reaction mixture was cooled to rt and then it was diluted with EtOAc and washed with water. The aqueous layer was extracted with EtOAc. The organic layers was washed with brine, dried over sodium sulfate, filtered, and concentrated. Purification by reverse phase HPLC afforded the desired product (1.1 g, 77%) as a white solid. MS(ESI) m/z: 293.2 (M+H)$^+$. $^1$H NMR (500 MHz, MeOD) δ 8.54 (d, J=5.8 Hz, 1H), 8.11 (s, 1H), 8.02 (dd, J=5.8, 0.6 Hz, 1H), 5.79 (ddt, J=17.1, 10.2, 7.1 Hz, 1H), 5.11-5.03 (m, 2H), 4.86 (t, J=7.0 Hz, 1H), 2.69-2.55 (m, 2H), 1.40 (br. s., 9H) ppm.

220B. (S)-Methyl 2-(2-(1-((tert-butoxycarbonyl)amino)but-3-en-1-yl)pyridin-4-yl)-5-nitrobenzoate: A solution of 220A (0.2 g, 0.492 mmol), methyl 2-bromo-5-nitrobenzoate (0.141 g, 0.542 mmol), Cs$_2$CO$_3$ (0.802 g, 2.462 mmol) in DME (8 mL) and water (1.600 mL) was purged under argon for 5 min, then tetrakis(triphenylphosphine)palladium (0) (0.057 g, 0.049 mmol) was added, and the reaction mixture was heated at 90° C. After 4 h, the reaction was cooled to rt. The reaction mixture was partitioned between water/brine and EtOAc and the layers were separated. The organic layer was washed with brine, dried over Na$_2$SO$_4$, filtered, and concentrated. Purification by silica gel chromatography afforded the desired product (0.176 g, 84%) as a white solid. MS(ESI) m/z: 428.2 (M+H)$^+$. $^1$H NMR (500 MHz, CDCl$_3$) δ 8.78 (d, J=2.5 Hz, 1H), 8.65-8.61 (m, 1H), 8.41 (dd, J=8.4, 2.3 Hz, 1H), 7.51 (d, J=8.3 Hz, 1H), 7.17-7.10 (m, 2H), 5.75-5.58 (m, 2H), 5.11-5.02 (m, 2H), 4.90-4.83 (m, 1H), 3.74 (s, 3H), 2.68-2.59 (m, 2H), 1.44 (s, 9H) ppm.

220C. (S)-Methyl 2-(2-(1-((tert-butoxycarbonyl)amino)but-3-en-1-yl)pyridin-4-yl)-5-((methoxycarbonyl)amino)benzoate: To the solution of 220B (0.33 g, 0.772 mmol) in MeOH (7.72 mL) was added ammonium chloride (0.413 g, 7.72 mmol) and zinc (0.505 g, 7.72 mmol). The reaction was stirred at 55° C. for 5 h. The reaction was cooled to rt, filtered, and the filtrate was concentrated. The residue was partitioned between EtOAc and saturated NaHCO$_3$ and the layers were separated. The organic layer washed with water, brine, dried over Na$_2$SO$_4$, filtered, and concentrated to afford the aniline (0.317 g, 103%) as a yellow solid. MS(ESI) m/z: 398.2 (M+H)$^+$. To a cooled (~78° C.) clear solution of the aniline (0.317 g, 0.798 mmol) and pyridine (0.097 mL, 1.196 mmol) in DCM (7.98 mL) was added dropwise methyl chlorocarbonate (0.074 mL, 0.957 mmol). The reaction was stirred at −78° C. for 1 h, quenched with sat. NH$_4$Cl and then warmed to rt. The reaction was diluted with DCM and water and the layers were separated. The aqueous layer was extracted with DCM. The combined organic layers were washed with saturated NaHCO$_3$, brine, dried over Na$_2$SO$_4$, filtered and concentrated to give a brown foam. Purification by silica gel chromatography afforded the desired product (0.304 g, 84%) as a white solid. MS(ESI) m/z: 456.2 (M+H)$^+$. $^1$H NMR (500 MHz, CDCl$_3$) δ 8.54 (d, J=5.0 Hz, 1H), 7.89 (d, J=2.2 Hz, 1H), 7.72 (d, J=7.4 Hz, 1H), 7.28-7.21 (m, 2H), 7.11 (s, 1H), 7.08 (dd, J=5.2, 1.7 Hz, 1H), 5.74-5.64 (m, 2H), 5.09-5.01 (m, 2H), 4.88-4.81 (m, 1H), 3.81 (s, 3H), 3.66 (s, 3H), 2.67-2.55 (m, 2H), 1.44 (s, 9H) ppm.

220D. (S)-2-(2-(1-((tert-Butoxycarbonyl)amino)but-3-en-1-yl)pyridin-4-yl)-5-((methoxycarbonyl)amino)benzoic acid: To solution of 220C (0.304 g, 0.667 mmol) in MeOH (6.67 mL) was added 1 N NaOH (2.67 mL, 2.67 mmol). The reaction was stirred at rt. After 48 h, the reaction was neutralized with 1 N HCl and then it was concentrated to remove the MeOH. The residue was extracted with EtOAc (2×). The organic layers were combined and washed with brine, dried over Na$_2$SO$_4$, filtered, and concentrated to afford 220D (0.291 g, 99%) as a yellow solid. MS(ESI) m/z: 442.2 (M+H)$^+$. $^1$H NMR (500 MHz, MeOD) δ 8.45 (d, J=5.2 Hz, 1H), 8.01 (d, J=2.2 Hz, 1H), 7.73 (dd, J=8.3, 2.2 Hz, 1H), 7.36 (d, J=1.1 Hz, 1H), 7.30 (d, J=8.5 Hz, 1H), 7.26 (dd, J=5.2, 1.7 Hz, 1H), 5.84-5.74 (m, 1H), 5.14-5.04 (m, 2H), 4.80-4.74 (m, 1H), 3.77 (s, 3H), 2.65-2.45 (m, 2H), 1.42 (s, 9H) ppm.

220E. Methyl N-{3-[(but-3-en-2-yl)carbamoyl]-4-{2-[(1S)-1-{[(ten-butoxy)carbonyl]amino}but-3-en-1-yl]pyridin-4-yl}phenyl}carbamate: To a solution of 220D (0.29 g, 0.657 mmol), but-3-en-2-amine, HCl (0.085 g, 0.788 mmol), EDC (0.252 g, 1.314 mmol) and HOBT (0.201 g, 1.314 mmol) in DMF (5 mL) was added TEA (0.275 mL, 1.971 mmol). The reaction was stirred at rt. After 24 h, the reaction was diluted with EtOAc, washed with water (2×), brine, dried over Na₂SO₄, filtered, and concentrated. Purification by silica gel chromatography afforded the desired product (0.31 g, 95%) as a white solid. MS(ESI) m/z: 495.3 (M+H)⁺. ¹H NMR (500 MHz, CDCl₃) δ 8.54 (d, J=5.2 Hz, 1H), 7.72 (d, J=7.7 Hz, 1H), 7.59 (d, J=1.9 Hz, 1H), 7.30 (d, J=8.5 Hz, 1H), 7.26-7.20 (m, 3H), 5.74-5.54 (m, 3H), 5.35-5.30 (m, 1H), 5.09-4.89 (m, 4H), 4.87-4.81 (m, 1H), 4.60-4.51 (m, 1H), 3.80 (s, 3H), 2.66-2.54 (m, 2H), 1.43 (s, 9H), 1.05-1.01 (m, 3H) ppm.

220F and 220G. Methyl N-[(11E,14S)-14-{[(tert-butoxy)carbonyl]amino}-10-methyl-8-oxo-9,16-diazatricyclo[13.3.1.0²,⁷]nonadeca-1(19),2(7),3,5,11,15,17-heptaen-5-yl]carbamate, Diastereomer A and methyl N-[(11E,14S)-14-{[(tert-butoxy)carbonyl]amino}-10-methyl-8-oxo-9,16-diazatricyclo[13.3.1.0²,⁷]nonadeca-1(19),2(7),3,5,11,15,17-heptaen-5-yl]carbamate, Diastereomer B: The procedure was followed as described for Example 2J/2K, by replacing 21 with 220E. Purification by silica gel chromatography provided 220F (Diastereomer A) (0.073 g, 25%) as a brown solid and 220G (Diastereomer B) (0.052 g, 18%) as a brown solid. Diastereomer A: MS(ESI) m/z: 467.2 (M+H)⁺. Diastereomer B: MS(ESI) m/z: 467.2 (M+H)⁺.

Example 220. Methyl N-[(14S)-14-[1-(3-chloro-2-fluorophenyl)-5-methyl-1H-pyrazole-4-amido]-10-methyl-8-oxo-9,16-diazatricyclo[13.3.1.0²,⁷]nonadeca-1(19),2(7),3,5,15,17-hexaen-5-yl]carbamate, TFA salt: 220F (Diastereomer A) was converted to the title compound in three steps (hydrogenation, Boc-deprotection, and amide formation using Intermediate 25) according to the procedures described in Example 2. A white solid (0.008 g, 38%) was obtained as a homochiral compound. MS(ESI) m/z: 605.3 (M+H)⁺. ¹H NMR (500 MHz, MeOD) δ 8.73 (d, J=6.1 Hz, 1H), 8.30 (s, 1H), 8.04 (dd, J=6.1, 1.9 Hz, 1H), 7.95 (d, J=1.7 Hz, 1H), 7.85-7.78 (m, 2H), 7.75-7.69 (m, 2H), 7.46 (ddd, J=8.0, 6.5, 1.7 Hz, 1H), 7.41-7.35 (m, 1H), 5.23 (dd, J=11.8, 5.5 Hz, 1H), 4.28-4.21 (m, 1H), 3.78 (s, 3H), 2.35 (d, J=0.8 Hz, 3H), 2.27-2.10 (m, 2H), 1.99-1.90 (m, 1H), 1.63-1.53 (m, 1H), 1.37-1.26 (m, 1H), 1.04 (d, J=7.2 Hz, 3H), 0.56-0.44 (m, 1H) ppm. Analytical HPLC RT=6.04 min.

Example 221

Methyl N-[(14S)-14-[1-(3-chloro-2-fluorophenyl)-5-methyl-1H-pyrazole-4-amido]-10-methyl-8-oxo-9,16-diazatricyclo[13.3.1.0²,⁷]nonadeca-1(19),2(7),3,5,15,17-hexaen-5-yl]carbamate, TFA salt

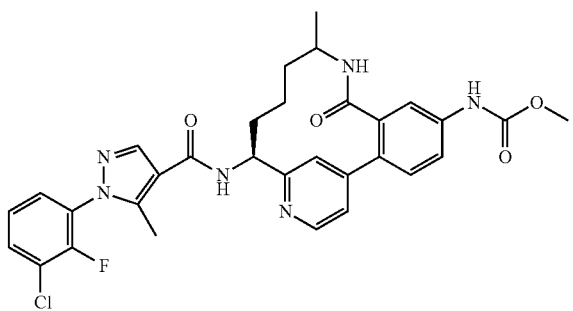 [SMILES: COC(=O)Nc1ccc2c(c1)C(=O)NC(C)CCC[C@H](NC(=O)c1cnn(-c3cccc(Cl)c3F)c1C)c1cc-2ccn1]

Example 221. Methyl N-[(14S)-14-[1-(3-chloro-2-fluorophenyl)-5-methyl-1H-pyrazole-4-amido]-10-methyl-8-oxo-9,16-diazatricyclo[13.3.1.0²,⁷]nonadeca-1(19),2(7),3,5,15,17-hexaen-5-yl]carbamate, TFA salt: 220G (Diastereomer B) was converted to the title compound in three steps (hydrogenation, Boc-deprotection, and amide formation using Intermediate 25) according to the procedures described in Example 2. A white solid (0.005 g, 50%) was obtained as a homochiral compound. MS(ESI) m/z: 5.95 (M+H)⁺. ¹H NMR (500 MHz, MeOD) δ 8.71 (d, J=6.1 Hz, 1H), 8.31 (s, 1H), 8.04 (s, 1H), 7.93 (dd, J=6.1, 1.4 Hz, 1H), 7.75-7.68 (m, 4H), 7.46 (ddd, J=8.0, 6.5, 1.7 Hz, 1H), 7.41-7.36 (m, 1H), 5.23 (dd, J=9.9, 5.2 Hz, 1H), 4.14-4.06 (m, 1H), 3.77 (s, 3H), 2.36 (d, J=1.1 Hz, 3H), 2.12-1.97 (m, 2H), 1.78-1.69 (m, 1H), 1.54-1.20 (m, 6H) ppm. Analytical HPLC RT=5.95 min.

Example 222

Methyl N-[(11R,15S)-15-[1-(3-chloro-2-fluorophenyl)-5-methyl-1H-pyrazole-4-amido]-11-methyl-9-oxo-8,17,19-triazatricyclo[14.2.1.0²,⁷]nonadeca-1(18),2,4,6,16(19)-pentaen-5-yl]carbamate, TFA salt

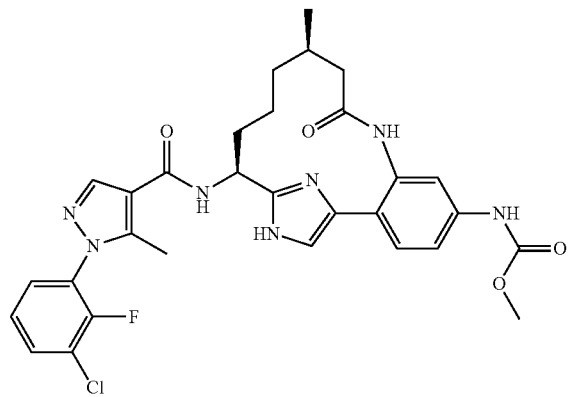 [SMILES: COC(=O)Nc1ccc2c(c1)NC(=O)C[C@H](C)CCC[C@H](NC(=O)c1cnn(-c3cccc(Cl)c3F)c1C)c1nc-2c[nH]1]

222A. tert-Butyl N-[(1S)-1-(4-{4-[(methoxycarbonyl)amino]-2-(3-methylpent-4-enamido)phenyl}-1-{[2-(trimethylsilyl)ethoxy]methyl}-1H-imidazol-2-yl)but-3-en-1-yl]carbamate (mixture of diastereomers): 222A was prepared according to the procedure described in Example 57E, by replacing pent-4-enoic acid with 3-methylpent-4-enoic acid. MS(ESI) m/z: 628.4 (M+H)⁺. ¹H NMR (400 MHz, MeOD) δ 8.45 (d, J=2.01 Hz, 1H), 7.51-7.58 (m, 2H), 7.35 (d, J=7.03 Hz, 1H), 5.80-5.94 (m, 2H), 5.61 (d, J=10.79 Hz, 1H), 5.36 (d, J=11.04 Hz, 1H), 5.20 (s, 1H), 5.04-5.13 (m, 2H), 4.92-5.03 (m, 2H), 3.75 (s, 3H), 3.62 (t, J=8.03 Hz, 2H), 2.73-2.87 (m, 3H), 2.40-2.57 (m, 2H), 1.45 (s, 9H), 1.14 (t, J=6.78 Hz, 3H), 0.96 (td, J=8.03, 5.52 Hz, 2H), -0.01-0.04 (m, 9H).

222B. tert-Butyl N-[(12E,15S)-5-[(methoxycarbonyl)amino]-11-methyl-9-oxo-17-{[2-(trimethylsilyl)ethoxy]methyl}-8,17,19-triazatricyclo[14.2.1.0²,⁷]nonadeca-1(18),2,4,6,12,16(19)-hexaen-15-yl]carbamate and Z-isomer: A flame-dried RBF, equipped with condenser, containing a solution of 222A (1.1 g, 1.752 mmol) and p-toluenesulfonic acid monohydrate (0.367 g, 1.927 mmol) in DCM (1600 mL) was degassed for 1 h with nitrogen. The reaction mixture was refluxed for 1 h under nitrogen atmosphere. Next, a solution of tricyclohexylphosphine[1,3-bis(2,4,6-trimethylphenyl)-4,5-dihydroimidazol-2-ylidene][benzylidene]ruthenium(IV)dichloride (0.596 g, 0.701 mmol) in DCM (15 mL), purged with nitrogen for 10 min, was added slowly. The reaction was stirred overnight at 45° C. The reaction was cooled to rt. The reaction mixture was washed with saturated NaHCO₃ (2×250 mL), brine solution (250 mL), dried by Na₂SO₄, filtered and concentrated to give a gummy brown solid. Purification using silica gel chromatography gave the desired product (0.88 g, 84%) as a brown solid and a mixture of E and Z isomers. MS(ESI) m/z: 600.4 (M+H)⁺.

222C (Diastereomer A). tert-Butyl N-[(11R,15S)-5-[(methoxycarbonyl)amino]-11-methyl-9-oxo-17-{2-(trimethylsilyl)ethoxy]methyl}-8,17,19-triazatricyclo[14.2.1.0$^{2,7}$]nonadeca-1(18),2,4,6,16(19)-pentaen-15-yl]carbamate and 222D (Diastereomer B), tert-butyl N-[(11S,15S)-5-[(methoxycarbonyl)amino]-11-methyl-9-oxo-17-{2-(trimethylsilyl)ethoxy]methyl}-8,17,19-triazatricyclo[14.2.1.0$^{2,7}$]nonadeca-1(18),2,4,6,16(19)-pentaen-15-yl]carbamate To the solution of 222B (2.1 g, 3.50 mmol) in MeOH (100 mL) was added platinum(IV) oxide (0.159 g, 0.700 mmol) and the reaction was stirred at rt under hydrogen atmosphere. After 30 h, the reaction was stopped and filtered through CELITE® washing with methanol (4×50 mL) and ethyl acetate (4×50 mL). The filtrate was concentrated to give a brown solid. The diastereomers were separated by chiral HPLC using Chiral OD-H column to give (Diastereomer A, 0.750 g, 34%) and (Diastereomer B, 0.700 g, 33%). 222C (Diastereomer A): MS(ESI) m/z: 602.2 (M+H)⁺. [α]$^{20.0}_D$=−44.48 (c 0.5, MeOH). ¹H NMR (300 MHz, MeOD) δ 8.11 (d, J=2.17 Hz, 1H), 7.39-7.45 (m, 2H), 7.33-7.38 (m, 1H), 5.50-5.59 (m, 2H), 5.33 (d, J=10.76 Hz, 1H), 3.75 (s, 3H), 3.60 (t, J=8.12 Hz, 2H), 2.36-2.49 (m, 1H), 2.26-2.35 (m, 2H), 2.16-2.25 (m, 1H), 1.82-1.93 (m, 1H), 1.75-1.82 (m, 1H), 1.46 (s, 9H), 1.22-1.33 (m, 1H), 1.07-1.16 (m, 1H), 1.04 (d, J=6.42 Hz, 3H), 0.95 (td, J=8.14, 4.49 Hz, 2H), 0.02 (s, 9H). 222D (Diastereomer B): MS(ESI) m/z: 602.2 (M+H)⁺. [α]$^{20.0}_D$=−66.40 (c 0.5, MeOH). ¹H NMR (400 MHz, DMSO-d₆) δ 12.02 (s, 1H), 9.66 (s, 1H), 8.30 (d, J=2.26 Hz, 1H), 7.65 (s, 1H), 7.43-7.52 (m, 2H), 7.25 (dd, J=8.41, 2.13 Hz, 1H), 5.27-5.39 (m, 2H), 3.67 (s, 3H), 3.50-3.56 (m, 2H), 2.53-2.60 (m, 2H), 2.46 (s, 1H), 2.04-1.95 (m, 2H), 1.93 (dd, J=13.30, 6.02 Hz, 2H), 1.41 (s, 9H), 0.99 (d, J=6.78 Hz, 3H), 0.89 (td, J=8.16, 3.26 Hz, 2H), −0.02 (s, 9H).

222E. Methyl N-[(11R,15S)-15-amino-11-methyl-9-oxo-8,17,19-triazatricyclo[14.2.1.0$^{2,7}$]nonadeca-1(18),2,4,6,16 (19)-pentaen-5-yl]carbamate, 2HCl: A sealed tube containing 222C (0.050 g, 0.083 mmol) in 4 M HCl in dioxane (1.5 mL, 49.4 mmol) was heated at 50° C. for 3 h. The reaction mixture was concentrated to give an off-white solid. Trituration from petroleum ether (3×5 mL) and diethyl ether (2×7 mL) gave the desired product (0.030 g, 97%) as an off white solid. MS(ESI) m/z: 372.2 (M+H)⁺. ¹H NMR (400 MHz, MeOD) δ 7.64 (d, J=7.03 Hz, 2H), 7.44-7.50 (m, 2H), 4.71 (dd, J=11.29, 4.27 Hz, 1H), 3.78 (s, 3H), 3.68 (s, 1H), 2.54 (dd, J=13.68, 2.89 Hz, 1H), 2.38-2.44 (m, 1H), 2.09-2.22 (m, 2H), 1.96-2.04 (m, 1H), 1.79 (d, J=6.27 Hz, 1H), 1.41 (d, J=9.54 Hz, 1H), 1.02 (d, J=6.53 Hz, 3H), 0.74 (d, J=6.78 Hz, 1H).

Example 222. Methyl N-[(11R,15S)-15-[1-(3-chloro-2-fluorophenyl)-5-methyl-1H-pyrazol-4-amido]-11-methyl-9-oxo-8,17,19-triazatricyclo[14.2.1.0$^{2,7}$]nonadeca-1(18),2,4,6,16(19)-pentaen-5-yl]carbamate, TFA salt: 222E was coupled with Intermediate 25 according to the procedure described in Example 2. An off white solid (0.009 g, 14%) was obtained. ¹H NMR (400 MHz, DMSO-d₆ two drops D₂O) δ 8.29-8.32 (m, 1H), 8.18-8.21 (m, 1H), 7.75-7.81 (m, 1H), 7.48-7.54 (m, 2H), 7.40-7.46 (m, 2H), 7.13-7.18 (m, 1H), 5.09 (d, J=12.30 Hz, 1H), 3.64 (s, 3H), 2.37 (s, 3H), 2.24-2.36 (m, 2H), 2.17-2.05 (m, 2H), 1.99-2.10 (m, 2H), 1.78-1.45 (m, 2H), 1.34 (d, J=13.80 Hz, 1H), 0.99 (d, J=6.78 Hz, 3H). MS(ESI) m/z: 608.3 (M+H)⁺. Analytical HPLC RT=6.20 min (Method A).

Example 223

Methyl N-[(10R,14S)-14-[1-(3-chloro-2-fluorophenyl)-5-methyl-1H-1,2,3-triazole-4-amido]-10-methyl-9-oxo-8,17,18-triazatricyclo[13.2.1.0$^{2,7}$]octadeca-1(18),2,4,6,15-pentaen-5-yl]carbamate, TFA salt

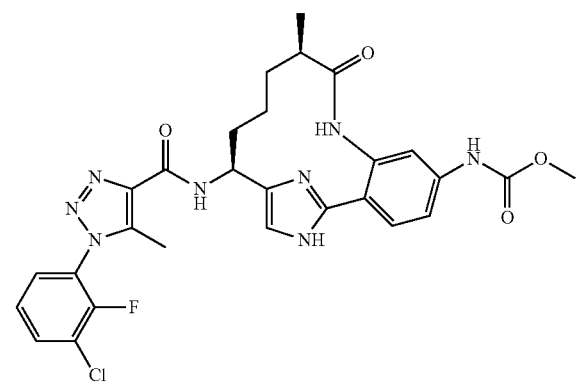 [SMILES: COC(=O)Nc1ccc2c(c1)NC(=O)[C@H](C)CCC[C@H](NC(=O)c1nnn(-c3cccc(Cl)c3F)c1C)c1c[nH]c-2n1]

223A. tert-Butyl N-(1-diazo-2-oxohex-5-en-3-yl)carbamate: To a cooled (−40° C.) solution of 2-((t-butoxycarbonyl) amino)pent-4-enoic acid (15 g, 69.7 mmol) in THF (250 mL) was added N-methylmorpholine (9.19 mL, 84 mmol) followed by the dropwise addition of isobutyl chloroformate (10.98 mL, 84 mmol). The reaction was stirred at −40° C. for 20 min, whereupon it was filtered to remove the salts. The filtrate was added to a solution of diazomethane (4.39 g, 105 mmol) in Et₂O (500 mL) [Generated from 1-methyl-3-nitro-1-nitrosoguanidine]. The reaction mixture was stirred at −40° C. for 3 h and then the reaction was allowed to warm to rt. After 1 h, the reaction was purged with nitrogen for 30 min to remove the excess diazomethane. The reaction mixture was washed with a saturated solution of NaHCO₃ (2×100 mL), water (2×50 mL), brine solution (1×80 mL), dried by Na₂SO₄, filtered and concentrated to give a yellow solid (16 g). Purification by normal phase chromatography afforded the desired product (12.5 g, 75%) as a yellow solid. ¹H NMR (300 MHz, CDCl₃) δ 5.66-5.83 (m, 1H), 5.48 (br. s., 1H), 5.19 (dd, J=3.21, 1.79 Hz, 1H), 5.03-5.16 (m, 2H), 4.24 (br. s., 1H), 2.35-2.62 (m, 2H), 1.46 (s, 9H).

223B. tert-Butyl N-(1-bromo-2-oxohex-5-en-3-yl)carbamate: To a cooled (−15° C.) suspension of 223A (15 g, 62.7 mmol) in diethyl ether (500 mL) was added dropwise HBr (~47% in water) (18.11 mL, 157 mmol). After 15 min., the reaction was allowed to warm slowly to 0° C. over 2.5 h. The reaction was diluted with diethyl ether (100 mL) and the reaction was washed with water (2×100 mL), saturated solution of NaHCO₃ (1×80 mL), brine solution (1×80 mL), dried by Na₂SO₄, filtered and concentrated to give the desired product (17 g, 93%) as a viscous yellow liquid which solidified in the refrigerator. ¹H NMR (400 MHz, CDCl₃) δ 5.62-5.76 (m, 1H), 5.12-5.21 (m, 2H), 5.08 (br. s., 1H), 4.57 (d, J=6.00 Hz, 1H), 3.99-4.12 (m, 2H), 2.38-2.67 (m, 2H), 1.43 (s, 9H).

223C. tert-Butyl N-[1-(1H-imidazol-4-yl)but-3-en-1-yl] carbamate: A pressure tube containing a solution of 223B (28 g, 96 mmol), formamidine acetate (19.95 g, 192 mmol) and K$_2$CO$_3$ (53.0 g, 383 mmol) in DMF (200 mL) was heated at 100° C. overnight. The reaction mixture was cooled to rt and concentrated. The residue was partitioned between water (200 mL) and ethyl acetate (500 mL) and the layers were separated. The aqueous layer was extracted with ethyl acetate (2×200 mL). The organic layers were combined and washed with brine (1×100 mL), dried by Na$_2$SO$_4$, filtered and concentrated to give the desired product (25.5 g, 84%) as a gummy brown solid. This was used in the next step without purification. MS(ESI) m/z: 238.2 (M+H)$^+$.

223D. tert-Butyl N-[1-(1-{[2-(trimethylsilyl)ethoxy]methyl}-1H-imidazol-4-yl)but-3-en-1-yl]carbamate: To a cooled (0° C.) solution of 223C (25.5 g, 107 mmol) in THF (260 mL) was added sodium hydride (4.73 g, 118 mmol). Following the addition, the reaction was allowed to warm to rt. After 30 min., the reaction was cooled to 0° C. and SEM-Cl (19.06 mL, 107 mmol) was added dropwise. The reaction was allowed to warm to rt and stirred overnight. The reaction mixture was concentrated to give a brown gummy solid. Purification by normal phase chromatography gave the desired product (11.5 g, 70%) as a gummy, brown solid. MS(ESI) m/z: 368.4 (M+H)$^+$. $^1$H NMR (400 MHz, CDCl$_3$) δ 7.51 (d, J=1.25 Hz, 1H), 6.87 (s, 1H), 5.71 (dd, J=17.13, 10.13 Hz, 1H), 5.20 (s, 2H), 4.99-5.10 (m, 3H), 4.73 (dd, J=13.88, 6.38 Hz, 1H), 3.43-3.48 (m, 2H), 2.55-2.63 (m, 2H), 1.43 (s, 9H), 0.86-0.91 (m, 2H), 0.02-0.03 (m, 9H).

223E. tert-Butyl N-[1-(2-bromo-1-{[2-(trimethylsilyl)ethoxy]methyl}-1H-imidazol-4-yl)but-3-en-1-yl]carbamate: To a cooled (−78° C.) solution of 223D (5.0 g, 13.60 mmol) in THF (100 mL) was added dropwise nBuLi (1.6 M in hexanes) (25.5 mL, 40.8 mmol). After 2 h, N-bromosuccinimide (2.421 g, 13.60 mmol) was added. After 2 h, the reaction mixture was quenched with a solution of saturated NH$_4$Cl (30 mL). The reaction mixture extracted with ethyl acetate (3×50 mL). The organic layers were combined and washed with brine (1×50 mL), dried by Na$_2$SO$_4$, filtered and concentrated to give a gummy yellow solid. Purification by normal phase chromatography gave the desired product (2.0 g, 26.5%) as a gummy, brown solid. MS(ESI) m/z: 446.0 (M+H)$^+$. $^1$H NMR (300 MHz, CDCl$_3$) δ 6.95 (s, 1H), 5.63-5.78 (m, 1H), 5.22 (s, 2H), 5.02-5.14 (m, 3H), 4.64-4.74 (m, 1H), 3.50-3.57 (m, 2H), 2.58 (t, J=6.61 Hz, 2H), 1.44 (s, 9H), 0.89-0.96 (m, 2H), 0.01 (s, 9H).

223F. tert-Butyl N-[(1S)-1-[2-(2-amino-4-nitrophenyl)-1-{[2-(trimethylsilyl)ethoxy]methyl}-1H-imidazol-4-yl]but-3-en-1-yl]carbamate (Enantiomer I) and 223G. tert-Butyl N-[(1R)-1-[2-(2-amino-4-nitrophenyl)-1-{[2-(trimethylsilyl)ethoxy]methyl}-1H-imidazol-4-yl]but-3-en-1-yl]carbamate (Enantiomer II): To a solution of 223E (3 g, 6.72 mmol) and (2-(2-amino-4-nitrophenyl)-5-methyl-1,3,2-dioxaborinan-5-yl)methylium (5.02 g, 20.16 mmol) in toluene (40 mL) was added phosphoric acid, potassium salt (4.28 g, 20.16 mmol) and water (10 mL). The reaction mixture was purged with nitrogen for 15 min. Next, PdCl$_2$(dppf)-CH$_2$Cl$_2$ adduct (0.274 g, 0.336 mmol) was added and the reaction was heated at 110° C. After 3 h, the reaction was cooled to rt. The reaction mixture was diluted with ethyl acetate (80 mL) and then it was washed with saturated NaHCO$_3$ (50 mL), water (50 mL), brine (50 mL), dried over Na$_2$SO$_4$, filtered and concentrated to give a gummy brown solid. Purification by normal phase chromatography gave a gummy brown solid. The enantiomers were separated by chiral HPLC using CHIRALPAK® AD-H 250×21 mm column (mobile phase: CO$_2$:80%, solvent: 20% (0.5% DEA in Methanol)) to give 223F (Enantiomer I, 0.42 g, 13%) and 223G (Enantiomer II, 0.545 g, 16%). 223F (Enantiomer I): MS(ESI) m/z: 503.9 (M+H)$^+$. $^1$H NMR (400 MHz, DMSO-d$_6$ with two drops D$_2$O) δ 7.56-7.62 (m, 2H), 7.39 (dd, J=8.53, 2.51 Hz, 1H), 7.20 (s, 1H), 5.65-5.75 (m, 1H), 5.23 (s, 2H), 4.95-5.08 (m, 2H), 4.55 (d, J=8.53 Hz, 1H), 3.40 (t, J=8.03 Hz, 2H), 2.32-2.49 (m, 2H), 1.33 (s, 9H), 0.69-0.77 (m, 2H), −0.14 (s, 9H). 223G (Enantiomer II): MS(ESI) m/z: 503.9 (M+H)$^+$. $^1$H NMR (400 MHz, DMSO-d$_6$ with two drops D$_2$O) δ 7.60-7.64 (m, 2H), 7.38 (dd, J=8.78, 2.26 Hz, 1H), 7.22 (s, 1H), 5.66-5.77 (m, 1H), 5.24 (s, 2H), 4.95-5.09 (m, 2H), 4.57 (d, J=8.53 Hz, 1H), 3.44 (t, J=8.03 Hz, 2H), 2.32-2.48 (m, 2H), 1.35 (s, 9H), 0.73-0.80 (m, 2H), −0.11 (s, 9H).

223H. tert-Butyl N-[(1S)-1-(2-{2-[(2R)-2-methylbut-3-enamido]-4-nitrophenyl}-1-{[2-(trimethylsilyl)ethoxy]methyl}-1H-imidazol-4-yl)but-3-en-1-yl]carbamate: To a cooled (0° C.) solution of 223F (0.650 g, 1.291 mmol) in DCM (10 mL) was added pyridine (0.313 mL, 3.87 mmol) followed by DMAP (0.015 g, 0.129 mmol). Next, freshly prepared Intermediate 48 (0.383 g, 3.23 mmol) in DCM (0.5 mL) was added dropwise. After 20 min, the reaction was concentrated. Purification by normal phase chromatography provided the desired product (0.740 g, 98%) as a yellow oil. MS(ESI) m/z: 586.5 (M−H). $^1$H NMR (300 MHz, MeOD) δ 9.34 (t, J=1.37 Hz, 1H), 8.05 (d, J=1.32 Hz, 2H), 7.35 (s, 1H), 6.98 (d, J=8.12 Hz, 1H), 5.76-6.04 (m, 2H), 5.36 (m, 2H), 5.04-5.26 (m, 4H), 4.80 (d, J=6.66 Hz, 1H), 3.65 (t, J=7.8 Hz, 2H), 3.25-3.30 (m, 1H), 2.64-2.79 (m, 1H), 2.50-2.61 (m, 1H), 1.46 (s, 9H), 1.32 (d, J=6.9, 3H), 0.93 (t, J=8.1 Hz, 3H), 0.01 (s, 9H).

223I. tert-Butyl N-[(10R,11E,14S)-10-methyl-5-nitro-9-oxo-17-{[2-(trimethylsilyl)ethoxy]methyl}-8,17,18-triazatricyclo[13.2.1.0$^{2,7}$]octadeca-1(18),2,4,6,11,15-hexaen-14-yl]carbamate: A flame-dried 3 neck 1 L RBF containing the solution of 223H (0.42 g, 0.717 mmol) and p-toluenesulfonic acid monohydrate (0.15 g, 0.789 mmol) in DCM (700 mL) was purged with argon for 1 h. Next, the reaction was warmed to reflux. After 1 h, a solution of tricyclohexylphosphine[1,3-bis(2,4,6-trimethylphenyl)-4,5-dihydroimidazol-2-ylidene][benzylidine]ruthenium(IV)dichloride (0.244 g, 0.287 mmol) in DCM (6 mL) was added dropwise. The reaction was allowed to stir at reflux overnight. The reaction mixture was cooled to rt, washed with saturated NaHCO$_3$ (2×80 mL), brine (80 mL), dried by Na$_2$SO$_4$, filtered and concentrated to give a gummy brown solid. Purification by normal phase chromatography afforded the title compound (0.225 gm, 56%) as a gummy, yellow solid. MS(ESI) m/z: 558.5 (M+H)$^+$. $^1$H NMR (400 MHz, CDCl$_3$) δ 12.80 (br. s., 1H), 9.33 (br. s., 1H), 7.94-8.04 (m, 2H), 6.99 (d, J=8.00 Hz, 1H), 6.01-5.25 (m, 1H), 5.19-5.27 (m, 4H), 5.14 (d, J=7.50 Hz, 2H), 3.64-3.73 (m, 2H), 3.60 (m, 2H), 1.54 (s, 9H), 0.94-1.01 (m, 3H), 0.00 (s, 9H).

223J. tert-Butyl N-[(10R,14S)-5-amino-10-methyl-9-oxo-17-{[2-(trimethylsilyl)ethoxy]methyl}-8,17,18-triazatricyclo[13.2.1.0$^{2,7}$]octadeca-1(18),2(7),3,5,15-pentaen-14-yl]carbamate: A solution of 223I (0.210 g, 0.377 mmol) in EtOAc (20 mL) was purged with nitrogen and vacuum. This was repeated 3 times. Next, platinum(IV) oxide (0.043 g, 0.188 mmol) was added and the reaction was purged with H$_2$ gas for several minutes (H$_2$ filled in balloon). The reaction was stirred vigorously under a hydrogen atmosphere. After 16 h, the reaction was diluted with methanol (5 mL) and then it was filtered through CELITE® bed, washing with methanol (2×5 mL). The filtrate was concentrated to give 223J (0.200 g, 95%) as a white solid. MS(ESI) m/z: 530.2

(M+H)+. 1H NMR (400 MHz, CDCl3) δ 12.15 (br. s., 1H), 7.56 (d, J=8.51 Hz, 1H), 7.48 (d, J=2.25 Hz, 1H), 6.86 (s, 1H), 6.46 (dd, J=8.50, 2.50 Hz, 1H), 5.09-5.18 (m, 3H), 5.29-5.12 (m, 1H), 3.90-3.60 (m, 2H), 3.55-3.62 (m, 2H), 2.45-1.90 (m, 1H), 1.86-1.97 (m, 2H), 1.66-1.78 (m, 3H), 1.47 (s, 9H), 1.26 (s, 2H), 0.92-0.98 (m, 3H), 0.01 (s, 9H).

223K. tert-Butyl N-[(10R,14S)-5-[(methoxycarbonyl)amino]-10-methyl-9-oxo-17-{[2-(trimethylsilyl)ethoxy]methyl}-8,17,18-triazatricyclo[13.2.1.0$^{2,7}$]octadeca-1(18),2(7),3,5,15-pentaen-14-yl]carbamate: To the cooled (0° C.) solution of 223J (0.195 g, 0.368 mmol) in DCM (5 mL) was added pyridine (0.045 mL, 0.552 mmol) followed by the dropwise addition of methyl chloroformate (0.043 mL, 0.552 mmol). After 10 min., the reaction was allowed to warm to rt. After 1 h, the reaction was diluted with DCM (30 mL) and then it was washed with saturated NaHCO3 (2×20 mL), brine (20 mL), dried by Na2SO4, filtered and concentrated to give a gummy brown solid. Purification by normal phase chromatography provided the title compound (0.145 g, 67%) as a yellow solid. MS(ESI) m/z: 588.2 (M+H)+. 1H NMR (400 MHz, MeOD) δ 7.71 (d, J=8.53 Hz, 1H), 7.64 (s, 1H), 7.44 (dd, J=8.28, 2.26 Hz, 1H), 7.12 (s, 1H), 5.19-5.27 (m, 2H), 3.78 (s, 3H), 3.64-3.73 (m, 2H), 2.58 (t, J=6.27 Hz, 1H), 2.01-2.11 (m, 1H), 1.76 (dt, J=6.40, 3.58 Hz, 2H), 1.52-1.62 (m, 2H), 1.47 (s, 9H), 1.35-1.41 (m, 2H), 1.07 (d, J=7.03 Hz, 3H), 0.99 (dt, J=8.91, 6.59 Hz, 2H), 0.05 (s, 9H).

223L. Methyl N-[(10R,14S)-14-amino-10-methyl-9-oxo-8,17,18-triazatricyclo[13.2.1.0$^{2,7}$]octadeca-1(18),2(7),3,5,15-pentaen-5-yl]carbamate: To a solution of 223K (0.030 g, 0.051 mmol) in DCM (1 mL) was added TFA (1 mL, 12.98 mmol). After 1 h, additional TFA (0.4 mL) was added. After 1 h, the reaction was concentrated to give a white solid. Petroleum ether (5 mL) was added and the mixture was stirred. The solvent was removed with a dropper. This was repeated with diethyl ether (2×7 mL) and the solid was dried under high vacuum to give the desired product (0.040 g, 93%) as a white solid. MS(ESI) m/z: 358.4 (M+H)+. 1H NMR (400 MHz, MeOD) δ 7.68 (d, J=2.01 Hz, 1H), 7.62 (d, J=8.53 Hz, 1H), 7.50-7.55 (m, 1H), 7.39 (s, 1H), 4.63 (dd, J=8.78, 5.77 Hz, 1H), 3.79 (s, 3H), 2.17-2.30 (m, 1H), 1.81-1.95 (m, 2H), 1.65-1.80 (m, 2H), 1.34-1.55 (m, 2H), 1.12 (d, J=7.03 Hz, 3H).

Example 223. Methyl N-[(10R,14S)-14-[1-(3-chloro-2-fluorophenyl)-5-methyl-1H-1,2,3-triazole-4-amido]-10-methyl-9-oxo-8,17,18-triazatricyclo[13.2.1.0$^{2,7}$]octadeca-1(18),2,4,6,15-pentaen-5-yl]carbamate, TFA salt: To a solution of 223L (0.010 g, 0.028 mmol) in DMF (1.0 mL) was added Intermediate 21 (0.0071 g, 0.028 mmol), EDC (0.0085 mg, 0.042 mmol), HOBT (0.0064 mg, 0.042 mmol) and Hunig's base (0.024 mL, 0.140 mmol). The reaction was stirred at rt overnight. The reaction was concentrated to give a gummy solid. Purification by reverse phase HPLC afforded the title compound (2.8 mg, 13%) as an off-white solid. 1H NMR (400 MHz, MeOD) δ 7.79-7.79 (m, 2H), 7.58-7.66 (m, 2H), 7.46-7.53 (m, 2H), 7.13 (s, 1H), 5.37 (t, J=4.52 Hz, 1H), 3.78 (s, 3H), 2.68 (m, 1H), 2.54 (d, J=1.00 Hz, 3H), 2.18-2.25 (m, 2H), 2.00-2.09 (m, 2H), 1.63 (m, 2H), 1.23 (d, J=7.03 Hz, 3H). MS(ESI) m/z: 593.0 (M+H)+. Analytical HPLC RT=6.38 min.

Example 224

Methyl N-[(10S,14S)-14-[1-(3-chloro-2-fluorophenyl)-5-methyl-1H-1,2,3-triazole-4-amido]-10-methyl-9-oxo-8,17,18-triazatricyclo[13.3.1.0$^{2,7}$]nonadeca-1(19),2,4,6,15,17-hexaen-5-yl]carbamate, TFA salt

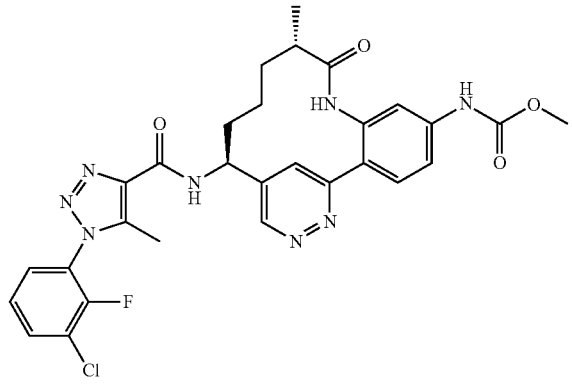 [SMILES: COC(=O)Nc1ccc2c(c1)NC(=O)[C@@H](C)CCC[C@H](NC(=O)c1nnn(-c3cccc(Cl)c3F)c1C)c1cnnc-2c1]

224A. tert-Butyl N-[(3,6-dichloropyridazin-4-yl)methyl]carbamate: A mixture of 3,6-dichloropyridazine (0.765 g, 5.14 mmol) in water (25 mL) was heated to 75° C. 2-((tert-Butoxycarbonyl)amino)acetic acid (1 g, 5.71 mmol) and ammonium formate (0.072 g, 1.142 mmol) were added. Then, a solution of silver nitrate (0.194 g, 1.142 mmol) in water (1 mL) was added dropwise over 2 min. To the resulting dark brown solution was added dropwise a solution of ammonium persulfate (5.21 g, 22.83 mmol) in water (30 mL) over 25 min. A purple precipitate formed. The reaction mixture was stirred for additional 40 min, and then cooled to rt. The reaction mixture was poured onto ice, basified with aq. ammonia, keeping the temperature below 5° C. The reaction mixture was extracted with ethyl acetate and the organic layer was dried over sodium sulfate, filtered and concentrated. Purification by normal phase chromatography afforded the desired product (0.3 g, 18%) as an off-white solid. MS(ESI) m/z: 278.1 (M+H)+. 1H NMR (300 MHz, CDCl3) δ 7.51 (s, 1H), 5.15 (br. s., 1H), 4.40 (s, 2H), 1.49 (s, 9H).

224B. tert-Butyl N-[1-(3,6-dichloropyridazin-4-yl)but-3-en-1-yl]carbamate: To a cooled (−78° C.) solution of 224A (2 g, 7.19 mmol) in tetrahydrofuran (25 mL) was added TMEDA (3.2 mL, 21.20 mmol). To the resulting light green color solution was added dropwise n-butyllithium (1.6 M in hexane) (25.2 mL, 40.3 mmol). Following the addition, the reaction was allowed to warm to −40° C. over 30 min. The reaction was cooled to −78° C. and then allyl bromide (2.7 mL, 31.2 mmol) was added dropwise. After 1 h, the reaction was quenched with the addition of saturated ammonium chloride (25 mL) and the reaction was warmed to rt. The reaction mixture was diluted with ethyl acetate, washed with 1 N HCl (15 mL), saturated sodium bicarbonate (15 mL), brine (15 mL), dried over Na2SO4, filtered, and concentrated. Purification by normal phase chromatography gave the desired product (0.93 g, 41%) as a buff colored solid. MS(ESI) m/z: 318.2 (M+H)+. 1H NMR (400 MHz, MeOD) δ 7.76-7.76 (m, 1H), 5.85-5.86 (m, 1H), 5.17 (d, J=1.00 Hz, 2H), 4.88-4.88 (m, 1H), 2.55-2.57 (m, 1H), 2.41-2.43 (m, 1H), 1.42-1.44 (m, 9H).

224C. tert-Butyl N-[(1S)-1-[6-(2-amino-4-nitrophenyl)-3-chloropyridazin-4-yl]but-3-en-1-yl]carbamate (Enantiomer I) and 224D. tert-Butyl N-[(1R)-1-[6-(2-amino-4-nitrophenyl)-3-chloropyridazin-4-yl]but-3-en-1-yl]carbamate (Enantiomer II): A mixture of 224B (0.5 g, 1.571 mmol) in toluene (10 mL) and ethanol (1 mL) was degassed using nitrogen gas. Next, 2-(5,5-dimethyl-1,3,2-dioxaborinan-2-yl)-5-nitroaniline (0.452 g, 1.807 mmol) and sodium carbonate (0.500 g, 4.71 mmol) were added. The reaction mixture was degassed with nitrogen for 10 min. Then, tetrakis(triphenylphosphine)palladium(0) (0.082 g, 0.071 mmol) was added and the reaction was heated to 100° C. After 16 h, the reaction was cooled to rt and filtered through a plug of CELITE®. The filtrate was washed with water, brine, dried over $Na_2SO_4$, filtered, and concentrated. Purification by normal phase chromatography gave the desired product (0.2 g, 30%) as a pale yellow solid. The enantiomers were separated by chiral HPLC using CHIRALCEL® OJ-H to give 224C (Enantiomer I) as a pale yellow solid and 224D (Enantiomer II) as a pale yellow solid. 224C (Enantiomer I): (ESI) m/z: 420.2 (M+H)$^+$. $^1$H NMR (300 MHz, MeOD) δ 8.11 (s, 1H), 7.72-7.79 (m, 2H), 7.54 (dd, J=8.73, 2.31 Hz, 1H), 5.83-5.95 (m, 1H), 5.14-5.20 (m, 2H), 5.01 (br. s, 1H), 2.41-2.71 (m, 2H), 1.39-1.49 (m, 9H). $[α]^{20}_D$=−62 (c 0.1, MeOH). 224D (Enantiomer II): MS(ESI) m/z: 420.2 (M+H)$^+$. $^1$H NMR (300 MHz, MeOD) δ 8.11 (s, 1H), 7.74-7.76 (m, 2H), 7.54 (dd, J=8.69, 2.36 Hz, 1H), 5.81-5.95 (m, 1H), 5.14-5.20 (m, 2H), 4.96-5.06 (m, 1H), 2.14-2.43 (m, 2H), 1.39-1.50 (m, 9H). $[α]^{20}_D$=78.4 (c 0.1, MeOH).

224E. tert-Butyl N-[(1S)-1-{3-chloro-6-[2-(2-methylbut-3-enamido)-4-nitrophenyl]pyridazin-4-yl}but-3-en-1-yl]carbamate: To a cooled (0° C.) solution of 224C (0.1 g, 0.238 mmol) in dichloromethane (1 mL) and pyridine (0.058 mL, 0.715 mmol) was added Intermediate 48 (0.031 g, 0.262 mmol). The reaction was allowed to warm to rt. After 35 min., the reaction was concentrated. Purification by normal phase chromatography afforded the desired product (0.1 g, 84%) as a pale yellow semi solid. MS(ESI) m/z: 502.2 (M+H)$^+$. $^1$H NMR (300 MHz, DMSO-d$_6$) δ 10.63-10.64 (d, J=6.03 Hz, 1H), 8.93-8.95 (m, 1H), 8.17-8.19 (m, 2H), 7.92-7.93 (m, 1H), 7.70-7.71 (m, 1H), 5.87-5.91 (m, 1H), 5.13-5.20 (m, 4H), 4.99-5.11 (m, 1H), 3.19-3.22 (m, 1H), 2.51-2.53 (m, 1H), 2.45-2.49 (m, 1H), 1.72-1.79 (m, 1H), 1.36-1.51 (m, 9H), 1.27 (d, J=6.73 Hz, 3H).

224F. tert-Butyl N-[(1S)-1-{6-[4-amino-2-(2-methylbut-3-enamido)phenyl]-3-chloropyridazin-4-yl}but-3-en-1-yl]carbamate: A mixture of 224E (0.24 g, 0.478 mmol) in acetic acid (5 mL) and water (1.667 mL) was heated to 70° C. under $N_2$. Next, finely powdered iron (0.134 g, 2.391 mmol) was added. After 30 min, the reaction was cooled to rt and filtered through CELITE®. The filtrate was neutralized with 10% NaOH solution. The mixture was extracted with DCM. The organic layer was washed with brine, dried over $Na_2SO_4$, filtered, and concentrated. The crude product was washed with diethyl ether (2×5 mL) and dried to give the desired product (0.19 g, 84%) as a pale pink solid. This material was used in the next step without further purification. MS(ESI) m/z: 502.2 (M+H)$^+$. $^1$H NMR (400 MHz, DMSO-d$_6$) δ 11.61-11.63 (d, J=7.21 Hz, 1H), 8.07-8.32 (m, 1H), 7.65-7.69 (m, 2H), 7.46-7.48 (m, 1H), 6.46-6.48 (m, 1H), 5.80-5.88 (m, 4H), 5.20-5.24 (m, 1H), 5.12-5.14 (m, 3H), 4.99-5.10 (m, 1H), 3.19-3.22 (m, 1H), 2.51-2.53 (m, 1H), 2.45-2.49 (m, 1H), 1.72-1.79 (m, 1H), 1.36 (s, 9H), 1.27 (m, 3H).

224G. tert-Butyl N-[(1S)-1-(3-chloro-6-{4-[(methoxycarbonyl)amino]-2-(2-methylbut-3-enamido)phenyl}pyridazin-4-yl)but-3-en-1-yl]carbamate: To a cooled (−60° C.) solution of 224F (0.06 g, 0.127 mmol) in DCM (4 mL) was added pyridine (0.011 mL, 0.140 mmol). Next, a solution of methyl chloroformate (9.85 μL, 0.127 mmol) in DCM was added dropwise. After 30 min, the reaction was diluted with DCM and washed with saturated sodium bicarbonate, brine, dried over $Na_2SO_4$, filtered, and concentrated. Purification by normal phase chromatography gave the desired product (0.021 g, 31%) as a pale pink solid. MS(ESI) m/z: 530.2 (M+H)$^+$. $^1$H NMR (400 MHz, DMSO-d$_6$) δ 10.83-10.84 (d, J=7.21 Hz, 1H), 9.96 (s, 1H), 8.27 (s, 1H), 8.07 (s, 1H), 7.70-7.71 (m, 1H), 7.61-7.63 (dd, J=8.28, 6.90 Hz, 1H), 7.48-7.51 (m, 1H), 5.77-5.92 (m, 2H), 5.12-5.20 (m, 4H), 4.92-5.10 (m, 1H), 3.70 (s, 3H), 3.14-3.18 (m, 1H), 2.45-2.50 (m, 2H), 1.72-1.79 (m, 1H), 1.36 (s, 9H), 1.27 (d, J=7.03 Hz, 3H).

224H. Methyl N-[(11E,14S)-14-{[(tert-butoxy)carbonyl]amino}-16-chloro-10-methyl-9-oxo-8,17,18-triazatricyclo[13.3.1.0$^{2,7}$]nonadeca-1(19),2(7),3,5,11,15,17-heptaen-5-yl]carbamate: A solution of 224G (0.1 g, 0.189 mmol) in 1,2-dichloroethane (40 mL) was degassed with argon for 25 mins Next, Grubbs II (0.064 g, 0.075 mmol) was added and the reaction was heated at 120° C. under microwave conditions for 30 min. The reaction mixture was filtered through CELITE®, and the filtrate was washed with saturated sodium bicarbonate, brine, dried over $Na_2SO_4$, filtered and concentrated. Purification by normal phase chromatography gave 224H (0.02 g, 22%) as an off white solid. MS(ESI) m/z: 501.2 (M+H)$^+$. $^1$H NMR (300 MHz, DMSO-d$_6$) δ 9.98 (s, 1H), 7.9-8.01 (m, 2H), 7.79-7.85 (m, 1H), 7.74 (s, 1H), 7.34-7.4 (m, 2H), 5.82-5.93 (m, 1H), 5.68-5.79 (m, 1H), 4.94-5.06 (m, 1H), 3.71 (s, 3H), 3.20-3.29 (m, 1H), 2.38-0.63 (m, 2H), 1.30 (s, 9H), 0.90-0.97 (m, 3H).

224I. Methyl N-[(10S,14S)-14-{[(tert-butoxy)carbonyl]amino}-10-methyl-9-oxo-8,17,18-triazatricyclo[13.3.1.0$^{2,7}$]nonadeca-1(19),2(7),3,5,15,17-hexaen-5-yl]carbamate: A mixture of 224H (0.025 g, 0.050 mmol) and ammonium formate (0.001 mg, 0.025 mmol) in methanol (10 mL) was purged with $N_2$ for 10 min. Next, Pd/C (0.042 g, 0.398 mmol) was added to the reaction. After 16 h, the reaction was filtered through CELITE® and the filtrate was concentrated. The crude material was washed with diethyl ether (2×5 mL) and dried to give the desired product (0.019 g, 81%) as a black solid. MS(ESI) m/z: 470.2 (M+H)$^+$.

224J. Methyl N-[(10S,14S)-14-amino-10-methyl-9-oxo-8,17,18-triazatricyclo[13.3.1.0$^{2,7}$]nonadeca-1(19),2,4,6,15,17-hexaen-5-yl]carbamate: To a cooled (0° C.) solution of 224I (0.027 g, 0.058 mmol) in DCM (3 mL) was added TFA (0.250 mL, 3.24 mmol). The reaction was allowed to warm to rt. After 2 h, the reaction was concentrated. The crude material was washed with diethyl ether (2×3 mL), ethyl acetate (2×5 mL), DCM (5×15 mL) and dried to give the desired product (0.018 g, 52%) as a reddish brown solid. MS(ESI) m/z: 370.6 (M+H)$^+$.

Example 224. Methyl N-[(10S,14S)-14-[1-(3-chloro-2-fluorophenyl)-5-methyl-1H-1,2,3-triazole-4-amido]-10-methyl-9-oxo-8,17,18-triazatricyclo[13.3.1.0$^{2,7}$]nonadeca-1(19),2,4,6,15,17-hexaen-5-yl]carbamate, TFA salt: To a solution of 224J (0.018 g, 0.049 mmol) in DMF (1 mL) was added Intermediate 21 (0.012 g, 0.049 mmol), HOBT (0.011 g, 0.073 mmol), EDC (0.014 g, 0.073 mmol), and DIPEA (0.043 mL, 0.244 mmol). The reaction mixture was stirred at rt overnight. The reaction was concentrated to give a gummy solid. Purification by reverse phase HPLC provided the desired product (3.5 mg, 12%) as an off white solid. $^1$H NMR (400 MHz, DMSO-d$_6$) δ 9.96 (s, 1H), 9.59 (s, 1H), 9.35 (d, J=7.53 Hz, 1H), 9.23 (d, J=1.76 Hz, 1H), 8.32 (s, 1H), 7.95 (ddd, J=8.28, 6.90, 1.63 Hz, 1H), 7.69-7.78 (m, 1H), 7.86 (d, J=8.53 Hz, 1H), 7.49-7.60 (m, 2H), 7.44 (d, J=2.0 Hz, 1H), 4.99-5.11 (m, 1H), 3.71 (s, 3H), 2.40 (s, 3H), 2.26 (dd, J=15.56, 7.53 Hz, 1H), 1.89-2.04 (m, 2H), 1.63-1.75 (m, 1H), 1.46-1.57 (m, 1H), 1.30-1.43 (m, 2H), 1.13 (d, J=7.03 Hz, 3H). MS(ESI) m/z: 607.2 (M+H)$^+$. Analytical HPLC RT=8.40 min (Method A).

The following Examples in Table 12 were made by using coupling acids with amines. The acids used are as indicated in the below table in the Intermediate section. Various coupling reagents could be used other than the one described in Example 34 like BOP, PyBop, EDC/HOBt, HATU or T3P. Boc and SEM deprotection was achieved when necessary.

TABLE 12

| Example # | Stereochemistry | Structure | M + H | RT, min Method |
|---|---|---|---|---|
| 225 | Homochiral | 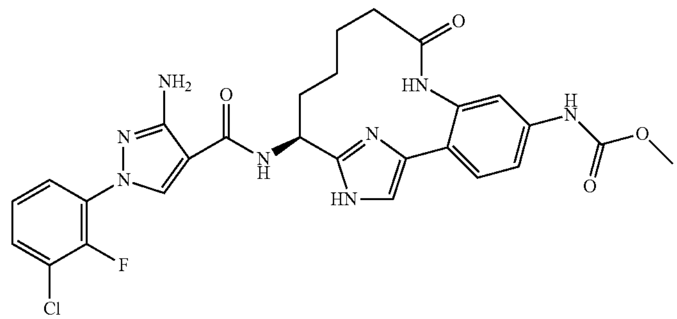 [SMILES: COC(=O)Nc1ccc2c(c1)NC(=O)CCCC[C@H](NC(=O)c1cn(-c3cccc(Cl)c3F)nc1N)c1nc-2c[nH]1] | 581.2 | 4.63 D |
| 226 | Homochiral | 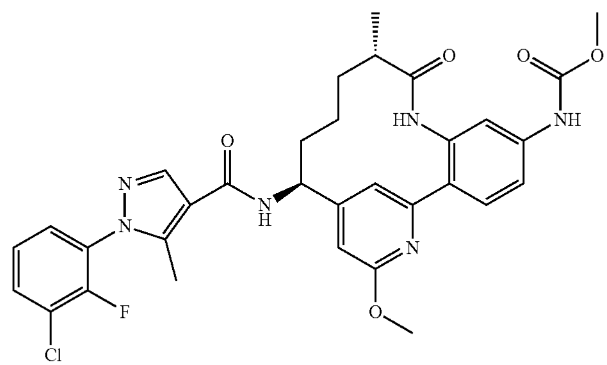 [SMILES: COC(=O)Nc1ccc2c(c1)NC(=O)[C@@H](C)CCC[C@H](NC(=O)c1cnn(-c3cccc(Cl)c3F)c1C)c1cc(OC)nc-2c1] | 635.6 | 8.42 A |
| 227 | Homochiral | 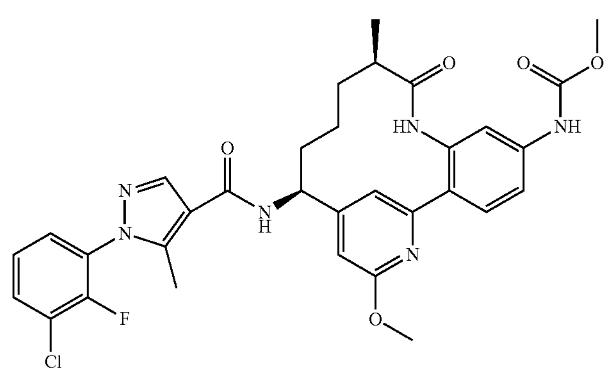 [SMILES: COC(=O)Nc1ccc2c(c1)NC(=O)[C@H](C)CCC[C@H](NC(=O)c1cnn(-c3cccc(Cl)c3F)c1C)c1cc(OC)nc-2c1] | 635.6 | 8.22 A |

TABLE 12-continued

| Example # | Stereochemistry | Structure | M + H | RT, min Method |
|---|---|---|---|---|
| 228 | Homochiral | 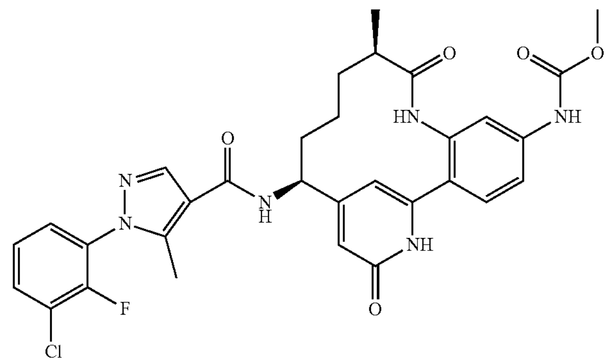 [SMILES: COC(=O)Nc1ccc2c(c1)NC(=O)[C@H](C)CCC[C@H](NC(=O)c1cnn(-c3cccc(Cl)c3F)c1C)c1cc-2[nH]c(=O)c1] | 621.6 | 7.10 A |
| 229 | Homochiral | 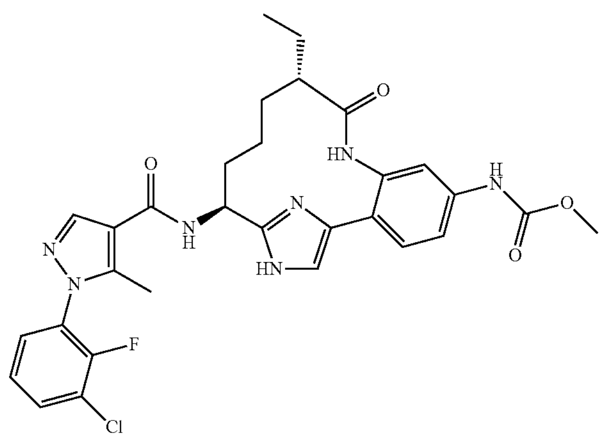 [SMILES: CC[C@H]1CCC[C@H](NC(=O)c2cnn(-c3cccc(Cl)c3F)c2C)c2nc(c[nH]2)-c2ccc(NC(=O)OC)cc2NC1=O] | 608.3 | 6.00 A |
| 230 | Homochiral | 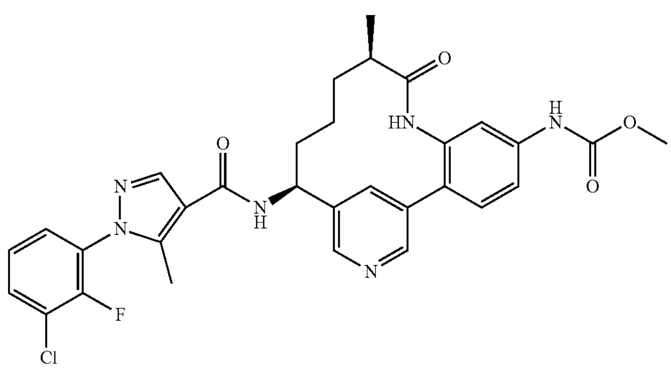 [SMILES: COC(=O)Nc1ccc2c(c1)NC(=O)[C@H](C)CCC[C@H](NC(=O)c1cnn(-c3cccc(Cl)c3F)c1C)c1cncc-2c1] | 606.3 | 6.13 A |
| 231 | Diastereomer mixture | 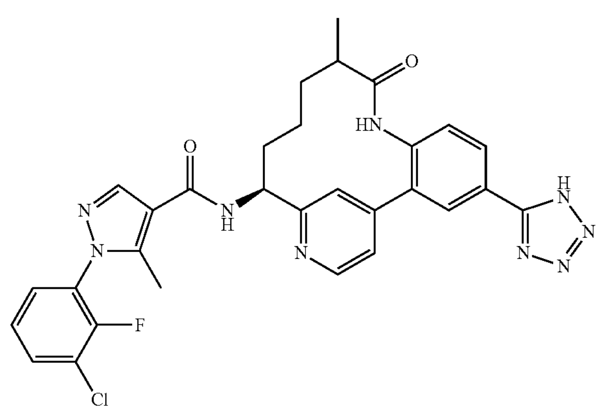 [SMILES: Cc1c(C(=O)N[C@H]2CCCC(C)C(=O)Nc3ccc(-c4nnn[nH]4)cc3-c3ccnc2c3)cnn1-c1cccc(Cl)c1F] | 600.1 | 5.99 A |

TABLE 12-continued

| Example # | Stereochemistry | Structure | M + H | RT, min Method |
|---|---|---|---|---|
| 232 | Homochiral | 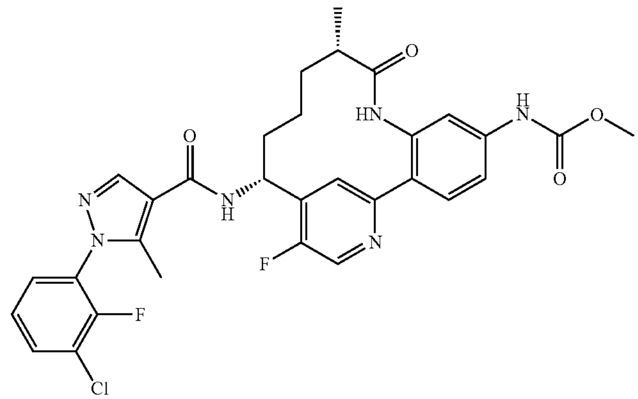 [SMILES: COC(=O)Nc1ccc2c(c1)NC(=O)[C@@H](C)CCC[C@@H](NC(=O)c1cnn(-c3cccc(Cl)c3F)c1C)c1cc-2ncc1F] | 623.0 | 8.15 A |
| 233 | Homochiral | 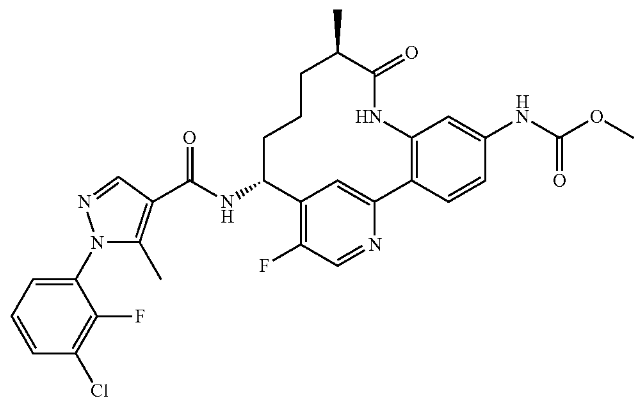 [SMILES: COC(=O)Nc1ccc2c(c1)NC(=O)[C@H](C)CCC[C@@H](NC(=O)c1cnn(-c3cccc(Cl)c3F)c1C)c1cc-2ncc1F] | 623.0 | 8.02 A |
| 234 | Homochiral | 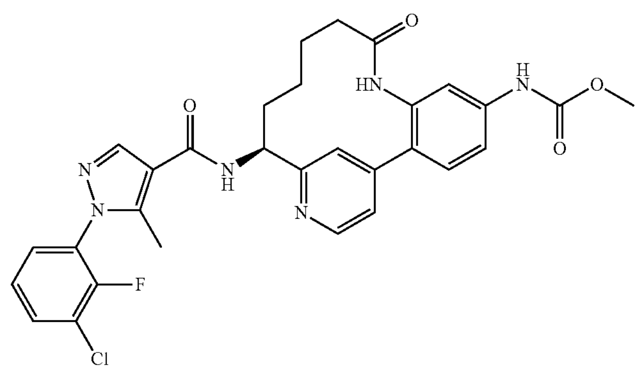 [SMILES: COC(=O)Nc1ccc2c(c1)NC(=O)CCCC[C@H](NC(=O)c1cnn(-c3cccc(Cl)c3F)c1C)c1cc-2ccn1] | 591.0 | 5.91 A |
| 235 | Homochiral | 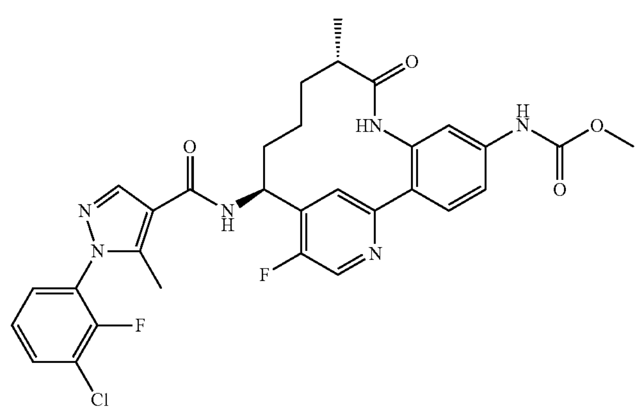 [SMILES: COC(=O)Nc1ccc2c(c1)NC(=O)[C@@H](C)CCC[C@H](NC(=O)c1cnn(-c3cccc(Cl)c3F)c1C)c1cc-2ncc1F] | 622.9 | 8.66 A |

TABLE 12-continued

| Example # | Stereochemistry | Structure | M + H | RT, min Method |
|---|---|---|---|---|
| 236 | Homochiral | 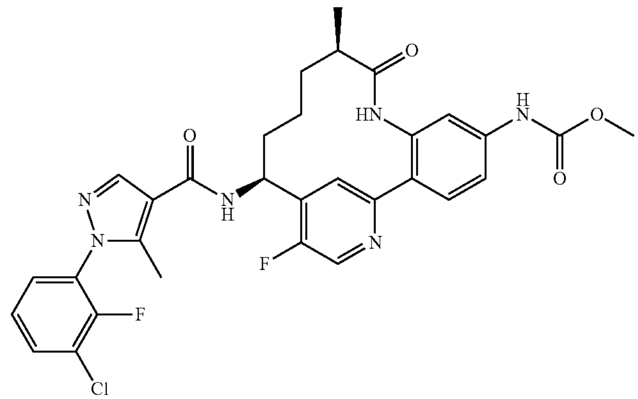 [SMILES: COC(=O)Nc1ccc2c(c1)NC(=O)[C@H](C)CCC[C@H](NC(=O)c1cnn(-c3cccc(Cl)c3F)c1C)c1cc-2ncc1F] | 622.9 | 8.79 A |
| 237 | Homochiral | 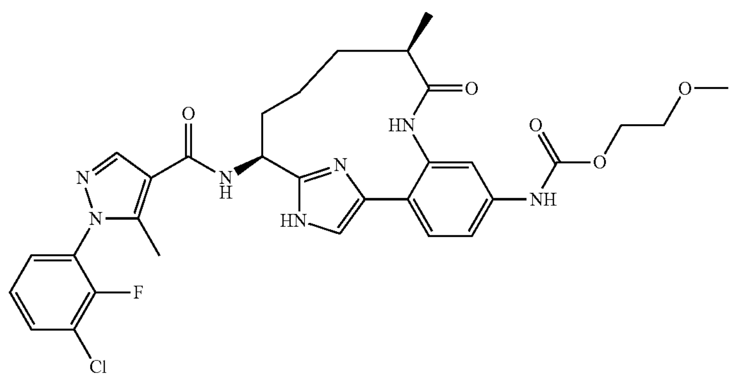 [SMILES: COCCOC(=O)Nc1ccc2c(c1)NC(=O)[C@H](C)CCC[C@H](NC(=O)c1cnn(-c3cccc(Cl)c3F)c1C)c1nc-2c[nH]1] | 638.3 | 5.95 A |
| 238 | Homochiral | 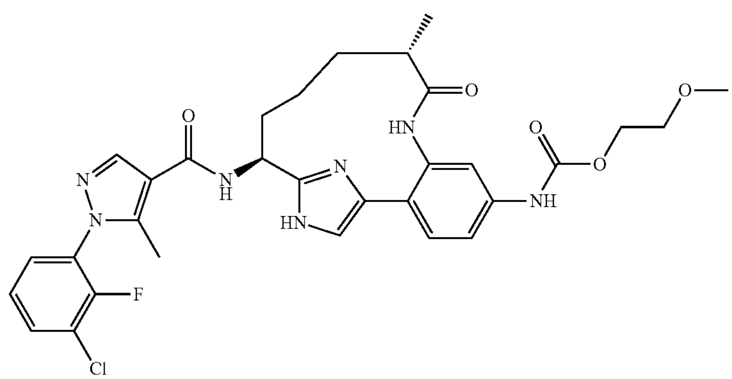 [SMILES: COCCOC(=O)Nc1ccc2c(c1)NC(=O)[C@@H](C)CCC[C@H](NC(=O)c1cnn(-c3cccc(Cl)c3F)c1C)c1nc-2c[nH]1] | 638.3 | 6.00 A |
| 239 | Homochiral | 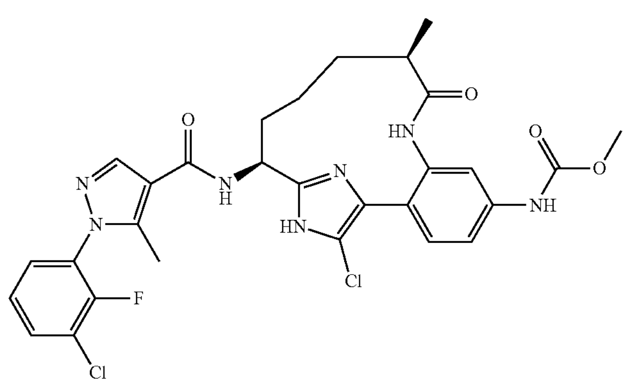 [SMILES: COC(=O)Nc1ccc2c(c1)NC(=O)[C@H](C)CCC[C@H](NC(=O)c1cnn(-c3cccc(Cl)c3F)c1C)c1nc-2c(Cl)[nH]1] | 628.2 | 7.54 A |

TABLE 12-continued
| Example # | Stereochemistry | Structure | M + H | RT, min Method |
|---|---|---|---|---|
| 240 | Homochiral | 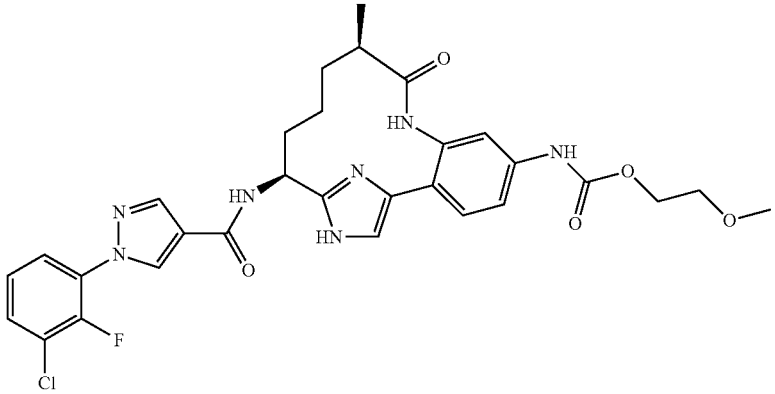 [SMILES: COCCOC(=O)Nc1ccc2c(c1)NC(=O)[C@H](C)CCC[C@H](NC(=O)c1cnn(-c3cccc(Cl)c3F)c1)c1nc-2c[nH]1] | 624.3 | 6.70 A |
| 241 | Homochiral | 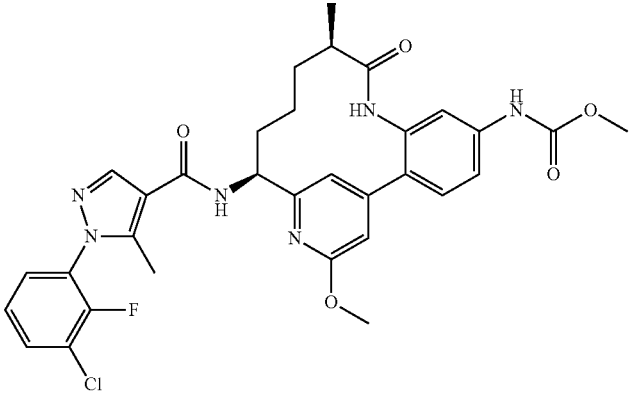 [SMILES: COC(=O)Nc1ccc2c(c1)NC(=O)[C@H](C)CCC[C@H](NC(=O)c1cnn(-c3cccc(Cl)c3F)c1C)c1cc-2cc(OC)n1] | 634.9 | 6.85 A |
| 242 | Homochiral | 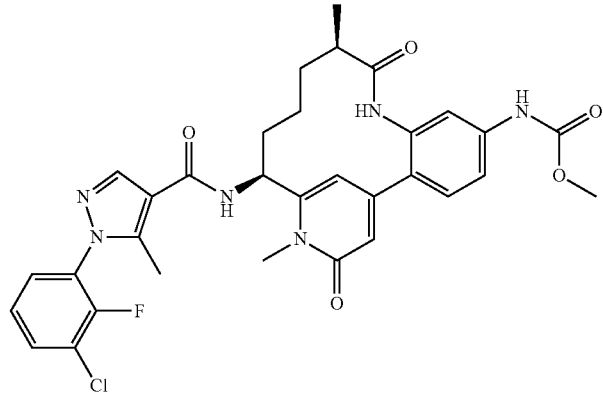 | 635.0 | 6.25 B |
| 243 | Homochiral | 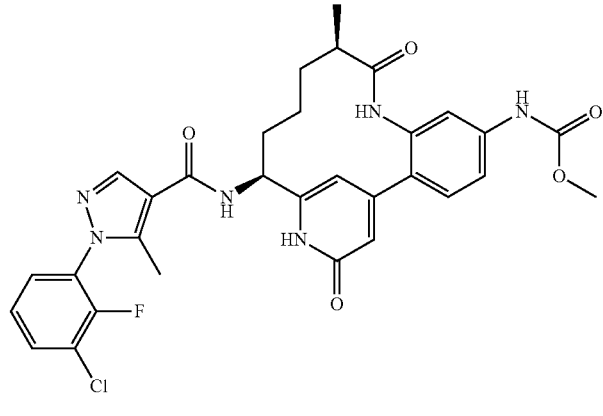 [SMILES: COC(=O)Nc1ccc2c(c1)NC(=O)[C@H](C)CCC[C@H](NC(=O)c1cnn(-c3cccc(Cl)c3F)c1C)c1cc-2cc(=O)[nH]1] | 621.1 | 4.99 A |

TABLE 12-continued
| Example # | Stereochemistry | Structure | M + H | RT, min Method |
|---|---|---|---|---|
| 244 | Homochiral | 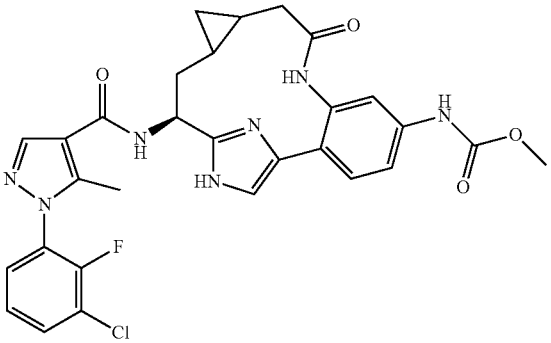 [SMILES: COC(=O)Nc1ccc2c(c1)NC(=O)CC1CC1C[C@H](NC(=O)c1cnn(-c3cccc(Cl)c3F)c1C)c1nc-2c[nH]1] | 591.9 | 5.24 A |
| 245 | Homochiral | 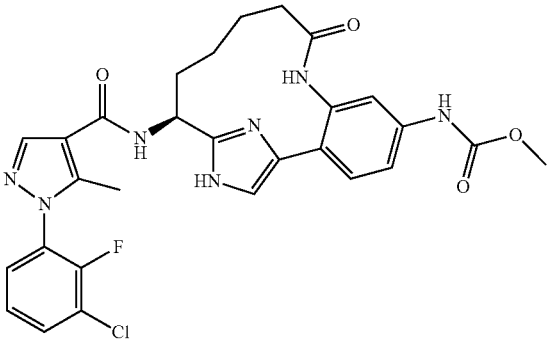 [SMILES: COC(=O)Nc1ccc2c(c1)NC(=O)CCCC[C@H](NC(=O)c1cnn(-c3cccc(Cl)c3F)c1C)c1nc-2c[nH]1] | 579.9 | 5.24 A |
| 246 | Homochiral | 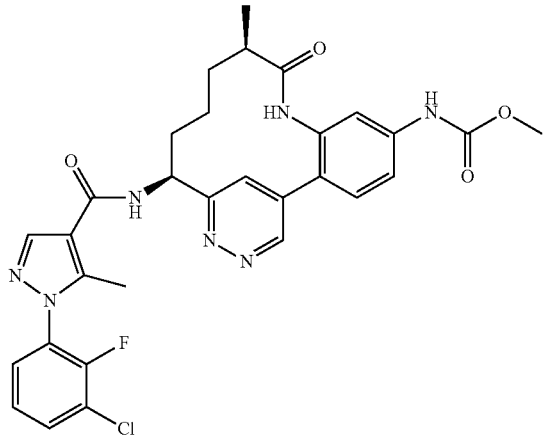 [SMILES: COC(=O)Nc1ccc2c(c1)NC(=O)[C@H](C)CCC[C@H](NC(=O)c1cnn(-c3cccc(Cl)c3F)c1C)c1cc-2cnn1] | 606.3 | 8.15 A |
| 247 | Homochiral | 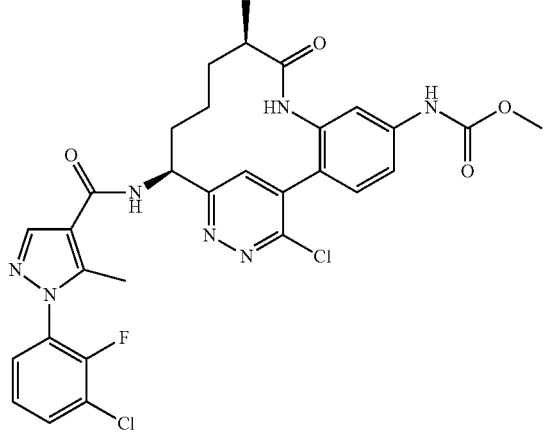 [SMILES: COC(=O)Nc1ccc2c(c1)NC(=O)[C@H](C)CCC[C@H](NC(=O)c1cnn(-c3cccc(Cl)c3F)c1C)c1cc-2c(Cl)nn1] | 640.2 | 9.86 A |

TABLE 12-continued

| Example # | Stereochemistry | Structure | M + H | RT, min Method |
|---|---|---|---|---|
| 248 | Homochiral | 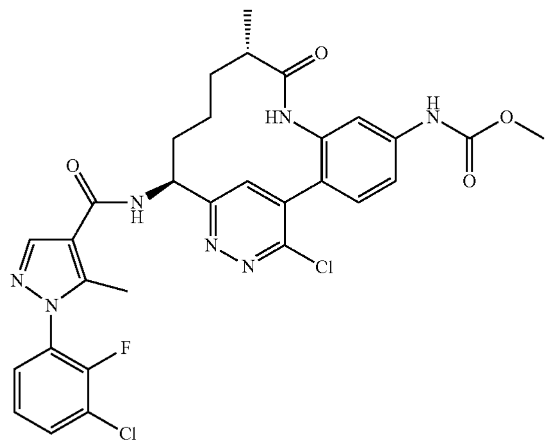 [SMILES: COC(=O)Nc1ccc2c(c1)NC(=O)[C@@H](C)CCC[C@H](NC(=O)c1cnn(-c3cccc(Cl)c3F)c1C)c1cc-2c(Cl)nn1] | 640.3 | 9.70 A |
| 249 | Homochiral | 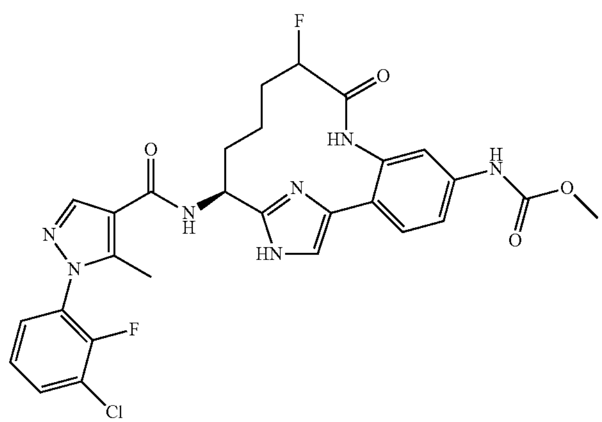 [SMILES: COC(=O)Nc1ccc2c(c1)NC(=O)C(F)CCC[C@H](NC(=O)c1cnn(-c3cccc(Cl)c3F)c1C)c1nc-2c[nH]1] | 598.0 | 5.30 A |
| 250 | Homochiral | 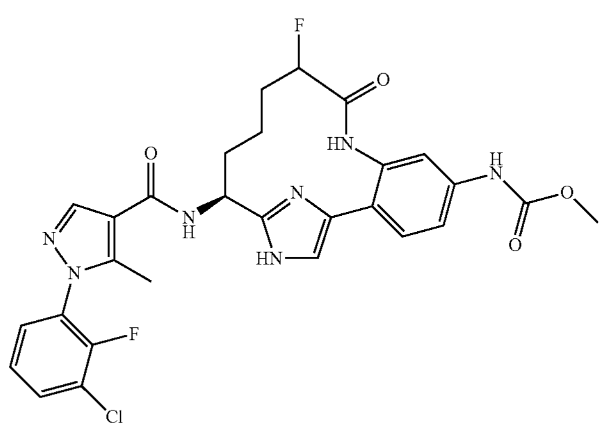 [SMILES: COC(=O)Nc1ccc2c(c1)NC(=O)C(F)CCC[C@H](NC(=O)c1cnn(-c3cccc(Cl)c3F)c1C)c1nc-2c[nH]1] | 598.1 | 6.28 A |

TABLE 12-continued

| Example # | Stereochemistry | Structure | M + H | RT, min Method |
|---|---|---|---|---|
| 251 | Homochiral | 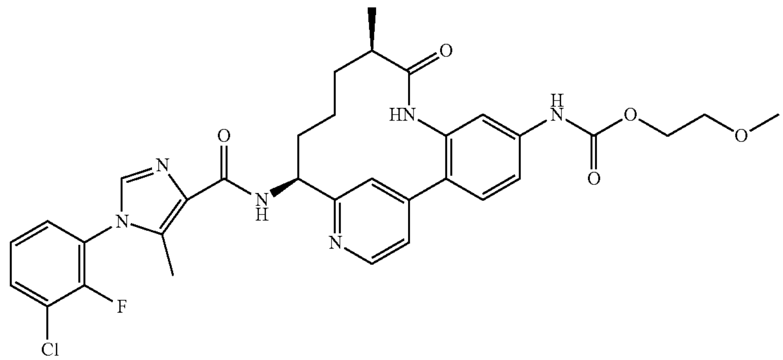 [SMILES: COCCOC(=O)Nc1ccc2c(c1)NC(=O)[C@H](C)CCC[C@H](NC(=O)c1ncn(-c3cccc(Cl)c3F)c1C)c1cc-2ccn1] | 649.3 | 5.20 D |
| 252 | Homochiral | 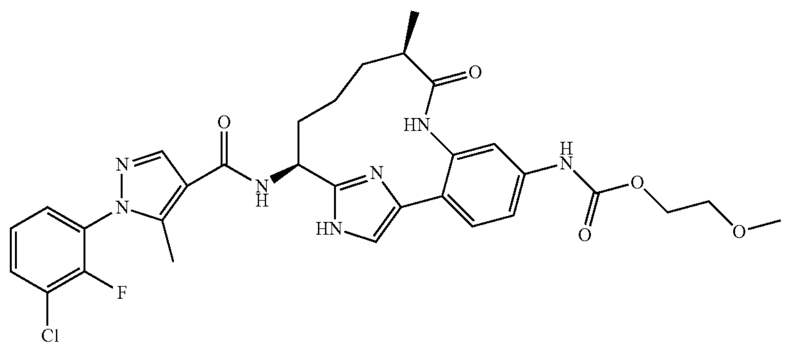 [SMILES: COCCOC(=O)Nc1ccc2c(c1)NC(=O)[C@H](C)CCC[C@H](NC(=O)c1cnn(-c3cccc(Cl)c3F)c1C)c1nc-2c[nH]1] | 638.1 | 5.06 E |
| 253 | Diastereomer mixture | 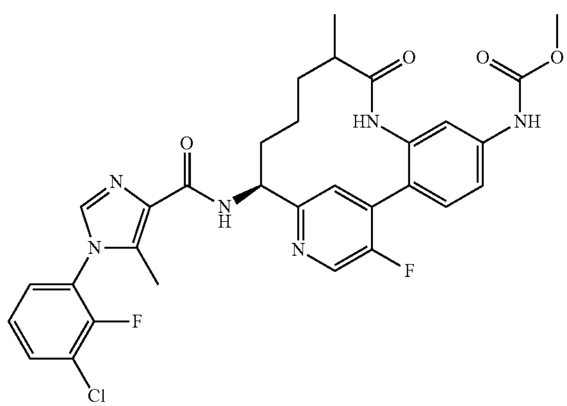 | 623.2 | 7.50 A |
| 254 | Homochiral | 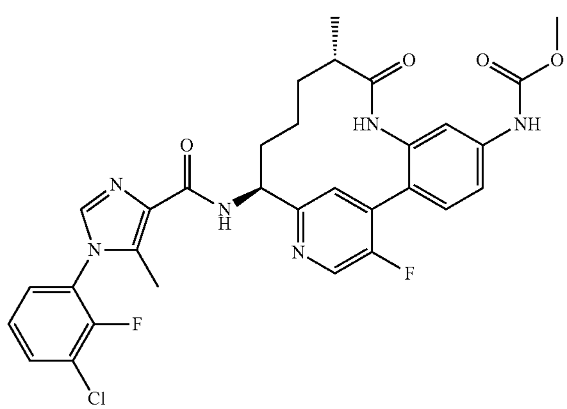 [SMILES: COC(=O)Nc1ccc2c(c1)NC(=O)C(C)CCC[C@H](NC(=O)c1ncn(-c3cccc(Cl)c3F)c1C)c1cc-2c(F)cn1] | 623.1 | 7.50 A |

TABLE 12-continued

| Example # | Stereochemistry | Structure | M + H | RT, min Method |
|---|---|---|---|---|
| 255 | Homochiral | 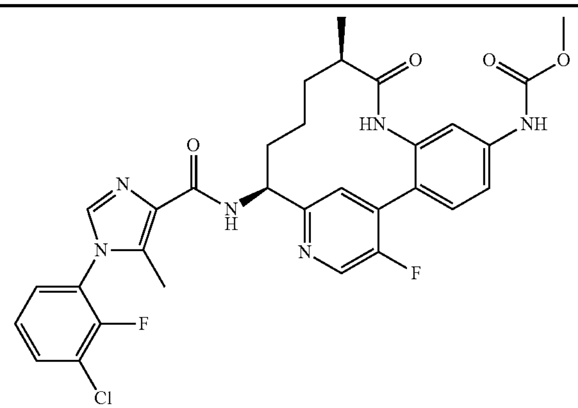 | 623.1 | 7.50 A |
| 256 | Homochiral | 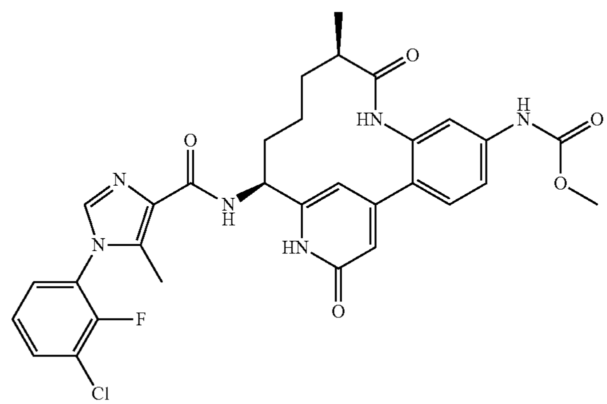 | 621.0 | 4.91 A |
| 257 | Homochiral | 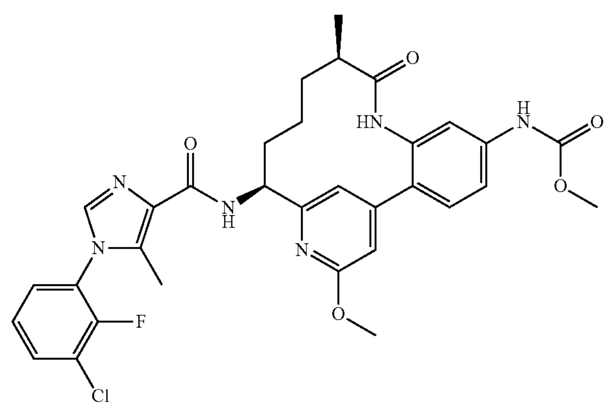 | 635.1 | 5.19 A |
| 258 | Homochiral | 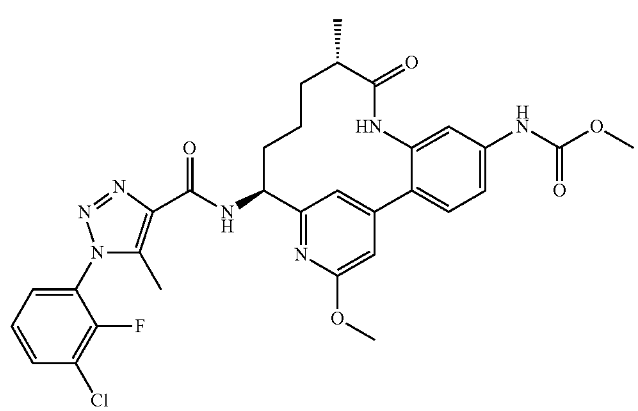 | 635.9 | 7.25 A |

TABLE 12-continued

| Example # | Stereochemistry | Structure | M + H | RT, min Method |
|---|---|---|---|---|
| 259 | Homochiral | 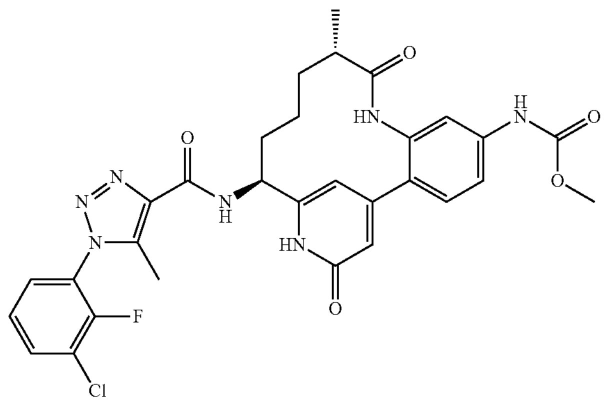 | 622.0 | 6.20 B |
| 260 | Homochiral | 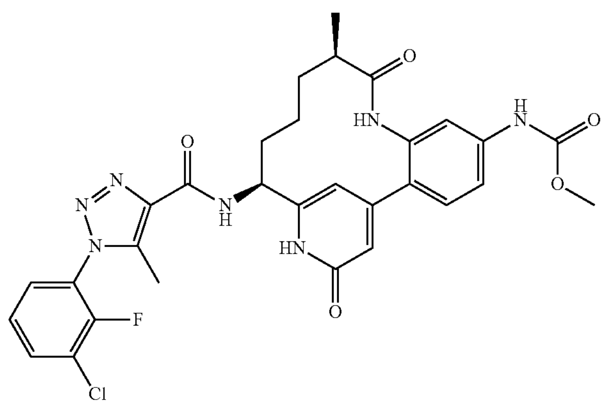 | 622.0 | 6.22 B |
| 261 | Homochiral | 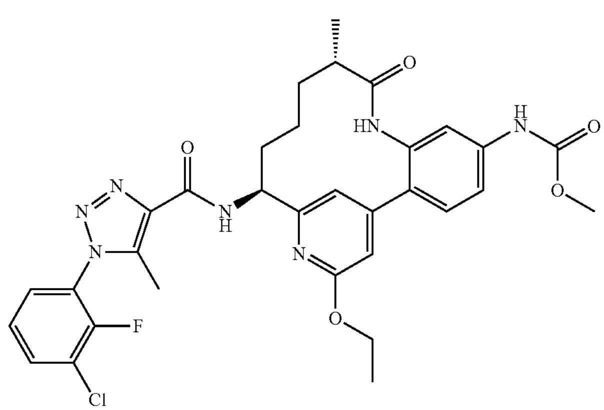 | 650.2 | 3.59 B |

TABLE 12-continued

| Example # | Stereochemistry | Structure | M + H | RT, min Method |
|---|---|---|---|---|
| 262 | Homochiral | 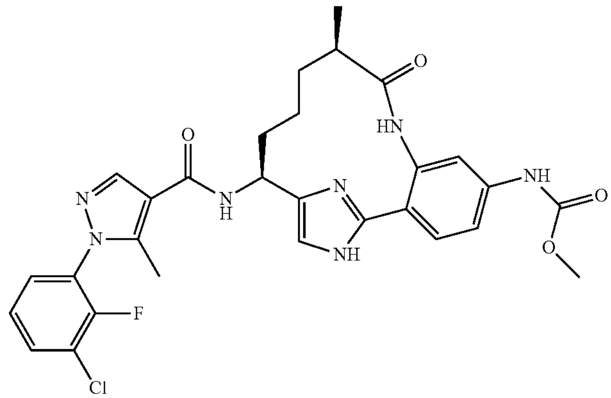 [SMILES: COC(=O)Nc1ccc2c(c1)NC(=O)[C@H](C)CCC[C@H](NC(=O)c1cnn(-c3cccc(Cl)c3F)c1C)c1c[nH]c-2n1] | 594.2 | 5.75 A |
| 263 | Homochiral | 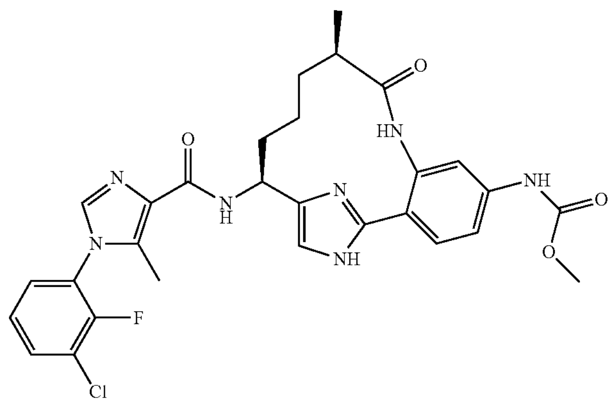 [SMILES: COC(=O)Nc1ccc2c(c1)NC(=O)[C@H](C)CCC[C@H](NC(=O)c1ncn(-c3cccc(Cl)c3F)c1C)c1c[nH]c-2n1] | 593.8 | 6.31 A |
| 264 | Homochiral | 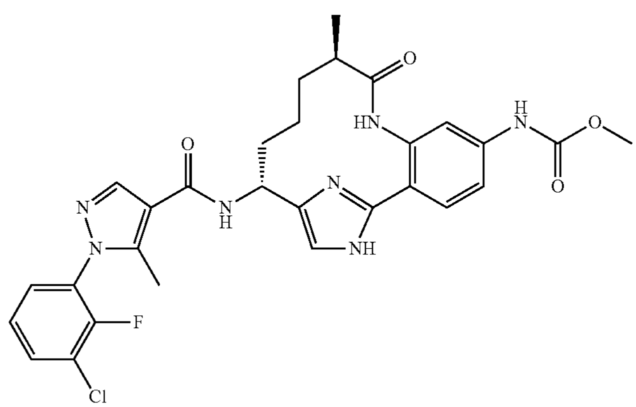 [SMILES: COC(=O)Nc1ccc2c(c1)NC(=O)[C@H](C)CCC[C@@H](NC(=O)c1cnn(-c3cccc(Cl)c3F)c1C)c1c[nH]c-2n1] | 592.0 | 6.24 A |
| 265 | Homochiral | 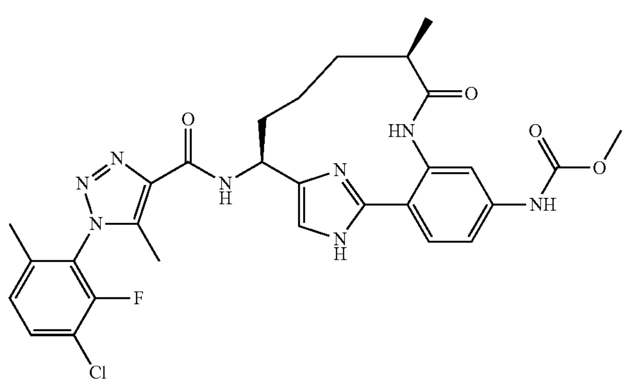 [SMILES: COC(=O)Nc1ccc2c(c1)NC(=O)[C@H](C)CCC[C@H](NC(=O)c1nnn(-c3c(C)ccc(Cl)c3F)c1C)c1c[nH]c-2n1] | 609.4 | 6.96 A |

TABLE 12-continued

| Example # | Stereochemistry | Structure | M + H | RT, min Method |
|---|---|---|---|---|
| 266 | Homochiral | 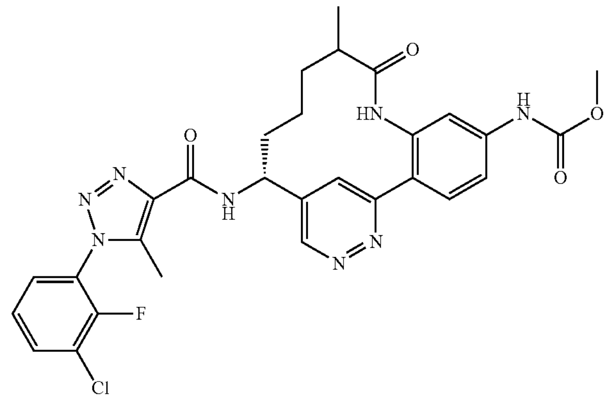 [SMILES: COC(=O)Nc1ccc2c(c1)NC(=O)C(C)CCC[C@@H](NC(=O)c1nnn(-c3cccc(Cl)c3F)c1C)c1cnnc-2c1] | 605.0 | 8.47 A |
| 267 | Homochiral | 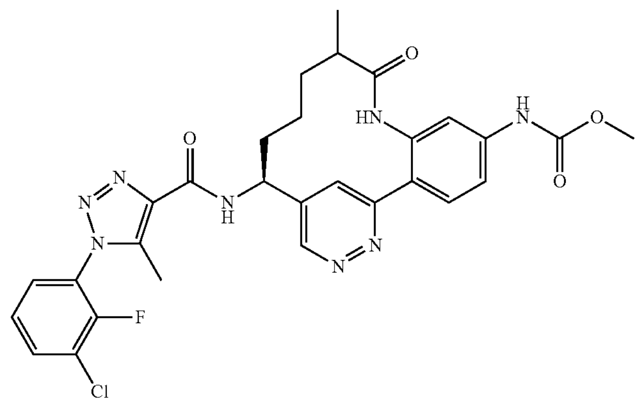 [SMILES: COC(=O)Nc1ccc2c(c1)NC(=O)C(C)CCC[C@H](NC(=O)c1nnn(-c3cccc(Cl)c3F)c1C)c1cnnc-2c1] | 605.0 | 8.40 A |
| 268 | Homochiral | 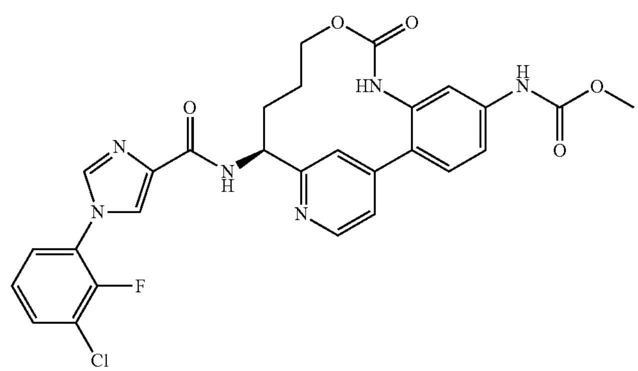 [SMILES: COC(=O)Nc1ccc2c(c1)NC(=O)OCCC[C@H](NC(=O)c1cn(-c3cccc(Cl)c3F)cn1)c1cc-2ccn1] | 579.2 | 6.33 A |
| 269 | Homochiral | 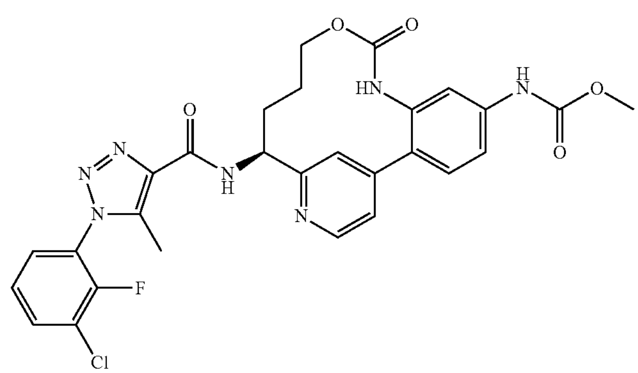 [SMILES: COC(=O)Nc1ccc2c(c1)NC(=O)OCCC[C@H](NC(=O)c1nnn(-c3cccc(Cl)c3F)c1C)c1cc-2ccn1] | 594.1 | 7.00 A |

TABLE 12-continued

| Example # | Stereochemistry | Structure | M + H | RT, min Method |
|---|---|---|---|---|
| 270 | Homochiral | 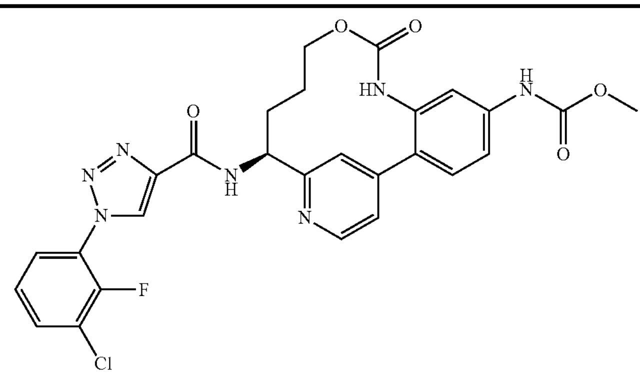 | 579.2 | 7.04 A |
| 271 | Homochiral | 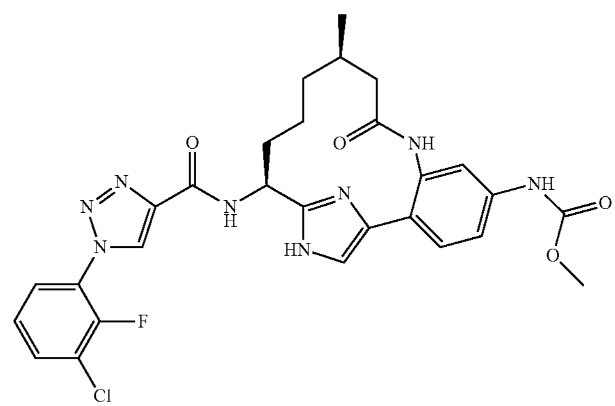 [SMILES: COC(=O)Nc1ccc2c(c1)NC(=O)C[C@H](C)CCC[C@H](NC(=O)c1cn(-c3cccc(Cl)c3F)nn1)c1nc-2c[nH]1] | 595.5 | 6.48 A |
| 272 | Homochiral | 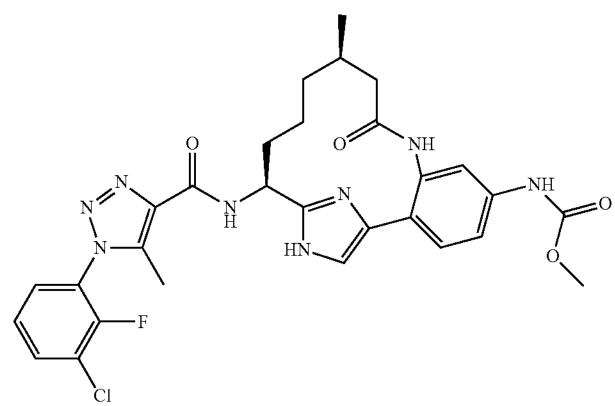 [SMILES: COC(=O)Nc1ccc2c(c1)NC(=O)C[C@H](C)CCC[C@H](NC(=O)c1nnn(-c3cccc(Cl)c3F)c1C)c1nc-2c[nH]1] | 609.4 | 6.75 A |
| 273 | Homochiral | 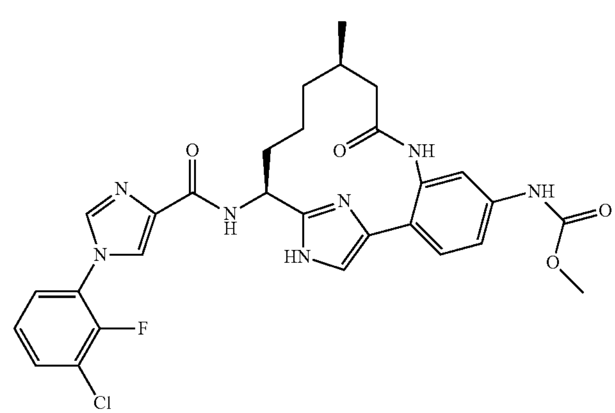 [SMILES: COC(=O)Nc1ccc2c(c1)NC(=O)C[C@H](C)CCC[C@H](NC(=O)c1cn(-c3cccc(Cl)c3F)cn1)c1nc-2c[nH]1] | 594.2 | 6.19 A |

TABLE 12-continued

| Example # | Stereochemistry | Structure | M + H | RT, min Method |
|---|---|---|---|---|
| 274 | Homochiral | 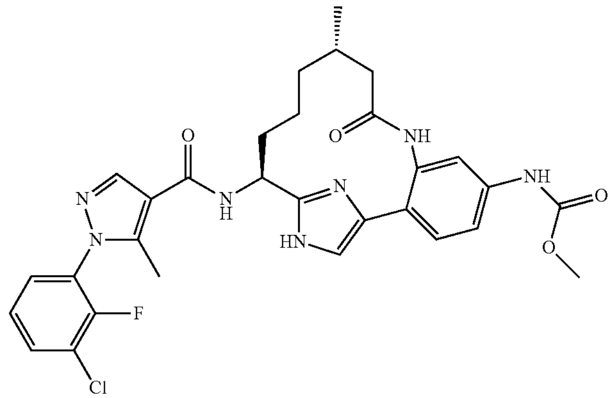 [SMILES: COC(=O)Nc1ccc2c(c1)NC(=O)C[C@@H](C)CCC[C@H](NC(=O)c1cnn(-c3cccc(Cl)c3F)c1C)c1nc-2c[nH]1] | 609.3 | 6.43 A |
| 275 | Homochiral | 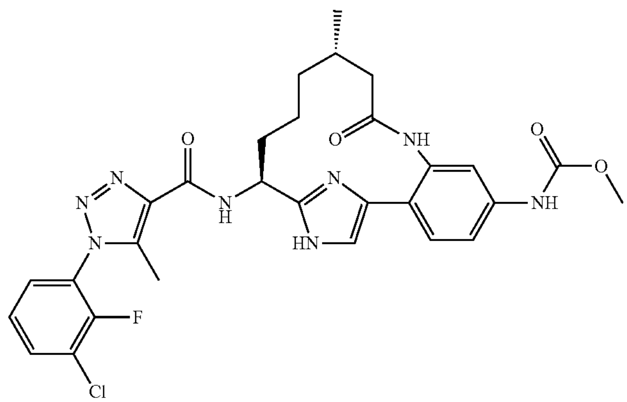 [SMILES: COC(=O)Nc1ccc2c(c1)NC(=O)C[C@@H](C)CCC[C@H](NC(=O)c1nnn(-c3cccc(Cl)c3F)c1C)c1nc-2c[nH]1] | 609.3 | 6.60 A |
| 276 | Homochiral | 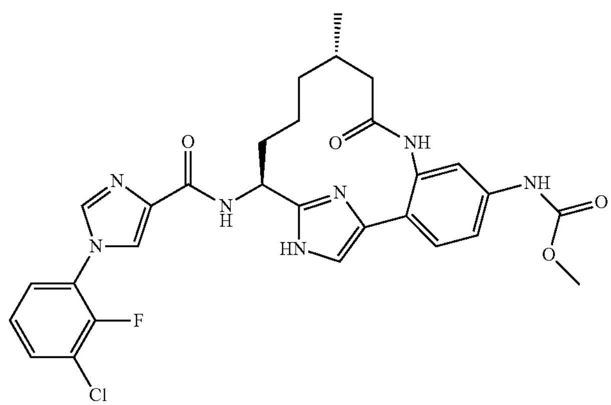 [SMILES: COC(=O)Nc1ccc2c(c1)NC(=O)C[C@@H](C)CCC[C@H](NC(=O)c1cn(-c3cccc(Cl)c3F)cn1)c1nc-2c[nH]1] | 594.0 | 6.14 A |
| 277 | Homochiral | 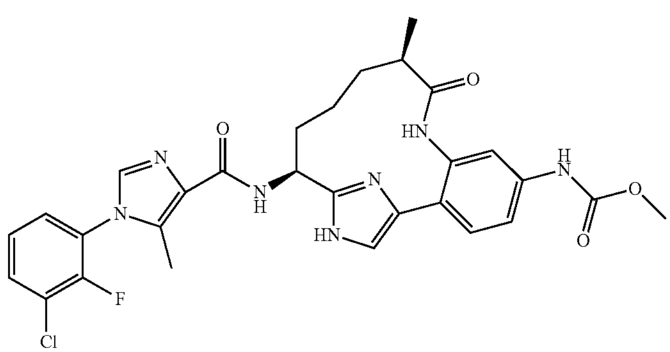 [SMILES: COC(=O)Nc1ccc2c(c1)NC(=O)[C@H](C)CCC[C@H](NC(=O)c1ncn(-c3cccc(Cl)c3F)c1C)c1nc-2c[nH]1] | 594.1 | 5.02 D |

TABLE 12-continued

| Example # | Stereochemistry | Structure | M + H | RT, min Method |
|---|---|---|---|---|
| 278 | Diastereomer mixture | 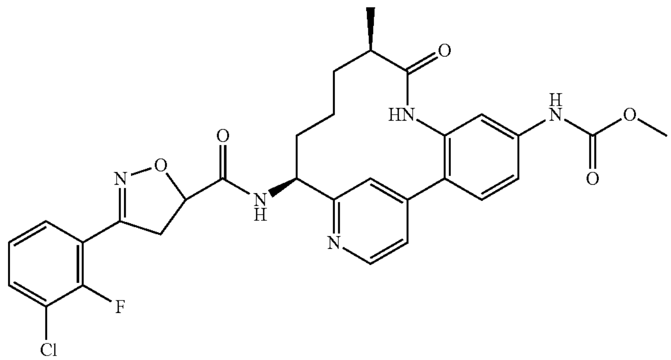 [SMILES: COC(=O)Nc1ccc2c(c1)NC(=O)[C@H](C)CCC[C@H](NC(=O)C1CC(c3cccc(Cl)c3F)=NO1)c1cc-2ccn1] | 594.2 | 5.94 6.05 D |
| 279 | Homochiral | 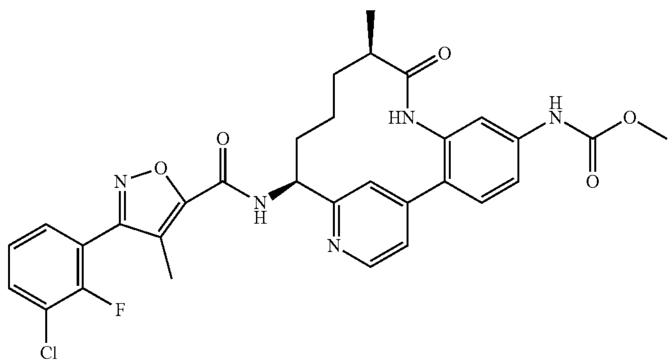 [SMILES: COC(=O)Nc1ccc2c(c1)NC(=O)[C@H](C)CCC[C@H](NC(=O)c1onc(-c3cccc(Cl)c3F)c1C)c1cc-2ccn1] | 606.2 | 9.27 A |
| 280 | Homochiral | 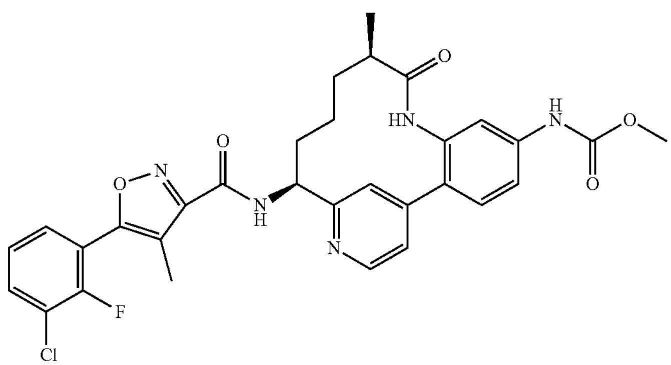 [SMILES: COC(=O)Nc1ccc2c(c1)NC(=O)[C@H](C)CCC[C@H](NC(=O)c1noc(-c3cccc(Cl)c3F)c1C)c1cc-2ccn1] | 606.1 | 7.19 A |
| 281 | Homochiral | 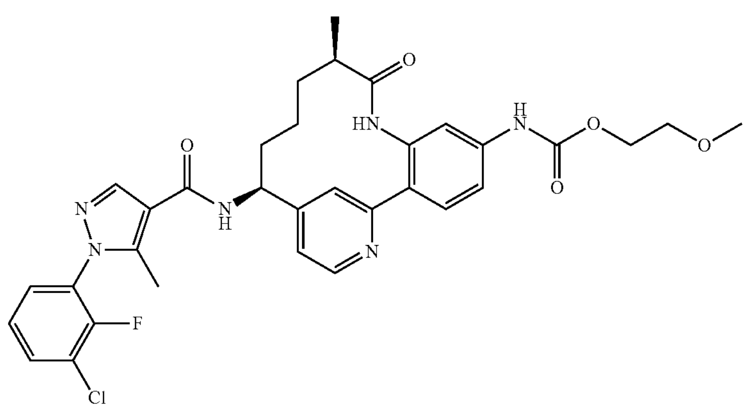 [SMILES: COCCOC(=O)Nc1ccc2c(c1)NC(=O)[C@H](C)CCC[C@H](NC(=O)c1cnn(-c3cccc(Cl)c3F)c1C)c1ccnc-2c1] | | |

What is claimed is:

1. A compound of Formula (Ia):

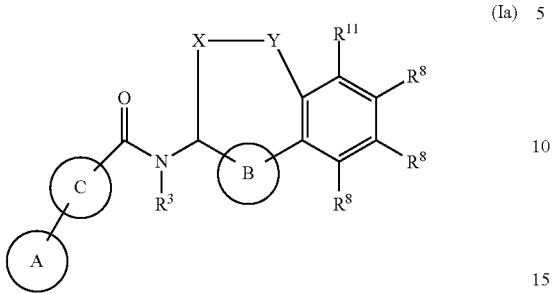

or a stereoisomer, a tautomer, a pharmaceutically acceptable salt, a solvate thereof, wherein:
ring A is selected from aryl and a 5- to 6-membered heterocycle comprising carbon atoms and 1-4 heteroatoms selected from N, NH, N($C_{1-4}$ alkyl), $S(O)_p$, and O, wherein said aryl and heterocycle are optionally substituted with $R^1$;
ring B is pyridine optionally substituted with $R^{10}$;
ring C is a 4- to 6-membered heterocycle comprising: carbon atoms and 1-4 heteroatoms selected from N, $NR^9$, $S(O)_p$, and O, wherein said heterocycle is optionally substituted with $R^2$;
X is selected from $C_{4-8}$ alkylene and $C_{4-8}$ alkenylene, wherein said alkylene and alkenylene are substituted with $R^4$ and $R^5$; alternatively one or more of the carbon atoms of said alkylene and alkenylene may be replaced by O, C=O, $S(O)_p$, NH, and N($C_{1-4}$ alkyl);
Y is —$CR^6R^7$—NH—;
$R^1$ is selected from H, halogen, $NO_2$, $C_{1-6}$ alkyl, OH, haloalkyl, alkoxy, haloalkoxy, —C(=O)$C_{1-3}$ alkyl, and CN;
$R^2$ is selected from H, =O, OH, $NH_2$, $CF_3$, halogen, $C_{1-4}$ alkyl (optionally substituted with OH), $C_{1-3}$ alkoxy, and C(O)$C_{1-3}$ alkyl;
$R^3$ is selected from H and $C_{1-4}$ alkyl;
alternatively, $R^2$ and $R^3$, together with the atoms to which they are directly or indirectly attached, form a ring;
$R^4$ and $R^5$ are independently selected from H, halogen, $C_{1-6}$ alkyl, OH, $NH_2$, —$CH_2NH_2$, $C_{1-4}$ haloalkyl, —$OCH_2F$, —$OCHF_2$, —$OCF_3$, NH($C_{1-4}$ alkyl), N($C_{1-4}$ alkyl)$_2$, $C_{1-4}$ alkoxy, —$CH_2OH$, and —$CH_2O(C_{1-4}$ alkyl); when $R^4$ and $R^5$ are not attached to the same carbon atom, they may be taken together with the carbon atoms to which they are attached to form a carbocycle;
$R^6$ is selected from H, halogen, C(O)OH, and C(O)O($C_{1-4}$ alkyl);
$R^7$ is selected from H, $C_{1-4}$ alkyl, and $CF_3$;
alternatively, $R^6$ and $R^7$ together are =O;
$R^8$ is, independently at each occurrence, selected from H, halogen, haloalkyl, CN, —$(CH_2)_n$OH, $NR^{12}R^{12}$, —$CH_2NH_2$, C(O)OH, —$(CH_2)_n$—NHC(O)$OR^{12}$, —NHC(O)$R^{12}$, —NHC(O)C(O)$R^{12}$, —NHC(N=CN) $NHR^{12}$, —NHC(NH)$NHR^{12}$, —N=CHN$R^{12}R^{12}$, —NHC(O)N$R^{12}R^{12}$, —NHS(O)$_2C_{1-4}$ alkyl, —$(CH_2)_n$ —CONR$^{12}R^{12}$, —$(CH_2)_n$C(O)O($C_{1-4}$ alkyl), —NHC (O)OCH$_2$(C(CH$_2$)$_2$)O—(CH$_2$)$_n$—$C_{3-10}$ carbocycle, —$(CH_2)_n$—$C_{3-10}$ carbocycle, and —$(CH_2)_n$-4-10-membered heterocycle wherein said carbocycle and heterocycle are optionally substituted with $R^{13}$;
$R^9$ is selected from H and $C_{1-4}$ alkyl;
$R^{10}$ is selected from H, halogen, CN, =O, OH, $NH_2$, $C_{3-6}$ cycloalkyl, $C_{1-4}$ alkyl, $C_{1-4}$ alkoxy, and $C_{1-4}$ haloalkyl;
$R^{11}$ is selected from H, halogen, and methyl;
$R^{12}$ is selected from H, $C_{1-4}$ alkyl (optionally substituted with halogen, hydroxy, alkoxy, carboxy, alkoxycarbonyl, and arylalkyloxy), —$(CH_2)_n$—$C_{3-10}$ carbocycle and —$(CH_2)_n$-4-10-membered heterocycle, wherein said carbocycle and heterocycle are optionally substituted with $R^{13}$;
$R^{13}$ is selected from OH, halogen, $C_{1-6}$ alkyl, $C_{3-6}$ cycloalkyl, —$(CH_2)_n$—C(=O)OH, —$(CH_2)_n$—C (=O)O$C_{1-4}$ alkyl, —$(CH_2)_n$—O$C_{1-4}$ alkyl, and =O;
n is, independently at each occurrence, selected from 0, 1, 2, 3, and 4;
p is, independently at each occurrence, selected from 0, 1, and 2.

2. The compound of claim 1 having Formula (IIa):

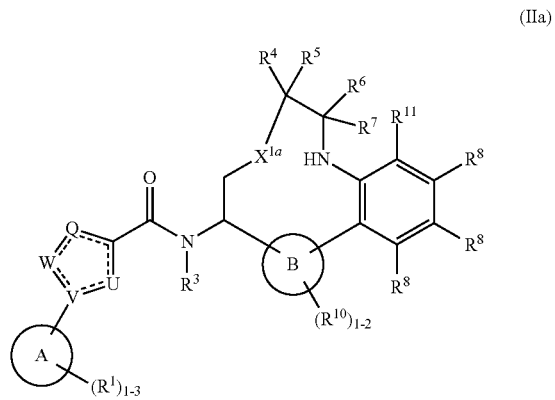

or a stereoisomer, a tautomer, a pharmaceutically acceptable salt, a solvate thereof, wherein:
ring A is selected from aryl and a 5- to 6-membered heterocycle comprising: carbon atoms and 1-3 heteroatoms selected from N, NH, and N($C_{1-4}$ alkyl);
ring B is selected from pyridine and pyridone;
$X^{1a}$ is selected from $C_{2-4}$ alkylene and $C_{2-4}$ alkenylene wherein said $C_{2-4}$ alkylene and $C_{2-4}$ alkenylene are optionally substituted with $R^4$ and $R^5$; alternatively, one or more of the carbon atoms of said alkylene may be replaced by O and C=O;
U, V, W, and Q are each independently selected from N, $NR^9$, S, O, C, $CR^2$, and $CHR^2$;
--- is an optional bond;
$R^1$ is, independently at each occurrence, selected from H, halogen, $NO_2$, $C_{1-6}$ alkyl, OH, $C_{1-6}$ haloalkyl, $C_{1-6}$ alkoxy, $C_{1-6}$ haloalkoxy, and CN;
$R^2$ is selected from H, =O, OH, $NH_2$, $CF_3$, halogen, $C_{1-4}$ alkyl (optionally substituted with OH), $C_{1-3}$ alkoxy, and C(O)$C_{1-3}$ alkyl;
$R^3$ is H;
$R^4$ and $R^5$ are independently selected from H, halogen, $C_{1-6}$ alkyl, OH, and $NH_2$; when $R^4$ and $R^5$ are not attached to the same carbon atom, they may be taken together with the carbon atoms to which they are attached to form a carbocycle;

$R^6$ is selected from H, halogen, C(O)OH, and C(O)O(C$_{1-4}$ alkyl);

$R^7$ is selected from H, C$_{1-4}$ alkyl, and CF$_3$;

alternatively, $R^6$ and $R^7$ together are =O;

$R^8$ is, independently at each occurrence, selected from H, halogen, haloalkyl, CN, —(CH$_2$)$_n$OH, NR$^{12}$R$^{12}$, C(O)OH, —(CH$_2$)$_n$—NHC(O)OR$^{12}$, —NHC(O)R$^{12}$, —NHC(O)NR$^{12}$R$^{12}$, —NHS(O)$_2$C$_{1-4}$ alkyl, —(CH$_2$)$_n$—CONR$^{12}$R$^{12}$, —(CH$_2$)$_n$C(O)O(C$_{1-4}$ alkyl), —(CH$_2$)$_n$—C$_{3-10}$ carbocycle, and —(CH$_2$)$_n$-4-10-membered heterocycle optionally substituted with R$^{13}$;

$R^9$ is selected from H and C$_{1-4}$ alkyl;

$R^{10}$ is, independently at each occurrence, selected from H, halogen, CN, =O, OH, NH$_2$, C$_{3-6}$ cycloalkyl, C$_{1-4}$ alkyl, C$_{1-4}$ alkoxy, and C$_{1-4}$ haloalkyl;

$R^{11}$ is H;

$R^{12}$ is selected from H, C$_{1-4}$ alkyl (optionally substituted with halogen, hydroxy, alkoxy, carboxy, alkoxycarbonyl), —(CH$_2$)$_n$—C$_{3-10}$ carbocycle and —(CH$_2$)$_n$-4-10-membered heterocycle, wherein said carbocycle and heterocycle are optionally substituted with R$^{13}$;

$R^{13}$ is selected from OH, halogen, C$_{1-6}$ alkyl, C$_{3-6}$ cycloalkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, and =O; and n is, independently at each occurrence, selected from 0, 1, 2, and 3.

3. The compound of claim 2, or a stereoisomer, a tautomer, a pharmaceutically acceptable salt, a solvate thereof, wherein:

ring A is selected from phenyl, piperidine, and pyridine;

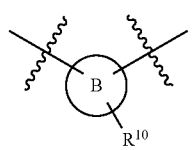

is selected from

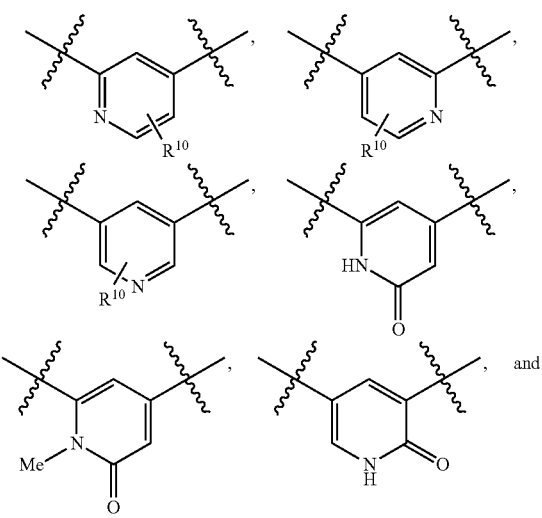

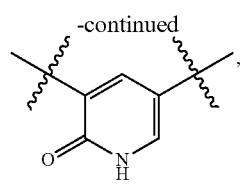

and $R^{10}$ is selected from H, F, Cl, C$_{1-4}$ alkyl, C$_{1-4}$ alkoxy, and CN.

4. A compound of claim 3 having Formula (IIIa):

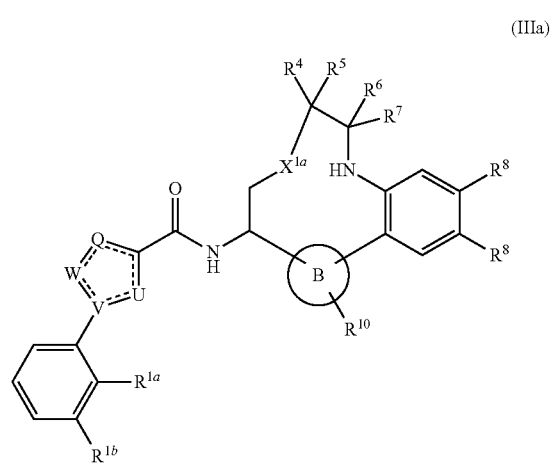

(IIIa)

or a stereoisomer, a tautomer, a pharmaceutically acceptable salt, a solvate thereof, wherein:

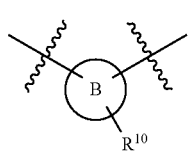

is independently selected from

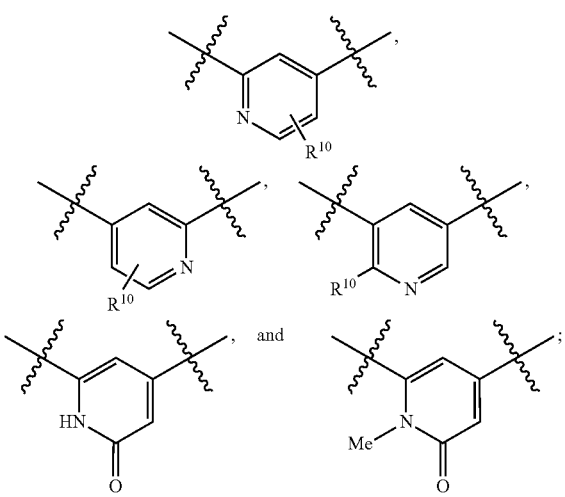

$X^{1a}$ is selected from —CR$^4$R$^5$—CR$^4$R$^5$—, —CR$^4$R$^5$—CR$^4$R$^5$—CR$^4$R$^5$—, and —CR$^4$=CR$^5$CR$^4$R$^5$—, wherein one or more —CR$^4$R$^5$— may be replaced by O or C=O;

U, V, W, and Q are each independently selected from N, NR$^9$, S, C, CR$^2$, and CHR$^2$;

R$^{1a}$ and R$^{1b}$ are each independently selected from H, halogen, OH, CN, CH$_3$, OCH$_3$, CF$_3$, and OCHF$_2$;

R$^2$ is selected from H, NH$_2$, CF$_3$, halogen, and C$_{1-4}$ alkyl (optionally substituted with OH), C$_{1-3}$ alkoxy, and C(O)C$_{1-3}$ alkyl;

R$^4$ is selected from H, F, Cl, OH, and C$_{1-4}$ alkyl;

R$^5$ is selected from H, F, and C$_{1-4}$ alkyl;

R$^6$ is independently selected from H, C(O)OH, and C(O)O(C$_{1-4}$ alkyl);

R$^7$ is selected from H, C$_{1-4}$ alkyl, and CF$_3$;

alternatively, R$^6$ and R$^7$ together are =O;

R$^8$ is, independently at each occurrence, selected from H, halogen, haloalkyl, CN, —(CH$_2$)$_n$OH, NR$^{12}$R$^{12}$, —CH$_2$NH$_2$, C(O)OH, and —NHC(O)OR$^{12}$, —(CH$_2$)$_n$—C$_{3-10}$ carbocycle, and —(CH$_2$)$_n$-4-10-membered heterocycle optionally substituted with R$^{13}$;

R$^9$ is selected from H and C$_{1-4}$ alkyl;

R$^{10}$ is selected from H, halogen, methyl, ethyl, methoxy, ethoxy, and CN;

R$^{12}$ is selected from H, C$_{1-4}$ alkyl (optionally substituted with F, OH, —O(C$_{1-4}$ alkyl), —C(O)OH, —C(O)O(C$_{1-4}$ alkyl)), —(CH$_2$)$_n$—C$_{3-10}$ carbocycle and —(CH$_2$)$_n$-4-10-membered heterocycle, wherein said carbocycle and heterocycle are optionally substituted with R$^{13}$;

R$^{13}$ is selected from OH, halogen, C$_{1-6}$ alkyl, C$_{3-6}$ cycloalkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, and =O; and n is, independently at each occurrence, selected from 0, 1, 2, and 3.

5. The compound of claim 4 having Formula (IVa):

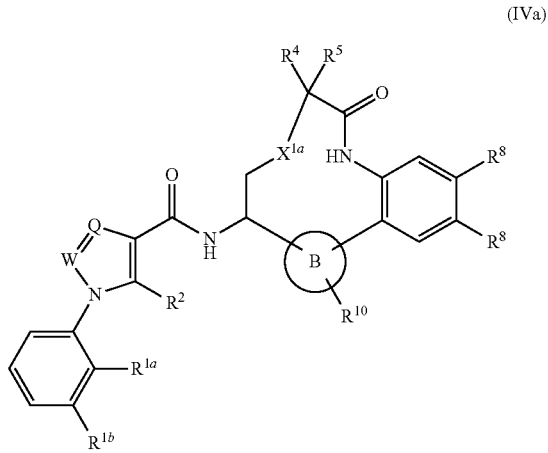

(IVa)

or a stereoisomer, a tautomer, a pharmaceutically acceptable salt, a solvate thereof, wherein:

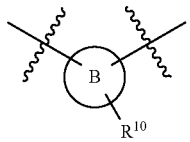

is independently selected from

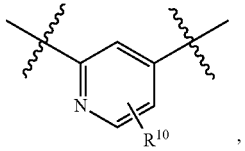
,

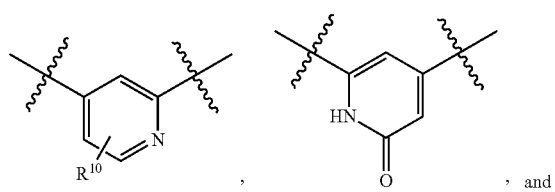
, and

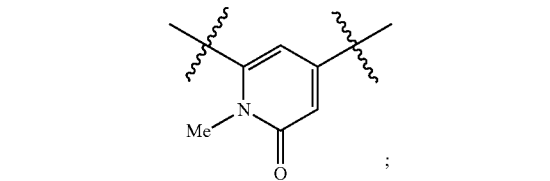
;

W and Q are each independently selected from N and CR$^2$;

R$^{1a}$ is selected from H, F, and Cl;

R$^{1b}$ is selected from H, F, Cl, OH, CN, CH$_3$, OCH$_3$, CF$_3$, and OCHF$_2$;

R$^2$ is selected from H, NH$_2$, CF$_3$, F, Cl, and C$_{1-4}$ alkyl;

R$^4$ is selected from H, F, methyl, ethyl, propyl, and isopropyl;

R$^5$ is H and F;

R$^8$ is, independently at each occurrence, selected from H, halogen, haloalkyl, CN, —(CH$_2$)$_n$OH, NR$^{12}$R$^{12}$, C(O)OH, and —NHC(O)OR$^{12}$;

R$^{10}$ is selected from H, halogen, methyl, ethyl, methoxy, ethoxy, and CN;

R$^{12}$ is selected from H, C$_{1-4}$ alkyl (optionally substituted with F, OH, —O(C$_{1-4}$ alkyl), —C(O)OH, —C(O)O(C$_{1-4}$ alkyl)), —(CH$_2$)$_n$—C$_{3-10}$ carbocycle and —(CH$_2$)$_n$-4-10-membered heterocycle, wherein said carbocycle and heterocycle are optionally substituted with R$^{13}$;

R$^{13}$ is selected from OH, halogen, C$_{1-6}$ alkyl, C$_{3-6}$ cycloalkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, and =O; and n is, independently at each occurrence, selected from 0, 1, 2, and 3.

6. The compound of claim 5 having Formula (Va):

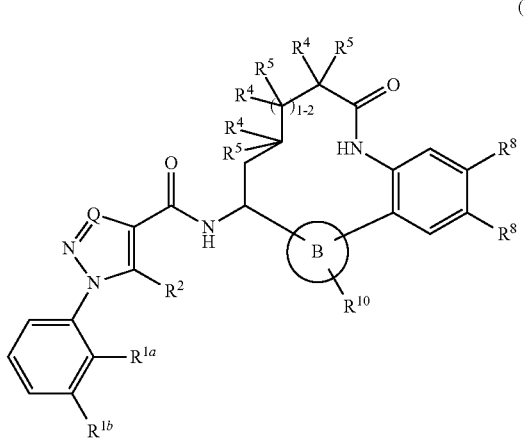

or a stereoisomer, a tautomer, a pharmaceutically acceptable salt, a solvate thereof, wherein:

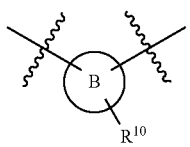

is independently selected from

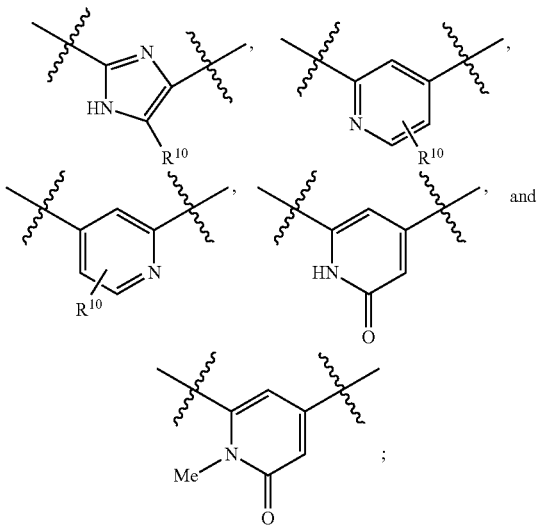

Q is selected from N and $CR^2$;
$R^{1a}$ is selected from H and F;
$R^{1b}$ is Cl;
$R^2$ is selected from H, $NH_2$, F, Cl, and methyl;
$R^4$ is selected from H, OH, methyl, ethyl, and isopropyl;
$R^5$ is H and F;
$R^8$ is, independently at each occurrence, selected from H, —$(CH_2)_n$OH, $NR^{12}R^{12}$, C(O)OH, and —NHC(O)OR$^{12}$;
$R^{10}$ is selected from H, halogen, methyl, ethyl, methoxy, ethoxy, and CN;

$R^{12}$ is selected from H, $C_{1-4}$ alkyl (optionally substituted with F, OH, —O($C_{1-4}$ alkyl), —C(O)OH, —C(O)O ($C_{1-4}$ alkyl)), —$(CH_2)_n$—$C_{3-10}$ carbocycle, and —$(CH_2)_n$-4-10-membered heterocycle, wherein said carbocycle and heterocycle are optionally substituted with $R^{13}$;
$R^{13}$ is selected from OH, halogen, $C_{1-6}$ alkyl, $C_{3-6}$ cycloalkyl, —$(CH_2)_n$—C(=O)OH, —$(CH_2)_n$—C(=O)O$C_{1-4}$ alkyl, —$(CH_2)_n$—O$C_{1-4}$ alkyl, and =O; and
n is, independently at each occurrence, selected from 0, 1, 2, and 3.

7. The compound of claim 5 having Formula (VIa):

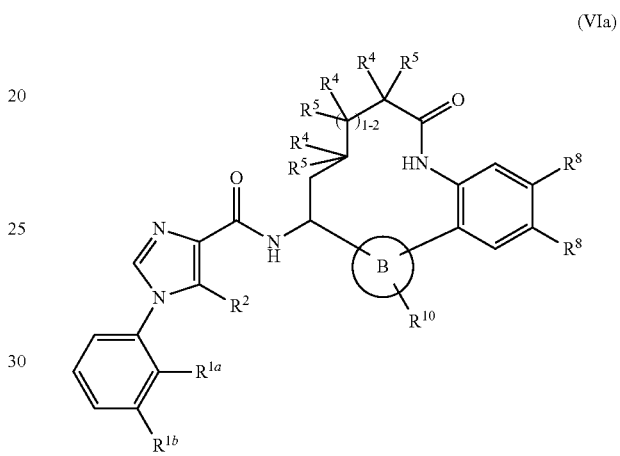

or a stereoisomer, a tautomer, a pharmaceutically acceptable salt, a solvate thereof, wherein:

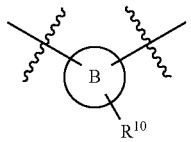

is independently selected from

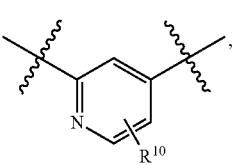

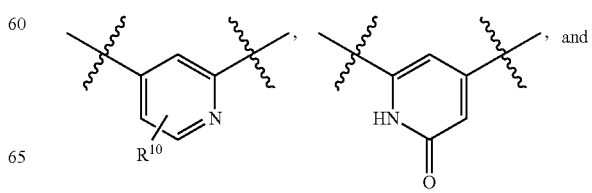

-continued

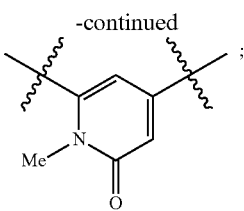

$R^{1b}$ is Cl;

$R^2$ is selected from H, NH$_2$, F, Cl, and methyl;

$R^4$ is selected from H, OH, methyl, ethyl, and isopropyl;

$R^5$ is H and F;

$R^8$ is, independently at each occurrence, selected from H, —(CH$_2$)$_n$OH, NR$^{12}$R$^{12}$, C(O)OH, and —NHC(O)OR$^{12}$;

$R^{10}$ is selected from H, halogen, methyl, ethyl, methoxy, ethoxy, and CN;

$R^{12}$ is selected from H, C$_{1-4}$ alkyl (optionally substituted with F, OH, —O(C$_{1-4}$ alkyl), —C(O)OH, —C(O)O(C$_{1-4}$ alkyl)), —(CH$_2$)$_n$—C$_{3-10}$ carbocycle and —(CH$_2$)$_n$-4-10-membered heterocycle, wherein said carbocycle and heterocycle are optionally substituted with R$^{13}$;

$R^{13}$ is selected from OH, halogen, C$_{1-6}$ alkyl, C$_{3-6}$ cycloalkyl, —(CH$_2$)$_n$—C(═O)OH, —(CH$_2$)$_n$—C(═O)OC$_{1-4}$ alkyl, —(CH$_2$)$_n$—OC$_{1-4}$ alkyl, and ═O; and n is, independently at each occurrence, selected from 0, 1, 2, and 3.

8. The compound of claim 4 having Formula (VIIa):

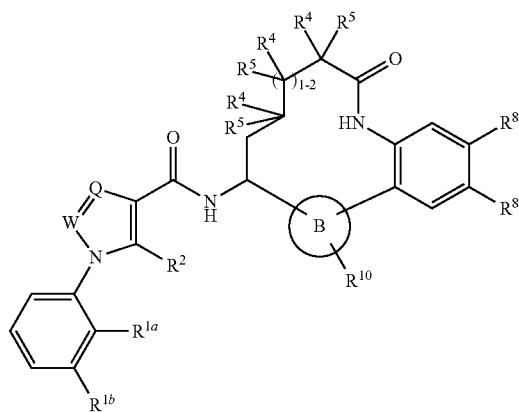

(VIIa)

or a stereoisomer, a tautomer, a pharmaceutically acceptable salt, a solvate thereof, wherein:

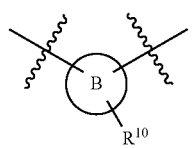

is independently selected from

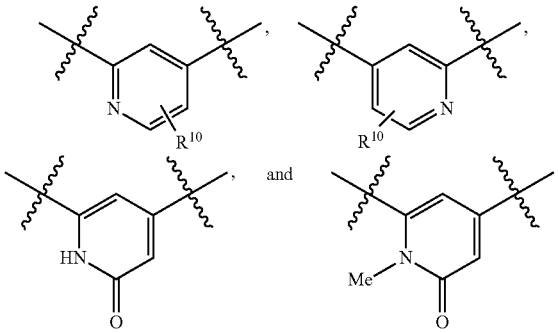

W is selected from N and CR$^2$;

Q is selected from N and CR$^2$;

$R^{1a}$ is selected from H and F;

$R^{1b}$ is Cl;

$R^2$ is selected from H, Cl, NH$_2$, and methyl;

$R^4$ is selected from H, F, methyl, ethyl, OH;

$R^5$ is selected from H and F;

$R^8$ is selected from H, NHR$^{12}$, —(CH$_2$)$_n$OH, —NHC(N═CN)NHR$^{12}$, —C(O)OH, —NHC(O)OR$^{12}$, and —(CH$_2$)$_n$-4-10-membered heterocycle optionally substituted with R$^{13}$;

$R^{10}$ is selected from H, F, Cl, C$_{1-2}$ alkyl, methoxy, ethoxy, and CN;

$R^{12}$ is selected from H, C$_{1-4}$ alkyl (optionally substituted with F, OH, —OC$_{1-4}$ alkyl, —C(O)OH, —C(O)OC$_{1-4}$ alkyl, —O-arylalkyl), —(CH$_2$)$_n$—C$_{3-6}$ cycloalkyl and —(CH$_2$)$_n$-4-6-membered heterocycle comprising carbon atoms and 1-4 heteroatoms selected from N, NH, N(C$_{1-4}$ alkyl), and O wherein said heterocycle is optionally substituted with R$^{13}$;

$R^{13}$ is selected from OH, OC$_{1-4}$ alkyl, C$_{1-6}$ alkyl (optionally substituted with alkoxy), C$_{3-6}$ cycloalkyl, and ═O; and n is, independently at each occurrence, selected from 0, 1, 2, and 3.

9. The compound of claim 8, or a stereoisomer, a tautomer, a pharmaceutically acceptable salt thereof, wherein:

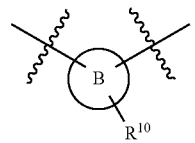

is independently selected from

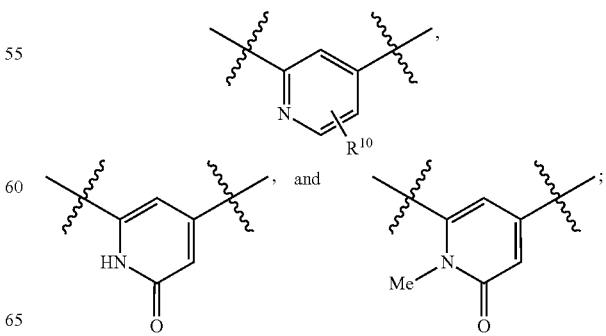

W is selected from N and $CR^2$;
Q is selected from N and $CR^2$;
$R^{1a}$ is selected from H and F;
$R^{1b}$ is Cl;
$R^2$ is selected from H, Cl, $NH_2$, and methyl;
$R^4$ is selected from H, F, methyl, ethyl, OH;
$R^5$ is selected from H and F;
$R^8$ is selected from H, $NHR^{12}$, —C(O)OH, and —NHC(O)$OR^{12}$;
$R^{10}$ is selected from H, F, Cl, methyl, methoxy, ethoxy, and CN;
$R^{12}$ is selected from H, $C_{1-4}$ alkyl (optionally substituted with F, OH, —$OC_{1-4}$ alkyl, —C(O)OH, —C(O)$OC_{1-4}$ alkyl), —$(CH_2)_n$—$C_{3-6}$ cycloalkyl and —$(CH_2)_n$-4-6-membered heterocycle comprising carbon atoms and 1-4 heteroatoms selected from N, NH, N($C_{1-4}$ alkyl), and O wherein said heterocycle is optionally substituted with $R^{13}$;
$R^{13}$ is selected from OH, $OC_{1-4}$ alkyl, $C_{1-6}$ alkyl (optionally substituted with alkoxy), $C_{3-6}$ cycloalkyl, and =O; and
n is, independently at each occurrence, selected from 0, 1, 2, and 3.

10. A pharmaceutical composition comprising one or more compounds according to claim 1 and a pharmaceutically acceptable carrier or diluent.

11. A method for the treatment and/or prophylaxis of a thromboembolic disorder, comprising: administering to a patient in need thereof a therapeutically effective amount of a compound of claim 1, or a stereoisomer, a tautomer, or a pharmaceutically acceptable salt thereof.

12. A method according to claim 11, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

13. A method according to claim 12, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

14. The compound of claim 1 selected from the group consisting of:
methyl N-[(14S)-14-[1-(3-chlorophenyl)-3-(2-hydroxyethyl)-1H-pyrazole-4-amido]-16-fluoro-10-methyl-9-oxo-8,17-diazatricyclo[13.3.1.0$^{2,7}$]nonadeca-1(19),2,4,6,15,17-hexaen-5-yl]carbamate (1);
methyl N-[(10R,14S)-14-[1-(3-chlorophenyl)pyrrolidine-3-amido]-10-methyl-9-oxo-8,16-diazatricyclo[13.3.1.0$^{2,7}$]nonadeca-1(19),2(7),3,5,15,17-hexaen-5-yl]carbamate (2);
methyl N-[(14S)-14-[1(3-chloro-2-fluorophenyl)-1H-pyrazole-4-amido]-9-oxo-8,16-diazatricyclo[13.3.1.0$^{2,7}$]nonadeca-1(19),2(7),3,5,15,17-hexaen-5-yl]carbamate (21);
methyl N-[(14S)-14-[1-(3-chloro-2-fluorophenyl)-1H-1,2,3-triazole-4-amido]-10-ethyl-9-oxo-8,16-diazatricyclo[13.3.1.0$^{2,7}$]nonadeca-1(19),2(7),3,5,15,17-hexaen-5-yl]carbamate (24);
methyl N-[(14S)-14-[1-(3-chloro-2-fluorophenyl)-1H-1,2,3-triazole-4-amido]-10-ethyl-9-oxo-8,16-diazatricyclo[13.3.1.0$^{2,7}$]nonadeca-1(19),2(7),3,5,15,17-hexaen-5-yl]carbamate (25);
ethyl (9R,14S)-14-[1-(3-chloro-2-fluorophenyl)-1H-pyrazole-4-amido]-5-[(methoxycarbonyl)amino]-8,16-diazatricyclo[13.3.1.0$^{2,7}$]nonadeca-1(19),2(7),3,5,15,17-hexaene-9-carboxylate(26);
methyl N-[(14S)-14-[1-(3-chloro-2-fluorophenyl)-1H-pyrazole-4-amido]-16-fluoro-10-methyl-9-oxo-8,17-diazatricyclo[13.3.1.0$^{2,7}$]nonadeca-1(19),2(7),3,5,15,17-hexaen-5-yl]carbamate (28);
methyl N-[(14S)-14-[1-(3-chloro-2-fluorophenyl)-1H-1,2,3-triazole-4-amido]-10-methyl -9,17-dioxo-8,16-diazatricyclo[13.3.1.0$^{2,7}$]nonadeca-1(18),2,4,6,15(19)-pentaen-5-yl]carbamate (29);
ethyl N-[(14S)-14[1-(3-chloro-2-fluorophenyl)-1H-1,2,3-triazole-4-amido]-10-methyl-9,17-dioxo-8,16-diazatricyclo[13.3.1.0$^{2,7}$]nonadeca-1(18),2,4,6,15(19)-pentaen-5-yl]carbamate (30);
methyl N-[(14S)-14-[1-(3-chloro-2-fluorophenyl)-1H-pyrazole-4-amido]-10-methyl-9-oxo -8,18-diazatricyclo[13.3.1.0$^{2,7}$]nonadeca-1(19),2(7),3,5,15,17-hexaen-5-yl]carbamate (31);
methyl N-[(14S)-14-[1-(3-chloro-2-fluorophenyl)-1H-pyrazole-4-amido]-16-fluoro-9-oxo -8,17-diazatricyclo[13.3.1.0$^{2,7}$]nonadeca-1(19),2(7),3,5,15,17-hexaen-5-yl]carbamate (32);
methyl N-[(12E,15S)-15-[1-(3-chloro-2-fluorophenyl)-1H-1,2,3-triazole-4-amido]-9,18-dioxo-8,17-diazatricyclo[14.3.1.0$^{2,7}$]icosa-1(19),2,4,6,12,16(20)-hexaen-5-yl]carbamate (33);
methyl ((10R,14S)-14-(((1-(3-chloro-2-fluorophenyl)-1H-1,2,3-triazol-4-yl)carbonyl)amino)-10-methyl-9-oxo-8,18-diazatricyclo[13.3.1.0$^{2,7}$]nonadeca-1(19),2,4,6,15,17-hexaen-5-yl)carbamate (59);
methyl ((10S,14S)-14-(((1-(3 -chloro-2-fluorophenyl)-1H-1,2,3-triazol-4-yl)carbonyl)amino)-10-methyl-9-oxo-8,18-diazatricyclo[13.3.1.0$^{2,7}$]nonadeca-1(19),2,4,6,15,17-hexaen-5-yl)carbamate (60);
methyl N-[(10R,14S)-14-[1-(3-chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaen-5-yl]carbamate (61);
methyl N-[(10R,14S)-14-[1-(3-chloro-2-fluorophenyl)-5-methyl-1H-imidazole-4-amido]-10-methyl-9-oxo-8,16-diazatricyclo[613.3.1.0$^{2,7}$]nonadeca-1(19),2(7),3,5,15,17-hexaen-5-yl]carbamate (62);
methyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate (63);
methyl N-[(10R,14S)-14-[1-(3 -chloro-2-fluorophenyl)-5-methyl-1H-1,2,3-triazole-4-amido]-16-fluoro-10-methyl-9-oxo-8,18-diazatricyclo[13.3.1.0$^{2,7}$]nonadeca-1(19),2(7),3,5,15,17-hexaen-5-yl]carbamate (86);
methyl N-[(10R,14S)-14-[1-(3-chloro-2-fluorophenyl)-5-methyl-1H-1,2,3-triazole-4-amido]-6-fluoro-10-methyl-9-oxo-8,16-diazatricyclo[13.3.1.0$^{2,7}$]nonadeca-1(19),2(7),3,5,15,17-hexaen-5-yl]carbamate (87);
methyl N-[(14S)-14[1-(3-chloro-2-fluorophenyl)-5-methyl-1H-1,2,3-triazole-4-amido]-13-methyl-9-oxo-8,16-diazatricyclo[13.3.1.0$^{2,7}$]nonadeca-1(19),2(7),3,5,15,17-hexaen-5-yl]carbamate (88);

N-[(10R,14S)-5-amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-1,2,3-triazole-4-carboxamide (89);

N-[(10R,14S)-5-amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide, (90);

N-[(10S,14S)-5-amino-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide (91);

N-[(10R,14S)-5-amino-10-methyl-9-oxo-8,18-diazatricyclo[13.3.1.0$^{2,7}$]nonadeca-1(19),2(7),3,5,15,17-hexaen-14-yl]-1-(3-chloro-2-fluorophenyl)-5-methyl-1H-pyrazole-4-carboxamide (92);

N-[(10R,14S)-5-amino-10-methyl-9-oxo-8,18-diazatricyclo[13.3.1.0$^{2,7}$]nonadeca-1(19),2(7),3,5,15,17-hexaen-14-yl]-1-(3-chloro-2-fluorophenyl)-5-methyl-1H-imidazole-4-carboxamide (93);

1-(3-chloro-2-fluorophenyl)-5-methyl-N-[(10R,14S)-10-methyl-5-[(methylcarbamoyl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide (94);

propan-2-yl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate (95);

1-(3-chloro-2-fluorophenyl)-N-R10R,14S)-5-[(dimethylcarbamoyl)amino]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (135);

1-(3-chloro-2-fluorophenyl)-N-[(10R,14S)-5-methanesulfonamido-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (136);

1-(3-chloro-2-fluorophenyl)-5-methyl-N-[(10R,14S)-10-methyl-9-oxo-5-(trifluoroacetamido)-8,16-diazatricyclo[13.3.1.0$^{2,7}$]nonadeca-1(19),2(7),3,5,15,17-hexaen-14-yl]-1H -1,2,3-triazole-4-carboxamide (137);

1-(3-chloro-2-fluorophenyl)-N-[(10R,14S)-5-acetamido-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (138);

fluoromethyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate (139);

fluoromethyl N-[(10R,14S)-14-[1-(3-chloro-2-fluorophenyl)-5-methyl-1H-pyrazole-4-amido]-10-methyl-9-oxo-8,18-diazatricyclo[13.3.1.0$^{2,7}$]nonadeca-1(19),2(7),3,5,15,17-hexaen-5-yl]carbamate (140);

1-(3-chloro-2-fluorophenyl)-N-[(10R,14S)-5-(2-methoxyacetamido)-10-methyl-9-oxo-8,16-diazatricyclo[13.3.1.0$^{2,7}$]nonadeca-1(19),2(7),3,5,15,17-hexaen-14-yl]-5-methyl-1H- 1,2,3-triazole-4-carboxamide (141);

1-(3-chloro-2-fluorophenyl)-N-[(10S,14S)-5-(2-methoxyacetamido)-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (142);

1-(3-chloro-2-fluorophenyl)-5-methyl-N-[(10R,14S)-10-methyl-9-oxo-5-(2-oxopropanamido)-8,16-diazatricyclo[13.3.1.0$^{2,7}$]nonadeca-1(19),2(7),3,5,15,17-hexaen-14-yl]-1H-1,2,3-triazole-4-carboxamide (143);

1-(3-chloro-2-fluorophenyl)-N-[(10R,14S)-5-(2-hydroxypropanamido)-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (144);

2-hydroxypropyl N-[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamate (145);

tert-butyl 2-{[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]carbamoyl}acetate (146);

1-(3-chloro-2-fluorophenyl)-N-[(10R,14S)-5-[(E)-2-cyano-1-methylcarbamimidamido]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (147);

1-(3-chloro-2-fluorophenyl)-N-[(10S,14S)-5-[(E)-2-cyano-1-methylcarbamimidamido]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (148);

1-(3-chloro-2-fluorophenyl)-N-[(10R,14S)-5-{[6-(methoxymethyl)pyrimidin-4-yl]amino}-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (149);

1-(3-chloro-2-fluorophenyl)-N-[(10R,14S)-5[(E)-[(dimethylamino)methylidene]amino]-10-methyl-9-oxo-8,16-diazatricyclo[13.3.1.0$^{2,7}$]nonadeca-1(19),2(7),3,5,15,17-hexaen-14-yl]-5-methyl-1H-1,2,3-triazole-4-carboxamide (150);

ethyl 2-{[(10R,14S)-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaen-5-yl]amino}acetate (156);

methyl (10R,14S)-5-amino-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaene-4-carboxylate (157);

(10R,14S)-5-amino-14-[1-(3-chloro-2-fluorophenyl)-5-methyl-1H-1,2,3-triazole-4-amido]-10-methyl-9-oxo-8,16-diazatricyclo[13.3.1.0$^{2,7}$]nonadeca-1(19),2(7),3,5,15,17-hexaene-4-carboxylic acid (158);

1-(3-chloro-2-fluorophenyl)-5-methyl-N-[(10R,14S)-10-methyl-5-[(5-methyl-1,3,4-oxadiazol-2-yl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide (159);

N-[(10R,14S)-5-carbamimidamido-10-methyl-9-oxo-8,16-diazatricyclo[13.3.1.0$^{2,7}$]nonadeca-1(19),2(7),3,5,15,17-hexaen-14-yl]-1-(3-chloro-2-fluorophenyl)-5-methyl-1H-1,2,3-triazole-4-carboxamide (160);

1-(2-fluorophenyl)-5-methyl-N-[(10S,14S)-10-methyl-5-[(5-methyl-1,3,4-oxadiazol-2-yl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide (161);

1-(3-chloro-2-fluorophenyl)-5-methyl-N-[(10R,14S)-10-methyl-5-[(1,3,4-oxadiazol-2-yl)amino]-9-oxo-8,16-diazatricyclo[13.3.1.0$^{2,7}$]nonadeca-1(19),2(7),3,5,15,17-hexaen-14-yl]-1H-1,2,3-triazole-4-carboxamide (162);

N-[(10R,14S)-5-bromo-10-methyl-9-oxo-8,16-diazatricyclo[13.3.1.0$^{2,7}$]nonadeca-1(19),2(7),3,5,15,17- hexaen-14-yl]-1-(3-chloro-2 fluorophenyl)-5-methyl-1H-1,2,3-triazole-4 carboxamide (163);

1-(3-chloro-2-fluorophenyl)-5-methyl-N-[(10R,14S)-10-methyl-9-oxo-5-(1H-pyrazol-5-yl)-8,16-diazatricyclo[13.3.1.0$^{2,7}$]nonadeca-1(19),2(7),3,5,15,17-hexaen-14-yl]-1H-1,2,3-triazole-4-carboxamide (164);

1-(3-chloro-2-fluorophenyl)-5-methyl-N-[(10S,14S)-10-methyl-9-oxo-5-(1H-pyrazol-5-yl)-8,16-diazatricyclo[13.3.1.0$^{2,7}$]nonadeca-1(19),2(7),3,5,15,17-hexaen-14-yl]-1H-1,2,3-triazole-4-carboxamide (165);

1-(3-chloro-2-fluorophenyl)-5-methyl-N-[(10R,14S)-10-methyl-9-oxo-5-[(1,3-thiazol-2-yl)amino]-8,16-diazatricyclo[13.3.1.0$^{2,7}$]nonadeca-1(19),2(7),3,5,15,17-hexaen-14-yl]-1H-1,2,3-triazole-4-carboxamide (166);

1-(3-chloro-2-fluorophenyl)-5-methyl-N-[(10S,14S)-10-methyl-9-oxo-5-[(1,3-thiazol-2-yl)amino]-8,16-diazatricyclo[13.3.1.0$^{2,7}$]nonadeca-1(19),2(7),3,5,15,17-hexaen-14-yl]-1H-1,2,3-triazole-4-carboxamide (167);

1-(3-chloro-2-fluorophenyl)-5-methyl-N-[(10R,14S)-10-methyl-9-oxo-5-(2-oxo-1,2-dihydropyridin-3-yl)-8,16-diazatricyclo[13.3.1.0$^{2,7}$]nonadeca-1(19),2(7),3,5,15,17-hexaen-14-yl]-1H-1,2,3-triazole-4-carboxamide (172);

methyl N-[(10R,14S)-14-[1-(3-chloro-2-fluorophenyl)-5-methyl-1H-1,2,3-triazole-4-amido]-10-methyl-9,11-dioxo-8,16-diazatricyclo[13.3.1.0$^{2,7}$]nonadeca-1(19),2(7),3,5,15,17-hexaen-5-yl]carbamate (173);

methyl N-[(10R,14S)-14-[1-(3-chloro-2-fluorophenyl)-5-methyl-1H-1,2,3-triazole-4-amido]-10-methyl-9,12-dioxo-8,16-diazatricyclo[13.3.1.0$^{2,7}$]nonadeca-1(19),2(7),3,5,15,17-hexaen-5-yl]carbamate (174);

methyl N-[(10R,12R,14S)-14-[1-(3-chloro-2-fluorophenyl)-5-methyl-1H-pyrazole-4-amido]-12-hydroxy-10-methyl-9-oxo-8,16-diazatricyclo[13.3.1.0$^{2,7}$]nonadeca-1(19),2(7),3,5,15,17-hexaen-5-yl]carbamate (175);

methyl N-[(10R,12S,14S)-14-[1-(3-chloro-2-fluorophenyl)-5-methyl-1H-pyrazole-4-amido]-12-hydroxy-10-methyl-9-oxo-8,16-diazatricyclo[13.3.1.0$^{2,7}$]nonadeca-1(19),2(7),3,5,15,17-hexaen-5-yl]carbamate (176);

methyl N-[(10R,14S)-14-[1-(3-chloro-2-fluorophenyl)-5-methyl-1H-pyrazole-4-amido]-11-hydroxy-10-methyl-9-oxo-8,16-diazatricyclo[13.3.1.0$^{2,7}$]nonadeca-1(19),2(7),3,5,15,17-hexaen-5-yl]carbamate (177);

methyl N-[(10R,14S)-14-[1-(3-chloro-2-fluorophenyl)-5-methyl-1H-pyrazole-4-amido]-11-hydroxy-10-methyl-9-oxo-8,16-diazatricyclo[13.3.1.0$^{2,7}$]nonadeca-1(19),2(7),3,5,15,17-hexaen-5-yl]carbamate (178);

methyl N-[(10S,14S)-14-[1-(3-chloro-2-fluorophenyl)-5-methyl-1H-pyrazole-4-amido]-11-fluoro-10-methyl-9-oxo-8,16-diazatricyclo[13.3.1.0$^{2,7}$]nonadeca-1(19),2(7),3,5,15,17-hexaen-5-yl]carbamate (179);

methyl N-[(14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0$^{2,7}$]nonadeca-1(19),2(7),3,5,15,17-hexaen-5-yl]carbamate (180);

methyl N-[(10S,14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0$^{2,7}$]nonadeca-1(19),2(7),3,5,15,17-hexaen-5-yl]carbamate (181);

methyl N-[(10R,14S)-14-[1-(3-chloro-2-fluorophenyl)-5-methyl-1H-1,2,3-triazole-4-amido]-18-fluoro-10-methyl-9-oxo-8,16-diazatricyclo[13.3.1.0$^{2,7}$]nonadeca-1(19),2(7),3,5,15,17-hexaen-5-yl]carbamate (182);

methyl N-[(14S)-14-[1-(3-chloro-2-fluorophenyl)-5-methyl-1H-1,2,3-triazole-4-amido]-10,18-dimethyl-9-oxo-8,16-diazatricyclo[13.3.1.0$^{2,7}$]nonadeca-1(19),2(7),3,5,15,17-hexaen-5-yl]carbamate (183);

methyl (10R,14S)-14-[1-(3-chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylate (184);

(10R,14S)-14-[1-(3-chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylic acid (185);

(10S,14S)-14-[1-(3-chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-4-carboxylic acid (186);

(10R,14S)-14-[1-(3-chloro-2-fluorophenyl)-5-methyl-1H-pyrazole-4-amido]-10-methyl-9-oxo-8,16-diazatricyclo[13.3.1.0$^{2,7}$]nonadeca-1(19),2(7),3,5,15,17-hexaene-5-carboxylic acid (187);

(14S)-14-[1-(3-chloro-2-fluorophenyl)-5-methyl-1H-pyrazole-4-amido]-9-oxo-8,16-diazatricyclo[13.3.1.0$^{2,7}$]nonadeca-1(19),2(7),3,5,15,17-hexaene-4-carboxylic acid (188);

(10R,14S)-14-C-1-(3-chloro-2-fluorophenyl)-5-methyl-1H-pyrazole-4-N,10-dimethyl-9-oxo-8,16-diazatricyclo[13.3.1.0$^{2,7}$]nonadeca-1(19),2(7),3,5,15,17-hexaene-4,14-diamido (189);

(10R,14S)-14-C-1-(3-chloro-2-fluorophenyl)-5-methyl-1H-pyrazole-4-10-methyl-9-oxo-8,16-diazatricyclo[13.3.1.0$^{2,7}$]nonadeca-1(19),2(7),3,5,15,17-hexaene-5,14-diamido (190);

(10S,14S)-14-C-1-(3-chloro-2-fluorophenyl)-5-methyl-1H-pyrazole-4-10-methyl-9-oxo-8,16-diazatricyclo[13.3.1.0$^{2,7}$]nonadeca-1(19),2(7),3,5,15,17-hexaene-5,14-diamido (191);

(14S)-14-C-1-(3-chloro-2-fluorophenyl)-5-methyl-1H-pyrazole-4-9-oxo-8,16-diazatricyclo[13.3.1.0$^{2,7}$]nonadeca-1(19),2(7),3,5,15,17-hexaene-5,14-diamido (192);

(14S)-14-C-1-(3-chloro-2-fluorophenyl)-5-methyl-1H-pyrazole-4-5-N,5-N-dimethyl-9-oxo-8,16-diazatricyclo[13.3.1.0$^{2,7}$]nonadeca-1(19),2(7),3,5,15,17-hexaene-5,14-diamido (193);

1-(3-chloro-2-fluorophenyl)-5-methyl-N-[(10R,14S)-10-methyl-9-oxo-5-(1H-1,2,4-triazol-5-y1)-8,16-diazatricyclo[13.3.1.0$^{2,7}$]nonadeca-1(19),2(7),3,5,15,17-hexaen-14-yl]-1H-pyrazole-4-carboxamide (194);

1-(3-chloro-2-fluorophenyl)-5-methyl-N-[(10R,14S)-10-methyl-5-(5-methyl-4H-1,2,4-triazol-3-yl)-9-oxo-8,16-diazatricyclo[13.3.1.0$^{2,7}$]nonadeca-1(19),2(7),3,5,15,17-hexaen-14-yl]-1H-pyrazole-4-carboxamide (195);

1-(3-chloro-2-fluorophenyl)-N-[(10R,14S)-5-(hydroxymethyl)-10-methyl-9-oxo-8,16-diazatricyclo[13.3.1.0$^{2,7}$]nonadeca-1(19),2(7),3,5,15,17-hexaen-14-yl]-5-methyl-1H-pyrazole-4-carboxamide (196);

1-(3-chloro-2-fluorophenyl)-5-methyl-N-[(14S)-10-methyl-5-(3-methyl-1,2,4-oxadiazol-5-yl)-9-oxo-8,16-diazatricyclo[13.3.1.0$^{2,7}$]nonadeca-1(19),2(7),3,5,15,17-hexaen-14-yl]-1H-pyrazole-4-carboxamide (197);

1-(3-chloro-2-fluorophenyl)-5-methyl-N-[(14S)-9-oxo-4-(2H-1,2,3,4-tetrazol-5-yl)-8,16-diazatricyclo[13.3.1.0$^{2,7}$]nonadeca-1(19),2(7),3,5,15,17-hexaen-14-yl]-1H-pyrazole-4-carboxamide (198);

methyl N-[(10R,14 S)-14-[1-(3-chloro-2-fluorophenyl)-5-methyl-1H-1,2,3-triazole-4-amido]-17-methoxy-10-methyl-9-oxo-8,16-diazatricyclo[13.3.1.0$^{2,7}$]nonadeca-1(18),2,4,6,15(19),16-hexaen-5-yl]carbamate (199);

methyl N-[(10R,14S)-14-[1-(3-chloro-2-fluorophenyl)-5-methyl-1H-1,2,3-triazole-4-amido]-17-ethoxy-10-methyl-9-oxo-8,16-diazatricyclo[13.3.1.0$^{2,7}$]nonadeca-1(18),2,4,6,15(19),16-hexaen-5-yl]carbamate (200);

methyl N-[(10R,14 S)-14-[1-(3-chloro-2-fluorophenyl)-5-methyl-1H-1,2,3-triazole-4-amido]-10,16-dimethyl-9,17-dioxo-8,16-diazatricyclo[13.3.1.0$^{2,7}$]nonadeca-1(18),2,4,6,15(19)-pentaen-5-yl] carbamate (201);

methyl N-[(14S)-14-[1-(3-chloro-2-fluorophenyl)-5-methyl-1H-pyrazole-4-amido]-9-oxo-11-oxa-8,16-diazatricyclo[13.3.1.0$^{2,7}$]nonadeca-1(19),2(7),3,5,15,17-hexaen-5-yl]carbamate (217);

methyl N-[(14S)-14-[1-(3-chloro-2-fluorophenyl)-5-methyl-1H-pyrazole-4-amido]-9-oxo-10-oxa-8,16-diazatricyclo[13.3.1.0$^{2,7}$]nonadeca-1(19),2,4,6,15,17-hexaen-5-yl]carbamate (219);

methyl N-[(14S)-14-[1-(3-chloro-2-fluorophenyl)-5-methyl-1H-pyrazole-4-amido]-10-methyl-8-oxo-9,16-diazatricyclo[13.3.1.0$^{2,7}$]nonadeca-1(19),2(7),3,5,15,17-hexaen-5-yl]carbamate (220);

methyl N-[(14S)-14-[1-(3-chloro-2-fluorophenyl)-5-methyl-1H-pyrazole-4-amido]-10-methyl-8-oxo-9,16-diazatricyclo[13.3.1.0$^{2,7}$]nonadeca-1(19),2(7),3,5,15,17-hexaen-5-yl]carbamate (221).

\* \* \* \* \*